(12) United States Patent
Shiraishi et al.

(10) Patent No.: US 6,936,602 B1
(45) Date of Patent: Aug. 30, 2005

(54) BENZAZEPINE DERIVATIVES, PROCESS FOR THE PREPARATION OF THE SAME AND USES THEREOF

(75) Inventors: Mitsuru Shiraishi, Amagasaki (JP); Masanori Baba, Kogoshima (JP); Yoshio Aramaki, Itami (JP); Naoyuki Kanzaki, Ibaraki (JP); Osamu Nishimura, Kawanishi (JP)

(73) Assignee: Takeda Chemical Industries, Ltd., Osaka (JP)

(*) Notice: Subject to any disclaimer, the term of this patent is extended or adjusted under 35 U.S.C. 154(b) by 277 days.

(21) Appl. No.: 10/018,321

(22) PCT Filed: Jun. 15, 2000

(86) PCT No.: PCT/JP00/03879

§ 371 (c)(1),
(2), (4) Date: Dec. 12, 2001

(87) PCT Pub. No.: WO00/76993

PCT Pub. Date: Dec. 21, 2000

(30) Foreign Application Priority Data

May 16, 1999 (JP) ............................................. 11/170345

(51) Int. Cl.$^7$ .................... A61K 31/55; A61P 31/00; C07D 223/16
(52) U.S. Cl. ................. 514/213.01; 514/81; 514/86; 514/220; 514/230.5; 514/253.01; 514/253.09; 514/255.05; 514/263.23; 514/263.4; 514/274; 514/307; 514/314; 514/365; 514/471; 540/495; 540/593; 544/92; 544/243; 544/244; 544/265; 544/277; 544/312; 544/314; 544/317; 544/336; 544/360; 544/364; 546/146; 546/169; 548/204
(58) Field of Search ................... 514/213.01; 540/593

(56) References Cited

U.S. PATENT DOCUMENTS

| 5,716,944 A | 2/1998 | Sohda et al. ............... 514/119 |
| 6,166,006 A * | 12/2000 | Shiraishi et al. ........ 514/213.01 |
| 6,172,061 B1 * | 1/2001 | Nishimura et al. ...... 514/231.5 |

FOREIGN PATENT DOCUMENTS

| EP | 0 825 186 | 2/1998 |
| JP | 7025756 | 1/1995 |
| JP | 7025757 | 1/1995 |
| WO | WO 96/01267 | 1/1996 |
| WO | WO 99/32100 | 7/1999 |
| WO | WO 99/32468 | 7/1999 |
| WO | WO 00/10965 | 3/2000 |
| WO | WO 00/37455 | 6/2000 |
| WO | WO 00/68203 | 11/2000 |

OTHER PUBLICATIONS

HORUK, Chemokine Receptors, Cytokine and Growth Factor Reviews, Dec. 2001, vol. 12, No. 4, pp. 313–335.*

M. Baba et al. "A Small–Molecule, Nonpeptide CCR5 Antagonist with Highly Potent and Selective Anti–HIV–I Activity", Proc. Natl. Acad. Sci USA (May 1999) vol. 96, pp. 5698–5703.

* cited by examiner

*Primary Examiner*—Brenda Coleman
(74) *Attorney, Agent, or Firm*—Elaine M. Ramesh; Mark Chao

(57) ABSTRACT

Compounds of the general formula (I):

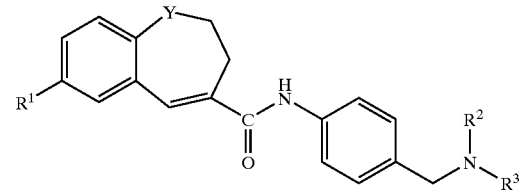

or salts thereof, which exhibit CCR5 antagonism and exert preventive and therapeutic effects against HIV infections: wherein $R^1$ is a 5- to 6-membered aromatic ring which bears a substituent represented by the general formula: R-$Z^1$-X-$Z^2$- (wherein $R^1$ is hydrogen or optionally substituted hydrocarbyl; X is optionally substituted alkylene; and $Z^1$ and $Z^2$ are each a heteroatom) and may be further substituted, with R being optionally bonded to the aromatic ring to form another ring; Y is optionally substituted imino; and $R^2$ and $R^3$ are each optionally substituted aliphatic hydrocarbyl or an optionally Substituted hetero-alicyclic group.

27 Claims, No Drawings

BENZAZEPINE DERIVATIVES, PROCESS FOR THE PREPARATION OF THE SAME AND USES THEREOF

This application is the National Stage of International Application No. PCT/JP00/03879, filed on Jun. 15, 2000.

TECHNICAL FIELD

The present invention relates to a novel benzazepine derivative, production and use thereof.

BACKGROUND ART

Recently, HIV (human immunodeficiency virus) protease inhibitors are developed for method of the treatment of AIDS (acquired immunological deficient syndrome) and use of the protease inhibitors in combination with conventional two HIV reverse transcriptase inhibitors provides with a further progress of the treatment of AIDS. However, these drugs and their combination use are not sufficient for the eradications of AIDS, and development of new anti-AIDS drugs having different activity and mechanism are sought for.

As a receptor from which HIV invades to a target cell, CD4 is so far known, and recently CCR5 as a second receptor of macrophage-tropic HIV and CXCR4 as a second receptor of T cell-tropic HIV, each of which is G protein-coupled chemokine receptor having seven transmembrane domains, are respectively found out. These chemokine receptors are thought to play an essential role in establishment and spread of HIV infection. In fact, it is reported that a person who is resistant to HIV infection in spite of several exposures retains mutation of homo deletion of CCR5 gene. Therefore, a CCR5 antagonist is expected to be a new anti-HIV drug. However, so far, there has been no report that a CCR5 antagonist is developed as a therapeutic agent of AIDS.

DISCLOSURE OF THE INVENTION

In order to investigate an anti-AIDS drug having CCR5 antagonistic activity, it is necessary to clone CCR5 gene from human tissue derived cDNA library, to ligate said gene with a vector for expression in animal cells, to introduce said gene into animal cells and to obtain cells expressing CCR5. In addition, with using this transformant, it is necessary to screen a compound which strongly inhibits binding of CC chemokine RANTES, natural ligand, to CCR5. However, so far there has been almost no report of a low molecular weight compound which has this CCR5 antagonistic activity and is suitable for oral administration. The present invention is to provide a novel anilide derivative which is useful for the treatment or prevention of infectious diseases of HIV and, in particular, AIDS and also which is suitable for oral administration, production and use thereof.

The present inventors diligently made extensive studies on compounds having CCR5 antagonistic activity and, as a result, they found that a benzazepine derivative of the following formula (I) or a salt thereof [hereinafter, referred to as Compound (I) in some cases] possesses CC chemokine receptor (CCR) antagonistic activity, in particular, potent CCR5 antagonistic activity and clinically desirable pharmaceutical effect (e.g. remarkable inhibition of HIV infection to human peripheral mononuclear cells, etc.) and also that Compound (I) has superior absorbability when orally administered. Based on the finding, the present invention was accomplished.

More specifically, the present invention relates to
(1) A compound of the formula (I):

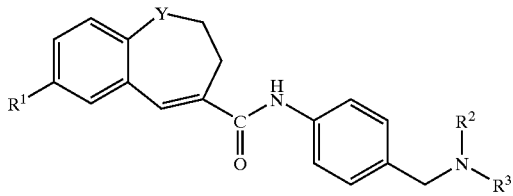

wherein $R^1$ is a 5- to 6-membered aromatic ring which has a group of the formula: $R-Z^1-X-Z^2-$ wherein R is a hydrogen atom or an optionally substituted hydrocarbon group, X is an optionally substituted alkylene chain, and $Z^1$ and $Z^2$ are respectively hetero-atoms, and which may have a further substituent, the group R may bind to the 5- to 6-membered aromatic ring to form a ring, Y is an optionally substituted imino group, $R^2$ and $R^3$ are respectively an optionally substituted aliphatic hydrocarbon group or an optionally substituted alicyclic heterocyclic group; or a salt thereof;
(2) A pro-drug of the compound as described in the above (1) or a salt thereof;
(3) The compound as described in the above (1), wherein the 5- to 6-membered aromatic ring is benzene, furan or thiophene;
(4) The compound as described in the above (1), wherein the 5- to 6-membered aromatic ring is benzene;
(5) The compound as described in the above (1), wherein R is an optionally halogenated lower alkyl group;
(6) The compound as described in the above (1), wherein X is $-(CH_2)_n-$ (n is an integer of 1–4);
(7) The compound as described in the above (1), wherein $Z^1$ and $Z^2$ are respectively $-O-$, $-S(O)_m-$ (m is an integer of 0–2) or $-N(R^4)-$ ($R^4$ is a hydrogen atom or an optionally substituted lower alkyl group);
(8) The compound as described in the above (1), wherein $Z^1$ is $-O-$ or $-S(O)_m-$ (m is an integer of 0–2);
(9) The compound as described in the above (1), wherein $Z^1$ is $-O-$;
(10) The compound as described in the above (1), wherein $Z^2$ is $-O-$ or $-N(R^4)-$ ($R^4$ is a hydrogen atom or an optionally substituted lower alkyl group);
(11) The compound as described in the above (1), wherein $Z^2$ is $-O-$;
(12) The compound as described in the above (1), wherein Y is $-N(R^5)-$ ($R^5$ is a hydrogen atom, an optionally substituted hydrocarbon group or an optionally substituted acyl group);
(13) The compound as described in the above (12), wherein ($R^5$) is $C_{1-4}$ alkyl, formyl or $C_{2-5}$ alkanoyl;
(14) The compound as described in the above (12), wherein $R^5$ is a group represented by the formula $-(CH_2)_k-R^6$: wherein k is 0 or 1, and $R^6$ is an optionally substituted 5- to 6-membered monocyclic aromatic group;
(15) The compound as described in the above (1), wherein $R^2$ is an optionally substituted straight chain hydrocarbon group;
(16) The compound as described in the above (1), wherein $R^2$ is an optionally substituted lower alkyl group;
(17) The compound as described in the above (1), wherein $R^3$ is an optionally substituted alicyclic hydrocarbon group or an optionally substituted alicyclic heterocyclic group;
(18) The compound as described in the above (17), wherein the alicyclic hydrocarbon group is a lower cycloalkyl group;

(19) The compound as described in the above (17), wherein the alicyclic hydrocarbon group is cyclohexyl;
(20) The compound as described in the above (17), wherein the alicyclic heterocyclic group is a saturated alicyclic heterocyclic group;
(21) The compound as described in the above (17), wherein the alicyclic heterocyclic group is tetrahydropyranyl, tetrahydrothiopyranyl or piperidyl;
(22) The compound as described in the above (17), wherein the alicyclic heterocyclic group is tetrahydropyranyl;
(23) The compound selected from the class consisting of
7-(4-ethoxyethoxyphenyl)-1-ethyl-N-[4-[[N-methyl-N-(tetrahydropyran-4-yl)amino]methyl]phenyl]-2,3-dihydro-1-benzazepine-4-carboxamide;
1-ethyl-7-(4-propoxyethoxyphenyl)-N-[4-[[N-methyl-N-(tetrahydropyran-4-yl)amino]methyl]phenyl]-2,3-dihydro-1-benzazepine-4-carboxamide;
7-(4-butoxyethoxyphenyl)-1-ethyl-N-[4-[[N-methyl-N-(tetrahydropyran-4-yl)amino]methyl]phenyl]-2,3-dihydro-1-benzazepine-4-carboxamide;
7-(4-ethoxyethoxyphenyl)-1-formyl-N-[4-[[N-methyl-N-(tetrahydropyran-4-yl)amino]methyl]phenyl]-2,3-dihydro-1-benzazepine-4-carboxamide,
1-formyl-7-(4-propoxyethoxyphenyl)-N-[4-[[N-methyl-N-(tetrahydropyran-4-yl)amino]methyl]phenyl]-2,3-dihydro-1-benzazepine-4-carboxamide,
7-(4-butoxyethoxyphenyl)-1-formyl-N-[4-[[N-methyl-N-(tetrahydropyran-4-yl)amino]methyl]phenyl]-2,3-dihydro-1-benzazepine-4-carboxamide,
7-(4-butoxyethoxyphenyl)-N-[4-[[N-methyl-N-(tetrahydropyran-5-yl)amino]methyl]phenyl]-1-propyl-2,3-dihydro-1-benzazepine-4-carboxamide,
N-[4-[[N-methyl-N-(tetrahydropyran-5-yl)amino]methyl]phenyl]-7-(4-propoxyethoxyphenyl)-1-propyl-2,3-dihydro-1-benzazepine-4-carboxamide,
1-benzyl-7-(4-butoxyethoxyphenyl)-N-[4-[[N-methyl-N-(tetrahydropyran-4-yl)amino]methyl]phenyl]-2,3-dihydro-1-benzazepine-4-carboxamide,
7-(4-butoxyethoxyphenyl)-1-cyclopropylmethyl-N-[4-[[N-methyl-N-(tetrahydropyran-4-yl)amino]methyl]phenyl]-2,3-dihydro-1-benzazepine-4-carboxamide,
7-(4-butoxyethoxyphenyl)-N-[4-[[N-methyl-N-(tetrahydropyran-4-yl)amino]methyl]phenyl]-1-phenyl-2,3-dihydro-1-benzazepine-4-carboxamide,
7-(4-butoxyethoxyphenyl)-1-(3,4-methylenedioxy)phenyl-N-[4-[[N-methyl-N-(tetrahydropyran-4-yl)amino]methyl]phenyl]-2,3-dihydro-1-benzazepine-4-carboxamide,
7-(4-butoxyethoxyphenyl)-1-(2-methyloxazol-5-yl)-N-[4-[[N-methyl-N-(tetrahydropyran-4-yl)amino]methyl]phenyl]-2,3-dihydro-1-benzazepine-4-carboxamide,
1-allyl-7-(4-butoxyethoxyphenyl)-N-[4-[[N-methyl-N-(tetrahydropyran-4-yl)amino]methyl]phenyl]-2,3-dihydro-1-benzazepine-4-carboxamide,
7-(4-butoxyethoxyphenyl)-N-[4-[[N-methyl-N-(tetrahydropyran-4-yl)amino]methyl]phenyl]-1-(3-thienyl)methyl-2,3-dihydro-1-benzazepine-4-carboxamide,
7-(4-butoxyethoxyphenyl)-N-[4-[[N-methyl-N-(tetrahydropyran-4-yl)amino]methyl]phenyl]-1-(thiazol-2-yl)methyl-2,3-dihydro-1-benzazepine-4-carboxamide,
7-(4-butoxyethoxyphenyl)-1-(1-methylpyrazol-4-yl)methyl-N-[4-[[N-methyl-N-(tetrahydropyran-4-yl)amino]methyl]phenyl]-2,3-dihydro-1-benzazepine-4-carboxamide,
7-(4-butoxyethoxyphenyl)-1-(3-methylisothiazol-4-yl)methyl-N-[4-[[N-methyl-N-(tetrahydropyran-5-yl)amino]methyl]phenyl]-2,3-dihydro-1-benzazepine-4-carboxamide,
7-(4-butoxyethoxyphenyl)-1-(1-ethylpyrazol-4-yl)methyl-N-[4-[[N-methyl-N-(tetrahydropyran-4-yl)amino]methyl]phenyl]-2,3-dihydro-1-benzazepine-4-carboxamide,
7-(4-butoxyethoxyphenyl)-1-isobutyl-N-[4-[[N-methyl-N-(tetrahydropyran-5-yl)amino]methyl]phenyl]-2,3-dihydro-1-benzazepine-4-carboxamide,
1-isobutyl-N-[4-[[N-methyl-N-(tetrahydropyran-5-yl)amino]methyl]phenyl]-7-(4-propoxyethoxyphenyl)-2,3-dihydro-1-benzazepine-4-carboxamide,
7-(4-butoxyethoxyphenyl)-N-[4-[[N-methyl-N-(tetrahydropyran-4-yl)amino]methyl]phenyl]-1-(thiazol-5-yl)methyl-2,3-dihydro-1-benzazepine-4-carboxamide,
7-(4-butoxyethoxyphenyl)-N-[4-[[N-methyl-N-(tetrahydropyran-4-yl)amino]methyl]phenyl]-1-(1-methyltetrazol-5-yl)methyl-2,3-dihydro-1-benzazepine-4-carboxamide, and
7-(4-butoxyethoxyphenyl)-N-[4-[[N-methyl-N-(tetrahydropyran-4-yl)amino]methyl]phenyl]-1-(2-methyltetrazol-5-yl)methyl-2,3-dihydro-1-benzazepine-4-carboxamide, or salt thereof;
(24) A pro-drug of the compound as described in the above (23) or a salt thereof;
(25) A method for producing a compound of the formula:

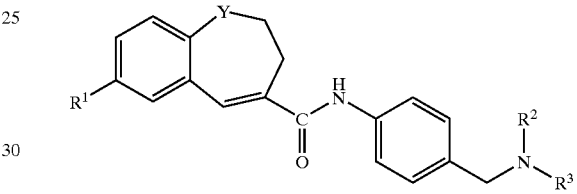

wherein each symbol is as described in the above (1), or a salt thereof, which comprises subjecting a compound of the formula:

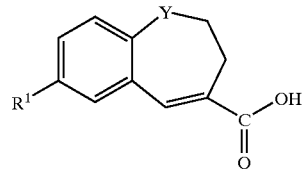

wherein each symbol is as described in the above (1), a salt or a reactive derivative thereof to a condensation reaction with a compound of the formula:

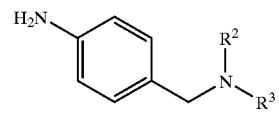

wherein each symbol is as described in the above (1), or a salt thereof;
(26) A pharmaceutical composition which comprises the compound as described in the above (1) or a salt thereof;
(27) The composition as described in the above (26), which is a CC chemokine receptor (CCR) antagonist;
(28) The pharmaceutical composition as described in the above (26), which is a CCR5 antagonist;
(29) The composition as described in the above (26), which is for the treatment or prevention of infectious disease of HIV;
(30) The composition as described in the above (26), which is for the treatment or prevention of AIDS;

(31) The composition as described in the above (26), which is for the prevention of the progression of AIDS;

(32) The composition as described in the above (29), which is used in combination with a protease inhibitor and/or a reverse transcriptase inhibitor;

(33) The composition as described in the above (32), wherein the reverse transcriptase inhibitor is zidovudine, didanosine, zalcitabine, lamivudine, stavudine, nevirapine, delavirdine, efavirenz or abacavir;

(34) The composition as described in the above (32), wherein the protease inhibitor is saquinavir, ritonavir, indinavir or nelfinavir;

(35) Use of the compound as described in the above (1) or a salt thereof in combination with a protease inhibitor and/or a reverse transcriptase inhibitor for the treatment or prevention of infectious diseases of HIV;

(36) A method for antagonizing a CC chemokine receptor (CCR) in a mammal, which comprises administering an effective amount of a compound described in the above (1) or a salt thereof to a mammal;

(37) Use of a compound described in the above (1) or a salt thereof in preparation of a medicament for antagonizing a CC chemokine receptor (CCR); etc.

In the above formula(I), examples of the "5- to 6-membered aromatic ring" of the "5- to 6-membered aromatic ring which has a group of the formula: $R-Z^1-X-Z^2-$ wherein R is a hydrogen atom or an optionally substituted hydrocarbon group, X is an optionally substituted alkylene chain, and $Z^1$ and $Z^2$ are respectively hetero-atoms, and which may have a further substituent" represented by $R^1$ include a 6-membered aromatic hydrocarbon such as benzene, etc.; 5- to 6-membered aromatic heterocyclic ring containing 1 to 4 hetero-atoms consisting of 1 to 2 kinds of hetero-atoms selected from oxygen atom, sulfur atom and nitrogen atom such as furan, thiophene, pyrrole, imidazole, pyrazole, thiazole, oxazole, isothiazole, isoxazole, tetrazole, pyridine, pyrazine, pyrimidine, pyridazine, triazole, etc.; and the like. Among others, benzene, furan, thiophene, pyridine, etc. are preferable, benzene, furan or thiophene is more preferable, and in particular, benzene is preferable.

Examples of the "hydrocarbon group" of the "optionally substituted hydrocarbon group" represented by R include (1) alkyl (e.g., $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc., more preferable lower ($C_{1-4}$) alkyl, etc,);

(2) cycloalkyl (e.g., $C_{3-7}$ cycloalkyl, etc. such as cyclopropyl, cyclobutyl, cyclopentyl, cyclohexyl, cycloheptyl, etc.);

(3) alkenyl (e.g., $C_{2-10}$ alkenyl such as allyl, crotyl, 2-pentenyl, 3-hexenyl, etc., preferably lower ($C_{2-6}$) alkenyl, etc.);

(4) cycloalkenyl (e.g., $C_{3-7}$ cycloalkenyl, etc. such as 2-cyclopentenyl, 2-cyclohexenyl, 2-cyclopentenylmethyl, 2-cyclohexenylmethyl, etc.);

(5) alkynyl, (e.g., $C_{2-10}$ alkynyl, such as ethynyl, 1-propynyl, 2-propynyl, 1-butynyl, 2-pentynyl, 3-hexynyl, etc., preferably lower ($C_{2-6}$) alkynyl, etc.);

(6) aralkyl (e.g., phenyl-$C_{1-4}$ alkyl (e.g., benzyl, phenethyl, etc.), etc.);

(7) aryl (e.g., phenyl, naphthyl, etc.);

(8) cycloalkyl-alkyl (e.g., $C_{3-7}$ cycloalkyl-$C_{1-4}$ alkyl such as cyclopropylmethyl, cyclobutylmethyl, cyclopentylmethyl, cyclohexylmethyl, cycloheptylmethyl, etc.), and the like.

Examples of the substituents, which the above-mentioned (1) alkyl, (2) cycloalkyl, (4) cycloalkenyl, (5) alkynyl, (6) aralkyl, (7) aryl and (8) cycloalkylalkyl may have, include halogen (e.g., fluorine, chlorine, bromine, iodine, etc.), nitro, cyano, hydroxy group, an optionally substituted thiol group (e.g., thiol, $C_{1-4}$ alkylthio, etc.), an optionally substituted amino group (e.g., amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.; etc.), an optionally esterified or amidated carboxyl group (e.g., carboxyl, $C_{1-4}$ alkoxycarbonyl, carbamoyl, mono-$C_{1-4}$ alkylcarbamoyl, di-$C_{1-4}$ alkylcarbamoyl, etc.), an optionally halogenated $C_{1-4}$ alkyl (e.g., trifluoromethyl, methyl, ethyl, etc.), an optionally halogenated $C_{1-4}$ alkoxy (e.g., methoxy, ethoxy, propoxy, butoxy, trifluoromethoxy, trifluoroethoxy, etc.), $C_{1-4}$ alkylenedioxy (e.g., —O—CH$_2$—O—, —O—CH$_2$—CH$_2$—O, etc.), optionally substituted sulfonamide [e.g., a group formed by binding of an optionally substituted amino group (e.g., amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.; etc.) to —SO$_2$—], formyl, $C_{2-4}$ alkanoyl (e.g., acetyl, propionyl, etc.), $C_{1-4}$ alkylsulfonyl (e.g., methanesulfonyl, ethanesulfonyl, etc.), etc., and the number of the substituents are preferably 1 to 3.

Examples of the "heterocyclic group" of the "optionally substituted heterocyclic group" as substituents of "optionally substituted hydrocarbon group" represented by R include a group formed by removing one hydrogen atom from aromatic heterocyclic ring or non-aromatic heterocyclic ring. Examples of the aromatic heterocyclic ring include 5- to 6-membered aromatic heterocyclic ring containing 1 to 4 hetero-atoms consisting of 1 to 2 kinds of hetero-atoms selected from oxygen atom, sulfur atom and nitrogen atom such as furan, thiophene, pyrrole, imidazole, pyrazole, thiazole, oxazole, isothiazole, isoxazole, tetrazole, pyridine, pyrazine, pyrimidine, pyridazine, triazole, oxadiatole, thiadiazole, etc. Examples of the non-aromatic heterocycle include 5- to 6-membered non-aromatic heterocycle containing 1 to 4 hetero-atoms consisting of 1 to 2 kinds of hetero-atoms selected from nitrogen atom, sulfur atom and oxygen atom, such as tetrahydrofuran, tetrahydrothiophene, dioxolane, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran and tetrahydropyran, as well as non-aromatic heterocycles in which some or all of the bonds of the aforementioned non-aromatic heterocycle are saturated bonds, and the like (preferably, aromatic heterocycles such as pyrazole, thiazole, oxazole, tetrazole, etc.).

The "heterocyclic group" of the "optionally substituted heterocyclic group" as the substituent for the "optionally substituent hydrocarbon group" represented by R, may have 1 to 3 substituents at an optional replaceable position. Examples of such the substituent include halogen (e.g., fluorine, chlorine, bromine and iodine), nitro, cyano, a hydroxy group, an optionally substituted thiol group (e.g., thiol, $C_{1-4}$ alkylthio etc.), an optionally substituted amino group (e.g., amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.; etc.), an optionally esterified or amidated carboxyl group (e.g., carboxyl, $C_{1-4}$ alkoxycarbonyl, carbamoyl, mono-$C_{1-4}$ alkylcarbamoyl, di-$C_{1-4}$ alkylcarbamoyl etc.), optionally halogenated $C_{1-4}$ alkyl (e.g., trifluoromethyl, methyl, ethyl, etc.), optionally halogenated $C_{1-4}$ alkoxy (e.g., methoxy, ethoxy, propoxy, butoxy, trifluoromethoxy, trifluoroethoxy, etc.), $C_{1-4}$ alkylenedioxy (e.g., —O—CH$_2$—O—, —O—CH$_2$—CH$_2$—O—, etc.), optionally substituted sulfonamide [e.g., an optionally substituted amino group (e.g., amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.; etc.) binding to —SO$_2$—], formyl, $C_{2-4}$ alkanoyl (e.g., acetyl, propionyl, etc.), $C_{1-4}$ alkylsulfonyl (e.g., methanesulfonyl, ethanesulfonyl, etc.), etc. (preferably, $C_{1-4}$ alkyl, etc.).

When the group of the formula: R-$Z^1$-X-$Z^2$- wherein each symbol is as defined above is a monovalent group, that is it does not bind to the 5- to 6-membered aromatic ring to form a ring, as the group R, an optionally substituted alkyl group is preferable, an optionally halogenated lower alkyl group is more preferable, and in particular, an optionally halogenated $C_{1-4}$ alkyl group is preferable.

Examples of the "optionally substituted alkylene chain" represented by X include an optionally substituted straight or branched $C_{1-6}$ alkylene, etc. In said alkylene chain, a straight portion is preferably constituted by 1–4 carbon atoms, and in particular, an optionally substituted straight $C_{1-4}$ alkylene (preferably ethylene or propylene) is preferable as X.

Examples of the substituent, which the "alkylene chain" of the "optionally substituted alkylene chain" represented by X may have, include any one which can bind to a divalent chain constituting the straight portion, for example, $C_{1-6}$ lower alkyl (e.g., methyl, ethyl, propyl, isopropyl, butyl, isobutyl, sec-butyl, tert-butyl, pentyl, isopentyl, neopentyl, hexyl, etc.), lower ($C_{3-7}$) cycloalkyl (e.g., cyclopropyl, cyclobutyl, cyclopentyl, cyclohexyl, cycloheptyl, etc.), formyl, lower ($C_{2-7}$) alkanoyl (e.g., acetyl, propionyl, butyryl, etc.), an optionally esterified phosphono group, an optionally esterified carboxyl group, hydroxy group, oxo, etc., and more preferably $C_{1-6}$ lower alkyl (preferably $C_{1-3}$ alkyl), hydroxy group, oxo, etc.

Examples of the optionally esterified phosphono group include a group of the formula: P(O)(O$R^7$)(O$R^8$) wherein $R^7$ and $R^8$ are independently hydrogen, a $C_{1-6}$ alkyl group or a $C_{3-7}$ cycloalkyl group, and $R^7$ and $R^8$ may bind to each other to form a 5- to 7-membered ring.

In the above formula, examples of the $C_{1-6}$ alkyl group represented by $R^7$ and $R^8$ include methyl, ethyl, propyl, isopropyl, butyl, isobutyl, sec-butyl, tert-butyl, pentyl, isopentyl, neopentyl, hexyl, etc., and examples of the $C_{3-7}$ cycloalkyl include cyclopropyl, cyclobutyl, cyclopentyl, cyclohexyl, cycloheptyl, etc. Among others, a straight $C_{1-6}$ lower alkyl is preferable and $C_{1-3}$ lower alkyl is more preferable. The groups $R^7$ and $R^8$ may be the same or different, and preferably the groups $R^7$ and $R^8$ are the same. When $R^7$ and $R^8$ may bind to each other to form a 5- to 7-membered ring, the groups $R^7$ and $R^8$ bind to each other to represent a straight $C_{2-4}$ alkylene chain of the formula: —(CH$_2$)$_2$—, —(CH$_2$)$_3$—, —(CH)$_4$—, etc. Said chain may have a substituent, and examples of the substituent include hydroxy group, halogen, etc.

Examples of the optionally esterified carboxyl group include a carboxyl group and an ester formed by binding a carboxyl group to a $C_{1-6}$ alkyl group or a $C_{3-7}$ cycloalkyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, etc.).

As the group X, an optionally substituted $C_{1-4}$ alkylene is preferable, $C_{1-4}$ alkylene which may be substituted with $C_{1-3}$ alkyl, hydroxy group or oxo is more preferable, and in particular, a group of the formula: —(CH$_2$)$_n$— (n is an integer of 1–4) is preferable.

Examples of the hetero-atom represented by $Z^1$ and $Z^2$ include —O—, S(O)$_m$— (m is an integer of 0–2), —N($R^4$)— ($R^4$ is a hydrogen atom or an optionally substituted lower alkyl group), etc. As the group $Z^1$, —O— or —S(O)$_m$— (m is an integer of 0–2) is preferable, and —O— is more preferable. As the group $Z^2$,—O— or —N($R^4$)— ($R^4$ is a hydrogen atom or an optionally substituted lower alkyl group) is preferable, and —O— is more preferable.

Examples of the "optionally substituted lower alkyl group" represented by $R^4$ include the same as the above "optionally substituted lower alkyl group" exemplified with respect to the "optionally substituted hydrocarbon group" represented by R.

Examples of the further substituent, which the "5- to 6-membered ring" of the "5- to 6-membered aromatic ring which has a group of the formula: R-$Z^1$-X-$Z^2$- wherein each symbol is as defined above, and which may have a further substituent" represented by $R^1$ may have, in addition to the group of the formula: R-$Z^1$-X-$Z^2$—, include a halogen atom, nitro, cyano, an optionally substituted alkyl, an optionally substituted cycloalkyl, an optionally substituted hydroxy group, an optionally substituted thiol group (wherein a sulfur atom may be oxidized to form an optionally substituted sulfinyl group or an optionally substituted sulfonyl group), an optionally substituted amino group, an optionally substituted acyl group, an optionally esterified or amidated carboxyl group, an optionally substituted aromatic group and the like.

Examples of the halogen as the substituents for $R^1$ include fluorine, chlorine, bromine, iodine, etc. Among others, fluorine and chlorine are preferable.

Examples of the alkyl in the optionally substituted alkyl as the substituents for $R^1$ include a straight or branched $C_{1-10}$ alkyl such as methyl, ethyl, propyl, isopropyl, butyl, isobutyl, sec-butyl, tert-butyl, pentyl isopentyl, neopentyl, hexyl, heptyl, octyl, nonyl, decyl, etc., and preferably lower ($C_{1-6}$) alkyl. Examples of the substituents in the optionally substituted alkyl include halogen (e.g., fluorine, chlorine, bromine, iodine, etc.), nitro, cyano, hydroxy group, an optionally substituted thiol group (e.g., thiol, $C_{1-6}$ alkylthio, etc.), an optionally substituted amino group (e.g., amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.; etc.), an optionally esterified or amidated carboxyl group (e.g., carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkoxy (e.g., methoxy, ethoxy, propoxy, butoxy, trifluoromethoxy, trifluoroethoxy, etc.), an optionally halogenated $C_{1-4}$ alkoxy-$C_{1-4}$ alkoxy (e.g., methoxymethoxy, methoxyethoxy, ethoxyethoxy, trifluoromethoxyethoxy, trifluoroethoxyethoxy, etc.), formyl, $C_{2-4}$ alkanoyl (e.g. acetyl, propionyl, etc.), $C_{1-4}$ alkylsulfonyl (e.g. methanesulfonyl, ethanesulfonyl, etc.), etc., and the number of substituents is preferably 1 to 3.

Examples of the cycloalkyl in the optionally substituted cycloalkyl as the substituents for $R^1$ include $C_{3-7}$ cycloalkyl, etc. such as cyclopropyl, cyclobutyl, cyclopentyl, cyclohexyl, cycloheptyl, etc. Examples of the substituents in the optionally substituted cycloalkyl include halogen (e.g., fluorine, chlorine, bromine, iodine, etc.), nitro, cyano, hydroxy group, an optionally substituted thiol group (e.g., thiol, $C_{1-4}$ alkylthio, etc.), an optionally substituted amino group (e.g., amino, mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.; etc.), an optionally esterified or amidated carboxyl group (e.g., carboxyl, $C_{1-4}$ alkoxycarbonyl, carbamoyl, mono-$C_{1-4}$ alkylcarbamoyl, di-$C_{1-4}$ alkylcarbamoyl, etc.), an optionally halogenated $C_{1-4}$ alkyl (e.g., trifluoromethyl, methyl, ethyl, etc.), an optionally halogenated $C_{1-4}$ alkoxy (e.g., methoxy, ethoxy, propoxy, butoxy, trifluoromethoxy, trifluoroethoxy, etc.), formyl, $C_{2-4}$ alkanoyl (e.g., acetyl, propionyl, etc.), $C_{1-4}$ alkylsulfonyl (e.g. methanesulfonyl, ethanesulfonyl, etc.), etc., and the number of the substituents are preferably 1 to 3.

Examples of the substituents in the optionally substituted hydroxy group as the substituents for $R^1$ include
(1) an optionally substituted alkyl (e.g., $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);
(2) an optionally substituted cycloalkyl which may contain a hetero-atom (e.g., $C_{3-7}$ cycloalkyl such as cyclopropyl, cyclobutyl, cyclopentyl, cyclohexyl, cycloheptyl, etc.; a saturated 5- to 6-membered heterocyclic ring group containing 1–2 hetero-atoms such as tetrahydrofuranyl, tetrahydrothienyl, pyrrolidinyl, pyrazolidinyl, piperidyl, piperazinyl, morpholinyl, thiomorpholinyl, tetrahydropyranyl, tetrahydrothiopyranyl, etc.; etc., (preferably, tetrahydropyranyl, etc.));
(3) an optionally substituted alkenyl (e.g., $C_{2-10}$ alkenyl such as allyl, crotyl, 2-pentenyl, 3-hexenyl, etc., preferably lower ($C_{2-6}$) alkenyl, etc.);
(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);
(5) an optionally substituted aralkyl (e.g. phenyl-$C_{1-4}$ alkyl (e.g. benzyl, phenethyl, etc.), etc.);
(6) formyl or an optionally substituted acyl (e.g. $C_{2-4}$ alkanoyl (e.g. acetyl, propionyl, butyryl, isobutyryl, etc.), $C_{1-4}$ alkylsulfonyl (e.g. methanesulfonyl, ethanesulfonyl, etc.), etc.);
(7) an optionally substituted aryl (e.g. phenyl, naphthyl, etc.); etc.

Examples of the substituents which the above-mentioned (1) optionally substituted alkyl, (2) optionally substituted cycloalkyl, (3) optionally substituted alkenyl, (4) optionally substituted cycloalkenyl, (5) optionally substituted aralkyl, (6) optionally substituted acyl and (7) optionally substituted aryl may have include halogen (e.g., fluorine, chlorine, bromine, iodine, etc.), nitro, cyano, hydroxy group, an optionally substituted thiol group (e.g., thiol, $C_{1-4}$ alkylthio, etc.), an optionally substituted amino group (e.g. amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.; etc.), an optionally esterified or amidated carboxyl group (e.g., carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g., trifluoromethyl, methyl, ethyl, etc.), an optionally halogenated $C_{1-6}$ alkoxy (e.g., trifluoromethoxy, trifluoroethoxy, etc.; preferably an optionally halogenated $C_{1-4}$ alkoxy), formyl, $C_{2-4}$ alkanoyl (e.g., acetyl, propionyl, etc.), $C_{1-4}$ alkoxy), $C_{1-4}$ alkylsulfonyl (e.g., methanesulfonyl, ethanesulfonyl, etc.), an optionally substituted 5- to 6-membered aromatic heterocyclic ring (e.g., 5- to 6-membered aromatic heterocyclic ring containing 1 to 4 hetero-atoms consisting of 1 to 2 kinds of hetero-atoms selected from oxygen atom, sulfur atom and nitrogen atom such as furan, thiophene, pyrrole, imidazole, pyrazole, thiazole, oxazole, isothiazole, isoxazole, tetrazole, pyridine, pyrazine, pyrimidine, pyridazine, triazole, etc.; examples of the substituents which said heterocyclic ring may have include halogen (e.g., fluorine, chlorine, bromine, iodine, etc.), nitro, cyano, hydroxy group, thiol group, amino group, carboxyl group, an optionally halogenated $C_{1-4}$ alkyl (e.g., trifluoromethyl, methyl, ethyl, etc.), an optionally halogenated $C_{1-4}$ alkoxy (e.g., methoxy, ethoxy, propoxy, butoxy, trifluoromethoxy, trifluoroethoxy, etc.), formyl, $C_{2-4}$ alkanoyl (e.g., acetyl, propionyl, etc.), $C_{1-4}$ alkylsulfonyl (e.g., methanesulfonyl, ethanesulfonyl, etc.), etc.; and the number of the substituents are preferable 1 to 3.], etc., and the number of the substituents are preferably 1 to 3.

Examples of the substituents in the optionally substituted thiol group as the substituents for $R^1$ are the same as the above-described substituents of the optionally substituted hydroxy group as the substituents for $R^1$, and among others,
(1) an optionally substituted alkyl (e.g., $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc. preferably lower ($C_{1-6}$) alkyl, etc.);
(2) an optionally substituted cycloalkyl (e.g., $C_{3-7}$ cycloalkyl, etc. such as cyclopropyl, cyclobutyl, cyclopentyl, cyclohexyl, cycloheptyl, etc.);
(3) an optionally substituted aralkyl (e.g., phenyl-$C_{1-4}$ alkyl (e.g. benzyl, phenethyl, etc.), etc.);
(4) an optionally substituted aryl (e.g., phenyl, naphthyl, etc.); etc. are preferable.

Examples of the substituents which the above-mentioned (1) optionally substituted alkyl, (2) optionally substituted cycloalkyl, (3) optionally substituted aralkyl and (4) optionally substituted aryl may have include halogen (e.g., fluorine, chlorine, bromine, iodine, etc.), nitro, cyano, hydroxy group, an optionally substituted thiol group (e.g., thio, $C_{1-4}$ alkylthio, etc.), an optionally substituted amino group (e.g., amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine., pyrrole, imidazole, etc.; etc.), an optionally esterified or amidated carboxyl group (e.g., carboxyl, $C_{1-4}$ alkoxycarbonyl, carbamoyl, mono-$C_{1-4}$ alkylcarbamoyl, di-$C_{1-4}$ alkylcarbamoyl, etc.), an optionally halogenated $C_{1-4}$ alkyl (e.g., trifluoromethyl, methyl, ethyl, etc.), an optionally halogenated $C_{1-4}$ alkoxy (e.g., methoxy, ethoxy, propoxy, butoxy, trifluoromethoxy, trifluoroethoxy, etc.), formyl, $C_{2-4}$ alkanoyl (e.g., acetyl, propionyl, etc.), $C_{1-4}$ alkylsulfonyl (e.g., methanesulfonyl, ethanesulfonyl, etc.), etc., and the number of the substituents are preferably 1 to 3.

Examples of the substituents of the optionally substituted amino group as the substituents for $R^1$ include an amino group which may have the same one to two substituents as those of the above-described substituents of "the optionally substituted hydroxy group as the substituents for $R^1$", etc. Among others,
(1) an optionally substituted alkyl (e.g., $C_{1-10}$ alkyl such as methyl, ethyl, propyl, isopropyl, butyl, isobutyl, sec-butyl, tert-butyl, pentyl, isopentyl, neopentyl, hexyl, heptyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g., $C_{3-7}$ cycloalkyl, etc. such as cyclopropyl, cyclobutyl cyclopentyl, cyclohexyl, cycloheptyl, etc.);

(3) an optionally substituted alkenyl (e.g., $C_{2-10}$ alkenyl such as allyl, crotyl, 2-pentenyl, 3-hexenyl, etc., preferably lower ($C_{2-6}$) alkenyl, etc.);

(4) an optionally substituted cycloalkenyl (e.g., $C_{3-7}$ cycloalkenyl, etc. such as 2-cyclopentenyl, 2-cyclohexenyl, 2-cyclopentenylmethyl, 2-cyclohexenylmethyl, etc.);

(5) formyl or an optionally substituted acyl (e.g., $C_{2-4}$ alkanoyl (e.g., acetyl, propionyl, butyryl, isobutyryl, etc.), $C_{1-4}$ alkylsulfonyl (e.g., methanesulfonyl, ethanesulfonyl, etc.), etc.);

(6) an optionally substituted aryl (e.g., phenyl, naphthyl, etc.); etc. are preferable.

Examples of the substituents, which each of the above-described (1) optionally substituted alkyl, (2) optionally substituted cycloalkyl, (3) optionally substituted alkenyl, (4) optionally substituted cycloalkyl, (5) optionally substituted acyl and (6) optionally substituted aryl may have, include halogen (e.g., fluorine, chlorine, bromine, iodine, etc.), nitro, cyano, hydroxy group, an optionally substituted thiol group (e.g., thiol, $C_{1-4}$ alkylthio, etc.), an optionally substituted amino group (e.g., amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.; etc.), an optionally esterified or amidated carboxyl group (e.g., carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g., trifluoromethyl, methyl, ethyl, etc.), an optionally halogenated $C_{1-4}$ alkoxy (e.g., methoxy, ethoxy, propoxy, butoxy, trifluoromethoxy, trifluoroethoxy, etc.), formyl, $C_{2-4}$ alkanoyl (e.g., acetyl, propionyl, etc.), $C_{1-4}$ alkylsulfonyl (e.g., methanesulfonyl, ethanesulfonyl, etc.), etc., and the number of the substituents are preferably 1 to 3.

The substituents in the optionally substituted amino group as the substituents for $R^1$ may bind to each other to form a cyclic amino group (e.g., 5- to 6-membered cyclic amino, etc. such as tetrahydropyrrole, piperazine, piperidine, morpholine, thiomorpholine, pyrrole, imidazole, etc.). Said cyclic amino group may have a substituent and examples of the substituents include halogen (e.g., fluorine, chlorine, bromine, iodine, etc.), nitro cyano, hydroxy group, an optionally substituted thiol group (e.g., thiol, $C_{1-4}$ alkylthio, etc.), an optionally substituted amino group (e.g., amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.; etc.), an optionally esterified or amidated carboxyl group (e.g., carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g., trifluoromethyl, methyl, ethyl, etc.), an optionally halogenated $C_{1-4}$ alkoxy (e.g., methoxy, ethoxy, propoxy, butoxy, trifluoromethoxy, trifluoroethoxy, etc.), formyl, $C_{2-4}$ alkanoyl (e.g., acetyl, propionyl, etc.), $C_{1-4}$ alkylsulfonyl (e.g., methanesulfonyl, ethanesulfonyl, etc.), etc., and the number of the substituents are preferably 1 to 3.

Examples of the optionally substituted acyl as the substituents for $R^1$ include (1) hydrogen;

(2) an optionally substituted alkyl (e.g., $C_{1-10}$ alkyl such as methyl, ethyl, propyl, isopropyl, butyl, isobutyl, sec-butyl, tert-butyl, pentyl, isopentyl, neopentyl, hexyl, octyl, nonyl, decyl, etc., preferably lower ($C_{1-6}$) alkyl, etc.);

(3) an optionally substituted cycloalkyl (e.g. $C_{3-7}$ cycloalkyl, etc. such as cyclopropyl, cyclobutyl, cyclopentyl, cyclohexyl, cycloheptyl, etc.);

(4) an optionally substituted alkenyl (e.g., $C_{2-10}$ alkenyl such as allyl, crotyl, 2-pentenyl, 3-hexenyl, etc., preferably lower ($C_{2-6}$) alkenyl, etc.);

(5) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(6) an optionally substituted 5- to 6-membered monocyclic aromatic group (e.g., phenyl, 5- to 6-membered aromatic heterocyclic group (e.g., 5- to 6-membered aromatic heterocyclic group containing 1 to 4 hetero-atoms consisting of 1 to 2 kinds of hetero-atoms selected from oxygen atom, sulfur atom and nitrogen atom, such as furyl, thienyl, pyrrolyl, imidazolyl, pyrazolyl, thiazolyl, oxazolyl, isothiazolyl, isoxazolyl, tetrazolyl, pyridyl, pyrazyl, pyrimidinyl, pyridazinyl, triazolyl, etc.);

(7) an optionally substituted 5- to 6-membered monocyclic non-aromatic heterocylic group (e.g., a group which is formed by removing one hydrogen atom from a 5- to 6-membered monocyclic non-aromatic heterocycle containing 1 to 4 hetero-atoms consisting of 1 to 2 kinds of hetero-atoms selected from nitrogen atom, sulfur atom and nitrogen atom, such as tetrahydrofuran, tetrahydrothiophene, dioxolane, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, etc.; preferably dioxolanyl, etc) which is bound to a carbonyl group or a sulfonyl group (e.g., acetyl, propionyl, butyryl, isobutyryl, valeryl, isovaleryl, pivaloyl, hexanoyl, butanoyl, octanoyl, cyclobutanecarbonyl, cyclopentanecarbonyl, cyclohexanecarbonyl, cyclobutanecarbonyl, crotonyl, 2-cycohexenecarbonyl, benzoyl, nicotinyl, methanesulfonyl, ethanesulfonyl, etc.). Examples of the substituents, which the above-mentioned (2) optionally substituted alkyl, (3) optionally substituted cycloalkyl, (4) optionally substituted alkenyl, (5) optionally substituted cycloalkenyl, (6) optionally substituted 5- to 6-membered monocyclic aromatic group and (7) optionally substituted 5- to 6-membered mono-cyclic non-aromatic heterocycle may have, include halogen (e.g., fluorine, chlorine, bromine, iodine, etc.), nitro, cyano, hydroxy group, an optionally substituted thiol group (e.g., thiol, $C_{1-4}$ alkylthio, etc.), an optionally substituted amino group (e.g., amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.; etc.), an optionally esterified or amidated carboxyl group (e.g. carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g., trifluoromethyl, methyl, ethyl, etc.), an optionally halogenated $C_{1-4}$ alkoxy (e.g. methoxy, ethoxy, propoxy, butoxy, trifluoromethoxy, trifluoroethoxy, etc.), $C_{1-4}$ alkylenedioxy (e.g., —O—CH$_2$—O—, —O—CH$_2$—CH$_2$—O—, etc.), optionally substituted sulfonamide [e.g., an optionally substituted amino group (e.g. amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.) which is bound to —SO$_2$—, etc.], formyl, $C_{2-4}$ alkanoyl (e.g., acetyl, propionyl, etc.), $C_{1-4}$ alkylsulfonyl (e.g., methanesulfonyl, ethanesulfonyl, etc.), etc., and the number of the substituents are preferably 1 to 3.

Examples of the optionally esterified carboxyl group as the substituents for $R^1$ include (1) hydrogen;
(2) an optionally substituted alkyl (e.g., $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);
(3) an optionally substituted cycloalkyl (e.g., $C_{3-7}$ cycloalkyl, etc. such as cyclopropyl, cyclobutyl, cyclopentyl, cyclohexyl, cycloheptyl, etc.);
(4) an optionally substituted alkenyl (e.g., $C_{2-10}$ alkenyl such as allyl, crotyl, 2-pentenyl, 3-hexenyl, etc., preferably lower ($C_{2-6}$) alkenyl, etc.);
(5) an optionally substituted cycloalkenyl (e.g., $C_{3-7}$ cycloalkenyl, etc. such as 2-cyclopentenyl, 2-cyclohexenyl, 2-cyclopentenylmethyl, 2-cyclohexenylmethyl, etc.);
(6) an optionally substituted aryl (e.g., phenyl, naphthyl, etc.); etc., and preferably carboxyl, lower ($C_{1-6}$) alkoxycarbonyl, aryloxycarbonyl (e.g., methoxycarbonyl, ethoxycarbonyl, propoxycarbonyl, phenoxycarbonyl, naphthoxycarbonyl, etc.), etc.

Examples of the substituents, which the above-mentioned (2) optionally substituted alkyl, (3) optionally substituted cycloalkyl, (4) optionally substituted alkenyl, (5) optionally substituted cycloalkenyl and (6) optionally substituted aryl may have, include halogen (e.g., fluorine, chlorine, bromine, iodine, etc.), nitro, cyano, hydroxy group, an optionally substituted thiol group (e.g., thiol, $C_{1-4}$ alkylthio, etc.), an optionally substituted amino group (e.g., amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.; etc.), an optionally esterified or amidated carboxyl group (e.g., carboxyl, $C_{1-4}$ alkoxycarbonyl, carbamoyl, mono-$C_{1-4}$ alkyl carbamoyl, di-$C_{1-4}$ alkylcarbamoyl, etc.), an optionally halogenated $C_{1-4}$ alkyl, (e.g., trifluoromethyl, methyl, ethyl, etc.), an optionally halogenated $C_{1-4}$ alkoxy (e.g., methoxy, ethoxy, propoxy, butoxy, trifluoromethoxy, trifluoroethoxy, etc.), formyl, $C_{2-4}$ alkanoyl (e.g., acetyl, propionyl, etc.) $C_{1-4}$ alkylsulfonyl (e.g. methanesulfonyl, ethanesulfonyl, etc.), etc., and the number of substituents is preferably 1 to 3.

Examples of the optionally amidated carboxyl group as the substituent for $R^1$ include a carbonyl group binding to "an optionally substituted amino group", etc. which is the same as that of the above-described "optionally substituted amino group as the substituents for $R^1$" and among others, carbamoyl, mono-$C_{1-6}$ alkylcarbamoyl, di-$C_{1-6}$ alkylcarbamoyl, etc. are preferable.

Examples of the aromatic group in the optionally substituted aromatic group as the substituents for $R^1$ include 5- to 6-membered aromatic homocyclic or heterocyclic ring such as phenyl, pyridyl, furyl, thienyl, pyrrolyl, imidazolyl, pyrazolyl, thiazolyl, oxazolyl, isothiazolyl, isoxazolyl, tetrazolyl, pyrazinyl pyrimidinyl, pyridazinyl, triazolyl, oxadiazolyl, thiadiazolyl, etc.; fused aromatic heterocyclic ring such as benzofuran, indole, benzothiophene, benzoxazole, benzothiazole, indazole, benzimidazole, quinoline, isoquinoline, quinoxaline, phthalazine, quinazoline, cinnoline, etc.; etc. Examples of the substituents for these aromatic groups include halogen (e.g., fluorine, chlorine, bromine, iodine, etc.), nitro, cyano, hydroxy group, an optionally substituted thiol group (e.g., thiol, $C_{1-4}$ alkylthio, etc.), an optionally substituted amino group (e.g., amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.; etc.), an optionally esterified or amidated carboxyl group (e.g., carboxyl, $C_{1-4}$ alkoxy-carbonyl, carbamoyl, mono-$C_{1-4}$ alkylcarbamoyl, di-$C_{1-4}$ alkylcarbamoyl, etc.), an optionally halogenated $C_{1-4}$ alkyl (e.g., trifluoromethyl, methyl, ethyl, etc.), an optionally halogenated $C_{1-4}$ alkoxy (e.g., methoxy, ethoxy, propoxy, butoxy, trifluoromethoxy, trifluoroethoxy, etc.), formyl, $C_{2-4}$ alkanoyl (e.g., acetyl, propionyl, etc.), $C_{1-4}$ alkylsulfonyl (e.g., methanesulfonyl, ethanesulfonyl, etc.), etc., and the number of the substituents are preferably 1 to 3.

The number of the above-mentioned substituents for $R^1$ is 1–4 (preferably 1–2) and they may be the same or different and present at any possible position on the ring represented by $R^1$.

When the group represented by R binds to the 5- to 6-membered aromatic ring to form a ring, the group of the formula: $R-Z^1-X-Z^2-$ wherein each symbol is as defined above (as the group R is preferably hydrogen atom) forms a divalent group such as lower ($C_{1-6}$) alkylenedioxy (e.g., —O—CH$_2$—O—, —O—CH$_2$—CH$_2$—O—, —O—CH$_2$—CH$_2$—CH$_2$—O—, etc.), oxy-lower ($C_{1-6}$) alkylene-amino (e.g., —O—CH$_2$—NH—, —O—CH$_2$—CH$_2$—NH—, etc.), oxy-lower ($C_{1-6}$) alkylenethio (e.g., —O—CH$_2$—S—, —O—CH$_2$—CH$_2$—S—, etc.), lower ($C_{1-6}$) alkylenediamino (e.g., —NH—CH$_2$—NH—, —NH—CH$_2$—CH$_2$—NH—, etc.), thia-lower ($C_{1-6}$) alkylene-amino (e.g., —S—CH$_2$—NH—, —S—CH$_2$—CH$_2$—NH—, etc.), etc.

Preferred examples of the further substituent, which the "5- to 6-membered ring" of the "5- to 6-membered aromatic ring which has a group of the formula: $R-Z^1-X-Z^2-$ wherein each symbol is as defined above, and which may have a further substituent" represented by $R^1$ may have, in addition to the group of the formula: $R-Z^1-X-Z^2-$, include, in particular, a lower ($C_{1-4}$) alkyl optionally substituted with a halogen or a lower ($C_{1-4}$) alkoxy (e.g., methyl, ethyl, t-butyl, trifluoromethyl, methoxymethyl, ethoxymethyl, propoxymethyl, butoxymethyl, methoxyethyl, ethoxyethoxy, propoxyethyl, butoxyethyl, etc.), a lower ($C_{1-4}$) alkoxy optionally substituted with a halogen or a lower ($C_{1-4}$) alkoxy (e.g., methoxy, ethoxy, propoxy, butoxy, t-butoxy, trifluoromethoxy, methoxymethoxy, ethoxymethoxy, propoxymethoxy, butoxymethoxy, methoxyethoxy, ethoxyethoxy, propoxyethoxy, butoxyethoxy, methoxypropoxy, ethoxypropoxy, propoxypropoxy, butoxypropoxy, etc.), halogen (e.g., fluorine, chlorine, etc.), nitro, cyano, an amino group optionally substituted with 1–2 lower ($C_{1-4}$) alkyl groups, formyl group or lower ($C_{2-4}$) alkanoyl groups (e.g., amino, methylamino, dimethylamino, formylamino, acetylamino, etc.), 5- to 6-membered cyclic amino (e.g., 1-pyrrolidinyl, 1-piperazinyl, 1-piperidinyl, 4-morpholino, 4-thiomorpholino, 1-imidazolyl, 4-tetrahydropyranyl, etc.), etc.

When $R^1$ is a benzene, the "group of the formula: $R-Z^1-X-Z^2-$" is preferably present at para position and the further substituent, which the "5- to 6-membered aromatic ring which may have, in addition to the group of the formula: $R-Z^1-X-Z^2-$ is preferably present at meta position.

In the above formula, examples of the "optionally substituted imino group" represent by Y include a divalent group of the formula: $-N(R^5)-$ wherein $R^5$ is hydrogen atom or a substituent, etc.

As $R^5$, hydrogen atom, an optionally substituted hydrocarbon group, an optionally substituted heterocyclic group, an optionally substituted hydroxy group, an optionally substituted thiol group (the sulfur atom may be oxidized to form an optionally substituted sulfinyl group or an optionally substituted sulfonyl group), an optionally substituted amino group, an optionally esterified or amidated carboxyl group, and an optionally substituted acyl group, etc. are preferable, and hydrogen atom, an optionally substituted hydrocarbon group, an optionally substituted heterocyclic group and an optionally substituted acyl group, etc. are more preferable.

As the preferable $R^5$, hydrogen atom, an optionally substituted hydrocarbon group, an optionally substituted acyl group, etc. are preferable, $C_{1-4}$ alkyl, $C_{1-4}$ alkylsulfonyl, formyl, $C_{2-5}$ alkanoyl etc. are more preferable, $C_{1-4}$ alkyl, formyl, $C_{2-5}$ alkanoyl etc. are further more preferable, and in particular, formyl or ethyl is preferable. As other preferably $R^5$, there is a group represented by the formula —(CH$_2$)$_k$—R$^1$ [wherein k represents 0 or 1, $R^6$ represents an optionally substituted 5- to 6-membered monocyclic aromatic group (similar to "(6) an optionally substituted 5- to 6-membered monocyclic aromatic group" exemplified with respect to an optionally substituted acyl group as the substituent for $R^1$; preferably phenyl, pyrazolyl, thiazolyl, oxazolyl, tetrazolyl, etc., each being optionally substituent with halogen, optionally halogenated $C_{1-4}$ alkyl, optionally halogenated $C_{1-4}$ alkoxy, etc.)].

Example of the "optionally substituted hydrocarbon group" as $R^5$ are the same as the "optionally substituted hydrocarbon group" of R. Examples of the "optionally substituted heterocyclic group" as $R^5$ include the same "optionally substituted heterocyclic group" as the substituent for the "optionally substituted hydrocarbon group" represented by R, and examples of the "optionally substituted hydroxy group", the "optionally substituted thiol group", the "optionally substituted amino group", the "optionally esterified or amidated carboxyl group" and the "optionally substituted acyl group" as $R^5$ include the same "optionally substituted hydroxy group", "optionally substituted thiol group", "optionally substituted amino group", "optionally esterified or amidated carboxyl group" and "optionally substituted acyl group" as the substituent for $R^1$.

In the above formula (I), examples of the "optionally substituted aliphatic hydrocarbon group" (aliphatic straight chain hydrocarbon group and aliphatic cyclic hydrocarbon group) represented by $R^2$ and $R^3$ include (1) an optionally substituted alkyl (e.g., $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);
(2) an optionally substituted cycloalkyl (e.g. $C_{3-8}$ cycloalkyl such as cyclopropyl, cyclobutyl, cyclopentyl, cyclohexyl, cycloheptyl, cyclooctyl, etc.; etc.), provided that
(2-1) said cycloalkyl may contain one hetero-atom selected from a sulfur atom, an oxygen atom and a nitrogen atom to form oxirane, thiolane, aziridine, tetrahydrofuran, tetrahydrothiophene, pyrrolidine, tetrahydropyran, tetrahydrothiopyran, tetrahydrothiopyran-1-oxide, piperidine, etc. (preferably, 6-membered ring such as tetrahydropyran, tetrahydrothiopyran, piperidine, etc.); that
(2-2) said cycloalkyl may be fused with a benzene ring to form indane, tetrahydronaphthalene, etc. (preferably, indane, etc.); and that
(2-3) said cycloalkyl may have a bridging through a straight chain constituted by 1–2 carbon atoms to form a bridged hydrocarbon residue such as bicyclo[2.2.1]heptyl, bicyclo[2.2.2]octyl, bicyclo[3.2.1]octyl, bicyclo[3.2.2]nonyl, etc., preferably, a cyclohexyl group, etc. having a bridging through a straight chain constituted by 1–2 carbon atoms, and more preferably bicycle[2.2.1]heptyl, etc.;
(3) an optionally substituted alkenyl (e.g., $C_{2-10}$ alkenyl such as allyl, crotyl, 2-pentenyl, 3-hexenyl etc., preferably lower ($C_{2-6}$)alkenyl, etc.);
(4) an optionally substituted cycloalkenyl (e.g., $C_{3-7}$ cycloalkenyl, etc. such as 2-cyclopentenyl, 2-cyclohexenyl, 2-cyclopentenylmethyl; 2-cyclohexenylmethyl, etc.); etc.

Examples of the substituents, which the above-mentioned (1) optionally substituted alkyl, (2) optionally substituted cycloalkyl, (3) optionally substituted alkenyl and (4) optionally substituted cycloalkenyl may have, include halogen (e.g., fluorine, chlorine, bromine, iodine, etc.), an optionally halogenated lower ($C_{1-4}$) alkyl, an optionally halogenated lower $C_{1-4}$ alkoxy (e.g., methoxy, ethoxy, propoxy, butoxy, trifluoromethoxy, trifluoroethoxy, etc.), $C_{1-4}$ alkylenedioxy (e.g., —O—CH$_2$—O—, —O—CH$_2$—CH$_2$—O—, etc.), formyl, $C_{2-4}$ alkanoyl (e.g., acetyl, propionyl, etc.), $C_{1-4}$ alkylsulfonyl (e.g., methanesulfonyl, ethanesulfonyl, etc.), phenyl-lower ($C_{1-4}$) alkyl, $C_{3-7}$ cycloalkyl, cyano, nitro, hydroxy group, an optionally substituted thiol group (e.g., thiol, $C_{1-4}$ alkylthio, etc.), an optionally substituted amino group (e.g., amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.; etc.), an optionally esterified or amidated carboxyl group (e.g., carboxyl, $C_{1-4}$ alkoxy-carbonyl, carbamoyl, mono-$C_{1-4}$ alkylcarbamoyl, di-$C_{1-4}$ alkylcarbamoyl, etc.), a lower ($C_{1-4}$) alkoxy-carbamoyl, oxo group (preferably, halogen, an optionally halogenated lower ($C_{1-4}$) alkyl, an optionally halogenated lower ($C_{1-4}$) alkoxy, phenyl-lower ($C_{1-4}$) alkyl, $C_{3-7}$ cycloalkyl, cyano, hydroxy group, etc.), etc., and the number of the substituents are preferably 1 to 3.

Preferred examples of the "optionally substituted aliphatic hydrocarbon group" represented by $R^2$ and $R^3$ include
(1) a lower ($C_{1-6}$) straight or branched alkyl which may have 1–3 substituents selected from the class consisting of halogen, cyano, hydroxy group and $C_{3-7}$ cycloalkyl;
(2) $C_{5-8}$ cycloalkyl which may be substituted with 1–3 substituents selected from the class consisting of a halogen, an optionally halogenated lower ($C_{1-4}$) alkyl and a phenyl-lower ($C_{1-4}$) alkyl, which may contain a heteroatom selected from the class consisting of a sulfur atom, an oxygen atom and a nitrogen atom, which may be fused with a benzene ring and which may have a bridging through a $C_{1-2}$ straight chain (e.g., cyclopentyl, cyclohexyl, cycloheptyl, cyclooctyl, tetrahydropyranyl, tetrahydrothiapyranyl, piperidinyl, indanyl, tetrahydronaphthalenyl, piperidinyl, indanyl, tetrahydronaphthalenyl, bicyclo[2.2.1]heptyl, etc., each of which may be substituted); etc.

In the above formula (I), example of the "optionally substituted alicyclic (non-aromatic) heterocyclic group" represented by $R^2$ and $R^3$ include 5- to 6-membered non-aromatic heterocyclic ring containing 1 to 4 hetero-atoms consisting of 1 to 2 kinds of hetero-atoms selected from oxygen atom, sulfur atom and nitrogen atom such as tetrahydrofuran, tetrahydrothiophene, dioxolane, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran etc. Among others, a 5- to 6-membered non-aromatic heterocyclic ring containing 1 hetero-atom such as tetrahydrofuran, piperidine, tetrahydropyran, tetrahydrothiopyran, etc. and so on are preferable.

Examples of the substituent, which the "alicylic heterocyclic group" in the "optionally substituted alicyclic heterocyclic group" represented by $R^2$ and $R^3$ may have, include halogen (e.g., fluorine, chlorine, bromine, iodine, etc.), an optionally halogenated lower ($C_{1-4}$) alkyl, an optionally halogenated $C_{1-4}$ alkoxy (e.g., methoxy, ethoxy, propoxy, butoxy, trifluoromethoxy, trifluoroethoxy, etc.), $C_{1-4}$ alkylenedioxy (e.g., —O—CH$_2$—O—, —O—CH$_2$—CH$_2$—O—, etc.), formyl, $C_{2-4}$ alkanoyl (e.g., acetyl, propionyl, etc.), $C_{1-4}$ alkylsulfonyl (e.g., methanesulfonyl, ethanesulfonyl, etc.), phenyl-lower($C_{1-4}$) alkyl, $C_{3-7}$ cycloalkyl, cyano, nitro, hydroxy group, an optionally substituted thiol group (e.g., thiol, $C_{1-4}$ alkylthio, etc.), an optionally substituted amino group (e.g. amino; mono-$C_{1-4}$ alkylamino; di-$C_{1-4}$ alkylamino; 5- to 6-membered cyclic amino such as tetrahydropyrrole, piperazine, piperidine, morpholine, thiomorpholine, pyrrole, imidazole, etc.; etc.), an optionally esterified or amidated carboxyl group (e.g., carboxyl, $C_{1-4}$ alkoxy-carbonyl, carbamoyl, mono-$C_{1-4}$ alkylcarbamoyl, di-$C_{1-4}$ alkylcarbamoyl, etc.), a lower ($C_{1-4}$) alkoxy-carbonyl, oxo group (preferably, halogen, an optionally halogenated lower ($C_{1-4}$) alkyl, an optionally halogenated lower ($C_{1-4}$) alkoxy, phenyl-lower ($C_{1-4}$) alkyl, $C_{3-7}$ cycloalkyl, cyano, hydroxy group, etc.), etc., and the number of the substituents are preferably 1 to 3.

Among others, as $R^2$, an optionally substituted acyclic hydrocarbon group (e.g., alkyl, alkenyl, etc., each of which may be substituted) is preferable, an optionally substituted lower $C_{1-6}$ alkyl group is more preferable, and in particular, an optionally substituted methyl group is preferable.

As $R^3$, an optionally substituted alicyclic hydrocarbon group (e.g., cycloalkyl, cycloalkenyl, etc., each of which may be substituted; preferably, an optionally substituted lower $C_{3-8}$ cycloalkyl group; and more preferably, an optionally substituted cyclohexyl) or an optionally substituted alicyclic heterocyclic group (preferably, an optionally substituted saturated alicyclic heterocyclic group (preferably, 6-membered ring group); more preferably, an optionally substituted tetrahydropyranyl, an optionally substituted tetrahydrothiopyranyl or an optionally substituted piperidyl; an in particular, an optionally substituted tetrahydropyranyl) is preferable.

As the compound represented by the above formula (I),
7-(4-ethoxyethoxyphenyl)-1-ethyl-N-[4-[[N-methyl-N-(tetrahydropyran-4-yl)amino]methyl]phenyl]-2,3-dihydro-1-benzazepine-4-carboxamide;

1-ethyl-7-(4-propoxyethoxyphenyl)-N-[4-[[N-methyl-N-(tetrahydropyran-4-yl)amino]methyl]phenyl]-2,3-dihydro-1-benzazepine-4-carboxamide;

7-(4-butoxyethoxyphenyl)-1-ethyl-N-[4-[[N-methyl-N-(tetrahydropyran-4-yl)amino]methyl]phenyl]-2,3-dihydro-1-benzazepine-4-carboxamide;

7-(4-ethoxyethoxyphenyl)-1-formyl-N-[4-[[N-methyl-N-(tetrahydropyran-4-yl)amino]methyl]phenyl]-2,3-dihydro-1-benzazepine-4-carboxamide;

1-formyl-7-(4-propoxyethoxyphenyl)-N-[4-[[N-methyl-N-(tetrahydropyran-4-yl)amino]methyl]phenyl]-2,3-dihydro-1-benzazepine-4-carboxamide;

7-(4-butoxyethoxyphenyl)-1-formyl-N-[4-[[N-methyl-N-(tetrahydropyran-4-yl)amino]methyl]phenyl]-2,3-dihydro-1-benzazepine-4-carboxamide;

7-(4-butoxyethoxyphenyl)-N-[4-[[N-methyl-N-(tetrahydropyran-5-yl)amino]methyl]phenyl]-1-propyl-2,3-dihydro-1-benzazepine-4-carboxamide;

N-[4-[[N-methyl-N-(tetrahydropyran-5-yl)amino]methyl]phenyl]-7-(4-propoxyethoxyphenyl)-1-propyl-2,3-dihydro-1-benzazepine-4-carboxamide, 1-benzyl-7-(4-butoxyethoxyphenyl)-N-[4-[[N-methyl-N-(tetrahydropyran-4-yl)amino]methyl]phenyl]-2,3-dihydro-1-benzazepine-4-carboxamide, 7-(4-butoxyethoxyphenyl)-1-cyclopropylmethyl-N-[4-[[N-methyl-N-(tetrahydropyran-4-yl)amino]methyl]phenyl]-2,3-dihydro-1-benzazepine-4-carboxamide, 7-(4-butoxyethoxyphenyl)-N-[4-[[N-methyl-N-(tetrahydropyran-4-yl)amino]methyl]phenyl]-1-phenyl-2,3-dihydro-1-benzazepine-4-carboxamide, 7-(4-butoxyethoxyphenyl)-1-(3,4-methylenedioxy)phenyl-N-[4-[[N-methyl-N-(tetrahydropyran-4-yl)amino]methyl]phenyl]-2,3-dihydro-1-benzazepine-4-carboxamide, 7-(4-butoxyethoxyphenyl)-1-(2-methyloxazol-5-yl)-N-[4-[[N-methyl-N-(tetrahydropyran-4-yl)amino]methyl]phenyl]-2,3-dihydro-1-benzazepine-4-carboxamide, 1-allyl-7-(4-butoxyethoxyphenyl)-N-[4-[[N-methyl-N-(tetrahydropyran-4-yl)amino]methyl]phenyl]-2,3-dihydro-1-benzazepine-4-carboxamide, 7-(4-butoxyethoxyphenyl)-N-[4-[[N-methyl-N-(tetrahydropyran-4-yl)amino]methyl]phenyl]-1-(3-thienyl)methyl-2,3-dihydro-1-benzazepine-4-carboxamide, 7-(4-butoxyethoxyphenyl)-N-[4-[[N-methyl-N-(tetrahydropyran-4-yl)amino]methyl]phenyl]-1-(thiazol-2-yl)methyl-2,3-dihydro-1-benzazepine-4-carboxamide, 7-(4-butoxyethoxyphenyl)-1-(1-methylpyrazol-4-yl)methyl-N-[4-[[N-methyl-N-(tetrahydropyran-4-yl)amino]methyl]phenyl]-2,3-dihydro-1-benzazepine-4-carboxamide, 7-(4-butoxyethoxyphenyl)-1-(3-methylisothiazol-4-yl)methyl-N-[4-[[N-methyl-N-(tetrahydropyran-5-yl)amino]methyl]phenyl]-2,3-dihydro-1-benzazepine-4-carboxamide, 7-(4-butoxyethoxyphenyl)-1-(1-ethylpyrazol-4-yl)methyl-N-[4-[[N-methyl-N-(tetrahydropyran-4-yl)amino]methyl]phenyl]-2,3-dihydro-1-benzazepine-4-carboxamide, 7-(4-butoxyethoxyphenyl)-1-isobutyl-N-[4-[[N-methyl-N-(tetrahydropyran-5-yl)amino]methyl]phenyl]-2,3-dihydro-1-benzazepine-4-carboxamide, 1-isobutyl-N-[4-[[N-methyl-N-(tetrahydropyran-5-yl)amino]methyl]phenyl]-7-(4-propoxyethoxyphenyl)-2,3-dihydro-1-benzazepine-4-carboxamide, 7-(4-butoxyethoxyphenyl)-N-[4-[[N-methyl-N-(tetrahydropyran-4-yl)amino]methyl]phenyl]-1-(thiazol-5-yl)methyl-2,3-dihydro-1-benzazepine-4-carboxamide, 7-(4-butoxyethoxyphenyl)-N-[4-[[N-methyl-N-(tetrahydropyran-4-yl)amino]methyl]phenyl]-1-(1-methyltetrazol-5-yl)methyl-2,3-dihydro-1-benzazepine-4-carboxamide, 7-(4-butoxyethoxyphenyl)-N-[4-[[N-methyl-N-(tetrahydropyran-4-yl)amino]methyl]phenyl]-1-(2-methyltetrazol-5-yl)methyl-2,3-dihydro-1-benzazepine-4-carboxamide etc. are preferable.

Examples of the salts of the compound represented by the formula (I) include a pharmaceutically acceptable salt such as a salt with inorganic base, a salt with organic base, a salt with inorganic acid, a salt with organic acid, a salt with basic or acidic amino acid, etc. Suitable examples of the salt with the inorganic base include a salt with alkali metal (e.g. sodium, potassium, etc.), alkaline earth metal (e.g. calcium, magnesium, etc.), aluminum, ammonium, etc. Suitable examples of the salt with the organic base include a salt with trimethylamine, triethylamine, pyridine, picoline, ethanolamine, diethanolamine, triethanolamine, dicyclohexylamine, N,N'-dibenzylethylenediamine, etc.

Suitable examples of the salt with the inorganic acid include a salt with hydrochloric acid, hydrobromic acid, nitric acid, sulfuric acid, phosphoric acid, etc. Suitable examples of the salt with the organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Suitable examples of the salt with the basic amino acid include a salt with arginine, lysine, ornithine, etc. Suitable examples of the salt with the acidic amino acid include a salt with aspartic acid, glutamic acid, etc. The compound of the formula (I) of the present invention may be hydrated or non-hydrated. When the compound of the formula (I) of the present invention exists as configuration isomer, diastereomer, conformer, etc., it is possible to isolate individual isomers with a per se known separation and purification method, if desired. When the compound of the formula (I) of the present invention is racemate, it can be separated into (S)-isomer and (R)-isomer with usual optical resolution and individual optical isomers and a mixture thereof are included in the scope of the present invention.

The pro-drug of the compound of the formula (I) or a salt thereof of the present invention [hereinafter, referred to as Compound (I) in some cases] means a compound which is converted to Compound (I) under the physiological condition or with a reaction due to an enzyme, an gastric acid, etc. in the living body, that is, a compound which is converted to Compound (I) with oxidation, reduction, hydrolysis, etc. according to an enzyme; a compound which is converted to Compound (I) with hydrolysis by gastric acid, etc.; etc. Examples of the pro-drug of Compound (I) include a compound wherein an amino group of Compound (I) is substituted with acyl, alkyl, phosphoric acid, etc. (e.g. a compound wherein an amino group of Compound (I) is substituted with eicosanyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl, etc,); a compound wherein an hydroxy group of Compound (1) is substituted with acyl, alkyl, phosphoric acid, boric acid, etc. (e.g. a compound wherein an hydroxy group of Compound (I) is modified with acetyl, palmitoyl, propanoyl, pivaloyl, succinyl, fumaryl, alanyl, dimethylaminomethylcarbonyl, etc.); a compound wherein a carboxyl group of Compound (I) is modified with ester, amide, etc. (e.g. a compound wherein a carboxyl group of Compound (I) is modified with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.); etc. These pro-drugs can be produced by per se known method from Compound (I).

The pro-drug of Compound (I) may be a compound which is converted into Compound (I) under the physiological conditions as described in "Pharmaceutical Research and Development", Vol.7 (Drug Design), pages 163–198 published in 1990 by Hirokawa Publishing Co.

Compound (I) may be labeled with isotope (e.g. $^3$H, $^{14}$C, $^{35}$S, $^{125}$I, etc), etc.

The present compound of the formula (I) or a salt thereof alone or as an admixture with a pharmaceutically acceptable carrier (e.g. solid formulations such as tablets, capsules, granules, powders, etc.; liquid formulations such as syrups, injections, etc.) may be orally or non-orally (preferably orally) administered.

Examples of non-oral formulations include injections, drops, suppositories, pessaries, etc. In particular, pessary is useful for the prevention of infectious diseases of HIV.

Examples of the carriers include various organic or inorganic carriers which are generally used in this field. For example, an excipient, a lubricant, a binder, a disintegrating agent, etc. are used in solid formulations, and a solvent, a solubilizer, a suspending agent, an isotonizing agent, a buffer, a soothing agent, etc. are used in liquid formulations. In addition, if desired, an appropriate additive such as a preservative, an antioxidant, a colorant, a sweetener, etc. may be used. Suitable examples of the excipient include lactose, sucrose, D-mannitol, starch, crystalline cellulose, light silicic acid anhydride, etc. Suitable examples of the lubricant include magnesium stearate, calcium stearate, talc, colloidal silica, etc. Suitable examples of the binder include crystalline cellulose, sucrose, D-mannitol, dextrin, hydroxypropyl cellulose, hydroxypropylmethyl cellulose, polyvinyl-pyrrolidone, etc. Suitable examples of the disintegrating agent include starch, carboxymethyl cellulose, carboxymethyl cellulose calcium, croscarmellose sodium, sodium carboxymethyl starch, etc. Suitable examples of the solvent include water for injection, alcohol, propylene glycol, macrogol, sesame oil, corn oil, etc. Suitable examples of the solubilizer include polyethylene glycol, propylene glycol, D-mannitol, benzyl benzoate, ethanol, trisaminomethane, cholesterol, triethanolamine, sodium carbonate, sodium citrate, etc. Suitable examples of the suspending agent include surfactants such as stearyl triethanolamine, sodium laurylsulfate, laurylaminopropionic acid, lecithin, benzalkonium chloride, benzethonium chloride, glycerin monostearate, etc.; hydrophilic polymers such as polyvinylalcohol, polyvinylpyrrolidone, sodium carboxymethyl cellulose, methyl cellulose, hydroxymethylcellulose, hydroxyethyl cellulose, hydroxypropyl cellulose, etc. Suitable examples of the isotonizing agent include sodium chloride, glycerin, D-mannitol, etc. Suitable examples of the buffer include a buffer solution of phosphate, acetate, carbonate, citrate, etc. Suitable examples of the soothing agent include benzylalcohol, etc. Suitable examples of the preservative include p-hydroxybenzoic acid esters, chlorobutanol, benzylalcohol, phenethylalcohol, dehydroacetic acid, sorbic acid, etc. Suitable examples of the antioxidant include sulfites, ascorbic acid, etc.

The present invention further provides production methods of the compound of the formula (I) or a salt thereof.

The compound of the formula (I) or a salt thereof can be produced in accordance with per se known methods, for example, the methods described in JP-A-73476/1996, or analogous methods thereto, etc.

A salt of the compound of the formulas (II), (III), (IV), (V), (I-1) and (I-2) (hereinafter, abbreviated as Compound (II), Compound (III), Compound (IV), Compound (V), Compound (I-1) and Compound (I-2), respectively, in some cases) may be similar to that of Compound (I).

In the following reactions, when the starting compounds have, as substituents, amino group, carboxyl group and/or hydroxy group, these groups may be protected by conventional protective groups such as those generally employed in peptide chemistry, etc. After the reaction, if necessary, the protective groups may be removed to obtain the desired compound.

Examples of an amino-protective group include an optionally substituted $C_{1-6}$ alkylcarbonyl (e.g., acetyl, propionyl, etc.), formyl, phenylcarbonyl, $C_{1-6}$ alkyloxycarbonyl (e.g., methoxycarbonyl, ethoxycarbonyl, t-butoxycarbonyl, etc.), phenyloxycarbonyl (e.g., benzoxycarbonyl, etc.), $C_{7-10}$ aralkyloxycarbonyl (e.g., benzyloxycarbonyl, etc.), trityl, phthaloyl, etc. These protective groups may be substituted by 1 to 3 substituents such as halogen atom (e.g., fluorine, chlorine, bromine, iodine, etc.), $C_{1-6}$ alkylcarbonyl (e.g., acetyl, propionyl, butyryl, etc.), nitro group, etc.

Examples of a carboxyl-protective group include an optionally substituted $C_{1-6}$ alkyl (e.g., methyl, ethyl, propyl, isopropyl, butyl, tert-butyl, etc.), phenyl, trityl, silyl, etc. These protective groups may be substituted by 1 to 3 substituents such as halogen atom (e.g., fluorine, chlorine, bromine, iodine, etc.), $C_{1-6}$ alkylcarbonyl (e.g., acetyl, propionyl, butyryl, etc.), formyl, nitro group, etc.

Examples of a hydroxy-protective group include an optionally substituted $C_{1-6}$ alkyl (e.g., methyl, ethyl, propyl, isopropyl, butyl, tert-butyl, etc.), phenyl, $C_{7-10}$ aralkyl (e.g., benzyl, etc.), $C_{1-6}$ alkylcarbonyl (e.g., acetyl, propionyl, etc.), formyl, phenyloxycarbonyl, $C_{7-10}$ aralkyloxycarbonyl (e.g., benzyloxycarbonyl, etc.), pyranyl, furanyl, silyl, etc. These protective groups may be substituted by 1 to 4 substituents such as halogen atom (e.g., fluorine, chlorine, bromine, iodine, etc.), $C_{1-6}$ alkyl, phenyl, $C_{7-10}$ aralkyl, nitro group, etc.

These protective group may be introduced or removed by per se known methods (e.g. a method described in Protective Groups in Organic Chemistry (J. F. W. McOmie et al.; Plenum Press Inc.). For example, employable method for removing the protective groups is a method using an acid, a base, reduction, ultraviolet ray, hydrazine, phenylhydrazine, sodium N-methyldithiocarbamate, tetrabutylammonium fluoride, palladium acetate, etc.

[Method A]

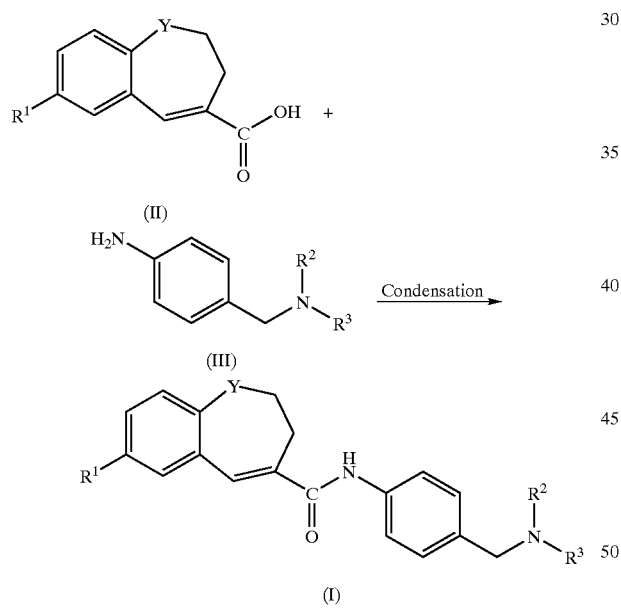

wherein each symbol is as defined above.

This production method is carried out by reacting Compound (II) with Compound (III) to obtain the anilide Compound (I).

The condensation reaction of Compounds (II) and (III) is carried out by usual methods for peptide synthesis. Said methods for peptide synthesis are employed according to optional known methods, for example, methods described in "Peptide Synthesis" written by M. Bodansky and M. A. Ondetti, Interscience, New York, 1966; "The Proteins", volume 2, written by F. M. Finn and K. Hofmann, H. Nenrath and R. L. Hill edition, Academic Press Inc., New York, 1976; "peputido-gosei no kiso to jikken (Basis and Experiment of Peptide Synthesis)" written by Nobuo Izumiya et al., Maruzen K. K., 1985; etc., as well as azide method, chloride method, acid anhydride method, mixed acid anhydride method, DCC method, active ester method, method using Woodward reagent K, carbonyldiimidazole method, oxidation-reduction method, DCC/HONB method, etc. and in addition WSC method, method using diethyl cyanophosphate (DEPC), etc. The condensation reaction can be carried out in a solvent.

Examples of the solvents to be employed in the reaction include anhydrous or hydrous N,N-dimethylformamide (DMF), dimethyl sulfoxide (DMSO), pyridine, chloroform, dichloromethane, tetrahydrofuran (THF), dioxane, acetonitrile, or a suitable mixture of these solvents.

Usually, about 1–2 moles of the Compound (III) are used per 1 mole of the Compound (II). The reaction temperature is generally about −20° C. to about 50° C., preferably about −10° C. to about 30° C. and the reaction time is generally about 1 to about 100 hours, preferably about 2 to about 40 hours. The thus obtained anilide derivative (I) can be isolated and purified by known separation and purification methods such as concentration, concentration under reduced pressure, extraction, crystallization, recrystallization, solvent convert, chromatography, etc.

In addition, the compound of the formula (II) or a salt thereof is a novel compound and useful as an intermediate for producing the compound of the formula (I) or a salt thereof.

[Method B]

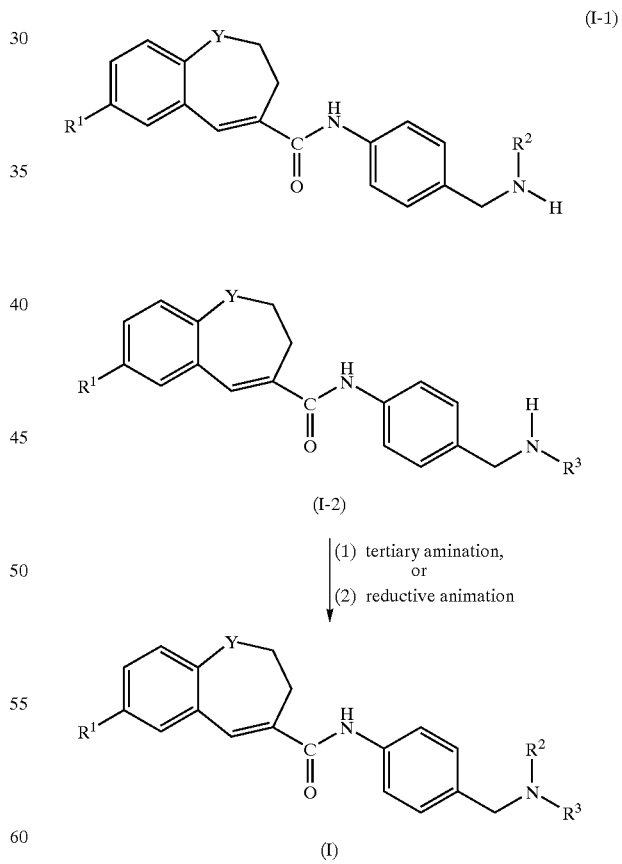

(1) Compound (I) can be produced by reacting Compound (I-1) or (I-2) with halogenated alkyl or halogenated aralkyl. Examples of a halogen atom include chlorine, bromine, iodine, etc. and usually about 1 to 2 moles of the halogenated alkyl or halogenated aralkyl is used per mole of Compound (I-1) or (I-2). If necessary, the reaction smoothly proceeds by addition of about equal to three-fold moles of a base such as triethylamine, diisopropylethylamine, pyridine, lithium hydride, sodium hydride, sodium methoxide, sodium ethoxide, sodium carbonate, potassium carbonate, sodium hydrogen carbonate and further sodium iodide, potassium iodide, etc.

This tertiary amination reaction is carried out in an inert solvent such as methanol, ethanol, propanol, isopropanol, n-butanol, tetrahydrofuran, diethyl ether, dimethoxyethane, 1,4-dioxane, toluene, benzene, xylene, dichloromethane, chloroform, 1,2-dichloroethane, dimethylformamide (DMF), dimethyl sulfoxide (DMSO), pyridine, etc., or a mixture of these solvents. The reaction temperature is generally about 0° C. to 180° C., and the reaction time is generally about 1 hour to about 40 hours. This reaction is preferably carried out under inert gas (e.g. nitrogen, argon, etc.) atmosphere.

(2) Compound (I) having a tertiary amino can be produced by reacting Compound (I-1) or (I-2) with an aldehyde compound in the presence of a reductive amination reagent such as triacetoxysodium borohydride, sodium cyanoborohydride, sodium borohydride, etc. The conditions of this reductive amination reaction vary depending on the reagent to be used. For example, when sodium triacetoxyborohydride is used, reaction is carried out in an inert solvent such as dichloromethane, chloroform, 1,2-dichloroethane, tetrahydrofuran, diethyl ether, dioxane, acetonitrile, dimethylformamide (DMF), etc., or a mixture of these solvents. In this case, about 1 to 2 moles of the reagent is used per mole of Compound (I-1) or (I-2). The reaction temperature is generally about 0° C. to about 80° C., and the reaction time is generally about 1 hour to about 40 hours. This reaction is preferably carried out under inert gas (e.g. nitrogen, argon, etc.) atmosphere.

[Method C]

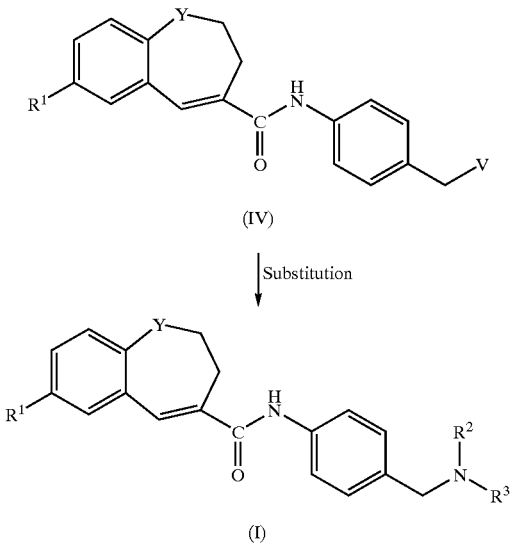

wherein V in the Compound (IV) is a halogen atom (chlorine, bromine, iodine, etc.), or a sulfonyloxy group (methanesulfonyloxy group, trifluoromethanesulfonyloxy group, benzenesulfonyloxy group, toluenesulfonyloxy group, etc.), and the other symbols are as defined above.

Compound (I) having a tertiary amino group can be produced by reacting Compound (IV) and a secondary amine compound. Usually, about 1 to 3 moles of the secondary amine compound is used per mole of Compound (IV). If necessary, the reaction smoothly proceeds by addition of about equal to three-fold moles of a base such as triethylamine, diisopropylethylamine, pyridine, lithium hydride, sodium hydride, sodium methoxide, sodium ethoxide, sodium carbonate, potassium carbonate, sodium hydrogen carbonate and further sodium iodide, potassium iodide, etc. This substitution reaction is carried out in an inert solvent such as methanol, ethanol, propanol, isopropanol, n-butanol, tetrahydrofuran, diethyl ether, dimethoxyethane, 1,4-dioxane, toluene, benzene, xylene, dichloromethane, chloroform, 1,2-dichloroethane, dimethylformamide (DMF), dimethyl sulfoxide (DMSO), pyridine, etc., or a mixture of these solvents. The reaction temperature is generally about −10° C. to about 180° C., and the reaction time is generally about 1 hour to about 40 hours. The reaction is carried out preferably under inert gas (e.g. nitrogen, argon, etc.) atmosphere.

[Method D]

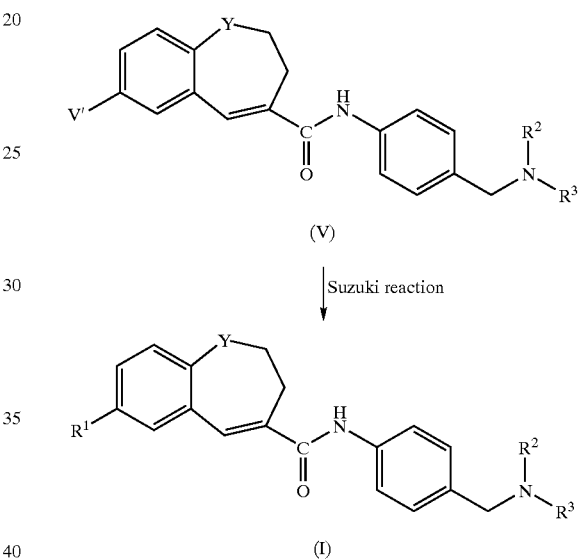

wherein V' in Compound (V) is a halogen atom (bromine, iodine, etc.) or a sulfonyloxy group (trifluoromethanesulfonyloxy group, etc.), and the other symbols are as defined above.

Compound (I) wherein the group $R^1$ is a 5- to 6-membered aromatic ring group can be produced by subjecting Compound (V) to, for example, Suzuki reaction [cross condensation reaction of aryl borate with e.g. aryl halide or aryloxytrifluoromethane-sulfonate in the presence of a palladium catalyst; A. Suzuki et al., Synth. Commun. 1981, 111, 513]. Usually, about 1–1.5 times moles of aryl borate is used per mole of Compound (V) to obtain Compound (I).

The thus obtained Compound (I) can be isolated and purified by known separation and purification methods such as concentration, concentration under reduced pressure, extraction, crystallization, recrystallization, solvent convert, chromatography, etc.

Compound (II) used as a starting material can be produced by a known method (e.g. method described in JP-A-73476/1996, etc.) or the methods analogous thereto. For example, Compound (II) can be produced by a method described in the following Reaction Scheme I or II, a method described in the following Reference Examples or the methods analogous thereto.

Reaction Scheme I

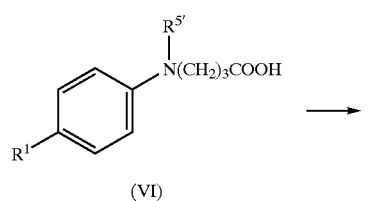
(VI)

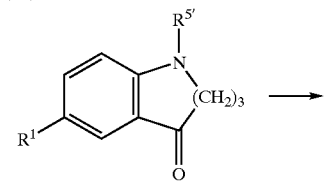
(VII)

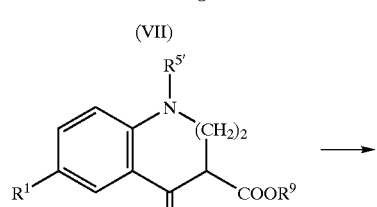
(VIII)

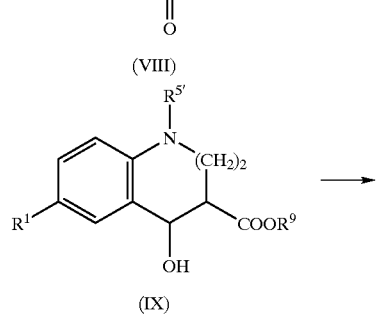
(IX)

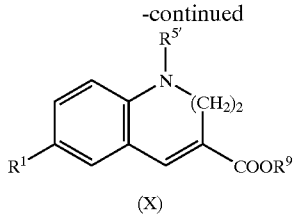
(X)

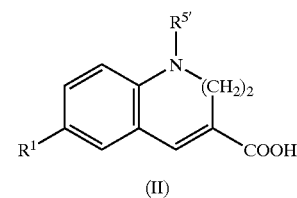
(II)

wherein $R^9$ is a $C_{1-4}$ alkyl group, $R^{5'}$ has the same meaning as the substituent represented by $R^5$, and the other symbols are as defined above.

In this reaction, the Compound (VI) is heated with polyphosphoric acid, or Compound (VI) is converted to acid chloride with thionyl chloride, oxalyl chloride, phosphorus oxychloride, phosphorus pentachloride, etc., followed by subjecting the resulting acid chloride to usual Friedel-Crafts reaction and cyclizing the same to produce Compound (VII). Compound (VII) is then reacted with carbonate ester in the presence of a base to produce ketoester (VIII). Compound (VIII) is subjected to reduction with catalytic hydrogenation or sodium borohydride, etc. to produce Compound (IX). Compound (IX) is subjected to dehydration by the conventional method to produce Compound (X). Compound (X) is subjected to ester hydrolysis to produce unsaturated carboxylic acid (II).

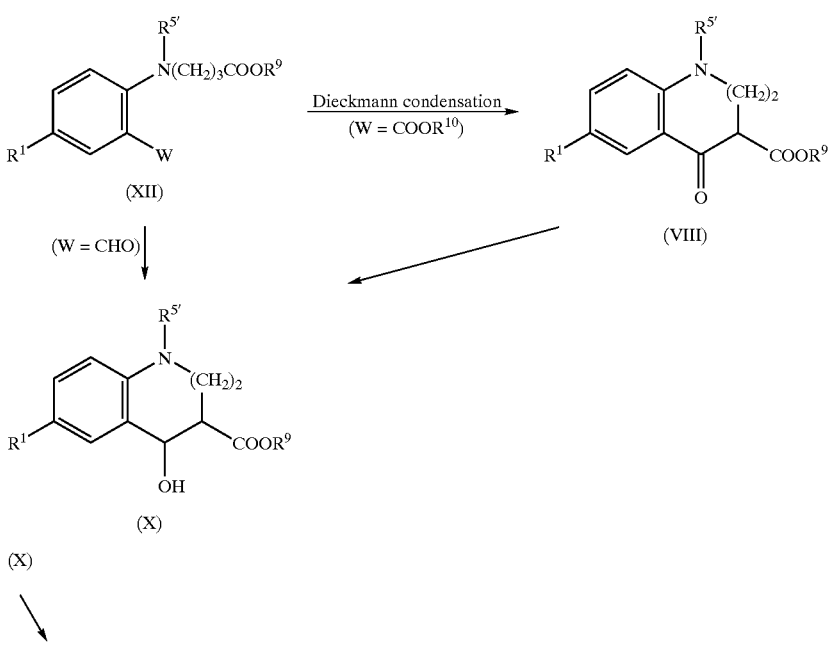

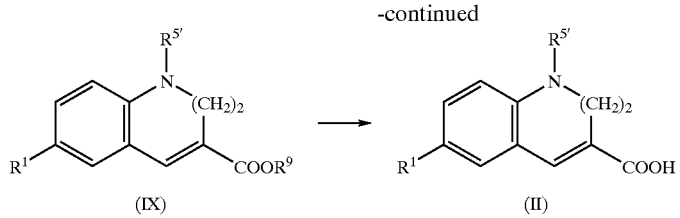

wherein $R^{10}$ is $C_{1-4}$ alkyl group and the other symbols are as defined above.

The Compound (VIII) or (IX) can be produced by subjecting the Compound (XII) to Dieckmann condensation (J. P. Schaefer and J. J. Bloomfield, Org. Reactions, 1967, 15, 1). Compound (VIII) or (IX) is subjected to the reactions as described in Reaction Scheme I to produce unsaturated carboxylic acid (II).

Compound (III) can be produced by a known method (e.g. method described in JP-A-73476/1996, etc.) or the methods analogous thereto. For example, Compound (III) can be produced by a method described in the following Reaction Scheme III, a method described in the following Reference Examples or the methods analogous thereto.

Reaction Scheme III

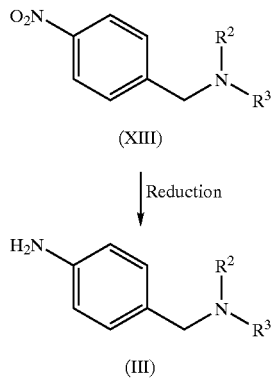

The reduction of Compound (XIII) can be carried out by per se known methods, for example, reduction with a metal, reduction with metal hydride, reduction with metal hydride complex compound, reduction with-metal hydride complex compound, reduction with diborane or substituted borane, catalytic hydrogenation, etc. That is, this reaction is carried out by treating Compound (XIII) with a reducing agent. Examples of the reducing agent include metal such as reduced iron, zinc powder, etc.; alkali metal borohydride (e.g., sodium borohydride, lithium borohydride, etc.); metal hydride complex compound such as aluminum lithium hydride, etc.; metal hydride such as sodium hydride etc.; organic tin compound (triphenyltin hydride, etc.), metal complex compound and metal salt such as nickel compound, zinc compound etc.; catalytic reducing agent using hydrogen and transition metal catalyst such as palladium, platinum, rhodium, etc.; diborane; etc. Among others, as the reducing agent, catalytic reducing agent using hydrogen and transition metal catalyst such as palladium, platinum, rhodium, etc.; metal such as reduced iron, etc. are preferable. The reaction is carried out in a solvent which does not affect the reaction. Examples of the solvent include benzene, toluene, xylene, chloroform, carbon tetrachloride, dichloromethane, 1,2-dichloroethane, 1,1,2,2-tetrachloroethane, diethyl ether, tetrahydrofuran, dioxane, methanol, ethanol, propanol, isopropanol, 2-methoxyethanol, N,N-dimethylformamide, acetic acid, or a mixture of these solvents, etc. The solvent is appropriately selected depending on kind of the reducing agent. The reaction temperature is generally about −20° C. to about 150° C., preferably about 0° C. to about 100° C., and the reaction time is generally about 1 to about 24 hours.

The resultant Compound (II) or (III) can be separated and purified with known separation and purification methods such as concentration, concentration under reduced pressure, extraction, crystallization, solvent conversion, chromatography, etc.

The compound of the formula (I) or a salt thereof of the present invention may be used in combination with other drug for the treatment or prevention of infectious diseases of HIV (in particular, a pharmaceutical composition for the treatment or prevention of AIDS). In this case, these drugs can be formulated by mixing individually or simultaneously with pharmaceutically acceptable carriers, excipients, binders, diluents or the like, which can be administered-orally or non-orally as a pharmaceutical composition for the treatment or prevention of infectious diseases of HIV. In the case of formulating these effective components individually, while the individually formulated agents can be administered in the form of their mixture prepared by using e.g. a diluent when administered, the individually formulated agents can also be administered separately or simultaneously or with time intervals to the one and same subject. A kit for administering the individually formulated effective components in the form of their mixture prepared by using e.g., a diluent when administered (e.g., a kit for injection which comprises two or more ampoules each comprising a powdery component and a diluent for mixing and dissolving two or more components when administered, etc.), a kit for administering the individually formulated agents simultaneously or with time intervals to the one and the same subject (e.g., a kit for tablets to be administered simultaneously or with time intervals, characterized by having two or more tablets each comprising an agent and said tablets being put in one or separate bags and, if necessary, a column to describe time to be administered each agent, etc.), etc. are also included by the pharmaceutical composition of the present invention.

Example of the other pharmaceutical agent for the treatment or prevention of infectious disease of HIV to be used in combination with the compound of the formula (I) or a salt thereof of the present invention include nucleotide reverse transcriptase inhibitors such as zidovudine, didanosine, zalcitabine, lamivudine, stavudine, abacavir, adefovir, adefovir dipivoxil, fozivudine tidoxil, etc.; non-nucleotide reverse transcriptase inhibitors (including an agent having anti-oxidation activity such as immunocal, oltipraz, etc.) such as nevirapine, delavirdine, efavirenz, loviride, immunocal, oltipraz, etc.; protease inhibitors such as saquinavir, ritonavir, indinavir, nelfinavir, amprenavir, palinavir, lasinavir, etc.; etc.

As the nucleotide reverse transcriptase inhibitor, zidovudine, didanosine, zalcitabine, lamivudine, stavudine, etc. are preferable; as the non-nucleotide reverse transcriptase inhibitor, nevirapine, delavirdine etc. are preferable; and as the protease inhibitor, saquinavir, ritonavir, indinavir, nelfinavir etc. are preferable.

The compound of the formula (I) or a salt thereof of the present invention may be used in combination with, for example, CXCR4 antagonist (CXCR4 being a second receptor of T cell-tropic HIV-1) such as AMD-3100, etc., antibody against HIV-1 surface antigen. HIV-1 vaccine, etc., in addition to the above-mentioned protease inhibitor, nucleotide reverse transcriptase inhibitor, etc.

The compound of the formula (I) or a salt thereof of the present invention has CC chemokine receptor (CCR) antagonistic activity, in particular, potent CCR5 antagonistic activity and, therefore, can be used for the treatment or prevention of various infectious diseases of HIV, for example, AIDS in human. The compound of the formula (I) or a salt thereof of the present invention is low toxic and safely used.

The compound of the formula (I) or a salt thereof of the present invention can be used as CCR5 antagonist for the treatment or prevention of AIDS and also for the prevention of the progression of the AIDS.

The dose per day of the compound of the formula (I) or a salt thereof varies depending on the condition and body weight of a patient, administration route, etc. Typical daily dose per adult patient (body weight: 50 Kg) for oral administration is about 5–100 mg, preferably about 10–600 mg, more preferably about 10–300 mg, and in particular about 15–150 mg, as active ingredient [the compound of the formula (I) or a salt thereof] and the compound of the formula (I) or a salt thereof is administered once or 2–3 times per day.

When the compound of the formula (I) or a salt thereof is used in combination with a reverse transcriptase inhibitor and/or a protease inhibitor, the dose of the reverse transcriptase inhibitor or the protease inhibitor ranges, for example, from about 1/200–1/2 or more of the usual dose to about 2–3 times or less of the usual dose. In case that two or more drugs are used in combination, each dose of the drugs is appropriately adjusted if one drug affects metabolism of the other drug, while each dose of the drugs when they are used in combination is generally the same as the dose when they are used alone.

Usual doses of the typical reverse transcriptase inhibitors and the protease inhibitors are as follows:
zidovudine: 100 mg
didanosine: 125–200 mg
zalcitabine: 0.75 mg
lamivudine: 10 mg
stavudine: 30–40 mg
saquinavir: 600 mg
ritonavir: 600 mg
indinavir: 800 mg
nelfinavir: 750 mg In case of combination use of the compound of the formula (I) or a salt thereof with a reverse transcriptase inhibitor and/or a protease inhibitor, preferred embodiments are shown-below.
(1) A drug containing about 10–300 mg of the compound of the formula (I) or a salt thereof and a drug containing about 50–200 mg of zidovudine to one adult patient (body weight: 50 Kg) are administered. Each of the drugs may be administered to the one and the same subject simultaneously or with time intervals of 12 hours or less.
(2) A drug containing about 10–300 mg of the compound of the formula (I) or a salt thereof and a drug containing about 300–1200 mg of saquinavir to one adult patient (body weight: 50 Kg) are administered. Each of the drugs may be administered to the one and the same subject simultaneously or with time intervals of 12 hours or less.

BEST MODE FOR CARRYING OUT THE INVENTION

The present invention is hereinafter described in more detail by means of the following Test Example. Formulation Example, Reference Examples and Working Examples, which are mere examples of the present invention and are not construed as limitative to the present invention.

The following gene manipulation is carried out in accordance with methods described in textbook (Maniatis et al., Molecular Cloning, Cold Spring Harbor Laboratory, 1989) or protocol attached to reagents.

EXAMPLES

Test Example
(1) Cloning of Human CCR5 Chemokine Receptor
Cloning of CCR5 gene was carried out by a PCR method from human spleen cDNA. With using 0.5 ng of spleen cDNA (Toyobo, QUICK-Clone cDNA) as template, PCR was performed in DNA Thermal Cycler 480 (Perkin-Elmer) (reaction conditions: 30 cycles of 95° C. for 1 minute, 60° C. for 1 minute, and 75° C. for 5 minutes) by adding each 25 pmol of primers of a primer set,
SEQ ID NO.: 1 described in Test Example (1) of WO 99/32100 [length of sequence: 34; type of sequence: nucleic acid; strandedness: single; topology: straight; kind of sequence: other nucleic acid synthetic DNA, and
SEQ ID NO.: 2 described in Test Example (1) of WO 99/32100 [length of sequence: 34; type of sequence: nucleic acid; strandedness: single; topology: straight; kind of sequence: other nucleic acid synthetic DNA which were designed referring to nucleotide sequence of CCR5 gene reported by Samson et. al. (Biochemistry, 35(11), 3362–3367 (1996)) and by using TaKaRa EX Taq (Takara Shuzo). The resultant PCR product was subjected to agarose gel electrophoresis to collect about 1.0 kb DNA fragment, which was subjected to Original TA Cloning Kit (Funakoshi) to carry out cloning of CCR5 gene.
(2) Preparation of Plasmid for Expression of Human CCR5
The plasmid obtained in the above (1) was digested with restriction enzymes XbaI (Takara Shuzo) and BamHI (Takara Shuzo) and subjected to agarose gel electrophoresis to collect about 1.0 kb DNA fragment.

The DNA fragment was mixed with plasmid pcDNA3.1 (Funakoshi) for expression in animal cells, said plasmid being digested with XbaI and BamHI, and they were ligated with DNA Ligation Kit Ver.2 (Takara Shuzo). The resulting plasmid was subjected to transformation of competent cell of *E. coli* JM109 (Takara Shuzo) to obtain plasmid pCKR5.
(3) Introduction of Plasmid for Expression of Human CCR5 into CHO-K1 Cell and Expression of Said Plasmid in CHO-K1 Cell CHO-K1 cells were grown in 750 ml of tissue culture flask (Becton Dickinson) using Ham's F12 medium (Nihon Pharmaceutical) containing 10% fetal calf serum (Life Tech Oriental) and taken off with 0.5 g/L trypsin-0.2 g/L EDTA (Life Tech Oriental). The cells were washed with PBS (Life Tech Oriental), centrifuged (1000 rpm, 5 minutes), and suspended in PBS. With using Gene Pulser (Bio-Rad Laboratories), DNA was introduced into the cells under the conditions shown below. That is, to the cuvette of 0.4 cm gap were added $8 \times 10^6$ cells and 10 µg of plasmid pCKR5 for expression of human CCR5, and electroporation was carried out under 0.25 kV of voltage and 960 µF of capacitance. The cells were transferred into Ham's F12 medium containing 10% fetal calf serum, and cultivated for 24 hours. The cells were again taken off and centrifuged, and suspended in Ham's F12 medium containing 10% fetal calf serum and 500 µg/ml of geneticin (Life Tech Oriental). The suspension was diluted to give $10^4$ cells/ml of the suspension, which was inoculated on a 96 well plate (Becton Dickinson) to give geneticin resistant cells.

The resulting geneticin resistant cells were cultivated in 96 well plate (Becton Dickinson), and cells expressing CCR5 were selected from the geneticin resistant cells. That is, in assay buffer (Ham's F12 medium containing 0.5% BSA and 20 mM HEPES (Wako Pure Chemical, pH7.2)) to which was added 200 pM of [$^{125}$I]-RANTES (Amersham) as a ligand, a binding reaction was carried out at room temperature for 46 minutes, and the buffer was washed with cooled PBS. To the buffer was added 50 µl/well of 1M NaOH, and the mixture was stirred. Radioactivity was determined with a y-counter to select CCR5/CHO cells which specifically bind to the ligand.

(4) Evaluation of Test Compounds Based on CCR5 Antagonistic Activity

The CCR5/CHO cells were inoculated on 96 well microplate ($5 \times 10^4$ cells/well) and cultivated for 24 hours. The medium was removed by means of suction, and to each well was added an assay buffer containing Test Compound (1 µM) and then 100 pM of [$^{125}$I]-RANTES (Amersham) as a ligand. A binding assay was carried out at room temperature for 40 minutes, and an assay buffer was removed by means of suction. Each well was washed twice with cooled PBS, and 200 µl of Microscint-20 (Packard Instrument, Inc.) was added to each well. Radio-activity was determined with Top-Count Micro Scintillation Counter (Packard Instrument, Inc.).

According to the method described above, inhibitory rate of Test Compound to CCR5 binding was measured. The results are shown in Table 1.

TABLE 1

| Compound Number | Inhibitory Rate (%) |
|---|---|
| 1 | 93 |
| 2 | 96 |
| 14 | 96 |
| 16 | 96 |
| 17 | 99 |
| 19 | 100 |
| 20 | 94 |
| 23 | 97 |
| 26 | 100 |
| 27 | 100 |
| 33 | 98 |
| 35 | 100 |
| 39 | 98 |
| 43 | 100 |
| 45 | 100 |
| 49 | 100 |
| 50 | 100 |
| 58 | 99 |
| 68 | 95 |
| 69 | 100 |
| 71 | 100 |
| 77 | 97 |
| 79 | 100 |
| 84 | 97 |
| 85 | 100 |
| 98 | 100 |
| 101 | 100 |

TABLE 1-continued

| Compound Number | Inhibitory Rate (%) |
|---|---|
| 102 | 100 |
| 104 | 98 |
| 112 | 100 |

(5) Inhibitory Effect on HIV-1 Infection to MAGI-CCR5 Cell

The plasmid where β-galactosidase gene was ligated downstream of HIV-1 LTR was introduced into CD4 positive HeLa cell, to which human CCR5 was further introduced to obtain transformant MAGI-CCR5.

By using said transformant MAGI-CCR5, a degree of HIV-1 infection was calculated using β-galactosidase activity (blue color due to decomposition of 5-bromo-4-chloro-3-indolyl-β-D-galactopyranoside) as an index. Specifically, MAGI-CCR5 cells were suspended in DMEM medium containing 10% serum to prepare $5 \times 10^4$ cells/ml suspension. To each well of 96 well plate was inoculated 200 µl of the suspension, and the cells were cultivated at 37° C. overnight. The medium was removed by means of suction, and to the residue was added 100 µl of the above medium containing 1.6 µM of Test Compound and 100 µl of the above medium containing 300 PFU of HIV-1 BA-L cells. The cells were cultivated at 37° C. for 2 days. The medium was removed by means of suction. To the residue was added 200 µl of a cell fixative (PBS containing 1% formaldehyde and 0.2% glutaraldehyde), and the mixture was allowed to stand at room temperature for 5 minutes and washed twice with PBS. To the mixture was added 100 µl of staining solution (PBS containing 4 µM potassium ferrocyanide, 4 µM potassium ferricyanide, 2 µM $MgCl_2$ and 0.4 mg/ml X-gal), and the mixture was allowed to stand at 37° C. for 50 minutes and washed twice with PBS. The number of blue cells was counted by a microscope and defined as the number of cells infected with HIV-1. According to this method, inhibition rate of HIV-1 infection was determined. The results are shown in Table 2.

TABLE 2

| Compound Number | Inhibitation Rate (%) |
|---|---|
| 1 | 85 |
| 14 | 91 |
| 16 | 94 |
| 17 | 94 |

The pharmaceutical composition for antagonizing CCR5 (e.g., a medicament for the treatment or prevention of infectious disease of HIV, a medicament for the treatment or prevention of AIDS, etc.) comprising the compound of the formula (I) or a salt thereof of the present invention, as an active ingredient, can be prepared, for example, by the following prescriptions:

Formulation Example

1. Capsule (1) Compound obtained in Working Example 1 40 mg
(2) lactose 70 mg
(3) fine crystalline cellulose 9 mg
(4) magnesium stearate 1 mg
   1 capsule 120 mg (1), (2), (3) and ½ of (4) are mixed and then granulated. To the granules is added the remainder of (4), and the whole is filled into a gelatin capsule.

2. Tablet
(1) Compound obtained in Working Example 1 40 mg
(2) lactose 58 mg
(3) corn starch 18 mg
(4) fine crystalline cellulose 3.5 mg
(5) magnesium stearate 0.5 mg
1 capsule 120 mg (1), (2), (3), ⅔ of (4) and ½ of (5) are mixed and then granulated. To the granules are added the 1 remainders of (4) and (5), followed by subjecting the mixture to compression molding.

Reference Example 1

In DMF (14 ml) was dissolved 1-formyl-7-(4-morpholinophenyl)-2,3-dihydro-1H-1-benzazepine-4-carboxylic acid (0.18 g). To the solution was added, under ice-cooling, thionyl chloride (0.1 ml), and the mixture was stirred at room temperature for 30 minutes. Under reduced pressure, the solvent was evaporated, and the residue was suspended in THF (50 ml). The suspension was added dropwise to a solution of 4-[N-methyl-N-(tetrahydro-2H-pyran-4-yl)aminomethyl]aniline (0.13 g) and triethylamine (0.33 ml) in THF (5 ml), under ice-cooling, and the mixture was stirred under nitrogen atmosphere at room temperature for 2 hours. Under reduced pressure, the solvent was evaporated. To the residue was added water, and the mixture was extracted with ethyl acetate. The organic layer was washed with water and saturated brine and dried with anhydrous magnesium sulfate, and the solvent was evaporated to give crude crystals, which were recrystallized from ethanol/hexane to give 1-formyl-N-[4-[[N-methyl-N-(tetrahydro-2H-pyran-4-yl)amino]methyl]phenyl]-7-(4-morpholinophenyl)-2,3-dihydro-1H-1-benzazepine-4-carboxamide (0.16 g) as colorless crystals.

mp 234–243° C.

$^1$H-NMR (δ ppm, CDCl$_3$) 1.70–1.75 (4H, m), 2.21 (3H, s), 2.60–2.67 (1H, m), 3.03 (2H, t, J=5.4 Hz), 3.21–3.26 (4H, m), 3.37 (2H, dt, J=2.8, 11.2 Hz), 3.58 (2H, s), 3.87–3.95 (6H, m), 4.02–4.07 (2H, m), 7.00 (2H, d, J=8.8 Hz), 7.19 (1H, d, J=8.6 Hz), 7.32 (2H, d, J=8.4 Hz), 7.47–7.59 (7H, m), 7.69 (1H, d, J=2.2 Hz), 8.55 (1H, s).

IR (KBr) ν: 2953, 2845, 1667 cm$^{-1}$.

Anal. Calcd. for $C_{35}H_{40}N_4O_4$: C, 72.39; H, 6.94; N, 9.65. Found C, 72.03; H, 6.65; N, 9.49.

Reference Example 2

In DMF (5 ml) was dissolved 7-(4-ethoxyphenyl)-1-formyl-2,3-dihydro-1H-1-benzazepine-4-carboxylic acid (0.2 g). To the solution was added, under ice-cooling, thionyl chloride (0.11 ml), and the mixture was stirred at room temperature for 30 minutes. Under reduced pressure, the solvent was evaporated, and the residue was suspended in THF (15 ml). The suspension was added dropwise to a solution of 4-[N-methyl-N-(tetrahydro-2H-pyran-4-yl)aminomethyl]aniline (0.15 g) and triethylamine (0.41 ml) in THF (5 ml), under ice-cooling, and the mixture was stirred under nitrogen atmosphere at room temperature overnight. Under reduced pressure, the solvent was evaporated. To the residue was added water, and the mixture was extracted with ethyl acetate. The organic layer was washed with water and saturated brine and dried with anhydrous magnesium sulfate, and the solvent was evaporated to give crude crystals, which were recrystallized from ethyl acetate/hexane to give 7-(4-ethoxyphenyl)-1-formyl-N-[4-[[N-methyl-N-(tetrahydro-2H-pyran-4-yl)amino]methyl]phenyl]-2,3-dihydro-1H-1-benzazepine-4-carboxamide (0.25 g) as colorless crystals.

mp 211–215° C.

$^1$H-NMR (δ ppm, CDCl$_3$) 1.45 (3H, t, J=6.9 Hz), 1.59–1.75 (4H, m), 2.21 (3H, s), 2.60–2.68 (1H, m), 3.04 (2H, t, J=5.5 Hz), 3.37 (2H, dt, J=2.8, 11.3 Hz), 3.58 (2H, s), 3.93 (2H, t, J=5.5 Hz), 4.01–4.18 (4H, m), 6.99 (2H, d, J=8.8 Hz), 7.19 (1H, d, J=8.6 Hz), 7.32 (2H, d, J=8.4 Hz), 7.46–7.58 (6H, m), 7.68 (1H, d, J=2.0 Hz), 8.55 (1H, s).

IR (KBr) ν: 2940, 1667 cm$^{-1}$.

Anal. Calcd. for $C_{33}H_{37}N_3O_4.0.2H_2O$: C, 72.96; H, 6.94; N, 7.73. Found C, 72.89; H, 6.91; N, 7.59.

Reference Example 3

In DMF (5 ml) was dissolved 7-(3-diethoxyphenyl)-1-formyl-2,3-dihydro-1H-1-benzazepine-4-carboxylic acid (0.25 g). To the solution was added, under ice-cooling, thionyl chloride (0.12 ml), and the mixture was stirred at room temperature for 30 minutes. Under reduced pressure, the solvent was evaporated, and the residue was suspended in THF (25 ml). The solution was added dropwise to a solution of 4-[N-methyl-N-(tetrahydro-2H-pyran-4-yl)aminomethyl]aniline (0.16 g) and triethylamine (0.46 ml) in THF (4 ml), under ice-cooling, and the mixture was stirred under nitrogen atmosphere at room temperature for 5 hours. Under reduced pressure, the solvent was evaporated. To the residue was added water, and the mixture was extracted with ethyl acetate. The organic layer was washed with water and saturated brine and dried with anhydrous magnesium sulfate, and the solvent was evaporated to give crude crystals, which were recrystallized from ethyl acetate/diethyl ether to give 7-(3,4-diethoxyphenyl)-1-formyl-N-[4-[[N-methyl-N-(tetrahydro-2H-pyran-4-yl)amino]methyl]phenyl]-2,3-dihydro-1H-1-benzazepine-4-carboxamide (0.26 g) as yellow crystals.

mp 145–148° C.

$^1$H-NMR (δ ppm, CDCl$_3$) 1.49 (3H, t, J=7.0 Hz), 1.50 (3H, t, J=7.0 Hz), 1.62–1.75 (4H, m), 2.21 (3H, s), 2.61–2.70 (1H, m), 3.04 (2H, t, J=5.4 Hz), 3.38 (2H, dt, J=3.0, 11.2 Hz), 3.58 (2H, s), 3.93 (2H, t, J=5.4 Hz), 3.95–4.10 (2H, m), 4.10–4.24 (4H, m), 6.97 (1H, d, J=8.8 Hz), 7.11–7.21 (3H, m), 7.33 (2H, d, J=8.4 Hz), 7.49–7.59 (4H, m), 7.68 (1H, d, J=2.0 Hz), 8.55 (1H, s).

IR (KBr) ν: 2980, 2944, 1667 cm$^{-1}$.

Anal. Calcd. for $C_{35}H_{41}N_3O_5.0.2H_2O$: C, 71.58; H, 7.10; N, 7.15. Found C, 71.40; H, 7.00; N, 7.22.

Reference Example 4

In DMF (10 ml) was dissolved 1-methanesulfonyl-7-(4-morpholinophenyl)-2,3-dihydro-1H-1-benzazepine-4-carboxylic acid (0.3 g). To the solution was added, under ice-cooling, thionyl chloride (0.15 ml), and the mixture was stirred at room temperature for 30 minutes. Under reduced pressure, the solvent was evaporated, and the residue was suspended in THF (50 ml). The suspension was added dropwise to a solution of 4-[N-methyl-N-(tetrahydro-2H-pyran-4-yl)aminomethyl]aniline (0.19 g) and triethylamine (0.5 ml) in THF (5 ml), under ice-cooling, and the mixture was stirred under nitrogen atmosphere at room temperature overnight. Under reduced pressure, the solvent was evaporated. To the residue was added water, and the mixture was extracted with ethyl acetate. The organic layer was washed with water and saturated brine and dried with anhydrous magnesium sulfate, and the solvent was evaporated to give crude crystals, which were recrystallized from ethyl acetate/ ethanol to give 1-methanesulfonyl-N-[4-[[N-methyl-N-(tetrahydro-2H-pyran-4-yl)amino]methyl]phenyl]-7-(4-morpholinophenyl)-2,3-dihydro-1H-1-benzazepine-4-carboxamide (0.26 g) as pale crystals.

mp 239–243° C.

$^1$H-NMR (δ ppm, CDCl$_3$) 1.70–1.77 (4H, m), 2.22 (3H, s), 2.60–2.70 (1H, m), 2.89 (3H, s), 3.13 (2H, t-like), 3.21–3.26 (4H, m), 3.37 (2H, dt, J=2.6, 11.5 Hz), 3.59 (2H, s), 3.87–3.91 (6H, m), 4.02–4.11 (2H, m), 7.00 (2H, d, J=8.8 Hz), 7.34 (2H, d, J=8.8 Hz), 7.50–7.66 (9H, m).

IR (KBr) v: 2951, 2847, 1661, 1609, 1520 cm$^{-1}$.

Anal. Calcd. for C$_{35}$H$_{42}$N$_4$O$_5$.0.3H$_2$O: C, 66.08; H, 6.75; N, 8.81. Found C, 66.06; H, 6.50; N, 8.55.

Reference Examples 5

In DMF (12 ml) was suspended 7-(4-ethoxyphenyl)-1-methanesulfonyl-2,3-dihydro-1H-1-benzazepine-4-carboxylic acid (0.13 g). To the suspension was added, under ice-cooling, thionyl chloride (0.04 ml) and DMF (catalytic amount), and the mixture was stirred at room temperature for 2 hours. Under reduced pressure, the solvent was evaporated, and the residue was dissolved in THF (15 ml). The solution was added dropwise to a solution of 4-[N-methyl-N-(tetrahydro-2H-pyran-4-yl)aminomethyl]aniline (0.08 g) and triethylamine (0.14 ml) in THF (5 ml), under ice-cooling, and the mixture was stirred under nitrogen atmosphere at room temperature overnight. Under reduced pressure, the solvent was evaporated. To the residue was added water, and the mixture was extracted with ethyl acetate. The organic layer was washed with water and saturated brine and dried with anhydrous magnesium sulfate, and the solvent was evaporated to give crude crystals, which were recrystallized from ethyl acetate/hexane to give 7-(4-ethoxyphenyl)-1-methanesulfonyl-N-[4-[[N-methyl-N-(tetrahydro-2H-pyran-4-yl)amino]methyl]phenyl]-2,3-dihydro-1H-1-benzazepine-4-carboxamide (0.16 g) as colorless crystals.

mp 184–186° C.

$^1$H-NMR (δ ppm, CDCl$_3$) 1.45 (3H, t, J=7.0 Hz), 1.64–1.75 (4H, m), 2.21 (3H, s), 2.61–2.72 (1H, m), 2.88 (3H, s), 3.13 (2H, t, J=5.3 Hz), 3.37 (2H, dt, J=2.6, 11.2 Hz), 3.59 (2H, s), 3.91 (2H, t, J=5.3 Hz), 4.01–4.07 (2H, m), 4.09 (2H, q, J=7.0 Hz), 6.98 (2H, d, J=8.8 Hz), 7.33 (2H, d, J=8.8 Hz), 7.48–7.68 (9H, m).

IR (KBr) v: 2946, 2843, 1661, 1609, 1518, 1495 cm$^{-1}$.

Anal. Calcd. for C$_{33}$H$_{39}$N$_3$O$_5$S: C, 67.21; H, 6.67; N, 7.13. Found C, 67.25; H, 6.33; N, 7.05.

Reference Example 6

In DMF (8 ml) was dissolved 1-methoxycarbonyl-7-(4-morpholinophenyl)-2,3-dihydro-1H-1-benzazepine-4-carboxylic acid (0.15 g). To the solution was added, under ice-cooling, thionyl chloride (0.07 ml), and the mixture was stirred at room temperature for 30 minutes. Under reduced pressure, the solvent was evaporated, and the residue was suspended in THF (25 ml). The suspension was added dropwise to a solution of 4-[N-methyl-N-(tetrahydro-2H-pyran-4-yl)aminomethyl]aniline (0.12 g) and triethylamine (0.26 ml) in THF (5 ml), under ice-cooling, and the mixture was stirred under nitrogen atmosphere at room temperature for 4 hours. Under reduced pressure, the solvent was evaporated. To the residue was added water, and the mixture was extracted with ethyl acetate. The organic layer was washed with water and saturated brine and dried with anhydrous magnesium sulfate, and the solvent was evaporated. The residue was purified with silica gel column chromatography (elution solvent: methanol/triethylamine/ethyl acetate) to give crude crystals, which were recrystallized from ethyl acetate/hexane to give 1-methoxycarbonyl-N-[4-[[N-methyl-N-(tetrahydro-2H-pyran-4-yl)amino]methyl]phenyl]-7-(4-morpholinophenyl)-2,3-dihydro-1H-1-benzazepine-4-carboxamide (0.14 g) as colorless crystals.

mp 193–197° C.

$^1$H-NMR (δ ppm, CDCl$_3$) 1.57–1.80 (4H, m), 2.21 (3H, s), 2.65 (1H, br), 3.03 (2H, br), 3.20–3.23 (4H, m), 3.37 (2H, dt, J=3.0, 9.9 Hz), 3.58 (2H, s), 3.78 (3H, s), 3.78 (2H, br), 3.87–3.92 (4H, m), 4.01–4.14 (2H, m), 6.99 (2H, d, J=9.2 Hz), 7.30–7.60 (10H, m).

IR (KBr) v: 2957, 2855, 1701 cm$^{-1}$.

Anal. Calcd. for C$_{36}$H$_{42}$N$_4$O$_5$.0.2H$_2$O: C, 70.38; H, 6.96; N, 9.12. Found C, 70.35; H, 6.81; N, 9.09.

Reference Example 7

In a mixture of water:ethanol:toluene (1:1:10, v/v, 18.0 ml) were dissolved 3,4-diethylphenyl borate (264 mg) and 7-bromo-1-methyl-N-[4-[[N-methyl-N-(tetrahydro-2H-pyran-4-yl)amino]methyl]phenyl]-2,3-dihydro-1H-1-benzazepine-4-carboxamide (406 mg), and to the solution was added potassium carbonate (162 mg). The mixture was stirred under argon atmosphere at room temperature for 30 minutes, and to the mixture was added tetrakistriphenylphosphinepalladium (39 mg). The mixture was refluxed under argon atmosphere for 13 hours, diluted with ethyl acetate and washed with water and saturated brine, and the organic layer was dried with anhydrous magnesium sulfate. The solvent was evaporated under reduced pressure, and the residue was purified with silica gel column chromatography (45 g, ethyl acetate:ethanol=20:1) and recrystallized from ethanol to give 7-(3,4-diethylphenyl)-1-methyl-N-[4-[[N-methyl-N-(tetrahydro-2H-pyran-4-yl)amino]methyl]phenyl]-2,3-dihydro-1H-1-benzazepine-4-carboxamide (263 mg, 55%) as yellow crystals.

mp 127–129° C.

$^1$H-NMR (200 MHz, CDCl$_3$) δ 1.47 (3H, t, J=7.0 Hz), 1.48 (3H, t, J=7.0 Hz), 1.69–1.76 (4H, m), 2.21 (3H, s), 2.53–2.74 (1H, m), 2.96 (2H, t, J=4.5 Hz), 3.09 (3H, s), 3.31–3.43 (4H, m), 3.57 (2H, s), 4.01–4.07 (2H, m), 4.13 (2H, q, J=7.0 Hz), 4.17 (2H, q, J=7.0 Hz), 6.87 (1H, d, J=8.6 Hz), 6.93 (1H, d, J=9.0 Hz), 7.07 (1H, dd, J=6.9, 2.1 Hz), 7.09 (1H, s), 7.30 (2H, d, J=8.6 Hz), 7.41–7.42 (2H, m), 7.48 (1H, dd, J=9.1, 2.3 Hz), 7.54 (2H, d, J=8.6 Hz), 7.59 (1H, s).

IR (KBr) 1653, 1599, 1514, 1503, 1478, 1406, 1312, 1246, 1188, 1140, 1044 cm$^{-1}$.

Anal. Calcd. for C$_{35}$H$_{43}$N$_3$O$_4$: C, 73.78; H, 7.61; N, 7.38. Found C, 73.49; H, 7.54; N, 7.15.

Reference Example 8

In a mixture of THF and ethanol (1:1, v/v, 30.0 ml) was dissolved ethyl 1-[(4-methylphenyl)sulfonyl]-7-[4-(4-morpholino)phenyl]-2,3-dihydro-1H-1-benzazepine-4-carboxylate (454 mg). To the solution was added 1N Sodium hydroxide solution (3.0 ml), and the mixture was stirred at room temperature for 62 hours. To the mixture was added 1N hydrochloric acid to make the solution weak acidic, and the mixture was extracted with ethyl acetate. The organic layer was dried with anhydrous magnesium sulfate. The solvent was evaporated under reduced pressure to give 1-[(4-methylphenyl)sulfonyl]-7-[4-(4-morpholino)phenyl]-2,3-dihydro-1H-1-benzazepine-4-carboxylic acid as white crystals. The obtained 1-[(4-methylphenyl)sulfonyl]-7-[4-

(4-morpholino)phenyl]-2,3-dihydro-1H-1-benzazepine-4-carboxylic acid was suspended in DMF (15.0 ml). To the suspension was added thionyl chloride (0.15 ml), and the mixture was stirred at room temperature for 1 hour. Under reduced pressure, the solvent was evaporated, and the residue was dissolved in dichloromethane (10.0 ml). On the other hand, to 4-[[(N-methyl-N-tetrahydro-2H-pyran-4-yl)amino]methyl]aniline dihydrochloride (296 mg) was added dichloromethane (15.0 ml), and then was added triethylamine (0.88 ml). To the obtained mixture was added dropwise at 0° C. the previously prepared acid chloride solution, and the mixture was stirred at room temperature for 3 hours. To the mixture was added water, and the separated organic layer was dried with anhydrous magnesium sulfate. The solvent was evaporated under reduced pressure, and the residue was recrystallized from ethanol to give 1-[(4-methylphenyl)sulfonyl]-N-[4-[[N-methyl-N-(tetrahydro-2H-pyran-4-yl)amino]methyl]phenyl]-7-[4-(4-morpholino)phenyl]-2,3-dihydro-1H-1-benzazepine-4-carboxamide (359 mg, 60%) as white crystals.

mp 258–262° C.

$^1$H-NMR (200 MHz, CDCl$_3$) δ 1.70–1.77 (4H, m), 2.21 (3H, s), 2.35 (3H, s), 2.53–2.74 (1H, m), 2.98 (2H, t, J=5.5 Hz), 3.23 (4H, t, J=4.9 Hz), 3.38 (2H, td, J=10.4, 3.2 Hz), 3.58 (2H, s), 3.89 (4H, t, J=4.8 Hz), 3.99 (2H, t, J=5.4 Hz), 4.01–4.09 (2H, m), 6.99 (2H, d, J=8.8 Hz), 6.97–7.06 (2H, m), 7.19 (2H, d, J=7.6 Hz), 7.29–7.34 (2H, m), 7.45 (2H, d, J=8.6 Hz), 7.53 (2H, d, J=8.6 Hz), 7.50–7.65 (5H, m).

IR (KBr) 1663, 1609, 1605, 1518, 1495, 1345, 1308, 1233, 1159, 1121, 1090, 928, 816, 733, 671 cm$^{-1}$.

Anal. Calcd. for C$_{41}$H$_{46}$N$_4$O$_5$S (0.1H$_2$O additive): C, 69.49; H, 6.57; N, 7.91. Found C, 69.27; H, 6.63; N, 7.92.

Reference Example 9

In DMF (15.0 ml) was suspended 1-acetyl-7-[4-(4-morpholino)phenyl]-2,3-dihydro-1H-1-benzazepine-4-carboxylic acid (365 mg). To the suspension was added thionyl chloride (0.17 ml), and the mixture was stirred at room temperature for 1 hour. Under reduced pressure, the solvent was evaporated, and the residue was dissolved in dichloromethane (10.0 ml). On the other hand, to 4-[[N-methyl-N-(tetrahydro-2H-pyran-4-yl)amino]methyl]aniline dihydrochloride (327 mg) was added dichloromethane (15.0 ml), and then was added triethylamine (0.97 ml). To the obtained mixture: was added dropwise the previously prepared acid chloride suspension at 0° C., and the mixture was stirred at room temperature for 3 hours. To the mixture was added water, and the separated organic layer was dried with anhydrous magnesium sulfate. The solvent was evaporated under reduced pressure, and the residue was purified with silica gel column chromatography (50 g, ethyl acetate:ethanol=9:1) and washed with hexane/ethyl acetate to give 1-acetyl-N-[4-[[N-methyl-N-(tetrahydro-2H-pyran-4-yl)amino]methyl]phenyl]-7-[4-(4-morpholino)phenyl]-2,3-dihydro-1H-1-benzazepine-4-carboxamide (116 mg, 21%) as pale yellow crystals.

mp 141–145° C.

$^1$H-NMR (200 MHz, CDCl$_3$) δ 1.65–1.87 (4H, m), 2.09 (3H, s), 2.23 (3H, s), 2.61–2.78 (1H, m), 2.81–3.05 (3H, m), 3.24 (4H, t, J=4.7 Hz), 3.37 (2H, td, J=11.4, 2.7 Hz), 3.60 (2H, s), 3.90 (4H, t, J=4.8 Hz), 4.02–4.07 (2H, m), 4.75–4.91 (1H, m), 7.23–7.27 (1H, m), 7.34 (2H, d, J=8.4 Hz), 7.52–7.69 (8H, m).

IR (KBr) 1657, 1609, 1514, 1497, 1451, 1395, 1314, 1258, 1235 cm$^{-1}$.

Anal. Calcd. for C$_{36}$H$_{42}$N$_4$O$_4$ (1.2H$_2$O additive): C, 70.15; H, 7.26; N, 9.09. Found C, 69.91; H, 7.05;.N, 9.03.

Reference Example 10

In water:ethanol:toluene (1:1:10, v/v, 18.0 ml) were dissolved (4-diethylamino)phenyl borate (234 mg) and 7-bromo-1-methyl-N-[4-[[N-methyl-N-(tetrahydro-2H-pyran-4-yl)amino]methyl]phenyl]-2,3-dihydro-1H-1-benzazepine-4-carboxamide (391 mg). To the solution was added potassium carbonate (268 mg), and the mixture was stirred under argon atmosphere at room temperature for 30 minutes. To the mixture was added tetrakistriphenylphosphinepalladium (37 mg), and the mixture was heated to reflux under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (45 g, ethyl acetate:ethanol=20:1) and recrystallized from ethanol to give 7-(4-diethylaminophenyl)-1-methyl-N-(4-[[N-methyl-N-(tetrahydro-2H-pyran-4-yl)amino]methyl]phenyl]-2,3-dihydro-1H-1-benzazepine-4-carboxamide (145 mg, 33%) as yellow crystals.

mp 178–180° C.

$^1$H NMR (200 MHz, CDCl$_3$) δ 1.19 (6H, t, J=7.0 Hz), 1.64–1.76 (4H, m), 2.21 (3H, s), 2.54–2.72 (1H, m), 2.95 (2H, t, J=4.5 Hz), 3.07 (3H, s), 3.31–3.44 (4H, m), 3.39 (4H, q, J=7.1 Hz), 3.57 (2H, s), 4.01–4.07 (2H, m), 6.74 (2H, d, J=9.0 Hz), 6.86 (1H, d, J=8.6 Hz), 7.30 (2H, d, J=8.4 Hz), 7.41–7.59 (8H, m).

IR (KBr). 2948, 1644, 1597, 1514, 1497, 1406, 1312, 1283, 1246, 1188, 1071, 810, 733 cm$^{-1}$.

Anal. Calcd. for C$_{35}$H$_{44}$N$_4$O$_2$ (0.1H$_2$O additive): C, 75.80; H, 6.03; N, 10.10. Found C, 75.51; H, 7.95; N, 10.10.

Reference Example 11

In water: ethanol: toluene (1:1:10, v/v, 18.0 ml) were dissolved 4-propoxyphenyl borate (203 mg) and 7-bromo-1-methyl-N-[4-[[N-methyl-N-(tetrahydro-2H-pyran-4-yl)amino]methyl]phenyl]-2,3-dihydro-1H-benzazepine-4-carboxamide (455 mg). To the solution was added potassium carbonate (312 mg), and the mixture was stirred under argon atmosphere at room temperature for 30 minutes. To the mixture was added tetrakistriphenylphosphinepalladium (43 mg), and the mixture was heated to reflux under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (30 g, ethyl acetate:ethanol:triethyleamine=100:5:1) and recrystallized from ethanol/hexane to give 1-methyl-N-[4-[[N-methyl-N-(tetrahydro-2H-pyran-4-yl)amino]methyl]phenyl]-7-(4-propoxyphenyl)-2,3-dihydro-1H-1-benzazepine-4-carboxamide (349 mg, 69%) as yellow crystals.

mp 149–151° C.

$^1$H NMR (200 MHz, CDCl$_3$) δ 1.05 (3H, t, J=7.4 Hz), 1.63–1.76 (4H, m), 1.83 (2H, sextet, J=7.2 Hz), 2.20 (3H, s), 2.53–2.73 (1H, m), 2.95 (2H, t, J=4.5 Hz), 3.07 (3H, s), 3.31–3.43 (4H, m), 3.56 (2H, s), 3.96 (2H, t, J=6.6 Hz), 4.01–4.07 (2H, m), 6.87 (1H, d, J=8.4 Hz), 6.95 (2H, d, J=8.8 Hz), 7.29 (2H, d, J=8.6 Hz), 7.39 (1H, s), 7.43 (1H, dd, J=8.6, 2.2 Hz), 7.47 (2H, d, J=8.6 Hz), 1H (d) was concealed under 7.49, 7.54 (2H, d, J=8.6 Hz), 7.62 (1H, 5).

IR (KBr) 2946, 1651, 1607, 1514, 1505, 1312, 1242, 1182, 814 cm$^{-1}$.

Anal. Calcd. for $C_{34}H_{41}N_3O_3$ (0.1$H_2O$ additive): C, 75.41; H, 7.67; N, 7.76. Found C, 75.30; H, 7.75; N, 7.82.

Reference Example 12

In DMF (10.0 ml) was suspended 1-formyl-7-(4-propoxyphenyl)-2,3-dihydro-1H-1-benzazepine-4-carboxylic acid (433 mg). To the suspension was added thionyl chloride (0.22 ml), and the mixture was stirred at room temperature for 30 minutes. Under reduced pressure, the solvent was evaporated, and to the mixture was added THF (15.0 ml). On the other hand, to 4-[[N-methyl-N-tetrahydro-2H-pyran-4-yl)amino]methyl]aniline dihydrochloride (434 mg) was added THF (10.0 ml) and then added triethylamine (1.29 ml). The previously prepared acid chloride suspension was added dropwise at 0° C. The mixture was stirred at room temperature for 4 hours. To the mixture was added water, and the mixture was washed with water and saturated brine, and the organic layer was dried with anhydrous magnesium sulfate. The solvent was evaporated under reduced pressure, and the residue was recrystallized from ethanol to give 1-formyl-N-[4-[[N-methyl-N-(tetrahydro-2H-pyran-4-yl)amino]methyl]phenyl]-7-(4-propoxyphenyl)-2,3-dihydro-1H-1-benzazepine-4-carboxamide (554 mg, 81%) as white crystals.

mp 207–209° C.

$^1$H NMR (200 MHz, $CDCl_3$) δ 1.06 (3H, t, J=7.4 Hz), 1.63–1.77 (4H, m), 1.85 (2H, sextet, J=7.0 Hz), 2.21 (3H, s), 2.57–2.72 (1H, m), 3.04 (2H, t, J=4.8 Hz), 3.37 (2H, td, J=11.4, 3.1 Hz), 3.57 (2H, s), 3.90–4.08 (6H, m), 7.00 (2H, d, J=9.0 Hz), 7.20 (1H, d, J=8.2 Hz), 7.32 (2H, d, J=8.4 Hz), 7.47–7.54 (6H, m), 7.57 (1H, dd, J=8.0, 2.2 Hz), 7.68 (1H, d, J=2.0 Hz), 8.56 (1H, s).

IR (KBr) 1669, 1609, 1522, 1497, 1360, 1314, 1252 $cm^{-1}$.

Anal. Calcd. for $C_{34}H_{39}N_3O_4$: C, 73.75; H, 7.10; N, 7.59. Found C, 73.48; H, 7.11; N, 7.50.

Reference Example 13

In THF (10.0 ml) and catalytic amount of DMF was suspended 1-methylsulfonyl-7-(4-propoxyphenyl)-2,3-dihydro-1H-1-benzazepine-4-carboxylic acid (236 mg). To the suspension was added oxalyl chloride (0.13 ml), and the mixture was stirred at room temperature for 1 hour. Under reduced pressure, the solvent was evaporated. To the residue was added THF (10.0 ml). On the other hand, to 4-[[N-methyl-N-(tetrahydro-2H-pyran-4-yl)amino]methyl]aniline dihydrochloride (207 mg) was added THF (10.0 ml), and then was added triethylamine (0.61 ml). To the obtained mixture was added dropwise at 0° C. the previously prepared acid chloride suspension, and the mixture was stirred at room temperature for 3.5 hours. To the mixture was added ethyl acetate, and the mixture was washed with water, 1N sodium hydroxide solution, water and saturated brine. The organic layer was dried with anhydrous magnesium sulfate. The solvent was evaporated under reduced pressure, and the residue was purified with silica gel column chromatography (10 g, ethyl acetate:ethanol:triethylamine=100:10:1) and recrystallized from ethanol to give 1-methylsulfonyl-N-[4-[[N-methyl-N-(tetrahydro-2H-pyran-4-yl amino]methyl] phenyl]-7-(4-propoxyphenyl)-2,3-dihydro-1H-1-benzazepine-4-carboxamide (205 mg, 58%) as white crystals.

mp 199–202° C.

$^1$H NMR (200 MHz, $CDCl_3$) δ 1.06 (3H, t, J=7.4 Hz), 1.63–1.79 (4H, m), 1.85 (2H, sextet, J=7.0 Hz), 2.21 (3H, s), 2.54–2.74 (1H, m), 2.98 (3H, s), 3.14 (2H, t, J=5.2 Hz), 3.38 (2H, td, J=11.3, 3.2 Hz), 3.58 (2H, s), 3.89–4.07 (6H, m), 6.96–7.03 (2H, m), 7.33 (2H, d, J=8.4 Hz), 7.47–7.67 (9H, m).

IR (KBr) 1653, 1609, 1518, 1493, 1341, 1314, 1248, 1154 $cm^{-1}$.

Anal. Calcd. for $C_{34}H_{41}N_3O_5S$: C, 67.64; H, 6.84; N, 6.96. Found C, 67.37; H, 6.77; N, 6.89.

Reference Example 14

In THF (10.0 ml) and catalytic amount of DMF was suspended 7-(4-ethoxy-3-fluorophenyl)-1-methylsulfonyl-2,3-dihydro-1H-1-benzazepine-4-carboxylic acid (182 mg). To the suspension was added oxalyl chloride (0.12 ml), and the mixture was stirred at room temperature for 1 hour. Under reduced pressure, the solvent was evaporated, and to the residue was added THF (10.0 ml). On the other hand, to 4-[[N-methyl-N-(tetrahydro-2H-pyran-4-yl)amino]methyl] aniline dihydrochloride (158 mg) was added THF (10.0 ml), and then was added triethylamine (0.47 ml). To the obtained mixture was added dropwise at 0° C. the previously prepared acid chloride suspension, and the mixture was stirred at room temperature for 3 hours. To the mixture was added ethyl acetate, and the mixture was washed with water, 1N sodium hydroxide solution, water and saturated brine. The organic layer was dried with anhydrous magnesium sulfate. The solvent was evaporated under reduced pressure, and the residue was purified with silica gel column chromatography (15 g, ethyl acetate→ethyl acetate:ethanol:triethylamine= 100:10:1), and recrystallized from ethanol to give 7-(4-ethoxy-3-fluorophenyl]-1-methylsulfonyl-N-[4-[[N-methyl-N-(tetrahydro-2H-pyran-4-yl)amino]methyl]phenyl]-2,3-dihydro-1H-1-benzazepine-4-carboxamide (140 mg, 51%) as white crystals.

mp 199–202° C.

$^1$H NMR (200 MHz, $CDCl_3$) δ 1.49 (3H, t, J=7.0 Hz), 1.64–1.77 (4H, m), 2.21 (3H, s), 2.57–2.70 (1H, m), 2.89 (3H, s), 3.14 (2H, t, J=5.4 Hz), 3.38 (2H, td, J=11.3, 2.9 Hz), 3.57 (2H, s), 3.91 (2H, t, J=5.7 Hz), 4.02–4.07 (2H, m), 4.17 (2H, q, J=6.9 Hz), 7.04 (1H, t, J=8.8 Hz), 7.28–7.35 (3H, m), 7.48–7.61 (7H, m), 7.65 (1H, d, J=8.4 Hz).

IR (KBr) 1661, 1522, 1497, 1343, 1310, 1269, 1238, 1154, 1138 $cm^{-1}$.

Anal. Calcd. for $C_{33}H_{38}FN_3O_5S$ (0.3$H_2O$ additive)] C, 64.64; H, 6.35; N, 6.85. Found C, 64.46; H, 6.41; N, 6.80.

Reference Example 15

In DMF (5.5 ml) was dissolved 7-(4-ethoxy-3-fluorophenyl)-1-formyl-2,3-dihydro-1H-1-benzazepine-4-carboxylic acid (398 mg). To the solution was added thionyl chloride (0.20 ml), and the mixture was stirred at room temperature for 30 minutes. Under reduced pressure, the solvent was evaporated, and to the residue was added THF (10.0 ml). On the other hand, to 4-[[N-methyl-N-(tetrahydro-2H-pyran-4-yl)amino]methyl]aniline dihydrochloride (394 mg) was added THF (10.0 ml), and then was added triethylamine (1.17 ml). To the obtained mixture was added dropwise at 0° C. the previously prepared acid chloride suspension, and the mixture was stirred at room temperature for 4 hours. To the mixture was added ethyl acetate, and the mixture was washed with water, 1N sodium hydroxide solution, water and saturated brine. The organic layer was dried with anhydrous magnesium sulfate. The solvent was evaporated under reduced pressure, and the residue was recrystallized from ethanol to give 7-(4-ethoxy-3-fluorophenyl)-1-formyl-N-[4-[[N-methyl-N-(tetrahydro- 2H-pyran-4-yl)amino]methyl]phenyl]-2,3-dihydro-1H-1-benzazepine-4-carboxamide (453 mg, 73%) as white crystals.

mp 193–196° C.

$^1$H NMR (200 MHz, CDCl$_3$) δ 1.49 (3H, t, J=7.0 Hz), 1.64–1.75 (4H, m), 2.21 (3H, s), 2.58–2.74 (1H, m), 3.04 (2H, t, J=5.0 Hz), 3.37 (2H, td, J=11.3, 3.1 Hz), 3.58 (2H, s), 3.92 (2H, t, J=5.3 Hz), 4.02–4.07 (2H, m), 4.17 (2H, q, J=7.1 Hz), 7.05 (1H, t, J=8.6 Hz), 7.20 (1H, d, J=8.4 Hz), 7.29–7.37 (5H, m), 7.45 (1H, s), 7.54 (2H, d, J=8.4 Hz), 7.56 (1H, s), 7.66 (1H, d, J=2.0 Hz), 8.55 (1H, s).

IR (KBr) 1667, 1514, 1501, 1360, 1314, 1269, 1238 cm$^{-1}$.

Anal. Calcd. for C$_{33}$H$_{36}$FN$_3$O$_4$ (0.1H$_2$O additive): C, 70.85; H, 6.52; N, 7.51. Found C, 70.55; H, 6.54; N, 7.45.

Reference Example 16

A solution of methyl 5-bromo-N-tosylanthranylate (200 g) in DMF (450 ml) was added dropwise, under ice-cooling, to a suspension of 60% sodium hydride (25 g) in DMF (50 ml). Under nitrogen atmosphere, the mixture was stirred at room temperature for 2 hours, and to the mixture were added sodium iodide (78 g) and ethyl 4-bromobutyrate (82 ml). The mixture was stirred under nitrogen atmosphere at 85° C. for 24 hours, and to the mixture was added potassium t-butoxide (70 g) under ice-cooling. The mixture was stirred at 85° C. for 1.5 hours, and the solvent was evaporated. To the residue was added ice-water, and the mixture was extracted with ethyl acetate. The organic layer was washed with water and saturated brine and dried with anhydrous magnesium sulfate, and the solvent was evaporated to give ethyl (methyl) 7-bromo-5-hydroxy-1-tosyl-2,3-dihydro-1H-1-benzazepine-4-carboxylate (mixture) (153 g) as white crystals.

$^1$H NMR (δ ppm, CDCl$_3$) 1.31 (1.5H, t, J=7.1 Hz), 2.29 (2H, t, J=6.4 Hz), 2.40 (3H, s), 3.72 (1.5H, s), 4.08 (2H, t, J=6.4 Hz), 4.17 (1H, q, J=7.1 Hz), 7.17 (2H, d, J=8.2 Hz), 7.38 (2H, d, J=8.0 Hz), 7.41–7.46 (1H, m), 7.60–7.66 (2H, m), 11.83 (0.5H, s), 11.91 (0.5H, s).

Reference Example 17

To ethyl (methyl) 7-bromo-5-hydroxy-1-tosyl-2,3-dihydro-1H-1-benzazepine-4-carboxylate (mixture) (32.4 g) were added acetic acid (200 ml) and concentrated sulfuric acid (120 ml), and the mixture was stirred at 80° C. for 2.5 hours. The mixture was poured into ice-water, and the mixture was neutralized with sodium hydroxide solution and extracted with ethyl acetate. The organic layer was washed with water and saturated brine and dried with anhydrous magnesium sulfate, and the solvent was evaporated. The residue was purified with silica gel column chromatography (hexane/ethyl acetate) to give 7-bromo-1,2,3,4-tetrahydro-1-benzazepin-5-one (8.55 g) as pale yellow crystals.

mp 99–101° C.

$^1$H NMR (δ ppm, CDCl$_3$) 2.18 (2H, quint, J=7.1 Hz), 2.82 (2H, t, J=7.2 Hz), 3.25 (2H, t, J=6.6 Hz), 4.65 (1H, br), 6.65 (1H, d, J=8.6 Hz), 7.20 (1H, dd, J=2.2, 8.6 Hz), 7.82 (1H, d, J=2.2 Hz).

IR (KBr) ν: 3364, 2955, 1661 cm$^{-1}$.

Reference Example 18

In THF (200 ml) were dissolved 7-bromo-1,2,3,4-tetrahydro-1-benzazepin-5-one (7 g) and dimethylaminopyridine (22 g). To the solution was added di-t-butyl dicarbonate (60 g), and the mixture was refluxed for 1.5 hours. The solvent was evaporated. To the residue was added water, and the mixture was extracted with ethyl acetate. The organic layer was washed with 1M citric acid solution, water and saturated brine, and dried with anhydrous magnesium sulfate, and the solvent was evaporated. The residue was purified with silica gel column chromatography (ethyl acetate/hexane) to give a mixture of 7-bromo-1-(t-butoxycarbonyl)-1,2,3,4-tetrahydro-1-benzazepin-5-one and 7-bromo-1-(t-butoxycarbonyl)-5-(t-butoxycarbonyloxy)-2,3-dihydro-1H-1-benzazepine (24.6 g) as yellow oil.

$^1$H NMR (δ ppm, CDCl$_3$) 1.43 (4.5H, s), 1.49 (9H, s), 2.15 (1H, quint, J=6.8 Hz), 2.76 (2H, t, J=6.8 Hz), 3.73 (2H, t, J=6.8 Hz), 5.97 (0.5H, t, J=4.6 Hz), 7.17 (0.5H, br), 7.35 (1H, br), 7.54–7.59 (1H, m), 7.98 (0.5H, d, J=2.6 Hz).

Reference Example 19

In dimethyl carbonate (400 ml) was dissolved a mixture (3.3 g) of 7-bromo-1-(t-butoxycarbonyl)-1,2,3,4-tetrahydro-1-benzazepin-5-one and 7-bromo-1-(t-butoxycarbonyl)-5-(t-butoxycarbonyloxy)-2,3-dihydro-1H-1-benzazepine. To the solution was added sodium methoxide (23.0 g), and the mixture was refluxed under nitrogen atmosphere for 2.5 hours and poured into ice-water. To the mixture was added 1M citric acid solution, and the mixture was extracted with ethyl acetate. The organic layer was washed with water and saturated brine and dried with anhydrous magnesium sulfate, and the solvent was evaporated. The residue was purified with silica gel column chromatography (ethyl acetate/hexane) to give methyl 7-bromo-1-(t-butoxycarbonyl)-1,2,3,4-tetrahydro-1-benzazepin-5-one-4-carboxylate (23.8 g) as yellow oil.

$^1$H NMR (δ ppm, CDCl$_3$) 1.36 (4.5H, s), 1.52 (4.5H, s), 2.43–2.55 (2H, m), 3.39–3.54 (0.5H, m), 3.72 (1.5H, s), 3.84 (1.5H, s), 3.89–4.04 (2H, m), 7.12 (0.5H, br), 7.42 (0.5H, br), 7.51 (0.5H, dd, J=2.2, 8.4 Hz), 7.58 (0.5H, dd, J=2.4, 8.6 Hz), 7.82 (0.5H, d, J=2.2 Hz), 8.00 (0.5H, d, J=2.2 Hz).

Reference Example 20

In THF (150 ml) was dissolved methyl 7-bromo-1-(t-butoxycarbonyl)-1,2,3,4-tetrahydro-1-benzazepin-5-one-4-carboxylate (7.2 g). To the solution was added sodium borohydride (0.7 g) at −40° C., and then was added dropwise methanol (15 ml). The mixture was stirred at −15° C. for 1 hour. To the mixture was added 1M citric acid, and the mixture was extracted with ethyl acetate. The organic layer was washed with water and saturated brine and dried with anhydrous magnesium sulfate, and the solvent was evaporated. The residue was dissolved in THF (150 ml), and to the solution was added triethylamine (7.5 ml). To the mixture was added dropwise, under ice-cooling, methanesulfonyl chloride (2.1 ml). Under nitrogen atmosphere, the mixture was stirred at room temperature for 1.5 hours, and to the mixture was added dropwise DBU (13.5 ml) at room temperature. The mixture was stirred at 90° C. for 10 minutes, and the solvent was evaporated. To the residue was added water, and the mixture was extracted with ethyl acetate. The organic layer was washed with water and saturated brine and dried with anhydrous magnesium sulfate, and the solvent was evaporated. The residue was purified with silica gel column chromatography (ethyl acetate/hexane) to give methyl 7-bromo-1-(t-butoxycarbonyl)-2,3-dihydro-1H-1-benzazepine-4-carboxylate (5.18 g) as colorless crystals.

mp 144–145° C.

$^1$H NMR (δ ppm, CDCl$_3$) 1.47 (9H, s), 2.89 (2H, t, J=4.8 Hz), 3.61 (2H, br), 3.83 (3H, s), 7.27 (1H, br), 7.39 (1H, dd, J=1.8, 8.4 Hz), 7.54–7.55 (2H, m).

IR (KBr) ν: 2978, 1709 cm$^{-1}$.

Anal. Calcd. for $C_{17}H_{20}BrNO_4$: C, 53.42; H, 5.27; N, 3.66. Found C, 53.58; H, 5.12; N, 3.52.

Reference Example 21

In ethyl acetate (50 ml) was dissolved methyl 7-bromo-1-(t-butoxycarbonyl)-2,3-dihydro-1H-1-benzazepine-4-carboxylate (1.5 g). To the solution was added 6N hydrochloric acid (2 ml), and the mixture was heated to stir at 80° C. for 2 hours, neutralized with 1N sodium hydroxide solution and extracted with ethyl acetate. The organic layer was washed with water and saturated brine and dried with anhydrous magnesium sulfate. The solvent was evaporated to give methyl 7-bromo-2,3-dihydro-1H-1-benzazepine-4-carboxylate (1.0 g) as yellow crystals.

mp 143–145° C.

$^1$H NMR ($\delta$ ppm, $CDCl_3$) 2.85 (2H, t, J=4.8 Hz), 3.35 (2H, t, J=4.8 Hz), 3.80 (3H, s), 4.62 (1H, br), 6.49 (1H, d, J=8.4 Hz), 7.15 (1H, dd, J=2.4, 8.4 Hz), 7.37 (1H, d, J=2.4 Hz), 7.53 (1H, s).

IR (KBr) $\nu$: 3384, 2949, 1694 $cm^{-1}$.

Anal. Calcd. for $C_{12}H_{12}BrNO_2$: C, 51.09; H, 4.29; N, 4.96. Found C, 51.17; H, 4.32; N, 4.97.

Reference Example 22

To anhydrous acetic acid (0.84 ml) was added dropwise formic acid (0.4 ml), under ice-cooling, and the mixture was stirred, under nitrogen atmosphere, at 50° C. for 2 hours. To the mixture was added THF (5 ml), and to the mixture was added dropwise, under ice-cooling, a solution of methyl 7-bromo-2,3-dihydro-1H-1-benzazepine-4-carboxylate (1.0 g) in THF (15 ml). The mixture was stirred at room temperature overnight. The solvent was evaporated, and to the residue was added water. The mixture was extracted with ethyl acetate. The organic layer was washed with sodium hydrogen carbonate solution, water and saturated brine and dried with anhydrous magnesium sulfate. The solvent was evaporated to give methyl 7-bromo-1-formyl-2,3-dihydro-1H-1-benzazepine-4-carboxylate (1.07 g) as colorless crystals.

mp 175–176° C.

$^1$H NMR ($\delta$ ppm, $CDCl_3$) 2.93 (2H, t, J=5.3 Hz), 3.80 (2H, t, J=5.3 Hz), 3.83 (3H, s), 7.01 (1H, d, J=8.5 Hz), 7.50 (1H, dd, J=2.2, 8.5 Hz), 7.58 (1H, s), 7.65 (1H, d, J=2.2 Hz), 8.46 (1H, s).

IR (KBr) $\nu$: 2951, 1713, 1680 $cm^{-1}$.

Anal. Calcd. for $C_{13}H_{12}BrNO_3$: C, 50.34; H, 3.90; N, 4.52. Found C, 50.43; H, 3.75; N, 4.45.

Reference Example 23

To a mixture of methyl 7-bromo-1-formyl-2,3-dihydro-1H-1-benzazepine-4-carboxylate (3.51 g), 4-morpholinophenyl borate (3.51 g) and potassium carbonate (3.75 g) was added a mixture of water (20 ml), ethanol (20 ml) and toluene (100 ml), and the mixture was stirred under argon atmosphere at room temperature for 40 minutes. To the mixture was added tetrakis(triphenylphosphine) palladium (0.52 g), and the mixture was refluxed under argon atmosphere for 12 hours and extracted with ethyl acetate. The organic layer was washed with water and saturated brine, and dried with anhydrous magnesium sulfate. The solvent was evaporated, and the residue was purified with silica gel column chromatography (ethyl acetate/hexane) to give methyl 1-formyl-7-(4-morpholinophenyl)-2,3-dihydro-1H-1-benzazepine-4-carboxylate (3.64 g) as pale yellow crystals.

mp 178–181° C.

$^1$H NMR ($\delta$ ppm, $CDCl_3$) 2.95 (2H, t, J=5.1 Hz), 3.23 (4H, t, J=4.9 Hz), 3.82–3.92 (6H, m), 3.84 (3H, s), 6.97–7.04 (2H, m), 7.17 (1H, d, J=8.2 Hz), 7.45–7.60 (3H, m), 7.69 (1H, d, J=2.2 Hz), 7.76 (1H, s), 8.53 (1H, s).

IR (KBr) $\nu$: 2951, 2830, 1709, 1674 $cm^{-1}$.

Reference Example 24

In methanol (250 ml) and THF (250 ml) was dissolved methyl 1-formyl-7-(4-morpholinophenyl)-2,3-dihydro-1H-1-benzazepine-4-carboxylate (3.54 g). To the solution was added 1N sodium hydroxide solution (90 ml), and the mixture was stirred at room temperature overnight and concentrated. To the mixture was added water, and the mixture was neutralized with 1N hydrochloric acid and extracted with ethyl acetate. The organic layer was dried with anhydrous magnesium sulfate, and the solvent was evaporated to give 1-formyl-7-(4-morpholinophenyl)-2,3-dihydro-1H-1-benzazepine-4-carboxylic acid (3.30 g) as colorless crystals.

mp 247–257° C. (dec.).

$^1$H NMR ($\delta$ ppm, DMSO-$d_6$) 2.75 (2H, t-like), 3.14–3.19 (4H, m), 3.70–3.78 (6H, m), 7.03 (2H, d, J=8.8 Hz), 7.36 (1H, d, J=8.4 Hz), 7.62–7.71 (4H, m), 7.87 (1H, s), 8.51 (1H, s).

IR (KBr) $\nu$: 1671 $cm^{-1}$.

Anal. Calcd. for $C_{22}H_{22}N_2O_4 \cdot 0.7H_2O$: C, 67.57; H, 6.03; N, 7.16. Found C, 67.48; H, 5.74; N, 6.98.

Reference Example 25

A mixture of methyl 7-bromo-1-(t-butoxycarbonyl)-2,3-dihydro-1H-1-benzazepine-4-carboxylate (2.0 g), 4-morpholinophenyl borate (1.2 g), and 1M potassium carbonate solution (15 ml), ethanol (15 ml) and toluene (100 ml) was stirred under argon atmosphere at room temperature for 20 minutes. To the mixture was added tetrakis (triphenylphosphine)palladium (0.24 g), and the mixture was refluxed under argon atmosphere for 12 hours and extracted with ethyl acetate. The organic layer was washed with water and saturated brine, and dried with anhydrous magnesium sulfate. The solvent was evaporated under reduced pressure, and the residue was purified with silica gel column chromatography (ethyl acetate/hexane) to give methyl 1-(t-butoxycarbonyl)-7-(4-morpholinophenyl)-2,3-dihydro-1H-1-benzazepine-4-carboxylate (3.64 g) as pale yellow crystals.

mp 183–185° C.

$^1$H-NMR ($\delta$ ppm, $CDCl_3$) 1.49 (9H, s), 2.90 (2H, t, J=5.0 Hz), 3.19–3.24 (4H, m), 3.69 (2H, br), 3.83 (3H, s), 3.87–3.91 (4H, m), 6.98 (2H, d, J=9.0 Hz), 7.48 (2H, br), 7.52 (2H, d, J=9.0 Hz), 7.58 (1H, s), 7.73 (1H, s).

IR (KBr) $\nu$: 2973, 1705 $cm^{-1}$.

Anal. Calcd. for $C_{27}H_{32}N_2O_5$: C, 69.81; H, 6.94; N, 6.03. Found C, 69.57; H, 6.76; N, 5.76.

Reference Example 26

In ethyl acetate (100 ml) was dissolved methyl 1-(t-butoxycarbonyl)-7-(4-morpholinophenyl)-2,3-dihydro-1H-1-benzazepine-4-carboxylate (2.0 g). To the solution was added 6N hydrochloric acid (40 ml), and the mixture was stirred at 80° C. for 30 minutes, neutralized with 1N sodium hydroxide solution and extracted with ethyl acetate. The organic layer was washed with water and saturated brine and dried with anhydrous magnesium sulfate, and the solvent was evaporated to give 7-(4-morpholinophenyl)-2,3-dihydro-1H-1-benzazepine-4-carboxylate (1.46 g) as yellow crystals.

mp 175–182° C. (dec.).

$^1$H-NMR (δ ppm, CDCl$_3$) 2.89 (2H, t, J=4.5 Hz), 3.17–3.22 (4H, m), 3.41 (2H, t, J=4.5 Hz), 3.81 (3H, s), 3.87–3.91 (4H, m), 6.67 (1H, d, J=8.3 Hz), 6.97 (2H, d, J=8.8 Hz), 7.33 (1H, dd, J=2.0, 8.3 Hz), 7.45–7.50 (3H, m), 7.73 (1H, s).

IR (KBr) ν: 3378, 2953, 1694 cm$^{-1}$.

Anal. Calcd. for C$_{22}$H$_{24}$N$_2$O$_3$·0.2H$_2$O: C, 71.80; H, 6.68; N, 7.61. Found C, 71.51; H, 6.72; N, 7.47.

Reference Example 27

To anhydrous acetic acid (0.2 ml) was added dropwise formic acid (0.1 ml), under ice-cooling, and the mixture was heated to stir under nitrogen atmosphere at 50° C. for 2 hours. To the mixture was added THF (5 ml), and then to the mixture was added dropwise, under ice-cooling, a solution of methyl 7-(4-morpholinophenyl)-2,3-dihydro-1H-1-benzazepine-4-carboxylate (0.3 g) in THF (15 ml). The mixture was stirred at room temperature for 1.5 hours. The solvent was evaporated, and to the residue was added water. The mixture was extracted with ethyl acetate. The organic layer was washed with sodium hydrogen carbonate solution, water and saturated brine, and dried with anhydrous magnesium sulfate, and the solvent was evaporated to give methyl 1-formyl-7-(4-morpholinophenyl)-2,3-dihydro-1H-1-benzazepine-4-carboxylate (0.3 g) as pale yellow crystals.

Reference Example 28

A mixture of methyl 7-bromo-1-(t-butoxycarbonyl)-2,3-dihydro-1H-1-benzazepine-4-carboxylate (1.0 g), 4-ethoxyphenyl borate (0.5 g), 1M potassium carbonate solution (8 ml), ethanol (8 ml) and toluene (50 ml) was stirred under argon atmosphere at room temperature for 30 minutes. To the mixture was added tetrakis (triphenylphosphine)palladium (0.12 g), and the mixture was refluxed overnight under argon atmosphere and extracted with ethyl acetate. The organic layer was washed with water and saturated brine and dried with anhydrous magnesium sulfate, and the solvent was evaporated under reduced pressure. The residue was purified with silica gel column chromatography (ethyl acetate/hexane) to give methyl 1-(t-butoxycarbonyl)-7-(4-morpholinophenyl)-2,3-dihydro-1H-1-benzazepine-4-carboxylate (1.1 g) as colorless crystals.

$^1$H-NMR (δ ppm, CDCl$_3$) 1.38–1.49 (12H, m), 2.91 (2H, t, J=5.3 Hz), 3.68 (2H, br), 3.83 (3H, s), 4.09 (2H, q, J=7.0 Hz), 6.97 (2H, d, J=8.8 Hz), 7.47–7.55 (4H, m), 7.58 (1H, s), 7.74 (1H, 4).

IR (KBr) ν: 2980, 1705 cm$^{-1}$.

Reference Example 29

In ethyl acetate (50 ml) was dissolved methyl 1-(t-butoxycarbonyl)-7-(4-ethoxyphenyl)-2,3-dihydro-1H-1-benzazepine-4-carboxylate (1.1 g). To the solution was added 6N hydrochloric acid (10 ml) and the mixture was stirred at 80° C. for 40 minutes, neutralized with 1N sodium hydroxide solution and extracted with ethyl acetate. The organic layer was washed with water and saturated brine and dried with anhydrous magnesium sulfate, and the solvent was evaporated to give methyl 7-(4-ethoxyphenyl)-2,3-dihydro-1H-1-benzazepine-4-carboxylate (0.78 g) as yellow crystals.

mp 157–158° C.

$^1$H-NMR (δ ppm, CDCl$_3$) 1.43 (3H, t, J=7.0 Hz), 2.88 (2H, t, J=4.6 Hz), 3.40 (2H, t, J=4.6 Hz), 3.81 (3H, s), 4.07 (2H, q, J=7.0 Hz), 6.66 (1H, d, J=8.3 Hz), 6.94 (2H, d, J=9.2 Hz), 7.31 (1H, dd, J=2.2, 8.3 Hz), 7.41–7.47 (3H, m), 7.73 (1H, s).

IR (KBr) ν: 3380, 2980, 2948, 1699 cm$^{-1}$.

Reference Example 30

To anhydrous acetic acid (0.18 ml) was added dropwise formic acid (0.09 ml) under ice-cooling, and the mixture was stirred under nitrogen atmosphere at 50° C. for 2 hours. To the mixture was added THF (2 ml) and then was added dropwise, under ice-cooling a solution of methyl 7-(4-ethoxyphenyl)-2,3-dihydro-1H-1-benzazepine-4-carboxylate (0.25 g) in THF (15 ml), and the mixture was stirred at room temperature for 4 hours. The solvent was evaporated, and to the residue was added water. The mixture was extracted with ethyl acetate. The organic layer was washed with sodium hydrogen carbonate solution, water and saturated brine, and dried with anhydrous magnesium sulfate, and the solvent was evaporated to give methyl 7-(4-ethoxyphenyl)-1-formyl-2,3-dihydro-1H-1-benzazepine-4-carboxylate (0.24 g) as yellow crystals.

mp 133–135° C.

$^1$H-NMR (δ ppm, CDCl$_3$) 1.45 (3H, t, J=6.9 Hz), 2.95 (2H, t, J=4.9 Hz), 3.82–3.88 (5H, m), 4.09 (2H, q, J=6.9 Hz), 6.99 (2H, d, J=8.8 Hz), 7.17 (1H, d, J=8.0 Hz), 7.49–7.58 (3H, m), 7.68 (1H, d, J=2.2 Hz), 7.75 (1H, s), 8.53 (1H, s).

IR (KBr) ν: 2980, 2948, 1709, 1678 cm$^{-1}$.

Reference Example 31

In methanol (25 ml) and THF (30 ml) was dissolved methyl 7-(4-ethoxyphenyl)-1-formyl-2,3-dihydro-1H-1-benzazepine-4-carboxylate (0.24 g). To the solution was added 1N sodium hydroxide solution (5 ml) and the mixture was stirred at room temperature overnight and concentrated. To the residue was added water, and the mixture was neutralized with 1N hydrochloric acid and extracted with ethyl acetate. The organic layer was washed with water and saturated brine and dried with anhydrous magnesium sulfate, and the solvent was evaporated to give 7-(4-ethoxyphenyl)-1-formyl-2,3-dihydro-1H-1-benzazepine-4-carboxylic acid (0.23 g) as pale yellow crystals.

mp 224–226° C.

$^1$H-NMR (δ ppm, CDCl$_3$) 1.46 (3H, t, J=6.9 Hz), 2.97 (2H, t, J=5.1 Hz), 3.88 (2H, t, J=5.1 Hz), 4.10 (2H, q, J=6.9 Hz), 7.00 (2H, d, J=8.8 Hz), 7.20 (1H, d, J=8.1 Hz), 7.53 (2H, d, J=8.8 Hz), 7.59 (1H, dd, J=2.0, 8.1 Hz), 7.70 (1H, d, J=2.0 Hz), 7.86 (1H, s), 8.56 (1H, s).

IR (KBr) ν: 2982, 1669, 1682 cm$^{-1}$.

Anal. Calcd. for C$_{20}$H$_{19}$NO$_4$·0.4H$_2$O: C, 69.71; H, 5.79; N, 4.06. Found C, 69.80; H, 6.00; N, 3.80.

Reference Example 32

A mixture of methyl 7-bromo-1-(t-butoxycarbonyl)-2,3-dihydro-1H-1-benzazepine-4-carboxylate (1.0 g), 4-(2-ethoxyethoxy)phenyl borate (0.6 g), 1M potassium carbonate solution (8 ml), ethanol (8 ml) and toluene (50 ml) was stirred under argon atmosphere at room temperature for 20 minutes. To the mixture was added tetrakis (triphenylphosphine)palladium (0.12 g), and the mixture was refluxed overnight under argon atmosphere and extracted with ethyl acetate. The organic layer was washed with water and saturated brine and dried with anhydrous magnesium sulfate, and the solvent was evaporated under reduced pressure. The residue was purified with silica gel column chromatography (ethyl acetate/hexane) to give methyl 1-(t-butoxycarbonyl)-7-[4-12-ethoxyethoxy)phenyl]-2,3-dihydro-1H-1-benzazepine-4-carboxylate (1.1 g) as colorless oil.

$^1$H-NMR (δ ppm, CDCl$_3$) 1.26 (3H, t, J=7.1 Hz), 1.49 (9H, s), 2.91 (2H, t, J=4.8 Hz), 3.63 (2H, q, J=7.1 Hz), 3.68 (2H, br), 3.83 (2H, t, J=4.9 Hz), 3.83 (3H, s), 4.17 (2H, t, J=4.9 Hz), 7.00 (2H, d, J=8.8 Hz), 7.47–7.53 (4H, m), 7.58 (1H, s), 7.73 (1H, s).

IR (neat) ν: 2976, 1705 cm$^{-1}$.

Reference Example 33

In ethyl acetate (50 ml) was dissolved methyl 1-(t-butoxycarbonyl)-7-[4-(2-ethoxyethoxy)phenyl]-2,3-dihydro-1H-1-benzazepine-4-carboxylate (1.1 g). To the solution was added 6N hydrochloric acid (20 ml), and the mixture was stirred at 80° C. for 45 minutes, neutralized with 1N sodium hydroxide solution and was extracted with ethyl acetate. The organic layer was washed with water and saturated brine and dried with anhydrous magnesium sulfate, and the solvent was evaporated to give methyl 7-[4-(2-ethoxyethoxy)phenyl]-2,3-dihydro-1H-1-benzazepine-4-carboxylate (0.7 g) as yellow crystals.

mp 102–108° C.

$^1$H-NMR (δ ppm, CDCl$_3$) 1.26 (3H, t, J=7.0 Hz), 2.88 (2H, t, J=4.7 Hz), 3.40 (2H, t, J=4.7 Hz), 3.62 (2H, q, J=7.0 Hz), 3.81 (3H, s), 3.82 (2H, t, J=5.0 Hz), 4.16 (2H, t, J=5.0 Hz), 6.67 (1H, d, J=8.5 Hz), 6.97 (2H, d, J=8.8 Hz), 7.31 (1H, dd, J=2.2, 8.5 Hz), 7.42–7.47 (3H, m), 7.73 (1H, s).

IR (KBr) ν: 3370, 2976, 2946, 2870, 1698 cm$^{-1}$.

Anal. Calcd. for C$_{22}$H$_{25}$NO$_4$: C, 71.91; H, 6.86; N, 3.81. Found C, 71.88; H, 6.79; N, 3.78.

Reference Example 34

To anhydrous acetic acid (0.25 ml) was added formic acid (0.13 ml) under ice-cooling, and the mixture was stirred under nitrogen atmosphere at 50° C. for 2 hours. To the mixture was added THF (2 ml) and then was added dropwise, under ice-cooling, a solution of methyl 7-[4-(2-ethoxyethoxy)phenyl]-2,3-dihydro-1H-1-benzazepine-4-carboxylate (0.25 g) in THF (10 ml), and the mixture was stirred at room temperature overnight. The solvent was evaporated, and to the residue was added water. The mixture was extracted with ethyl acetate. The organic layer was washed with sodium hydrogen carbonate solution, water and saturated brine, and dried with anhydrous magnesium sulfate, and the solvent was evaporated to give methyl 7-[4-(2-ethoxyethoxy)phenyl]-1-formyl-2,3-dihydro-1H-1-benzazepine-4-carboxylate (0.2 g) as colorless crystals.

mp 138–142° C.

$^1$H-NMR (δ ppm, CDCl$_3$) 1.27 (3H, t, J=6.9 Hz), 2.95 (2H, t, J=5.1 Hz), 3.63 (2H, q, J=6.9 Hz), 3.81–3.88 (7H, m), 4.19 (2H, t, J=5.0 Hz), 7.03 (2H, d, J=8.8 Hz), 7.17 (1H, d, J=8.2 Hz), 7.48–7.59 (3H, m), 7.68 (1H, d, J=2.2 Hz), 7.75 (1H, s).

IR (KBr) ν: 2872, 1709, 1678 cm$^{-1}$.

Anal. Calcd. for C$_{23}$H$_{23}$NO$_5$: C, 69.86; H, 6.37; N, 3.54. Found C, 69.88; H, 6.43; N, 3.49.

Reference Example 35

In methanol (25 ml) and THF (25 ml) was dissolved methyl 7-[4-(2-ethoxyethoxy)phenyl]-1-formyl-2,3-dihydro-1H-1-benzazepine-4-carboxylate (0.2 g). To the solution was added 1N sodium hydroxide solution (5 ml), and the mixture was stirred at room temperature overnight and concentrated. To the residue was added water, and the mixture was neutralized with 1N hydrochloric acid and extracted with ethyl acetate. The organic layer was washed with water and saturated brine and dried with anhydrous magnesium sulfate, and the solvent was evaporated to give 7-[4-(2-ethoxyethoxy)phenyl]-1-formyl-2,3-dihydro-1H-1-benzazepine-4-carboxylic acid (0.19 g) as colorless crystals.

mp 190–192° C.

$^1$H-NMR (δ ppm, CDCl$_3$) 1.27 (3H, t, J=7.0 Hz), 2.97 (2H, t, J=4.4 Hz), 3.64 (2H, q, J=7.0 Hz), 3.81–3.90 (4H, m), 4.19 (2H, t, J=5.0 Hz), 7.03 (2H, d, J=8.8 Hz), 7.19 (1H, d, J=8.2 Hz), 7.52 (2H, d, J=8.8 Hz), 7.59 (1H, dd, J=2.2, 8.2 Hz), 7.69 (1H, d, J=2.2 Hz), 7.85 (1H, s), 8.55 (1H, s).

IR (KBr) ν: 2936, 2872, 1682, 1671 cm$^{-1}$.

Anal. Calcd. for C$_{22}$H$_{23}$NO$_5$: C, 69.28; H, 6.08; N, 3.67. Found C, 69.00; H, 6.31; N, 3.56.

Reference Example 36

A mixture of methyl 7-bromo-1-formyl-2,3-dihydro-1H-1-benzazepine-4-carboxylate (20 g), 4-(2-ethoxyethoxy)phenyl borate (14.9 g), 1M potassium carbonate solution (130 ml), ethanol (130 ml) and toluene (1000 ml) was stirred under argon atmosphere at room temperature for 30 minutes. To the mixture was added tetrakis(triphenylphosphine) palladium (3 g), and the mixture was refluxed under argon atmosphere for 15 hours and extracted with ethyl acetate. The organic layer was washed with water and saturated brine and dried with anhydrous magnesium sulfate, and the solvent was evaporated under reduced pressure. The residue was purified with silica gel column chromatography (ethyl acetate/hexane) to give methyl 7-[4-(2-ethoxyethoxy)phenyl]-1-formyl-2,3-dihydro-1H-1-benzazepine-4-carboxylate (25.2 g) as colorless crystals.

Reference Example 37

A mixture of methyl 7-bromo-1-(t-butoxycarbonyl)-2,3-dihydro-1H-1-benzazepine-4-carboxylate (1.0 g), 4-(3-ethoxypropoxy)phenyl borate (0.62 g), 1M potassium carbonate solution (8 ml), ethanol (8 ml) and toluene (50 ml) was stirred under argon atmosphere at room temperature for 30 minutes. To the mixture was added tetrakis(triphenylphosphine)palladium (0.12 g), and the mixture was refluxed overnight under argon atmosphere and extracted with ethyl acetate. The organic layer was washed with water and saturated brine and dried with anhydrous magnesium sulfate, and the solvent was evaporated under reduced pressure. The residue was purified with silica gel column chromatography (ethyl acetate/hexane) to give methyl 1-(t-butoxycarbonyl)-7-[4-(3-ethoxypropoxy)phenyl]-2,3-dihydro-1H-1-benzazepine-4-carboxylate (1.2 g) as colorless crystals.

mp 125–128° C.

$^1$H-NMR (δ ppm, CDCl$_3$) 1.21 (3H, t, J=7.0 Hz), 1.49 (9H, s), 2.02–2.14 (2H, m), 2.91 (2H, t, J=4.2 Hz), 3.51 (2H, q, J=7.0 Hz), 3.62 (2H, t, J=6.3 Hz), 3.65 (2H, br), 3.83 (3H, s), 4.12 (2H, t, J=6.2 Hz), 6.98 (2H, d, J=8.8 Hz), 7.40–7.55 (4H, m), 7.57 (1H, s), 7.73 (1H, s).

IR (KBr) ν: 2976, 2948, 2872, 1705 cm$^{-1}$.

Reference Example 38

In ethyl acetate (50 ml) was dissolved methyl 1-(t-butoxycarbonyl)-7-[4-(3-ethoxypropoxy)phenyl]-2,3- dihydro-1H-1-benzazepine-4-carboxylate (1.2 g). To the solution was added 6N hydrochloric acid (10 ml), and the mixture was stirred at 80° C. for 30 minutes, neutralized with 1N sodium hydroxide solution and extracted with ethyl acetate. The organic layer was washed with water and saturated brine and dried with anhydrous magnesium sulfate, and the solvent was evaporated to give methyl 7-[4-(3-ethoxypropoxy)phenyl]-2,3-dihydro-1H-1-benzazepine-4-carboxylate (0.8 g) as yellow crystals.

mp 99–102° C.

$^1$H-NMR (δ ppm, CDCl$_3$) 1.21 (3H, t, J=7.0 Hz), 2.01–2.13 (2H, m), 2.88 (2H, t, J=4.7 Hz), 3.41 (2H, t, J=4.7 Hz), 3.51 (2H, q, J=7.0 Hz), 3.62 (2H, t, J=6.2 Hz), 3.81 (3H, s), 4.10 (2H, t, J=6.2 Hz), 4.78 (1H, br), 6.67 (1H, d, J=8.5 Hz), 6.95 (2H, d, J=8.8 Hz), 7.32 (1H, dd, J=2.2, 8.5 Hz), 7.43–7.47 (3H, m), 7.73 (1H, s).

IR (KBr) ν: 3374, 2949, 2868, 1699 cm$^{-1}$.

Anal. Calcd. for C$_{23}$H$_{27}$NO$_4$: C, 72.42; H, 7.13; N, 3.67. Found C, 72.24; H, 7.04; N, 3.67.

Reference Example 39

To anhydrous acetic acid (0.22 ml) was added dropwise formic acid (0.11 ml) under ice-cooling, and the mixture was stirred under nitrogen atmosphere at 50° C. for 2 hours. To the mixture was added THF (2 ml) and then was added dropwise, under ice-cooling, a solution of methyl 7-[4-(3-ethoxypropoxy)phenyl]-2,3-dihydro-1H-1-benzazepine-4-carboxylate (0.35 g) in THF (15 ml), and the mixture was stirred at room temperature overnight. The solvent was evaporated, and to the residue was added water. The mixture was extracted with ethyl acetate. The organic layer was washed with sodium hydrogen carbonate solution, water and saturated brine, and dried with anhydrous magnesium sulfate, and the solvent was evaporated to give methyl 7-[4-(3-ethoxypropoxy) phenyl]-1-formyl-2,3-dihydro-1H-1-benzazepine-4-carboxylate (0.36 g) as colorless crystals.

mp 112–113° C.

$^1$H-NMR (δ ppm, CDCl$_3$) 1.22 (3H, t, J=7.0 Hz), 2.03–2.15 (2H, m), 2.95 (2H, t, J=4.8 Hz), 3.52 (2H, q, J=7.0 Hz), 3.63 (2H, t, J=6.3 Hz), 3.84 (3H, s), 3.84 (2H, t, J=4.8 Hz), 4.13 (2H, t, J=6.3 Hz), 7.01 (2H, d, J=8.8 Hz), 7.17 (1H, d, J=8.2 Hz), 7.52 (2H, d, J=8.8 Hz), 7.56 (1H, dd, J=2.2, 8.8 Hz), 7.68 (1H, d, J=2.2 Hz), 7.75 (1H, s), 8.53 (1H, s).

IR (KBr) ν: 2951, 2872, 1709, 1678 cm$^{-1}$.

Anal. Calcd. for C$_{24}$H$_{27}$NO$_5$·0.2H$_2$O: C, 69.78; H, 6.69; N, 3.39. Found C, 69.98; H, 6.79; N, 3.28.

Reference Example 40

In methanol (25 ml) and THF (25 ml) was dissolved methyl 7-[4-(3-ethoxypropoxy)phenyl]-1-formyl-2,3-dihydro-1H-1-benzazepine-4-carboxylate (0.31 g). To the solution was added 1N sodium hydroxide solution (8 ml), and the mixture was stirred at 50° C. for 1.5 hours and concentrated. To the residue was added water, and the mixture was neutralized with 1N hydrochloric acid and extracted with ethyl acetate. The organic layer was washed with water and saturated brine and dried with anhydrous magnesium sulfate, and the solvent was evaporated to give 7-[4-(3-ethoxypropoxy)phenyl]-1-formyl-2,3-dihydro-1H-1-benzazepine-4-carboxylic acid (0.3 g) as colorless crystals.

mp 179–181° C.

$^1$H-NMR (δ ppm, CDCl$_3$) 1.22 (3H, t, J=7.1 Hz), 2.03–2.15 (2H, m), 2.97 (2H, t, J=5.5 Hz), 3.52 (2H, q, J=7.1 Hz), 3.63 (2H, t, J=6.3 Hz), 3.88 (2H, t, J=5.5 Hz), 4.13 (2H, t, J=6.0 Hz), 7.01 (2H, d, J=8.8 Hz), 7.19 (1H, d, J=8.1 Hz), 7.52 (2H, d, J=8.8 Hz), 7.58 (1H, dd, J=2.0, 8.1 Hz), 7.69 (1H, d, J=2.0 Hz), 7.85 (1H, s), 8.55 (1H, s).

IR (KBr) ν: 3036, 2870, 1682 cm$^{-1}$.

Anal. Calcd. for C$_{23}$H$_{25}$NO$_5$: C, 69.86; H, 6.37; N, 3;54. Found C, 69.64; H, 6.32; N, 3.55.

Reference Example 41

A mixture of methyl 7-bromo-1-(t-butoxycarbonyl)-2,3-dihydro-1H-1-benzazepine-4-carboxylate (1.0 g), 3,4-diethoxyphenyl borate (0.63 g), 1M potassium carbonate solution (8 ml), ethanol (8 ml) and toluene (50 ml) was stirred under argon atmosphere at room temperature for 30 minutes. To the mixture was added tetrakis (triphenylphosphine)palladium (0.12 g), and the mixture was refluxed overnight under argon atmosphere and extracted with ethyl acetate. The organic layer was washed with water and saturated brine and dried with anhydrous magnesium sulfate, and the solvent was evaporated under reduced pressure. The residue was purified with silica gel column chromatography (ethyl acetate/hexane) to give methyl 1-benzazepine-4-carboxylate (1.3 g) as colorless crystals.

mp 168–173° C.

$^1$H-NMR (δ ppm, CDCl$_3$) 1.45–1.53 (15H, m), 2.90 (2H, t, J=5.0 Hz), 3.68 (2H, br), 3.83 (3H, s), 4.09–4.23 (4H, m), 6.95 (1H, d, J=9.2 Hz), 7.09–7.14 (2H, m), 7.40–7.52 (2H, m), 7.57 (1H, s), 7.74 (1H, s).

IR (KBr) ν: 2980, 1705 cm$^{-1}$.

Anal. Calcd. for C$_{27}$H$_{33}$NO$_6$: C, 69.36; H, 7.11; N, 3.00. Found C, 69.17; H, 7.11; N, 2.93.

Reference Example 42

In ethyl acetate (50 ml) was dissolved methyl 1-(t-butoxycarbonyl)-7-(3,4-diethoxyphenyl)-2,3-dihydro-1H-1-benzazepine-4-carboxylate (1.3 g). To the solution was added 6N hydrochloric acid (10 ml), and the mixture was stirred at 80° C. for 1 hour, neutralized with 1N sodium hydroxide solution and extracted with ethyl acetate. The organic layer was washed with water and saturated brine and dried with anhydrous magnesium sulfate, and the solvent was evaporated to give methyl 7-(3,4-diethoxyphenyl)-2,3-dihydro-1H-1-benzazepine-4-carboxylate (0.7 g) as yellow crystals.

mp 159–164° C.

$^1$H-NMR (δ ppm, CDCl$_3$) 1.43–1.52 (6H, m), 2.89 (2H, t, J=4.8 Hz), 3.41 (2H, t, J=4.8 Hz), 3.81 (3H, s), 4.08–4.22 (4H, m), 6.67 (1H, d, J=8.4 Hz), 6.92 (1H, d, J=9.2 Hz), 7.03–7.07 (2H, m), 7.31 (1H, dd, J=2.2, 8.2 Hz), 7.45 (1H, d, J=2.2 Hz), 7.73 (1H, s).

IR (KBr) ν: 3391, 2980, 1688 cm$^{-1}$.

Anal. Calcd. for C$_{22}$H$_{25}$NO$_4$·0.2H$_2$O: C, 71.21; H, 6.90; N, 3.77. Found C, 71.23; H, 6.88; N, 3.67.

Reference Example 43

To anhydrous acetic acid (0.22 ml) was added dropwise formic acid (0.11 ml) under ice-cooling, and the mixture was stirred under nitrogen atmosphere at 50° C. for 2 hours. To the mixture was added THF (2 ml) and then was added dropwise, under ice-cooling, a solution of methyl 7-(3,4-diethoxyphenyl)-2,3-dihydro-1H-1-benzazepine-4-carboxylate (0.35 g) in THF (20 ml), and the mixture was stirred at room temperature overnight. The solvent was evaporated, and to the residue was added water. The mixture was extracted with ethyl acetate. The organic layer was washed with sodium hydrogen carbonate solution, water and saturated brine, and dried with anhydrous magnesium sulfate, and the solvent was evaporated to give methyl 7-(3,4-diethoxyphenyl)-1-formyl-2,3-dihydro-1H-1-benzazepine-carboxylate (0.35 g) as colorless crystals.

mp 152–153° C.

$^1$H-NMR (δ ppm, CDCl$_3$) 1.45–1.54 (6H, m), 2.95 (2H, t, J=5.3 Hz), 3.82–3.88 (5H, m), 4.10–4.24 (4H, m), 6.97 (1H, d, J=8.8 Hz), 7.11–7.19 (3H, m), 7.56 (1H, dd, J=2.2, 8.4 Hz), 7.67 (1H, d, J=2.2 Hz), 7.76 (1H, s), 8.53 (1H, s).

IR (KBr) ν: 2980, 1709, 1678 cm$^{-1}$.

Anal. Calcd. for C$_{23}$H$_{25}$NO$_5$·0.2H$_2$O: C, 69.23; H, 6.42; N, 3.51. Found C, 69.39; H, 6.39; N, 3.48.

Reference Example 44

In methanol (25 ml) and THF (25 ml) was dissolved methyl 7-(3,4-diethoxyphenyl)-1-formyl-2,3-dihydro-1H-1-benzazepine-4-carboxylate (0.33 g). To the solution was added 1N sodium hydroxide solution (8 ml), and the mixture was stirred at room temperature overnight and concentrated. To the residue was added water, and the mixture was neutralized with 1N hydrochloric acid and extracted with ethyl acetate. The organic layer was washed with water and saturated brine and dried with anhydrous magnesium sulfate, and the solvent was evaporated to give 7-(3,4-diethoxyphenyl)-1-formyl-2,3-dihydro-1H-1-benzazepine-4-carboxylic acid (0.32 g) as colorless crystals.

mp 228–233° C. (dec.).

$^1$H-NMR (δ ppm, CDCl$_3$) 1.49 (3H, t, J=7.0 Hz), 1.50 (3H, t, J=7.0 Hz), 2.97 (2H, t, J=5.5 Hz), 3.88 (2H, t, J=5.5 Hz), 4.11–4.24 (4H, m), 6.97 (1H, d, J=8.7 Hz), 7.11–7.21 (3H, m), 7.59 (1H, dd, J=2.0, 8.7 Hz), 7.69 (1H, d, J=2.0 Hz), 7.86 (1H, s), 8.55 (1H, s).

IR (KBr) ν: 2980, 1682, 1669 cm$^{-1}$.

Anal. Calcd. for C$_{22}$H$_{23}$NO$_5$: C, 69.28; H, 6.08; N, 3.67. Found C, 69.31; H, 6.23; N, 3.60.

Reference Example 45

A mixture of methyl 7-bromo-1-formyl-2,3-dihydro-1H-1-benzazepine-4-carboxylate (0.25 g), 4-(2-butoxyethoxy)phenyl borate (0.23 g), 1M potassium carbonate solution (2.5 ml), ethanol (2.5 ml) and toluene (25 ml) was stirred under argon atmosphere at room temperature for 30 minutes. To the mixture was added tetrakis(triphenylphosphine)palladium (0.04 g), and the mixture was refluxed overnight under argon atmosphere and extracted with ethyl acetate. The organic layer was washed with water and saturated brine and dried with anhydrous magnesium sulfate, and the solvent was evaporated under reduced pressure. The residue was purified with silica gel column chromatography (ethyl acetate/hexane) to give methyl 7-[4-(2-butoxyethoxy)phenyl]-1-formyl-2.3-dihydro-1H-1-benzazepine-4-carboxylate (0.23 g) as colorless oil.

$^1$H-NMR (δ ppm, CDCl$_3$) 0.94 (3H, t, J=7.2 Hz), 1.34–1.45 (2H, m), 1.55–1.69 (2H, m), 2.94 (2H, t, J=5.0 Hz), 3.56 (2H, t, J=6.6 Hz), 3.79–3.87 (7H, m), 4.18 (2H, t, J=5.0 Hz), 7.02 (2H, d, J=9.2 Hz), 7.17 (1H, d, J=8.4 Hz), 7.48–7.58 (3H, m), 7.68 (1H, d, J=2.2 Hz), 7.75 (1H, s), 8.53 (1H, s).

IR (neat) ν: 2938, 2870, 1713, 1682 cm$^{-1}$.

Reference Example 46

In methanol (25 ml) and THF (25 ml) was dissolved methyl 7-[4-(2-butoxyethoxy)phenyl]-1-formyl-2,3-dihydro-1H-1-benzazepine-4-carboxylate (0.23 g). To the solution was added 1N sodium hydroxide solution (5 ml), and the mixture was stirred at 55° C. for 1.5 hours and concentrated. To the residue was added water, and the mixture was neutralized with 1N hydrochloric acid and extracted with ethyl acetate. The organic layer was washed with water and saturated brine and dried with anhydrous magnesium sulfate, and the solvent was evaporated to give 7-[4-(2-butoxyethoxy)phenyl]-1-formyl-2,3-dihydro-1H-1-benzazepine-4-carboxylic acid (0.24 g) as colorless amorphous.

$^1$H-NMR (δ ppm, CDCl$_3$) 0.94 (3H, t, J=7.3 Hz), 1.27–1.45 (2H, m), 1.55–1.66 (2H, m), 2.97 (2H, t, J=4.9 Hz), 3.57 (2H, t, J=6.8 Hz), 3.80–3.90 (4H, m), 4.18 (2H, t, J=4.9 Hz), 7.06 (2H, d, J=8.8 Hz), 7.19 (1H, d, J=8.2 Hz), 7.52 (2H, d, J=8.8 Hz), 7.58 (1H, dd, J=2.0, 8.2 Hz), 7.69 (1H, d, J=2.0 Hz), 7.85 (1H, s), 8.55 (1H, s).

IR (KBr) ν: 2955, 2934, 2867, 1682, 1669 cm$^{-1}$.

Reference Example 47

A mixture of methyl 7-bromo-1-formyl-2,3-dihydro-1H-1-benzazepine-4-carboxylate (0.2 g), 4-[N-(2-ethoxyethyl)-N-methylamino]phenyl borate (0.17 g), potassium carbonate (0.2 g), water (1.1 ml), ethanol (1.1 ml) and toluene (10.7 ml) was stirred under argon atmosphere at room temperature for 30 minutes. To the mixture was added tetrakis(triphenylphosphine)palladium (0.03 g), and the mixture was refluxed overnight under argon atmosphere and extracted with ethyl acetate. The organic layer was washed with water and saturated brine and dried with anhydrous magnesium sulfate, and the solvent was evaporated under reduced pressure. The residue was purified with silica gel column chromatography (ethyl acetate/hexane) to give methyl 7-[4-[N-(2-ethoxyethyl)-N-methylamino]phenyl]-1-formyl-2,3-dihydro-1H-1-benzazepine-4-carboxylate (0.22 g) as colorless amorphous.

$^1$H-NMR (δ ppm, CDCl$_3$) 1.21 (3H, t, J=7.0 Hz), 2.91–2.97 (2H, m), 3.05 (3H, s), 3.52 (2H, q, J=7.0 Hz), 3.58–3.63 (4H, m), 3.81–3.88 (2H, m), 3.84 (3H, s), 6.81 (2H, d, J=8.8 Hz), 7.14 (1H, d, J=8.2 Hz), 7.46–7.57 (3H, m), 7.67 (1H, d, J=2.0 Hz), 7.75 (1H, s), 8.52 (1H, s).

IR (KBr) ν: 1707, 1678, 1610, 1503, 1358, 1261, 1234, 1196 cm$^{-1}$.

Reference Example 48

In methanol (6.6 ml) and THF (4.4 ml) was dissolved methyl 7-[4-[N-(2-ethoxyethyl)-N-methylamino]phenyl]-1-formyl-2,3-dihydro-1H-1-benzazepine-4-carboxylate (0.22 g). To the solution was added 1N sodium hydroxide solution (2.2 ml), and the mixture was stirred at room temperature overnight and concentrated. To the residue was added water, and the mixture was neutralized with 1N hydrochloric acid and extracted with ethyl acetate. The organic layer was washed with water and saturated brine and dried with anhydrous magnesium sulfate, and the solvent was evaporated to give 7-[4-[N-(2-ethoxyethyl)-N-methylamino]phenyl]-1-formyl-2,3-dihydro-1H-1-benzazepine-4-carboxylic acid (0.18 g) as colorless amorphous.

$^1$H-NMR (δ ppm, CDCl$_3$) 1.10 (3H, t, J=7.4 Hz), 2.68–2.81 (2H, m), 2.97 (3H, s), 3.26–3.38 (2H, m), 3.44 (2H, q, J=7.0 Hz), 3.54 (3H, s), 3.68–3.73 (2H, m), 6.79 (2H, d, J=8.8 Hz), 7.36 (1H, d, J=8.8 Hz), 7.56–7.73 (4H, m), 7.86 (1H, s), 8.52 (1H, s).

IR (KBr) ν: 2975, 2876, 1678, 1611, 1503, 1312, 1431, 1292, 1273, 1194, 1117, 810 cm$^{-1}$.

Reference Example 49

A mixture of methyl 7-bromo-1-formyl-2,3-dihydro-1H-1-benzazepine-4-carboxylate (0.2 g), 4-[N-(2-ethoxyethyl)-N-ethylamino]phenyl borate (0.46 g), 1M potassium carbonate solution (3.2 ml), ethanol (3.2 ml) and toluene (25 ml) was stirred under argon atmosphere at room temperature for 30 minutes. To the mixture was added tetrakis (triphenylphosphine)palladium (0.03 g), and the mixture was refluxed overnight under argon atmosphere and extracted with ethyl acetate. The organic layer was washed with water and saturated brine and dried with anhydrous magnesium sulfate, and the solvent was evaporated under reduced pressure. The residue was purified with silica gel column chromatography (ethyl acetate/hexane) to give methyl 7-[4-[N-(2-ethoxyethyl)-N-ethylamino]phenyl]-1-formyl-2,3-dihydro-1H-1-benzazepine-4-carboxylate (0.23 g) as green amorphous.

$^1$H-NMR ($\delta$ ppm, CDCl$_3$) 1.17–1.26 (6H, m), 2.94 (2H, t, J=4.8 Hz), 3.42–3.64 (8H, m), 3.82–3.87 (5H, m), 6.78 (2H, d, J=8.8 Hz), 7.13 (1H, d, J=8.1 Hz), 7.47 (2H, d, J=8.8 Hz), 7.54 (1H, dd, J=2.1, 8.1 Hz), 7.66 (1H, d, J=2.1 Hz), 7.75 (1H, s), 8.51 (1H, s).

IR (KBr) $\nu$: 2973, 2868, 1709, 1678 cm$^{-1}$.

Reference Example 50

In methanol (25 ml) and THF (25 ml) was dissolved methyl 7-[4-[N-(2-ethoxyethyl)-N-ethylamino]phenyl]-1-formyl-2,3-dihydro-1H-1-benzazepine-4-carboxylate (0.23 g). To the solution was added 1N sodium hydroxide solution (5.5 ml), and the mixture was stirred at room temperature overnight and concentrated. To the residue was added water, and the mixture was neutralized with 1N hydrochloric acid and extracted with ethyl acetate. The organic layer was washed with water and saturated brine and dried with anhydrous magnesium sulfate, and the solvent was evaporated to give 7-[4-[N-(2-ethoxyethyl)-N-ethylamino]phenyl]-1-formyl-2,3-dihydro-1H-1-benzazepine-4-carboxylic acid (0.2 g) as pale green crystals.

mp 182–184° C.

$^1$H-NMR ($\delta$ ppm, CDCl$_3$) 1.17–1.30 (6H, m), 2.97 (2H, t, J=5.7 Hz), 3.43–3.65 (8H, m), 3.87 (2H, t, J=5.7 Hz), 6.79 (2H, d, J=8.8 Hz), 7.16 (1H, d, J=8.4 Hz), 7.48 (2H, d, J=8.8 Hz), 7.58 (1H, dd, J=2.0, 8.4 Hz), 7.68 (1H, d, J=2.0 Hz), 7.86 (1H, s), 8.54 (1H, s).

IR (KBr) $\nu$: 2973, 2872, 1682 cm$^{-1}$.

Reference Example 51

A mixture of methyl 7-bromo-1-formyl-2,3-dihydro-1H-1-benzazepine-4-carboxylate (0.25 g), 4-[N-ethyl-N-(2-propoxyethyl)amino]phenyl borate (0.3 g), 1M potassium carbonate solution (2.5 ml), ethanol (2.5 ml) and toluene (25 ml) was stirred under argon atmosphere at room temperature for 30 minutes. To the mixture was added tetrakis (triphenylphosphine)palladium (0.04 g), and the mixture was refluxed overnight under argon atmosphere and extracted with ethyl acetate. The organic layer was washed with water and saturated brine, and dried with anhydrous magnesium sulfate. The solvent was evaporated, and the residue was purified with silica gel column chromatography (ethyl acetate/hexane) to give methyl 7-[4-[N-ethyl-N-(2-propoxyethyl)amino]phenyl]-1-formyl-2,3-dihydro-1H-1-benzazepine-4-carboxylate (0.31 g) as green oil.

$^1$H-NMR ($\delta$ ppm, CDCl$_3$) 0.93 (3H, t, J=7.3 Hz), 1.21 (3H, t, J=7.0 Hz), 1.59–1.66 (2H, m), 2.94 (2H, t, J=5.2 Hz), 3.39–3.64 (8H, m), 3.82–3.87 (5H, m), 6.78 (2H, d, J=9.0 Hz), 7.14 (1H, d, J=8.2 Hz), 7.47 (2H, d, J=9.0 Hz), 7.55 (1H, dd, J=2.0, 8.2 Hz), 7.66 (1H, d, J=2.0 Hz), 7.75 (1H, s), 8.52 (1H, s).

IR (neat) $\nu$: 2942, 2867, 1709, 1682 cm$^{-1}$.

Reference Example 52

In methanol (25 ml) and THF (25 ml) was dissolved methyl 7-[4-[N-ethyl-N-(2-propoxyethyl)amino]phenyl]-1-formyl-2,3-dihydro-1H-1-benzazepine-4-carboxylate (0.31 g). To the solution was added 1N sodium hydroxide solution (7 ml), and the mixture was stirred at 60° C. for 1.5 hours and concentrated. To the residue was added water, and the mixture was neutralized with 1N hydrochloric acid and extracted with ethyl acetate. The organic layer was washed with water and saturated brine and dried with anhydrous magnesium sulfate, and the solvent was evaporated to give 7-[4-[N-ethyl-N-(2-propoxyethyl)amino]phenyl]-1-formyl-2,3-dihydro-1H-1-benzazepine-4-carboxylic acid (0.29 g) as pale yellow crystals.

mp 169–171° C.

$^1$H-NMR ($\delta$ ppm, CDCl$_3$) 0.93 (3H, t, J=7.5 Hz), 1.21 (3H, t, J=7.0 Hz), 1.56–1.66 (2H, m), 2.96 (2H, t, J=5.0 Hz), 3.39–3.62 (8H, m), 3.87 (2H, t, J=5.0 Hz), 6.78 (2H, d, J=8.8 Hz), 7.16 (1H, d, J=8.0 Hz), 7.47 (2H, d, J=8.8 Hz), 7.58 (1H, dd, J=2.0, 8.0 Hz), 7.68 (1H, d, J=2.0 Hz), 7.84 (1H, s), 8.54 (1H, s).

IR (KBr) $\nu$: 2967, 2870, 1680 cm$^{-1}$.

Reference Example 53

In THF (50 ml) were dissolved methyl 7-(4-morpholinophenyl)-2,3-dihydro-1H-1-benzazepine-4-carboxylate (0.7 g) and pyridine (1.2 ml). To the solution was added methanesulfonic anhydride (1.5 g), and the mixture was stirred under nitrogen atmosphere at 50 for 3 hours. The solvent was evaporated, and to the residue was added water. The mixture was extracted with ethyl acetate. The organic layer was washed with water and saturated brine and dried with anhydrous magnesium sulfate, and the solvent was evaporated. The residue was purified with silica gel column chromatography (ethyl acetate/hexane) to give methyl 7-methanesulfonyl-7-(4-morpholinophenyl)-2,3-dihydro-1H-1-benzazepine-4-carboxylate (0.4 g) as pale yellow crystals.

mp 224–226° C. (dec.).

$^1$H-NMR ($\delta$ ppm, CDCl$_3$) 2.78 (3H, s), 3.05 (2H, t, J=5.0 Hz), 3.21–3.26 (4H, m), 3.85–3.92 (9H, m), 6.99 (2H, d, J=9.2 Hz), 7.50–7.58 (3H, m), 7.63–7.69 (2H, m), 7.80 (1H, s).

IR (KBr) $\nu$: 2953, 1709 cm$^{-1}$.

Reference Example 54

In methanol (100 ml) and THF (100 ml) was dissolved methyl 1-methanesulfonyl-7-(4-morpholinophenyl)-2,3-dihydro-1H-1-benzazepine-4-carboxylate (0.4 g). To the solution was added 1N sodium hydroxide solution (10 ml), and the mixture was stirred at room temperature overnight. To the mixture was added 1N sodium hydroxide solution (5 ml), and the mixture was stirred at 60° C. for 1.5 hours and concentrated. To the residue was added water, and the mixture was neutralized with 1N hydrochloric acid and extracted with ethyl acetate. The organic layer was washed with water and saturated brine and dried with anhydrous magnesium sulfate, and the solvent was evaporated to give 1-methanesulfonyl-7-(4-morpholinophenyl)-2,3-dihydro-1H-1-benzazepine-4-carboxylic acid (0.36 g) as pale yellow crystals.

mp 264–275° C. (dec.).

¹H-NMR (δ ppm, CDCl₃+CD₃OD) 2.79 (3H, s), 3.02 (2H, t, J=5.1 Hz), 3.21–3.26 (4H, m), 3.84–3.92 (6H, m), 7.00 (2H, d, J=8.8 Hz), 7.50–7.58 (3H, m), 7.64–7.68 (2H, m), 7.83 (1H, s).

IR (KBr) ν: 2969, 2832, 1671 cm⁻¹.

Anal. Calcd. for $C_{22}H_{24}N_2O_5S$: C, 61.66; H, 5.65; N, 6.54. Found C, 61.48; H, 5.81; N, 6.25.

Reference Example 55

In THF (25 ml) were dissolved methyl 7-(4-ethoxyphenyl)-2,3-dihydro-1H-1-benzazepine-4-carboxylate (0.25 g) and pyridine (0.6 ml). To the solution was added methanesulfonic anhydride (0.67 g), and the mixture was stirred under nitrogen atmosphere at 40° C. overnight. To the mixture was added methanesulfonic anhydride (0.13 g), and the mixture was stirred at 40° C. for 4 hours. The solvent was evaporated. To the residue was added water, and the mixture was extracted with ethyl acetate. The organic layer was washed with water and saturated brine and dried with anhydrous magnesium sulfate, and the solvent was evaporated. The residue was purified with silica gel column chromatography (ethyl acetate/hexane) to give methyl 7-(4-ethoxyphenyl)-1-methanesulfonyl-2,3-dihydro-1H-1-benzazepine-4-carboxylate (0.14 g) as pale yellow crystals.

mp 175–181° C.

¹H-NMR (δ ppm, CDCl₃) 1.45 (3H, t, J=7.1 Hz), 2.78 (3H, s), 3.05 (2H, t, J=4.9 Hz), 3.84–3.89 (5H, m), 4.09 (2H, q, J=7.1 Hz), 6.98 (2H, d, J=8.8 Hz), 7.49–7.57 (3H, m), 7.63 (1H, d, J=2.2 Hz), 7.67 (1H, d, J=8.4 Hz), 7.80 (1H, s).

IR (KBr) ν: 2984, 1711 cm⁻¹.

Reference Example 56

In methanol (25 ml) and THF (25 ml) was dissolved methyl 7-(4-ethoxyphenyl)-1-methanesulfonyl-2,3-dihydro-1H-1-benzazepine-4-carboxylate (0.14 g). To the solution was added 1N sodium hydroxide solution (3 ml), and the mixture was stirred at room temperature overnight and concentrated. To the residue was added water, and the mixture was neutralized with 1N hydrochloric acid and extracted with ethyl acetate. The organic layer was washed with water and saturated brine and dried with evaporated to give 7-(4-ethoxyphenyl)-1-methanesulfonyl-2,3-dihydro-1H-1-benzazepine-4-carboxylic acid (0.13 g) as pale yellow crystals.

mp 237–242° C. (dec.).

¹H-NMR (δ ppm, CDCl₃) 1.46 (3H, t, J=7.0 Hz), 2.81 (3H, s), 3.08 (2H, t, J=5.9 Hz), 3.89 (2H, t, J=5.9 Hz), 4.10 (2H, q, J=7.0 Hz), 6.99 (2H, d, J=8.8 Hz), 7.52 (2H, d, J=8.8 Hz), 7.58 (1H, dd, J=2.0, 8.4 Hz), 7.65 (1H, d, J=2.0 Hz), 7.70 (1H, d, J=8.4 Hz), 7.91 (1H, s).

IR (KBr) ν: 2984, 1669 cm⁻¹.

Reference Example 57

In THF (30 ml) were dissolved methyl 7-[4-(2-ethoxyethoxy)phenyl]-2,3-dihydro-1H-1-benzazepine-4-carboxylate (0.25 g) and pyridine (0.5 ml). To the solution was added methanesulfonic anhydride (0.6 g), and the mixture was stirred under nitrogen atmosphere at 50° C. overnight. To the mixture was added methanesulfonic anhydride (0.1 g), and the mixture was stirred at 50° C. for 2 hours. The solvent was evaporated. To the residue was added water, and the mixture was extracted with ethyl acetate. The organic layer was washed with water and saturated brine and dried with anhydrous magnesium sulfate, and the solvent was evaporated. The residue was purified with silica gel column chromatography (ethyl acetate/hexane) to give methyl 7-[4-(2-ethoxyethoxy)phenyl]-1-1-methanesulfonyl-2,3-dihydro-1H-1-benzazepine-4-carboxylate (0.13 g) as pale yellow crystals.

mp 143–146° C.

¹H-NMR (δ ppm, CDCl₃) 1.27 (3H, t, J=6.9 Hz), 2.78 (3H, s), 3.06 (2H, t, J=5.2 Hz), 3.63 (2H, q, J=6.9 Hz), 3.81–3.89 (7H, m), 4.19 (2H, t, J=4.9 Hz), 7.03 (2H, d, J=8.8 Hz), 7.49–7.57 (3H, m), 7.64 (1H, d, J=2.0 Hz), 7.68 (1H, d, J=8.4 Hz), 7.81 (1H, s).

IR (KBr) ν: 2932, 2872, 1709 cm⁻¹.

Reference Example 58

In methanol (20 ml) and THF (20 ml) was dissolved methyl 7-[4-(2- ethoxyethoxy)phenyl]-1-methanesulfonyl-2,3-dihydro-1-benzazepine-4-carboxylate (0.13 g). To the solution was added 1N sodium hydroxide solution (3 ml), and the mixture was stirred at room temperature overnight and concentrated. To the residue was added water, and the mixture was neutralized with 1N hydrochloric acid and extracted with ethyl acetate. The organic layer was washed with water and saturated brine and dried with anhydrous magnesium sulfate, and the solvent was evaporated to give 7-[4-(2-ethoxyethoxy)phenyl]-1-methanesulfonyl-2,3-dihydro-1H-1-benzazepine-4-carboxylic acid (0.12 g) as pale yellow crystals.

mp 222–225° C.

¹H-NMR (δ ppm, CDCl₃) 1.27 (3H, t, J=7.1 Hz), 2.81 (3H, s), 3.08 (2H, t, J=5.1 Hz), 3.63 (2H, q, J=7.1 Hz), 3.81–3.91 (4H, m), 4.19 (2H, t, J=4.8 Hz), 7.03 (2H, d, J=8.8 Hz), 7.52 (2H, d, J=8.8 Hz), 7.57 (1H, dd, J=2.2, 9.0 Hz), 7.64 (1H, d, J=2.2 Hz), 7.67 (1H, d, J=9.0 Hz), 7.90 (1H, s).

IR (KBr) ν: 2978, 2872, 1694, 1669 cm⁻¹.

Reference Example 59

In THF (35 ml) were dissolved methyl 7-[4-(3-ethoxypropoxy)phenyl]-2,3-dihydro-1H-1-benzazepine-4-carboxylate (0.4 g) and pyridine (0.75 ml). To the solution was added methanesulfonic anhydride (0.92 g), and the mixture was stirred under nitrogen atmosphere at room temperature overnight. To the mixture was added methanesulfonic anhydride (0.25 g), and the mixture was stirred at 50° C. overnight. The solvent was evaporated. To the residue was added water, and the mixture was extracted with ethyl acetate. The organic layer was washed with water and saturated brine and dried with anhydrous magnesium sulfate, and the solvent was evaporated. The residue was purified with silica gel column chromatography (ethyl acetate/hexane) to give methyl 7-[4-(3-ethoxypropoxy)phenyl]-1-methanesulfonyl-2,3-dihydro-1H-1-benzazepine-4-carboxylate (0.26 g) as pale yellow crystals.

mp 127–129° C.

¹H-NMR (δ ppm, CDCl₃) 1.22 (3H, t, J=7.0 Hz), 2.02–2.15 (2H, m), 2.78 (3H, s), 3.05 (2H, t, J=5.5 Hz), 3.51 (2H, q, J=7.0 Hz), 3.62 (2H, t, J=6.2 Hz), 3.85 (3H, s), 3.86 (2H, t, J=5.5 Hz), 4.12 (2H, t, J=6.2 Hz), 7.00 (2H, d, J=8.8 Hz), 7.51 (2H, d, J=8.8 Hz), 7.55 (1H, dd, J=2.2, 8.4 Hz), 7.63 (1H, d, J=2.2 Hz), 7.67 (1H, d, J=8.4 Hz), 7.80 (1H, s).

IR (KBr) ν: 2951, 2872, 1711 cm⁻¹.

Reference Example 60

In methanol (25 ml) and THF (25 ml) was dissolved methyl 7-[4-(3-ethoxypropoxy)phenyl]-1-methanesulfonyl- 2,3-dihydro-1H-1-benzazepine-4-carboxylate (0.22 g). To the solution was added 1N sodium hydroxide solution (5 ml), and the mixture was stirred at room temperature overnight and concentrated. To the residue was added water, and the mixture was neutralized with 1N hydrochloric acid and extracted with ethyl acetate. The organic layer was washed with water and saturated brine and dried with anhydrous magnesium sulfate, and the solvent was evaporated to give 7-[4-(3-ethoxypropoxy)phenyl]-1-methanesulfonyl-2,3-dihydro-1H-1-benzazepine-4-carboxylic acid (0.23 g) as pale yellow crystals.

mp 210–212° C.

$^1$H-NMR (δ ppm, CDCl$_3$) 1.22 (3H, t, J=7.2 Hz), 2.03–2.15 (2H, m), 2.81 (3H, s), 3.08 (2H, t, J=5.5 Hz), 3.52 (2H, q, J=7.2 Hz), 3.63 (2H, t, J=6.0 Hz), 3.89 (2H, t, J=5.5 Hz), 4.13 (2H, t, J=6.2 Hz), 7.00 (2H, d, J=8.8 Hz), 7.52 (2H, d, J=8.8 Hz), 7.57 (1H, dd, J=1.8, 8.4 Hz), 7.65 (1H, d, J=1.8 Hz), 7.69 (1H, d, J=8.4 Hz), 7.91 (1H, s).

IR (KBr) ν: 3036, 2870, 1671 cm$^{-1}$.

Anal. Calcd. for C$_{23}$H$_{27}$NO$_6$S: C, 62.00; H, 6.11; N, 3.14. Found C, 62.17; H, 5.99; N, 3.17.

Reference Example 61

In dimethyl carbonate (15 ml) was dissolved 7-bromo-1,2,3,4-tetrahydro-1-benzazepin-5-one (0.68 g). To the solution was added sodium methoxide (0.92 g), and the mixture was refluxed under nitrogen atmosphere for 8 hours and poured into ice-water. To the mixture was added 1N hydrochloric acid, and the mixture was extracted with ethyl acetate. The organic layer was washed with water and saturated brine and dried with anhydrous magnesium sulfate, and the solvent was evaporated. The residue was purified with silica gel column chromatography (ethyl acetate/hexane) to give pale yellow oil (0.88 g), which was dissolved in THF (30 ml). To the solution was added sodium borohydride (0.1 g) at −40° C. and then was added dropwise methanol (3 ml), and the mixture was stirred at −15° C. for 1 hour. To the mixture was added water, and the mixture was extracted with ethyl acetate. The organic layer was washed with water and saturated brine and dried with anhydrous magnesium sulfate, and the solvent was evaporated. The residue was dissolved in THF (25 ml), and to the solution was added triethylamine (0.7 ml), and then was added dropwise, under ice-cooling, methanesulfonyl chloride (0.6 ml). Under nitrogen atmosphere, the mixture was stirred at room temperature overnight, and to the mixture was added dropwise DBU (2.5 ml) at room temperature. The mixture was refluxed for 30 minutes, and the solvent was evaporated. To the residue was added water, and the mixture was extracted with ethyl acetate. The organic layer was washed with water and saturated brine and dried with anhydrous magnesium sulfate, and the solvent was evaporated. The residue was purified with silica gel column chromatography (ethyl acetate/hexane) to give methyl 7-bromo-1-methoxycarbonyl-2,3-dihydro-1H-1-benzazepine-4-carboxylate (0.3 g) as colorless crystals.

mp 135–136° C.

$^1$H-NMR (δ ppm, CDCl$_3$) 2.92 (2H, t, J=5.1 Hz), 3.70 (2H, br), 3.74 (3H, s), 3.82 (3H, s), 7.26 (1H, br), 7.42 (1H, dd, J=2.2, 8.4 Hz), 7.56–7.57 (2H, m).

IR (KBr) ν: 2951, 1713 cm$^{-1}$.

Anal. Calcd. for C$_{14}$H$_{14}$BrNO$_4$: C, 49.43; H, 4.15; N, 4.12. Found C, 49.53; H, 4.08; N, 4.06.

Reference Example 62

A mixture of methyl 7-bromo-1-methoxycarbonyl-2,3-dihydro-1H-1-benzazepine-4-carboxylate (0.3 g), 4-morpholinophenyl borate (0.22 g), 1M potassium carbonate solution (2.5 ml), ethanol (2.5 ml) and toluene (25 ml) was stirred under argon atmosphere at room temperature for 30 minutes. To the mixture was added tetrakis(triphenylphosphine)palladium (0.04 g), and the mixture was refluxed overnight under argon atmosphere and extracted with ethyl acetate. The organic layer was washed with water and saturated brine and dried with anhydrous magnesium sulfate, and the solvent was evaporated under reduced pressure. The residue was purified with silica gel column chromatography (ethyl acetate/hexane) to give methyl 1-methoxycarbonyl-7-(4-morpholinophenyl)-2,3-dihydro-1H-1-benzazepine-4-carboxylate (0.31 g) as pale yellow crystals.

mp 216–220° C.

$^1$H-NMR (δ ppm, CDCl$_3$) 2.94 (2H, t, J=5.4 Hz), 3.20–3.25 (4H, m), 3.75 (2H, br), 3.76 (3H, br), 3.83 (3H, s), 3.87–3.92 (4H, m), 6.99 (2H, d, J=9.0 Hz), 7.39 (1H, br), 7.50–7.55 (3H, m), 7.60 (1H, s), 7.73 (1H, s).

IR (KBr) ν: 2953, 1713 cm$^{-1}$.

Anal. Calcd. for C$_{24}$H$_{26}$N$_2$O$_5$·0.2H$_2$O: C, 67.65; H, 6.25; N, 6.57. Found C, 67.50; H, 6.10; N, 6.58.

Reference Example 63

In methanol (40 ml) and THF (60 ml) was dissolved methyl 1-methoxycarbonyl-7-(4-morpholinophenyl)-2,3-dihydro-1H-1-benzazepine-4-carboxylate (0.31 g). To the solution was added 1N sodium hydroxide solution (5 ml), and the mixture was stirred at room temperature overnight. To the mixture was added 1N sodium hydroxide solution (2.5 ml), and the mixture was stirred at room temperature overnight and concentrated. The residue was neutralized with 1N hydrochloric acid, precipitated crystals were filtered and washed with water to give 1-methoxycarbonyl-7-(4-morpholinophenyl)-2,3-dihydro-1H-1-benzazepine-4-carboxylic acid (0.29 g) as colorless crystals.

mp 274–279° C. (dec.).

$^1$H-NMR (δ ppm, DMSO-d$_6$) 2.78 (2H, t-like), 3.16–3.18 (4H, m), 3.60 (2H, br), 3.66 (3H, s), 3.75–3.77 (4H, m), 7.03 (2H, d, J=6 Hz), 7.40 (1H, d, J=8.4 Hz), 7.58–7.69 (4H, m), 7.79 (1H, s), 12.65 (1H, br).

IR (KBr) ν: 2969, 1705, 1678 cm$^{-1}$.

Anal. Calcd. for C$_{23}$H$_{24}$N$_2$O$_5$·0.5H$_2$O: C, 66.17; H, 6.04; N, 6.71. Found C, 66.15; H, 5.74; N, 6.68.

Reference Example 64

In pyridine (10.0 ml) were dissolved ethyl 4-(4-bromo-2-formylphenyl)aminobutyrate (3.16 g) and tosyl chloride (2.88 g), and the mixture was stirred at 50° C. for 62 hours. The mixture was diluted with ethyl acetate, washed with 1N hydrochloric acid and saturated brine, and the organic layer was dried with anhydrous magnesium sulfate. The solvent was evaporated under reduced pressure, and the residue was purified with silica gel column chromatography (150 g, hexane:ethyl acetate=6:1→4:1) to give ethyl 4-(4-bromo-2-formylphenyl)-4-[(4-methylphenyl)sulfonyl]aminobutyrate (1.47 g, 31%) as brown oil.

$^1$H-NMR (200 MHz, CDCl$_3$) δ 1.23 (3H, t, J=7.0 Hz), 1.77 (2H, quint, J=7.2 Hz), 2.35 (2H, t, J=7.1 Hz), 2.45 (3H, s), 3.27–3.38 (1H, m), 3.88–3.96 (1H, m), 4.09 (2H, q, J=6.9 Hz), 6.60 (1H, d, J=8.6 Hz), 7.29 (2H, d, J=9.2 Hz), 7.44 (2H, d, J=8.4 Hz), 7.59 (1H, dd, J=8.5, 2.5 Hz), 8.15 (1H, d, J=2.6 Hz), 10.35 (1H, s).

IR (KBr) 1732, 1694, 1474, 1377, 1350, 1184, 1163, 723, 655, 579 cm$^{-1}$.

Reference Example 65

In a mixture of t-butanol and toluene (1:10, v/v, 66.0 ml) was dissolved ethyl 4-(4-bromo-2-formylphenyl)-4-[(4-methylphenyl)sulfonyl]aminobutyrate (1456 mg). To the solution was added at room temperature potassium t-butoxide (384 mg), and the mixture was stirred at 100° C. for 1 hour. To the mixture was added 1N hydrochloric acid to convert weakly acidic solution, and the mixture was extracted with ethyl acetate. The organic layer was washed with water and saturated brine and dried with anhydrous magnesium sulfate, and the solvent was evaporated under reduced pressure. The residue was purified with silica gel column chromatography (75 g, hexane:ethyl acetate=6:1) to give ethyl 7-bromo-1-[(4-methylphenyl)sulfonyl]-2,3-dihydro-1H-1-benzazepine-4-carboxylate (413 mg, 30%) as yellow amorphous.

$^1$H-NMR (200 MHz, CDCl$_3$) δ 1.29 (3H, t, J=7.2 Hz), 2.35 (3H, s), 2.86 (2H, td, J=5.8, 1.4 Hz), 3.87 (2H, t, J=6.1 Hz), 4.19 (2H, q, J=7.1 Hz), 7.13 (2H, d, J=8.0 Hz), 7.15–7.19 (1H, m), 7.39–7.55 (5H, m).

IR (KBr) 1709, 1485, 1350, 1246, 1194, 1163, 1090, 710, 696, 662 cm$^{-1}$.

Reference Example 66

In a mixture of water ethanol toluene (1:1:10 v/v, 18.0 ml) were dissolved 4-(4-morpholino)phenyl borate (278 mg) and ethyl 7-bromo-1-[(4-methylphenyl)sulfonyl]-2,3-dihydro-1H-1-benzazepine-4-carboxylate (403 mg). To the solution was added potassium carbonate (297 mg), and the mixture was stirred under argon atmosphere at room temperature for 30 minutes. To the mixture was added tetrakistriphenylphosphinepalladium (41 mg), and the mixture was refluxed under argon atmosphere for 13 hours. The mixture was diluted with ethyl acetate, and washed with water and saturated brine. The organic layer was dried with anhydrous magnesium sulfate, and the solvent was evaporated under reduced pressure. The residue was purified with silica gel column chromatography (45 g, hexane:ethyl acetate= 4:1→3:1) to give ethyl 7-[(4-methylphenyl)sulfonyl]-7-[4-(4-morpholino)phenyl]-2,3-dihydro-1H-1-benzazepine-4-carboxylate (460 mg, 96%) as yellow crystals.

$^1$H-NMR (200 MHz, CDCl$_3$) δ 1.30 (3H, t, J=7.2 Hz), 2.34 (3H, s), 2.87 (2H, t, J=5.3 Hz), 3.23 (4H, t, J=4.9 Hz), 3.90 (4H, t, J=4.8 Hz), 3.90–3.95 (2H, m), 4.20 (2H, q, J=7.1 Hz), 6.99 (2H, d, J=9.0 Hz), 7.12 (2H, d, J=8.2 Hz), 7.36 (1H, s), 7.45 (2H, d, J=8.4 Hz), 7.53 (2H, d, J=8.6 Hz), 7.46–7.68 (3H, m).

IR (KBr) 1705, 1609, 1493, 1348, 1233, 1161, 1123, 1092, 932, 818, 671 cm$^{-1}$.

Reference Example 67

In THF (10.0 ml) was dissolved methyl 7-[4-(4-morpholino)phenyl]-2,3-dihydro-1H-1-benzazepine-4-carboxylate (369 mg), and to the solution were added pyridine (0.11 ml) and acetyl chloride (0.086 ml) at room temperature or at 0° C. The mixture was stirred at room temperature for 30 minutes, and diluted with ethyl acetate and washed with water and saturated brine. The organic layer was dried with anhydrous magnesium sulfate, and the solvent was evaporated under reduced pressure to give methyl 1-acetyl-7-[4-(4-morpholino)phenyl]-2,3-dihydro-1H-1-benzazepine-4-carboxylate (400 mg, 97%) as pale yellow amorphous.

$^1$H-NMR (200 MHz, CDCl$_3$) δ 2.05 (3H, s), 2.74–3.19 (3H, m), 3.24 (4H, t, J=4.8 Hz), 3.83 (3H, s), 3.90 (4H, t, J=4.8 Hz), 4.73–4.85 (1H, m), 7.01 (2H, d, J=8.8 Hz), 7.23 (1H, d, J=8.2 Hz), 7.54 (2H, d, J=8.8 Hz), 7.51–7.56 (1H, m), 7.67 (1H, d, J=1.8 Hz), 7.74 (1H, s).

IR (KBr) 1709, 1659, 1609, 1497, 1389, 1233, 1123 cm$^{-1}$.

Reference Example 68

In a mixture of THF and ethanol (1:1, v/v, 10.0 ml) was dissolved methyl 1-acetyl-7-[4-(4-morpholino)phenyl]-2,3-dihydro-1H-1-benzazepine-4-carboxylate (394 mg). To the solution was added 1N sodium hydroxide solution (3.0 ml), and the mixture was stirred at room temperature for 12 hours. To the mixture was added 1N hydrochloric acid to convert to a weakly acidic solution, and the mixture was extracted with ethyl acetate. The organic layer was dried with anhydrous magnesium sulfate. The solvent was evaporated under reduced pressure to give 1-acetyl-7-[4-(4-morpholino)phenyl]-2,3-dihydro-1H-1-benzazepine-4-carboxylic acid (372 mg, 98%) as pale yellow crystals.

$^1$H-NMR (200 MHz, DMSO-d$_6$) δ 1.95 (3H, s), 2.75 (3H, br), 3.17 (4H, t, J=4.7 Hz), 3.76 (4H, t, J=4.8 Hz), 4.54 (1H, br), 7.03 (2H, d, J=8.8 Hz), 7.46 (1H, d, J=8.2 Hz), 7.63–7.72 (4H, m), 7.88 (1H, s).

Reference Example 69

In THF (500 ml) was dissolved methyl anthranylate (247.8 g, 130 mol). To the solution were added pyridine (205.7 g, 2.60 ml) and tosyl chloride (260.2 g, 1.37 mol) at room temperature, and the mixture was stirred for 14.5 hours (overnight). To the mixture were added ethyl acetate and water to carry out extraction, and the organic layer was washed with 1N hydrochloric acid, water and saturated brine, and dried with anhydrous magnesium sulfate. Under reduced pressure, the solvent was evaporated to give crystals which were washed with ethyl acetate and IPE (isopropyl ether) to give white crystals of methyl N-tosylanthranylate (348.0 g). The mother liquor was treated by the same procedure to give methyl N-tosylanthranylate (32.4 g).

Yield, 380.4 g (96%).

mp 111–112° C.

$^1$H-NMR (CDCl$_3$, 200 MHz) δ 2.36 (3H, s), 3.88 (3H, s), 7.03 (1H, td, J=7.6, 1.7 Hz), 7.22 (2H, d, J=8.0 Hz), 7.45 (1H, td, J=7.9, 1.5 Hz), 7.67–7.78 (1H, m), 7.75 (2H, d, J=8.4 Hz), 7.92 (1H, dd, J=8.0, 1.6 Hz), 10.63 (1H, brs).

IR (KBr) 3173, 1688, 1493, 1260, 1161, 1090, 567 cm$^{-1}$.

Reference Example 70

In 85% acetic acid solution (1000 ml) were suspended methyl N-tosylanthranylate (100 g, 328 mmol) and sodium acetate (29.6 g, 361 mmol). To the solution was added dropwise at room temperature a solution of bromine (21.0 ml, 408 mmol) in 85% acetic acid solution (100 ml), and the mixture was stirred at 70° C. for 2 hours. To the mixture was added sodium thiosulfate pentahydrate at room temperature, and excess bromine was reduced. The mixture was concentrated under reduced pressure, and to the residue were added water and ethyl acetate. The separated organic layer was washed with potassium carbonate solution and saturated brine and dried with anhydrous magnesium sulfate. Under reduced pressure, the solvent was evaporated to give crystals, which were washed with IPE to give white crystals of methyl 5-bromo-N-tosylanthranylate (116.9 g). The mother liquor was treated by the same procedure to give methyl 5-bromo-N-tosylanthranylate (6.9 g).

Yield, 123.5 g (98%).

mp 123–124° C.

¹H-NMR (CDCl₃, 200 MHz) δ 2.38 (3H, s), 3.89 (3H, s), 7.24 (2H, d, J=9.2 Hz), 7.53 (1H, dd, J=8.8, 2.2 Hz), 7.61 (1H, d, J=8.6 Hz), 7.73 (2H, d, J=8.0 Hz), 8.03 (1H, d, J=2.2 Hz), 10.52 (1H, brs).

Reference Example 71

In a mixture of water:ethanol toluene (1:1:10, v/v. 42.0 ml) were dissolved 4-propoxyphenyl borate (746 mg) and methyl 7-bromo-1-(t-butoxycarbonyl)-2,3-dihydro-1H-1-benzazepine-4-carboxylate (1320 mg). To the solution was added potassium carbonate (1145 mg), and the mixture was stirred under argon atmosphere at room temperature for 30 minutes. To the mixture was added tetrakistriphenylphosphinepalladium (160 mg), and the mixture was heated to reflux under argon atmosphere for 14.5 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (75 g, hexane:ethyl acetate=3:1) to give methyl 1-(t-butoxycarbonyl)-7-(4-propoxyphenyl)-2,3-dihydro-1H-1-benzazepine-4-carboxylate as yellow amorphous. The obtained methyl 1-(t-butoxycarbonyl)-7-(4-propoxyphenyl)-2,3-dihydro-1H-1-benzazepine-4-carboxylate was dissolved in ethyl acetate (80 ml). To the solution was added 6N hydrochloric acid (20 ml) at room temperature, and the mixture was stirred at 100° C. for 30 minutes and neutralized with 1N sodium hydroxide and saturated sodium hydrogen carbonate solution. The separated organic layer was washed with saturated sodium hydrogen carbonate solution, water and saturated brine, and dried with anhydrous magnesium sulfate. The solvent was evaporated under reduced pressure to give crystals, which were washed with ethyl acetate/hexane to give methyl 7-(4-propoxyphenyl)-2,3-dihydro-1H-1-benzazepine-4-carboxylate (947 mg) as yellow crystals. The mother liquor was concentrated, and the residue was purified with silica gel column chromatography (15 g, hexane:ethyl acetate= 4:1) to give desired product (147 mg).

Yield, 1094 mg (94%).

mp 134–137° C.

¹H-NMR (200 MHz, CDCl₃) δ 1.05 (3H, t, J=8.1 Hz), 1.83 (2H, sextet, J=7.0 Hz), 2.88 (2H, t, J=4.4 Hz), 3.40 (2H, t, J=4.8 Hz), 3.81 (3H, s), 3.96 (2H, t, J=6.6 Hz), 6.67 (1H, d, J=8.4 Hz), 6.90–6.98 (2H, m), 7.32 (1H, dd, J=8.4, 2.2 Hz), 7.45 (2H, d, J=8.4 Hz), 7.46 (1H, d, J=1.8 Hz), 7.73 (1H, s).

IR (KBr) 3384, 2963, 1698, 1609, 1499, 1269, 1242, 1209, 1177, 818 cm⁻¹.

Anal. Calcd. for $C_{21}H_{23}NO_3$ (0.1H₂O additive): C, 74.36; H, 6.89; N, 4.13. Found C, 74.31; H, 6.81; N, 4.10.

Reference Example 72

To anhydrous acetic acid (0.65 ml) was added formic acid (0.32 ml) at 0° C., and the mixture was stirred at 60° C. for 2 hours, air-cooled and diluted with THF (10 ml). In THF (10 ml) was dissolved methyl 7-(4 propoxyphenyl)-2,3-dihydro-1H-1-benzazepine-4-carboxylate (520 mg), and the solution was added dropwise to the previously prepared solution of formic anhydride in THF, at 0° C. The mixture was stirred at room temperature for 1.5 hours. The solvent was evaporated under reduced pressure, and the residue was diluted with ethyl acetate, washed with saturated sodium hydrogen carbonate solution, water and saturated brine, and dried with anhydrous magnesium sulfate. The solvent was evaporated under reduced pressure to give crystals, which were washed with ethyl acetate/hexane to give methyl 1-formyl-7-(4-propoxyphenyl)-2,3-dihydro-1H-1-benzazepine-4-carboxylate (563 mg) as white crystals.

mp 151.5–153° C.

¹H-NMR (200 MHz, CDCl₃) δ 1.07 (3H, t, J=7.5 Hz), 1.85 (2H, sextet, J=7.1 Hz), 2.92 (2H, t, J=5.1 Hz), 3.84 (3H, s), 3.85 (2H, t, J=5.5 Hz), 3.98 (2H, t, J=6.6 Hz), 6.98–7.02 (2H, m), 7.17 (1H, d, J=8.0 Hz), 7.48–7.54 (2H, m), 7.56 (1H, dd, J=8.2, 2.2 Hz), 7.68 (1H, d, J=2.0 Hz), 7.76 (1H, s), 8.53 (1H, s).

IR (KBr) 1709, 1678, 1497, 1358, 1236, 1192, 824 cm⁻¹.

Anal. Calcd. for $C_{22}H_{23}NO_4$: C, 72.31; H, 6.34; N, 3.83. Found C, 72.35; H, 6.45; N, 3.83.

Reference Example 73

In THF (15.0 ml) was dissolved methyl 7-(4-propoxyphenyl)-2,3-dihydro-1H-1-benzazepine-4-carboxylate (431 mg). To the solution was added pyridine (1.0 ml) and then was added a solution of methanesulfonic anhydride (1.11 g) in THF (5.0 ml), at room temperature, and the mixture was stirred at 50° C. for 15 hours. The mixture was diluted with ethyl acetate, and washed with water, 1N hydrochloric acid, water and saturated brine, and the organic layer was dried with anhydrous magnesium sulfate. The solvent was evaporated under reduced pressure to give crystals, which were washed with ethyl acetate to give methyl 1-methylsulfonyl-7-(4-propoxyphenyl)-2,3-dihydro-1H-1-benzazepine-4-carboxylate (238 mg) as white crystals. The mother liquor was concentrated, and the residue was purified with silica gel column chromatography (15 g, hexane:ethyl acetate=2:1) to give desired product. The obtained methyl 1-methylsulfonyl-7-(4-propoxyphenyl)-2, 3-dihydro-1H-1-benzazepine-4-carboxylate was collected and dissolved in a mixture of THF and ethanol (1:1, v/v, 40 ml). To the solution was added 1N sodium hydroxide solution (14.0 ml), and the mixture was stirred at room temperature for 18 hours. The mixture was a little concentrated, and to the residue was added 1N hydrochloric acid to convert weakly acidic solution. The mixture was extracted with ethyl acetate, and the organic layer was washed with water and saturated brine, and dried with anhydrous magnesium sulfate. The solvent was evaporated under reduced pressure to give crystals, which were washed with ethyl acetate/hexane to give 1-methylsulfonyl-7-(4-propoxyphenyl)-2,3-dihydro-1H-1-benzazepine-4-carboxylic acid (273 mg, 53%) as white crystals.

mp 261–263° C. (dec.).

¹H-NMR (200 MHz, DMSO-d₆) δ 1.00 (3H, t, J=7.3 Hz), 1.76 (2H, sextet, J=7.0 Hz), 2.91 (2H, t-like), 3.08 (3H, s), 3.71 (2H, t-like), 3.98 (2H, t, J=6.6 Hz), 7.02 (2H, d, J=8.6 Hz), 7.51 (1H, d, J=4 Hz), 7.61–7.65 (1H, m), 7.67 (2H, d, J=8.8 Hz), 7.75 (1H, s), 7.86 (1H, d, J=1.4 Hz).

IR (KBr) 1669, 1499, 1435, 1341, 1273, 1248, 1144, 970, 824, 787 cm⁻¹.

Anal. Calcd. for $C_{21}H_{23}NO_5S$ (0.2H₂O additive): C, 62.27; H, 5.82; N, 3.46. Found C, 62.17; H, 5.87; N, 3.45.

Reference Example 74

In a mixture of THF and ethanol (1:1, v/v. 24.0 ml) was dissolved methyl 1-formyl-7-(4-propoxyphenyl)-2,3-dihydro-1H-1-benzazepine-4-carboxylate (501 mg). To the solution was added 1N sodium hydroxide solution (15.0 ml), and the mixture was stirred at room temperature for 16 hours. The mixture was a little concentrated, and to the residue was added 1N hydrochloric acid to convert weakly acidic solution. The mixture was extracted with ethyl acetate. The organic layer was washed with water and saturated brine, and dried with anhydrous magnesium sulfate. The solvent was evaporated under reduced pressure to give crystals, which were washed with ethyl acetate/hexane to give 1-formyl-7-(4-propoxyphenyl)-2,3-dihydro-1H-1-benzazepine-4-carboxylic acid (482 mg) as white crystals.

mp 215–217° C.

$^1$H-NMR (200 MHz, DMSO-d$_6$) δ 1.03 (3H, t, J=7.4 Hz), 1.71–1.84 (2H, m), 2.79 (2H, t, J=5.4 Hz), 3.75 (2H, t, J=5.6 Hz), 3.98 (2H, t, J=6.5 Hz), 7.00 (2H, d, J=8.8 Hz), 7.34 (1H, d, J=8.4 Hz), 7.59–7.65 (3H, m), 7.73 (1H, s), 7.82 (1H, d, J=1.6 Hz), 8.53 (1H, s).

IR (KBr) 1701, 1682, 1644, 1501, 1366, 1294, 1256, 1233, 1186, 820 cm$^{-1}$.

Anal. Calcd. for $C_{21}H_{21}NO_4$: C, 71.78; H, 6.02; N, 3.99. Found C, 72.08; H, 6.12; N, 4.06.

Reference Example 75

In a mixture of water:ethanol toluene (1:1:10, v/v, 42.0 ml) were dissolved 4-ethoxy-3-fluorophenyl borate (754 mg) and methyl 7-bromo-1-(t-butoxycarbonyl)-2,3-dihydro-1H-1-benzazepine-4-carboxylate (1305 mg). To the solution was added potassium carbonate (1132 mg), and the mixture was stirred under argon atmosphere at room temperature for 30 minutes. To the mixture was added tetrakistriphenylphosphinepalladium (158 mg), and the mixture was heated to reflux under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (75 g, hexane:ethyl acetate=4:1) to give methyl 1-(t-butoxycarbonyl)-7-(4-ethoxy-3-fluorophenyl)-2,3-dihydro-1H-1-benzazepine-4-carboxylate as yellow amorphous. The obtained methyl 1-(t-butoxycarbonyl)-7-(4-ethoxy-3-fluorophenyl)-2,3-dihydro-1H-1-benzazepine-4-carboxylate was dissolved in ethyl acetate (80 ml). To the solution was added 1N hydrochloric acid (15 ml) at room temperature, and the mixture was stirred at 100° C. for 1 hour and neutralized with 1N sodium hydroxide and saturated sodium hydrogen carbonate solution. To the mixture was added ethyl acetate, and the separated organic layer was washed with saturated sodium hydrogen carbonate solution, water and saturated brine, and dried with anhydrous magnesium sulfate. The solvent was evaporated under reduced pressure, and the residue was purified with silica gel column chromatography (50 g, hexane:ethyl acetate=9:1→4:1→2:1) to give methyl 7-(4-ethoxy-3-fluorophenyl)-2,3-dihydro-1H-1-benzazepine-4-carboxylate (1007 mg, 86%) as yellow crystals.

mp 134–137° C.

$^1$H-NMR (200 MHz, CDCl$_3$) δ 1.47 (3H, t, J=7.0 Hz), 2.89 (2H, t, J=4.4 Hz), 3.41 (2H, q, J=4.8 Hz), 3.81 (3H, s), 4.14 (2H, q, J=7.1 Hz), 4.63 (1H, brs), 6.67 (1H, d, J=8.2 Hz), 6.94–7.03 (1H, m), 7.19–7.31 (3H, m), 7.44 (1H, d, J=2.2 Hz), 7.71 (1H, s).

IR (KBr) 3385, 1696, 1624, 1503, 1478, 1435, 1312, 1292,1235, 1211, 1173 cm$^{-1}$.

Anal. Calcd. for $C_{20}H_{20}FNO_3$: C, 70.37; H, 5.91; N, 4.10. Found C, 70.35; H, 5.73; N, 4.03.

Reference Example 76

To anhydrous acetic acid (0.63 ml) was added formic acid (0.31 ml) at 0° C., and the mixture was stirred at 60° C. for 2 hours, cooled and diluted with THF (10 ml). In THF (10 ml) was dissolved methyl 7-(4-ethoxy-3-fluorophenyl)-2,3-dihydro-1H-1-benzazepine-4-carboxylate (510 mg), and the solution was added dropwise to the previously prepared solution of formic anhydride in THF, at 0° C. The mixture was stirred at room temperature for 2 hours, and the solvent was evaporated under reduced pressure. The residue was diluted with ethyl acetate, washed with saturated sodium hydrogen carbonate solution, water and saturated brine, and dried with anhydrous magnesium sulfate. The solvent was evaporated under reduced pressure to give crystals, which were washed with ethyl acetate/hexane to give methyl 7-(4-ethoxy-3-fluoropheny)-1-formyl-2,3-dihydro-1H-1-benzazepine-4-carboxylate (490 mg, 89%) as white crystals.

mp 126–127.5° C.

$^1$H-NMR (200 MHz, CDCl$_3$) δ 1.49 (3H, t, J=7.0 Hz), 2.95 (2H, td, J=5.5, 1.1 Hz), 3.83–3.88 (2H, m), 3.84 (3H, s), 4.17 (2H, q, J=7.1 Hz), 7.05 (1H, t, J=8.7 Hz), 7.19 (1H, d, J=8.0 Hz), 7.28–7.37 (2H, m), 7.54 (1H, dd, J=8.2, 2.2 Hz), 7.66 (1H, d, J=2.2 Hz), 7.75 (1H, s), 8.54 (1H, s).

IR (KBr) 1707, 1674, 1501, 1269, 1236 cm$^{-1}$.

Anal. Calcd. for $C_{21}H_{20}FNO_4$: C, 68.28; H, 5.46; N, 3.79. Found C, 68.18; H, 5.52; N, 3.70.

Reference Example 77

In THF (10.0 ml) was dissolved methyl 7-(4-ethoxy-3-fluorophenyl)-2,3-dihydro-1H-1-benzazepine-4-carboxylate (345 mg). To the solution was added pyridine (0.82 ml), and to the mixture was added a solution of methanesulfonic anhydride (880 mg) in THF (5.0 ml), at room temperature. The mixture was stirred at room temperature for 37.5 hours, diluted with ethyl acetate, and washed with water, 1N hydrochloric acid, water and saturated brine, and the organic layer was dried with anhydrous magnesium sulfate. The solvent was evaporated under reduced pressure to give crystals, which were washed with ethyl acetate/hexane to give methyl 7-(4-ethoxy-3-fluorophenyl)-1-methylsulfonyl-2,3-dihydro-1H-1-benzazepine-4-carboxylate (193 mg) as white crystals. The mother liquor was concentrated, and the residue was purified with silica gel column chromatography (15 g, hexane:ethyl acetate=3:1) to give desired product. The obtained methyl 7-(4-ethoxy-3-fluorophenyl)-1-methylsulfonyl-2,3-dihydro-1H-1-benzazepine-4-carboxylate was collected and dissolved in a mixture of THF and ethanol (1:1, v/v, 10.0 ml). To the solution was added 1N sodium hydroxide solution (3.6 ml), and the mixture was stirred at room temperature for 16.5 hours. The mixture was a little concentrated, and to the residue was added 1N hydrochloric acid to convert weakly acidic solution. The mixture was extracted with ethyl acetate, and the organic layer was washed with water and saturated brine, and dried with anhydrous magnesium sulfate. The solvent was evaporated under reduced pressure to give crystals, which were washed with ethyl acetate/hexane to give 7-(4-ethoxy-3-fluorophenyl)-1-methylsulfonyl-2,3-dihydro-1H-1-benzazepine-4-carboxylic acid (213 mg, 52%) as white crystals.

mp 237–239° C.

$^1$H-NMR (200 MHz, DMSO-d$_6$) δ 1.38 (3H, t, J=7.0 Hz), 2.90 (2H, t, J=5.4 Hz), 3.09 (3H, s), 3.70 (2H, t, J=4.8 Hz), 4.16 (2H, q, J=7.1 Hz), 7.23 (1H, d, J=8.9 Hz), 7.50–7.56 (2H, m), 7.63–7.71 (2H, m), 7.76 (1H, s), 7.94 (1H, d, J=1.6 Hz).

IR (KBr) 1686, 1669, 1622, 1499, 1350, 1271, 1150, 970, 801, 783 cm$^{-1}$.

Anal. Calcd. for $C_{20}H_{20}FNO_5S$ (0.3H$_2$O additive): C, 58.47; H, 5.05; N, 3.41. Found C, 58.50; H, 4.94; N, 3.44.

Reference Example 78

In a mixture of THF and ethanol (1:1, v/v, 20.0 ml) was dissolved methyl 7-(4-ethoxy-3-fluorophenyl)-1-formyl-2,3-dihydro-1H-1-benzazepine-4-carboxylate (441 mg). To the solution was added 1N sodium hydroxide solution (12.0 ml), and the mixture was stirred at room temperature for 16 hours. The mixture was a little concentrated, and to the residue was added 1N hydrochloric acid to convert weakly acidic solution. The mixture was extracted with ethyl acetate, and the organic layer was washed with water and saturated brine, and dried with anhydrous magnesium sulfate. The solvent was evaporated under reduced pressure to give crystals, which were washed with ethyl acetate/hexane to give 7-(4-ethoxy-3-fluorophenyl)-1-formyl-2,3-dihydro-1H-1-benzazepine-4-carboxylic acid (435 mg) as white crystals.

mp 220–222° C.

$^1$H-NMR (200 MHz, DMSO-d$_6$) δ 1.37 (3H, t, J=7.0 Hz), 2.74 (2H, t-like), 3.71 (2H, t-like), 4.16 (2H, q, J=6.9 Hz), 7.24 (1H, t, J=8.8 Hz), 7.41 (1H, d, J=8.4 Hz), 7.53–7.58 (1H, m), 7.65–7.75 (3H, m), 7.99 (1H, d-like), 8.53 (1H, s).

IR (KBr) 1705, 1655, 1499, 1362, 1304, 1292, 1273, 1231, 1217, 1196, 1134, 816 cm$^{-1}$.

Anal. Calcd. for C$_{20}$H$_{18}$FNO$_4$ (0.2H$_2$O additive): C, 66.92; H, 5.17; N, 3.90. Found C, 66.80; H, 5.28; N, 3.81.

Reference Example 79

In a mixture of water:ethanol:toluene (1:1:10, v/v, 36.0 ml) were dissolved 4-[(2-methylthio)ethoxy]phenyl borate (760 mg) and methyl 7-bromo-1-(t-butoxycarbonyl)-2,3-dihydro-1H-1-benzazepine-4-carboxylate (1141 mg). To the solution was added potassium carbonate (990 mg), and the mixture was stirred under argon atmosphere at room temperature for 30 minutes. To the mixture was added tetrakistriphenylphosphinepalladium (138 mg) and the mixture was heated to reflux under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (50 g, hexane:ethyl acetate=9:1→4:1) to give methyl 1-(t-butoxycarbonyl)-7-[4-(2-methylthio)ethoxyphenyl]-2,3-dihydro-1H-1-benzazepine-4-carboxylate (1370 mg, 98%) as white crystals.

mp 142.5–143.5° C.

$^1$H-NMR (200 MHz, CDCl$_3$) δ 1.50 (9H, s), 2.24 (3H, s), 2.89–2.95 (4H, m), 3.63–3.70 (2H, br), 3.84 (3H, s), 4.21 (2H, t, J=6.8 Hz), 6.99 (2H, d, J=8.8 Hz), 7.46–7.58 (5H, m), 7.74 (1H, s).

IR (KBr) 1703, 1497, 1391, 1238, 1163 cm$^{-1}$.

Anal. Calcd. for C$_{26}$H$_{31}$NO$_5$S: C, 66.50; H, 6.65; N, 2.98. Found C, 66.27; H, 6.68; N, 3.04.

Reference Example 80

In ethyl acetate (80 ml) was dissolved methyl 1-(t-butoxycarbonyl)-7-[4-(2-methylthio)ethoxyphenyl]-2,3-dihydro-1H-1-benzazepine-4-carboxylate (1320 mg). To the solution was added 1N hydrochloric acid (15 ml) at room temperature, and the mixture was stirred at 90° C. for 1.5 hours and neutralized with 1N sodium hydroxide and saturated sodium hydrogen carbonate solution. To the mixture was added ethyl acetate, and the separated organic layer was washed with saturated sodium hydrogen carbonate solution, water and saturated brine, and dried with anhydrous magnesium sulfate. The solvent was evaporated under reduced pressure to give crystals, which were washed with ethyl acetate/hexane to give methyl 7-[4-(2-methylthio)ethoxyphenyl]-2,3-dihydro-1H-1-benzazepine-4-carboxylate (9 10 mg) as yellow crystals. The mother liquor was concentrated under reduced pressure, and the residue was purified with silica gel column chromatography (20 g, hexane:ethyl acetate=4:1) to give methyl 7-[4-(2-methylthio)ethoxyphenyl]-2,3-dihydro-1H-1-benzazepine-4-carboxylate (910 mg) as yellow crystals.

Yield, 1020 mg (98%).

mp 114.5–117° C.

$^1$H-NMR (200 MHz, CDCl$_3$) δ 2.24 (3H, s), 2.89 (2H, t, J=4.2 Hz), 2.91 (2H, t, J=6.8 Hz), 3.41 (2H, t, J=4.7 Hz), 3.81 (3H, s), 4.20 (2H, t, J=6.9 Hz), 4.63–4.72 (1H, br), 6.68 (1H, d, J=8.4 Hz), 6.96 (2H, d, J=8.8 Hz), 7.32 (1H, dd, J=8.2, 2.2 Hz), 7.46 (1H, d, J=2.6 Hz), 7.47 (2H, d, J=8.8 Hz), 7.73 (1H, s).

IR (KBr) 3380, 1698, 1609, 1499, 1269, 1244, 1209, 1174 cm$^{-1}$.

Anal. Calcd. for C$_{21}$H$_{23}$NO$_3$S: C, 68.27; H, 6.27; N, 3.79. Found C, 68.16; H, 6.22; N, 3.75.

Reference Example 81

To anhydrous acetic acid (0.65 ml) was added formic acid (0.32 ml) at 0° C., and the mixture was stirred at 55° C. for 2 hours, air-cooled and diluted with THF (10 ml). In THF (15 ml) was dissolved methyl 7-[4-(2-methylthio)ethoxyphenyl]-2,3-dihydro-1H-1-benzazepine-4-carboxylate (565 mg), and the solution was added dropwise to the previously prepared solution of formic anhydride in THF, at 0° C. The mixture was stirred at room temperature for 2 hours, and the solvent was evaporated under reduced pressure. The residue was diluted with ethyl acetate, washed with saturated sodium hydrogen carbonate solution, water and saturated brine, and dried with anhydrous magnesium sulfate. The solvent was evaporated under reduced pressure to give crystals, which were washed with ethyl acetate/hexane to give methyl 1-formyl-7-[4-(2-methylthio)ethoxyphenyl]-2,3-dihydro-1H-1-benzazepine-4-carboxylate (578 mg, 95%) as white crystals.

mp 160–162° C.

$^1$H-NMR (200 MHz, CDCl$_3$) δ 2.24 (3H, s), 2.93 (2H, t, J=6.7 Hz), 2.95 (2H, t, J=4.6 Hz), 3.83–3.88 (2H, m), 3.84 (3H, s), 4.22 (2H, t, J=6.8 Hz), 6.97–7.04 (2H, m), 7.18 (1H, d, J=8.2 Hz), 7.49–7.55 (2H, m), 7.56 (1H, dd, J=8.2, 2.2 Hz), 7.68 (1H, d, J=1.8 Hz), 7.76 (1H, s), 8.53 (1H, s).

IR (KBr) 1705, 1673, 1607, 1497, 1435, 1358, 1236, 1192, 824 cm$^{-1}$.

Anal. Calcd. for C$_{22}$H$_{23}$NO$_4$S: C, 66.48; H, 5.83; N, 3.52. Found C, 66.23; H, 5.93; N, 3.41.

Reference Example 82

In THF (10.0 ml) were dissolved methyl 7-[4-(2-methylthio)ethoxyphenyl]-2,3-dihydro-1-benzazepine-4-carboxylate (374 mg) and pyridine (0.82 ml). To the solution was added a solution of methanesulfonic anhydride (882 mg) in THF (5.0 ml), at room temperature, and the mixture was stirred at 50° C. for 13 hours. The mixture was diluted with ethyl acetate and washed with water, 1N hydrochloric acid, water and saturated brine, and the organic layer was dried with anhydrous magnesium sulfate. The solvent was evaporated under reduced pressure, and the residue was purified with silica gel column chromatography (25 g, hexane:ethyl acetate=4:1→1:1) to give crystals, which were washed with ethyl acetate/hexane to give methyl 1-methylsulfonyl-7-[4-(2-methylthio)ethoxyphenyl]-2,3-dihydro-1H-1-benzazepine-4-carboxylate (201 mg, 44%) as white crystals.

mp 157–159° C.

$^1$H-NMR (200 MHz, CDCl$_3$) δ 2.24 (3H, s), 2.78 (3H, s), 2.92 (2H, t, J=6.8 Hz), 3.05 (2H, td-like, J=5.4 Hz (t)), 3.86 (3H, s), 3.87 (2H, t, J=5.9 Hz), 4.22 (2H, t, J=6.7 Hz), 7.00 (2H, d, J=8.8 Hz), 7.49–7.57 (3H, m), 7.64 (1H, d, J=2.0 Hz), 7.68 (1H, d, J=8.4 Hz), 7.81 (1H, s).

IR (KBr) 1709, 1493, 1343, 1248, 1155 cm$^{-1}$.

Anal. Calcd. for $C_{22}H_{25}NO_5S_2$: C, 59.04; H, 5.63; N, 3.13. Found C, 58.91; H, 5.65; N, 3.08.

Reference Example 83

In a mixture of THF and ethanol (1:1, v/v, 40.0 ml) was dissolved methyl 1-formyl-7-[4-(2-methylthio)ethoxyphenyl]-2,3-dihydro-1H-1-benzazepine-4-carboxylate (531 mg). To the solution was added 1N sodium hydroxide solution (13.5 ml), and the mixture was stirred at room temperature for 14 hours. The mixture was a little concentrated, and to the residue was added 1N hydrochloric acid to convert weakly acidic solution. The mixture was extracted with ethyl acetate, and the organic layer was washed with water and saturated brine, and dried with anhydrous magnesium sulfate. The solvent was evaporated under reduced pressure to give crystals, which were washed with ethyl acetate/hexane to give 1-formyl-7-[4-(2-methylthio)ethoxyphenyl]-2,3-dihydro-1H-1-benzazepine-4-carboxylic acid (470 mg, 92%) as white crystals.

mp 199–201° C.

$^1$H-NMR (200 MHz, DMSO-d$_6$) δ 2.18 (3H, s), 2.76 (2H, t-like), 2.87 (2H, t, J=6.6 Hz), 3.72 (2H, t-like), 4.21 (2H, t, J=6.2 Hz), 7.04 (2H, d, J=8.8 Hz), 7.40 (1H, d, J=8.8 Hz), 7.67–7.74 (4H, m), 7.91 (1H, s), 8.53 (1H, s).

IR (KBr) 1688, 1671, 1501, 1422, 1364, 1292, 1256, 1194, 1182, 1019, 822 cm$^{-1}$.

Anal. Calcd. for $C_{21}H_{21}NO_4S$: C, 65.78; H, 5.52; N, 3.65. Found C, 65.49; H, 5.62; N, 3.58.

Reference Example 84

In a mixture of THF and ethanol (1:1, v/v, 20.0 ml) was dissolved methyl 1-methylsulfonyl-7-[4-(2-methylthio)ethoxyphenyl]-2,3-dihydro-1H-1-benzazepine-4-carboxylate (169 mg). To the solution was added 1N sodium hydroxide solution (5.5 ml), and the mixture was stirred at room temperature for 14 hours. The mixture was a little concentrated, and to the residue was added 1N hydrochloric acid to convert weakly acidic solution. The mixture was extracted with ethyl acetate, and the organic layer was washed with water and saturated brine, and dried with anhydrous magnesium sulfate. The solvent was evaporated under reduced pressure to give crystals, which were washed with ethyl acetate/hexane to give 1-methylsulfonyl-7-[4-(2-methylthio)ethoxyphenyl]-2,3-dihydro-1H-1-benzazepine-4-carboxylic acid (157 mg, 96%) as white crystals.

mp 234–239° C. (dec.).

$^1$H-NMR (200 MHz, DMSO-d$_6$) δ 2.17 (3H, s), 2.87 (2H, t, J=6.6 Hz), 2.90 (2H, t-like), 3.08 (3H, s), 3.70 (2H, t-like), 4.21 (2H, t, J=6.6 Hz), 7.05 (2H, d, J=8.8 Hz), 7.51 (1H, d, J=8.0 Hz), 7.61–7.75 (4H, m), 7.86 (1H, d-like).

IR (KBr) 1669, 1495, 1437, 1343, 1271, 1250, 1240, 1144, 824, 517 cm$^{-1}$.

Anal. Calcd. for $C_{21}H_{23}NO_5S_2$: C, 58.18; H, 5.35; N, 3.23. Found C, 58.39; H, 5.39; N, 3.17.

Reference Example 85

In a mixture of water ethanol toluene (1:1:10, v/v, 42.0 ml) were dissolved 4-(2-propoxy)ethoxyphenyl borate (920 mg) and methyl 7-bromo-1-(t-butoxycarbonyl)-2,3-dihydro-1H-1-benzazepine-4-carboxylate (1308 mg). To the solution was added potassium carbonate (1135 mg), and the mixture was stirred under argon atmosphere at room temperature for 30 minutes. To the mixture was added tetrakistriphenylphosphinepalladium (119 mg), and the mixture was heated to reflux under argon atmosphere for 14.5 hours. The mixture was diluted with ethyl acetate, and washed with water and saturated brine, and the organic layer was dried with anhydrous magnesium sulfate. The solvent was evaporated under reduced pressure and the residue was purified with silica gel column chromatography (50 g, hexane:ethyl acetate= 9:1→3:1) to give methyl 1-(t-butoxycarbonyl)-7-[4-(2-propoxy)ethoxyphenyl]-2.3-dihydro-1H-1-benzazepine-4-carboxylate (1536 mg, 93%) as colorless oil.

$^1$H-NMR (200 MHz, CDCl$_3$) δ 0.95 (3H, t, J=7.4 Hz), 1.49 (9H, s), 1.66 (2H, sextet, J=7.1 Hz), 2.91 (2H, t, J=4.7 Hz), 3.52 (2H, t, J=6.7 Hz), 3.55–3.82 (2H, br), 3.82 (2H, t, J=4.9 Hz), 3.83 (3H, s), 4.18 (2H, t, J=4.9 Hz), 7.01 (2H, d, J=8.8 Hz), 7.45–7.58 (5H, m), 7.74 (1H, s).

IR (KBr) 1705, 1497, 1391, 1287, 1236, 1163, 1086 cm$^{-1}$.

Reference Example 86

In ethyl acetate (80 ml) was dissolved methyl 1-(t-butoxycarbonyl)-7-[4-(2-propoxy)ethoxyphenyl]-2,3-dihydro-1H-1-benzazepine-4-carboxoylate (1536 mg). To the solution was added 1N hydrochloric acid (20 ml) at room temperature, and the mixture was stirred at 90° C. for 1 hour and neutralized with saturated sodium hydrogen carbonate solution, and to the mixture was added ethyl acetate. The separated organic layer was washed with saturated sodium hydrogen carbonate solution, water and saturated brine, and dried with anhydrous magnesium sulfate. The solvent was evaporated under reduced pressure to give crystals, which were washed with ethyl acetate/hexane to give methyl 7-[4-(2-propoxy)ethoxyphenyl]-2,3-dihydro-1H-1-benzazepine-4-carboxylate (523 mg) as yellow crystals. The mother liquor was concentrated under reduced pressure, and the residue was purified with silica gel column chromatography (65 g, hexane:ethyl acetate=3:1) to give methyl 7-[4-(2-propoxy)ethoxyphenyl]-2,3-dihydro-1H-1-benzazepine-4-carboxylate (606 mg) as yellow crystals.

Yield, 1129 mg (93%).

mp 86–88° C.

$^1$H-NMR (200 MHz, CDCl$_3$) δ 0.94 (3H, t, J=7.4 Hz), 1.65 (2H, sextet, J=7.2 Hz), 2.89 (2H, t, J=4.5 Hz), 3.40 (2H, brs), 3.51 (2H, t, J=6.8 Hz), 3.81 (3H, s and 2H, t, J=4.9 Hz), 4.16 (2H, t, J=5.0 Hz), 4.60 (1H, brs), 6.67 (1H, d, J=8.4 Hz), 6.95–7.01 (2H, m), 7.32 (1H, dd, J=8.2, 2.2 Hz), 7.42–7.48 (2H, m), 7.46 (1H, d, J=2.0 Hz), 7.73 (1H, s).

IR (KBr) 3380, 1698, 1611, 1501, 1269, 1246, 1209, 1177, 820 cm$^{-1}$.

Anal. Calcd. for $C_{23}H_{27}NO_4$: C, 72.42; H, 7.13; N, 3.67. Found C, 72.28; H, 7.09; N, 3.73.

Reference Example 87

To anhydrous acetic acid (0.51 ml) was added formic acid, (0.25 ml) at 0° C., and the mixture was stirred at 55° C. for 2 hours, air-cooled and diluted with THF (10 ml). In THF (15 ml) was dissolved methyl 7-[4-(2-propoxy)ethoxyphenyl]-2,3-dihydro-1H-1-benzazepine-4-carboxylate (462 mg), and the solution was added dropwise to the previously prepared solution of formic anhydride in THF, at 0° C. The mixture was stirred at room temperature for 2 hours, and the solvent was evaporated under reduced pressure. The residue was diluted with ethyl acetate, washed with saturated sodium hydrogen carbonate solution, water and saturated brine, and dried with anhydrous, magnesium sulfate. The solvent was evaporated under reduced pressure to give crystals, which were washed with ethyl acetate/hexane to give methyl 1-formyl-7-[4-(2-propoxy)ethoxyphenyl]-2,3-dihydro-1H-1-benzazepine-4-carboxylate (496 mg) as white crystals.

mp 107–108° C.

$^1$H-NMR (200 MHz, CDCl$_3$) δ 0.95 (3H, t, J=7.3 Hz), 1.62 (2H, sextet, J=7.2 Hz), 2.95 (2H, t, J=4.7 Hz), 3.52 (2H, t, J=6.7 Hz), 3.80–3.88 (4H, m), 3.84 (3H, s), 4.18 (2H, t, J=4.9 Hz), 7.03 (2H, d, J=8.8 Hz), 7.17 (1H, d, J=8.0 Hz), 7.51 (2H, d, J=8.8 Hz), 7.56 (1H, dd, J=8.0, 2.2 Hz), 7.68 (1H, d, J=1.8 Hz), 7.75 (1H, s), 8.53 (1H, s).

IR (KBr) 1709, 1678, 1360, 1291, 1236, 1192, 824 cm$^{-1}$.

Anal. Calcd. for C$_{24}$H$_{27}$NO$_5$: C, 70.40; H, 6.65; N, 3.42. Found C, 70.37; H, 6.64; N, 3.41.

Reference Example 88

In THF (20.0 ml) were dissolved methyl 7-[4-(2-propoxy)ethoxyphenyl]-2,3-dihydro-1H-1-benzazepine-4-carboxylate (600 mg) and pyridine (1.53 ml). To the solution was added a solution of methanesulfonic anhydride (1.64 g) in THF (10.0 ml), at room temperature, and the mixture was stirred at 50° C. for 14.5 hours. The mixture was diluted with ethyl acetate, and washed with water, 1N hydrochloric acid, water and saturated brine, and the organic layer was dried with anhydrous magnesium sulfate. The solvent was evaporated under reduced pressure, and the residue was purified with silica gel column chromatography (35 g, hexane:ethyl acetate=4:1→2:1) to give crystals, which were washed with ethyl acetate/hexane to give methyl 1-methylsulfonyl-7-[4-(2-propoxy)ethoxyphenyl]-2,3-dihydro-1H-1-benzazepine-4-carboxylate (231 mg) as white crystals. The mother liquor was concentrated under reduced pressure, and the residue was purified with silica gel column chromatography (350 g, hexane:ethyl acetate=3:1→2:1) to give methyl 1-methylsulfonyl-7-[4-(2-propoxy)ethoxyphenyl]-2,3-dihydro-1H-1-benzazepine-4-carboxylate (170 mg) as white crystals.

Yield, 402 mg (56%).

mp 119–121° C.

$^1$H-NMR (200 MHz, CDCl$_3$) δ 0.95 (3H, t, J=7.4 Hz), 1.65 (2H, sextet, J=7.3 Hz), 2.78 (3H, s), 3.05 (2H, t, J=5.5 Hz), 3.52 (2H, t, J=6.8 Hz), 3.80–3.89 (4H, m), 3.85 (3H, s), 4.18 (2H, t, J=5.0 Hz), 7.02 (2H, d, J=8.8 Hz), 7.51 (2H, d, J=8.8 Hz), 7.54 (1H, dd, J=8.4, 2.2 Hz), 7.63 (1H, d, J=1.8 Hz), 7.67 (1H, d, J=8.4 Hz), 7.80 (1H, s).

IR (KBr) 1709, 1493, 1345, 1289, 1248, 1188, 1155, 1132, 1103 cm$^{-1}$.

Anal. Calcd. for C$_{24}$H$_{29}$NO$_6$S (0.4H$_2$O additive): C, 61.76; H, 6.44; N, 3.00. Found C, 61.61; H, 6.22; N, 2.96.

Reference Example 89

In a mixture of THF and ethanol (1:1, v/v, 30.0 ml) was dissolved methyl 1-formyl-7-[4-(2-propoxy)ethoxyphenyl]-2,3-dihydro-1H-1-benzazepine-4-carboxylate (445 mg). To the solution was added 1N sodium hydroxide solution (11.0 ml), and the mixture was stirred at room temperature for 13 hours. The mixture was a little concentrated, and to the residue was added 1N hydrochloric acid to convert weakly acidic solution. The mixture was extracted with ethyl acetate, and the organic layer was washed with water and saturated brine, and dried with anhydrous magnesium sulfate. The solvent was evaporated under reduced pressure to give crystals, which were washed with ethyl acetate/hexane to give 1-formyl-7-[4-(2-propoxy)ethoxyphenyl]-2,3-dihydro-1H-1-benzazepine-4-carboxylic acid (430 mg) as white crystals.

mp 165–166° C.

$^1$H-NMR (200 MHz, DMSO-d$_6$) δ 0.88 (3H, t, J=7.5 Hz), 1.54 (2H, sextet, J=7.1 Hz), 2.75 (2H, t, J=6.8 Hz), 3.72 (4H, t, J=4.6 Hz), 4.15 (2H, t, J=4.6 Hz), 7.04 (2H, d, J=8.8 Hz), 7.40 (1H, d, J=8.0 Hz), 7.69 (2H, d, J=8.8 Hz), 7.67–7.74 (2H, m), 7.92 (1H, d, J=1.8 Hz), 8.53 (1H, s).

IR (KBr) 1682, 1499, 1360, 1291, 1258, 1246, 1192, 1130, 820 cm$^{-1}$.

Anal. Calcd. for C$_{23}$H$_{25}$NO$_5$: C, 69.86; H, 6.37; N, 3.54. Found C, 69.69; H, 6.38; N, 4.59.

Reference Example 90

In a mixture of THF and ethanol (1:1, v/v, 30.0 ml) was dissolved methyl 1-methylsulfonyl-7-[4-(2-propoxy)ethoxyphenyl]-2,3-dihydro-1H-1-benzazepine-4-carboxylate (354 mg). To the solution was added 1N sodium hydroxide solution (7.7 ml), and the mixture was stirred at room temperature for 15.5 hours. The mixture was a little concentrated, and to the residue was added 1N hydrochloric acid to convert weakly acidic solution. The mixture was extracted with ethyl acetate, and the organic layer was washed with water and saturated brine, and dried with anhydrous magnesium sulfate. The solvent was evaporated under reduced pressure to give crystals, which were washed with ethyl acetate/hexane to give 1-methylsulfonyl-7-[4-(2-propoxy)ethoxyphenyl]-2,3-dihydro-1H-1-benzazepine-4-carboxylic acid (337 mg, 98%) as white crystals.

mp 213–215° C.

$^1$H-NMR (200 MHz, DMSO-d$_6$) δ 0.88 (3H, t, J=7.3 Hz), 1.54 (2H, sextet, J=7.0 Hz), 2.50 (3H, s), 3.33 (2H, t-like), 3.43 (2H, t, J=6.6 Hz), 3.72 (4H, t-like), 4.15 (2H, t-like), 7.04 (2H, d, J=8.8 Hz), 7.51 (1H, d, J=8.0 Hz), 7.63–7.75 (4H, m), 7.88 (1H, s).

IR (KBr) 1669, 1493, 1341, 1294, 1271, 1250, 1154, 1128, 785, 519 cm$^{-1}$.

Anal. Calcd. for C$_{23}$H$_{27}$NO$_6$S (0.1H$_2$O additive): C, 61.75; H, 6.13; N, 3.13. Found C, 61.50; H, 5.88; N, 3.01.

Reference Example 91

In THF (1000 ml) was dissolved 4-[[N-(benzyloxy)carbonyl]amino]butyric acid (50.0 g). To the solution were added propyl bromide (77.5 g) and sodium iodide (94.4 g), and to the mixture was gradually added at −5° C. 60% sodium hydride (25.2 g). Under nitrogen atmosphere, the mixture was stirred at 0° C. for 15 minutes and then at 75° C. for 4 days. The mixture was concentrated under reduced pressure, and to the residue was added water. The aqueous layer was adjusted to pH11 with sodium hydroxide (granule) and washed with ether (twice). The aqueous layer was adjusted to pH2 with concentrated hydrochloric acid and washed with ethyl acetate (thrice). The organic layer was washed with 1M sodium thiosulfate solution and saturated brine, and dried with anhydrous magnesium sulfate. The solvent was evaporated under reduced pressure to give 4-[[N-(benzyloxy)carbonyl]-N-propylamino]butyric acid (35.8 g, 61%).

¹H-NMR (200 MHz, CDCl₃) δ 0.88 (3H, t, J=7.3 Hz), 1.50–1.57 (2H, m), 1.85–1.90 (2H, m), 2.34–2.41 (2H, m), 3.17–3.30 (4H, m), 5.13 (2H, s), 7.35 (5H, s).

Reference Example 92

To 4-[[N-(benzyloxy)carbonyl]-N-propylamino]butyric acid (35.8 g) was added t-butanol (350 ml), and then was added di-t-butyl dicarbonate (140 g). To the mixture was added dimethylaminopyridine (4.69 g), and the mixture was stirred at room temperature for 30 minutes. The mixture was concentrated under reduced pressure, and the residue was purified with silica gel column chromatography to give pale yellow oil of t-butyl 4-[[N-(benzyloxy)carbonyl]-N-propylamino]butyrate (23.8 g, 55%).

¹H-NMR (200 MHz, CDCl₃) δ 0.88 (3H, t, J=7.3 Hz), 1.45 (9H, s), 1.52–1.59 (2H, m), 1.81–1.84 (2H, m), 2.23 (2H, t, J=7.1 Hz), 3.17–3.27 (4H, m), 5.13 (2H, s), 7.35 (5H, s).

IR (KBr) 2969, 1728, 1703, 1476, 1456, 1422, 1368, 1242, 1155, 1136 cm⁻¹.

Reference Example 93

In methanol (250 ml) was dissolved t-butyl 4-[[N-(benzyloxy)carbonyl]-N-propylamino]butyrate (23.7 g), and to the solution was added 10% palladium on carbon (2.37 g). The mixture was stirred under hydrogen atmosphere at room temperature for 2 hours, and 10% palladium on carbon was removed. The solvent was evaporated under reduced pressure to give colorless oil of t-butyl 4-propylaminobutyrate [16.8 g (containing methanol)].

¹H-NMR (200 MHz, CDCl₃) δ 0.92 (3H, t, J=7.1 Hz), 1.45 (9H, s), 1.47–1.67 (4H, m), 1.70–1.85 (2H, m), 2.25 (2H, q, J=7.9 Hz), 2.60 (2H, dt, J=11.6, 7.2 Hz), 3.21 (1H, m).

IR (KBr) 2967, 2936, 1728, 1480, 1456, 1424, 1368, 1246, 1155 cm⁻¹.

Reference Example 94

To a solution of t-butyl 4-propylaminobutyrate (14.2 g, 70.7 mmol) in DMF (20 ml) were added 5-bromo-2-fluorobenzaldehyde (14.4 g, 70.9 mmol) and potassium carbonate (14.7 g, 106 mmol) at room temperature, and the mixture was stirred at 80° C. for 94 hours. The mixture was diluted with ethyl acetate, washed with water and saturated brine, and dried with anhydrous magnesium sulfate. The solvent was evaporated under reduced pressure, and the residue was purified with silica gel column chromatography (hexane:ethyl acetate=10:1) to give yellow oil of t-but yl 4-(4-bromo-2-formylphenyl)propylaminobutyrate (14.2 g, 52%).

¹H-NMR (200 MHz, CDCl₃) δ 0.84 (3H, t, J=7.8 Hz), 1.45 (9H, s), 1.42–1.63 (2H, m), 1.81 (2H, quint, J=7.4 Hz), 2.19 (2H, t, J=7.5 Hz), 3.09 (2H, t, J=7.6 Hz), 3.17 (2H, t, J=7.5 Hz), 7.06 (1H, d, J=8.8 Hz), 7.56 (1H, dd, J=8.7, 2.5 Hz), 7.90 (1H, d, J=2.6 Hz), 10.24 (1H, s).

IR (KBr) 2971, 1730, 1694, 1480, 1368, 1244, 1157 cm⁻¹.

Reference Example 95

In a mixture of t-butanol and toluene (1:10, v/v, 440 ml) was dissolved t-butyl 4-(4-bromo-2-formylphenyl)propylbutyrate (14.1 g). To the solution was added sodium t-butoxide (5.29 g) at room temperature, and the mixture was heated to reflux for 1 hour (90° C.), air-cooled, diluted with ethyl acetate, washed with water, 0.5N sodium hydroxide solution, water and saturated brine, and dried with anhydrous magnesium sulfate. The solvent was evaporated under reduced pressure, and the residue was purified with silica gel column chromatography (hexane:ethyl acetate= 4:1) to give yellow oil of t-butyl 7-bromo-1-propyl-2,3-dihydro-1H-1-benzazepine-4-carboxylate (8.07 g, 60%).

¹H-NMR (200 MHz, CDCl₃) δ 0.95 (3H, t, J=7.5 Hz), 1.53 (9H, s), 1.68 (2H, sextet, J=7.6 Hz), 2.75 (2H, t, J=4.4 Hz), 3.18–3.26 (4H, m), 6.67 (1H, d, J=9.2 Hz), 7.22 (1H, dd, J=8.8, 2.6 Hz), 7.39 (1H, d, J=2.6 Hz), 7.46 (1H, s).

IR (KBr) 2969, 1698, 1497, 1368, 1269, 1254, 1159 cm⁻¹.

Reference Example 96

In ethyl acetate (80 ml) was dissolved t-butyl 7-bromo-1-propyl-2,3-dihydro-1H-1-benzazepine-4-carboxylate (8.05 g). To the solution was added a solution of 4N hydrochloric acid in ethyl acetate (80 ml), and the mixture was stirred at room temperature for 12 hours. To the mixture was added water, and the mixture was adjusted to pH2 with saturated sodium hydrogen carbonate solution and extracted with ethyl acetate. The organic layer was dried with anhydrous magnesium sulfate. The solvent was evaporated under reduced pressure, and the residue of solid was washed with hexane-ethyl acetate to give yellow crystals of 7-bromo-1-propyl-2,3-dihydro-1H-1-benzazepine-4-carboxylic acid (2.61 g, 39%).

mp 172–173° C.

¹H-NMR (200 MHz, CDCl₃) δ 0.95 (3H, t, J=7.3 Hz), 1.70 (2H, sextet, J=7.5 Hz), 2.81 (2H, t, J=4.6 Hz), 3.22–3.29 (4H, m), 6.70 (1H, d, J=8.8 Hz), 7.25 (1H, dd, J=8.8, 2.6 Hz), 7.43 (1H, d, J=2.0 Hz), 7.69 (1H, s).

IR (KBr) 2963, 1674, 1497, 1410, 1277, 1171 cm⁻¹.

Anal. Calcd. for $C_{14}H_{16}BrNO_2$: C, 54.21; H, 5.20; N, 4.52. Found C, 54.17; H, 5.05; N, 4.42.

Reference Example 97

In DMF (12 ml) was dissolved 7-bromo-1-propyl-2,3-dihydro-1H-1-benzazepine-4-carboxylic acid (2430 mg, 7.83 mmol). To the solution was added thionyl chloride (1.4 ml), and the mixture was stirred at room temperature for 30 minutes. The solvent was evaporated under reduced pressure, and the residue was suspended in THF (50 ml). To 4-[[N-methyl-N-(tetrahydro-2H-pyran-4-yl)amino]methyl] aniline dihydrochloride (2757 mg) was added THF (40 ml), and to the mixture was added dropwise triethylamine (8.2 ml). The mixture was stirred at room temperature for 30 minutes, and to the mixture was added dropwise the previously prepared acid chloride suspension in THF, at 0° C. The mixture was stirred at room temperature for 21 hours, and the mixture was concentrated. To the mixture was added ethyl acetate, and the mixture was washed with water and saturated brine, and dried with anhydrous magnesium sulfate. The solvent was evaporated under reduced pressure, and the residue was purified with silica gel column chromatography (ethyl acetate→ethyl acetate:ethanol=10:1) and recrystallized from ethyl acetate-hexane to give yellow crystals of 7-bromo-N-[4-[[N-methyl-N-(tetrahydro-2H-pyran-4-yl)amino]methyl]phenyl]-1-propyl-2,3-dihydro-1H-1-benzazepine-4-carboxamide (3219 mg, 80%).

mp 134–136° C.

¹H-NMR (200 MHz, CDCl₃) δ 0.97 (3H, t, J=7.5 Hz), 1.60–1.80 (6H, m), 2.21 (3H, s), 2.57–2.70 (1H, m), 2.89 (2H, t, J=4.6 Hz), 3.22–3.30 (4H, m), 3.37 (2H, td, J=11.1, 2.8 Hz), 3.57 (2H, s), 4.01–4.07 (2H, m), 6.71 (1H, d, J=9.2 Hz), 7.19 (1H, s), 7.24 (1H, dd, J=9.0, 2.6 Hz), 7.30 (2H, d, J=8.4 Hz), 7.41 (1H, d, J=2.6 Hz), 7.50 (1H, s), 7.52 (2H, d, J=8.4 Hz).

IR (KBr) 2957, 1645, 1597, 1514, 1497, 1406, 1314, 1246, 1173 cm$^{-1}$.

Anal. Calcd. for $C_{27}H_{34}BrN_3O_2$: C, 63.28; H, 6.69; N, 8.20. Found C, 63.19; H, 6.54; N, 8.05.

Working Example 1

Production of Compound 1

In DMF (10 ml) was dissolved 7-[4-(2-ethoxyethoxy)phenyl]-1-formyl-2,3-dihydro-1H-1-benzazepine 4-carboxylic acid (0.18 g). To the solution was added, under ice-cooling, thionyl chloride (0.09 ml), and the mixture was stirred at room temperature for 30 minutes. Under reduced pressure, the solvent was evaporated, and the residue was dissolved in THF (20 ml). The solution was added dropwise to a solution of 4-[N-methyl-N-(tetrahydro-2H-pyran-4-yl)aminomethyl]aniline (0.12 g) and triethylamine (0.33 ml) in THF (10 ml), under ice-cooling, and the mixture was stirred under nitrogen atmosphere at room temperature overnight. Under reduced pressure, the solvent was evaporated. To the residue was added water, and the mixture was extracted with ethyl acetate. The organic layer was washed with water and saturated brine and dried with anhydrous magnesium sulfate, and the solvent was evaporated to give crude crystals, which were recrystallized from ethyl acetate/hexane to give 7-[4-(2-ethoxyethoxy)phenyl]-1-formyl-N-[4-[[N-methyl-N-(tetrahydro-2H-pyran-4-yl)amino]methyl]phenyl]-2,3-dihydro-1H-1-benzazepine-4-carboxamide (Compound 1) (0.23 g) as colorless crystals.

mp 192–194° C.

$^1$H-NMR (δ ppm, CDCl$_3$) 1.26 (3H, t, J=7.0 Hz), 1.59–1.75 (4H, m), 2.21 (3H, s), 2.59–2.70 (1H, m), 3.02 (2H, t, J=5.1 Hz), 3.37 (2H, dt, J=1.5, 11.4 Hz), 3.57 (2H, s), 3.63 (2H, q, J=7.0 Hz), 3.83 (2H, t, J=4.8 Hz), 3.91 (2H, t, J=5.1 Hz), 4.01–4.07 (2H, m), 4.18 (2H, t, J=4.8 Hz), 7.02 (2H, d, J=8.8 Hz), 7.18 (1H, d, J=8.4 Hz), 7.31 (2H, d, J=8.4 Hz), 7.45–7.57 (6H, m), 7.65 (1H, br), 7.66 (1H, d, J=1.8 Hz), 8.54 (1H, s).

IR (KBr) ν: 3297, 2946, 2847, 1669 cm$^{-1}$.

Anal. Calcd. for $C_{35}H_{41}N_3O_5$: C, 72.02; H, 7.08; N, 7.20. Found C, 71.90; H, 6.79; N, 7.05.

Working Example 2

Production of Compound 2

In DMF (5 ml) was dissolved 7-[4-(3-ethoxypropoxy)phenyl]-1-formyl-2,3-dihydro-1H-1-benzazepine-4-carboxylic acid (0.25 g). To the solution was added, under ice-cooling, thionyl chloride (0.12 ml), and the mixture was stirred at room temperature for 30 minutes. Under reduced pressure, the solvent was evaporated, and the residue was suspended in THF (15 ml). The suspension was added dropwise to a solution of 4-[N-methyl-N-(tetrahydro-2H-pyran-4-yl)aminomethyl]aniline (0.16 g) and triethylamine (0.44 ml) in THF (5 ml), under ice-cooling, and the mixture was stirred under nitrogen atmosphere at room temperature overnight. Under reduced pressure, the solvent was evaporated. To the residue was added water, and the mixture was extracted with ethyl acetate. The organic layer was washed with water and saturated brine and dried with anhydrous magnesium sulfate, and the solvent was evaporated to give crude crystals, which were recrystallized from ethyl acetate/hexane to give 7-[4-(3-ethoxypropoxy)phenyl]-1-formyl-N-[4-[[N-methyl-N-(tetrahydro-2H-pyran-4-yl)amino]methyl]phenyl]-2,3-dihydro-1H-1-benzazepine-4-carboxamide (Compound 2) (0.29 g) as colorless crystals.

mp 166–169° C.

$^1$H-NMR (δ ppm, CDCl$_3$) 1.22 (3H, t, J=7.0 Hz), 1.64–1.82 (4H, m), 2.02–2.15 (2H, m), 2.21 (3H, s), 2.60–2.68 (1H, m), 3.03 (2H, t, J=5.5 Hz), 3.37 (2H, dt, J=2.6, 11.2 Hz), 3.46–3.66 (6H, m), 3.92 (2H, t, J=5.5 Hz), 4.02–4.07 (2H, m), 4.13 (2H, t, J=6.3 Hz), 7.01 (2H, d, J=8.8 Hz), 7.19 (1H, d, J=8.2 Hz), 7.32 (2H, d, J=8.6 Hz), 7.47–7.60 (6H, m), 7.68 (1H, d, J=2.0 Hz), 8.55 (1H, s).

IR (KBr) ν: 2946, 2849, 1669 cm$^{-1}$.

Anal. Calcd. for $C_{36}H_{43}N_3O_5$: C, 72.34; H, 7.25; N, 7.03. Found C, 72.54; H, 7.11; N, 7.00.

Working Example 3

Production of Compound 3

In DMF (5 ml) was dissolved 7-[4-(2-butoxyethoxy)phenyl]-1-formyl-2,3-dihydro-1H-1-benzazepine-4-carboxylic acid (0.23 g). To the solution was added, under ice-cooling, thionyl chloride (0.11 ml), and the mixture was stirred at room temperature for 30 minutes. Under reduced pressure, the solvent was evaporated, and the residue was dissolved in THF (25 ml). The solution was added dropwise to a solution of 4-[N-methyl-N-(tetrahydro-3H-pyran-4-yl)aminomethyl]aniline (0.15 g), and triethylamine (0.4 ml) in THF (5 ml), under ice-cooling, and the mixture was stirred under nitrogen atmosphere at room temperature overnight. Under reduced pressure, the solvent was evaporated. To the residue was added water, and the mixture was extracted with ethyl acetate. The organic layer was washed with water and saturated brine and dried with anhydrous magnesium sulfate, and the solvent was evaporated to give crude crystals, which were recrystallized from ethanol to give 7-[4-(2-butoxyethoxy)phenyl]-1-formyl-N-[[4-[N-methyl-N-(tetrahydro-2H-pyran-4-yl)amino]methyl]phenyl]-2,3-dihydro-1H-1-benzazepine-4-carboxamide (Compound 3) (0.23 g) as colorless crystals.

mp 171–173° C.

$^1$H-NMR (δ ppm, CDCl$_3$) 0.94 (3H, t, J=7.2 Hz), 1.31–1.49 (2H, m), 1.55–1.65 (2H, m), 1.70–1.75 (4H, m), 2.21 (3H, s), 2.60–2.71 (1H, m), 3.04 (2H, t, J=5.5 Hz), 3.37 (2H, dt, J=3.2, 11.3 Hz), 3.53–3.59 (4H, m), 3.82 (2H, t, J=4.9 Hz), 3.92 (2H, t, J=5.5 Hz), 4.01–4.07 (2H, m), 4.18 (2H, t, J=4.9 Hz), 7.03 (2H, d, J=8.8 Hz), 7.19 (1H, d, J=8.2 Hz), 7.32 (2H, d, J=8.4 Hz), 7.46–7.56 (6H, m), 7.68 (1H, d, J=1.8 Hz), 8.55 (1H, s).

IR (KBr) ν: 2940, 1669, 1518, 1497 cm$^{-1}$.

Anal. Calcd. for $C_{37}H_{45}N_3O_5$: C, 72.64; H, 7.41; N, 6.87. Found C, 72.49; H, 7.11; N, 6.71.

Working Example 4

Production of Compound 4

In DMF (3.5 ml) was dissolved 7-[4-[N-(2-ethoxyethyl)-N-methylamino]phenyl]-1-formyl-2,3-dihydro-1H-1-benzazepine-4-carboxylic acid (0.17 g). To the solution was added, under ice-cooling, thionyl chloride (0.08 ml), and the mixture was stirred at room temperature for 30 minutes. Under reduced pressure, the solvent was evaporated, and the residue was dissolved in THF (25 ml). The solution was added dropwise to a solution of 4-[N-methyl-N-(tetrahydro-2H-pyran-4-yl)aminomethyl]aniline (0.11 g) and triethylamine (0.31 ml) in THF (6.5 ml), under ice-cooling, and the mixture was stirred under nitrogen atmosphere at room temperature for 1 hour, poured into water and extracted with ethyl acetate. The organic layer was washed with water and saturated brine and dried with anhydrous magnesium sulfate, and the solvent was evaporated. The residue was purified with silica gel column chromatography (ethyl acetate/ethanol) to give crude crystals, which were recrystallized from ethanol to give 7-[4-[N-(2-ethoxyethyl)-N-methylamino]phenyl]-1-formyl-N-[4-[[N-methyl-N-(tetrahydro-2H-pyran-4-yl)amino]methyl]phenyl]-2,3-dihydro-1H-1-benzazepine-4-carboxamide (Compound 4) (0.14 g) as pale yellow crystals.

mp 157–158° C.

$^1$H-NMR (δ ppm, CDCl$_3$) 1.21 (3H, t, J=7.4 Hz), 1.59–1.82 (4H, m), 2.20 (3H, s), 2.64 (1H, m), 2.96–3.06 (2H, m), 3.05 (3H, s), 3.30–3.43 (2H, m), 3.52 (2H, q, J=7.0 Hz), 3.57 (2H, s), 3.56–3.63 (2H, m), 3.88–3.94 (2H, m), 3.99–4.07 (2H, m), 6.80 (2H, d, J=8.8 Hz), 7.16 (1H, m), 7.29–7.56 (7H, m), 7.66 (1H, s), 8.53 (1H, s).

IR (KBr) ν: 2946, 2849, 1669, 1609, 1505, 1360, 1316, 1204, 1113, 814 cm$^{-1}$.

Working Example 5

Production of Compound 5

In DMF (5 ml) was dissolved 7-[4-[N-(2-ethoxyethyl)-N-ethylamino]phenyl]-1-formyl-2,3-dihydro-1H-1-benzazepine-4-carboxylic acid (0.2 g). To the solution was added, under ice-cooling, thionyl chloride (0.09 ml), and the mixture was stirred at room temperature for 30 minutes. Under reduced pressure, the solvent was evaporated, and the residue was dissolved in THF (25 ml). The solution was added dropwise a solution of 4-[N-methyl-N-(tetrahydro-2H-pyran-4-yl)aminomethyl]aniline (0.20 g) and triethylamine (0.35 ml) in THF (5 ml), under ice-cooling, and the mixture was stirred under nitrogen atmosphere stirred at room temperature overnight. Under reduced pressure, the solvent was evaporated. To the residue was added water, and the mixture was extracted with ethyl acetate. The organic layer was washed with water and saturated brine and dried with anhydrous magnesium sulfate, and the solvent was evaporated to give crude crystals, which were recrystallized from ethyl acetate/hexane to give 7-[4-[N-(2-ethoxyethyl)-N-ethylamino]phenyl]-1-formyl-N-[4-[[N-methyl-N-(tetrahydro-2H-pyran-4-yl)amino]methyl]phenyl]-2,3-dihydro-1H-1-benzazepine-4-carboxamide (Compound 5) (0.23 g) as pale yellow crystals.

mp 162–164° C.

$^1$H-NMR (δ ppm, CDCl$_3$) 1.17–1.30 (6H, m), 1.70–1.80 (4H, m), 2.21 (3H, s), 2.55–2.75 (1H, m), 3.03 (2H, t, J=5.2 Hz), 3.33–3.62 (12H, m), 3.92 (2H, t, J=5.2 Hz), 4.01–4.14 (2H, m), 6.78 (2H, d, J=8.8 Hz), 7.16 (1H, d, J=8.4 Hz), 7.32 (2H, d, J=8.4 Hz), 7.45–7.56 (6H, m), 7.66 (1H, d, J=2.0 Hz), 8.54 (1H, s).

IR (KBr) ν: 2849, 1661, 1609, 1552, 1501 cm$^{-1}$.

Anal. Calcd. for C$_{37}$H$_{46}$N$_4$O$_4$.0.2H$_2$O: C, 72.33; H, 7.61; N, 9.12. Found C, 72.30; H, 7.70; N, 9.23.

Working Example 6

Production of Compound 6

In DMF (7 ml) was dissolved 7-[4-[N-ethyl-N-(2-propoxyethyl)amino]phenyl]-1-formyl-2,3-dihydro-1H-1-benzazepine-4-carboxylic acid (0.25 g). To the solution was added, under ice-cooling, thionyl chloride (0.11 ml), and the mixture was stirred at room temperature for 30 minutes. Under reduced pressure, the solvent was evaporated, and the residue was dissolved in THF (25 ml). The solution was added dropwise to a solution of 4-[N-methyl-N-(tetrahydro-2H-pyran-4-yl)aminomethyl]aniline (0.16 g) and triethylamine (0.41 ml) in THF (5 ml), under ice-cooling, and the mixture was stirred under nitrogen atmosphere at room temperature overnight. Under reduced pressure, the solvent was evaporated. To the residue was added water, and the mixture was extracted with ethyl acetate. The organic layer was washed with water and saturated brine and dried with anhydrous magnesium sulfate, and the solvent was evaporated to give crude crystals, which were recrystallized from ethyl acetate/hexane to give 7-[4-[N-ethyl-N-(2-propoxyethyl)amino]phenyl]-1-formyl-N-[4-[[N-methyl-N-(tetrahydro-2H-pyran-4-yl)amino]methyl]phenyl]-2,3-dihydro-1H-1-benzazepine-4-carboxamide (Compound 6) (0.27 g) as pale yellow crystals.

mp 146–149° C.

$^1$H-NMR (δ ppm, CDCl$_3$) 0.93 (3H, t, J=7.3 Hz), 1.20 (3H, t, J=6.9 Hz), 1.59–1.75 (6H, m), 2.21 (3H, s), 2.55–2.75 (1H, m), 3.03 (2H, t, J=5.4 Hz), 3.31–3.61 (12H, m), 3.92 (2H, t, J=5.4 Hz), 4.01–4.14 (2H, m), 6.78 (2H, d, J=9.2 Hz), 7.16 (1H, d, J=8.4 Hz), 7.32 (2H, d, J=8.4 Hz), 7.45–7.56 (6H, m), 7.66 (1H, d, J=2.2 Hz), 8.54 (1H, s).

IR (KBr) ν: 2942, 1669 cm$^{-1}$.

Anal. Calcd. for C$_{38}$H$_{48}$N$_4$O$_4$.0.3H$_2$O: C, 72.42; H, 7.77; N, 8.89. Found C, 72.57; H, 7.53; N, 8.59

Working Example 7

Production of Compound 7

In THF (15 ml) was suspended 7-[4-(2-ethoxyethoxy)phenyl]-1-methanesulfonyl-2,3-dihydro-1H-1-benzazepine-4-carboxylic acid (0.14 g). To the suspension were added, under ice-cooling, thionyl chloride (0.04 ml) and DMF (catalytic amount), and the mixture was stirred at room temperature for 1.5 hours. Under reduced pressure, the solvent was evaporated, and the residue was dissolved in THF (15 ml). The solution was added dropwise to a solution of 4-[N-methyl-N-(tetrahydro-2H-pyran-4-yl)aminomethyl] aniline (0.08 g) and triethylamine (0.14 ml) in THF (15 ml), under ice-cooling, and the mixture was stirred under nitrogen atmosphere at room temperature for 1 hour. Under reduced pressure, the solvent was evaporated. To the residue was added water, and the mixture was extracted with ethyl acetate. The organic layer was washed with water and saturated brine and dried with anhydrous magnesium sulfate, and the solvent was evaporated to give 7-[4-(2-ethoxyethoxy)phenyl]-1-methanesulfonyl-N-[4-[[N-methyl-N-(tetrahydro-2H-pyran-4-yl)amino]methyl]phenyl]-2,3-dihydro-1H-1-benzazepine-4-carboxamide (Compound 7) (0.15 g) as colorless amorphous.

$^1$H-NMR (δ ppm, CDCl$_3$) 1.26 (3H, t, J=7.0 Hz), 1.60–1.76 (4H, m), 2.22 (3H, s), 2.67 (1H, br), 2.89 (3H, s), 3.14 (2H, t, J=5.2 Hz), 3.37 (2H, dt, J=3.0, 11.0 Hz), 3.59 (2H, s), 3.63 (2H, q, J=7.0 Hz), 3.83 (2H, t, J=4.8 Hz), 3.92 (2H, t, J=5.2 Hz), 4.01–4.07 (2H, m), 4.18 (2H, t, J=4.6 Hz), 7.02 (2H, d, J=8.8 Hz), 7.33 (2H, d, J=8.8 Hz), 7.49–7.67 (8H, m).

IR (KBr) ν: 2934, 2849, 1661, 1609, 1520, 1495 cm$^{-1}$.

Anal. Calcd. for C$_{35}$H$_{43}$N$_3$O$_6$S: C, 66.33; H, 6.84; N, 6.63. Found C, 66.39; H, 6.76; N, 6.57.

Working Example 8

Production of Compound 8

In THF (5 ml) was dissolved 7-[4-(3-ethoxypropoxy)phenyl]-1-methanesulfonyl-2,3-dihydro-1H-1-benzazepine- 4-carboxylic acid (0.20 g). To the solution were added, under ice-cooling, thionyl chloride (0.06 ml) and DMF (catalytic amount), and the mixture was stirred at room temperature for 2 hours. Under reduced pressure, the solvent was evaporated, and the residue was dissolved in THF (15 ml). The solution was added dropwise to a solution of 4-[N-methyl-N-(tetrahydro-2H-pyran-4-yl)aminomethyl] aniline (0.11 g) and triethylamine (0.19 ml) in THF (5 ml), under ice-cooling, and the mixture was stirred under nitrogen atmosphere at room temperature overnight. Under reduced pressure, the solvent was evaporated. To the residue was added water, and the mixture was extracted with ethyl acetate. The organic layer was washed with water and saturated brine and dried with anhydrous magnesium sulfate, and the solvent was evaporated to give crude crystals, which were recrystallized from ethyl acetate/hexane to give 7-[4-(3-ethoxypropoxy)phenyl)-1-methanesulfonyl-N-[4-[[N-methyl-N-(tetrahydro-2H-pyran-4-yl)amino]methyl]phenyl]-2,3-dihydro-1H-1-benzazepine-4-carboxamide (Compound 8) (0.22 g) as colorless crystals.

mp 157–160° C.

$^1$H-NMR (δ ppm, CDCl$_3$) 1.22 (3H, t, J=7.0 Hz), 1.65–1.76 (4H, m), 2.06–2.15 (2H, m), 2.22 (3H, s), 2.55–2.78 (1H, m), 2.89 (3H, s), 3.14 (2H, t, J=5.1 Hz), 3.38 (2H, dt, J=2.6, 11.2 Hz), 3.46–3.65 (6H, m), 3.92 (2H, t, J=5.1 Hz), 3.95–4.15 (4H, m), 7.00 (2H, d, J=9.2 Hz), 7.34 (2H, d, J=8.4 Hz), 7.49–7.67 (9H, m).

IR (KBr) ν: 2926, 2851, 1671, 1595, 1524 cm$^{-1}$.

Working Example 9

Production of Compound 9

In a mixture of water:ethanol:toluene (1:1:10, v/v, 18.0 ml) were dissolved 4-(2-ethoxyethoxy)phenyl borate (315 mg) and 7-bromo-1-methyl-N-[4-[[N-methyl-N-(tetrahydro-2H-pyran-4-yl)amino]methyl]phenyl]-2,3-dihydro-1H-1-benzazepine-4-carboxamide (485 mg). To the solution was added potassium carbonate (332 mg), and the mixture was stirred under argon atmosphere at room temperature for 30 minutes. To the mixture was added tetrakistriphenylphosphinepalladium (46 mg), and the mixture was heated to reflux under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (30 g, ethyl acetate:ethanol=9:1) and recrystallized from ethanol to give 7-[4-(2-ethoxyethoxy)phenyl]-1-methyl-N-[4-[[N-methyl-N-(tetrahydro-2H-pyran-4-yl)amino]methyl]phenyl]-2,3-dihydro-1H-1-benzazepine-4-carboxamide (Compound 9) (230 mg, 40%) as yellow crystals.

mp 122–125° C.

$^1$H-NMR (200 MHz, CDCl$_3$) δ 1.26 (3H, t, J=7.0 Hz), 1.23–1.76 (4H, m), 2.20 (3H, s), 2.53–2.71 (1H, m), 2.94 (2H, t, J=4.4 Hz), 3.07 (3H, s), 3.32 (2H, t, J=4.5 Hz), 3.37 (2H, td, J=11.4, 2.9 Hz), 3.56 (2H, s), 3.62 (2H, q, J=7.0 Hz), 3.81 (2H, t, J=4.9 Hz), 4.01–4.07 (2H, m), 4.16 (2H, t, J=5.0 Hz), 6.86 (1H, d, J=8.6 Hz), 6.97 (2H, d, J=8.8 Hz), 7.29 (2H, d, J=9.0 Hz), 7.38 (1H, s), 7.43 (1H, dd, J=8.6, 2.2 Hz), 7.47 (2H, d, J=8.8 Hz), 1H (d) was concealed under 7.49, 7.54 (2H, d, J=8.6 Hz), 7.66 (1H, s).

IR (KBr) 2946, 2847, 1653, 1607, 1501, 1312, 1244, 1186, 1119, 814 cm$^{-1}$.

Anal. Calcd. for C$_{35}$H$_{43}$N$_3$O$_4$: C, 73.78; H, 7.61; N, 7.38. Found C, 73.93; H, 7.39; N, 7.44.

Working Example 10

Production of Compound 10

In DMF (5.0 ml) was dissolved 1-methylsulfonyl-7-[4-(2-methylthio)ethoxyphenyl]-2,3-dihydro-1H-1-benzazepine-4-carboxylic acid (207 mg). To the solution was added thionyl chloride (0.09 ml), and the mixture was stirred at room temperature for 30 minutes. Under reduced pressure, the solvent was evaporated, and to the residue was added THF (10.0 ml). On the other hand, to 4-[[N-methyl-N-(tetrahydro-2H-pyran-4-yl)amino]methyl]aniline dihydrochloride (168 mg) was added THF (5.0 ml), and then was added triethylamine (0.50 ml). To the obtained mixture was added dropwise at 0° C. the previously prepared acid chloride suspension, and the mixture was stirred at room temperature for 4 hours. To the mixture was added ethyl acetate, and the mixture was washed with water and saturated brine. The organic layer was dried with anhydrous magnesium sulfate. The solvent was evaporated under reduced pressure, and the residue was purified with silica gel column chromatography (15 g, ethyl acetate→ethyl acetate:ethanol:triethylamine=100:10:1) and recrystallized from ethanol to give 1-methylsulfonyl-N-[4-[[N-methyl-N-(tetrahydro-2H-pyran-4-yl)amino]methyl]phenyl]-7-[4-(2-methylthio)ethoxyphenyl]-2,3-dihydro-1H-1-benzazepine-4-carboxamide (Compound 10) (176 mg, 58%) as white crystals.

mp 174–177° C.

$^1$H-NMR (200 MHz, CDCl$_3$) δ 1.64–1.77 (4H, m), 2.21 (3H, s), 2.24 (3H, s), 2.60–2.72 (1H, m), 2.89 (3H, s), 2.92 (2H, t, J=6.9 Hz), 3.14 (2H, t, J=5.3 Hz), 3.38 (2H, td, J=11.4, 2.9 Hz), 3.58 (2H, s), 3.92 (2H, t, J=5.3 Hz), 4.02–4.07 (2H, m), 4.22 (2H, t, J=6.8 Hz), 7.00 (2H, d, J=8.8 Hz), 7.33 (2H, d, J=8.4 Hz), 7.50–7.67 (9H, m).

IR (KBr) 1655, 1607, 1517, 1493, 1341, 1314, 1248, 1154 cm$^{-1}$.

Anal. Calcd. for C$_{34}$H$_{41}$N$_3$O$_5$S$_2$: C, 64.22; H, 6.50; N, 6.61. Found C, 64.03; H, 6.51; N, 6.55.

Working Example 11

Production of Compound 11

In DMF (10.0 ml) was dissolved 1-formyl-7-[4-(2-methylthio)ethoxyphenyl]-2,3-dihydro-1H-1-benzazepine-4-carboxylic acid (484 mg). To the solution was added thionyl chloride (0.23 ml), and the mixture was stirred at room temperature for 30 minutes. Under reduced pressure, the solvent was evaporated, and to the residue was added THF (10.0 ml). On the other hand, to 4-[[N-methyl-N-(tetrahydro-2H-pyran-4-yl)amino]methyl]aniline dihydrochloride (444 mg) was added THF (10.0 ml), and then was added triethylamine (1.32 ml). To the obtained mixture was added dropwise at 0° C. the previously prepared acid chloride suspension, and the mixture was stirred at room temperature for 3 hours. To the mixture was added ethyl acetate and the mixture was washed with water and saturated brine. The organic layer was dried with anhydrous magnesium sulfate. The solvent was evaporated under reduced pressure, and the residue was purified with silica gel column chromatography (30 g, ethyl acetate→ethyl acetate:ethanol:triethylamine=100:10:1) and recrystallized from ethanol to give 1-formyl-N-[4-[[N-methyl-N-(tetrahydro-2H-pyran-4-yl)amino]methyl]phenyl]-7-[4-(2-methylthio)ethoxyphenyl]-2,3-dihydro-1H-1-benzazepine-4-carboxamide (Compound 11) (555 mg, 75%) as white crystals.

mp 180–183° C.

¹H-NMR (200 MHz, CDCl₃) δ 1.64–1.77 (4H, m), 2.21 (3H, s), 2.24 (3H, s), 2.59–2.67 (1H, m), 2.92 (2H, t, J=6.8 Hz), 3.04 (2H, t, J=4.6 Hz), 3.37 (2H, td, J=11.2, 2.9 Hz), 3.57 (2H, s), 3.92 (2H, t, J=5.3 Hz), 4.01–4.07 (2H, m), 4.22 (2H, t, J=6.8 Hz), 7.01 (2H, d, J=8.8 Hz), 7.20 (1H, d, J=8.0 Hz), 7.32 (2H, d, J=8.8 Hz), 7.47–7.58 (7H, m), 7.68 (1H, d, J=1.8 Hz), 8.55 (1H, s).

IR (KBr) 1667, 1607, 1514, 1497, 1360, 1314, 1246, 824 cm⁻¹.

Anal. Calcd. for $C_{34}H_{39}N_3O_4S$ (0.2$H_2O$ additive): C, 69.29; H, 6.74; N, 7.13. Found C, 69.09; H, 6.58; N, 7.01.

Working Example 12

Production of Compound 12

In a mixture of water:ethanol:toluene (1:1:10, v/v, 18.0 ml) were dissolved 4-(2-propoxyethoxy)phenyl borate (242 mg) and 7-bromo-1-methyl-N-[4-[[N-methyl-N-(tetrahydro-2H-pyran-4-yl)amino]methyl]phenyl]-2,3-dihydro-1H-1-benzazepine-4-carboxamide (436 mg). To the solution was added potassium carbonate (299 mg), and the mixture was stirred under argon atmosphere at room temperature for 30 minutes. To the mixture was added tetrakistriphenylphosphinepalladium (42 mg), and the mixture was heated to reflux under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (30 g, ethyl acetate:ethanol:triethylamine=180:20:1) and recrystallized from ethanol/hexane to give 1-methyl-N-[4-[[N-methyl-N-(tetrahydro-2H-pyran-4-yl)amino]methyl]phenyl]-7-[4-(2-propoxyethoxy)phenyl]-2,3-dihydro-1H-benzazepine-4-carboxamide (Compound 12) (186 mg, 35%) as yellow crystals.

mp 136–138° C.

¹H-NMR (200 MHz, CDCl₃) δ 0.94 (3H, t, J=7.3 Hz), 1.65 (2H, sextet, J=7.2 Hz), 1.69–1.76 (4H, m), 2.21 (3H, s), 2.57–2.72 (1H, m), 2.96 (2H, t, J=4.4 Hz), 3.09 (3H, s), 3.32–3.43 (4H, m), 3.51 (2H, t, J=6.8 Hz), 3.56 (2H, s), 3.81 (2H, t, J=5.0 Hz), 4.01–4.06 (2H, m), 4.16 (2H, t, J=4.9 Hz), 6.88 (1H, d, J=8.4 Hz), 6.98 (2H, d, J=8.8 Hz), 7.30 (2H, d, J=8.6 Hz), 7.40–7.56 (8H, m).

IR 1651, 1607, 1514, 1501, 1312, 1244, 1186 cm⁻¹.

Anal. Calcd. for $C_{36}H_{45}N_3O_4$ (0.3$H_2O$ additive): C, 73.39; H, 7.80; N, 7.13. Found C, 73.12; H, 7.67; N, 7.08.

Working Example 13

Production of Compound 13

In a mixture of water ethanol:toluene (1:1:10, v/v, 18.0 ml) were dissolved 4-(3-ethoxypropoxy)phenyl borate (250 mg) and 7-bromo-1-methyl-N-[4-[[N-methyl-N-(tetrahydro-2H-pyran-4-yl)amino]methyl]phenyl]-2,3-dihydro-1H-1-benzazepine-4-carboxamide (450 mg). To the solution was added potassium carbonate (308 mg), and the mixture was stirred under argon atmosphere at room temperature for 30 minutes. To the mixture was added tetrakistriphenylphosphinepalladium (43 mg), and the mixture was refluxed under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (25 g, ethyl acetate:ethanol:triethylamine=100:10:1) and recrystallized from ethanol/hexane to give 7-[4-(3-ethoxypropoxy) phenyl]-1-methyl-N-[4-[[N-methyl-N-(tetrahydro-2H-pyran-4-yl)amino]methyl]phenyl]-2,3-dihydro-1H-1-benzazepine-4-carboxamide (Compound 13) (359 mg, 66%) as yellow crystals.

mp 98–100° C.

¹H-NMR (200 MHz, CDCl₃) δ 1.21 (3H, t, J=6.9 Hz), 1.63–1.79 (4H, m), 2.07 (2H, quint, J=6.3 Hz), 2.21 (3H, s), 2.54–2.75 (1H, m), 2.96 (2H, t, J=4.4 Hz), 3.09 (3H, s), 3.31–3.43 (4H, m), 3.51 (2H, q, J=7.0 Hz), 3.56 (2H, s), 3.62 (2H, t, J=6.3 Hz), 4.00–4.07 (2H, m), 4.10 (2H, t, J=6.2 Hz), 6.88 (1H, d, J=8.6 Hz), 6.97 (2H, d, J=8.8 Hz), 7.30 (2H, d, J=8.6 Hz), 7.40–7.56 (3H, m), 7.40 (1H, s), 7.48 (2H, d, J=9.0 Hz), 7.54 (2H, d, J=8.6 Hz).

IR (KBr) 1647, 1607, 1514, 1501, 1312, 1244, 1182, 1115 cm⁻¹.

Anal. Calcd. for $C_{36}H_{45}N_3O_4$ (0.2$H_2O$ additive): C, 73.62; H, 7.79; N, 7.15. Found C, 73.53; H, 7.63; N, 7.11.

Working Example 14

Production of Compound 14

In DMF (9.5 ml) was dissolved 1-formyl-7-[4-(2-propoxy)ethoxyphenyl]-2,3-dihydro-1H-1-benzazepine-4-carboxylic acid (379 mg). To the solution was added thionyl chloride (0.18 ml), and the mixture was stirred at room temperature for 30 minutes. Under reduced pressure, the solvent was evaporated, and to the residue was added THF (15.0 ml). On the other hand, to 4-[[N-methyl-N-(tetrahydro-2H-pyran-4-yl)amino]methyl]aniline dihydrochloride (337 mg) was added THF (10.0 ml), and then was added triethylamine (1.00 ml). To the obtained mixture was added dropwise at 0° C. the previously prepared acid chloride suspension, and the mixture was stirred at room temperature for 15 hours. To the mixture was added ethyl acetate, and the mixture was washed with water and saturated brine. The organic layer was dried with anhydrous magnesium sulfate. The solvent was evaporated under reduced pressure, and the residue was purified with silica gel column chromatography (35 g, ethyl acetate→ethyl acetate:ethanol=10:1→ethyl acetate:ethanol:triethylamine= 100:10:1) and recrystallized from ethanol to give 1-formyl-N-[4-[[N-methyl-N-(tetrahydro-2H-pyran-4-yl)amino] methyl]phenyl]-7-[4-(2-propoxy)ethoxyphenyl]-2,3-dihydro-1H-1-benzazepine-4-carboxamide (Compound 14) (459 mg, 80%) as white crystals.

mp 187–189° C.

¹H-NMR (200 MHz, CDCl₃) δ 0.95 (3H, t, J=7.4 Hz), 1.57–1.74 (6H, m), 2.20 (3H, s), 2.56–2.72 (1H, m), 3.03 (2H, t, J=5.2 Hz), 3.37 (2H, td, J=11.0, 2.8 Hz), 3.52 (2H, t, J=6.8 Hz), 3.57 (2H, s), 3.82 (2H, t, J=4.9 Hz), 3.92 (2H, t, J=5.3 Hz), 4.01–4.07 (2H, m), 4.18 (2H, t, J=4.9 Hz), 7.03 (2H, d, J=8.8 Hz), 7.19 (1H, d, J=8.4 Hz), 7.31 (2H, d, J=8.4 Hz), 7.46–7.58 (7H, m), 7.67 (1H, s), 8.55 (1H, s).

IR (KBr) 1667, 1609, 1518, 1497, 1360, 1314, 1248, 824 cm⁻¹.

Anal. Calcd. for $C_{36}H_{43}N_3O_5$: C, 72.34; H, 7.25; N, 7.03. Found C, 72.39; H, 7.32; N, 7.08.

Working Example 15

Production of Compound 15

In DMF (6.5 ml) was dissolved 1-methylsulfonyl-7-[4-(2-propoxy)ethoxyphenyl]-2,3-dihydro-1H-1-benzazepine- 4-carboxylic acid (296 mg). To the solution was added thionyl chloride (0.12 ml), and the mixture was stirred at room temperature for 30 minutes. Under reduced pressure, the solvent was evaporated, and to the residue was added THF (15.0 ml). On the other hand, to 4-[[N-methyl-N-(tetrahydro-2H-pyran-4-yl)amino]methyl]aniline dihydrochloride (234 mg) was added THF (10.0 ml), and then was added triethylamine (0.69 ml). To the obtained mixture was added dropwise at 0° C. the previously prepared acid chloride suspension, and the mixture was stirred at room temperature for 3 hour. To the mixture was added ethyl acetate, and the mixture was washed with water and saturated brine. The organic layer was dried with anhydrous magnesium sulfate. The solvent was evaporated under reduced pressure, and the residue was purified with silica gel column chromatography (25 g, ethyl acetate→ethyl acetate:ethanol:triethylamine=100:10:1) and recrystallized from ethanol to give 1-methylsulfonyl N-[4-[[N-methyl-N-(tetrahydro-2H-pyran-4-yl)amino]methyl]phenyl]-7-[4-(2-propoxy)ethoxyphenyl]-2,3-dihydro-1H-1-benzazepine-4-carboxamide (Compound 15) (248 mg, 58%) as white crystals.

mp 161–162° C.

$^1$H-NMR (200 MHz, CDCl$_3$) δ 0.95 (3H, t, J=7.3 Hz), 1.65 (2H, sextet, J=7.1 Hz), 1.69–1.77 (4H, m), 2.21 (3H, s), 2.54–2.70 (1H, m), 2.88 (3H, s), 3.13 (2H, t, J=5.0 Hz), 3.37 (2H, td, J=11.4, 5.6 Hz), 3.52 (2H, t, J=6.8 Hz), 3.57 (2H, s), 3.82 (2H, t, J=4.8 Hz), 3.91 (2H, t, J=5.7 Hz), 4.01–4.07 (2H, m), 4.18 (2H, t, J=5.0 Hz), 7.00–7.04 (2H, m), 7.32 (2H, d, J=8.4 Hz), 7.50 (2H, d, J=8.8 Hz), 7.48–7.66 (7H, m).

IR (KBr) 1663, 1609, 1516, 1493, 1343, 1310, 1248, 1154, 667 cm$^{-1}$.

Anal. Calcd. for C$_{36}$H$_{45}$N$_3$O$_6$S: C, 66.74; H, 7.00; N, 6.49. Found C, 66.56; H, 7.03; N, 6.36.

Working Example 16

Production of Compound 16

In a mixture of water:ethanol:toluene (1:1:10, v/v, 18.0 ml) were dissolved 4-(2-ethoxyethoxy)phenyl borate (339 mg) and 7-bromo-1-ethyl-N-[4-[[N-methyl-N-(tetrahydro-2H-pyran-4-yl)amino]methyl]phenyl]-2,3-dihydro-1H-1-benzazepine-4-carboxamide (537 mg). To the solution was added potassium carbonate (357 mg), and the mixture was stirred under argon atmosphere at room temperature for 30 minutes. To the mixture was added tetrakistriphenylphosphinepalladium (50 mg), and the mixture was heated to reflux under argon atmosphere for 14 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (35 g, ethyl acetate→ethyl acetate ethanol=10:1→ethyl acetate:ethanol triethylamine= 100:10:0.5) and recrystallized from ethyl acetate/IPE to give 7-[4-(2-ethoxyethoxy)phenyl]-1-ethyl-N-[4-[[N-methyl-N-(tetrahydro-2H-pyran-4-yl)amino]methyl]phenyl]-2,3-dihydro-1H-1-benzazepine-4-carboxamide (Compound 16) (332 mg, 53%) as yellow crystals.

mp 114.5–116.5° C.

$^1$H-NMR (200 MHz, CDCl$_3$) δ 1.26 (3H, t, J=6.9 Hz), 1.32 (3H, t, J=7.1 Hz), 1.63–1.76 (4H, m), 2.21 (3H, s), 2.59–2.69 (1H, m), 2.91 (2H, t, J=4.8 Hz), 3.31–3.42 (4H, m), 3.44 (2H, q, J=7.0 Hz), 3.57 (2H, s), 3.64 (2H, t, J=6.9 Hz), 3.82 (2H, t, J=4.8 Hz), 4.01–4.06 (2H, m), 4.16 (2H, t, J=5.0 Hz), 6.91 (1H, d, J=8.8 Hz), 6.98 (2H, d, J=9.2 Hz), 7.30 (2H, d, J=8.4 Hz), 7.40 (1H, s), 7.47 (2H, d, J=9.2 Hz), 7.53 (2H, d, J=8.4 Hz), 7.40–7.56 (3H, m).

IR (KBr) 1651, 1607, 1514, 1501, 1312, 1244, 1175, 1140, 1119 cm$^{-1}$.

Anal. Calcd. for C$_{36}$H$_{45}$N$_3$O$_4$ (0.2H$_2$O additive): C, 73.62; H, 7.79; N, 7.15. Found C, 73.45; H, 7.85; N, 7.05.

Working Example 17

Production of Compound 17

In a mixture of water:ethanol:toluene (1:1:10, v/v, 18.0 ml) were dissolved 4-(2-propoxyethoxy)phenyl borate (272 mg) and 7-bromo-1-ethyl-N-[4-[[N-methyl-N-(tetrahydro-2H-pyran-4-yl)amino]methyl]phenyl]-2,3-dihydro-1H-1-benzazepine-4-carboxamide (404 mg). To the solution was added potassium carbonate (269 mg), and the mixture was stirred under argon atmosphere at room temperature for 30 minutes. To the mixture was added tetrakistriphenylphosphinepalladium (37 mg), and the mixture was heated to reflux under argon atmosphere for 14 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (30 g, ethyl acetate→ethyl acetate:ethanol=10:1→ethyl acetate:ethanol:triethylamine= 100:10:0.5) and recrystallized from ethyl acetate/IPE to give 1-ethyl-N-[4-[[N-methyl-N-(tetrahydro-2H-pyran-4-yl) amino]methyl]phenyl]-7-[4-(2-propoxyethoxy)phenyl]-2,3-dihydro-1H-1-benzazepine-4-carboxamide (Compound 17) (221 mg, 46%) as yellow crystals.

mp 106–108° C.

$^1$H-NMR (200 MHz, CDCl$_3$) δ 0.94 (3H, t, J=7.5 Hz), 1.32 (3H, t, J=6.9 Hz), 1.65 (2H, sextet, J=7.1 Hz), 1.70–1.76 (4H, m), 2.21 (3H, s), 2.56–2.69 (1H, m), 2.92 (2H, t, J=4.0 Hz), 3.31–3.46 (6H, m), 3.51 (2H, t, J=6.8 Hz), 3.56 (2H, s), 3.81 (2H, t, J=4.9 Hz), 4.01–4.06 (2H, m), 4.16 (2H, t, J=5.0 Hz), 6.92 (1H, d, J=8.4 Hz), 6.98 (2H, d, J=8.8 Hz), 7.30 (2H, d, J=8.8 Hz), 7.40 (1H, s), 7.47 (2H, d, J=8.8 Hz), 7.54 (2H, d, J=8.8 Hz), 7.40–7.56 (3H, m).

IR (KBr)2928, 1651, 1645, 1607, 1514, 1501, 1314, 1244, 1175 cm$^{-1}$.

Anal. Calcd. for C$_{37}$H$_{47}$N$_3$O$_4$ (0.3H$_2$O additive): C, 73.67; H, 7.95; N, 6.97. Found C, 73.52; H, 7.76; N, 6.95.

Working Example 18

Production of Compound 18

In a mixture of water:ethanol:toluene (1:1:10, v/v, 18.0 ml) were dissolved 4-(2-butoxyethoxy)phenyl borate (324 mg) and 7-bromo-1-methyl-N-[4-[[N-methyl-N-(tetrahydro-2H-pyran-4-yl)amino]methyl]phenyl]-2,3-dihydro-1H-1-benzazepine-4-carboxamide (440 mg). To the solution was added potassium carbonate (301 mg), and the mixture was stirred under argon atmosphere at room temperature for 30 minutes. To the mixture was added tetrakistriphenylphosphinepalladium (42 mg), and the mixture was refluxed under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (30 g, ethyl acetate→ethyl acetate:ethanol=10:1→ethyl acetate:ethanol:triethylamine=

100:10:0.5) and recrystallized from ethyl acetate/IPE to give 7-[4-(2-butoxyethoxy)phenyl]-1-methyl-N-[4-[[N-methyl-N-(tetrahydro-2H-pyran-4-yl)amino]methyl]phenyl]-2,3-dihydro-1H-1-benzazepine-4-carboxamide (Compound 18) (287 mg, 53%) as yellow crystals.

mp 107–110° C.

$^1$H-NMR (200 MHz, CDCl$_3$) δ 0.93 (3H, t, J=7.2 Hz), 1.39 (2H, sextet, J=7.3 Hz), 1.55–1.79 (6H, m), 2.21 (3H, s), 2.57–2.75 (1H, m), 2.96 (2H, t, J=4.4 Hz), 3.09 (3H, s), 3.31–3.38 (2H, m), 3.37 (2H, td, J=11.6, 2.7 Hz), 3.55 (2H, t, J=6.6 Hz), 3.57 (2H, s), 3.81 (2H, t, J=5.0 Hz), 4.00–4.08 (2H, m), 4.16 (2H, t, J=4.9 Hz), 6.88 (1H, d, J=8.6 Hz), 6.96–7.01 (2H, m), 7.30 (2H, d, J=8.4 Hz), 7.40–7.56 (4H, m), 7.48 (2H, d, J=9.0 Hz), 7.54 (2H, d, J=8.6 Hz).

IR (KBr) 2955, 2936, 1651, 1607, 1514, 1312, 1244, 1186 cm$^{-1}$.

Anal. Calcd. for C$_{37}$H$_{47}$N$_3$O$_4$ (0.1H$_2$O additive): C, 74.12; H, 7.93; N, 7.01. Found C, 73.90; H, 7.82; N, 7.12.

Working Example 19

Production of Compound 19

In a mixture of water:ethanol:toluene (1:1:10, v/v, 18.0 ml) were dissolved 4-(2-butoxyethoxy)phenyl borate (301 mg) and 7-bromo-1-ethyl-N-[4-[[N-methyl-N-(tetrahydro-2H-pyran-4-yl)amino]methyl]phenyl]-2,3-dihydro-1H-1-benzazepine-4-carboxamide (420 mg). To the solution was added potassium carbonate (279 mg), and the mixture was stirred under argon atmosphere at room temperature for 30 minutes. To the mixture was added tetrakistriphenylphosphinepalladium (39 mg), and the mixture was refluxed under argon atmosphere for 14 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (30 g, ethyl acetate→ethyl acetate:ethanol=10:1→ethyl acetate:ethanol:triethylamine= 100:10 0.5) and recrystallized from ethyl acetate/IPE to give 7-[4-(2-butoxyethoxy)phenyl]-1-ethyl-N-[4-[[N-methyl-N-(tetrahydro-2H-pyran-4-yl)amino]methyl]phenyl]-2,3-dihydro-1-H-1-benzazepine-4-carboxamide (Compound 19) (218 mg, 42%) as yellow crystals.

mp 102–106° C.

$^1$H-NMR (200 MHz, CDCl$_3$) δ 0.93 (3H, t, J=7.1 Hz), 1.32 (3H, t, J=7.0 Hz), 1.39 (2H, sextet, J=7.4 Hz), 1.54–1.76 (6H, m), 2.21 (3H, s), 2.54–2.72 (1H, m), 2.92 (2H, t, J=4.6 Hz), 3.31–3.50 (6H, m), 3.55 (2H, t, J=6.6 Hz), 3.57 (2H, s), 3.81 (2H, t, J=4.9 Hz), 4.01–4.07 (2H, m), 4.16 (2H, t, J=5.0 Hz), 6.92 (1H, d, J=8.6 Hz), 6.98 (2H, d, J=8.8 Hz), 7.30 (2H, d, J=4 Hz), 7.40 (1H, s), 7.44–7.56 (3H, m), 7.47 (2H, d, J=9.0 Hz), 7.54 (2H, d, J=8.4 Hz).

IR (KBr) 2953, 2932, 1651, 1605, 1514, 1501, 1406, 1314, 1244, 1175 cm$^{-1}$.

Anal. Calcd. for C$_{38}$H$_{49}$N$_3$O$_4$ (0.2H$_2$O additive): C, 74.16; H, 8.09; N, 6.83. Found C, 73.92; H, 8.19; N, 6.59.

Working Example 20

Production of Compound 20

In a mixture of water:ethanol:toluene (1:1:10, v/v, 18.0 ml) were dissolved 4-[(2-ethoxy)ethoxy]-3-fluorophenyl borate (355 mg) and 7-bromo-1-formyl-N-(4-[[N-methyl-N-(tetrahydro-2H-pyran-4-yl)amino]methyl]phenyl]-2,3-dihydro-1H-1-benzazepine-4-carboxamide (517 mg). To the solution was added potassium carbonate (344 mg), and the mixture was stirred under argon atmosphere at room temperature for 30 minutes. To the mixture was added tetrakistriphenylphosphinepalladium (48 mg), and the mixture was heated to reflux under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (30 g, ethyl acetate→ethyl acetate:ethanol=10:1→ethyl acetate:ethanol:triethylamine=100:10 :1) and recrystallized from ethanol to give 7-[4-(2-ethoxy)ethoxy-3-fluorophenyl]-1-formyl-N-[4-[[N-methyl-N-(tetrahydro-2H-pyran-4-yl)amino]methyl]phenyl]-2,3-dihydro-1H-1-benzazepine-4-carboxamide (Compound 20) (476 mg, 76%) as white crystals.

mp 188–191° C.

$^1$H-NMR (200 MHz, CDCl$_3$) δ 1.26 (3H, t, J=7.1 Hz), 1.64–1.77 (4H, m), 2.20 (3H, s), 2.57–2.72 (1H, m), 3.04 (2H, t, J=5.2 Hz), 3.37 (2H, td, J=11.3, 2.9 Hz), 3.57 (2H, s), 3.63 (2H, q, J=7.0 Hz), 3.85 (2H, t, J=4.9 Hz), 3.92 (2H, t, J=5.6 Hz), 4.01–4.07 (2H, m), 4.25 (2H, t, J=4.9 Hz), 7.09 (1H, t, J=8.6 Hz), 7.20 (1H, d, J=8.2 Hz), 7.29–7.36 (2H, m), 7.32 (2H, d, J=8.0 Hz), 7.45 (1H, s), 7.53 (2H+1H, d, J=8.8 Hz), 7.56 (1H, s), 7.65 (1H, d, J=2.2 Hz), 8.55 (1H, s).

IR (KBr) 1669, 1501, 1358, 1314, 1269, 1238, 1198, 1138, 1125 cm$^{-1}$.

Anal. Calcd. for C$_{35}$H$_{40}$FN$_3$O$_4$: C, 69.86; H, 6.70; N, 6.98. Found C, 69.66; H, 6.40; N, 6.71.

Working Example 21

Production of Compound 21

In a mixture of water ethanol:toluene (1:1:10; v/v, 18.0 ml) were dissolved 3-chloro-4-(2-ethoxy)ethoxyphenyl borate (280 mg) and 7-bromo-1-formyl-N-[4-[[N-methyl-N-(tetrahydro-2H-pyran-4-yl)amino]methyl]phenyl]-2,3-dihydro-1H-1-benzazepine-4-carboxamide (380 mg). To the solution was added potassium carbonate (253 mg), and the mixture was stirred under argon atmosphere at room temperature for 30 minutes. To the mixture was added tetrakistriphenylphosphinepalladium (35 mg), and the mixture was heated to reflux under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (25 g, ethyl acetate→ethyl acetate:ethanol=10:1→ethyl acetate:ethanol:triethylamine=100:10:0.5) and recrystallized from ethanol to give 7-[3-chloro4-(2-ethoxy)ethoxyphenyl]-1-formyl-N-[4-[[N-methyl-N-(tetrahydro-2H-pyran-4-yl)amino]methyl]phenyl]-2,3-dihydro-1H-1-benzazepine-4-carboxamide (Compound 21) (342 mg, 73%) as white crystals.

mp 198–200° C.

$^1$H-NMR (200 MHz, CDCl$_3$) δ 1.26 (3H, t, J=6.9 Hz), 1.64–1.76 (4H, m), 2.20 (3H, s), 2.57–2.69 (1H, m), 3.04 (2H, t, J=5.2 Hz), 3.37 (2H, td, J=11.1, 2.9 Hz), 3.57 (2H, s), 3.67 (2H, q, J=7.0 Hz), 3.88 (2H, t, J=5.0 Hz), 3.91 (2H, t, J=6.0 Hz), 4.01–4.06 (2H, m), 4.24 (2H, t, J=4.9 Hz), 7.05 (1H, d, J=8.4 Hz), 7.20 (1H, d, J=8.2 Hz), 7.32 (2H, d, J=8.4 Hz), 7.43 (1H, dd, J=8.6, 2.4 Hz), 7.44 (1H, s), 7.54 (2H+1H, d, J=8.4 Hz), 7.56 (1H, s), 7.61 (1H, d, J=2.2 Hz), 7.65 (1H, d, J=2.2 Hz), 8.55 (1H, s).

IR (KBr) 1669, 1599, 1516, 1493, 1360, 1314, 1292, 1260, 1140, 1065 cm$^{-1}$.

Anal. Calcd. for $C_{35}H_{40}ClN_3O_5$: C, 68.00; H, 6.52; N, 6.80. Found C, 67.71; H, 6.43; N, 6.71.

Working Example 22

Production of Compound 22

In a mixture of water ethanol toluene (1:1:10, v/v, 18.0 ml) were dissolved 4-(3-propoxy)propoxyphenyl borate (270 mg) and 7-bromo-1-formyl-N-[4-[[N-methyl-N-(tetrahydro-2H-pyran-4-yl)amino]methyl]phenyl]-2,3-dihydro-1H-1-benzazepine-4-carboxamide (377 mg). To the solution was added potassium carbonate (251 mg), and the mixture was stirred under argon atmosphere at room temperature for 30 minutes. To the mixture was added tetrakistriphenylphosphinepalladium (35 mg), and the mixture was heated to reflux under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (25 g, ethyl acetate→ethyl acetate:ethanol=10:1→ethyl acetate:ethanol:triethylamine=100:10:0.5) and recrystallized from ethanol to give 1-formyl-N-[4-[[N-methyl-N-(tetrahydro-2H-pyran-4-yl)amino]methyl]phenyl]-7-[4-(3-propoxy)propoxyphenyl]-2,3-dihydro-1H-1-benzazepine-4-carboxamide (Compound 22) (304 mg, 66%) as white crystals.

mp 174–177° C.

$^1$H-NMR (200 MHz, CDCl$_3$) δ 0.92 (3H, t, J=7.3 Hz), 1.60 (2H, sextet, J=7.1 Hz), 1.69–1.76 (4H, m), 2.08 (2H, quint, J=6.2 Hz), 2.20 (3H, s), 2.59–2.69 (1H, m), 3.03 (2H, t, J=4.9 Hz), 3.31–3.41 (2H, m), 3.41 (2H, t, J=6.6 Hz), 3.57 (2H, s), 3.61 (2H, t, J=6.0 Hz), 3.92 (2H, t, J=5.3 Hz), 4.01–4.09 (2H, m), 4.12 (2H, t, J=6.4 Hz), 7.00 (2H, d, J=8.8 Hz), 7.19 (1H, d, J=8.0 Hz), 7.31 (2H, d, J=8.4 Hz), 7.46 (1H, s), 7.51 (2H, d, J=8.4 Hz), 7.54 (2H, d, J=8.4 Hz), 7.49–7.58 (2H, m), 7.67 (1H, d, J=1.8 Hz), 8.54 (1H, s).

IR (KBr) 2940, 1669, 1607, 1516, 1497, 1360, 1314, 1248, 1119 cm$^{-1}$.

Anal. Calcd. for $C_{37}H_{45}N_3O_4$: C, 72.64; H, 7.41; N, 6.87. Found C, 72.46; H, 7.62; N, 6.95

Working Example 23

Production of Compound 23

In a mixture of water:ethanol:toluene (1:1:10, v/v, 18.0 ml) were dissolved 3-ethoxy-4-(2-propoxy)ethoxyphenyl borate (324 mg) and 7-bromo-1-formyl-N-[4-[[N-methyl-N-(tetrahydro-2H-pyran-4-2,3-dihydro-1H-1-benzazepine-4-carboxamide (401 mg). To the solution was added potassium carbonate (267 mg), and the mixture was stirred under argon atmosphere at room temperature for 30 minutes. To the mixture was added tetrakistriphenylphosphinepalladium (37 mg), and the mixture was heated to reflux under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (25 g, ethyl acetate→ethyl acetate:ethanol=10:1→ethyl acetate:ethanol:triethylamine=100:10:0.5) and recrystallized from ethyl acetate/IPE to give 7-[3-ethoxy-4-(2-propoxy)ethoxyphenyl]-1-formyl-N-[4-[[N-methyl-N-(tetrahydro-2H-pyran-4-yl)amino]methyl]phenyl]-2,3-dihydro-1H-1-benzazepine-4-carboxamide (Compound 23) (317 mg, 61%) as white crystals.

mp 117–119° C.

$^1$H-NMR (200 MHz, CDCl$_3$) δ 0.94 (3H, t, J=7.3 Hz), 1.48 (3H, t, J=6.9 Hz), 1.64 (2H, sextet, J=7.2 Hz), 1.64–1.76 (4H, m), 2.20 (3H, s), 2.57–2.70 (1H, m), 3.03 (2H, t, J=3.6 Hz), 3.37 (2H, td, J=11.2, 2.7 Hz), 3.53 (2H, t, J=6.7 Hz), 3.56 (2H, s), 3.84 (2H, t, J=5.1 Hz), 3.92 (2H, t, J=5.3 Hz), 4.01–4.07 (2H, m), 4.16 (2H, q, J=7.1 Hz), 4.22 (2H, t, J=5.2 Hz), 7.03 (1H, d, J=8.8 Hz), 7.10 (1H, s), 7.11 (1H, dd, J=8.4, 2.2 Hz), 7.18 (1H, d, J=8.4 Hz), 7.32 (2H, d, J=8.4 Hz), 7.50 (2H, d, J=8.4 Hz), 7.54 (1H, d, J=8.4 Hz), 7.57 (1H, d, J=2.6 Hz), 7.60 (1H, s), 7.57 (1H, d, J=1.8 Hz), 8.54 (1H, s).

IR (KBr) 2942, 1671, 1597, 1514, 1499, 1408, 1360, 1316, 1254, 1202, 1140 cm$^{-1}$.

Anal. Calcd. for $C_{38}H_{47}N_3O_6$ (0.1H$_2$O additive): C, 70.92; H, 7.39; N, 6.53. Found C, 70.71; H, 7.36; N, 6.47.

Working Example 24

Production of Compound 24

In a mixture of water:ethanol:toluene (1:1:10, v/v, 18.0 ml) were dissolved (2,3-dihydro-1,4-benzodioxin-6-yl) borate (221 mg) and 7-bromo-1-methyl-N-[4-[[N-methyl-N-(tetrahydro-2H-pyran-4-yl)amino]methyl]phenyl]-2,3-dihydro-1H-1-benzazepine-4-carboxamide (397 mg). To the solution was added potassium carbonate (272 mg), and the mixture was stirred under argon atmosphere at room temperature for 30 minutes. To the mixture was added tetrakistriphenylphosphinepalladium (38 mg), and the mixture was heated to reflux under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (35 g, ethyl acetate:ethanol=20:1) and recrystallized from ethanol to give 7-(2,3-dihydro-1,4-benzodioxin-6-yl)-1-methyl-N-[4-[[N-methyl-N-(tetrahydro-2H-pyran-4-yl)amino]methyl]phenyl]-2,3-dihydro-1H-1-benzazepine-4-carboxamide (Compound 24) (215 mg, 49%) as yellow crystals.

mp 164–165° C.

$^1$H-NMR (200 MHz, CDCl$_3$) δ 1.63–1.76 (4H, m), 2.20 (3H, s), 2.53–2.73 (1H, m), 2.95 (2H, t, J=4.4 Hz), 3.07 (3H, s), 3.31–3.43 (4H, m), 3.56 (2H, s), 4.01–4.07 (2H, m), 4.29 (4H, s), 6.86 (1H, d, J=8.4 Hz), 6.90 (1H, d, J=9.6 Hz), 7.05 (1H, dd, J=10.4, 2.2 Hz), 7.07 (1H, s), 7.29 (2H, d, J=6 Hz), 7.37–7.55 (3H, m), 7.54 (2H, d, J=8.6 Hz), 7.62 (1H, s).

IR (KBr) 2948, 1644, 1597, 1514, 1497, 1406, 1312, 1283, 1246, 1188, 1071, 810, 733 cm$^{-1}$.

Anal. Calcd. for $C_{33}H_{37}N_3O_4$ (0.2H$_2$O additive): C, 72.96; H, 6.94; N, 7.73. Found C, 72.86; H, 6.91; N, 7.70.

Working Example 25

Production of Compound 25

In a mixture of water:ethanol:toluene (1:1:10. v/v, 18.0 ml) were dissolved 4-(2-ethoxyethoxy)phenyl borate (246 mg) and 7-bromo-1-propyl-N-[4-[[N-methyl-N-(tetrahydro-2H-pyran-4-yl)amino]methyl]phenyl]-2,3-dihydro-1H-1-benzazepine-4-carboxamide (400 mg). To the solution was added potassium carbonate (259 mg), and the mixture was stirred under argon atmosphere at room temperature for 30 minutes. To the mixture was added tetrakistriphenylphosphinepalladium (36 mg), and the mixture was heated to reflux under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (30 g, ethyl acetate→ethyl acetate:ethanol=10:1) and recrystallized from ethyl acetate-IPE to give 7-[4-(2-ethoxyethoxy)phenyl]-N-[4-[[N-methyl-N-(tetrahydro-2H-pyran-4-yl)amino]methyl]phenyl]-1-propyl-2,3-dihydro-1H-1-benzazepine-4-carboxamide (Compound 25) (216 mg, 46%) as yellow crystals.

mp 144–147° C.

$^1$H-NMR (200 MHz, CDCl$_3$) δ 0.99 (3H, t, J=7.4 Hz), 1.26 (3H, t, J=6.9 Hz), 1.63–1.84 (6H, m), 2.20 (3H, s), 2.56–2.69 (1H, m), 2.91 (2H, t, J=4.4 Hz), 3.28–3.43 (6H, m), 3.56 (2H, s), 3.62 (2H, q, J=7.0 Hz), 3.81 (2H, t, J=4.9 Hz), 4.01–4.06 (2H, m), 4.16 (2H, t, J=4.8 Hz), 6.90 (1H, d, J=8.6 Hz), 6.98 (2H, d, J=8.8 Hz), 7.29 (2H, d, J=8.4 Hz), 7.37–7.55 (8H, m).

IR (KBr) 2957, 2940, 1644, 1605, 1499, 1406, 1312, 1240, 1177, 1140, 1121 cm$^{-1}$.

Anal. Calcd. for C$_{37}$H$_{47}$N$_3$O$_4$: C, 74.34; H, 7.92; N, 7.02. Found C, 74.13; H, 7.76; N, 7.17.

Working Example 26

Production of Compound 26

In a mixture of water:ethanol toluene (1:1:10, v/v, 18.0 ml) were dissolved 4-(2-propoxyethoxy)phenyl borate (260 mg) and 7-bromo-1-propyl-N-[4-[[N-methyl-N-(tetrahydro-2H-pyran-4-yl)amino]methyl]phenyl]-2,3-dihydro-1H-1-benzazepine-4-carboxamide (396 mg). To the solution was added potassium carbonate (256 mg), and the mixture was stirred under argon atmosphere at room temperature for 30 minutes. To the mixture was added tetrakistriphenylphosphinepalladium (36 mg), and the mixture was heated to reflux under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (25 g, ethyl acetate→ethyl acetate ethanol=10:1) and recrystallized from ethyl acetate-IPE to give N-[4-[[N-methyl-N-(tetrahydro-2H-pyran-4-yl)amino]methyl]phenyl]-7-[4-(2-propoxyethoxy)phenyl]-1-propyl-2,3-dihydro-1H-1-benzazepine-4-carboxamide (Compound 26) (252 mg, 53%) as yellow crystals.

mp 128–130° C.

$^1$H-NMR (200 MHz, CDCl$_3$) δ 0.94 (3H, t, J=7.5 Hz), 0.99 (3H, t, J=7.6 Hz), 1.59–1.81 (8H, m), 2.20 (3H, s), 2.56–2.69 (1H, m), 2.92 (2H, t-like), 3.28–3.43 (6H, m), 3.51 (2H, t, J=6.7 Hz), 3.56 (2H, s), 3.81 (2H, t, J=5.0 Hz), 4.01–4.06 (2H, m), 4.16 (2H, t, J=5.0 Hz), 6.90 (1H, d, J=8.4 Hz), 6.98 (2H, d, J=8.4 Hz), 7.29 (2H, d, J=8.8 Hz), 7.38–7.55 (8H, m).

IR (KBr) 2957, 2940, 1644, 1605, 1499, 1406, 1312, 1240, 1177, 1140, 1121 cm$^{-1}$.

Anal. Calcd. for C$_{38}$H$_{49}$N$_3$O$_4$: C, 74.60; H, 8.07; N, 6.87. Found C, 74.31; H, 8.21; N, 7.12.

Working Example 27

Production of Compound 27

In a mixture of water:ethanol:toluene (1:1:10, v/v, 24.0 ml) were dissolved 4-(2-butoxyethoxy)phenyl borate (519 mg) and 7-bromo-1-propyl-N-[4-[[N-methyl-N-(tetrahydro-2H-pyran-4-yl)amino]methyl]phenyl]-2,3-dihydro-1H-1-benzazepine-4-carboxamide (745 mg). To the solution was added potassium carbonate (482 mg), and the mixture was stirred under argon atmosphere at room temperature for 30 minutes. To the mixture was added tetrakistriphenylphosphinepalladium (67 mg), and the mixture was refluxed under argon atmosphere for 10 hours. The mixture was diluted with ethyl acetate, and washed with water and saturated brine, and the organic layer was dried with anhydrous magnesium sulfate. The solvent was evaporated under reduced pressure, and the residue was purified with silica gel column chromatography (35 g, ethyl acetate→ethyl acetate:ethanol=10:1) and recrystallized from ethyl acetate-IPE to give 7-[4-(2-butoxyethoxy)phenyl]-N-[4-[[N-methyl-N-(tetrahydro-2H-pyran-4-yl)amino]methyl]phenyl]-1-propyl-2,3-dihydro-1H-1-benzazepine-4-carboxamide (Compound 27) (453 mg, 50%) as yellow crystals.

mp 122–124° C.

$^1$H-NMR (200 MHz, CDCl$_3$) δ 0.93 (3H, t, J=7.1 Hz), 0.99 (3H, t, J=7.3 Hz), 1.39 (2H, sextet, J=7.2 Hz), 1.54–1.80 (8H, m), 2.20 (3H, s), 2.53–2.71 (1H, m), 2.91 (2H, t, J=4.0 Hz), 3.27–3.43 (6H, m), 3.52–3.58 (4H, m), 3.80 (2H, t, J=5.0 Hz), 4.01–4.06 (2H, m), 4.15 (2H, t, J=4.7 Hz), 6.89 (1H, d, J=8.8 Hz), 6.97 (2H, d, J=8.8 Hz), 7.29 (2H, d, J=8.4 Hz), 7.37–7.59 (8H, m).

IR (KBr) 2957, 2940, 1644, 1605, 1499, 1406, 1312, 1240, 1177, 1140, 1121 cm$^{-1}$.

Anal. Calcd. for C$_{39}$H$_{51}$N$_3$O$_4$: C, 74.85; H, 8.21; N, 6.71. Found C, 74.64; H, 8.36; N, 6.93.

Working Examples 28

Production of Compound 28

In 1N hydrochloric acid (50 ml) and THF (50 ml) was dissolved 7-[4-(2-butoxyethoxy)phenyl]-1-formyl-N-[4-[[N-methyl-N-(tetrahydro-2H-pyran-4-yl)amino]methyl]phenyl]-2,3-dihydro-1H-1-benzazepine-4-carboxamide (1.4 g). The solution was refluxed for 4.5 hours, concentrated, neutralized with 1N sodium hydroxide solution and extracted with ethyl acetate. The organic layer was washed with water and saturated brine and dried with anhydrous magnesium sulfate. The solvent was evaporated to give 7-[4-(2-butoxyethoxy)phenyl]-N-[4-[[N-methyl-N-(tetrahydro-2H-pyran-4-yl)amino]methyl]phenyl]-2,3-dihydro-1H-1-benzazepine-4-carboxamide (Compound 28) (1.0 g) as yellow crystals.

mp 119–123° C.

$^1$H-NMR (δ ppm, CDCl$_3$) 0.93 (3H, t, J=7.3 Hz), 1.34–1.75 (8H, m), 2.21 (3H, s), 2.60–2.65 (1H, m), 2.96 (2H, t-like), 3.32–3.58 (8H, m), 3.80 (2H, t, J=5.0 Hz), 4.01–4.07 (2H, m), 4.16 (2H, t, J=5.0 Hz), 4.57 (1H, br), 6.70 (1H, d, J=8.2 Hz), 6.98 (2H, d, J=9.0 Hz), 7.26–7.32 (4H, m), 7.43–7.56 (5H, m).

IR (KBr) ν: 3328, 2946, 2851, 1651, 1609, 1514, 1499 cm$^{-1}$.

Anal. Calcd. for C$_{36}$H$_{45}$N$_3$O$_4$·0.25H$_2$O: C, 73.50; H, 7.80; N, 7.14. Found C, 73.54; H, 7.79; N, 7.15.

Working Example 29

Production of Compound 29

In DMF (5 ml) was dissolved 1-propionyl-7-[4-(2-propoxyethoxy)phenyl]-2,3-dihydro-1H-1-benzazepine-4- carboxylic acid (0.2 g). Under ice-cooling, to the solution was added thionyl chloride (0.09 ml). The mixture was stirred at room temperature for 30 minutes. The solvent was evaporated under reduced pressure. In THF (15 ml) was dissolved the residue, which was added dropwise to a solution of 4-[N-methyl-N-(tetrahydro-2H-pyran-4-yl) aminomethyl]aniline (0.15 g) and triethylamine (0.34 ml) in THF (5 ml), under ice-cooling. The mixture was stirred at room temperature overnight under nitrogen atmosphere. The solvent was evaporated under reduced solvent. Water was added to the mixture, and the mixture was extracted with ethyl acetate. The organic layer was washed with water and saturated brine and dried with anhydrous magnesium sulfate. The solvent was evaporated to give crude crystals, which were recrystallized from ethyl acetate-hexane to give 1-propionyl-7-[4-(2-propoxyethoxy)phenyl]-N-[4-[[N-methyl-N-(tetrahydro-2H-pyran-4-yl)amino]methyl] phenyl]-2,3-dihydro-1H-1-benzazepine-4-carboxamide (Compound 29) (0.1 g) as pale yellow crystals.

mp 167–169° C.

$^1$H-NMR (δ ppm, CDCl$_3$) 0.95 (3H, t, J=7.3 Hz), 1.08 (3H, t, J=7.5 Hz), 1.58–1.75 (6H, m), 2.12–2.21 (1H, m), 2.21 (3H, s), 2.40–2.75 (2H, m), 2.75–3.00 (2H, m), 3.10–3.30 (1H, m), 3.37 (2H, dt, J=2.8, 11.2 Hz), 3.52 (2H, t, J=6.7 Hz), 3.58 (2H, s), 3.82 (2H, t, J=4.8 Hz), 4.01–4.06 (2H, m), 4.19 (2H, t, J=4.8 Hz), 4.81–4.88 (1H, m), 7.03 (2H, d, J=8.8 Hz), 7.24–7.34 (3H, m), 7.50–7.56 (6H, m), 7.67 (1H, s).

IR (KBr) ν: 2944, 1653 cm$^{-1}$.

Anal. Calcd. for $C_{38}H_{47}N_3O_5 \cdot 0.5H_2O$: C, 71.90; H, 7.62; N, 6.62. Found C, 71.84; H, 7.48; N, 6.71.

Working Example 30

Production of Compound 30

In DMF (6 ml) was dissolved 1-butyl-7-[4-(2-propoxyethoxy)phenyl]-2,3-dihydro-1H-1-benzazepine-4-carboxylic acid (0.30 g). Under ice-cooling, to the mixture was added thionyl chloride (0.15 ml). The mixture was stirred at room temperature for 30 minutes. The solvent was evaporated under reduced pressure. In THF (20 ml) was suspended the residue, and the suspension was added dropwise to a solution of 4-[N-methyl-N-(tetrahydro-2H-pyran-4-yl)aminomethyl]aniline (0.17 g) and triethylamine (0.42 ml) in THF (5 ml), under ice-cooling. The mixture was stirred at room temperature overnight under nitrogen atmosphere. The solvent was evaporated under reduced solvent. Water was added to the mixture, and the mixture was extracted with ethyl acetate. The organic layer was washed with water and saturated brine and dried with anhydrous magnesium sulfate. The solvent was evaporated, and the residue was purified with silica gel column chromatography (ethyl acetate/methanol/triethylamine). The material was dissolved in ethyl acetate-ethanol, and 6N hydrochloric acid was added to the solution. The solvent was evaporated. Diethyl ether was added to the residue, and the precipitates were filtered to give 1-butyl-7-[4-(2-propoxyethoxy) phenyl]-N-[4-[[N-methyl-N-(tetrahydro-2H-pyran-4-yl) amino]methyl]phenyl]-2,3-dihydro-1H-1-benzazepine-4-carboxamide dihydrochloride (Compound 30) (0.36 g) as pale yellow amorphous.

$^1$H-NMR (δ ppm, DMSO-d$_6$) 0.84–1.02 (6H, m), 1.30–1.45 (2H, m), 1.49–1.70 (4H, m), 1.70–1.95 (2H, m), 1.95–2.20 (2H, m), 2.58 (3H, d, J=5.0 Hz), 2.80–2.85 (2H, m), 3.20–3.46 (8H, m), 3.66–3.84 (3H, m), 3.96–4.14 (3H, m), 4.12 (2H, t, J=4.7 Hz), 4.39–4.45 (1H, m), 6.93–7.02 (3H, m), 7.41–7.63 (7H, m), 7.81 (2H, d, J=8.4 Hz), 10.00 (1H, s), 10.22 (1H, br).

IR (KBr) ν: 2691, 2930, 2872, 1653, 1609, 1518, 1501 cm$^{-1}$.

Anal. Calcd. for $C_{39}H_{51}N_3O_4 \cdot 2HCl \cdot H_2O$: C, 65.35; H, 7.73; N, 5.86. Found C, 65.04; H, 7.88; N, 5.66.

Working Example 31

Production of Compound 31

A mixture of 7-bromo-1-cyclopropyl-N-[4-[[N-methyl-N-(tetrahydro-2H-pyran-4-yl)amino]methyl]phenyl]-2,3-dihydro-1H-1-benzazepine-4-carboxamide (0.45 g), 4-(2-butoxyethoxy)phenyl borate (0.23 g), 1M potassium carbonate solution (1.5 ml), ethanol (1.5 ml) and toluene (25 ml) was stirred under argon atmosphere at room temperature for 30 minutes. To the mixture was added tetrakis (triphenylphosphine)palladium (0.05 g), and the mixture was refluxed for 3 hours under argon atmosphere and extracted with ethyl acetate. The organic layer was washed with water and saturated brine and dried with anhydrous magnesium sulfate, and the solvent was evaporated under reduced pressure. The residue was purified with silica gel column chromatography (ethyl acetate/methanol/triethylamine) to give crude crystals, which were recrystallized to give 7-[4-(2-butoxyethoxy)phenyl]-1-cyclopropyl-N-[4-[[N-methyl-N-(tetrahydro-2H-pyran-4-yl)amino] methyl]phenyl]-2,3-dihydro-1H-1-benzazepine-4-carboxamide (Compound 31) (0.25 g) as pale yellow crystals.

mp 117–120° C.

$^1$H-NMR (δ ppm, CDCl$_3$) 0.55–0.62 (2H, m), 0.85–0.93 (2H, m), 0.93 (3H, t, J=7.0 Hz), 1.21–1.76 (8H, m), 2.20 (3H, s), 2.56–2.76 (2H, m), 2.90 (2H, t-like), 3.34 (2H, dt, J=8.0, 11.4 Hz), 3.43–3.59 (6H, m), 3.80 (2H, t, J=5.0 Hz), 4.00–4.06 (2H, m), 4.16 (2H, t, J=5.0 Hz), 6.98 (2H, d, J=8.8 Hz), 7.25–7.36 (3H, m), 7.42–7.54 (7H, m).

Anal. Calcd. for $C_{39}H_{49}N_3O_4$: C, 75.09; H, 7.92; N, 6.74. Found C, 75.09; H, 8.14; N, 6.78.

Working Example 32

Production of Compound 32

In DMF (4 ml) was dissolved 1-benzyl-7-[4-(2-propoxyethoxy)phenyl]-2,3-dihydro-1H-1-benzazepine-4-carboxylic acid (0.15 g). Under ice-cooling, to the mixture was added thionyl chloride (0.06 ml). The mixture was stirred at room temperature for 30 minutes. The solvent was evaporated under reduced pressure. In THF (25 ml) was dissolved the residue, and then the solution was added dropwise to a solution of 4-[N-methyl-N-(tetrahydro-2H-pyran-4-yl)aminomethyl]aniline (0.09 g) and triethylamine (0.23 ml) in THF (10 ml), under ice-cooling. The mixture was stirred at room temperature overnight under nitrogen atmosphere. The solvent was evaporated under reduced pressure. Water was added to the mixture, and then the mixture was extracted with ethyl acetate. The organic layer was washed with water and saturated brine and dried with anhydrous magnesium sulfate. The solvent was evaporated, and the residue was purified with silica gel column chromatography (ethyl acetate/methanol/triethylamine). The material was dissolved in ethyl acetate, and 4N hydrochloric acid-ethyl acetate was added to the solution. The solvent was evaporated to give 1-benzyl-7-[4-(2-propoxyethoxy) phenyl]-N-[4-[[N-methyl-N-(tetrahydro-2H-pyran-4-yl) amino]methyl]phenyl]-2,3-dihydro-1H-1-benzazepine-4- carboxamide hydrochloride (Compound 32) (0.14 g) as yellow amorphous.

$^1$H-NMR ($\delta$ ppm, DMSO-d$_6$) 0.87 (3H, t, J=7.3 Hz), 1.48–1.59 (2H, m), 1.65–2.15 (4H, m), 2.57 (3H, d, J=4.8 Hz), 2.81 (2H, s), 3.25–3.45 (7H, m), 3.98–4.13 (5H, m), 4.39–4.46 (1H, m), 4.66 (2H, s), 6.86 (1H, d, J=8.8 Hz), 6.99 (2H, d, J=8.8 Hz), 7.27–7.57 (11H, m), 7.67 (1H, s), 7.81 (2H, d, J=8.4 Hz), 10.04 (1H, s), 10.44 (1H, br).

IR (KBr) $\nu$: 2963, 2868, 1655, 1607, 1518, 1499 cm$^{-1}$.

Anal. Calcd. for C$_{42}$H$_{49}$N$_3$O$_4$·HCl·1.5H$_2$O: C, 69.74; H, 7.39; N, 5.81. Found C, 69.35; H, 7.40; N, 5.84.

Working Example 33

Production of Compound 33

In THF (5 ml) was dissolved 1-benzyl-7-[4-(2-butoxyethoxy)phenyl]-2,3-dihydro-1H-1-benzazepine-4-carboxylic acid (0.3 g). Under ice-cooling, to the solution were added oxalyl (0.11 ml) and DMF (catalytic amount). The mixture was stirred at room temperature for 30 minutes, and the solvent was evaporated under reduced pressure. In THF (25 ml) was dissolved the residue, the solution was added dropwise to a solution of 4-[N-methyl-N-(tetrahydro-2H-pyran-4-yl)aminomethyl]aniline (0.15 g) and triethylamine (0.44 ml) in THF (10 ml), under ice-cooling. The mixture was stirred at room temperature under nitrogen atmosphere and the solvent was evaporated under reduced pressure. To the residue was added water, and the mixture was extracted with ethyl acetate. The organic layer was washed with water and saturated brine, and dried with anhydrous magnesium sulfate. The solvent was evaporated, and the residue was purified by silica gel column chromatography (ethyl acetate/methanol/triethylamine) to give crude crystals, which were recrystallized from ethyl acetate-hexane to give 1-benzyl-7-[4-(2-butoxyethoxy)phenyl]-N-[4-[[N-methyl-N-(tetrahydro-2H-pyran-4-yl)amino]methyl]phenyl]-2,3-dihydro-1H-1-benzazepine-4-carboxamide (Compound 33) (0.26 g) as pale yellow crystals.

mp 127–131° C.

$^1$H-NMR ($\delta$ ppm, CDCl$_3$) 0.93 (3H, t, J=7.1 Hz), 1.30–1.75 (8H, m), 2.21 (3H, s), 2.55–2.70 (1H, m), 2.85 (2H, t-like), 3.31–3.38 (4H, m), 3.52–3.58 (4H, m), 3.80 (2H, t, J=4.9 Hz), 4.01–4.05 (2H, m), 4.16 (2H, t, J=4.9 Hz), 4.61 (2H, s), 6.90 (1H, d, J=8.4 Hz), 6.98 (2H, d, J=8.8 Hz), 7.26–7.56 (14H, m).

IR (KBr) $\nu$: 2934, 2851, 1651, 1601, 1514, 1501 cm$^{-1}$.

Anal. Calcd. for C$_{43}$H$_{51}$N$_3$O$_4$·0.25H$_2$O: C, 76.13; H, 7.65; N, 6.19. Found C, 76.19; H, 7.55; N, 6.19.

Working Example 34

Production of Compound 34

In THF (3 ml) was dissolved 7-[4-(2-butoxyethoxy)phenyl]-1-cyclohexylmethyl-2,3-dihydro-1H-1-benzazepine-4-carboxylic acid (0.25 g). Under ice-cooling, to the solution were added oxalyl chloride (0.09 ml) and DMF (catalytic amount). The mixture was stirred at room temperature for 1 hour, and the solvent was evaporated under reduced pressure. In THF (25 ml) was dissolved the residue, and the solution was added dropwise to a solution of 4-[N-methyl-N-(tetrahydro-2H-pyran-4-yl)aminomethyl]aniline (0.14 g) and triethylamine (0.36 ml) in THF (5 ml), under ice-cooling. The mixture was stirred at room temperature under nitrogen atmosphere and the solvent was evaporated under reduced pressure. To the residue was added water, and the mixture was extracted with ethyl acetate. The organic layer was washed with water and saturated brine, and dried with anhydrous magnesium sulfate. The solvent was evaporated to give crude crystals, which were recrystallized from diethyl ether-ethyl acetate-hexane to give 7-[4-(2-butoxyethoxy)phenyl]-1-cyclohexylmethyl-N-[4-[[N-methyl-N-(tetrahydro-2H-pyran-4-yl)amino]methyl]phenyl]-2,3-dihydro-1H-1-benzazepine-4-carboxamide (Compound 34) (0.28 g) as pale yellow crystals.

mp 115–117° C.

$^1$H-NMR ($\delta$ ppm, CDCl$_3$) 0.93 (3H, t, J=7.3 Hz), 0.93–1.4 (19H, m), 2.21 (3H, s), 2.58–2.66 (1H, m), 2.91 (2H, t-like), 3.22 (2H, d, J=6.6 Hz), 3.30–3.46 (4H, m), 3.50–3.58 (4H, m), 3.80 (2H, t, J=4.9 Hz), 4.01–4.06 (2H, m), 4.16 (2H, t, J=4.9 Hz), 6.91 (1H, d, J=8.8 Hz), 6.98 (2H, d, J=8.8 Hz), 7.30 (2H, d, J=8.4 Hz), 7.37–7.56 (7H, m).

IR (KBr) $\nu$: 2924, 2849, 1651, 1605, 1516, 1499 cm$^{-1}$.

Anal. Calcd. for C$_{43}$H$_{57}$N$_3$O$_4$: C, 75.96; H, 8.45; N, 6.18. Found C, 75.93; H, 8.58; N, 6.21.

Working Example 35

Production of Compound 35

In THF (5 ml) was dissolved 7-[4-(2-butoxyethoxy)phenyl]-1-cyclopropylmethyl-2,3-dihydro-1H-1-benzazepine-4-carboxylic acid (0.35 g). Under ice-cooling, to the solution were added oxalyl chloride (0.14 ml) and DMF (catalytic amount). The mixture was stirred at room temperature for 1 hour, and the solvent was evaporated under reduced pressure. In THF (25 ml) was dissolved the residue, and the solution was added dropwise to a solution of 4-[N-methyl-N-(tetrahydro-2H-pyran-4-yl)aminomethyl]aniline (0.20 g) and triethylamine (0.56 ml) in THF (10 ml), under ice-cooling. The mixture was stirred at room temperature overnight under nitrogen atmosphere and the solvent was evaporated under reduced pressure. To the residue was added water, and the mixture was extracted with ethyl acetate. The organic layer was washed with water and saturated brine, and dried with anhydrous magnesium sulfate. The solvent was evaporated, and the residue was purified with silica gel column chromatography (ethyl acetate/methanol/triethylamine) to give crude crystals, which were recrystallized from ethyl acetate-hexane to give 7-[4-(2-butoxyethoxy)phenyl]-1-cyclopropylmethyl-N-[4-[[N-methyl-N-(tetrahydro-2H-pyran-4-yl)amino]methyl]phenyl]-2,3-dihydro-1H-1-benzazepine-4-carboxamide (Compound 35) (0.36 g) as yellow crystals.

mp 92–94° C.

$^1$H-NMR ($\delta$ ppm, CDCl$_3$) 0.26–0.33 (2H, m), 0.60–0.69 (2H, m), 0.93 (3H, t, J=7.4 Hz), 1.05–1.18 (1H, m), 1.22–2.05 (8H, m), 2.21 (3H, s), 2.59–2.67 (1H, m), 2.95 (2H, t-like), 3.25 (2H, d, J=6.2 Hz), 3.32–3.58 (8H, m), 3.80 (2H, t, J=5.0 Hz), 3.93–4.18 (4H, m), 6.95–7.00 (3H, m), 7.29 (2H, d, J=8.8 Hz), 7.41–7.58 (7H, m).

IR (KBr) $\nu$: 3289, 2940, 2870, 1651, 1607, 1516, 1499 cm$^{-1}$.

Anal. Calcd. for C$_{40}$H$_{51}$N$_3$O$_4$: C, 75.32; H, 8.06; N, 6.59. Found C, 75.21; H, 8.12; N, 6.49.

Working Example 36

Production of Compound 36

In THF (5 ml) was dissolved 1-cyclopropylmethyl-7-[4-(2-propoxyethoxy)phenyl]-2,3-dihydro-1H-1-benzazepine-4-carboxylic acid (0.25 g). Under ice-cooling, to the solution were added oxalyl chloride (0.11 ml) and DMF (catalytic amount). The mixture was stirred at room temperature for 1 hour, and the solvent was evaporated under reduced pressure. In THF (25 ml) was dissolved the residue, and the solution was added dropwise to a solution of 4-[N-methyl-N-(tetrahydro-2H-pyran-4-yl)aminomethyl]aniline (0.14 g) and triethylamine (0.41 ml) in THF (5 ml), under ice-cooling. The mixture was stirred at room temperature overnight under nitrogen atmosphere and the solvent was evaporated under reduced pressure. To the residue was added water, and the mixture was extracted with ethyl acetate. The organic layer was washed with water and saturated brine, and dried with anhydrous magnesium sulfate. The solvent was evaporated, and the residue was purified with silica gel column chromatography (ethyl acetate/methanol/triethylamine), which was dissolved in ethyl acetate. To the solution was added 4N hydrochloric acid-ethyl acetate, and the solvent was evaporated to give 1-cyclopropylmethyl-7-[4-(2-propoxyethoxy)phenyl]-N-[4-[[N-methyl-N-tetrahydro-2H-pyran-4-yl)amino]methyl]phenyl]-2,3-dihydro-1H-1-benzazepine-4-carboxamide dihydrochloride (Compound 36) (0.32 g) as pale yellow amorphous.

$^1$H-NMR ($\delta$ ppm, DMSO-$d_6$) 0.29–0.31 (2H, m), 0.54–0.57 (2H, m), 0.88 (2H, t, J=7.5 Hz), 1.06–1.13 (1H, m), 1.45–1.63 (2H, m), 1.70–2.20 (4H, m), 2.57 (3H, d, J=4.8 Hz), 2.89 (2H, br), 3.25–3.46 (9H, m), 3.69–3.74 (2H, m), 4.10–4.14 (5H, m), 4.37–4.45 (1H, m), 7.00 (2H, d, J=8.8 Hz), 7.03–7.11 (1H, m), 7.44–7.59 (6H, m), 7.68 (1H, s), 7.81 (2H, d, J=8.6 Hz), 10.07 (1H, s), 10.63 (1H, br).

Working Example 37

Production of Compound 37

In THF (5 ml) was dissolved 7-[4-(2-butoxyethoxy)phenyl]-1-cyclobutylmethyl-2,3-dihydro-1H-1-benzazepine-4-carboxylic acid (0.25 g). Under ice-cooling, to the solution were added oxalyl chloride (0.1 ml) and DMF (catalytic amount). The mixture was stirred at room temperature for 1 hour, and the solvent was evaporated under reduced pressure. In THF (25 ml) was dissolved the residue, the solution was added dropwise to a solution of 4-[N-methyl-N-(tetrahydro-2H-pyran-4-yl)aminomethyl]aniline (0.13 g) and triethylamine (0.4 ml) in THF (5 ml), under ice-cooling. The mixture was stirred at room temperature overnight under nitrogen atmosphere and the solvent was evaporated under reduced pressure. To the residue was added water, and the mixture was extracted with ethyl acetate. The organic layer was washed with water and saturated brine; and dried with anhydrous magnesium sulfate. The solvent was evaporated, and the residue was purified with silica gel column chromatography (ethyl acetate/methanol/triethylamine), which was dissolved in ethyl acetate. To the solution was added 4N hydrochloric acid-ethyl acetate, and the solvent was evaporated to give 7-[4-(2-butoxyethoxy)phenyl]-1-cyclobutylmethyl-N-[4-[[N-methyl-N-(tetrahydro-2H-pyran-4-yl)amino]methyl]phenyl]-2,3-dihydro-1H-1-benzazepine-4-carboxamide dihydrochloride (Compound 37) (0.27 g) as pale yellow amorphous.

$^1$H-NMR ($\delta$ ppm, DMSO-$d_6$) 0.89 (3H, t, J=7.1 Hz), 1.24–1.58 (4H, m), 1.73–2.15 (1H, m), 2.57 (3H, d, J=4.8 Hz), 2.60–2.85 (3H, m), 3.20–3.49 (10H, m), 3.96–4.13 (5H, m), 4.38–4.44 (1H, m), 6.97–7.02 (3H, m), 7.40–7.63 (7H, m), 7.80 (2H, d, J=8.8 Hz), 10.02 (1H, s), 10.41 (1H, s).

Anal. Calcd. for $C_{41}H_{53}N_3O_4 \cdot 2HCl \cdot 1.5H_2O$: C, 65.50; H, 7.78; N, 5.59. Found C, 65.51; H, 7.77; N, 5.24.

Working Example 38

Production of Compound 38

In DMF (6 ml) was dissolved 1-phenyl-7-[4-(2-propoxyethoxy)phenyl]-2,3-dihydro-1H-1-benzazepine-4-carboxylic acid (0.2 g). Under ice-cooling, to the mixture was added thionyl chloride (0.08 ml). The mixture was stirred at room temperature for 30 minutes. The solvent was evaporated under reduced pressure. In THF (20 ml) was suspended the residue, the suspension was added dropwise to a solution of 4-[N-methyl-N-(tetrahydro-2H-pyran-4-yl)aminomethyl]aniline (0.12 g) and triethylamine (0.31 ml) in THF (5 ml), under ice-cooling. The mixture was stirred at room temperature overnight under nitrogen atmosphere. The solvent was evaporated under reduced pressure. Water was added to the mixture, the mixture was extracted with ethyl acetate. The organic layer was washed with water and saturated brine and dried with anhydrous magnesium sulfate. The solvent was evaporated, the residue was purified with silica gel column chromatography (ethyl acetate/methanol/triethylamine), which was dissolved in ethyl acetate-ethanol, 4N hydrochloric acid-ethyl acetate was added to the solution, and the solvent was evaporated to give 1-phenyl-7-[4-(2-propoxyethoxy)phenyl]-N-[4-[[N-methyl-N-(tetrahydro-2H-pyran-4-yl)amino]methyl]phenyl]-2,3-dihydro-1H-1-benzazepine-4-carboxamide hydrochloride (Compound 38) (0.17 g) as yellow crystals.

mp 223–224° C.

$^1$H-NMR ($\delta$ ppm, DMSO-$d_6$) 0.88 (3H, t, J=7.3 Hz), 1.45–1.60 (2H, m), 1.70–1.95 (2H, m), 1.95–2.15 (2H, m), 2.58 (3H, d, J=4.8 Hz), 2.84 (2H, br), 3.22–3.46 (4H, m), 3.72 (2H, t, J=4.7 Hz), 3.75–4.12 (5H, m), 4.15 (2H, t, J=4.7 Hz), 4.39–4.46 (1H, m), 6.80–6.90 (1H, m), 6.98–7.07 (4H, m), 7.20–7.30 (3H, m), 7.47–7.57 (4H, m), 7.65 (2H, d, J=8.8 Hz), 7.79 (2H, d, J=8.8 Hz), 7.85 (1H, s), 9.96 (1H, br), 10.07 (1H, s).

IR (KBr) ν: 2961, 2928, 2863, 1651, 1520, 1495 cm$^{-1}$.

Anal. Calcd. for $C_{41}H_{47}N_3O_4 \cdot HCl \cdot 0.5H_2O$: C, 71.23; H, 7.14; N, 6.08. Found C, 71.56; H, 7.17; N, 6.18.

Working Example 39

Production of Compound 39

In THF (5 ml) was dissolved 7-[4-(2-butoxyethoxy)phenyl]-1-phenyl-2,3-dihydro-1H-1-benzazepine-4-carboxylic acid (0.25 g). Under ice-cooling, to the solution were added oxalyl chloride (0.1 ml) and DMF (catalytic amount). The mixture was stirred at room temperature for 1 hour, and the solvent was evaporated under reduced pressure. In THF (25 ml) was suspended the residue, the suspension was added dropwise to a solution of 4-[N-methyl-N-(tetrahydro-2H-pyran-4-yl)aminomethyl]aniline (0.13 g) and triethylamine (0.38 ml) in THF (5 ml), under ice-cooling. The mixture was stirred at room temperature overnight under nitrogen atmosphere and the solvent was evaporated under reduced pressure. To the residue was added water, and the mixture was extracted with ethyl acetate. The organic layer was washed with water and saturated brine, and dried with anhydrous magnesium sulfate. The solvent was evaporated, and the residue was purified with silica gel column chromatography (ethyl acetate/methanol/triethylamine) to give 7-[4-(2-butoxyethoxy)phenyl]-1-phenyl-N-[4-[[N-methyl-N-(tetrahydro-2H-pyran-4-yl)amino]methyl]phenyl]-2,3-dihydro-1H-1-benzazepine-4-carboxamide (Compound 39) (0.21 g) as yellow amorphous.

¹H-NMR (δ ppm, CDCl₃) 0.93 (3H, t, J=7.3 Hz), 1.27–1.49 (2H, m), 1.55–1.74 (6H, m), 2.19 (3H, s), 2.58–2.66 (1H, m), 2.93 (2H, t, J=4.8 Hz), 3.36 (2H, dt, J=3.2, 10.8 Hz), 3.52–3.59 (4H, m), 3.81 (2H, t, J=5.0 Hz), 3.89 (2H, t, J=4.8 Hz), 4.00–4.06 (2H, m), 4.17 (2H, t, J=5.0 Hz), 6.88–7.02 (5H, m), 7.21–7.30 (4H, m), 7.41 (1H, dd, J=2.2, 8.6 Hz), 7.48–7.53 (6H, m), 7.64 (1H, d, J=2.2 Hz).

IR (KBr) ν: 2953, 2934, 2847, 1653, 1595, 1520, 1495 cm⁻¹.

Anal. Calcd. for $C_{42}H_{49}N_3O_4 \cdot 0.25H_2O$: C, 75.93; H, 7.51; N, 6.32. Found C, 75.80; H, 7.40; N, 6.30.

Working Example 40

Production of Compound 40

In THF (5 ml) was dissolved 7-[4-(2-butoxyethoxy)phenyl]-1-(3-methoxyphenyl)-2,3-dihydro-1H-1-benzazepine-4-carboxylic acid (0.15 g). Under ice-cooling, to the solution were added oxalyl chloride (0.06 ml) and DMF (catalytic amount). The mixture was stirred at room temperature for 30 minutes, and the solvent was evaporated under reduced pressure. In THF (30 ml) was dissolved the residue, and the solution was added dropwise to a solution of 4-[N-methyl-N-(tetrahydro-2H-pyran-4-yl)aminomethyl]aniline (0.07 g) and triethylamine (0.2 ml) in THF (5 ml), under ice-cooling. The mixture was stirred at room temperature overnight under nitrogen atmosphere and the solvent was evaporated under reduced pressure. To the residue was added water, and the mixture was extracted with ethyl acetate. The organic layer was washed with water and saturated brine, and dried with anhydrous magnesium sulfate. The solvent was evaporated, and the residue was purified with silica gel column chromatography (ethyl acetate/methanol/triethylamine) to give crude crystals, which were recrystallized from ethyl acetate-hexane to give 7-[4-(2-butoxyethoxy)phenyl]-1-(3-methoxyphenyl)-N-(4-[[N-methyl-N-(tetrahydro-2H-pyran-4-yl)amino]methyl]phenyl]-2,3-dihydro-1H-1-benzazepine-4-carboxamide (Compound 40) (0.11 g) as pale yellow crystals.

mp 94–97° C.

¹H-NMR (δ ppm, CDCl₃) 0.93 (3H, t, J=7.4 Hz), 1.27–1.76 (8H, m), 2.20 (3H, s), 2.58–2.69 (1H, m), 2.95 (2H, t-like), 3.36 (2H, dt, J=3.4, 11.5 Hz), 3.52–3.59 (4H, m), 3.76 (3H, s), 3.76–3.87 (4H, m), 4.00–4.06 (2H, m), 4.17 (2H, t, J=4.9 Hz), 6.43–6.62 (3H, m), 7.00 (2H, d, J=8.8 Hz), 7.14–7.30 (3H, m), 7.40 7.54 (7H, m), 7.64 (1H, d, J=1.8 Hz).

IR (KBr) ν: 2955, 2845, 1661, 1595, 1516, 1493 cm⁻¹.

Anal. Calcd. for $C_{43}H_{51}N_3O_5$: C, 74.86; H, 7.45; N, 6.09. Found C, 74.52; H, 7.66; N, 6.19.

Working Example 41

Production of Compound 41

In THF (5 ml) was dissolved 7-[4-(2-butoxyethoxy)phenyl]-1-(4-methoxyphenyl)-2,3-dihydro-1H-1-benzazepine-4-carboxylic acid (0.2 g). Under ice-cooling, to the solution were added oxalyl chloride (0.08 ml) and DMF (catalytic amount). The mixture was stirred at room temperature for 1 hour, and the solvent was evaporated under reduced pressure. In THF (20 ml) was dissolved the residue, and the solution was added dropwise to a solution of 4-[N-methyl-N-(tetrahydro-2H-pyran-4-yl)aminomethyl]aniline (0.1 g) and triethylamine (0.3 ml) in THF (5 ml), under ice-cooling. The mixture was stirred at room temperature overnight under nitrogen atmosphere and the solvent was evaporated under reduced pressure. To the residue was added water, and the mixture was extracted with ethyl acetate. The organic layer was washed with water and saturated brine, and dried with anhydrous magnesium sulfate. The solvent was evaporated, and the residue was purified with silica gel column chromatography (ethyl acetate/methanol/triethylamine) to give 7-[4-(2-butoxyethoxy)phenyl]-1-(4-methoxyphenyl)-N-[4-[[N-methyl-N-(tetrahydro-2H-pyran-4-yl)amino]methyl]phenyl]-2,3-dihydro-1H-1-benzazepine-4-carboxamide (Compound 41) (0.22 g) as yellow amorphous.

¹H-NMR (δ ppm, CDCl₃) 0.93 (3H, t, J=7.1 Hz), 1.26–1.48 (2H, m), 1.54–1.74 (6H, m), 2.20 (3H, s), 2.58–2.66 (1H, m), 2.90 (2H, t-like), 3.37 (2H, dt, J=2.2, 12.7 Hz), 3.52–3.58 (4H, m), 3.78–3.83 (7H, m), 4.01–4.06 (2H, m), 4.16 (2H, t, J=4.9 Hz), 6.85–7.05 (7H, m), 7.26–7.34 (2H, m), 7.46–7.59 (7H, m).

Working Example 42

Production of Compound 42

In THF (5 ml) was dissolved 7-[4-(2-butoxyethoxy)phenyl]-1-(4-propoxyphenyl)-2,3-dihydro-1H-1-benzazepine-4-carboxylic acid (0.2 g). Under ice-cooling, to the solution were added oxalyl chloride (0.05 ml) and DMF (catalytic amount). The mixture was stirred at room temperature for 1 hour, and the solvent was evaporated under reduced pressure. In THF (20 ml) was dissolved the residue, and the solution was added dropwise to a solution of 4-[N-methyl-N-(tetrahydro-2H-pyran-4-yl)aminomethyl]aniline (0.11 g) and triethylamine (0.3 ml) in THF (5 ml), under ice-cooling. The mixture was stirred at room temperature overnight under nitrogen atmosphere and the solvent was evaporated under reduced pressure. To the residue was added water, and the mixture was extracted with ethyl acetate. The organic layer was washed with water and saturated brine, and dried with anhydrous magnesium sulfate. The solvent was evaporated, and the residue was purified with silica gel column chromatography (ethyl acetate/methanol/triethylamine) to give 7-[4-(2-butoxyethoxy)phenyl]-1-(4-propoxyphenyl)-N-[4-[[N-methyl-N-(tetrahydro-2H-pyran-4-yl)amino]methyl]phenyl]-2,3-dihydro-1H-1-benzazepine-4-carboxamide (Compound 42) (0.2 g) as yellow amorphous.

¹H-NMR (δ ppm, CDCl₃) 0.93 (3H, t, J=7.3 Hz), 1.04 (3H, t, J=7.3 Hz), 1.34–1.48 (2H, m), 1.54–1.86 (8H, m), 2.20 (3H, s), 2.58–2.69 (1H, m), 2.88 (2H, t-like), 3.36 (2H, dt, J=3.4, 11.0 Hz), 3.52–3.58 (5H, m), 3.78–3.83 (4H, m), 3.90 (2H, t, J=10.1 Hz), 4.00–4.17 (4H, m), 6.84–7.03 (7H, m), 7.26–7.33 (2H, m), 7.45–7.61 (7H, m).

IR (KBr) ν: 2936, 2872, 1651, 1607, 1495 cm⁻¹.

Working Example 43

Production of Compound 43

In THF (5 ml) was dissolved 7-[4-(2-butoxyethoxy)phenyl]-1-(3,4-methylenedioxyphenyl)-2,3-dihydro-1H-1-benzazepine-4-carboxylic acid (0.25 g). Under ice-cooling, to the solution were added oxalyl chloride (0.1 ml) and DMF (catalytic amount). The mixture was stirred at room temperature for 1 hour, and the solvent was evaporated under reduced pressure. In THF (30 ml) was dissolved the residue, and the solution was added dropwise to a solution of 4-[N-methyl-N-(tetrahydro-2H-pyran-4-yl)aminomethyl]aniline (0.13 g) and triethylamine (0.35 ml) in THF (5 ml), under ice-cooling. The mixture was stirred at room temperature overnight under nitrogen atmosphere and the solvent was evaporated under reduced pressure. To the residue was added water, and the mixture was extracted with ethyl acetate. The organic layer was washed with water and saturated brine, and dried with anhydrous magnesium sulfate. The solvent was evaporated, and the residue was purified with silica gel column chromatography (ethyl acetate/methanol/triethylamine) to give 7-[4-(2-butoxyethoxy)phenyl]-1-(3,4-methylenedioxyphenyl)-N-[4-[[N-methyl-N-(tetrahydro-2H-pyran-4-yl)amino)methyl]phenyl]-2,3-dihydro-1H-1-benzazepine-4-carboxamide (Compound 43) (0.28 g) as yellow amorphous.

$^1$H-NMR ($\delta$ ppm, CDCl$_3$) 0.93 (3H, t, J=7.3 Hz), 1.22–1.48 (4H, m), 1.54–1.74 (4H, m), 2.20 (3H, s), 2.58–2.67 (1H, m), 2.91 (2H, t-like), 3.37 (2H, dt, J=3.0, 11.2 Hz), 3.52–3.59 (4H, m), 3.78–3.83 (4H, m), 4.01–4.19 (4H, m), 5.95 (2H, s), 6.50 (H, dd, J=2.2, 8.4 Hz), 6.61 (1H, d, J=2.2 Hz), 6.76 (1H, d, J=8.4 Hz), 6.97–7.03 (3H, m), 7.26–7.37 (3H, m), 7.46–7.59 (7H, m).

IR (KBr) ν: 2951, 2872, 1651, 1607, 1514, 1487 cm$^{-1}$.

Working Example 44

Production of Compound 17

In phosphorus oxychloride (25 ml) was dissolved 1-(N-acetylglycyl)-7-[4-(2-butoxyethoxy)phenyl]-N-[4-[[N-methyl-N-(tetrahydro-2H-pyran-4-yl)amino]methyl]phenyl]-2,3-dihydro-1H-1-benzazepine-4-carboxamide (0.5 g). The solution was heated to stir at room temperature for 7 hours and at 50° C. for 2 hours, and the solvent was evaporated. To the residue was added sodium hydrogen carbonate solution, and the mixture was extracted with ethyl acetate. The organic layer was washed with water and saturated brine, and dried with anhydrous magnesium sulfate. The solvent was evaporated, and the residue was purified with basic silica gel column chromatography (ethyl acetate/hexane). The resulting crude crystals were recrystallized from ethyl acetate-hexane to give 7-[4-(2-butoxyethoxy)phenyl]-1-(2-methyloxazol-5-yl)-N-[4-[[N-methyl-N-(tetrahydro-2H-pyran-4-yl)amino]methyl]phenyl]-2,3-dihydro-1H-1-benzazepine-4-carboxamide (Compound 44) (0.26 g) as pale yellow crystals.

mp 125–128° C.

$^1$H-NMR ($\delta$ ppm, CDCl$_3$) 0.93 (3H, t, J=7.3 Hz), 1.22–1.48 (2H, m), 1.54–1.76 (6H, m), 2.20 (3H, s), 2.41 (3H, s), 2.55–2.70 (1H, m), 2.96 (2H, t-like), 3.36 (2H, dt, J=2.6, 11.0 Hz), 3.52–3.58 (4H, m), 3.72 (2H, t-like), 3.80 (2H, t, J=4.8 Hz), 4.00–4.06 (2H, m), 4.15 (2H, t, J=4.8 Hz), 6.33 (1H, s), 6.98 (2H, d, J=8.8 Hz), 7.08 (1H, d, J=8.4 Hz), 7.26–7.56 (8H, m), 7.76 (1H, s).

IR (KBr) ν: 2936, 2870, 1651, 1516, 1495 cm$^{-1}$.

Anal. Calcd. for C$_{40}$H$_{48}$N$_4$O$_5$: C, 72.26; H, 7.28; N, 8.43. Found C, 72.16; H, 7.10; N, 8.51.

Working Example 45

Production of Compound 45

In DMF (20 ml) were suspended 7-[4-(2-butoxyethoxy)phenyl]-1-(2-methylthiazol-4-yl)-2,3-dihydro-1H-1-benzazepine-4-carboxylic acid (0.13 g), 4-[N-methyl-N-(tetrahydro-2H-pyran-4-yl)aminomethyl]aniline dihydrochloride (0.1 g) and 1-hydroxybenzotriazole (0.06 g). Under ice-cooling, to the suspension were added 1-ethyl-3-(3-dimethylaminopropyl)carbodiimide hydrochloride (0.15 g), triethylamine (0.18 ml) and 4-dimethylaminopyridine (catalytic amount), and the mixture was stirred at room temperature overnight, which was poured into water and extracted with ethyl acetate. The organic layer was washed with water and saturated brine, and dried with anhydrous magnesium sulfate, and the solvent was evaporated. The residue was purified with silica gel column (ethyl acetate/methanol/triethylamine) to give crude crystals, which were recrystallized from ethyl acetate-diethyl ether-hexane to give 7-[4-(2-butoxyethoxy)phenyl]-1-(2-methylthiazol-4-yl)-N-[4-[[N-methyl-N-(tetrahydro-2H-pyran-4-yl)amino]methyl]phenyl]-2,3-dihydro-1H-1-benzazepine-4-carboxamide (Compound 45) (0.087 g) as pale yellow crystals.

mp 115–123° C.

$^1$H-NMR ($\delta$ ppm, CDCl$_3$) 0.93 (3H, t, J=7.3 Hz), 1.30–1.45 (2H, m), 1.55–1.76 (6H, m), 2.21 (3H, s), 2.55–2.75 (1H, m), 2.67 (3H, s), 2.94 (2H, t-like), 3.36 (2H, dt, J=2.6, 11.2 Hz), 3.52–3.59 (4H, m), 3.81 (2H, t, J=4.9 Hz), 4.01–4.19 (6H, m), 5.93 (1H, s), 7.00 (2H, d, J=8.8 Hz), 7.31 (1H, s), 7.43–7.60 ( 9H, m).

IR (KBr) ν: 2932, 2870, 2843, 1659, 1597, 1526, 1518, 1495 cm$^{-1}$.

Working Example 46

Production of Compound 46

In DMF (20 ml) were suspended 7-[4-(2-butoxyethoxy)phenyl]-1-(4-sulfamoylphenyl)-2,3-dihydro-1H-1-benzazepine-4-carboxylic acid (0.15 g), 4-[N-methyl-N-(tetrahydro-2H-pyran-4-yl)aminomethyl]aniline dihydrochloride (0.11 g) and 1-hydroxybenzotriazole (0.06 g). Under ice-cooling, to the suspension were added 1-ethyl-3-(3-dimethylaminopropyl)carbodiimide hydrochloride (0.16 g), triethylamine (0.2 ml) and 4-dimethylaminopyridine (catalytic amount), and the mixture was stirred at room temperature overnight, The solvent was evaporated, water was added to the residue, and the mixture was extracted with ethyl acetate. The organic layer was washed with water and saturated brine, and dried with anhydrous magnesium sulfate, and the solvent was evaporated. The residue was purified with silica gel column (ethyl acetate/methanol/triethylamine) to give crude crystals, which were recrystallized from ethyl acetate-hexane to give 7-[4-(2-butoxyethoxy)phenyl]-N-[4-[[N-methyl-N-(tetrahydro-2H-pyran-4-yl)amino]methyl]phenyl]-1-(4-sulfamoylphenyl)-2,3-dihydro-1H-1-benzazepine-4-carboxamide (Compound 46) (0.085 g) as yellow crystals.

$^1$H-NMR ($\delta$ ppm, CDCl$_3$) 0.93 (3H, t, J=7.2 Hz), 1.33–1.48 (2H, m), 1.54–1.75 (6H, m), 2.15 (3H, s), 2.57–2.67 (1H, m), 2.78–2.94 (2H, m), 3.33 (2H, t, J=10.3 Hz), 3.46–3.58 (4H, m), 3.78–3.82 (4H, m), 3.97–4.02 (2H, m), 4.06–4.14 (2H, m), 6.78 (2H, d, J=9.2 Hz), 6.97 (2H, d, J=8.8 Hz), 7.19–7.29 (3H, m), 7.36–7.63 (9H, m), 8.16 (1H, s).

Working Example 47

Production of Compound 47

In DMF (25 ml) were suspended 7-[4-(2-butoxyethoxy)phenyl]-1-(N,N-dimethyl-4-sulfamoylphenyl)-2,3-dihydro-1H-1-benzazepine-4-carboxylic acid (0.3 g), 4-[N-methyl-N-(tetrahydro-2H-pyran-4-yl)aminomethyl]aniline dihydrochloride (0.19 g) and 1-hydroxybenzotriazole (0.07 g). Under ice-cooling, to the suspension were added 1-ethyl-3-(3-dimethylaminopropyl)carbodiimide hydrochloride (0.15 g), triethylamine (0.37 ml) and 4-dimethylaminopyridine (catalytic amount), and the mixture was stirred at room temperature overnight. The solvent was evaporated, water was added to the residue, and the mixture was extracted with ethyl acetate. The organic layer was washed with water and saturated brine, and dried with anhydrous magnesium sulfate, and the solvent was evaporated. The residue was purified with silica gel column (ethyl acetate/methanol/triethylamine) to give crude crystals, which were recrystallized from ethyl acetate-hexane to give 7-[4-(2-butoxyethoxy)phenyl]-1-(N,N-dimethyl-4-sulfamoylphenyl)-N-[4-[[N-methyl-N-(tetrahydro-2H-pyran-4-yl)amino]methyl]phenyl]-2,3-dihydro-1H-1-benzazepine-4-carboxamide (Compound 47) (0.12 g) as colorless crystals.

mp 94–98° C.

$^1$H-NMR (δ ppm, CDCl$_3$) 0.94 (3H, t, J=7.1 Hz), 1.22–1.74 (8H, m), 2.20 (3H, s), 2.55–2.70 (1H, m), 2.70 (6H, s), 3.02 (2H, t-like), 3.36 (2H, dt, J=2.6, 11.0 Hz), 3.53–3.60 (4H, m), 3.82 (2H, t, J=5.0 Hz), 3.85–4.14 (4H, m), 4.18 (2H, t, J=5.0 Hz), 6.96 (2H, d, J=8.8 Hz), 7.03 (2H, d, J=8.8 Hz), 7.30 (2H, d, J=8.4 Hz), 7.37–7.63 (9H, m), 7.70 (1H, d, J=2.2 Hz).

Working Example 48

Production of Compound 48

In THF (7 ml) was dissolved 7-[4-(2-butoxyethoxy) phenyl]-1-(N-methyl-4-sulfamoylphenyl)-2,3-dihydro-1H-1-benzazepine-4-carboxylic acid (0.4 g). Under ice-cooling, to the solution were added oxalyl chloride (0.19 ml) and DMF (catalytic amount). The mixture was stirred at room temperature for 1 hour, and the solvent was evaporated under reduced pressure. In THF (25 ml) was dissolved the residue, and the solution was added dropwise to a suspension of 4-[N-methyl-N-(tetrahydro-2H-pyran-4-yl) aminomethyl]aniline dihydrochloride (0.28 g) and triethylamine (0.5 ml) in THF (5 ml), under ice-cooling. The mixture was stirred at room temperature under nitrogen atmosphere for 1 hour and the solvent was evaporated under reduced pressure. To the residue was added water, and the mixture was extracted with ethyl acetate. The organic layer was washed with water and saturated brine, and dried with anhydrous magnesium sulfate. The solvent was evaporated, and the residue was purified with basic silica gel column chromatography (ethyl acetate) to give crude crystals, which were recrystallized from ethyl acetate-hexane to give 7-[4-(2-butoxyethoxy)phenyl]-1-(N-methyl-4-sulfamoylphenyl)-N-[4-[[N-methyl-N-tetrahydro-2H-pyran-4-yl)amino] methyl]phenyl]-2,3-dihydro-1H-1-benzazepine-4-carboxamide (Compound 48) (0.28 g) as pale yellow crystals.

mp 96–99° C.

$^1$H-NMR (δ ppm, CDCl$_3$) 0.93 (3H, t, J=7.3 Hz), 1.29–1.71 (8H, m), 2.17 (3H, s), 2.59 (3H, d, J=4.0 Hz), 2.60–2.70 (1H, m), 2.95 (2H, t-like), 3.35 (2H, dt, J=2.6, 11.4 Hz), 3.52–3.59 (4H, m), 3.79–3.88 (4H, m), 3.99–4.17 (4H, m), 4.66 (1H, br), 6.86 (2H, d, J=8.8 Hz), 6.99 (2H, d, J=8.4 Hz), 7.23–7.66 (12H, m), 8.05 (1H, d, J=9.6 Hz).

IR (KBr) ν: 2942, 2853, 1661, 1590, 1495 cm$^{-1}$.

Reference Example 98

Propionyl chloride (1.0 ml) was added dropwise to a suspension of methyl 7-(2-propoxyethoxy)-2,3-dihydro-1H-1-benzazepine-4-carboxylate (0.2 g) and potassium carbonate (2.2 g) in DMF (10 ml) under ice-cooling. The mixture was stirred at room temperature overnight under nitrogen atmosphere, and poured into water, which was extracted with ethyl acetate. The organic layer was washed with water and saturated brine, and dried with anhydrous magnesium sulfate. The solvent was evaporated and the residue was purified with silica gel column chromatography (ethyl acetate/hexane) to give methyl 1-propionyl-7-(2-propoxyethoxy)-2,3-dihydro-1H-1-benzazepine-4-carboxylate (0.2 g) as pale yellow oil.

$^1$H-NMR (δ ppm, CDCl$_3$) 0.95 (3H, t, J=7.3 Hz), 1.05 (3H, t, J=7.3 Hz), 1.57–1.75 (2H, m), 2.09–2.20 (1H, m), 2.41–2.53 (1H, m), 2.75–2.84 (2H, m), 2.88–3.10 (1H, m), 3.52 (2H, t, J=6.7 Hz), 3.80–3.83 (5H, m), 4.18 (2H, t, J=4.6 Hz), 4.75–4.80 (1H, m), 7.03 (2H, d, J=8.8 Hz), 7.24 (1H, d, J=8.4 Hz), 7.48–7.55 (3H, m), 7.65 (1H, d, J=1.8 Hz), 7.73 (1H, s).

IR (neat) ν: 2948, 2874, 1713, 1661 cm$^{-1}$.

Reference Example 99

In methanol (25 ml) and THF (25 ml) was dissolved methyl 1-propionyl-7-(2-propoxyethoxy)-2,3-dihydro-1H-1-benzazepine-4-carboxylate (0.2 g), and to the solution was added 1N sodium hydroxide solution (5 ml). The mixture was stirred at room temperature overnight, concentrated, and then neutralized with 1N hydrochloric acid and extracted with ethyl acetate. The organic layer was washed with water and saturated brine, and dried with anhydrous magnesium sulfate. The solvent was evaporated to give 1-propionyl-7-(2-propoxyethoxy)-2,3-dihydro-1H-1-benzazepine-4-carboxylic acid (0.2 g) as colorless crystals.

$^1$H-NMR (δ ppm, CDCl$_3$) 0.95 (3H, t, J=7.3 Hz), 1.07 (3H, t, J=7.5 Hz), 1.57–1.75 (2H, m), 2.12–2.22 (1H, m), 2.43–2.55 (1H, m), 2.78–2.88 (2H, m), 3.00–3.10 (1H, m), 3.53 (2H, t, J=6.8 Hz), 3.83 (2H, t, J=5.0 Hz), 4.19 (2H, t, J=5.0 Hz), 4.78–4.80 (1H, m), 7.03 (2H, d, J=8.6 Hz), 7.26 (1H, d, J=8.2 Hz), 7.51–7.56 (3H, m), 7.67 (1H, d, J=1.4 Hz), 7.83 (1H, s).

IR (KBr) ν: 2940, 2876, 1705 cm$^{-1}$.

Reference Example 100

In 1,2-dichloroethane (20) were dissolved methyl 7-bromo-2,3-dihydro-1H-1-benzazepine-4-carboxylate (1.0 g), n-butylaldehyde (1.3 ml) and acetic acid (0.41 ml), and to the solution was added sodium triacetoxyborohydride (3.8 g). The mixture was stirred at room temperature overnight, poured into water, neutralized with sodium hydrogen carbonate solution and extracted with ethyl acetate. The organic layer was washed with water and saturated brine, and dried with anhydrous magnesium sulfate. The solvent was evaporated and the residue was purified with silica gel column chromatography (ethyl acetate/hexane) to give methyl 7-bromo-1-butyl-2,3-dihydro-1H-1-benzazepine-4-carboxylate (0.9 g) as pale yellow oil.

$^1$H-NMR (δ ppm, CDCl$_3$) 0.96 (3H, t, J=7.2 Hz), 1.27–1.45 (2H, m), 1.56–1.72 (2H, m), 2.79 (2H, t, J=4.2 Hz), 3.19–3.31 (4H, m), 3.80 (3H, s), 6.69 (1H, d, J=8.8 Hz), 7.23 (1H, dd, J=2.5, 8.8 Hz), 7.42 (1H, d, J=2.5 Hz), 7.57 (1H, s).

Reference Example 101

A mixture of methyl 7-bromo-1-butyl-2,3-dihydro-1H-1-benzazepine-4-carboxylate (0.45 g), 4-(2-propoxyethoxy) phenyl borate (0.66 g), 1M potassium carbonate solution (4 ml), ethanol (4 ml) and toluene (25 ml) was stirred under argon atmosphere at room temperature for 30 minutes. To the mixture was added tetrakis(triphenylphosphine) palladium (0.12 g), and the mixture was refluxed overnight under argon atmosphere and extracted with ethyl acetate. The organic layer was washed with water and saturated brine and dried with anhydrous magnesium sulfate, and the solvent was evaporated under reduced pressure. The residue was purified with silica gel column chromatography (ethyl acetate/hexane) to give methyl 1-butyl-7-[4-(2-propoxyethoxy)phenyl]-2,3-dihydro-1H-1-benzazepine-4-carboxylate (0.5 g) as pale yellow oil.

$^1$H-NMR ($\delta$ ppm, CDCl$_3$) 0.91–1.01 (6H, m), 1.30–1.45 (2H, m), 1.57–1.73 (4H, m), 2.80 (2H, t, J=4.6 Hz), 3.25–3.37 (4H, m), 3.51 (2H, t, J=6.1 Hz), 3.78–3.83 (5H, m), 4.16 (2H, t, J=4.9 Hz), 6.87 (1H, d, J=8.4 Hz), 6.97 (2H, d, J=8.8 Hz), 7.37–7.51 (4H, m), 7.76 (1H, s).

IR (neat) v: 2959, 2928, 2870, 1698, 1607, 1501 cm$^{-1}$.

Reference Example 102

In methanol (25 ml) and THF (25 ml) was dissolved methyl 1-butyl-7-[4-(2-propoxyethoxy)phenyl]-2,3-dihydro-1H-1-benzazepine-4-carboxylate (0.5 g). To the solution was added 1N sodium hydroxide solution (17 ml), and the mixture was heated to stir at 50° C. for 5 hours, concentrated, neutralized with 1N hydrochloric acid and extracted with ethyl acetate. The organic layer was washed with water and saturated brine and dried with anhydrous magnesium sulfate. The solvent was evaporated to give 1-butyl-7-[4-(2-propoxyethoxy)phenyl]-2,3-dihydro-1H-1-benzazepine-4-carboxylic acid (0.38 g) as yellow crystals.

mp 176–177° C.

$^1$H-NMR ($\delta$ ppm, CDCl$_3$) 0.91–1.02 (6H, m), 1.35–1.46 (2H, m), 1.60–1.74 (4H, m), 2.84 (2H, t-like), 3.32–3.39 (4H, m), 3.52 (2H, t, J=6.8 Hz), 3.81 (2H, t, J=5.1 Hz), 4.17 (2H, t, J=5.1 Hz), 6.88 (1H, d, J=9.2 Hz), 6.98 (2H, d, J=8.8 Hz), 7.40–7.53 (4H, m), 7.88 (1H, s).

IR (KBr) v: 2959, 2932, 2872, 1669, 1607, 1501 cm$^{-1}$.

Anal. Calcd. for C$_{26}$H$_{33}$NO$_4$: C, 73.73; H, 7.85; N, 3.31. Found C, 73.42; H, 7.86; N, 3.25.

Reference Example 103

To cyclopropylamine (50 ml) was added dropwise t-butyl 4-bromobutyrate (33.5 g) at 40° C. To the mixture was added sodium iodide (22.6 g), and the mixture was refluxed overnight. The solvent was evaporated, and to the residue was added water. The mixture was extracted with ethyl acetate, and the organic layer was washed with water and saturated brine and dried with anhydrous magnesium sulfate. The solvent was evaporated, and the residue was purified by distillation under reduced pressure to give t-butyl N-cyclopropyl-4-aminobutyrate (12.6 g) as colorless oil.

bp 85–90° C./5 mm.

$^1$H-NMR ($\delta$ ppm, CDCl$_3$) 0.27–0.47 (4H, m), 1.45 (9H, s), 1.69–1.84 (2H, m), 2.08–2.15 (1H, m), 2.26 (2H, t, J=7.3 Hz), 2.71 (2H, t, J=7.3 Hz).

Reference Example 104

5-bromo-2-fluorobenzaldehyde (20 g), t-butyl N-cyclopropyl-4-aminobutyrate (14.5 g), sodium carbonate (13.8 g), water (70 ml) and DMSO (70 ml) were heated at 80° C. for 5 days and at 110° C. for 3 days, which was poured into water and extracted with ethyl acetate. The organic layer was washed with water and saturated brine and dried with anhydrous magnesium sulfate. The solvent was evaporated and the residue was purified with silica gel column chromatography (ethyl acetate/hexane) to give t-butyl N-(4-bromo-2-formylphenyl)-N-cyclopropyl-4-aminobutyrate (6.4 g) as red oil.

$^1$H-NMR ($\delta$ ppm, CDCl$_3$) 0.45–0.52 (2H, m), 0.72–0.78 (2H, m), 1.41 (9H, s), 1.88–1.98 (2H, m), 2.17 (2H, t, J=7.1 Hz), 2.66–2.73 (1H, m), 3.29 (2H, t, J=7.5 Hz), 7.13 (1H, d, J=8.8 Hz), 7.53 (1H, dd, J=2.6, 8.8 Hz), 7.84 (1H, d, J=2.6 Hz), 10.09 (1H, s).

Reference Example 105

In THF (10 ml) was dissolved t-butyl N-(4-bromo-2-formylphenyl)-N-cyclopropyl-4-aminobutyrate (1 g). To the solution was added potassium t-butoxide (0.59 g), and the mixture was heated at 55° C. for 1.5 hours. The solvent was evaporated, which was extracted with water. The aqueous layer was washed with ethyl acetate, and neutralized by addition of 1N hydrochloric acid, and extracted with ethyl acetate. The organic layer was washed with water and saturated brine, and dried with anhydrous magnesium sulfate. The solvent was evaporated to give 7-bromo-1-cyclopropyl-2,3-dihydro-1H-1-benzazepine-4-carboxylic acid (0.44 g) as yellow crystals.

mp 225–230° C. (dec.).

$^1$H-NMR ($\delta$ ppm, CDCl$_3$) 0.42–0.50 (2H, m), 0.80–0.84 (2H, m), 2.60–2.80 (3H, m), 3.24–3.34 (2H, m), 7.13 (1H, d, J=8.8 Hz), 7.38 (1H, dd, J=2.4, 8.8 Hz), 7.45 (1H, s), 7.53 (1H, d, J=2.4 Hz), 12.39 (1H, br).

Anal. Calcd. for C$_{14}$H$_{14}$BrNO$_2$: C, 54.56; H, 4.58; N, 4.55. Found C, 54.20; H, 4.60; N, 4.30.

Reference Example 106

In THF (15 ml) was dissolved 7-bromo-1-cyclopropyl-2,3-dihydro-1H-1-benzazepine-4-carboxylic acid (0.4 g). Under ice-cooling, to the solution were added oxalyl chloride (0.26 ml) and DMF (catalytic amount), and the mixture was stirred at room temperature for 30 minutes. The solvent was evaporated under reduced pressure. In THF (30 ml) was dissolved the residue, and the solution was added dropwise to a solution of 4-[N-methyl-N-(tetrahydro-2H-pyran-4-yl)aminomethyl]-aniline (0.34 g) and triethylamine (0.9 ml) in THF (5 ml) under ice-cooling. The mixture was stirred under nitrogen atmosphere at room temperature overnight. The solvent was evaporated under reduced pressure. Water was added to the residue, and the mixture was extracted with ethyl acetate. The organic layer was washed with water and saturated brine, and dried with anhydrous magnesium sulfate. The solvent was evaporated and the residue was purified with silica gel column chromatography (ethyl acetate/methanol/triethylamine) to give 7-bromo-1-cyclopropyl-N-[4-[[N-methyl-N-(tetrahydro-2H-pyran-4-yl)amino]methyl]phenyl]-2,3-dihydro-1H-1-benzazepine-4-carboxamide (0.55 g) as yellow crystals.

mp 133–136° C.

$^1$H-NMR ($\delta$ ppm, CDCl$_3$) 0.50–0.58 (2H, m), 0.79–0.88 (2H, m), 1.63–1.76 (4H, m), 2.20 (3H, s), 2.58–2.71 (2H, m), 2.86 (2H, t, J=8.8 Hz), 3.37 (2H, dt, J=3.0, 11.4 Hz), 3.46 (2H, t, J=4.9 Hz), 3.56 (2H, s), 4.01–4.07 (2H, m), 7.08 (1H, d, J=8.8 Hz), 7.14 (1H, s), 7.26–7.32 (2H, m), 7.37 (1H, d, J=2.6 Hz), 7.52 (2H, d, J=8.8 Hz), 7.57 (1H, s).

Anal. Calcd. for C$_{27}$H$_{32}$BrN$_3$O$_2$: C, 63.53; H, 6.32; N, 8.23. Found C, 63.30; H, 6.26; N, 8.15.

Reference Example 107

In DMF (3 ml) was dissolved methyl 7-bromo-2,3-dihydro-1H-1-benzazepine-4-carboxylate (0.3 g), and the solution was added dropwise to a suspension of 60% sodium hydride (0.05 g) in DMF (1 ml) under ice-cooling. The mixture was stirred under nitrogen atmosphere for 10 minutes. Benzyl bromide (0.15 ml) was added thereto, and the mixture was heated at 45° C. for 4 hours. The mixture was poured into water, and extracted with ethyl acetate. The organic layer was washed with water and saturated brine, and dried with anhydrous magnesium sulfate. The solvent was evaporated and the residue was purified with silica gel column chromatography (ethyl acetate/hexane) to give methyl 1-benzyl-7-bromo-2,3-dihydro-1H-1-benzazepine-4-carboxylate (0.3 g) as yellow oil.

$^1$H-NMR ($\delta$ ppm, CDCl$_3$) 2.75 (2H, t, J=4.9 Hz), 3.26 (2H, t, J=4.9 Hz), 3.80 (3H, s), 4.52 (2H, s), 6.67 (1H, d, J=8.8 Hz), 7.19 (1H, dd, J=2.4, 8.8 Hz), 7.22–7.45 (6H, m), 7.47 (1H, d, J=2.4 Hz), 7.63 (1H, s).

IR (neat) $\nu$: 1703 cm$^{-1}$.

Reference Example 108

A mixture of methyl 1-benzyl-7-bromo-2,3-dihydro-1H-1-benzazepine-4-carboxylate (0.3 g), 4-(2-propoxyethoxy)phenyl borate (0.24 g), 1M potassium carbonate solution (2.5 ml), ethanol (2.5 ml) and toluene (25 ml) was stirred under argon atmosphere at room temperature for 30 minutes. To the mixture was added tetrakis(triphenylphosphine)palladium (0.04 g), and the mixture was refluxed under argon atmosphere overnight. The mixture was extracted with ethyl acetate, and the organic layer was washed with water and saturated brine and dried with anhydrous magnesium sulfate. The solvent was evaporated under reduced pressure and the residue was purified with silica gel column chromatography (ethyl acetate/hexane) to give methyl 1-benzyl-7-[4-(2-propoxyethoxy)phenyl]-2,3-dihydro-1H-1-benzazepine-4-carboxylate (0.27 g) as yellow oil.

$^1$H-NMR ($\delta$ ppm, CDCl$_3$) 0.94 (3H, t, J=7.5 Hz), 1.58–1.70 (2H, m), 2.77 (2H, t, J=4.6 Hz), 3.32 (2H, t, J=4.6 Hz), 3.51 (2H, t, J=6.8 Hz), 3.78–3.83 (2H, m), 3.81 (3H, s), 4.07–4.18 (2H, m), 4.59 (2H, s), 6.87 (1H, d, J=8.4 Hz), 6.98 (2H, d, J=8.8 Hz), 7.26–7.41 (6H, m), 7.47 (2H, d, J=8.8 Hz), 7.56 (1H, d, J=2.2 Hz), 7.83 (1H, s).

IR (neat) $\nu$: 3027, 2874, 1701, 1499 cm$^{-1}$.

Reference Example 109

In methanol (10 ml) and THF (10 ml) was dissolved methyl 1-benzyl-7-[4-(2-propoxyethoxy)phenyl]-2,3-dihydro-1H-1-benzazepine-4-carboxylate (0.27 g). To the solution was added 1N sodium hydroxide solution (10 ml), and the mixture was stirred at room temperature overnight and concentrated, which was neutralized with 1N hydrochloric acid and extracted with ethyl acetate. The organic layer was washed with water and saturated brine and dried with anhydrous magnesium sulfate. The solvent was evaporated to give 1-benzyl-7-[4-(2-propoxyethoxy)phenyl]-2,3-dihydro-1H-1-benzazepine-4-carboxylic acid (0.16 g) as yellow crystals.

mp 139–142° C.

$^1$H-NMR ($\delta$ ppm, CDCl$_3$) 0.94 (3H, t, J=7.3 Hz), 1.59–1.70 (2H, m), 2.80 (2H, t, J=4.6 Hz), 3.34 (2H, t, J=4.6 Hz), 3.52 (2H, t, J=6.8 Hz), 3.78–3.84 (2H, m), 4.14–4.19 (2H, m), 4.61 (2H, s), 6.87 (1H, d, J=8.8 Hz), 6.98 (2H, d, J=8.8 Hz), 7.26–7.49 (8H, m), 7.57 (1H, d, J=2.2 Hz), 7.95 (1H, s).

IR (KBr) $\nu$: 2934, 2870, 1674, 1607, 1501 cm$^{-1}$.

Anal. Calcd. for C$_{29}$H$_{31}$NO$_4$: C, 76.12; H, 6.83; N, 3.06. Found C, 75.77; H, 6.95; N, 3.15.

Reference Example 110

In 1,2-dichloroethane (7 ml) were dissolved methyl 7-[4-(2-butoxyethoxy)phenyl]-2,3-dihydro-1H-1-benzazepine-4-carboxylate (0.4 g) and benzaldehyde (0.43 g). To the solution was added sodium triacetoxyborohydride (0.43 g), and the mixture was stirred under nitrogen atmosphere at room temperature overnight, poured into water, neutralized with sodium hydrogen carbonate solution and extracted with ethyl acetate. The organic layer was washed with water and saturated brine and dried with anhydrous magnesium sulfate. The solvent was evaporated to give methyl 1-benzyl-7-[4-(2-butoxyethoxy)phenyl]-2,3-dihydro-1H-1-benzazepine-4-carboxylate (0.49 g) as oil.

$^1$H-NMR ($\delta$ ppm, CDCl$_3$) 0.93 (3H, t, J=7.3 Hz), 1.30–1.48 (2H, m), 1.54–1.68 (2H, m), 2.77 (2H, t, J=4.7 Hz), 3.31 (2H, t, J=4.7 Hz), 3.55 (2H, t, J=6.6 Hz), 3.78–3.82 (5H, m), 4.15 (2H, t, J=4.8 Hz), 4.59 (2H, s), 6.86 (1H, d, J=8.8 Hz), 6.97 (2H, d, J=8.8 Hz), 7.26–7.68 (7H, m), 7.82–7.91 (3H, m).

IR (neat) $\nu$: 2934, 2870, 1703, 1607, 1501 cm$^{-1}$.

Reference Example 111

In methanol (25 ml) and THF (25 ml) was dissolved methyl 1-benzyl-7-[4-(2-butoxyethoxy)phenyl]-2,3-dihydro-1H-1-benzazepine-4-carboxylate (0.49 g). To the solution was added 1N sodium hydroxide solution (10 ml), and the mixture was heated at 50° C. overnight and concentrated, then neutralized with 1N hydrochloric acid and extracted with ethyl acetate. The organic layer was washed with water and saturated brine and dried with anhydrous magnesium sulfate. The solvent was evaporated to give 1-benzyl-7-[4-(2-butoxyethoxy)phenyl]-2,3-dihydro-1H-1-benzazepine-4-carboxylic acid (0.47 g) as yellow crystals.

mp 133–138° C.

$^1$H-NMR ($\delta$ ppm, CDCl$_3$) 0.93 (3H, t, J=7.4 Hz), 1.34–1.45 (2H, m), 1.54–1.65 (2H, m), 2.80 (2H, br), 3.34 (2H, br), 3.56 (2H, t, J=6.6 Hz), 3.80 (2H, t, J=5.0 Hz), 4.16 (2H, t, J=5.0 Hz), 4.61 (2H, s), 6.88 (1H, d, J=8.8 Hz), 6.98 (2H, d, J=8.8 Hz), 7.26–7.49 (8H, m), 7.57 (1H, d, J=2.2 Hz), 7.94 (1H, s).

IR (KBr) $\nu$: 2957, 2934, 2867, 1674, 1609, 1501 cm$^{-1}$.

Anal. Calcd. for C$_{30}$H$_{33}$NO$_4$: C, 76.41; H, 7.05; N, 2.97. Found C, 76.06; H, 7.15; N, 2.68.

Reference Example 112

In 1,2-dichloroethane (5 ml) were dissolved methyl 7-[4-(2-butoxyethoxy)phenyl]-2,3-dihydro-1H-1-benzazepine-4-carboxylate (0.3 g) and cyclohexanecarboaldehyde (0.43 g). To the solution was added sodium triacetoxyborohydride (0.43 g), and the mixture was stirred under nitrogen atmosphere at room temperature for 3.5 hours, poured into water, neutralized with sodium hydrogen carbonate solution and extracted with ethyl acetate. The organic layer was washed with water and saturated brine and dried with anhydrous magnesium sulfate. The solvent was evaporated to give methyl 7-[4-(2-butoxyethoxy)phenyl]-1-cyclohexylmethyl-2,3-dihydro-1H-1-benzazepine-4-carboxylate (0.37 g) as pale yellow oil.

$^1$H-NMR ($\delta$ ppm, CDCl$_3$) 0.89–1.81 (15H, m), 0.93 (3H, t, J=7.3 Hz), 2.81 (2H, t, J=4.2 Hz), 3.19 (2H, d, J=6.6 Hz), 3.29 (2H, t, J=4.8 Hz), 3.55 (2H, t, J=6.6 Hz), 3.78–3.82 (5H, m), 4.15 (2H, t, J=4.9 Hz), 6.87 (1H, d, J=8.8 Hz), 6.97 (2H, d, J=8.8 Hz), 7.36–7.51 (4H, m), 7.76 (1H, s).

IR (neat) $\nu$: 2930, 2849, 1699, 1607, 1499 cm$^{-1}$.

Reference Example 113

In methanol (25 ml) and THF (25 ml) was dissolved methyl 7-[4-(2-butoxyethoxy)phenyl]-1-cyclohexylmethyl-2,3-dihydro-1H-1-benzazepine-4-carboxylate (0.37 g). To the solution was added 1N sodium hydroxide solution (7.5 ml), and the mixture was stirred at room temperature overnight and concentrated, which was neutralized with 1N hydrochloric acid and extracted with ethyl acetate. The organic layer was washed with water and saturated brine and dried with anhydrous magnesium sulfate. The solvent was evaporated to give 7-[4-(2-butoxyethoxy)phenyl]-1-cyclohexylmethyl-2,3-dihydro-1H-1-benzazepine-4-carboxylic acid (0.32 g) as yellow crystals.

mp 124–125° C.

$^1$H-NMR (δ ppm, CDCl$_3$) 0.90–1.85 (15H, m), 0.93 (3H, t, J=7.2 Hz), 2.83 (2H, t-like), 3.22 (2H, d, J=6.6 Hz), 3.32 (2H, t-like), 3.56 (2H, t, J=6.6 Hz), 3.81 (2H, t, J=5.0 Hz), 4.16 (2H, t, J=5.0 Hz), 6.89 (1H, d, J=8.8 Hz), 6.98 (2H, d, J=8.8 Hz), 7.39–7.53 (4H, m), 7.88 (1H, s).

IR (KBr) ν: 2926, 1674, 1607, 1499 cm$^{-1}$.

Anal. Calcd. for C$_{30}$H$_{39}$NO: C, 75.44; H, 8.23; N, 2.93. Found C, 75.46; H, 8.23; N, 2.96.

Reference Example 114

In 1,2-dichloroethane (7 ml) were dissolved methyl 7-[4-(2-butoxyethoxy)phenyl]-2,3-dihydro-1H-1-benzazepine-4-carboxylate (0.4 g) and cyclopropanecarboaldehyde (0.3 g). To the solution was added sodium triacetoxyborohydride (0.43 g), and the mixture was stirred under nitrogen atmosphere at room temperature overnight, poured into water, neutralized with sodium hydrogen carbonate solution and extracted with ethyl acetate. The organic layer was washed with water and saturated brine and dried with anhydrous magnesium sulfate. The solvent was evaporated to give methyl 7-[4-(2-butoxyethoxy)phenyl]-1-cyclopropylmethyl-2,3-dihydro-1H-1-benzazepine-4-carboxylate (0.45 g) as yellow oil.

$^1$H-NMR (δ ppm, CDCl$_3$) 0.24–0.32 (2H, m), 0.58–0.67 (2H, m), 0.93 (3H, t, J=7.3 Hz), 1.08–1.15 (1H, m), 1.34–1.49 (2H, m), 1.55–1.68 (2H, m), 2.86 (2H, t, J=4.4 Hz), 3.23 (2H, d, J=6.6 Hz), 3.39 (2H, t, J=4.7 Hz), 3.55 (2H, t, J=6.6 Hz), 3.73–3.83 (5H, m), 4.11–4.18 (2H, m), 6.92–7.01 (3H, m), 7.38–7.53 (4H, m), 7.77 (1H, s).

IR (neat) ν: 2953, 2930, 2870, 1699, 1607, 1499 cm$^{-1}$.

Reference Example 115

In methanol (25 ml) and THF (25 ml) was dissolved methyl 7-[4-(2-butoxyethoxy)phenyl]-1-cyclopropylmethyl-2,3-dihydro-1H-1-benzazepine-4-carboxylate (0.45 g). To the solution was added 1N sodium hydroxide solution (10 ml), and the mixture was stirred at room temperature overnight and concentrated, which was neutralized with 1N hydrochloric acid and extracted with ethyl acetate. The organic layer was washed with water and saturated brine and dried with anhydrous magnesium sulfate. The solvent was evaporated to give 7-[4-(2-butoxyethoxy)phenyl]-1-cyclopropylmethyl-2,3-dihydro-1H-1-benzazepine-4-carboxylic acid (0.42 g) as yellow crystals.

mp 152–155° C.

$^1$H-NMR (δ ppm, CDCl$_3$) 0.25–0.33 (2H, m), 0.59–0.68 (2H, m), 0.93 (3H, t, J=7.3 Hz), 1.05–1.20 (1H, m), 1.30–1.49 (2H, m), 1.55–1.69 (2H, m), 2.87 (2H, t, J=4.6 Hz), 3.25 (2H, d, J=6.4 Hz), 3.42 (2H, t, J=4.6 Hz), 3.56 (2H, t, J=6.6 Hz), 3.81 (2H, t, J=5.0 Hz), 4.16 (2H, t, J=5.0 Hz), 6.93–7.00 (3H, m), 7.40–7.54 (4H, m), 7.89 (1H, s).

IR (KBr) ν: 2959, 2936, 2868, 1669, 1607, 1501 cm$^{-1}$.

Anal. Calcd. for C$_{27}$H$_{33}$NO$_4$: C, 74.45; H, 7.64; N, 3.22. Found C, 74.27; H, 7.45; N, 3.21.

Reference Example 116

In 1,2-dichloroethane (5 ml) were dissolved methyl 7-[4-(2-propoxyethoxy)phenyl]-2,3-dihydro-1H-1-benzazepine-4-carboxylate (0.3 g) and cyclopropanecarboaldehyde (0.22 g). To the solution was added sodium triacetoxyborohydride (0.33 g), and the mixture was stirred under nitrogen atmosphere at room temperature for 4 hours, poured into water, neutralized with sodium hydrogen carbonate solution and extracted with ethyl acetate. The organic layer was washed with water and saturated brine and dried with anhydrous magnesium sulfate. The solvent was evaporated to give methyl 1-cyclopropylmethyl-7-[4-(2-propoxyethoxy)phenyl]-2,3-dihydro-1H-1-benzazepine-4-carboxylate (0.34 g) as yellow oil.

$^1$H-NMR (δ ppm, CDCl$_3$) 0.24–0.32 (2H, m), 0.58–0.67 (2H, m), 0.94 (3H, t, J=7.5 Hz), 1.05–1.15 (1H, m), 1.60–1.74 (2H, m), 2.85 (2H, t, J=4.6 Hz), 3.23 (2H, d, J=6.6 Hz), 3.39 (2H, t, J=4.6 Hz), 3.51 (2H, t, J=6.7 Hz), 3.79–3.84 (5H, m), 4.16 (2H, t, J=5.0 Hz), 6.91–7.01 (3H, m), 7.38–7.52 (4H, m), 7.77 (1H, s).

IR (neat) ν: 2936, 2872, 1699, 1607, 1499 cm$^{-1}$.

Reference Example 117

In methanol (25 ml) and THF (25 ml) was dissolved methyl 1-cyclopropylmethyl-7-[4-(2-propoxyethoxy)phenyl]-2,3-dihydro-1H-1-benzazepine-4-carboxylate (0.34 g). To the solution was added 1N sodium hydroxide solution (7.5 ml), and the mixture was stirred at room temperature overnight, heated at 50° C. for 1 hour, concentrated, which was neutralized with 1N hydrochloric acid and extracted with ethyl acetate. The organic layer was washed with water and saturated brine and dried with anhydrous magnesium sulfate. The solvent was evaporated to give 1-cyclopropylmethyl-7-[4-(2-propoxyethoxy)phenyl]-2,3-dihydro-1H-1-benzazepine-4-carboxylic acid (0.30 g) as yellow crystals.

mp 154–156° C.

$^1$H-NMR (δ ppm, CDCl$_3$) 0.25–0.33 (2H, m), 0.59–0.68 (2H, m), 0.95 (3H, t, J=7.3 Hz), 1.05–1.18 (1H, m), 1.56–1.74 (2H, m), 2.87 (2H, t, J=4.8 Hz), 3.25 (2H, d, J=6.2 Hz), 3.42 (2H, t, J=4.8 Hz), 3.51 (2H, t, J=6.8 Hz), 3.81 (2H, t, J=4.9 Hz), 4.17 (2H, t, J=4.9 Hz), 6.93–7.00 (3H, m), 7.40–7.53 (4H, m), 7.88 (1H, s).

IR (KBr) ν: 2963, 1669, 1518 cm$^{-1}$.

Anal. Calcd. for C$_{26}$H$_{31}$NO$_4$: C, 74.08; H, 7.41; N, 3.32. Found C, 74.03; H, 7.53; N, 3.27.

Reference Example 118

In 1,2-dichloroethane (7 ml) were dissolved methyl 7-[4-(2-butoxyethoxy)phenyl]-2,3-dihydro-1H-1-benzazepine-4-carboxylate (0.4 g) and cyclobutanecarboaldehyde (0.5 g). To the solution was added sodium triacetoxyborohydride (0.43 g), and the mixture was stirred under nitrogen atmosphere at room temperature for 4 hours, poured into water, neutralized with sodium hydrogen carbonate solution and extracted with ethyl acetate. The organic layer was washed with water and saturated brine and dried with anhydrous magnesium sulfate. The solvent was evaporated to give methyl 7-[4-(2-butoxyethoxy)phenyl]-1-cyclobutylmethyl-2,3-dihydro-1H-1-benzazepine-4-carboxylate (0.47 g) as yellow oil.

$^1$H-NMR ($\delta$ ppm, CDCl$_3$) 0.93 (3H, t, J=7.3 Hz), 1.34–1.45 (2H, m), 1.54–2.13 (8H, m), 2.70–2.81 (3H, m), 3.26 (2H, t, J=4.8 Hz), 3.38 (2H, d, J=7.4 Hz), 3.55 (2H, t, J=6.6 Hz), 3.78–3.83 (5H, m), 4.16 (2H, t, J=4.9 Hz), 6.87 (1H, d, J=8.8 Hz), 6.97 (2H, d, J=8.8 Hz), 7.37–7.51 (4H, m), 7.75 (1H, s).

Reference Example 119

In methanol (25 ml) and THF (25 ml) was dissolved methyl 7-[4-(2-butoxyethoxy)phenyl]-1-cyclobutylmethyl-2,3-dihydro-1H-1-benzazepine-4-carboxylate (0.47 g). To the solution was added 1N sodium hydroxide solution (10 ml), and the mixture was heated at 50° C. overnight, concentrated, neutralized with 1N hydrochloric acid and extracted with ethyl acetate. The organic layer was washed with water and saturated brine and dried with anhydrous magnesium sulfate. The solvent was evaporated to give 7-[4-(2-butoxyethoxy)phenyl]-1-cyclobutylmethyl-2,3-dihydro-1H-1-benzazepine-4-carboxylic acid (0.40 g) as yellow crystals.

mp 110–112° C.

$^1$H-NMR ($\delta$ ppm, CDCl$_3$) 0.93 (3H, t, J=7.3 Hz), 1.30–2.00 (8H, m), 2.00–2.15 (2H, m), 2.71–2.80 (3H, m), 3.29 (2H, t, J=4.8 Hz), 3.39 (2H, d, J=7.0 Hz), 3.55 (2H, t, J=6.6 Hz), 3.80 (2H, t, J=5.0 Hz), 4.16 (2H, t, J=5.0 Hz), 6.88 (1H, d, J=8.8 Hz), 6.98 (2H, d, J=8.8 Hz), 7.39–7.51 (4H, m), 7.85 (1H, s).

Anal. Calcd. for C$_{28}$H$_{35}$NO$_4$: C, 74.80; H, 7.85; N, 3.12. Found C, 74.51; H, 7.92; N, 2.98.

Reference Example 120

In dichloromethane (15 ml) were dissolved methyl 7-bromo-2,3-dihydro-1H-1-benzazepine-4-carboxylate (0.5 g) and copper pivalate (0.05 g). To the solution was added triphenylbismuth diacetate (1.1 g), and the mixture was stirred at room temperature overnight, poured into water, stirred, neutralized with 1N sodium hydroxide solution and extracted with ethyl acetate. The organic layer was washed with water and saturated brine and dried with anhydrous magnesium sulfate. The solvent was evaporated and the residue was purified with silica gel column chromatography (ethyl acetate/hexane) to give methyl 7-bromo-1-phenyl-2,3-dihydro-1H-1-benzazepine-4-carboxylate (0.27 g) as yellow crystals.

mp 104–106° C.

$^1$H-NMR ($\delta$ ppm, CDCl$_3$) 2.82 (2H, t, J=4.4 Hz), 3.76 (2H, t, J=4.4 Hz), 3.78 (3H, s), 6.90–7.00 (4H, m), 7.22–7.30 (3H, m), 7.58 (1H, d, J=2.2 Hz), 7.62 (1H, s).

IR (KBr) v: 2949, 1705 cm$^{-1}$.

Anal. calcd for C$_{18}$H$_{16}$BrNO$_2$: C, 60.35; H, 4.50; N, 3.91. Found C, 60.16; H, 4.28; N, 3.85.

Reference Example 121

A mixture of methyl 7-bromo-1-phenyl-2,3-dihydro-1H-1-benzazepine-4-carboxylate (0.27 g), 4-(2-propoxyethoxy)phenyl borate (0.23 g), 1M potassium carbonate solution (3 ml), ethanol (3 ml) and toluene (25 ml) was stirred under argon atmosphere at room temperature for 30 minutes. To the mixture was added tetrakis(triphenylphosphine) palladium (0.04 g), and the mixture was refluxed under argon atmosphere overnight, and extracted with ethyl acetate. The organic layer was washed with water and saturated brine and dried with anhydrous magnesium sulfate. The solvent was evaporated under reduced pressure and the residue was purified with silica gel column chromatography (ethyl acetate/hexane) to give methyl 1-phenyl-7-[4-(2-propoxyethoxy)phenyl]-2,3-dihydro-1H-1-benzazepine-4-carboxylate (0.26 g) as yellow crystals.

mp 117–119° C.

$^1$H-NMR ($\delta$ ppm, CDCl$_3$) 0.95 (3H, t, J=7.5 Hz), 1.57–1.71 (2H, m), 2.85 (2H, t, J=4.6 Hz), 3.52 (2H, t, J=6.8 Hz), 3.79 (3H, s), 3.79–3.84 (4H, m), 4.18 (2H, t, J=5.0 Hz), 6.87–7.03 (5H, m), 7.16–7.30 (3H, m), 7.40 (1H, dd, J=5 2.2, 8.4 Hz), 7.51 (2H, d, J=8.8 Hz), 7.64 (1H, d, J=2.2 Hz), 7.80 (1H, s).

IR (KBr) v: 1705, 1493 cm$^{-1}$.

Anal. Calcd. for C$_{29}$H$_{31}$NO$_4$: C, 76.12; H, 6.83; N, 3.06. Found C, 75.81; H, 6.75; N, 2.77.

Reference Example 122

In methanol (25 ml) and THF (25 ml) was dissolved methyl 1-phenyl-7-[4-(2-propoxyethoxy)phenyl]-2,3-dihydro-1H-1-benzazepine-4-carboxylate (0.23 g). To the solution was added 1N sodium hydroxide solution (10 ml), and the mixture was heated at 50° C. overnight, concentrated, neutralized with 1N hydrochloric acid and extracted with ethyl acetate. The organic layer was washed with water and saturated brine and dried with anhydrous magnesium sulfate. The solvent was evaporated to give 1-phenyl-7-[4-(2-propoxyethoxy)phenyl]-2,3-dihydro-1H-1-benzazepine-4-carboxylic acid (0.23 g) as yellow crystals.

mp 135–139° C.

$^1$H-NMR ($\delta$ ppm, CDCl$_3$) 0.95 (3H, t, J=7.5 Hz), 1.60–1.71 (2H, m), 2.86 (2H, t-like), 3.52 (2H, t, J=6.7 Hz), 3.80–3.85 (4H, m), 4.18 (2H, t, J=4.8 Hz), 6.90–7.04 (5H, m), 7.17 (1H, d, J=8.5 Hz), 7.23–7.31 (2H, m), 7.40 (1H, dd, J=2.2, 8.5 Hz), 7.51 (2H, d, J=8–8 Hz), 7.65 (1H, d, J=2.2 Hz), 7.90 (1H, s).

IR (KBr) v: 2963, 2936, 2872, 1674, 1609, 1593, 1493 cm$^{-1}$.

Anal. Calcd. for C$_{28}$H$_{29}$NO$_4$: C, 75.82; H, 6.59; N, 3.16. Found C, 75.43; H, 6.37; N, 3.10.

Reference Example 123

In dichloromethane (10 ml) were dissolved methyl 7-[4-(2-butoxyethoxy)phenyl]-2,3-dihydro-1H-1-benzazepine-4-carboxylate (0.5 g) and copper pivalate (0.07 g). To the solution was added triphenylbismuth diacetate (0.78 g), and the mixture was stirred at room temperature overnight, poured into 3N hydrochloric acid, stirred, neutralized with 1N sodium hydroxide solution and extracted with ethyl acetate. The organic layer was washed with water and saturated brine and dried with anhydrous magnesium sulfate. The solvent was evaporated and the residue was purified with silica gel column chromatography (ethyl acetate/hexane) to give methyl 7-[4-(2-butoxyethoxy)phenyl]-1-phenyl-2,3-dihydro-1H-1-benzazepine-4-carboxylate (0.42 g) as yellow crystals.

mp 80–82° C.

$^1$H-NMR ($\delta$ ppm, CDCl$_3$) 0.94 (3H, t, J=7.1 Hz), 1.31–1.49 (2H, m), 1.56–1.69 (2H, m), 2.85 (2H, t, J=4.4 Hz), 3.56 (2H, t, J=6.6 Hz), 3.79–3.84 (7H, m), 4.17 (2H, t, J=4.9 Hz), 6.87–7.02 (5H, m), 7.16–7.30 (3H, m), 7.40 (1H, dd, J=2.2, 8.8 Hz), 7.51 (2H, d, J=8.4 Hz), 7.64 (1H, d, J=2.2 Hz), 7.80 (1H, s).

IR (KBr) ν: 2955, 2868, 1705, 1593, 1495 cm$^{-1}$.

Anal. Calcd. for $C_{30}H_{33}NO_4$: C, 76.41; H, 7.05; N, 2.97. Found C, 76.30; H, 7.17; N, 2.90.

Reference Example 124

In methanol (25 ml) and THF (25 ml) was dissolved methyl 7-[4-(2-butoxyethoxy)phenyl]-1-phenyl-2,3-dihydro-1H-1-benzazepine-4-carboxylate (0.37 g). To the solution was added 1N sodium hydroxide solution (7.5 ml), and the mixture was stirred at room temperature overnight, concentrated, neutralized with 1N hydrochloric acid and extracted with ethyl acetate. The organic layer was washed with water and saturated brine and dried with anhydrous magnesium sulfate. The solvent was evaporated to give 7-[4-(2-butoxyethoxy)phenyl]-1-phenyl-2,3-dihydro-1H-1-benzazepine-4-carboxylic acid (0.27 g) as yellow crystals.

mp 129–131° C.

$^1$H-NMR (δ ppm, CDCl$_3$) 0.94 (3H, t, J=7.2 Hz), 1.34–1.49 (2H, m), 1.55–1.69 (2H, m), 2.86 (2H, t, J=4.4 Hz), 3.56 (2H, t, J=6.6 Hz), 3.79–3.84 (4H, m), 4.17 (2H, t, J=4.8 Hz), 6.90–7.04 (5H, m), 7.17 (1H, d, J=8.6 Hz), 7.23–7.31 (2H, m), 7.40 (1H, dd, J=2.2, 8.6 Hz), 7.50 (2H, d, J=7.2 Hz), 7.64 (1H, d, J=1.8 Hz), 7.90 (1H, s).

IR (KBr) ν: 2957, 2870, 1674, 1609, 1593, 1493 cm$^{-1}$.

Anal. Calcd. for $C_{29}H_{31}NO_4$: C, 76.12; H, 6.83; N, 3.06. Found C, 76.18; H, 6.85; N, 3.21.

Reference Example 125

In dichloromethane (7 ml) were dissolved methyl 7-[4-(2-butoxyethoxy)phenyl]-2,3-dihydro-1H-1-benzazepine-4-carboxylate (0.25 g) and copper pivalate (0.04 g). To the solution was added tri(3-methoxyphenyl)bismuth diacetate (1.5 g), and the mixture was stirred at room temperature overnight, poured into 3N hydrochloric acid, stirred, neutralized with 1N sodium hydroxide solution and extracted with ethyl acetate. The organic layer was washed with water and saturated brine and dried with anhydrous magnesium sulfate. The solvent was evaporated and the residue was purified with silica gel column chromatography (ethyl acetate/hexane) to give methyl 7-[4-(2-butoxyethoxy)phenyl]-1-(3-methoxyphenyl)-2,3-dihydro-1H-1-benzazepine-4-carboxylate (0.16 g) as yellow oil.

$^1$H-NMR (δ ppm, CDCl$_3$) 0.94 (3H, t, J=7.2 Hz), 1.34–1.45 (2H, m), 1.55–1.65 (2H, m), 2.86 (2H, t, J=4.8 Hz), 3.56 (2H, t, J=6.6 Hz), 3.75 (3H, s), 3.79 (3H, s), 3.79–3.84 (4H, m), 4.17 (2H, t, J=4.9 Hz), 6.42–6.60 (3H, m), 7.00 (2H, d, J=8.8 Hz), 7.11–7.26 (2H, m), 7.41 (1H, dd, J=2.2, 8.4 Hz), 7.51 (2H, d, J=8.8 Hz), 7.64 (1H, d, J=2.2 Hz), 7.78 (1H, s).

IR (neat) ν: 2955, 2932, 2870, 1705 cm$^{-1}$.

Reference Example 126

In methanol (25 ml) and THF (25 ml) was dissolved methyl 7-[4-(2-butoxyethoxy)phenyl]-1-(3-methoxyphenyl)-2,3-dihydro-1H-1-benzazepine-4-carboxylate (0.16 g). To the solution was added 1N sodium hydroxide solution (2.8 ml), and the mixture was heated at 50° C. overnight, concentrated, neutralized with 1N hydrochloric acid and extracted with ethyl acetate. The organic layer was washed with water and saturated brine and dried with anhydrous magnesium sulfate. The solvent was evaporated to give 7-[4-(2-butoxyethoxy)phenyl]-1-(3-methoxyphenyl)-2,3-dihydro-1H-1-benzazepine-4-carboxylic acid (0.16 g) as yellow crystals.

mp 154–156° C.

$^1$H-NMR (δ ppm, CDCl$_3$) 0.94 (3H, t, J=7.4 Hz), 1.34–1.45 (2H, m), 1.55–1.65 (2H, m), 2.87 (2H, t-like), 3.56 (2H, t, J=6.6 Hz), 3.76 (3H, s), 3.79–3.84 (4H, m), 4.17 (2H, t, J=4.8 Hz), 6.45–6.61 (3H, m), 7.00 (2H, d, J=8.8 Hz), 7.13–7.24 (2H, m), 7.42 (1H, dd, J=2.2, 8.4 Hz), 7.51 (2H, d, J=8.8 Hz), 7.64 (1H, d, J=2.2 Hz), 7.88 (1H, s).

Anal. Calcd. for $C_{30}H_{33}NO_5$: C, 73.90; H, 6.82; N, 2.87. Found C, 73.73; H, 6.72; N, 2.83.

Reference Example 127

In dichloromethane (10 ml) were dissolved methyl 7-[4-(2-butoxyethoxy)phenyl]-2,3-dihydro-1H-1-benzazepine-4-carboxylate (0.3 g) and copper pivalate (0.06 g). To the solution was added tri(4-methoxyphenyl)bismuth diacetate (1.5 g), and the mixture was stirred at room temperature overnight, poured into 3N hydrochloric acid, stirred, neutralized with 1N sodium hydroxide solution and extracted with ethyl acetate. The organic layer was washed with water and saturated brine and dried with anhydrous magnesium sulfate. The solvent was evaporated and the residue was purified with silica gel column chromatography (ethyl acetate/hexane) to give methyl 7-[4-(2-butoxyethoxy)phenyl]-1-(4-methoxyphenyl)-2,3-dihydro-1H-1-benzazepine-4-carboxylate (0.38 g) as yellow oil.

$^1$H-NMR (δ ppm, CDCl$_3$) 0.93 (3H, t, J=7.2 Hz), 1.30–1.45 (2H, m), 1.55–1.65 (2H, m), 2.82 (2H, t, J=4.4 Hz), 3.56 (2H, t, J=6.6 Hz), 3.72–3.83 (10H, m), 4.16 (2H, t, J=4.4 Hz), 6.85–6.91 (3H, m), 6.96–7.04 (4H, m), 7.30 (1H, dd, J=2.2, 8.4 Hz), 7.48 (2H, d, J=8.8 Hz), 7.59 (1H, d, J=2.2 Hz), 7.82 (1H, s).

IR (neat) ν: 2955, 1705, 1609, 1508, 1491 cm$^{-1}$.

Reference Example 128

In methanol (25 ml) and THF (25 ml) was dissolved methyl 7-[4-(2-butoxyethoxy)phenyl]-1-(4-methoxyphenyl)-2,3-dihydro-1H-1-benzazepine-4-carboxylate (0.38 g). To the solution was added 1N sodium hydroxide solution (8 ml), and the mixture was heated at 50° C. overnight, concentrated, neutralized with 1N hydrochloric acid and extracted with ethyl acetate. The organic layer was washed with water and saturated brine and dried with anhydrous magnesium sulfate. The solvent was evaporated to give 7-[4-(2-butoxyethoxy)phenyl]-1-(4-methoxyphenyl)-2,3-dihydro-1H-1-benzazepine-4-carboxylic acid (0.27 g) as yellow crystals.

mp 164–166° C.

$^1$H-NMR (δ ppm, CDCl$_3$) 0.93 (3H, t, J=7.1 Hz), 1.34–1.49 (2H, m), 1.54–1.68 (2H, m), 2.83 (2H, t-like), 3.55 (2H, t, J=6.0 Hz), 3.74–3.83 (7H, m), 4.16 (2H, t, J=4.9 Hz), 6.85–7.06 (7H, m), 7.31 (1H, dd, J=2.2, 8.4 Hz), 7.47 (2H, d, J=8.8 Hz), 7.59 (1H, d, J=2.2 Hz), 7.92 (1H, s).

IR (KBr) ν: 2957, 2928, 2868, 1674, 1609, 1508, 1493 cm$^{-1}$.

Anal. Calcd. for $C_{30}H_{33}NO_5$: C, 73.90; H, 6.82; N, 2.87. Found C, 73.87; H, 6.89; N, 2.70.

Reference Example 129

In dichloromethane (7 ml) were dissolved methyl 7-[4-(2-butoxyethoxy)phenyl]-2,3-dihydro-1H-1-benzazepine-4-carboxylate (0.2 g) and copper pivalate (0.04 g). To the solution was added tri(4-propoxyphenyl)bismuth diacetate (1.1 g), and the mixture was stirred at room temperature overnight, poured into 3N hydrochloric acid, stirred, neutralized with 1N sodium hydroxide solution and extracted with ethyl acetate. The organic layer was washed with water and saturated brine and dried with anhydrous magnesium sulfate. The solvent was evaporated and the residue was purified with silica gel column chromatography (ethyl acetate/hexane) to give methyl 7-[4-(2-butoxyethoxy)phenyl]-1-(4-propoxyphenyl)-2,3-dihydro-1H-1-benzazepine-4-carboxylate (0.25 g) as yellow oil.

$^1$H-NMR (δ ppm, CDCl$_3$) 0.93 (3H, t, J=7.3 Hz), 1.04 (3H, t, J=7.5 Hz), 1.34–1.45 (2H, m), 1.54–1.68 (2H, m), 1.75–1.86 (2H, m), 2.81 (2H, t, J=4.4 Hz), 3.55 (2H, t, J=6.6 Hz), 3.71–3.83 (7H, m), 3.90 (2H, t, J=6.6 Hz), 4.14–4.18 (2H, m), 6.84–6.90 (3H, m), 6.96–7.02 (4H, m), 7.29 (1H, dd, J=2.2, 8.4 Hz), 7.48 (2H, d, J=6.6 Hz), 7.58 (1H, d, J=2.2 Hz), 7.82 (1H, s).

IR (neat) ν: 2957, 2934, 2870, 1705, 1622, 1609, 1507, 1489 cm$^{-1}$.

Reference Example 130

In methanol (50 ml) and THF (50 ml) was dissolved methyl 7-[4-(2-butoxyethoxy)phenyl]-1-(4-propoxyphenyl)-2,3-dihydro-1H-1-benzazepine-4-carboxylate (0.25 g). To the solution was added 1N sodium hydroxide solution (5 ml), and the mixture was heated at 50° C. overnight, concentrated, neutralized with 1N hydrochloric acid and extracted with ethyl acetate. The organic layer was washed with water and saturated brine and dried with anhydrous magnesium sulfate. The solvent was evaporated to give 7-[4-(2-butoxyethoxy)phenyl]-1-(4-propoxyphenyl)-2,3-dihydro-1H-1-benzazepine-4-carboxylic acid (0.21 g) as yellow crystals.

mp 182–185° C.

$^1$H-NMR (δ ppm, CDCl$_3$) 0.93 (3H, t, J=7.1 Hz), 1.04 (3H, t, J=7.6 Hz), 1.30–1.49 (2H, m), 1.54–1.68 (2H, m), 1.76–1.86 (2H, m), 2.83 (2H, t-like), 3.55 (2H, t, J=6.6 Hz), 3.76 (2H, t-like), 3.80 (2H, t, J=5.0 Hz), 3.91 (2H, t, J=6.6 Hz), 4.16 (2H, t, J=5.0 Hz), 6.84–7.05 (7H, m), 7.30 (1H, dd, J=2.2, 8.6 Hz), 7.47 (2H, d, J=8.8 Hz), 7.58 (1H, d, J=2.2 Hz), 7.92 (1H, s).

IR (KBr) ν: 2959, 2934, 2872, 1669, 1609, 1508, 1493 cm$^{-1}$.

Anal. Calcd. for C$_{32}$H$_{37}$NO$_5$: C, 74.54; H, 7.23; N, 2.72. Found C, 74.19; H, 7.32; N, 2.87.

Reference Example 131

In dichloromethane (7 ml) were dissolved methyl 7-[4-(2-butoxyethoxy)phenyl]-2,3-dihydro-1H-1-benzazepine-4-carboxylate (0.25 g) and copper pivalate (0.05 g). To the solution was added tri(3,4-methylenedioxyphenyl)bismuth diacetate (1.3 g), and the mixture was stirred at room temperature overnight, poured into 3N hydrochloric acid, stirred, neutralized with 1N sodium hydroxide solution and extracted with ethyl acetate. The organic layer was washed with water and saturated brine and dried with anhydrous magnesium sulfate. The solvent was evaporated and the residue was purified with silica gel column chromatography (ethyl acetate/hexane) to give methyl 7-[4-(2-butoxyethoxy)phenyl]-1-(3,4-methylenedioxyphenyl)-2,3-dihydro-1H-1-benzazepine-4-carboxylate (0.3 g) as yellow oil.

$^1$H-NMR (δ ppm, CDCl$_3$) 0.93 (3H, t, J=7.2 Hz), 1.30–1.49 (2H, m), 1.55–1.68 (2H, m), 2.82 (2H, t, J=4.6 Hz), 3.56 (2H, t, J=6.6 Hz), 3.73 (2H, t, J=4.9 Hz), 3.79–3.84 (5H, m), 4.17 (2H, t, J=4.9 Hz), 5.94 (2H, s), 6.49 (1H, dd, J=2.2, 8.4 Hz), 6.60 (1H, d, J=2.2 Hz), 6.75 (1H, d, J=8.4 Hz), 6.94–7.02 (3H, m), 7.33 (1H, dd, J=2.2, 8.4 Hz), 7.48 (2H, d, J=8.8 Hz), 7.59 (1H, d, J=2.2 Hz), 7.80 (1H, s).

IR (neat) ν: 2955, 2932, 2870, 1703, 1609, 1485 cm$^{-1}$.

Reference Example 132

In methanol (25 ml) and THF (25 ml) was dissolved methyl 7-[4-(2-butoxyethoxy)phenyl]-1-(3,4-methylenedioxyphenyl)-2,3-dihydro-1H-1-benzazepine-4-carboxylate (0.3 g). To the solution was added 1N sodium hydroxide solution (6 ml), and the mixture was refluxed for 2 hours, concentrated, neutralized with 1N hydrochloric acid and extracted with ethyl acetate. The organic layer was washed with water and saturated brine and dried with anhydrous magnesium sulfate. The solvent was evaporated to give 7-[4-(2-butoxyethoxy)phenyl]-1-(3,4-methylenedioxyphenyl)-2,3-dihydro-1H-1-benzazepine-4-carboxylic acid (0.26 g) as yellow crystals.

mp 145–148° C.

$^1$H-NMR (δ ppm, CDCl$_3$) 0.93 (3H, t, J=7.3 Hz), 1.30–1.49 (2H, m), 1.55–1.68 (2H, m), 2.84 (2H, t, J=5.2 Hz), 3.56 (2H, t, J=6.6 Hz), 3.74 (2H, t, J=5.2 Hz), 3.81 (2H, t, J=5.0 Hz), 4.17 (2H, t, J=5.0 Hz), 5.95 (2H, s), 6.52 (1H, dd, J=2.2, 8.4 Hz), 6.62 (1H, d, J=2.2 Hz), 6.76 (1H, d, J=8.4 Hz), 6.92–7.01 (3H, m), 7.34 (1H, dd, J=2.2, 8.4 Hz), 7.48 (2H, d, J=8.8 Hz), 7.59 (1H, d, J=2.2 Hz), 7.91 (1H, s).

IR (KBr) ν: 2932, 2867, 1678, 1609, 1486 cm$^{-1}$.

Anal. Calcd. for C$_{30}$H$_{31}$NO$_6$: C, 71.84; H, 6.23; N, 2.79. Found C, 71.61; H, 6.19; N, 2.62.

Reference Example 133

In THF (25 ml) were dissolved methyl 7-[4-(2-butoxyethoxy)phenyl]-2,3-dihydro-1H-1-benzazepine-4-carboxylate (1 g) and pyridine (2 ml). Under ice-cooling, to the solution was added dropwise chloroacetyl chloride (1 ml). The mixture was stirred under nitrogen atmosphere at room temperature for 1 hour, and the solvent was evaporated. To the residue was added water, and the mixture was extracted with ethyl acetate. The organic layer was washed with water and saturated brine and dried with anhydrous magnesium sulfate. The solvent was evaporated and the residue was purified with silica gel column chromatography (ethyl acetate/hexane) to give methyl 7-[4-(2-butoxyethoxy)phenyl]-1-chloroacetyl-2,3-dihydro-1H-1-benzazepine-4-carboxylate (1.1 g) as pale yellow oil.

$^1$H-NMR (δ ppm, CDCl$_3$) 0.94 (3H, t, J=7.2 Hz), 1.30–1.69 (4H, m), 2.78–3.13 (3H, m), 3.56 (2H, t, J=6.6 Hz), 3.80–3.84 (5H, m), 3.93 (1H, d, J=12.8 Hz), 4.11–4.20 (3H, m), 4.76–7.84 (1H, m), 7.03 (2H, d, J=8.8 Hz), 7.34 (1H, d, J=8.4 Hz), 7.50–7.58 (3H, m), 7.68 (1H, d, J=1.8 Hz), 7.74 (1H, s).

Reference Example 134

In DMF (30 ml) was dissolved methyl 7-[4-(2-butoxyethoxy)phenyl]-1-chloroacetyl-2,3-dihydro-1H-1-benzazepine-4-carboxylate (1.1 g). To the solution was added sodium azide (0.23 g), and the mixture was heated at 65° C. for 1 hour, poured into water and extracted with ethyl acetate. The organic layer was washed with water and saturated brine and dried with anhydrous magnesium sulfate. The solvent was evaporated, and the residue was purified with silica gel column chromatography (ethyl acetate/hexane) to give pale yellow oil (0.8 g), which was dissolved in THF (50 ml). To the solution were added triphenylphosphine (1.1 g) and water (catalytic amount), and the mixture was heated at 50° C. for 1.5 hours. The solvent was evaporated and, to the residue was added water, and the mixture was extracted with ethyl acetate. The organic layer was washed with water and saturated brine, and dried with anhydrous magnesium sulfate. The solvent was evaporated and the residue was purified with silica gel column chromatography (ethyl acetate/methanol/triethylamine) to give pale yellow oil (0.7 g), which was dissolved in THF (15 ml). To the solution were added pyridine (0.7 ml) and acetic anhydride (0.25 ml), and the mixture was stirred under nitrogen atmosphere at room temperature overnight. The solvent was evaporated and, to the residue was added water, and the mixture was extracted with ethyl acetate. The organic layer was washed with water and saturated brine and dried with anhydrous magnesium sulfate. The solvent was evaporated to give methyl 1-(N-acetylglycyl)-7-[4-(2-butoxyethoxy)phenyl]-2,3-dihydro-1H-1-benzazepine-4-carboxylate (0.67 g) as colorless crystals.

mp 130–134° C.

$^1$H-NMR (δ ppm, CDCl$_3$) 0.94 (3H, t, J=7.3 Hz), 1.26–1.69 (4H, m), 2.01 (3H, s), 2.76–3.12 (3H, m), 3.51–3.62 (3H, m), 3.78–3.83 (5H, m), 4.16 (2H, t, J=4.9 Hz), 4.33 (1H, dd, J=4.0, 18.0 Hz), 4.73–4.80 (1H, m), 6.42 (1H, br), 7.03 (2H, d, J=8.8 Hz), 7.28 (1H, d, J=7.8 Hz), 7.49–7.56 (3H, m), 7.65 (1H, d, J=2.2 Hz), 7.72 (1H, s).

IR (KBr) ν: 3316, 2951, 2934, 2870, 1713, 1661 cm$^{-1}$.

Anal. Calcd. for C$_{28}$H$_{34}$N$_2$O$_6$: C, 68.00; H, 6.93; N, 5.66. Found C, 67.84; H, 6.74; N, 5.61.

Reference Example 135

In methanol (50 ml) was dissolved methyl 1-(N-acetylglycyl)-7-[4-(2-butoxyethoxy)phenyl]-2,3-dihydro-1H-1-benzazepine-4-carboxylate (1.2 g). To the solution was added 1N sodium hydroxide solution (13 ml), and the mixture was stirred at room temperature overnight, concentrated, neutralized with 1N hydrochloric acid and extracted with ethyl acetate. The organic layer was washed with water and saturated brine and dried with anhydrous magnesium sulfate. The solvent was evaporated to give 1-(N-acetylglycyl)-7-[4-(2-butoxyethoxy)phenyl]-2,3-dihydro-1H-1-benzazepine-4-carboxylic acid (1.2 g) as colorless crystals.

mp 196–201° C.

$^1$H-NMR (δ ppm, CDCl$_3$) 0.94 (3H, t, J=7.3 Hz), 1.26–1.69 (4H, m), 2.02 (3H, s), 2.78–3.15 (3H, m), 3.53–3.62 (3H, m), 3.82 (2H, t, J=4.9 Hz), 4.19 (2H, t, J=4.9 Hz), 4.36 (1H, dd, J=4.0, 18.0 Hz), 4.75–4.82 (1H, m), 6.53 (1H, br), 7.03 (2H, d, J=8.8 Hz), 7.31 (1H, d, J=8.0 Hz), 7.50–7.58 (3H, m), 7.67 (1H, d, J=2.2 Hz), 7.81 (1H, s).

IR (KBr) ν: 2951, 2872, 1669 cm$^{-1}$.

Anal. Calcd. for C$_{27}$H$_{32}$N$_2$O$_6$: C, 66.86; H, 6.75; N, 5.78. Found C, 66.65; H, 6.73; N, 5.97.

Reference Example 136

In DMF (20 ml) were suspended 1-(N-acetylglycyl)-7-[4-(2-butoxyethoxy)phenyl]-2,3-dihydro-1H-1-benzazepine-4-carboxylic acid (0.85 g), 4-[N-methyl-N-(tetrahydro-2H-pyran-4-yl)aminomethyl]aniline dihydrochloride (0.52 g) and 1-hydroxybenzotriazole (0.3 g). Under ice-cooling, to the suspension were added 1-ethyl-3-(3-dimethylaminopropyl)carbodiimide hydrochloride (1 g), triethylamine (1.7 ml) and 4-dimethylaminopyridine (catalytic amount), and the mixture was stirred at room temperature overnight. The solvent was evaporated and, to the residue was added water, and the mixture was extracted with ethyl acetate. The organic layer was washed with water and saturated brine and dried with anhydrous magnesium sulfate. The solvent was evaporated and the residue was purified with basic silica gel column chromatography (ethyl acetate/methanol/triethylamine) to give 1-(N-acetylglycyl)-7-[4-(2-butoxyethoxy)phenyl]-N-[4-[[N-methyl-N-(tetrahydro-2H-pyran-4-yl)amino]methyl]phenyl]-2,3-dihydro-1H-1-benzazepine-4-carboxamide (1.1 g) as pale yellow amorphous.

$^1$H-NMR (δ ppm, CDCl$_3$) 0.93 (3H, t, J=7.4 Hz), 1.25–1.75 (8H, m), 2.05 (3H, s), 2.19 (3H, s), 2.55–2.70 (1H, m), 2.86–3.14 (3H, m), 3.37 (2H, dt, J=2.6, 11.0 Hz), 3.53–3.71 (5H, m), 3.82 (2H, t, J=5.0 Hz), 4.01–4.07 (2H, m), 4.11–4.28 (3H, m), 4.75–4.81 (1H, m), 6.49 (1H, br), 7.02 (2H, d, J=8.4 Hz), 7.24–7.33 (4H, m), 7.43–7.61 (6H, m), 8.09 (1H, s).

Reference Example 137

In toluene (25 ml) were suspended methyl 7-[4-(2-butoxyethoxy)phenyl]-1-chloroacetyl-2,3-dihydro-1H-1-benzazepine-4-carboxylate (0.75 g) and thioacetamide (0.36 g). The suspension was heated at 90° C. for 1 hour and extracted with ethyl acetate. The organic layer was washed with water and saturated brine and dried with anhydrous magnesium sulfate. The solvent was evaporated and the residue was purified with silica gel column chromatography (ethyl acetate/hexane) to give methyl 7-[4-(2-butoxyethoxy)phenyl]-1-(2-methylthiazol-4-yl)-2,3-dihydro-1H-1-benzazepine-4-carboxylate (0.17 g) as yellow oil.

$^1$H-NMR (δ ppm, CDCl$_3$) 0.94 (3H, t, J=7.2 Hz), 1.26–1.65 (4H, m), 2.67 (3H, s), 2.86 (2H, t, J=5.3 Hz), 3.56 (2H, t, J=6.6 Hz), 3.80 (3H, s), 3.81 (2H, t, J=4.9 Hz), 3.95 (2H, t, J=5.3 Hz), 4.17 (2H, t, J=4.9 Hz), 5.92 (1H, s), 7.00 (2H, d, J=8.8 Hz), 7.43 (2H, s), 7.51 (2H, d, J=8.8 Hz), 7.62 (1H, s), 7.77 (1H, s).

Reference Example 138

In dichloromethane (15 ml) was dissolved methyl 7-bromo-1-phenyl-2,3-dihydro-1H-1-benzazepine-4-carboxylate (0.68 g). Under ice-cooling, to the solution was added dropwise chlorosulfonic acid (0.32 ml). The mixture was stirred at room temperature for 30 minutes and, to the mixture was additionally added chlorosulfonic acid (0.2 ml), and the mixture was stirred at room temperature for 10 minutes. The reaction solution was added dropwise to aqueous ammonia (10 ml) under ice-cooling, and the mixture was stirred for 30 minutes. The solvent was evaporated and, to the residue was added hot ethyl acetate. The insolubles were filtered and the solvent in the filtrate was evaporated. The precipitated methyl 7-bromo-1-(4-sulfamoylphenyl)-2,3-dihydro-1H-1-benzazepine-4-carboxylate (0.33 g) was collected by filtration and washed with ethyl acetate-hexane to give the carboxylate as yellow crystals.

mp 200–203° C.

$^1$H-NMR (δ ppm, CDCl$_3$) 2.89 (2H, t, J=5.5 Hz), 3.78 (3H, s), 3.84 (2H, t, J=5.5 Hz), 4.65 (2H, s), 6.87 (2H, d, J=9.2 Hz), 7.18 (1H, d, J=8.4 Hz), 7.43 (1H, dd, J=2.2, 8.4 Hz), 7.60 (1H, s), 7.68 (1H, d, J=2.2 Hz), 7.73 (2H, d, J=9.2 Hz).

IR (KBr) ν: 1713 cm$^{-1}$.

Anal. Calcd. for C$_{18}$H$_{17}$BrN$_2$O$_4$S: C, 49.44; H, 3.92; N, 6.41. Found C, 49.30; H, 4.20; N, 6.04.

Reference Example 139

A mixture of methyl 7-bromo-1-(4-sulfamoylphenyl)-2,3-dihydro-1H-1-benzazepine-4-carboxylate (0.31 g), 4-(2- butoxyethoxy)phenyl borate (0.22 g), 1M potassium carbonate solution (3 ml), ethanol (5 ml) and toluene (50 ml) was stirred under argon atmosphere at room temperature for 30 minutes. To the mixture was added tetrakis(triphenylphosphine)palladium (0.04 g), and the mixture was refluxed under argon atmosphere for 3 hours and extracted with ethyl acetate. The organic layer was washed with water and saturated brine and dried with anhydrous magnesium sulfate. The solvent was evaporated under reduced pressure and the residue was purified with silica gel column chromatography (ethyl acetate/hexane) to give methyl 7-[4-(2-butoxyethoxy)phenyl]-1-(4-sulfamoylphenyl)-2,3-dihydro-1H-1-benzazepine-4-carboxylate (0.34 g) as yellow crystals.

mp 163–165° C.

$^1$H-NMR (δ ppm, CDCl$_3$) 0.94 (3H, t, J=7.3 Hz), 1.35–1.46 (2H, m), 1.56 1.66 (2H, m), 2.92 (2H, t, J=5.0 Hz), 3.57 (2H, t, J=6.6 Hz), 3.79 (3H, s), 3.79–3.92 (4H, m), 4.18 (2H, t, J=4.8 Hz), 4.73 (2H, s), 6.91 (2H, d, J=9.2 Hz), 7.03 (2H, d, J=8.8 Hz), 7.34 (1H, d, J=8.2 Hz), 7.50–7.56 (3H, m), 7.71–7.77 (41H, m).

IR (KBr) ν: 2957, 2934, 2870, 1705, 1590, 1493 cm$^{-1}$.

Anal. Calcd. for C$_{30}$H$_{34}$N$_2$O$_6$S.0.25H$_2$O: C, 65.43; H, 6.22; N, 5.09. Found C, 65.04; H, 6.35; N, 4.91.

Reference Example 140

In methanol (50 ml) and THF (15 ml) was dissolved methyl 7-[4-(2-butoxyethoxy)phenyl]-1-(4-sulfamoylphenyl)-2,3-dihydro-1H-1-benzazepine-4-carboxylate (0.34 g). To the solution was added 1N sodium hydroxide solution (10 ml), and the mixture was refluxed for 2 hours, concentrated, neutralized with 1N hydrochloric acid and extracted with ethyl acetate. The organic layer was washed with water and saturated brine and dried with anhydrous magnesium sulfate. The solvent was evaporated to give 7-[4-(2-butoxyethoxy)phenyl]-1-(4-sulfamoylphenyl)-2,3-dihydro-1H-1-benzazepine-4-carboxylic acid (0.3 g) as yellow crystals.

mp 185–195° C.

$^1$H-NMR (δ ppm, CDCl$_3$) 0.94 (3H, t, J=7.1 Hz), 1.27–1.46 (2H, m), 1.55–1.66 (2H, m), 2.92 (2H, t-like), 3.57 (2H, t, J=6.6 Hz), 3.82 (2H, t, J=4.9 Hz), 3.90 (2H, t-like), 4.19 (2H, t, J=4.9 Hz), 4.73 (2H, s), 6.93 (2H, d, J=8.8 Hz), 7.03 (2H, d, J=8.8 Hz), 7.35 (1H, d, J=8.0 Hz), 7.52–7.56 (3H, m), 7.72–7.76 (3H, m), 7.85 (1 H s).

Anal. Calcd. for C$_{29}$H$_{32}$N$_2$O$_6$S: C, 64.91; H, 6.01; N, 5.22. Found C, 65.08; H, 6.17; N, 5.03.

Reference Example 141

In dichloromethane (10 ml) was dissolved methyl 7-bromo-1-phenyl-2,3-dihydro-1H-1-benzazepine-4-carboxylate (0.4 g). Under ice-cooling, to the solution was added dropwise chlorosulfonic acid (0.74 ml). The mixture was stirred at room temperature for 30 minutes and, to the mixture was additionally added chlorosulfonic acid (0.37 ml), and the mixture was stirred at room temperature for 30 minutes. The reaction solution was added dropwise to 2M dimethylamine solution in methanol (35 ml) under ice-cooling, and the mixture was stirred overnight. The solvent was evaporated and, to the residue was added water, and the mixture was extracted with ethyl acetate. The organic layer was washed with water and saturated brine and dried with anhydrous magnesium sulfate. The solvent was evaporated to give methyl 7-bromo-1-(N,N-dimethyl-4-sulfamoylphenyl)-2,3-dihydro-1H-1-benzazepine-4-carboxylate (0.37 g) as yellow crystals.

mp 210–213° C.

$^1$H-NMR (δ ppm, CDCl$_3$) 2.69 (6H, s), 2.90 (2H, t, J=5.1 Hz), 3.79 (3H, s), 3.84 (2H, t, J=5.1 Hz), 6.89 (2H, d, J=9.2 Hz), 7.21 (1H, d, J=8.4 Hz), 7.44 (1H, dd, J=2.2, 8.4 Hz), 7.57–7.62 (3H, m), 7.68 (1H, d, J=2.2 Hz).

IR (KBr) ν: 2955, 1709, 1595, 1582, 1501, 1483 cm$^{-1}$.

Anal. Calcd. for C$_{20}$H$_{21}$BrN$_2$O$_4$S: C, 51.62; H, 4.55; N, 6.02. Found C, 51.60; H, 4.55; N, 5.78.

Reference Example 142

A mixture of methyl 7-bromo-1-(N,N-dimethyl-4-sulfamoylphenyl)-2,3-dihydro-1H-1-benzazepine-4-carboxylate (0.35 g), 4-(2-butoxyethoxy)phenyl borate (0.19 g), 1M potassium carbonate solution (2 ml), ethanol (2 ml) and toluene (50 ml) was stirred under argon atmosphere at room temperature for 30 minutes. To the mixture was added tetrakis(triphenylphosphine)palladium (0.04 g), and the mixture was refluxed under argon atmosphere for 6 hours and extracted with ethyl acetate. The organic layer was washed with water and saturated brine and dried with anhydrous magnesium sulfate. The solvent was evaporated under reduced pressure and the residue was purified with silica gel column chromatography (ethyl acetate/hexane) to give methyl 7-[4-(2-butoxyethoxy)phenyl]-1-(N,N-dimethyl-4-sulfamoylphenyl)-2,3-dihydro-1H-1-benzazepine-4-carboxylate (0.35 g) as colorless crystals.

mp 150–153° C.

$^1$H-NMR (δ ppm, CDCl$_3$) 0.94 (3H, t, J=7.3 Hz), 1.35–1.66 (4H, m), 2.69 (6H, s), 2.93 (2H, t-like), 3.57 (2H, t, J=6.6 Hz), 3.80 (3H, s), 3.80–3.89 (4H, m), 4.19 (2H, t, J=5.0 Hz), 6.94 (2H, d, J=8.8 Hz), 7.03 (2H, d, J=8.8 Hz), 7.38 (1H, d, J=8.4 Hz), 7.51–7.62 (5H, m), 7.71 (1H, s), 7.78 (1H, s).

IR (KBr) ν: 2959, 2868, 1709, 1590, 1495 cm$^{-1}$.

Anal. Calcd. for C$_{32}$H$_{38}$N$_2$O$_6$S: C, 66.41; H, 6.62; N, 4.84. Found C, 66.25; H, 6.89; N, 4.76.

Reference Example 143

In methanol (50 ml) and THF (50 ml) was dissolved methyl 7-[4-(2-butoxyethoxy)phenyl]-1-(N,N-dimethyl-4-sulfamoylphenyl)-2,3-dihydro-1H-1-benzazepine-4-carboxylate (0.34 g). To the solution was added 1N sodium hydroxide solution (10 ml), and the mixture was stirred at room temperature at 60° C. for 1 hour, concentrated, neutralized with 1N hydrochloric acid and extracted with ethyl acetate. The organic layer was washed with water and saturated brine and dried with anhydrous magnesium sulfate. The solvent was evaporated to give 7-[4-(2-butoxyethoxy)phenyl]-1-(N,N-dimethyl-4-sulfamoylphenyl)-2,3-dihydro-1H-1-benzazepine-4-carboxylic acid (0.33 g) as yellow crystals.

mp 236–238° C.

$^1$H-NMR (δ ppm, CDCl$_3$) 0.94 (3H, t, J=7.1 Hz), 1.30–1.50 (2H, m), 1.56–1.66 (2H, m), 2.69 (6H, s), 2.93 (2H, t-like), 3.57 (2H, t, J=6.6 Hz), 3.83 (2H, t, J=4.8 Hz), 3.91 (2H, t-like), 4.19 (2H, t, J=4.8 Hz), 6.96 (2H, d, J=9.2 Hz), 7.03 (2H, d, J=8.8 Hz), 7.39 (1H, d, J=8.6 Hz), 7.52–7.63 (5H, m), 7.72 (1H, d, J=2.2 Hz), 7.88 (1H, s).

IR (KBr) ν: 2959, 2934, 2872, 1671, 1590, 1501, 1491 cm$^{-1}$.

Anal. Calcd. for C$_{31}$H$_{36}$N$_2$O$_6$S: C, 65.94; H, 6.43; N, 4.96. Found C, 65.82; H, 6.46; N, 4.85.

Reference Example 144

In dichloromethane (20 ml) was dissolved methyl 7-bromo-1-phenyl-2,3-dihydro-1H-1-benzazepine-4- carboxylate (1 g). Under ice-cooling, to the solution was added dropwise chlorosulfonic acid (0.93 ml). The mixture was stirred at room temperature for 1 hour, and the reaction solution was added dropwise to 40% methylamine solution in water (25 ml) under ice-cooling. The mixture was stirred at room temperature overnight, concentrated and extracted with ethyl acetate. The organic layer was washed with water and saturated brine and dried with anhydrous magnesium sulfate. The solvent was evaporated to give methyl 7-bromo-1-(N-methyl-4-sulfamoylphenyl)-2,3-dihydro-1H-1-benzazepine-4-carboxylate (1 g) as yellow crystals.

mp 201–204° C.

$^1$H-NMR (δ ppm, CDCl$_3$) 2.65 (3H, d, J=5.4 Hz), 2.90 (2H, t, J=4.6 Hz), 3.79 (3H, s), 3.84 (2H, t, J=4.6 Hz), 4.23 (1H, q, J=5.4 Hz), 6.88 (2H, d, J=9.0 Hz), 7.30 (1H, d, J=8.8 Hz), 7.44 (1H, dd, J=2.2, 8.8 Hz), 7.57–7.69 (4H, m).

IR (KBr) ν: 3277, 2953, 1705, 1595, 1501 cm$^{-1}$.

Anal. Calcd. for C$_{19}$H$_{19}$BrN$_2$O$_4$S: C, 50.56; H, 4.24; N, 6.21. Found C, 50.62; H, 4.20; N, 6.48.

Reference Example 145

A mixture of methyl 7-bromo-1-(N-methyl-4-sulfamoylphenyl)-2,3-dihydro-1H-1-benzazepine-4-carboxylate (1 g), 4-(2-butoxyethoxy)phenyl borate (0.69 g), 1M potassium carbonate solution (8 ml), ethanol (8 ml) and toluene (100 ml) was stirred under argon atmosphere at room temperature for 30 minutes. To the mixture was added tetrakis(triphenylphosphine)palladium (0.13 g), and the mixture was refluxed under argon atmosphere for 2.5 hours and extracted with ethyl acetate. The organic layer was washed with water and saturated brine and dried with anhydrous magnesium sulfate. The solvent was evaporated under reduced pressure and the residue was purified with silica gel column chromatography (ethyl acetate/hexane) to give methyl 7-[4-(2-butoxyethoxy)phenyl]-1-(N-methyl4-sulfamoylphenyl)-2,3-dihydro-1H-1-benzazepine-4-carboxylate (1.1 g) as colorless crystals.

mp 142–146° C.

$^1$H-NMR (δ ppm, CDCl$_3$) 0.94 (3H, t, J=7.2 Hz), 1.35–1.46 (2H, m), 1.57–1.66 (2H, m), 2.65 (3H, d, J=5.6 Hz), 2.92 (2H, t, J=4.8 Hz), 3.56 (2H, t, J=6.6 Hz), 3.80 (3H, s), 3.80–3.92 (4H, m), 4.10–4.21 (3H, m), 6.92 (2H, d, J=8.8 Hz), 7.03 (2H, d, J=8.6 Hz), 7.36 (1H, d, J=8.4 Hz), 7.50–7.56 (3H, m), 7.67 (2H, d, J=8.8 Hz), 7.71 (1H, d, J=2.2 Hz), 7.77 (1H, s).

IR (KBr) ν: 2957, 1709, 1590, 1495 cm$^{-1}$.

Anal. Calcd. for C$_{31}$H$_{36}$N$_2$O$_6$S: C, 65.94; H, 6.43; N, 4.69. Found C, 65.76; H, 6.36; N, 4.81.

Reference Example 146

In methanol (100 ml) and THF (100 ml) was dissolved methyl 7-[4-(2-butoxyethoxy)phenyl]-1-(N-methyl-4-sulfamoylphenyl)-2,3-dihydro-1H-1-benzazepine-4-carboxylate (1.1 g). To the solution was added 1N sodium hydroxide solution (19 ml), and the mixture was heated at 50° C. for 6 hours, concentrated, neutralized with 1N hydrochloric acid and extracted with ethyl acetate. The organic layer was washed with water and saturated brine and dried with anhydrous magnesium sulfate. The solvent was evaporated to give 7-[4-(2-butoxyethoxy)phenyl]-1-(N-methyl-4-sulfamoylphenyl)-2,3-dihydro-1H-1-benzazepine-4-carboxylate (1 g) as pale yellow crystals.

mp 208–210° C.

$^1$H-NMR (δ ppm, CDCl$_3$) 0.94 (3H, t, J=7.1 Hz), 1.31–1.50 (2H, m), 1.55–1.69 (2H, m), 2.65 (3H, d, J=5.6 Hz), 2.92 (2H, t-like), 3.57 (2H, t, J=6.6 Hz), 3.82 (2H, t, J=5.0 Hz), 3.91 (2H, t-like), 4.19 (2H, t, J=5.0 Hz), 4.27 (1H, q, J=5.6 Hz), 6.94 (2H, d, J=8.8H), 7.03 (2H, d, J=8.6 Hz), 7.37 (1H, d, J=8.4 Hz), 7.52–7.56 (3H, m), 7.67 (2H, d, J=9.2 Hz), 7.71 (1H, d, J=2.2 Hz), 7.86 (1H, s).

IR (KBr) ν: 2595, 2932, 2872, 1682, 1493 cm$^{-1}$.

Anal. Calcd. for C$_{30}$H$_{34}$N$_2$O$_6$S: C, 65.43; H, 6.22; N, 5.09. Found C, 65.18; H, 6.01; N, 5.02.

Working Example 49

Production of Compound 49

One droplet of DMF was added to a solution of 1-allyl-7-(4-propoxyethoxyphenyl)-2,3-dihydro-1-benzazepine-4-carboxylic acid (180 mg) in tetrahydrofuran (10 ml). Then, thionyl chloride (152 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (30 ml), and the suspension was added to a solution of 4-[[N-methyl N-(tetrahydropyran-4-yl)amino]methyl] aniline (113 mg) and triethylamine (516 mg) in tetrahydrofuran (10 ml) at 0° C. The suspension was stirred under nitrogen atmosphere at room temperature overnight, to the mixture was added water, and the mixture was extracted with ethyl acetate twice. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give 1-allyl-N-[4-[[N-methyl-N-(tetrahydropyran-4-yl)amino]methyl]phenyl]-7-(4-propoxyethoxyphenyl)-2,3-dihydro-1-benzazepine-4-carboxamide (Compound 49) (125 mg) as yellow crystals.

mp 110.0–111.0° C.

$^1$H-NMR (200 MHz, CDCl$_3$) δ 0.94 (t, 3H, J=7.6 Hz), 1.59–1.80 (m, 6H), 2.21 (s, 3H), 2.65 (br, 1H), 2.91 (br, 2H), 3.30–3.43 (m, 4H), 3.51 (t, 2H, J=6.8 Hz), 3.57 (s, 2H), 3.80 (t, 2H, J=4.4 Hz), 3.97–4.06 (m, 4H), 4.16 (t, 2H, J=5.2 Hz), 5.28 (d, 2H, J=12.8 Hz), 5.95 (br, 1H), 6.89 (d, 1H, J=8.2 Hz), 6.99 (d, 2H, J=8.8 Hz), 7.30 (d, 2H, J=8.4 Hz), 7.37–7.56 (m, 5H).

Anal. Calcd. C$_{38}$H$_{47}$N$_3$O$_4$ Calcd. C, 74.18; H, 7.75; N, 6.83. Found C, 73.87; H, 7.95; N, 6.78

Working Example 50

Production of Compound 50

In toluene (15 ml), ethanol (1.5 ml) and water (1.5 ml) were suspended 1-allyl-7-bromo-N-[4-[[N-methyl-N-(tetrahydropyran-4-yl)amino]methyl]phenyl]-2,3-dihydro-1-benzazepine-4-carboxamide (262 mg), 4-butoxyethoxyphenyl borate (169 mg) and potassium carbonate (196 mg), and the suspension was stirred under argon atmosphere for 30 minutes. Then, to the mixture was added tetrakistriphenylphosphinepalladium (45 mg), and the mixture was heated under argon atmosphere at 100° C. for 6 hours. After allowing to cool, water was added thereto, and the mixture was extracted with ethyl acetate. The organic layer was washed with saturated brine and dried with magnesium sulfate. The solvent was evaporated under reduced pressure and the resulting residue was separated and purified with silica gel column chromatography (methanol:ethyl acetate=1:16), which was recrystallized from hexane-ethyl acetate to give 1-allyl-7-(4-butoxyethoxyphenyl)-N-[4-[[N-methyl-N-(tetrahydropyran-4-yl)amino]methyl]phenyl]-2,3-dihydro-1-benzazepine-4-carboxamide (Compound 50) (46 mg) as yellow crystals.

mp 103.0–104.0° C.

$^1$H-NMR (200 MHz, CDCl$_3$) δ 0.93 (t, 3H, J=7.4 Hz), 1.34–1.49 (m, 2H), 1.58–1.82 (m, 6 Hz), 2.21 (s, 3H), 2.67 (br, 1H), 2.90 (br, 2H), 3.32–3.43 (m, 4H), 3.52–3.58 (m, 4H), 3.80 (t, 2H, J=4.8 Hz), 3.93–4.10 (m, 4H), 4.16 (t, 2H, J=4.6 Hz), 5.29 (d, 2H, J=14.0 Hz), 5.95 (br, 1H), 6.90 (d, 1H, J=8.6 Hz), 6.98 (d, 2H, J=8.8 Hz), 7.30 (d, 2H, J=8.4 Hz), 7.38–7.56 (m, 8H).

Working Example 51

Production of Compound 51

One droplet of DMF was added to a solution of 1-(2-methoxybenzyl)-7-(4-propoxyethoxyphenyl)-2,3-dihydro-1-benzazepine-4-carboxylic acid (190 mg) in tetrahydrofuran (10 ml). Then, thionyl chloride (139 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (25 ml), and the suspension was added to a solution of 4-[[N-methyl-N-(tetrahydropyran-4-yl)amino]methyl]aniline (104 mg) and triethylamine (476 mg) in tetrahydrofuran (10 ml) at 0° C. The suspension was stirred under nitrogen atmosphere at room temperature for 3.5 hours, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give 1-(2-methoxybenzyl)-N-[4-[[N-methyl-N-(tetrahydropyran-4-yl)amino]methyl]phenyl]-7-(4-propoxyethoxyphenyl)-2,3-dihydro-1-benzazepine-4-carboxamide (Compound 51) (169 mg) as yellow crystals.

mp 118.0–119.0° C.

$^1$H-NMR (200 MHz, CDCl$_3$) δ 0.94 (t, 3H, J=7.4 Hz), 1.59–1.82 (m, 6H), 2.21 (s, 3H), 2.65 (br, 1H), 2.89 (br, 2H), 3.30–3.42 (m, 4H), 3.51 (t, 2H, J=7.0 Hz), 3.57 (s 2H), 3.80 (t, 2H, J=4.4 Hz), 3.89 (s, 3H), 4.04 (d, 2H, J=11.0 Hz), 4.16 (t, 2H, J=5.2 Hz), 4.59 (s, 2H), 6.82 (d, 1H, J=8.8 Hz), 6.92–6.99 (m, 4H), 7.16 (d, 1H, J=6.6 Hz), 7.28–7.35 (m, 4H), 7.43–7.56 (m, 7H).

Anal. Calcd. C$_{43}$H$_{51}$N$_3$O$_5$.0.2H$_2$O Calcd. C, 74.47; H, 7.42; N, 6.06. Found C, 74.20; H, 7.53; N, 6.02.

Working Example 52

Production of Compound 52

One droplet of DMF was added to a solution of 7-(4-butoxyethoxyphenyl)-1-(2-methoxybenzyl)-2,3-dihydro-1-benzazepine-4-carboxylic acid (236 mg) in tetrahydrofuran (10 ml). Then, thionyl chloride (164 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (25 ml), and the suspension was added to a solution of 4-[[N-methyl-N-(tetrahydropyran-4-yl)amino]methyl]aniline (121 mg) and triethylamine (558 mg) in tetrahydrofuran (10 ml) at 0° C. The suspension was stirred under nitrogen atmosphere at room temperature for 3.5 hours, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give 7-(4-butoxyethoxyphenyl)-1-(2-methoxybenzyl)-N-[4-[[N-methyl-N-(tetrahydropyran-4-yl)amino]methyl]phenyl]-2,3-dihydro-1-benzazepine-4-carboxamide (Compound 52) (236 mg) as yellow crystals.

mp 111.5–112.5° C.

$^1$H-NMR (200 MHz, CDCl$_3$) δ 0.93 (t, 3H, J=7.2 Hz), 1.25–1.44 (m, 2H), 1.50–1.80 (m, 6H), 2.21 (s, 3H), 2.65 (br, 1H), 2.90 (br, 2H), 3.32–3.42 (m, 4H), 3.52–3.57 (m, 4H), 3.80 (t, 2H, J=4.4 Hz), 3.89 (s, 3H), 4.04 (d, 2H, J=11.8 Hz), 4.15 (t, 2H, J=5.6 Hz), 4.59 (s, 2H), 6.82 (d, 1H, J=8.8 Hz), 6.92–6.99 (m, 4H), 7.16 (d, 1H, J=6.6 Hz), 7.26–7.32 (m, 4H), 7.44–7.57 (m, 7H).

Anal. Calcd. C$_{44}$H$_{53}$N$_3$O$_5$.0.1H$_2$O Calcd. C, 74.88; H, 7.60; N, 5.96: Found C, 74.62; H, 7.39; N, 5.89.

Working Example 53

Production of Compound 53

One droplet of DMF was added to a solution of 1-(3-methoxybenzyl)-7-(4-propoxyethoxyphenyl)-2,3-dihydro-1-benzazepine-4-carboxylic acid (110 mg) in tetrahydrofuran (10 ml). Then, thionyl chloride (80 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (25 ml), and the suspension was added to a solution of 4-[[N-methyl-N-(tetrahydropyran-4-yl)amino]methyl]aniline (60 mg) and triethylamine (273 mg) in tetrahydrofuran (10 ml) at 0° C. The suspension was stirred under nitrogen atmosphere at room temperature for 5 hours, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give 1-(3-methoxybenzyl)-N-[4-[[N-methyl-N-(tetrahydropyran-4-yl)amino]methyl]phenyl]-7-(4-propoxyethoxyphenyl)-2,3-dihydro-1-benzazepine-4-carboxamide (Compound 53) (62 mg) as yellow crystals.

mp 113.0–114.0° C.

$^1$H-NMR (200 MHz, CDCl$_3$) δ 0.94 (t, 3H, J=7.2 Hz), 1.56–1.80 (m, 6H), 2.21 (s, 3H), 2.62 (br, 1H), 2.86 (br, 2H), 3.32–3.45 (m, 4H), 3.51 (t, 2H, J=6.6 Hz), 3.57 (s, 2H), 3.78–3.83 (m, 5H), 4.03 (d, 2H, J=9.8 Hz), 4.16 (t, 2H, J=5.2 Hz), 4.58 (s, 2H), 6.82–6.92 (m, 4H), 6.98 (d, 2H, J=8.8 Hz), 7.26–7.38 (m, 4H), 7.45–7.56 (m, 7H).

Working Example 54

Production of Compound 54

One droplet of DMF was added to a solution of 7-(4-butoxyethoxyphenyl)-1-(3-methoxybenzyl)-2,3-dihydro-1- benzazepine-4-carboxylic acid (150 mg) in tetrahydrofuran (10 ml). Then, thionyl chloride (107 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (25 ml), and the suspension was added to a solution of 4-[[N-methyl-N-(tetrahydropyran-4-yl)amino]methyl]aniline (79 mg) and triethylamine (363 mg) in tetrahydrofuran (10 ml) at 0° C. The suspension was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give 7-(4-butoxyethoxyphenyl)-1-(3-methoxybenzyl)-N-[4-[[N-methyl-N-(tetrahydropyran-4-yl)amino]methyl]phenyl]-2,3-dihydro-1-benzazepine-4-carboxamide (Compound 54) (29 mg) as yellow crystals.

mp 107.5–108.5° C.

$^1$H-NMR (200 MHz, CDCl$_3$) δ 0.93 (t, 3H, J=7.0 Hz), 1.33–1.45 (m, 2H), 1.57–1.80 (m, 6H), 2.21 (s, 3H), 2.64 (br, 1H), 2.86 (br, 2H), 3.32–3.45 (m, 4H), 3.55 (t, 2H, J=6.6 Hz), 3.57 (s, 2H), 3.78–3.83 (m, 5H), 4.03 (d, 2H, J=9.4 Hz), 4.16 (t, 2H, J=5.0 Hz), 4.58 (s, 2H), 6.82–6.92 (m, 4H), 6.97 (d, 2H, J=8.8 Hz), 7.26–7.39 (m, 4H), 7.44–7.55 (m, 7H).

Anal. Calcd. C$_{44}$H$_{53}$N$_3$O$_5$ Calcd. C, 75.08; H, 7.59; N, 5.97. Found C, 74.74; H, 7.52; N, 5.91.

Working Example 55

Production of Compound 55

One droplet of DMF was added to a solution of 1-(4-methoxybenzyl)-7-(4-propoxyethoxyphenyl)-2,3-dihydro-1-benzazepine-4-carboxylic acid (110 mg) in tetrahydrofuran (10 ml). Then, thionyl chloride (96 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (30 ml), and the suspension was added to a solution of 4-[[N-methyl-N-(tetrahydropyran-4-yl)amino]methyl]aniline (71 mg) and triethylamine (328 mg) in tetrahydrofuran (10 ml) at 0° C. The suspension was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give 1-(4-methoxybenzyl)-N-[4-[[N-methyl-N-(tetrahydropyran-4-yl)amino]methyl]phenyl]-7-(4-propoxyethoxyphenyl)-2,3-dihydro-1-benzazepine-4-carboxamide (Compound 55) (86 mg) as yellow crystals.

mp 160.0–161.0° C.

$^1$H-NMR (200 MHz, CDCl$_3$) δ 0.94 (t, 3H, J=7.8 Hz), 1.58–1.80 (m, 6H), 2.21 (s, 3H), 2.64 (br, 1H), 2.81 (br, 2H), 3.32–3.42 (m, 4H), 3.51 (t, 2H, J=6.6 Hz), 3.57 (s, 2H), 3.78–3.82 (m, 5H), 4.03 (d, 2H, J=9.4 Hz), 4.16 (t, 2H, J=5.2 Hz), 4.54 (s, 2H), 6.89–7.00 (m, 5H), 7.22–7.41 (m, 5H), 7.45–7.56 (m, 7H).

Anal. Calcd. C$_{43}$H$_{51}$N$_3$O$_5$.0.4H$_2$O Calcd. C, 74.08; H, 7.43; N, 6.03. Found C, 73.82; H, 7.60; N, 5.99.

Working Example 56

Production of Compound 56

One droplet of DMF was added to a solution of 7-(4-butoxyethoxyphenyl)-1-(4-methoxybenzyl)-2,3-dihydro-1-benzazepine-4-carboxylic acid (140 mg) in tetrahydrofuran (10 ml). Then, thionyl chloride (100 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (25 ml), and the suspension was added to a solution of 4-[[N-methyl-N-(tetrahydropyran-4-yl)amino]methyl]aniline (74 mg) and triethylamine (344 mg) in tetrahydrofuran (10 ml) at 0° C. The suspension was stirred under nitrogen atmosphere at room temperature for 3.5 hours, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give 7-(4-butoxyethoxyphenyl)-1-(4-methoxybenzyl)-N-[4-[[N-methyl-N-(tetrahydropyran-4-yl)amino]methyl]phenyl]-2,3-dihydro-1-benzazepine-4-carboxamide (Compound 56) (89 mg) as yellow crystals.

mp 151.0–152.0° C.

$^1$H-NMR (200 MHz, CDCl$_3$) δ 0.93 (t, 3H, J=7.2 Hz), 1.26–1.46 (m, 2H), 1.50–1.80 (m, 6H), 2.21 (s, 3H), 2.64 (br, 1H), 2.81 (br, 2H), 3.28–3.42 (m, 4H), 3.52–3.60 (m, 4H), 3.77–3.82 (m, 5H), 4.03 (d, 2H, J=10.2 Hz), 4.16 (t, 2H, J=5.0 Hz), 4.54 (s, 2H), 6.89–7.22 (m, 5H), 7.20–7.40 (m, 5H), 7.45–7.56 (m, 7H).

Anal. Calcd. C$_{44}$H$_{53}$N$_3$O$_5$.0.3H$_2$O Calcd. C, 74.50; H, 7.62; N, 5.93. Found C, 74.34; H, 7.62; N, 5.96.

Working Example 57

Production of Compound 57

One droplet of DMF was added to a solution of 7-(4-propoxyethoxyphenyl)-1-(3-thienylmethyl)-2,3-dihydro-1-benzazepine-4-carboxylic acid (250 mg) in tetrahydrofuran (10 ml). Then, thionyl chloride (193 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (25 ml), and the suspension was added to a solution of 4-[[N-methyl-N-(tetrahydropyran-4-yl)amino]methyl]aniline (143 mg) and triethylamine (655 mg) in tetrahydrofuran (10 ml) at 0° C. The suspension was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give N-[4-[[N-methyl-N-(tetrahydropyran-4-yl)amino]methyl]phenyl]-7-(4-propoxyethoxyphenyl)-1-(3-thienylmethyl)-2,3-dihydro-1-benzazepine-4-carboxamide (Compound 57) (260 mg) as yellow crystals.

mp 131.5–132.5° C.

$^1$H-NMR (200 MHz, CDCl$_3$) δ 0.94 (t, 3H, J=7.4 Hz), 1.58–1.80 (m, 6H), 2.21 (s, 3H), 2.64 (br, 1H), 2.84 (br, 2H), 3.32–3.42 (m, 4H), 3.51 (t, 2H, J=7.0 Hz), 3.57 (s, 2H), 3.81 (t, 2H, J=4.2 Hz), 4.03 (d, 2H, J=10.6 Hz), 4.16 (t, 2H, J=5.2 Hz), 4.58 (s, 2H), 6.93–7.06 (m, 4H), 7.16 (br, 1H), 7.28–7.42 (m, 4H), 7.45–7.55 (m, 7H).

Anal. Calcd. C$_{40}$H$_{47}$N$_3$O$_4$S.0.1H$_2$O Calcd. C, 71.95; H, 7.13; N, 6.29. Found C, 71.66; H, 7.12; N, 6.22.

Working Example 58

Production of Compound 58

One droplet of DMF was added to a solution of 7-(4-butoxyethoxyphenyl)-1-(3-thienylmethyl)-2,3-dihydro-1-benzazepine-4-carboxylic acid (250 mg) in tetrahydrofuran (10 ml). Then, thionyl chloride (187 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (25 ml), and the suspension was added to a solution of 4-[[N-methyl-N-(tetrahydropyran-4-yl)amino]methyl]aniline (131 mg) and triethylamine (638 mg) in tetrahydrofuran (10 ml) at 0° C. The suspension was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give 7-(4-butoxyethoxyphenyl)-N-[4-[[N-methyl-N-(tetrahydropyran-4-yl)amino]methyl]phenyl]-1-(3-thienylmethyl)-2,3-dihydro-1-benzazepine-4-carboxamide (Compound 58) (233 mg) as yellow crystals.

mp 122.0–123.0° C.

$^1$H-NMR (200 MHz, CDCl$_3$) δ 0.93 (t, 3H, J=7.2 Hz), 1.34–1.50 (m, 2H), 1.60–1.75 (m, 6H), 2.21 (s, 3H), 2.60 (br, 1H), 2.84 (br, 2H), 3.32–3.45 (m, 4H), 3.52–3.58 (m, 4H), 3.80 (t, 2H, J=4.0 Hz), 4.05 (d, 2H, J=12.2 Hz), 4.16 (t, 2H, J=5.0 Hz), 4.58 (s, 2H), 6.93–7.06 (m, 4H), 7.16 (br, 1H), 7.32–7.42 (m, 4H), 7.45–7.55 (m, 7H).

Anal. Calcd. C$_{41}$H$_{49}$N$_3$O$_4$S Calcd. C, 72.43; H, 7.26; N, 6.18. Found C, 72.03; H, 7.44; N, 6.12.

Working Example 59

Production of Compound 59

One droplet of DMF was added to a solution of 7-(4-propoxyethoxyphenyl)-1-(2-thienylmethyl)-2,3-dihydro-1-benzazepine-4-carboxylic acid (240 mg) in tetrahydrofuran (10 ml). Then, thionyl chloride (184 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (30 ml), and the suspension was added to a solution of 4-[[N-methyl-N-(tetrahydropyran-4-yl)amino]methyl]aniline (137 mg) and triethylamine (629 mg) in tetrahydrofuran (10 ml) at 0° C. The suspension was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give N-[4-[[N-methyl-N-(tetrahydropyran-4-yl)amino]methyl]phenyl]-7-(4-propoxyethoxyphenyl)-1-(2-thienylmethyl)-2,3-dihydro-1-benzazepine-4-carboxamide (Compound 59) (152 mg) as yellow crystals.

mp 104.5–105.5° C.

$^1$H-NMR (200 MHz, CDCl$_3$) δ 0.94 (t, 3H, J=7.2 Hz), 1.57–1.80 (m, 6H), 2.21 (s, 3H), 2.62 (br, 1H), 2.88 (br, 2H), 3.32–3.41 (m, 4H), 3.51 (t, 2H, J=6.6 Hz), 3.57 (s, 2H), 3.81 (t, 2H, J=4.8 Hz), 4.04 (d, 2H, J=11.4 Hz), 4.16 (t, 2H, J=5.2 Hz), 4.73 (s, 2H), 6.96–7.05 (m, 5H), 7.26–7.32 (m, 3H), 7.40–7.60 (m, 8H).

Anal. Calcd. C$_{40}$H$_{47}$N$_3$O$_4$S Calcd. C, 72.15; H, 7.11; N, 6.31. Found C, 71.87; H, 6.92; N, 6.26.

Working Example 60

Production of Compound 60

One droplet of DMF was added to a solution of 7-(4-butoxyethoxyphenyl)-1-(2-thienylmethyl)-2,3-dihydro-1-benzazepine-4-carboxylic acid (110 mg) in tetrahydrofuran (10 ml). Then, thionyl chloride (82 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (20 ml), and the suspension was added to a solution of 4-[[N-methyl-N-(tetrahydropyran-4-yl)amino]methyl]aniline (61 mg) and triethylamine (279 mg) in tetrahydrofuran (10 ml) at 0° C. The suspension was stirred under nitrogen atmosphere at room temperature for 3 hours, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give 7-(4-butoxyethoxyphenyl)-N-[4-[[N-methyl-N-(tetrahydropyran-4-yl)amino]methyl]phenyl]-1-(2-thienylmethyl)-2,3-dihydro-1-benzazepine-4-carboxamide (Compound 60) (86 mg) as yellow crystals.

mp 84.0–85.0° C.

$^1$H-NMR (200 MHz, CDCl$_3$) δ 0.93 (t, 2H, J=7.2 Hz), 1.34–1.50 (m, 2H), 1.59–1.80 (m, 6H), 2.22 (s, 3H), 2.66 (br, 1H), 2.89 (br, 2H), 3.30–3.45 (m, 4H), 3.55 (t, 2H, J=6.6 Hz), 3.5B (s, 2H), 3.80 (t, 2H, J=4.0 Hz), 4.04 (d, 2H, J=12.6 Hz), 4.16 (t, 2H, J=5.4 Hz), 4.73 (s, 2H), 6.96–7.06 (m, 5H), 7.29–7.33 (m, 3H), 7.45–7.56 (m, 8H).

Anal. Calcd. C$_{41}$H$_{49}$N$_3$O$_4$S Calcd. C, 71.29; H, 7.33; N, 6.08. Found C, 71.14; H, 7.12; N, 6.01.

Working Example 61

Production of Compound 61

One droplet of DMF was added to a solution of 1-(3-furylmethyl)-7-(4-propoxyethoxyphenyl)-2,3-dihydro-1-benzazepine-4-carboxylic acid (200 mg) in tetrahydrofuran (10 ml). Then, thionyl chloride (159 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (25 ml), and the suspension was added to a solution of 4-[[N-methyl-N-(tetrahydropyran-4-yl)amino]methyl]aniline (118 mg) and triethylamine (546 mg) in tetrahydrofuran (10 ml) at 0° C. The suspension was stirred under nitrogen atmosphere at room temperature for 4.5 hours, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1 8), which was recrystallized from hexane-ethyl acetate to give 1-(3-furylmethyl)-N-[4-[[N-methyl-N-(tetrahydropyran-4-yl)amino]methyl]phenyl]-7-(4-propoxyethoxyphenyl)-2,3-dihydro-1-benzazepine-4-carboxamide (Compound 61) (153 mg) as yellow crystals.

mp 115.0–116.0° C.

$^1$H-NMR (200 MHz, CDCl$_3$) δ 0.94 (t, 3H, J=7.2 Hz), 1.59–1.85 (m, 6H), 2.21 (s, 3H), 2.65 (br, 1H), 2.85 (br, 2H), 3.32–3.43 (m, 4H), 3.51 (t, 2H, J=6.6 Hz), 3.57 (S, 2H), 3.81 (t, 2H, J=4.4 Hz), 4.04 (d, 2H, J=14.6 Hz), 4.17 (t, 2H, J=5.6 Hz), 4.41 (s, 2H), 6.40 (s, 1H), 6.96–7.01 (m, 3H), 7.30 (d, 2H, J=8.8 Hz), 7.43–7,56 (m, 10H).

Anal. Calcd. C$_{40}$H$_{47}$N$_3$O$_5$ Calcd. C, 73.93; H, 7.29; N, 6.47. Found C, 73.53; H, 7.32; N, 6.38.

Working Example 62

Production of Compound 62

One droplet of DMF was added to a solution of 7-(4-butoxyethoxyphenyl)-1-(3-furylmethyl)-2,3-dihydro-1-benzazepine-4-carboxylic acid (200 mg) in tetrahydrofuran (10 ml). Then, thionyl chloride (155 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (25 ml), and the suspension was added to a solution of 4-[[N-methyl-N-(tetrahydropyran-4-yl)amino]methyl]aniline (115 mg) and triethylamine (526 mg) in tetrahydrofuran (10 ml) at 0° C. The suspension was stirred under nitrogen atmosphere at room temperature for 4.5 hours, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give 7-(4-butoxyethoxyphenyl)-1-(3-furylmethyl)-N-[4-[[N-methyl-N-(tetrahydropyran-4-yl)amino]methyl]phenyl]-2,3-dihydro-1-benzazepine-4-carboxamide (Compound 62) (125 mg) as yellow crystals.

mp 116.0–117.0° C.

$^1$H-NMR (200 MHz, CDCl$_3$) δ 0.93 (t, 3H, J=7.4 Hz), 1.25–1.45 (m, 2H), 1.58–1.81 (m, 6H), 2.21 (s, 3H), 2.65 (br, 1H), 2.84 (br, 2H), 3.32–3.43 (m, 4H), 3.56 (t, 2H, J=7.0 Hz), 3.57 (s, 2H), 3.80 (t, 2H, J=4.8 Hz), 4.04 (d, 2H, J=10.6 Hz), 4.16 (t, 2H, J=5.4 Hz), 4.41 (s, 2H), 6.40 (d, 1H, J=0.8 Hz), 6.96–7.01 (m, 3H), 7.30 (d, 2H, J=8.8 Hz), 7.38–7.56 (m, 10H).

Anal. Calcd. C$_{41}$H$_{49}$N$_3$O$_5$·0.2H$_2$O Calcd. C, 73.81; H, 7.41; N, 6.30. Found C, 73.71; H, 7.43; N, 6.18.

Working Example 63

Production of Compound 63

One droplet of DMF was added to a solution of 7-(4-butoxyethoxyphenyl)-1-(2-ethoxybenzyl)-2,3-dihydro-1-benzazepine-4-carboxylic acid (200 mg) in tetrahydrofuran (10 ml). Then, thionyl chloride (138 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (30 ml), and the suspension was added to a solution of 4-[[N-methyl-N-(tetrahydropyran-4-yl)amino]methyl]aniline (103 mg) and triethylamine (476 mg) in tetrahydrofuran (10 ml) at 0° C. The suspension was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give 7-(4-butoxyethoxyphenyl)-1-(2-ethoxybenzyl)-N-[4-[[N-methyl-N-(tetrahydropyran-4-yl)amino]methyl]phenyl]-2,3-dihydro-1-benzazepine-4-carboxamide (Compound 63) (161 mg) as yellow crystals.

mp 104.5–105.5° C.

$^1$H-NMR (200 MHz, CDCl$_3$) δ 0.93 (t, 3H, J=7.0 Hz), 1.32–1.47 (m, 5H), 1.56–1.80 (m, 6H), 2.21 (s, 3H), 2.63 (br, 1H), 2.90 (br, 2H), 3.32–3.42 (m, 4H), 3.52–3.57 (m, 4H), 3.80 (t, 2H, J=4.8 Hz), 4.01–4.18 (m, 6H), 4.60 (s, 2H), 6.84 (d, 1H, J=8.8 Hz), 6.89–6.99 (m, 5H), 7.16 (d, 1H, J=6.2 Hz), 7.27–7.37 (m, 4H), 7.44–7.56 (m, 6H).

Anal. Calcd. C$_{45}$H$_{55}$N$_3$O$_5$ Calcd. C, 75.28; H, 7.72; N, 5.85. Found C, 74.94; H, 7.77; N, 5.67.

Working Example 64

Production of Compound 64

One droplet of DMF was added to a solution of 7-(4-butoxyethoxyphenyl)-1-(3-propoxybenzyl)-2,3-dihydro-1-benzazepine-4-carboxylic acid (200 mg) in tetrahydrofuran (10 ml). Then, thionyl chloride (134 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (30 ml), and the suspension was added to a solution of 4-[[N-methyl-N-(tetrahydropyran-4-yl)amino]methyl]aniline (100 mg) and triethylamine (455 mg) in tetrahydrofuran (10 ml) at 0° C. The suspension was stirred under nitrogen atmosphere at room temperature for 4.5 hours, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give 7-(4-butoxyethoxyphenyl)-N-[4-[[N-methyl-N-(tetrahydropyran-4-yl)amino]methyl]phenyl]-1-(3-propoxybenzyl)-2,3-dihydro-1-benzazepine-4-carboxamide (Compound 64) (207 mg) as yellow crystals.

mp 114.5–115.5° C.

$^1$H-NMR (200 MHz, CDCl$_3$) δ 0.93 (t, 3H, J=7.4 Hz), 1.02 (t, 3H, J=7.4 Hz), 1.34–1.45 (m, 2H), 1.57–1.85 (m, 8H), 2.21 (s, 3H), 2.63 (br, 1H), 2.86 (br, 2H), 3.30–3.46 (m, 4H), 3.52–3.59 (m, 4H), 3.80 (t, 2H, J=4.0 Hz), 3.91 (t, 2H, J=6.6 Hz), 4.04 (d, 2H, J=10.4 Hz), 4.16 (t, 2H, J=5.2 Hz), 4.57 (s, 2H), 6.85–7.00 (m, 6H), 7.26–7.40 (m, 4H), 7.45–7.56 (m, 7H).

Anal. Calcd. $C_{46}H_{57}N_3O_5$ Calcd. C, 75.48; H, 7.85; N, 5.74. Found C, 75.21; H, 7.85; N, 5.64.

Working Example 65

Production of Compound 65

One droplet of DMF was added to a solution of 7-(4-butoxyethoxyphenyl)-1-(2,5-dimethoxybenzyl)-2,3-dihydro-1-benzazepine-4-carboxylic acid (200 mg) in tetrahydrofuran (10 ml). Then, thionyl chloride (134 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (30 ml), and the suspension was added to a solution of 4-[[N-methyl-N-(tetrahydropyran-4-yl)amino]methyl]aniline (100 mg) and triethylamine (455 mg) in tetrahydrofuran (10 ml) at 0° C. The suspension was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8), which was recrystallized from hexane-ethyl acetate to give 7-(4-butoxyethoxyphenyl)-1-(2,5-dimethoxybenzyl)-N-[4-[[N-methyl-N-(tetrahydropyran-4-yl)amino]methyl]phenyl]-2,3-dihydro-1-benzazepine-4-carboxamide (Compound 65) (210 mg) as yellow crystals.

mp 143.0–144.0° C.

$^1$H-NMR (200 MHz, CDCl$_3$) δ 0.93 (t, 3H, J=7.4 Hz), 1.32–1.45 (m, 2H), 1.56–1.80 (m, 6H), 2.21 (s, 3H), 2.65 (br, 1H), 2.90 (br, 2H), 3.32–3.47 (m, 4H), 3.55 (t, 2H, J=2.0 Hz), 3.57 (s, 2H), 3.71 (s, 3H), 3.80 (t, 2H, J=4.0 Hz), 3.84 (s, 3H), 4.04 (d, 2H, J=14.2 Hz), 4.16 (t, 2H, J=5.6 Hz), 4.56 (s, 2H), 6.76–6.89 (m, 4H), 6.97 (d, 2H, J=8.8 Hz), 7.26–7.36 (m, 3H), 7.44–7.56 (m, 7H).

Anal. Calcd. $C_{45}H_{55}N_3O_6$ Calcd. C, 73.64; H, 7.55; N, 5.73. Found C, 73.37; H, 7.63; N, 5.66.

Working Example 66

Production of Compound 66

One droplet of DMF was added to a solution of 7-(4-butoxyethoxyphenyl)-1-(2-fluorobenzyl)-2,3-dihydro-1-benzazepine-4-carboxylic acid (200 mg) in tetrahydrofuran (10 ml). Then, thionyl chloride (146 mg) was added at 0° C., the temperature was returned to room temperature, and the mixture was stirred under nitrogen atmosphere for 1 hour. The solvent and excess thionyl chloride were evaporated under reduced pressure, the resulting residue was suspended in tetrahydrofuran (30 ml), and the suspension was added to a solution of 4-[[N-methyl-N-(tetrahydropyran-4-yl)amino]methyl]aniline (108 mg) and triethylamine (496 mg) in tetrahydrofuran (10 ml) at 0° C. The suspension was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:8) to give 7-(4-butoxyethoxyphenyl)-1-(2-fluorobenzyl)-N-[4-[[N-methyl-N-(tetrahydropyran-4-yl)amino]methyl]phenyl]-2,3-dihydro-1-benzazepine-4-carboxamide (Compound 66) (139 mg) as yellow amorphous.

$^1$H-NMR (200 MHz, CDCl$_3$) δ 0.93 (t, 3H, J=7.2 Hz), 1.30–1.50 (m, 2H), 1.51–1.82 (m, 6H), 2.21 (s, 3H), 2.64 (br, 1H), 2.88 (br, 2H), 3.30–3.45 (m, 4H), 3.50–3.62 (m, 4H), 3.80 (t, 2H, J=4.4 Hz), 4.04 (d, 2H, J=11.0 Hz), 4.16 (t, 2H, J=5.0 Hz), 4.65 (s, 2H), 6.86 (d, 1H, J=8.6 Hz), 6.98 (d, 2H, J=8.8 Hz), 7.07–7.16 (m, 2H), 7.20–7.60 (m, 12H).

Anal. Calcd. $C_{43}H_{50l}N_3O_4 \cdot 0.8H_2O$ Calcd. C, 73.13; H, 7.14; N, 5.95: Found, C, 72.93; H, 7.22; N, 5.79.

Working Example 67

Production of Compound 67

One droplet of DMF was added to a solution of 7-(4-butoxyethoxyphenyl)-1-[(1-methylimidazol-2-yl)methyl]-2,3-dihydro-1-benzazepine-4-carboxylic acid (140 mg) in tetrahydroturan (10 ml). Then, thionyl chloride (41 mg) was added at 0° C., the temperature was returned to room temperature, and the mixture was stirred under nitrogen atmosphere for 1 hour. Then, this mixture was added to a solution of 4-[[N-methyl-N-(tetrahydropyran-4-yl)amino]methyl]aniline (75 mg) and triethylamine (346 mg) in tetrahydrofuran (30 ml) at 0° C. The suspension was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, the resulting residue was separated and purified with basic silica gel column chromatography (ethyl acetate), which was recrystallized from hexane-ethyl acetate to give 7-(4-butoxyethoxyphenyl)-1-[(1-methylimidazol-2-yl)methyl]-N-[4-[[N-methyl-N-(tetrahydropyran-4-yl)amino]methyl]phenyl]-2,3-dihydro-1-benzazepine-4-carboxamide (Compound 67) (65 mg) as yellow crystals.

$^1$H-NMR (200 MHz, CDCl$_3$) δ 0.93 (t, 3H, J=7.0 Hz), 1.30–1.45 (m, 2H), 1.55–1.80 (m, 6H), 2.20 (s, 3H), 2.51 (br, 2H), 2.64 (br, 1H), 3.30–3.45 (m, 4H), 3.52–3.59 (m, 5H), 3.81 (t, 2H, J=4.8 Hz), 4.04 (d, 2H, J=10.2 Hz), 4.17 (t, 2H, J=5.2 Hz), 4.62 (s, 2H), 4.79 (s, 2H), 6.90 (d, 1H, J=1.2 Hz), 6.97–7.01 (m, 3H), 7.07 (d, 1H, J=8.0 Hz), 7.27–7.32 (m, 2H), 7.46–7.57 (m, 8H).

Working Example 68

Production of Compound 68

One droplet of DMF was added to a solution of 7-(4-butoxyethoxyphenyl)-1-(thiazol-2-yl)methyl-2,3-dihydro-1-benzazepine-4-carboxylic acid (70 mg) in dichloromethane (10 ml). Then, thionyl chloride (23 mg) was added at 0° C., the temperature was returned to room temperature, and the mixture was stirred under nitrogen atmosphere for 1 hour. Then, this solution was added to a solution of 4-[[N-methyl-N-(tetrahydropyran-4-yl)amino]methyl]aniline (42 mg) and triethylamine (385 mg) in dichloromethane (20 ml) at 0° C. The suspension was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:3) to give 7-(4-butoxyethoxyphenyl)-N-[4-[[N-methyl-N-(tetrahydropyran-4-yl)amino]methyl]phenyl]-1-(thiazol-2- yl)methyl-2,3-dihydro-1-benzazepine-4-carboxamide (Compound 68) (66 mg) as yellow amorphous.

$^1$H-NMR (200 MHz, CDCl$_3$) δ 0.93 (t, 3H, J=7.2 Hz), 1.33–1.45 (m, 2H), 1.58–1.80 (m, 6H), 2.21 (s, 3H), 2.65 (br, 1H), 2.95 (br, 2H), 3.30–3.57 (m, 8H), 3.80 (t, 2H, J=4.0 Hz), 4.04 (d, 2H, J=10.4 Hz), 4.16 (t, 2H, J=5.0 Hz), 4.88 (s, 2H), 6.96–7.03 (m, 3H), 7.26–7.60 (m, 8H), 7.80 (d, 1H, J=3.2 Hz).

Anal. Calcd. C$_{40}$H$_{48}$N$_4$O$_4$S Calcd. C, 70.56; H, 7.11; N, 8.23. Found C, 70.38; H, 7.12; N, 8.18.

Working Example 69

Production of Compound 69

One droplet of DMF was added to a solution of 7-(4-butoxyethoxyphenyl)-1-[(1-methypyrazol-4-yl)methyl]-2,3-dihydro-1-benzazepine-4-carboxylic acid (380 mg) in dichloromethane (20 ml). Then, thionyl chloride (124 mg) was added at 0° C., the temperature was returned to room temperature, and the mixture was stirred under nitrogen atmosphere for 1 hour. Then, this solution was added to a solution of 4-[[N-methyl N-(tetrahydropyran-4-yl)amino]methyl]aniline (229 mg) and triethylamine (2.1 g) in dichloromethane (30 ml) at 0° C. The suspension was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:3), which was recrystallized from hexane-ethyl acetate to give 7-(4-butoxyethoxyphenyl)-1-[(1-methylpyrazol-4-yl)methyl]-N-[4-[[N-methyl-N-(tetrahydropyran-4-yl)amino]methyl]phenyl]-2,3-dihydro-1-benzazepine-4-carboxamide (Compound 69) (338 mg) as yellow crystals.

$^1$H-NMR (200 MHz, CDCl$_3$) δ 0.93 (t, 3H, J=7.2 Hz), 1.34–1.45 (m, 2H), 1.50–1.80 (m, 6H), 2.21 (s, 3H), 2.63 (br, 1H), 2.85 (br, 2H), 3.28–3.45 (m, 4H), 3.52–3.59 (m, 4H), 3.80 (t, 2H, J=4.0 Hz), 3.90 (s, 3H), 4.04 (d, 2H, J=11.6 Hz), 4.16 (t, 2H, J=5.4 Hz), 4.44 (s, 2H), 6.96–7.01 (m, 3H), 7.15–7.22 (m, 3H), 7.26–7.39 (m, 3H), 7.45–7.55 (m, 9H).

Anal. Calcd. C$_{41}$H$_{51}$N$_5$O$_4$ Calcd. C, 72.64; H, 7.58; N, 10.33. Found C, 72.34; H, 7.59; N, 10.34.

Working Example 70

Production of Compound 70

One droplet of DMF was added to a solution of 7-(4-butoxyethoxyphenyl)-1-[(1-methylpyrazol-5-yl)methyl]-2,3-dihydro-1-benzazepine-4-carboxylic acid (200 mg) in tetrahydrofuran (10 ml). Then, thionyl chloride (150 mg) was added at 0° C., the temperature was returned to room temperature, and the mixture was stirred under nitrogen atmosphere for 1 hour. Then, this mixture was added to a solution of 4-[[N-methyl-N-(tetrahydropyran-4-yl)amino]methyl]aniline (111 mg) and triethylamine (1.0 g) in tetrahydrofuran (25 ml) at 0° C. The suspension was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, the resulting residue was separated and purified with basic silica gel column chromatography (methanol:ethyl acetate=1:3) to give 7-(4-butoxyethoxyphenyl)-1-[(1-methylpyrazol-5-yl)methyl]-N-[4-[[N-methyl-N-(tetrahydropyran-4-yl)amino]methyl]phenyl]-2,3-dihydro-1-benzazepine-4-carboxamide (Compound 70) (60 mg) as yellow amorphous.

$^1$H-NMR (200 MHz, CDCl$_3$) δ 0.93 (t, 3H, J=7.4 Hz), 1.34–1.45 (m, 2H), 1.50–1.80 (m, 6H), 2.21 (s, 3H), 2.40–2.70 (m, 3H), 3.30–3.45 (m, 4H), 3.52–3.59 (m, 4H), 3.79–3.84 (m, 5H), 4.04 (d, 2H, J=10.6 Hz), 4.17 (t, 2H, J=5.2 Hz), 4.55 (s, 2H), 6.25 (d, 1H, J=1.8 Hz), 6.93–7.02 (m, 3H), 7.30 (d, 2H, J=8.4 Hz), 7.42–7.57 (m, 9H).

Anal. Calcd. C$_{41}$H$_{51}$N$_5$O$_4$.0.2H$_2$O Calcd. C, 72.26; H, 7.60; N, 10.28. Found C, 72.02; H, 7.46; N, 10.03.

Working Example 71

Production of Compound 71

One droplet of DMF was added to a solution of 7-(4-butoxyethoxyphenyl)-1-[(3,5-dimethylisoxazol-4-yl)methyl]-2,3-dihydro-1-benzazepine-4-carboxylic acid (140 mg) in tetrahydrofuran (1 ml). Then, thionyl chloride (102 mg) was added at 0° C., the temperature was returned to room temperature, and the mixture was stirred under nitrogen atmosphere for 1 hour. Then, this mixture was added to a solution of 4-[[N-methyl-N-(tetrahydropyran-4-yl)amino]methyl]aniline (75 mg) and triethylamine (690 mg) in tetrahydrofuran (25 ml) at 0° C. The suspension was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, the resulting residue was separated and purified with silica gel column chromatography (methanol:ethyl acetate=1:3) to give 7-(4-butoxyethoxyphenyl)-1-[(3,5-dimethylisoxazol-4-yl)methyl]-N-[4-[[N-methyl-N-(tetrahydropyran-4-yl)amino]methyl]phenyl]-2,3-dihydro-1-benzazepine-4-carboxamide (Compound 71) (45 mg) as yellow amorphous.

$^1$H-NMR (200 MHz, CDCl$_3$) δ 0.93 (t, 3H, J=7.0 Hz), 1.33–1.45 (m, 2H), 1.50–1.80 (m, 6H), 2.22 (s, 6H), 2.41 (s, 3H), 2.67 (br, 2H), 3.20 (br, 2H), 3.30–3.44 (m, 2H), 3.52–3.59 (m, 4H), 3.81 (t, 2H, J=4.8 Hz), 4.04 (d, 2H, J=9.2 Hz), 4.17 (t, 2H, J=5.4 Hz), 4.29 (s, 2H), 6.95–7.02 (m, 3H), 7.31 (d, 2H, J=8.4 Hz), 7.42–7.57 (m, 8H).

Anal. Calcd. C$_{42}$H$_{52}$N$_4$O$_5$.0.2H$_2$O Calcd. C, 72.42; H, 7.52; N, 8.04. Found C, 72.15; H, 7.72; N, 7.81.

Working Example 72

Production of Compound 72

One droplet of DMF was added to a solution of 7-(4-butoxyethoxyphenyl)-1-(2-furylmethyl)-2,3-dihydro-1-benzazepine-4-carboxylic acid (200 mg) in tetrahydrofuran (10 ml). Then, thionyl chloride (155 mg) was added at 0° C., the temperature was returned to room temperature, and the mixture was stirred under nitrogen atmosphere for 1 hour. Then, the solvent and excess thionyl chloride were evaporated, and the resulting residue was suspended in tetrahydrofuran (15 ml) and added to a solution of 4-[[N-methyl-N-(tetrahydropyran-4-yl)amino]methyl]aniline (115 mg) and triethylamine (1.1 g) in tetrahydrofuran (10 ml) at 0° C. The mixture was stirred under nitrogen atmosphere at room temperature for 2.5 hours, to the mixture was added water, and the mixture was extracted with ethyl acetate. The organic layer was washed with saturated brine and dried with magnesium sulfate. The solvent was evaporated under reduced pressure, and the resulting residue was separated and purified with silica gel column chromatography (methanol:ethyl acetate=1:8), which was recrystallized from hexane-ethyl acetate to give 7-(4-butoxyethoxyphenyl)-1-(2-furylmethyl)-N-[4-[[N-methyl-N-(tetrahydropyran-4-yl)amino]methyl]phenyl]-2,3-dihydro-1-benzazepine-4-carboxamide (Compound 72) (199 mg) as yellow crystals.

$^1$H-NMR (200 MHz, CDCl$_3$) δ 0.93 (t, 3H, J=7.4 Hz), 1.37–1.48 (m, 2H), 1.58–1.80 (m, 6H), 2.22 (s, 3H), 2.65 (br, 1H), 2.85 (br, 2H), 3.27–3.46 (m, 4H), 3.52–3.57 (m, 4H), 3.81 (t, 2H, J=4.6 Hz), 4.03 (d, 2H, J=11.8 Hz), 4.16 (t, 2H, J=4.8 Hz), 4.51 (s, 2H), 6.29 (d, 1H, J=3.2 Hz), 6.38 (dd, 1H, J=2.8, 1.8 Hz), 6.98 (d, 2H, J=8.8 Hz), 7.09 (d, 1H, J=8.8 Hz), 7.31 (d, 2H, J=8.6 Hz), 7.40–7.56 (m, 9H).

Anal. Calcd. C$_{41}$H$_{49}$N$_3$O$_5$.0.1H$_2$O Calcd. C, 73.97; H, 7.42; N, 6.31. Found C, 73.77; H, 7.24; N, 6.28.

Working Example 73

Production of Compound 73

One droplet of DMF was added to a solution of 7-(4-butoxyethoxyphenyl)-1-(2-pyridylmethyl)-2,3-dihydro-1-benzazepine-4-carboxylic acid (50 mg) in dichloromethane (5 ml). Then, thionyl chloride (17 mg) was added at 0° C., the temperature was returned to room temperature, and the mixture was stirred under nitrogen atmosphere for 1 hour. Then, this solution was added to a solution of 4-[[N-methyl-N-(tetrahydropyran-4-yl)amino]methyl]aniline (31 mg) and triethylamine (287 mg) in dichloromethane (15 ml) at 0° C. The mixture was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, and the resulting residue was separated and purified with silica gel column chromatography (methanol:ethyl acetate=1:3) to give 7-(4-butoxyethoxyphenyl)-N-[4-[[N-methyl-N-(tetrahydropyran-4-yl)amino]methyl]phenyl]-1-(2-pyridylmethyl)-2,3-dihydro-1-benzazepine-4-carboxamide (Compound 73) (31 mg) as yellow amorphous.

$^1$H-NMR (200 MHz, CDCl$_3$) δ 0.93 (t, 3H, J=7.4 Hz), 1.30–1.44 (m, 2H), 1.52–1.82 (m, 6H), 2.22 (s, 3H), 2.65 (br, 1H), 2.93 (br, 2H), 3.30–3.58 (m, 8H), 3.80 (t, 2H, J=4.4 Hz), 4.04 (d, 2H, J=10.6 Hz), 4.15 (t, 2H, J=5.2 Hz), 4.73 (s, 2H), 6.85 (d, 1H, J=8.6 Hz), 6.97 (d, 2H, J=8.6 Hz), 7.20–7.37 (m, 5H), 7.44–7.71 (m, 8H), 8.65 (d, 1H, J=5.2 Hz).

Working Example 74

Production of Compound 74

To a solution of 7-(4-butoxyethoxyphenyl)-N-[4-[[methyl-N-(tetrapyran-4-yl)amino]methyl]phenyl]-2,3-dihydro-1-benzazepine-4-carboxamide (150 mg) and 1-methylpyrrol-2-carboxyaldehyde (140 mg) in 1,2-dichloroethane (10 ml) was added sodium triacetoxyborohydride (326 mg). The mixture was stirred under nitrogen atmosphere at room temperature for 4 days and, then, water was added thereto, and the mixture was extracted with ethyl acetate. The organic layer was washed with saturated brine and dried with magnesium sulfate. The solvent was evaporated under reduced pressure, and the resulting residue was purified with silica gel column chromatography (methanol:ethyl acetate=1:6) to give 7-(4-butoxyethoxyphenyl)-1-[(1-methylpyrrol-2-yl)methyl]-N-[4-[[N-methyl-N-(tetrahydropyran-4-yl)amino]methyl]phenyl]-2,3-dihydro-1-benzazepine-4-carboxamide (Compound 74) (8 mg) as yellow amorphous.

$^1$H-NMR (200 MHz, CDCl$_3$) δ 0.93 (t, 3H, J=7.4 Hz), 1.30–1.49 (m, 2H), 1.54–1.85 (m, 6H), 2.21 (s, 3H), 2.50 (br, 2H), 2.65 (br, 1H), 3.25–3.59 (m, 11H), 3.81 (t, 2H, J=4.4 Hz), 4.04 (d, 2H, J=11.8 Hz), 4.17 (t, 2H, J=5.2 Hz), 4.47 (s, 2H), 6.11 (t, 1H, J=2.8 Hz), 6.16 (s, 1H), 6.66 (s, 1H), 6.97–7.06 (m, 3H), 7.29 (d, 2H, J=9.8 Hz), 7.46–7.56 (m, 8H).

Working Example 75

Production of Compound 75

To a solution of 7-(4-butoxyethoxyphenyl)-N-[4-[[N-methyl-N-(tetrapyran-4-yl)amino]methyl]phenyl]-2,3-dihydro-1-benzazepine-4-carboxamide (130 mg) and 2-methyloxazol-4-carboxyaldehyde (100 mg) in 1,2-dichloroethane (10 ml) was added sodium triacetoxyborohydride (378 mg). The mixture was stirred under nitrogen atmosphere at room temperature for 5 days and, then, water was added thereto, and the mixture was extracted with ethyl acetate. The organic layer was washed with saturated brine and dried with magnesium sulfate. The solvent was evaporated under reduced pressure, and the resulting residue was purified with basic silica gel column chromatography (hexane:ethyl acetate=1:2) to give 7-(4-butoxyethoxyphenyl)-1-[(2-methyloxazol-4-yl)methyl]-N-[4-[[N-methyl-N-(tetrahydropyran-4-yl)amino]methyl]phenyl]-2,3-dihydro-1-benzazepine-4-carboxamide (Compound 75) (29 mg) as yellow amorphous.

$^1$H-NMR (200 MHz, CDCl$_3$) δ 0.93 (t, 3H, J=7.4 Hz), 1.34–1.45 (m, 2H), 1.54–1.80 (m, 6H), 2.21 (s, 3H), 2.48 (s, 3H), 2.63 (br, 1H), 2.90 (br, 2H), 3.30–3.45 (m, 4H), 3.52–3.58 (m, 4H), 3.80 (t, 2H, J=4.6 Hz), 4.04 (d, 2H, J=11.4 Hz), 4.16 (t, 2H, J=4.4 Hz), 4.43 (s, 2H), 6.96–7.05 (m, 3H), 7.30 (d, 2H, J=8.4 Hz), 7.38–7.55 (m, 9H).

Working Example 76

Production of Compound 76

One droplet of DMF was added to a solution of 7-(4-butoxyethoxyphenyl)-1-[(2-methylthiazol-4-yl)methyl]-2,3-dihydro-1-benzazepine-4-carboxylic acid (150 mg) in chloroform (10 ml). Then, thionyl chloride (47 mg) was added at 0° C., the temperature was returned to room temperature, and the mixture was stirred under nitrogen atmosphere for 1 hour. Then, this solution was added to a solution of 4-[[N-methyl-N-(tetrahydropyran-4-yl)amino]methyl]aniline (87 mg) and triethylamine (800 mg) in chloroform (20 ml) at 0° C. The mixture was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, and the resulting residue was separated and purified with silica gel column chromatography (methanol:ethyl acetate=1:3) to give 7-(4-butoxyethoxyphenyl)-1-[(2-methylthiazol-4-yl)methyl]-N-[4-[[N-methyl-N-(tetrahydropyran-4-yl)amino]methyl]phenyl]-2,3-dihydro-1-benzazepine-4-carboxamide (Compound 76) (37 mg) as yellow amorphous.

$^1$H-NMR (200 MHz, CDCl$_3$) δ 0.93 (t, 3H, J=7.0 Hz), 1.34–1.45 (m, 2H), 1.50–1.82 (m, 6H), 2.22 (s, 3H), 2.66 (br, 1H), 2.74 (s, 3H), 2.91 (br, 2H), 3.30–3.48 (m, 4H), 3.52–3.58 (m, 4H), 3.80 (t, 2H, J=4.4 Hz), 4.04 (d, 2H, J=11.4 Hz), 4.16 (t, 2H, J=5.4 Hz), 4.67 (s, 2H), 6.92–7.00 (m, 4H), 7.26–7.60 (m, 10H).

Working Example 77

Production of Compound 77

One droplet of DMF was added to a solution of 7-(4-butoxyethoxyphenyl)-1-[(3-methylthiazol-5-yl)methyl]-2, 3-dihydro-1-benzazepine-4-carboxylic acid (150 mg) in dichloromethane (10 ml). Then, thionyl chloride (47 mg) was added at 0° C., the temperature was returned to room temperature, and the mixture was stirred under nitrogen atmosphere for 1 hour. Then, this solution was added to a solution of 4-[[N-methyl-N-(tetrahydropyran-4-yl)amino]methyl]aniline (87 mg) and triethylamine (800 mg) in dichloromethane (20 ml) at 0° C. The mixture was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, and the resulting residue was separated and purified with silica gel column chromatography (methanol:ethyl acetate=1:3), which was recrystallized from hexane-ethyl acetate to give 7-(4-butoxyethoxyphenyl)-1-[(3-methylisothiazol-5-yl)methyl]-N-[4-[[N-methyl-N-(tetrahydropyran-5-yl)amino]methyl]phenyl]-2,3-dihydro-1-benzazepine-4-carboxamide (Compound 77) (96 mg) as yellow crystals.

$^1$H-NMR (200 MHz, CDCl$_3$) δ 0.93 (t, 3H, J=6.8 Hz), 1.34–1.45 (m, 2H), 1.50–1.80 (m, 6H), 2.21 (s, 3H), 2.49 (s, 3H), 2.64 (br, 1H), 2.94 (br, 2H), 3.31–3.41 (m, 4H), 3.52–3.58 (m, 4H), 3.80 (t, 2H, J=4.4 Hz), 4.04 (d, 2H, J=10.2 Hz), 4.16 (t, 2H, J=5.4 Hz), 4.79 (s, 2H), 6.90–7.01 (m, 4H), 7.31 (d, 2H, J=8.8 Hz), 7.38–7.56 (m, 8H).

Anal. Calcd. C$_{41}$H$_{50}$N$_4$O$_4$S Calcd. C, 70.86; H, 7.25; N, 8.06. Found C, 70.57; H, 7.01; N, 8.02.

Working Example 78

Production of Compound 78

One droplet of DMF was added to a solution of 7-(4-butoxyethoxyphenyl)-1-(2-thienylcarbonyl)-2,3-dihydro-1-benzazepine-4-carboxylic acid (100 mg) in dichloromethane (10 ml). Then, thionyl chloride (31 mg) was added at 0° C., the temperature was returned to room temperature, and the mixture was stirred under nitrogen atmosphere for 1 hour. Then, this solution was added to a solution of 4-[[N-methyl-N-(tetrahydropyran-4-yl)amino]methyl]aniline (57 mg) and triethylamine (520 mg) in dichloromethane (20 ml) at 0° C. The mixture was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, and the resulting residue was separated and purified with silica gel column chromatography (methanol:ethyl acetate=1:3), which was recrystallized hexane-ethyl acetate to give 7-(4-butoxyethoxyphenyl)-N-[4-[[N-methyl-N-(tetrahydropyran-5-yl)amino]methyl]phenyl]-1-(2-thienylcarbonyl)-2,3-dihydro-1-benzazepine-4-carboxamide (Compound 78) (43 mg) as colorless crystals.

$^1$H-NMR (200 MHz, CDCl$_3$) δ 0.94 (t, 3H, J=7.4 Hz), 1.34–1.45 (m, 2H), 1.50–1.81 (m, 6H), 2.21 (s, 3H), 2.62 (br, 1H), 3.10 (br, 2H), 3.37 (td, 2H, J=10.6, 2.8 Hz), 3.53–3.59 (m, 4H), 3.82 (t, 2H, J=4.4 Hz), 4.04 (d, 2H, J=12.6 Hz), 4.18 (t, 2H, J=5.0 Hz), 6.80–6.83 (m, 2H), 7.02 (d, 2H, J=8.8 Hz), 7.12 (d, 1H, J=8.0 Hz), 7.29–7.41 (m, 4H), 7.51–7.60 (m, 6H), 7.74 (d, 1H, J=2.2 Hz).

Anal. Calcd. C$_{41}$H$_{47}$N$_3$O$_5$S.0.2H$_2$O Calcd. C, 70.60; H, 6.85; N, 6.02. Found C, 70.46; H, 6.89; N, 5.97.

Working Example 79

Production of Compound 79

One droplet of DMF was added to a solution of 7-(4-butoxyethoxyphenyl)-1-[(1-ethylpyrazol-4-yl)methyl]-2,3-dihydro-1-benzazepine-4-carboxylic acid (150 mg) in dichloromethane (10 ml). Then, thionyl chloride (47 mg) was added at 0° C., the temperature was returned to room temperature, and the mixture was stirred under nitrogen atmosphere for 1 hour. Then, this solution was added to a solution of 4-[[N-methyl-N-(tetrahydropyran-4-yl)amino]methyl]aniline (88 mg) and triethylamine (805 mg) in dichloromethane (20 ml) at 0° C. The mixture was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, and the resulting residue was separated and purified with silica gel column chromatography (methanol:ethyl acetate=1:3), which was recrystallized from hexane-ethyl acetate to give 7-(4-butoxyethoxyphenyl)-1-[(1-ethylpyrazol-4-yl)methyl]-N-[4-[[N-methyl-N-(tetrahydropyran-5-yl)amino]methyl]phenyl]-2,3-dihydro-1-benzazepine-4-carboxamide (Compound 79) (99 mg) as yellow crystals.

$^1$H-NMR (200 MHz, CDCl$_3$) δ 0.93 (t, 3H, J=7.4 Hz), 1.34–1.85 (m, 11H), 2.21 (s, 3H), 2.64 (br, 1H), 2.84 (br, 2H), 3.29–3.46 (m, 4H), 3.52–3.59 (m, 4H), 3.80 (t, 2H, J=4.4 Hz), 4.04 (d, 2H, J=9.4 Hz), 4.11–4.18 (m, 4H), 4.44 (s, 2H), 6.96–7.01 (m, 3H), 7.28–7.36 (m, 3H), 7.40–7.56 (m, 9H).

Anal. Calcd. C$_{42}$H$_{53}$N$_5$O$_4$ Calcd. C, 72.91; H, 7.72; N, 10.12. Found C, 72.69; H, 8.00; N, 9.92.

Working Example 80

Production of Compound 80

One droplet of DMF was added to a solution of 2-methyldioxolane-2-ylacetic acid in tetrahydrofuran (10 ml). Then, thionyl chloride (80 mg) was added at 0° C., the temperature was returned to room temperature, and the mixture was stirred under nitrogen atmosphere for 1 hour. This solution was added to a solution of 7-(4-butoxyethoxyphenyl)-N-[4-[[N-methyl-N-(tetrahydropyran-5-yl)amino]methyl]phenyl]-2,3-dihydro-1-benzazepine-4-carboxamide (100 mg) and pyridine (528 mg) in tetrahydrofuran (20 ml) at 0° C. The mixture was stirred under nitrogen atmosphere at room temperature overnight, the insolubles were filtered off using Celite, to the mixture was added water, and the mixture was extracted with ethyl acetate. The organic layer was washed with saturated brine and dried with magnesium sulfate. The solvent was evaporated under reduced pressure, and the resulting residue was separated and purified with silica gel column chromatography (methanol:ethyl acetate=1:3), which was recrystallized from hexane-ethyl acetate to give 7-(4-butoxyethoxyphenyl)-1-(2-(2-methyl-1,3-dioxolan-2-yl)acetyl)-N-[4-[[N-methyl-N-(tetrahydropyran-5-yl)amino]methyl]phenyl]-2,3-dihydro-1-benzazepine-4-carboxamide (Compound 80) (60 mg) as colorless crystals.

$^1$H-NMR (200 MHz, CDCl$_3$) δ 0.94 (t, 3H, J=7.0 Hz), 1.34–1.85 (m, 11H), 2.21 (s, 3H), 2.50–3.05 (m, 5H), 3.20 (d, 1H, J=13.6 Hz), 3.38 (td, 2H, J=10.8, 3.6 Hz), 3.53–3.70 (m, 5H), 3.75–3.95 (m, 5H), 4.04 (d, 2H, J=10.2 Hz), 4.18 (t, 2H, J=5.4 Hz), 4.90 (d, 1H, J=13.2 Hz), 7.03 (d, 2H, J=9.2 Hz), 7.29–7.35 (m, 3H), 7.51–7.67 (m, 8H).

Anal. Calcd. C$_{42}$H$_{53}$N$_3$O$_7$.0.1H$_2$O Calcd. C, 70.68; H, 7.51; N, 5.89. Found C, 70.41; H, 7.33; N, 5.89.

Working Example 81

Production of Compound 81

A catalytic amount of N,N-dimethyl-4-aminopyridine was added to a solution of 7-butoxyethoxyphenyl)-1-[(4- methylthiazol-5-yl)methyl]-2,3-dihydro-1-benzazepine-4-carboxylic acid (150 mg), 4-[[N-methyl-N-(tetrahydropyran-4-yl)amino]methyl]aniline (88 mg) and 1-hydroxybenzotriazole (96 mg) in DMF (15 ml), followed by addition of 1-ethyl-3-(3-dimethylaminopropylcarbodiimide (137 mg). The mixture was stirred under nitrogen atmosphere at room temperature overnight. To the mixture was added water, and the mixture was extracted with ethyl acetate. The organic layer was washed with saturated brine and dried with magnesium sulfate. The solvent was evaporated under reduced pressure, and the resulting residue was separated and purified with silica gel column chromatography (methanol:ethyl acetate=1:3) to give 7-(4-butoxyethoxyphenyl)-N-[4-[[N-methyl-N-tetrahydropyran-5-yl)amino]methyl]phenyl]-1-[(4-methylthiazol-5-yl)methyl]-2,3-dihydro-1-benzazepine-4-carboxamide (Compound 81) (7 mg) as yellow amorphous.

$^1$H-NMR (200 MHz, CDCl$_3$) δ 0.93 (t, 3H, J=7.2 Hz), 1.34–1.47 (m, 2H), 1.51–1.80 (m, 6H), 2.21 (s, 3H), 2.52 (s, 3H), 2.63 (br, 1H), 2.84 (br, 2H), 3.33–3.42 (m, 4H), 3.52–3.59 (m, 4H), 3.81 (t, 2H, J=4.4 Hz), 4.04 (d, 2H, J=12.2 Hz), 4.16 (t, 2H, J=4.8 Hz), 4.67 (s, 2H), 6.95 (d, 1H, J=6.2 Hz), 6.99 (d, 2H, J=7.0 Hz), 7.30 (d, 2H, J=8.8 Hz), 7.40–7.56 (m, 8H), 8.68 (s, 1H).

Working Example 82

Production of Compound 82

One droplet of DMF was added to a solution of 7-(4-butoxyethoxyphenyl)-1-[(1-isopropylpyrazol-4-yl)methyl]-2,3-dihydro-1-benzazepine-4-carboxylic acid (150 mg) in dichloromethane (10 ml). Then, thionyl chloride (49 mg) was added at 0° C., the temperature was returned to room temperature, and the mixture was stirred under nitrogen atmosphere for 1 hour. Then, this solution was added to a solution of 4-[[N-methyl-N-(tetrahydropyran-4-yl)amino] methyl]aniline (90 mg) and triethylamine (830 mg) in dichloromethane (20 ml) at 0° C. The mixture was stirred under nitrogen atmosphere at room temperature overnight, to the mixture was added water, and the mixture was extracted with ethyl acetate. The organic layer was washed with saturated brine and dried with magnesium sulfate. The solvent was evaporated under reduced pressure, and the resulting residue was separated and purified with silica gel column chromatography (methanol:ethyl acetate=1:3), which was recrystallized to give 7-(4-butoxyethoxyphenyl)-1-[(1-isopropylpyrazol-4-yl)methyl]-N-[4-[[N-methyl-N-(tetrahydropyran-4-yl)amino]methyl]phenyl]-2,3-dihydro-1-benzazepine-4-carboxamide (Compound 82) (119 mg) as yellow crystals.

$^1$H-NMR (200 MHz, CDCl$_3$) δ 0.93 (t, 3H, J=7.2 Hz), 1.34–1.85 (m, 14H), 2.21 (s, 3H), 2.65 (br, 1H), 2.84 (br, 2H), 3.36–3.52 (m, 4H), 3.56–3.59 (m, 4H), 3.81 (t, 2H, J=4.4 Hz), 4.04 (d, 2H, J=11.8 Hz), 4.16 (t, 2H, J=5.0 Hz), 4.44–4.52 (m, 3H), 6.96–7.02 (m, 3H), 7.30 (d, 2H, J=8.6 Hz), 7.39–7.56 (m, 10H).

Anal. Calcd. C$_{43}$H$_{55}$N$_5$O$_4$ Calcd. C, 73.16; H, 7.85; N, 9.92. Found C, 72.99; H, 7.76; N, 9.75.

Reference Example 147

To a suspension of 60% sodium hydride (0.17 g) in DMF (5 ml) which had been washed with hexane three times was added dropwise a solution of methyl 7-bromo-2,3-dihydro-1-benzazepine-4-carboxylate (1.0 g) in DMF (10 ml) at 0° C. under nitrogen atmosphere. The temperature was returned to room temperature and the mixture was stirred for 1 hour. Then, a solution of allyl bromide (0.56 g) in DMF (5 ml) was added dropwise thereto at 0° C., the temperature was returned to room temperature, and the mixture was stirred at room temperature overnight. To the mixture were added ethyl acetate and water, and the mixture was separated. The organic layer was washed with saturated brine and dried with magnesium sulfate. The solvent was evaporated under reduced pressure and the resulting residue was purified with silica gel column chromatography (hexane:ethyl acetate=7:1) to give methyl 1-allyl-7-bromo-2,3-dihydro-1-benzazepine-4-carboxylate (0.38 g) as yellow oil.

$^1$H-NMR (200 MHz, CDCl$_3$) δ 2.79 (t, 2H, J=5.4 Hz), 3.22 (t, 2H, J=5.2 Hz), 3.80 (s, 3H), 3.89 (d, 2H, J=4.8 Hz), 5.16–5.28 (m, 2H), 5.81–5.97 (m, 1H), 6.58 (d, 1H, J=8.8 Hz), 7.23 (dd, 1H, J=8.8, 2.6 Hz), 7.4 (d, 1H, J=2.6 Hz), 7.59 (s, 1H).

Reference Example 148

In toluene (20 ml), ethanol (2 ml) and water (2 ml) were suspended methyl 1-allyl-7-bromo-2,3-dihydro-1-benzazepine-4-carboxylate (274 mg), 4-propoxyethoxyphenyl borate (248 mg) and potassium carbonate (307 mg), and the suspension was stirred under argon atmosphere for 30 minutes, Then, tetrakistriphenylphosphinepalladium (69 mg) was added thereto, and the mixture was heated under argon atmosphere at 100° C. for 8 hours. After allowing to cool, water was added thereto, and the mixture was extracted with ethyl acetate. The organic layer was washed with saturated brine and dried with magnesium sulfate. The solvent was evaporated under reduced pressure and the resulting residue was purified with silica gel column chromatography (hexane:ethyl acetate=4:1) to give methyl 1-allyl-7-(4-propoxyethoxyphenyl)-2,3-dihydro-1-benzazepine-4-carboxylate (269 mg) as yellow oil.

$^1$H-NMR (200 MHz, CDCl$_3$) δ 0.94 (t, 3H, J=7.8 Hz), 1.58–1.75 (m, 2H), 2.81 (t, 2H, J=5.6 Hz), 3.27 (t, 2H, J=4.4 Hz), 3.51 (t, 2H, J=6.6 Hz), 3.75–3.83 (m, 5H), 3.96 (d, 2H, J=5.2 Hz), 4.16 (t, 2H, J=4.8 Hz), 5.23–5.30 (m, 2H), 5.88–6.02 (m, 1H), 6.87 (d, 1H, J=8.8 Hz), 6.97 (d, 2H, J=8.4 Hz), 7.39 (dd, 1H, J=8.8, 2.2 Hz), 7.46 (d, 2H, J=8.4 Hz), 7.52 (d, 1H, J=2.2 Hz), 7.78 (s, 1H).

Reference Example 149

To a solution of methyl 1-allyl-7-(4-propoxyethoxyphenyl)-2,3-dihydro-1-benzazepine-4-carboxylate (262 mg) in a mixture of tetrahydrofuran (19 ml) and methanol (19 ml) was added 1N sodium hydroxide solution (6.3 ml), and the mixture was stirred at room temperature overnight. Then, water and 1N hydrochloric acid were added to make acidic (pH=4) at 0° C., and the mixture was extracted with ethyl acetate. The organic layer was washed with water and saturated brine and dried with magnesium sulfate. The solvent was evaporated under reduced pressure to give the solid, which was washed with hexane to give 1-allyl-7-(4-propoxyethoxyphenyl)-2,3-dihydro-1-benzazepine-4-carboxylic acid (199 mg) as yellow crystals.

mp 152.0–153.0° C.

$^1$H-NMR (200 MHz, CDCl$_3$) δ 0.94 (t, 3H, J=7.4 Hz), 1.56–1.74 (m, 2H), 3.00 (t, 2H, J=5.2 Hz), 3.30 (t, 2H, J=5.2 Hz), 3.51 (t, 2H, J=6.4 Hz), 3.81 (t, 2H, J=5.0 Hz), 3.97 (d, 2H, J=5.2 Hz), 4.16 (t, 2H, J=4.8 Hz), 5.24–5.30 (m, 2H), 5.89–6.10 (m, 1H), 6.88 (d, 1H, J=8.4 Hz), 6.98 (d, 2H, J=8.4 Hz), 7.40–7.49 (m, 3H), 7.53 (d, 1H, J=2.6 Hz), 7.88 (s, 1H).

Anal. Calcd. $C_{25}H_{29}NO_4 \cdot 0.1H_2O$ Calcd. C, 73.36; H, 7.19; N, 3.42. Found C, 73.11; H, 7.09; N, 3.25.

Reference Example 150

To a suspension of 60% sodium hydride (0.23 g) in tetrahydrofuran (5 ml) which had been washed with hexane three times was added dropwise a solution of methyl 7-bromo-2,3-dihydro-1-benzazepine-4-carboxylate (0.80 g) in tetrahydrofuran (10 ml) at 0° C. under nitrogen atmosphere. The temperature was returned to room temperature and the mixture was stirred for 30 minutes. Then, a solution of allyl bromide (5.12 g) in tetrahydrofuran (5 ml) was added dropwise thereto at 0° C., and the mixture was stirred at 60° C. for 5 days. To the mixture were added ethyl acetate and water, and the mixture was separated. The organic layer was washed with saturated brine and dried with magnesium sulfate. The solvent was evaporated under reduced pressure and the resulting residue was purified with silica gel column chromatography (hexane:ethyl acetate=5:1) to give allyl 1-allyl-7-bromo-2,3-dihydro-1-benzazepine-4-carboxylate (0.22 g) as yellow oil.

$^1$H-NMR (200 MHz, CDCl$_3$) δ 2.81 (t, 2H, J=5.8 Hz), 3.23 (t, 2H, J=5.2 Hz), 3.90 (d, 2H, J=4.8 Hz), 4.69–4.73 (m, 2H), 5.11–5.42 (m, 4H), 5.81–6.07 (m, 2H), 6.68 (d, 1H, J=9.2 Hz), 7.23 (dd, 1H, J=8.8, 2.2 Hz), 7.43 (d, 1H, J=2.4 Hz), 7.62 (s, 1H).

Reference Example 151

To a solution of allyl 1-allyl-7-bromo-2,3-dihydro-1-benzazepine-4-carboxylate (224 mg) in tetrahydrofuran (10 ml) were added tetrakistriphenylphosphinepalladium (74 mg) and morpholine (560 mg), and the mixture was stirred under argon atmosphere at room temperature for 2 hours. To the mixture was added water at 0° C., and the mixture was made acidic (pH=4) with 1N hydrochloric acid and extracted with ethyl acetate. The organic layer was washed with 1N hydrochloric acid, further with water and saturated brine and dried with magnesium sulfate. The solvent was evaporated under reduced pressure to give 1-allyl-7-bromo-2,3-dihydro-1-benzazepine-4-carboxylic acid (198 mg) as yellow amorphous.

$^1$H-NMR (200 MHz, CDCl$_3$) δ 2.80 (t, 2H, J=4.2 Hz), 3.23 (t, 2H, J=4.8 Hz), 3.91 (d, 2H, J=4.8 Hz), 5.17–5.28 (m, 2H), 5.84–5.98 (m, 1H), 6.69 (d, 1H, J=9.2 Hz), 7.24 (dd, 1H, J=8.8, 2.2 Hz), 7.43–7.73 (m, 2H).

Reference Example 152

1-allyl-7-bromo-2,3-dihydro-1-benzazepine-4-carboxylic acid (320 mg) was dissolved in tetrahydrofuran (15 ml), and DMF (0.3 ml) was added to the solution. Then, thionyl chloride (0.23 ml) was added thereto at 0° C., and the mixture was stirred under nitrogen atmosphere at room temperature for 2 hours. The solvent and excess thionyl chloride were evaporated under reduced pressure, and the resulting residue was suspended in tetrahydrofuran (25 ml), and the suspension was added to a solution of 4-[[N-methyl-N-(tetrahydropyran-4-yl)amino]methyl]aniline (275 mg) and triethylamine (1.27 g) in tetrahydrofuran (10 ml) at 0° C. The temperature was returned to room temperature, and the mixture was stirred overnight. To the mixture was added water, and the mixture was extracted with ethyl acetate twice. The organic layer was washed with saturated brine and dried with magnesium sulfate. The solvent was evaporated under reduced pressure and the resulting residue was separated and purified with silica gel column chromatography (methanol:ethyl acetate=1:8) to give 1-allyl-7-bromo-N-[4-[[N-methyl-N-(tetrahydropyran-4-yl)amino]methyl]phenyl]-2,3-dihydro-1-benzazepine-4-carboxamide (266 mg) as yellow oil.

$^1$H-NMR (200 MHz, CDCl$_3$) δ 1.75 (br, 4H), 2.21 (s, 3H), 2.65 (br, 1H), 2.88 (t, 2H, J=4.4 Hz), 3.29 (t, 2H, J=5.0 Hz), 3.37 (dt, 2H, J=8.2, 2.4 Hz), 3.57 (s, 2H), 3.92 (d, 2H, J=4.8 Hz), 4.04 (d, 2H, J=11.8 Hz), 5.20–5.30 (m, 2H), 5.85–5.96 (m, 1H), 6.72 (d, 1H, J=9.2 Hz), 7.22–7.32 (m, 3H), 7.42–7.54 (m, 4H).

Reference Example 153

To a solution of methyl 7-(propoxyethoxyphenyl)-2,3-dihydro-1-benzazepine-4-carboxylate (300 mg) and 2-methoxybenzaldehyde (535 mg) in 1,2-dichloroethane (10 ml) was added sodium triacetoxyborohydride (749 mg), and the mixture was stirred under nitrogen atmosphere at room temperature overnight. Then, water was added thereto and the mixture was extracted with ethyl acetate. The organic layer was washed with saturated brine and dried with magnesium sulfate. The solvent was evaporated under reduced pressure and the resulting residue was purified with silica gel column chromatography (hexane:ethyl acetate=3:1) to give methyl (1-(2-methoxybenzyl)-7-(4-propoxyethoxyphenyl)-2,3-dihydro-1-benzazepine-4-carboxylate (394 mg) as yellow oil.

$^1$H-NMR (200 MHz, CDCl$_3$) δ 0.94 (t, 3H, J=7.6 Hz), 1.58–1.70 (m, 2H), 2.82 (br, 2H), 3.35 (br, 2H), 3.51 (t, 2H, J=6.6 Hz), 3.78–3.94 (m, 8H), 4.16 (t, 2H, J=4.6 Hz), 4.57 (s, 2H), 6.78 (d, 1H, J=9.2 Hz), 6.88–6.99 (m, 4H), 7.15 (d, 1H, J=8.0 Hz), 7.26–7.44 (m, 2H), 7.46 (d, 2H, J=8.4 Hz), 7.55 (d, 1H, J=2.4 Hz), 7.84 (s, 1H).

Reference Example 154

To a solution of methyl 1-(2-methoxybenzyl)-7-(4-propoxyethoxyphenyl)-2,3-dihydro-1-benzazepine-4-carboxylate (394 mg) in a mixture of tetrahydrofuran (24 ml) and methanol (24 ml) was added 1N sodium hydroxide solution (8 ml), and the mixture was stirred at room temperature for 1 day. Then, to the mixture was added water at 0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, and the resulting solid was recrystallized from hexane-ethyl acetate to give 1-(2-methoxybenzyl)-7-(4-propoxyethoxyphenyl)-2,3-dihydro-1-benzazepine-4-carboxylic acid (217 mg) as yellow crystals.

$^1$H-NMR (200 MHz, CDCl$_3$) δ 0.94 (t, 3H, J=7.2 Hz), 1.59–1.70 (m, 2H), 2.84 (br, 2H), 3.37 (br, 2H), 3.51 (t, 2H, J=6.6 Hz), 3.81 (t, 2H, J=4.8 Hz), 3.89 (s, 3H), 4.16 (t, 2H, J=5.2 Hz), 4.58 (s, 2H), 6.80 (d, 1H, J=8.8 Hz), 6.91–7.00 (m, 4H), 7.14 (d, 1H, J=6.6 Hz), 7.29–7.36 (m, 2H), 7.46 (d, 2H, J=8.8 Hz), 7.55 (d, 1H, J=2.4 Hz), 7.94 (s, 1H).

Anal. Calcd. $C_{30}H_{33}NO_5$ Calcd. C, 73.90; H, 6.82; N, 2.87. Found C, 73.58; H, 6.66; N, 2.76.

Reference of Example 155

To a solution of methyl 7-(4-butoxyethoxyphenyl)-2,3-dihydro-1-benzazepine-4-carboxylate (300 mg) and 2-methoxybenzaldehyde (517 mg) in 1,2-dichloroethane (10 ml) was added sodium triacetoxyborohydride (724 mg), and the mixture was stirred under nitrogen atmosphere at room temperature overnight. Then, water was added to the mixture, and the mixture was extracted with ethyl acetate.

The organic layer was washed with saturated brine and dried with magnesium sulfate. The solvent was evaporated under reduced pressure, and the resulting residue was purified with silica gel column chromatography (hexane:ethyl acetate= 3:1) to give methyl 7-(4-butoxyethoxyphenyl)-1-(2-methoxybenzyl)-2,3-dihydro-1-benzazepine-4-carboxylate (391 mg) as yellow oil.

$^1$H-NMR (200 MHz, CDCl$_3$) δ 0.93 (t, 3H, J=7.4 Hz), 1.37–1.45 (m, 2H), 1.55–1.64 (m, 2H), 2.82 (br, 2H), 3.35 (br, 2H), 3.55 (t, 2H, J=6.6 Hz), 3.78–3.82 (m, 5H), 3.88 (s, 3H), 4.16 (t, 2H, J=5.6 Hz), 4.57 (s, 2H), 6.78 (d, 1H, J=8.4 Hz), 6.91–6.99 (m, 4H), 7.14 (d, 1H, J=6.4 Hz), 7.26–7.40 (m, 2H), 7.46 (d, 2H, J=8.8 Hz), 7.54 (d, 1H, J=2.4 Hz), 7.84 (s, 1H).

Reference Example 156

To a solution of methyl 7-(4-butoxyethoxyphenyl)-1-(2-methoxybenzyl)-2,3-dihydro-1-benzazepine-4-carboxylate (391 mg) in a mixture of tetrahydrofuran (24 ml) and methanol (24 ml) was added 1N sodium hydroxide solution (8 ml), and the mixture was stirred at room temperature for 1 day. Then, to the mixture was added water at 0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, and the resulting solid was recrystallized from hexane-ethyl acetate to give 7-(4-butoxyethoxyphenyl)-1-(2-methoxybenzyl)-2,3-dihydro-1-benzazepine-4-carboxylic acid (257 mg) as yellow crystals.

$^1$H-NMR (200 MHz, CDCl$_3$) δ 0.93 (t, 3H, J=7.0 Hz), 1.34–1.45 (m, 2H), 1.57–1.64 (m, 2H), 2.84 (br, 2H), 3.36 (br, 2H), 3.55 (t, 2H, J=6.6 Hz), 3.80 (t, 2H, J=4.8 Hz), 3.88 (s, 3H), 4.15 (t, 2H, J=5.2 Hz), 4.58 (s, 2H), 6.79 (d, 1H, J=9.2 Hz), 6.91–6.99 (m, 4H), 7.14 (d, 1H, J=7.4 Hz), 7.29–7.36 (m, 2H), 7.46 (d, 2H, J=8.8 Hz), 7.55 (d, 1H, J=2.4 Hz), 7.94 (s, 1H).

Anal. Calcd. C$_{31}$H$_{35}$NO$_5$ Calcd. C, 74.23; H, 7.03; N, 2.79. Found C, 73.96; H, 6.91; N, 2.75.

Reference Example 157

To a suspension of 60% sodium hydride (0.23 g) in tetrahydrofuran (5 ml) which had been washed with hexane three times was added dropwise a solution of methyl 7-bromo-2,3-dihydro-1-benzazepine-4-carboxylate (0.80 g) in tetrahydrofuran (10 ml) under nitrogen atmosphere at 0° C. The temperature was returned to room temperature and the mixture was stirred for 1 hour. Then, to the mixture was added dropwise a solution of 3-methoxybenzyl bromide (2.29 g) in tetrahydrofuran (5 ml) at 0° C. The temperature was returned to room temperature, and the mixture was stirred for 3 days. To the mixture were added ethyl acetate and water, and the mixture was separated. The organic layer was washed with saturated brine and dried with magnesium sulfate. The solvent was evaporated under reduced pressure and the resulting residue was purified with silica gel column chromatography (hexane:ethyl acetate=5:1) to give methyl 7-bromo-1-(3-methoxybenzyl)-2,3-dihydro-1-benzazepine-4-carboxylate (0.69 g) as yellow oil.

$^1$H-NMR (200 MHz, CDCl$_3$) δ 2.76 (t, 2H, J=5.8 Hz), 3.26 (t, 2H, J=3.8 Hz), 3.79–3.81 (m, 6H), 4.49 (s, 2H), 6.67 (d, 1H, J=8.8 Hz), 6.78–6.93 (m, 3H), 7.17–7.31 (m, 2H), 7.46 (d, 1H, J=2.2 Hz), 7.63 (z, 1H).

Reference Example 158

To a solution of methyl 7-bromo-1-(3-methoxybenzyl.)-2,3-dihydro-1-benzazepine-4-carboxylate (691 mg) in a mixture of tetrahydrofuran (50 ml) and methanol (50 ml) was added 1N sodium hydroxide solution (17 ml), and the mixture was stirred at room temperature for 3 days. Then, to the mixture was added water at 0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, and the resulting solid was recrystallized from hexane-ethyl acetate to give 7-bromo-1-(3-methoxybenzyl)-2,3-dihydro-1-benzazepine-4-carboxylic acid (369 mg) as yellow crystals.

$^1$H-NMR (200 MHz, CDCl$_3$) δ 2.78 (t, 2H, J=5.6 Hz), 3.29 (t, 2H, J=5.6 Hz), 3.79 (s, 3H), 4.51 (s, 2H), 6.68 (d, 1H, J=9.2 Hz), 6.78–6.84 (m, 3H), 7.20–7.32 (m, 2H), 7.48 (d, 1H, J=2.6 Hz), 7.73 (s, 1H).

Anal. Calcd. C$_{19}$H$_{18}$NO$_3$Br Calcd. C, 58.78; H, 4.67; N, 3.61. Found C, 58.81; H, 4.68; N, 3.61.

Reference Example 159

In toluene (20 ml), ethanol (2 ml) and water (2 ml) were suspended 7-bromo-1-(3-methoxybenzyl)-2,3-dihydro-1-benzazepine-4-carboxylic acid (300 mg), 4-propoxyethoxyphenyl borate (346 mg) and potassium carbonate (534 mg), and the suspension was stirred under argon atmosphere for 30 minutes. Then, to the suspension was added tetrakistriphenylphosphinepalladium (62 mg), and the mixture was heated at 100° C. for 6 hours under argon atmosphere. After allowing to cool, water was added to the mixture, which was made acidic (pH=4) with 1N hydrochloric acid and extracted with ethyl acetate twice. The organic layer was washed with water and saturated brine and dried with magnesium sulfate. The solvent was evaporated under reduced pressure, the resulting residue was purified with silica gel column chromatography (hexane:ethyl acetate=2:1) and the resulting solid was recrystallized from hexane-ethyl acetate to give 1-(3-methoxybenzyl)-7-(4-propoxyethoxyphenyl)-2,3-dihydro-1-benzazepine-4-carboxylic acid (118 mg) as yellow crystals.

$^1$H-NMR (200 MHz, CDCl$_3$) δ 0.94 (t, 3H, J=7.4 Hz), 1.60–1.70 (m, 2H), 2.81 (br, 2H), 3.34 (br, 2H), 3.51 (t, 2H, J=7.0 Hz), 3.80–3.84 (m, 5H), 4.16 (t, 2H, J=5.0 Hz), 4.58 (s, 2H), 6.85–6.90 (m, 4H), 6.98 (d, 2H, J=8.8 Hz), 7.26–7.45 (m, 2H), 7.47 (d, 2H, J=8.4 Hz), 7.56 (d, 1H, J=2.4 Hz), 7.93 (s, 1H).

Reference Example 160

In toluene (15 ml), ethanol (1.5 ml) and water (1.5 ml) were suspended 7-bromo-1-(3-methoxybenzyl)-2,3-dihydro-1-benzazepine-4-carboxylic acid (320 mg), 4-butoxyethoxyphenyl borate (246 mg) and potassium carbonate (285 mg), and the suspension was stirred under argon atmosphere for 30 minutes. Then, to the suspension was added tetrakistriphenylphosphinepalladium (64 mg), and the mixture was heated at 100° C. for 8 hours under argon atmosphere. After allowing to cool, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate= 5:1) to give methyl 7-(4-butoxyethoxyphenyl)-1-(3-methoxybenzyl)-2,3-dihydro-1-benzazepine-4-carboxylic acid (207 mg) as yellow oil.

$^1$H-NMR (200 MHz, CDCl$_3$) δ 0.93 (t, 3H, J=7.0 Hz), 1.30–1.50 (m, 2H), 1.55–1.65 (m, 2H), 2.78 (t, 2H, J=4.8

Hz), 3.31 (t, 2H, J=4.8 Hz), 3.55 (t, 2H, J=6.6 Hz), 3.78–3.82 (m, 8H), 4.16 (t, 2H, J=5.0 Hz), 4.56 (s, 2H), 6.77–6.90 (m, 4H), 6.97 (d, 2H, J=8.6 Hz), 7.24–7.29 (m, 1H), 7.36 (dd, 1H, J=8.4, 2.2 Hz), 7.46 (d, 2H, J=9.2 Hz), 7.55 (d, 1H, J=2.2 Hz), 7.82 (s, 1H).

Reference Example 161

To a solution of 7-bromo-1-(2-methoxybenzyl)-2,3-dihydro-1-benzazepine-4-carboxylic acid (202 mg) in a mixture of tetrahydrofuran (13 ml) and methanol (13 ml) was added 1N sodium hydroxide solution (4 ml), and the mixture was stirred at room temperature for 3 days. Then, to the mixture was added water at 0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, and the resulting solid was recrystallized from hexane-ethyl acetate to give 7-(4-butoxyethoxyphenyl)-1-(3-methoxybenzyl)-2,3-dihydro-1-benzazepine-4-carboxylic acid (161 mg) as yellow crystals.

$^1$H-NMR (200 MHz, CDCl$_3$) δ 0.93 (t, 3H, J=7.2 Hz), 1.34–1.45 (m, 2H), 1.54–1.65 (m, 2H), 2.81 (br, 2H), 3.34 (br, 2H), 3.55 (t, 2H, J=6.6 Hz), 3.78–3.83 (m, 5H), 4.16 (t, 2H, J=5.2 Hz), 4.58 (s, 2H), 6.82–6.90 (m, 4H), 6.98 (d, 2H, J=8.8 Hz), 7.29–7.41 (m, 2H), 7.46 (d, 2H, J=8.8 Hz), 7.56 (d, 1H, J=2.4 Hz), 7.93 (s, 1H).

Reference Example 162

To a suspension of 60% sodium hydride (0.16 g) in DMF (5 ml) which had been washed with hexane three times was added dropwise a solution of methyl 7-bromo-2,3-dihydro-1-benzazepine-4-carboxylate (1.00 g) in DMF (10 ml) under nitrogen atmosphere at 0° C. The temperature was returned to room temperature and the mixture was stirred for 1 hour. Then, to the mixture was added dropwise a solution of 4-methoxybenzyl bromide (0.67 g) in DMF (5 ml) at 0° C. To the mixture was added sodium iodide (0.83 g), and the mixture was heated at 60° C. overnight. To the mixture were added ethyl acetate and water, and the mixture was separated. The organic layer was washed with saturated brine and dried with magnesium sulfate. The solvent was evaporated under reduced pressure and the resulting residue was purified with silica gel column chromatography (hexane:ethyl acetate=5:1) to give methyl 7-bromo-1-(4-methoxybenzyl)-2,3-dihydro-1-benzazepine-4-carboxylate (0.92 g) as yellow oil.

$^1$H-NMR (200 MHz, CDCl$_3$) δ 2.72 (t, 2H, J=4.4 Hz), 3.23 (t, 2H, J=5.0 Hz), 3.80–3.82 (m, 6H), 4.46 (s, 2H), 6.70 (d, 1H, J=4.6 Hz), 6.90 (d, 2H, J=8.4 Hz), 7.22–7.29 (m, 1H), 7.46 (d, 1H, J=2.2 Hz), 7.62 (s, 1H).

Reference Example 163

To a solution of methyl 7-bromo-1-(4-methoxybenzyl)-2,3-dihydro-1-benzazepine-4-carboxylate (920 mg) in a mixture of tetrahydrofuran (70 ml) and methanol (70 ml) was added 1N sodium hydroxide solution (23 ml), and the mixture was stirred at room temperature for 1 day. Then, to the mixture was added water at 0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, and the resulting solid was recrystallized from hexane-ethyl acetate to give 7-bromo-1-(4-methoxybenzyl)-2,3-dihydro-1-benzazepine-4-carboxylic acid (644 mg) as yellow crystals.

$^1$H-NMR (200 MHz, CDCl$_3$) δ 2.74 (t, 2H, J=4.4 Hz), 3.26 (t, 2H, J=4.4 Hz), 3.82 (s, 3H), 4.48 (s, 2H), 6.71 (d, 1H, J=8.8 Hz), 6.89 (s, 2H), 7.16 (d, 2H, J=8.4 Hz), 7.23 (dd, 1H, J=8.8, 2.6 Hz), 7.48 (d, 1H, J=2.6 Hz), 7.73 (s, 1H).

Anal. Calcd. C$_{19}$H$_{18}$NO$_3$Br Calcd. C, 58.78; H, 4.67; N, 3.61. Found C, 58.60; H, 4.61; N, 3.57.

Reference Example 164

In toluene (20 ml), ethanol (2 ml) and water (2 ml) were suspended 7-bromo-1-(4-methoxybenzyl)-2,3-dihydro-1-benzazepine-4-carboxylic acid (300 mg), 4-propoxyethoxyphenyl borate (346 mg) and potassium carbonate (534 mg), and the suspension was stirred under argon atmosphere for 30 minutes. Then, to the suspension was added tetrakistriphenylphosphinepalladium (63 mg), and the mixture was heated at 100° C. for 4 hours under argon atmosphere. After allowing to cool, water was added to the mixture, which was made acidic (pH=4) with 1N hydrochloric acid and extracted with ethyl acetate. The organic layer was washed with water and saturated brine and dried with magnesium sulfate. The solvent was evaporated under reduced pressure, the resulting residue was purified with silica gel column chromatography (hexane:ethyl acetate=1:1) and the resulting solid was recrystallized from hexane-ethyl acetate to give 1-(4-methoxybenzyl)-7-(4-propoxyethoxyphenyl)-2,3-dihydro-1-benzazepine-4-carboxylic acid (117 mg) as yellow crystals.

$^1$H-NMR (200 MHz, CDCl$_3$) δ 0.94 (t, 3H, J=7.2 Hz), 1.60–1.70 (m, 2H), 2.76 (br, 2H), 3.31 (br, 2H), 3.51 (t, 2H, J=7.0 Hz), 3.79–3.84 (m, 5H), 4.16 (t, 2H, J=4.6 Hz), 4.54 (s, 2H), 6.88–7.00 (m, 5H), 7.22 (d, 2H, J=8.8 Hz), 7.39 (d, 1H, J=10.6 Hz), 7.47 (d, 2H, J=8.4 Hz), 7.56 (d, 1H, J=2.2 Hz), 7.92 (s, 1H).

Reference Example 165

In toluene (20 ml), ethanol (2 ml) and water (2 ml) were suspended 7-bromo-1-(4-methoxybenzyl)-2,3-dihydro-1-benzazepine-4-carboxylic acid (300 mg), 4-butoxyethoxyphenyl borate (368 mg) and potassium carbonate (534 mg), and the suspension was stirred under argon atmosphere for 30 minutes. Then, to the suspension was added tetrakistriphenylphosphinepalladium (63 mg), and the mixture was heated at 100° C. for 6 hours under argon atmosphere. After allowing to cool, water was added to the mixture, which was made acidic (pH=4) with 1N hydrochloric acid and extracted with ethyl acetate twice. The organic layer was washed with water and saturated brine and dried with magnesium sulfate. The solvent was evaporated under reduced pressure, the resulting residue was purified with silica gel column chromatography (hexane:ethyl acetate=2:1) and the resulting solid was washed with hexane to give 7-(4-butoxyethoxyphenyl)-1-(4-methoxybenzyl)-2,3-dihydro-1-benzazepine-4-carboxylic acid (149 mg) as yellow crystals.

$^1$H-NMR (200 MHz, CDCl$_3$) δ 0.93 (t, 3H, J=7.2 Hz), 1.25–1.41 (m, 2H), 1.58–1.65 (m, 2H), 2.76 (br, 2H), 3.31 (br, 2H), 3.56 (t, 2H, J=7.0 Hz), 3.78–3.82 (m, 5H), 4.16 (t, 2H, J=5.4 Hz), 4.54 (s, 2H), 6.88–7.000 (m, 5H), 7.22 (d, 2H, J=8.4 Hz), 7.39 (dd, 1H, J=10.2, 2.4 Hz), 7.47 (d, 2H, J=8.8 Hz), 7.57 (d, 1H, J=2.4 Hz), 7.92 (s, 1H).

Anal. Calcd. C$_{31}$H$_{35}$NO$_5$ Calcd. C, 74.23; H, 7.03; N, 2.79. Found C, 73.88; H, 6.78; N, 2.85.

Reference Example 166

To a solution of methyl 7-(4-propoxyethoxyphenyl)-2,3-dihydro-1-benzazepine-4-carboxylate (300 mg) and 3-thiophenecarboxyaldehyde (441 mg) in 1,2-dichloroethane (10 ml) was added sodium triacetoxyborohydride (416 mg), and the mixture was stirred under nitrogen atmosphere at room temperature overnight. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate=3:1) to give methyl 7-(4-propoxyethoxyphenyl)-1-(3-thienylmethyl)-2,3-dihydro-1-benzazepine-4-carboxylate (375 mg) as yellow oil.

$^1$H-NMR (200 MHz, CDCl$_3$) δ 0.94 (t, 3H, J=7.4 Hz), 1.60–1.70 (m, 2H), 2.76 (t, 2H, J=3.6 Hz), 3.31 (t, 2H, J=3.6 Hz), 3.51 (t, 2H, J=6.6 Hz), 3.79–3.83 (m, 5H), 4.16 (t, 2H, J=5.2 Hz), 4.56 (s, 2H), 6.90–7.04 (m, 4H), 7.12–7.14 (m, 1H), 7.32–7.45 (m, 2H), 7.47 (d, 2H, J=8.6 Hz), 7.55 (d, 1H, J=2.2 Hz), 7.81 (s, 1H).

Reference Example 167

To a solution of methyl 7-(4-propoxyethoxyphenyl)-1-(3-thienylmethyl)-2,3-dihydro-1-benzazepine-4-carboxylate (375 mg) in a mixture of tetrahydrofuran (24 ml) and methanol (24 ml) was added 1N sodium hydroxide solution (8 ml), and the mixture was stirred at room temperature overnight. Then, to the mixture was added water at 0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, and the resulting solid was recrystallized from hexane-ethyl acetate to give. 7-(4-propoxyethoxyphenyl)-1-(3-thienylmethyl)-2,3-dihydro-1-benzazepine-4-carboxylic acid (317 mg) as yellow crystals.

$^1$H-NMR (200 MHz, CDCl$_3$) δ 0.94 (t, 3H, J=7.4 Hz), 1.56–1.74 (m, 2H), 2.78 (t, 2H, J=4.4 Hz), 3.51 (t, 2H, J=6.8 Hz), 3.81 (t, 2H, J=4.4 Hz), 4.17 (t, 2H, J=5.2 Hz), 4.58 (s, 2H), 6.91–7.05 (m, 4H), 7.13 (br, 1H), 7.33–7.49 (m, 4H), 7.56 (d, 1H, J=2.2 Hz), 7.91 (s, 1H).

Anal. Calcd. C$_{27}$H$_{29}$NO$_4$S Calcd. C, 69.95; H, 6.31; N, 3.02. Found C, 69.78; H, 6.30; N, 3.01.

Reference Example 168

To a solution of methyl 7-(4-butoxyethoxyphenyl)-2,3-dihydro-1-benzazepine-4-carboxylate (300 mg) and 3-thiophenecarboxyaldehyde (426 mg) in 1,2-dichloroethane (10 ml) was added sodium triacetoxyborohydride (402 mg), and the mixture was stirred under nitrogen atmosphere at room temperature overnight. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate=3:1) to give methyl 7-(4-butoxyethoxyphenyl)-1-(3-thienylmethyl)-2,3-dihydro-1-benzazepine-4-carboxylate (373 mg) as yellow oil.

$^1$H-NMR (200 MHz, CDCl$_3$) δ 0.93 (t, 3H, J=7.4 Hz), 1.25–1.45 (m, 2H), 1.57–1.65 (m, 2H), 2.76 (t, 2H, J=3.6 Hz), 3.31 (t, 2H, J=4.6 Hz), 3.55 (t, 2H, J=6.6 Hz), 3.78–3.83 (m, 5H), 4.16 (t, 2H, J=5.2 Hz), 4.56 (s, 2H), 6.90–7.13 (m, 5H), 7.32–7.41 (m, 2H), 7.47 (d, 2H, J=8.8 Hz), 7.55 (s, 1H), 7.81 (s, 1H).

Reference Example 169

To a solution of methyl 7-(4-butoxyethoxyphenyl)-1-(3-thienylmethyl)-2,3-dihydro-1-benzazepine-4-carboxylate (373 mg) in a mixture of tetrahydrofuran (24 ml) and methanol (24 ml) was added 1N sodium hydroxide solution (8 ml), and the mixture was stirred at room temperature for 3 days. Then, to the mixture was added water at 0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, and the resulting solid was recrystallized from hexane-ethyl acetate to give 7-(4-butoxyethoxyphenyl)-1-(3-thienylmethyl)-2,3-dihydro-1-benzazepine-4-carboxylic acid (297 mg) as yellow crystals.

$^1$H-NMR (200 MHz, CDCl$_3$) δ 0.93 (t, 3H, J=7.2 Hz), 1.34–1.45 (m, 2H), 1.57–1.65 (m, 2H), 2.78 (t, 2H, J=4.0 Hz), 3.29 (t, 2H, J=4.0 Hz), 3.55 (t, 2H, J=6.6 Hz), 3.80 (t, 2H, J=4.8 Hz), 4.16 (t, 2H, J=5.2 Hz), 4.57 (s, 2H), 6.73–7.00 (m, 3H), 7.03 (dd, 1H, J=5.0, 1.4 Hz), 7.33–7.49 (m, 4H), 7.56 (d, 1H, J=1.8 Hz), 7.90 (s, 1H).

Anal. Calcd. C$_{28}$H$_{31}$NO$_4$S.0.1H$_2$O Calcd. C, 70.14; H, 6.56; N, 2.92. Found C, 69.85; H, 6.46; N, 2.86.

Reference Example 170

One droplet of pyridine was added to a solution of 2-hydroxymethylthiophene (1.0 g) in toluene (10 ml), followed by addition of thionyl chloride (1.56 g). The mixture was stirred at room temperature for 1 hour, ethyl acetate was added thereto, and the mixture was washed with water. The organic layer was washed with 1N sodium hydroxide solution, water and saturated brine, and dried with magnesium sulfate. The solvent was evaporated under reduced pressure to give 2-chloromethylthiophene (1.16 g) as deep brown oil.

$^1$H-NMR (200 MHz, CDCl$_3$) δ 4.82 (s, 2H), 6.93–7.00 (m, 1H), 7.09 (d, 1H, J=3.0 Hz), 7.31 (dd, 1H, J=5.2, 1.0 Hz).

Reference Example 171

To a suspension of 60% sodium hydride (0.16 g) in DMF (5 ml) which had been washed with hexane three times was added dropwise a solution of methyl 7-bromo-2,3-dihydro-1-benzazepine-4-carboxylate (1.00 g) in DMF (10 ml) under nitrogen atmosphere at 0° C. The temperature was returned to room temperature and the mixture was stirred for 1 hour. Then, to the mixture was added dropwise a solution of 2-chloromethylthiophene (1.07 g) in DMF (5 ml) at 0° C. To the mixture was added sodium iodide (0.83 g), and the mixture was heated at 60° C. overnight. To the mixture were added ethyl acetate and water, and the mixture was separated. The organic layer was washed with saturated brine and dried with magnesium sulfate. The solvent was evaporated under reduced pressure and the resulting residue was purified with silica gel column chromatography (hexane:ethyl acetate=5:1) to give methyl 7-bromo-1-(2-thienylmethyl)-2,3-dihydro-1-benzazepine-4-carboxylate (0.82 g) as yellow oil.

$^1$H-NMR (200 MHz, CDCl$_3$) δ 2.78 (t, 2H, J=3.6 Hz), 3.27 (t, 2H, J=3.6 Hz), 3.80 (s, 3H), 4.65 (s, 2H), 6.82 (d, 1H, J=7.8 Hz), 6.70–7.03 (m, 2H), 7.24–7.35 (m, 2H), 7.47 (d, 1H, J=2.8 Hz), 7.61 (s, 1H).

Reference Example 172

To a solution of methyl 7-bromo-1-(2-thienylmethyl)-2,3-dihydro-1-benzazepine-4-carboxylate (810 mg) in a mixture of tetrahydrofuran (60 ml) and methanol (60 ml) was added 1N sodium hydroxide solution (21 ml), and the mixture was stirred at room temperature overnight. Then, to the mixture was added water at 0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, and the resulting solid was recrystallized from hexane-ethyl acetate to give 7-bromo-1-(2-thienylmethyl)-2,3-dihydro-1-benzazepine-4-carboxylic acid (574 mg) as yellow crystals.

$^1$H-NMR (200 MHz, CDCl$_3$) δ 2.79 (t, 2H, J=4.4 Hz), 3.30 (t, 2H, J=4.8 Hz), 4.66 (s, 2H), 6.83 (d, 1H, J=4.4 Hz), 6.97–7.01 (m, 2H), 7.24–7.49 (m, 2H), 7.48 (d, 1H, J=2.4 Hz), 7.71 (s, 1H).

Anal. Calcd. C$_{16}$H$_{14}$NO$_2$SBr Calcd. C, 52.76; H, 3.87; N, 3.85. Found C, 52.80; H, 3.95; N, 3.68.

Reference Example 173

In toluene (30 ml), ethanol (3 ml) and water (3 ml) were suspended 7-bromo-1-(2-thienylmethyl)-2,3-dihydro-1-benzazepine-4-carboxylic acid (500 mg), 4-propoxyethoxyphenyl borate (615 mg) and potassium carbonate (949 mg), and the suspension was stirred under argon atmosphere for 30 minutes. Then, to the suspension was added tetrakistriphenylphosphinepalladium (111 mg), and the mixture was heated under argon atmosphere at 100° C. for 6 hours. After allowing to cool, water was added thereto, and the mixture was extracted with ethyl acetate. The organic layer was washed with saturated brine and dried with magnesium sulfate. The solvent was evaporated under reduced pressure and the resulting residue was purified with silica gel column chromatography (hexane:ethyl acetate= 1:1), which was recrystallized from hexane-ethyl acetate to give 7-(4-propoxyethoxyphenyl)-1-(2-thienylmethyl)-2,3-dihydro-1-benzazepine-4-carboxylic acid (269 mg).

$^1$H-NMR (200 MHz, CDCl$_3$) δ 0.94 (t, 3H, J=7.6 Hz), 1.59–1.74 (m, 2H), 2.79 (br, 2H), 3.30 (br, 2H), 3.51 (t, 2H, J=6.6 Hz), 3.81 (t, 2H, J=5.0 Hz), 4.15 (br, 2H), 4.68 (br, 2H), 6.90–7.10 (m, 5H), 7.23–7.26 (m, 1H), 7.43–7.47 (m, 3H), 7.54 (br, 1H), 7.90 (s, 1H).

Anal. Calcd. C$_{27}$H$_{29}$NO$_4$S.0.2H$_2$O Calcd. C, 69.41; H, 6.34; N, 3.00. Found C, 69.18; H, 6.05; N, 3.01.

Reference Example 174

To a solution of methyl 7-(4-butoxyethoxyphenyl)-2,3-dihydro-1-benzazepine-4-carboxylate (300 mg) and thiophene-2-carboxyaldehyde (422 mg) in 1,2-dichloroethane (10 ml) was added sodium triacetoxyborohydride (796 mg), and the mixture was stirred under nitrogen atmosphere at room temperature overnight. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate=3:1) to give methyl 7-(4-butoxyethoxyphenyl)-1-(2-thienylmethyl)-2,3-dihydro-1-benzazepine-4-carboxylate (373 mg) as yellow oil.

$^1$H-NMR (200 MHz, CDCl$_3$) δ 0.93 (t, 3H, J=7.0 Hz), 1.30–1.47 (m, 2H), 1.56–1.71 (m, 2H), 2.80 (t, 2H, J=5.4 Hz), 3.32 (t, 2H, J=5.4 Hz), 3.55 (t, 2H, J=7.0 Hz), 3.78–3.83 (m, 5H), 4.16 (t, 2H, J=5.0 Hz), 4.71 (s, 2H), 6.96–7.02 (m, 5H), 7.29 (dd, 1H, J=4.8, 1.4 Hz), 7.40–7.49 (m, 3H), 7.55 (d, 1H, J=2.2 Hz), 7.80 (s, 1H).

Reference Example 175

To a solution of methyl 7-(4-butoxyethoxyphenyl)-1-(3-thienylmethyl)-2,3-dihydro-1-benzazepine-4-carboxylate (373 mg) in a mixture of tetrahydrofuran (24 ml) and methanol (24 ml) was added 1N sodium hydroxide solution (8 ml), and the mixture was stirred at room temperature for 1 day. Then, to the mixture was added water at 0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, and the resulting solid was recrystallized from hexane-ethyl acetate to give 7-(4-butoxyethoxyphenyl)-1-(2-thienylmethyl)-2,3-dihydro-1-benzazepine-4-carboxylic acid (249 mg) as yellow crystals.

$^1$H-NMR (200 MHz, CDCl$_3$) δ 0.93 (t, 3H, J=7.4 Hz), 1.34–1.70 (m, 4H), 2.81 (t, 2H, J=3.6 Hz), 3.34 (t, 2H, J=3.6 Hz), 3.55 (t, 2H, J=6.6 Hz), 3.80 (t, 2H, J=4.2 Hz), 4.16 (t, 2H, J=5.6 Hz), 4.72 (s, 2H), 6.96–7.04 (m, 5H), 7.26–7.31 (m, 1H), 7.41–7.49 (m, 3H), 7.55 (d, 1H, J=2.2 Hz), 7.89 (s, 1H).

Anal. Calcd. C$_{28}$H$_{31}$NO$_4$S Calcd. C, 70.41; H, 6.54; N, 2.93. Found C, 70.15; H, 6.51; N, 2.79.

Reference Example 176

To a solution of methyl 7-(4-propoxyethoxyphenyl)-2,3-dihydro-1-benzazepine-4-carboxylate (300 mg) and 3-furaldehyde (378 mg) in 1,2-dichloroethane (10 ml) was added sodium triacetoxyborohydride (416 mg), and the mixture was stirred under nitrogen atmosphere at room temperature overnight. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate= 3:1) to give methyl 1-(3-furylmethyl)-7-(4-propoxyethoxyphenyl)-2,3-dihydro-1-benzazepine-4-carboxylate (362 mg) as yellow oil.

$^1$H-NMR (200 MHz, CDCl$_3$) δ 0.94 (t, 3H, J=7.4 Hz), 1.57–1.70 (m, 2H), 2.76 (t, 2H, J=5.2 Hz), 3.27 (t, 2H, J=5.2 Hz), 3.51 (t, 2H, J=7.0 Hz), 3.79–3.84 (m, 5H), 4.16 (t, 2H, J=5.2 Hz), 4.38 (s, 2H), 6.37 (d, 1H, J=0.8 Hz), 6.96–7.00 (m, 3H), 7.38–7.49 (m, 5H), 7.54 (d, 1H, J=2.2 Hz), 7.79 (s, 1H).

Reference Example 177

To a solution of methyl 1-(3-furylmethyl)-7-(4-propoxyethoxyphenyl)-2,3-dihydro-1-benzazepine-4-carboxylate (362 mg) in a mixture of tetrahydrofuran (24 ml) and methanol (24 ml) was added 1N sodium hydroxide solution (8 ml), and the mixture was stirred at room temperature for 5 days. Then, to the mixture was added water at –0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, and the resulting solid was washed with hexane to give 1-(3-furylmethyl)-7-(4-propoxyethoxyphenyl)-2,3-dihydro-1-benzazepine-4-carboxylic acid (307 mg) as yellow crystals.

$^1$H-NMR (200 MHz, CDCl$_3$) δ 0.95 (t, 3H, J=7.4 Hz), 1.60–1.70 (m, 2H), 2.80 (br, 2H), 3.30 (b, 2H), 3.52 (t, 2H, J=6.6 Hz), 3.81 (t, 2H, J=4.0 Hz), 4.17 (t, 2H, J=5.0 Hz), 4.40 (s, 2H), 6.39 (s, 1H), 6.95–7.01 (m, 3H), 7.39–7.49 (m, 5H), 7.54 (d, 1H, J=2.2 Hz), 7.89 (s, 1H).

Anal. Calcd. C$_{27}$H$_{29}$NO$_5$ Calcd. C, 72.46; H, 6.53; N, 3.13. Found C, 72.13; H, 6.45; N, 3.00.

Reference Example 178

To a solution of methyl 7-(4-butoxyethoxyphenyl)-2,3-dihydro-1-benzazepine-4-carboxylate (300 mg) and 3-furaldehyde (365 mg) in 1,2-dichloroethane (10 ml) was added sodium triacetoxyborohydride (402 mg), and the mixture was stirred under nitrogen atmosphere at room temperature for 5 days. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate= 1:1) to give methyl 7-(4-butoxyethoxyphenyl)-1-(3-furylmethyl)-2,3-dihydro-1-benzazepine-4-carboxylate (310 mg) as yellow oil.

$^1$H-NMR (200 MHz, CDCl$_3$) δ 0.93 (t, 3H, J=7.4 Hz), 1.34–1.50 (m, 2H), 1.56–1.69 (m, 2H), 2.76 (t, 2H, J=7.2 Hz), 3.28 (t, 2H, J=5.6 Hz), 3.55 (t, 2H, J=6.6 Hz), 3.78–3.83 (m, 5H), 4.16 (t, 2H, J=5.0 Hz), 4.38 (s, 2H), 6.38 (d, 1H, J=0.8 Hz), 6.93–7.00 (m, 3H), 7.39–7.49 (m, 5H), 7.54 (d, 1H, J=2.2 Hz), 7.79 (s, 1H).

Reference Example 179

To a solution of methyl 7-(4-butoxyethoxyphenyl)-1-(3-furylmethyl)-2,3-dihydro-1-benzazepine-4-carboxylate (310 mg) in a mixture of tetrahydrofuran (21 ml) and methanol (21 ml) was added 1N sodium hydroxide solution (7 ml), and the mixture was stirred at room temperature for 3 days. Then, to the mixture was added water at 0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, and the resulting solid was washed with hexane to give 7-(4-butoxyethoxyphenyl)-1-(3-furylmethyl)-2,3-dihydro-1-benzazepine-4-carboxylic acid (312 mg) as yellow crystals.

$^1$H-NMR (200 MHz, CDCl$_3$) δ 0.93 (t, 3H, J=7.2 Hz), 1.31–1.45 (m, 2H), 1.55–1.70 (m, 2H), 2.79 (t, 2H, J=4.6 Hz), 3.30 (t, 2H, J=4.6 Hz), 3.56 (t, 2H, J=6.6 Hz), 3.81 (t, 2H, J=4.8 Hz), 4.16 (t, 2H, J=5.0 Hz), 4.40 (s, 2H), 6.38 (s, 1H), 6.95–7.01 (m, 3H), 7.40–7.49 (m, 5H), 7.55 (d, 1H, J=2.2 Hz), 7.90 (s, 1H).

Anal. Calcd. C$_{28}$H$_{31}$NO$_5$.0.2H$_2$O Calcd. C, 72.29; H, 6.80; N, 3.01. Found C, 72.15; H, 6.95; N, 2.93.

Reference Example 180

To a solution of methyl 7-(4-butoxyethoxyphenyl)-2,3-dihydro-1-benzazepine-4-carboxylate (300 mg) and 2-ethoxybenzaldehyde (570 mg) in 1,2-dichloroethane (10 ml) was added sodium triacetoxyborohydride (402 mg), and the mixture was stirred under nitrogen atmosphere at room temperature for 5 days. Then, water was added to the mixture, and the mixture was extracted with ethyl acetate. The organic layer was washed with saturated brine and dried with magnesium sulfate. The solvent was evaporated under reduced pressure, and the resulting residue was unified with silica gel column chromatography (hexane:ethyl acetate= 3:1) to give methyl 7-(4-butoxyethoxyphenyl)-1-(2-ethoxybenzyl)-2,3-dihydro-1-benzazepine-4-carboxylate (402 mg) as yellow oil.

$^1$H-NMR (200 MHz, CDCl$_3$) δ 0.93 (t, 3H, J=7.4 Hz), 1.33–1.64 (m, 7H), 2.81 (t, 2H, J=4.4 Hz), 3.34 (t, 2H, J=4.4 Hz), 3.55 (t, 2H, J=6.6 Hz), 3.78–3.82 (m, 5H), 4.04–4.18 (m, 4H), 4.58 (s, 2H), 6.74–6.99 (m, 6H), 7.14 (d, 1H, J=7.8 Hz), 7.32 (dd, 1H, J=4, 2.6 Hz), 7.46 (d, 2H, J=8.8 Hz), 7.54 (d, 1H, J=2.2 Hz), 7.84 (s, 1H).

Reference Example 181

To a solution of methyl 7-(4-butoxyethoxyphenyl)-1-(2-ethoxybenzyl)-2,3-dihydro-1-benzazepine-4-carboxylate (402 mg) in a mixture of tetrahydrofuran (24 ml) and methanol (24 ml) was added 1N sodium hydroxide solution (8 ml), and the mixture was stirred at room temperature for 4 days. Then, to the mixture was added water at 0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, which was recrystallized from hexane ethyl acetate to give 7-(4-butoxyethoxyphenyl)-1-(2-ethoxybenzyl)-2,3-dihydro-1-benzazepine-4-carboxylic acid (297 mg) as yellow crystals.

$^1$H-NMR (200 MHz, CDCl$_3$) δ 0.93 (t, 3H, J=7.0 Hz), 1.34–1.47 (m, 5H), 1.50–1.65 (m, 2H), 2.83 (br, 2H), 3.37 (br, 2H), 3.55 (t, 2H, J=6.6 Hz), 3.80 (t, 2H, J=4.4 Hz), 4.10 (q, 2H, J=5.0 Hz), 4.16 (t, 2H, J=4.8 Hz), 4.59 (s, 2H), 6.82 (d, 1H, J=8.8 Hz), 6.90–6.99 (m, 5H), 7.15 (d, 1H, J=7.4 Hz), 7.26–7.37 (m, 1H), 7.46 (d, 2H, J=8.8 Hz), 7.56 (d, 1H, J=2.2 Hz), 7.94 (s, 1H).

Anal. Calcd. C$_{32}$H$_{37}$NO$_5$ Calcd. C, 74.54; H, 7.23; N, 2.72. Found C, 74.48; H, 7.17; N, 2.92.

Reference Example 182

To a solution of 3-hydroxybenzaldehyde (10.0 g) in DMF (120 ml) were added potassium carbonate (15.8 g) and 1-bromopropane (12.1 g), and the mixture was stirred under nitrogen atmosphere at room temperature overnight. Then, water was added to the mixture, which was extracted with ethyl acetate and washed with 1N sodium hydroxide solution twice, with water three times and with saturated brine once. After dried with magnesium sulfate, the solvent was evaporated under reduced pressure to give 3-propoxybenzaldehyde (13.4 g) as colorless liquid.

$^1$H-NMR (200 MHz, CDCl$_3$) δ 1.05 (t, 3H, J=7.4 Hz), 1.75–1.93 (m, 2H), 3.99 (t, 2H, J=6.6 Hz), 7.15–7.21 (m, 1H), 7.39 (d, 1H, J=2.6 Hz), 7.41–7.45 (m, 2H).

Reference Example 183

To a solution of methyl 7-(4-butoxyethoxyphenyl)-2,3-dihydro-1-benzazepine-4-carboxylate (300 mg) and 3-propoxybenzaldehyde (623 mg) in 1,2-dichloroethane (10 ml) was added sodium triacetoxyborohydride (804 mg), and the mixture was stirred under nitrogen atmosphere at room temperature for 5 days. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane ethyl acetate= 3:1) to give methyl 7-(4-butoxyethoxyphenyl)-1-(3-propoxybenzyl)-2,3-dihydro-1-benzazepine-4-carboxylate (412 mg) as yellow oil.

$^1$H-NMR (200 MHz, CDCl$_3$) δ 0.89–1.09 (m, 6H), 1.33–1.45 (m, 2H), 1.55–1.65 (m, 2H), 1.74–1.85 (m, 2H), 2.78 (t, 2H, J=5.2 Hz), 3.31 (t, 2H, J=5.2 Hz), 3.55 (t, 2H, J=7.0 Hz), 3.78–3.83 (m, 5H), 3.90 (t, 2H, J=6.6 Hz), 4.16 (t, 2H, J=5.4 Hz), 4.55 (s, 2H), 6.80–6.89 (m, 4H), 6.97 (d, 2H, J=8.8 Hz), 7.22–7.49 (m, 4H), 7.54 (d, 1H, J=2.2 Hz), 7.82 (s, 1H).

Reference Example 184

To a solution of methyl 7-(4-butoxyethoxyphenyl)-1-(3-propoxybenzyl)-2,3-dihydro-1-benzazepine-4-carboxylate (412 mg) in a mixture of tetrahydrofuran (24 ml) and methanol (24 ml) was added 1N sodium hydroxide solution (8 ml), and the mixture was stirred at room temperature for 4 days. Then, to the mixture was added water at 0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-(3-propoxybenzyl)-2,3-dihydro-1-benzazepine-4-carboxylic acid (308 mg) as yellow crystals.

$^1$H-NMR (200 MHz, CDCl$_3$) δ 0.93 (t, 3H, J=7.4 Hz), 1.03 (t, 3H, J=7.2 Hz), 1.30–1.50 (m, 2H), 1.50–1.70 (m, 2H), 1.74–1.85 (m, 2H), 2.81 (br, 2H), 3.35 (br, 2H), 3.56 (t, 2H, J=6.6 Hz), 3.81 (t, 2H, J=4.4 Hz), 4.16 (t, 2H, J=5.6 Hz), 4.57 (s, 2H), 6.81–6.91 (m, 4H), 6.98 (d, 2H, J=8.8 Hz), 7.24–7.35 (m, 1H), 7.38 (dd, 1H, J=8.4, 1.4 Hz), 7.47 (d, 2H, J=8.8 Hz), 7.56 (d, 1H, J=1.4 Hz), 7.93 (s, 1H).

Anal. Calcd. C$_{33}$H$_{39}$NO$_5$ Calcd. C, 74.83; H, 7.42; N, 2.64. Found C, 74.76; H, 7.38; N, 2.74.

Reference Example 185

To a solution of methyl 7-(4-butoxyethoxyphenyl)-2,3-dihydro-1-benzazepine-4-carboxylate (300 mg) and 2,5-dimethoxybenzaldehyde (631 mg) in 1,2-dichloroethane (10 ml) was added sodium triacetoxyborohydride (8042 mg), and the mixture was stirred under nitrogen atmosphere at room temperature for 5 days. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate= 3:1) to give methyl 7-(4-butoxyethoxyphenyl)-1-(2,5-dimethoxybenzyl)-2,3-dihydro-1-benzazepine-4-carboxylate (290 mg) as yellow oil.

$^1$H-NMR (200 MHz, CDCl$_3$) δ 0.93 (t, 3H, J=7.4 Hz), 1.37–1.45 (m, 2H), 1.55–1.70 (m, 2H), 3.82 (br, 2H), 3.34 (br, 2H), 3.55 (t, 2H, J=7.0 Hz), 3.70 (s, 3H), 3.78–3.84 (m, 8H), 4.16 (t, 2H, J=5.4 Hz), 4.53 (s, 2H), 6.75–6.83 (m, 4H), 6.97 (d, 2H, J=8.8 Hz), 7.30 (dd, 1H, J=8.8, 1.3 Hz), 7.46 (d, 2H, J=8.8 Hz), 7.57 (d, 1H, J=1.3 Hz), 7.83 (s, 1H).

Reference Example 186

To a solution of methyl 7-(4-butoxyethoxyphenyl)-1-(3-propoxybenzyl)-2,3-dihydro-1-benzazepine-4-carboxylate (290 mg) in a mixture of tetrahydrofuran (21 ml) and methanol (21 ml) was added 1N sodium hydroxide solution (7 ml), and the mixture was stirred at room temperature for 4 days. Then, to the mixture was added water at 0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-(2,5-dimethoxybenzyl)-2,3-dihydro-1-benzazepine-4-carboxylic acid (237 mg) as yellow crystals.

$^1$H-NMR (200 MHz, CDCl$_3$) δ 0.93 (t, 3H, J=6.8 Hz), 1.32–1.45 (m, 2H), 1.50–1.64 (m, 2H), 2.83 (br, 2H), 3.35 (br, 2H), 3.55 (t, 2H, J=6.6 Hz), 3.71 (s, 3H), 3.80 (t, 2H, J=5.0 Hz), 3.84 (s, 3H), 4.16 (t, 2H, J=5.6 Hz), 4.55 (s, 2H), 6.75–6.83 (m, 4H), 6.97 (d, 2H, J=8.8 Hz), 7.35 (dd, 1H, J=8.8, 1.3 Hz), 7.46 (d, 2H, J=8.8 Hz), 7.54 (d, 1H, J=1.3 Hz), 7.93 (s, 1H).

Anal. Calcd. C$_{32}$H$_{37}$NO$_6$.0.1H$_2$O Calcd. C, 72.05; H, 7.03; N, 2.63. Found C, 71.83; H, 7.18; N, 2.57.

Reference Example 187

To a solution of methyl 7-(4-butoxyethoxyphenyl)-2,3-dihydro-1-benzazepine-4-carboxylate (300 mg) and 2-fluorobenzaldehyde (471 mg) in 1,2-dichloroethane (10 ml) was added sodium triacetoxyborohydride (402 mg), and the mixture was stirred under nitrogen atmosphere at room temperature for 5 days. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate= 3:1) to give methyl-7-(4-butoxyethoxyphenyl)-1-(2-fluorobenzyl)-2,3-dihydro-1-benzazepine-4-carboxylate (382 mg) as yellow oil.

$^1$H-NMR (200 MHz, CDCl$_3$) δ 0.93 (t, 3H, J=7.0 Hz), 1.30–1.45 (m, 2H), 1.54–1.70 (m, 2H), 2.80 (t, 2H, J=4.0 Hz), 3.31 (t, 2H, J=5.2 Hz), 3.55 (t, 2H, J=6.6 Hz), 3.78–3.83 (m 5H), 4.16 (t, 2H, J=5.2 Hz), 4.63 (s, 2H), 6.82 (d, 1H, J=8.8 Hz), 6.95–7.48 (m, 9H), 7.56 (d, 1H, J=2.2 Hz), 7.82 (s, 1H).

Reference Example 188

To a solution of methyl 7-(4-butoxyethoxyphenyl)-1-(2-fluorobenzyl)-2,3-dihydro-1-benzazepine-4-carboxylate (382 mg) in a mixture of tetrahydrofuran (24 ml) and methanol (24 ml) was added 1N sodium hydroxide solution (8 ml), and the mixture was stirred at room temperature for 4 days. Then, to the mixture was added water at 0° C., and 1N hydrochloric acid was further added to make acidic (pH=4), and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-(2-fluorobenzyl)-2,3-dihydro-1-benzazepine-4-carboxylic acid (309 mg) as yellow crystals.

$^1$H-NMR (200 MHz, CDCl$_3$) δ 0.93 (t, 3H, J=7.2 Hz), 1.34–1.45 (m, 2H), 1.54–1.65 (m, 2H), 2.81 (br, 2H), 3.37 (br, 2H), 3.55 (t, 2H, J=6.8 Hz), 3.80 (t, 2H, J=4.4 Hz), 4.16 (t, 2H, J=5.6 Hz), 4.65 (s, 2H), 6.84 (d, 1H, J=8.4 Hz), 6.98 (d, 2H, J=8.8 Hz), 7.06–7.15 (m, 2H), 7.24–7.40 (m, 3H), 7.46 (d, 2H, J=8.8 Hz), 7.57 (d, 1H, J=2.6 Hz), 7.93 (s, 1H).

Anal. Calcd. C$_{30}$H$_{32}$NO$_4$F Calcd. C, 73.60; H, 6.59; N, 2.86. Found C, 73.48; H, 6.46; N, 3.01.

Reference Example 189

To a solution of methyl 7-(4-butaxyethoxyphenyl)-2,3-dihydro-1-benzazepine-4-carboxylate (500 mg) and 1-methyl-2-imidazolecarboxyaldehyde (696 mg) in 1,2-dichloroethane (20 ml) was added sodium triacetoxyborohydride (804 mg), and the mixture was stirred under nitrogen atmosphere at room temperature for 4 days. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (ethyl acetate) to give methyl 7-(4-butoxyethoxyphenyl)-1-(1-methylimidazol-2-yl)methyl]-2,3-dihydro-1-benzazepine-4-carboxylate (367 mg) as yellow oil.

$^1$H-NMR (200 MHz, CDCl$_3$) δ 0.93 (t, 3H, J=7.2 Hz), 1.38–1.45 (m, 2H), 1.54–1.65 (m, 2H), 2.41 (t, 2H, J=4.4 Hz), 3.30 (t, 2H, J=5.0 Hz), 3.51 (s, 3H), 3.56 (t, 2H, J=6.2 Hz), 3.79–3.83 (m, 5H), 4.17 (t, 2H, J=4.4 Hz), 4.61 (s, 2H), 6.88 (d, 1H, J=1.0 Hz), 6.97–7.06 (m, 4H), 7.44–7.50 (m, 3H), 7.56 (d, 2H, J=2.2 Hz), 7.77 (s, 1H).

Reference Example 190

To a solution of methyl 7-(4-butoxyethoxyphenyl)-1-[(1-methylimidazol-2-yl)methyl]-2,3-dihydro-1-benzazepine-4-carboxylate (367 mg) in a mixture of tetrahydrofuran (24 ml) and methanol (24 ml) was added 1N sodium hydroxide solution (8 ml), and the mixture was stirred at room temperature for 3 days. Then, to the mixture was added water at 0° C., and 1N hydrochloric acid was further added to neutralize, and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-[(1-methylimidazol-2-yl)methyl]-2,3-dihydro-1-benzazepine-4-carboxylic acid (285 mg) as yellow crystals.

$^1$H-NMR (200 MHz, CDCl$_3$) δ 0.93 (t, 3H, J=7.4 Hz), 1.30–1.50 (m, 2H), 1.54–1.70 (m, 2H), 2.47 (br, 2H), 3.32 (br, 2H), 3.54–3.59 (m, 5H), 3.80 (t, 2H, J=4.4 Hz), 4.16 (t, 2H, J=5.4 Hz), 4.68 (s, 2H), 6.88 (s, 1H), 6.98 (d, 2H, J=8.4 Hz), 7.03–7.07 (m, 2H), 7.45–7.49 (m, 3H), 7.57 (d, 1H, J=2.2 Hz), 7.85 (s, 1H).

Anal. Calcd. C$_{28}$H$_{35}$N$_3$O$_4$ Calcd. C, 70.42; H, 7.39; N, 8.80. Found C, 70.27; H, 7.43; N, 8.73.

Reference Example 191

To a solution of methyl 7-(4-butoxyethoxyphenyl)-2,3-dihydro-1-benzazepine-4-carboxylate (300 mg) and 2-thiazolecarboxyaldehyde (445 mg) in 1,2-dichloroethane (20 ml) was added sodium triacetoxyborohydride (416 mg), and the mixture was stirred under nitrogen atmosphere at room temperature for 1 day. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate= 2:1) to give methyl 7-(4-butoxyethoxyphenyl)-1-(thiazol-2-ylmethyl)-2,3-dihydro-1-benzazepine-4-carboxylate (212 mg) as yellow oil.

$^1$H-NMR (200 MHz, CDCl$_3$) δ 0.93 (t, 3H, J=7.2 Hz), 1.34–1.45 (m, 2H), 1.57–1.70 (m, 2H), 2.87 (t, 2H, J=4.4 Hz), 3.42 (t, 2H, J=4.4 Hz), 3.55 (t, 2H, J=6.6 Hz), 3.78–3.82 (m, 5H), 4.16 (t, 2H, J=5.6 Hz), 4.86 (s, 2H), 6.95–7.00 (m, 3H), 7.30 (d, 1H, J=3.2 Hz), 7.40 (dd, 1H, J=8.4, 2.2 Hz), 7.46 (d, 2H, J=8.6 Hz), 7.56 (d, 1H, J=2.6 Hz), 7.78–7.81 (m, 2H).

Reference Example 192

To a solution of methyl 7-(4-butoxyethoxyphenyl)-1-(thiazol-2-ylmethyl)-2,3-dihydro-1-benzazepine-4-carboxylate (212 mg) in a mixture of tetrahydrofuran (18 ml) and methanol (18 ml) was added 1N sodium hydroxide solution (6 ml), and the mixture was stirred at room temperature overnight. Then, to the mixture was added water at 0° C., and 1N hydrochloric acid was further added to neutral, and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-(thiazol-2-ylmethyl)-2,3-dihydro-1-benzazepine-4-carboxylic acid (153 mg) as yellow crystals.

$^1$H-NMR (200 MHz, CDCl$_3$) δ 0.93 (t, 3H, J=7.6 Hz), 1.34–1.45 (m, 2H), 1.54–1.65 (m, 21), 2.89 (br, 2H), 3.45 (br, 2H), 3.55 (t, 2H, J=6.6 Hz), 3.80 (t, 2H, J=4.4 Hz), 4.16 (t, 2H, J=5.6 Hz), 4.88 (s, 2H), 6.96–7.01 (m, 3H), 7.31 (d, 1H, J=3.2 Hz), 7.46–7.49 (m, 3H), 7.57 (d, 1H, J=2.6 Hz), 7.80 (d, 1H, J=3.4 Hz), 7.91 (s, 1H).

Anal. Calcd. C$_{27}$H$_{30}$N$_2$O$_4$S Calcd. C, 67.76; H, 6.32; N, 5.85. Found C, 67.76; H, 6.39; N, 5.70.

Reference Example 193

To a solution of methyl 7-bromo-2,3-dihydro-1-benzazepine-4-carboxylate (1.5 g) and 2-methoxybenzaldehyde (3.62 g) in 1,2-dichloroethane (50 ml) was added sodium triacetoxyborohydride (2.82 g), and the mixture was stirred under nitrogen atmosphere at room temperature for 1 day. Then, water was added to the mixture, and the mixture was extracted-with ethyl acetate. The organic layer was washed with saturated brine and dried with magnesium sulfate. The solvent was evaporated under reduced pressure, and the resulting residue was purified with silica gel column chromatography (hexane:ethyl acetate= 5:1) to give methyl 7-bromo-1-(2-methoxybenzyl)-2,3-dihydro-1-benzazepine-4-carboxylate (1.62 g) as yellow oil.

$^1$H-NMR (200 MHz, CDCl$_3$) δ 2.79 (t, 2H, J=5.2 Hz), 3.29 (t, 2H, J=5.6 Hz), 3.80 (s, 3H), 3.86 (s, 3H), 4.50 (s, 2H), 6.60 (d, 1H, J=9.2 Hz), 6.88–7.07 (m, 3H), 7.16 (dd, 1H, J=8.8, 2.6 Hz), 7.20–7.31 (m, 1H), 7.46 (d, 1H, J=2.6 Hz), 7.64 (s, 1H).

Reference Example 194

In toluene (25 ml), ethanol (2.5 ml) and water (2.5 ml) were suspended methyl 7-bromo-1-(2-methoxybenzyl)-2,3-dihydro-1-benzazepine-4-carboxylate (712 mg), 4-propoxyphenyl borate (416 mg) and potassium carbonate (636 mg), and the suspension was stirred under argon atmosphere for 30 minutes. Then, to the suspension was added tetrakistriphenylphosphinepalladium (143 mg) and the mixture was heated under argon atmosphere at 100° C. for 5 hours. After allowing to cool, water was added thereto, and the mixture was extracted with ethyl acetate. The organic layer was washed with saturated brine and dried with magnesium sulfate. The solvent was evaporated under reduced pressure and the resulting residue was purified with silica gel column chromatography (hexane:ethyl acetate= 3:1) to give methyl 7-(4-propoxyphenyl)-1-(2-methoxybenzyl)-2,3-dihydro-1-benzazepine-4-carboxylate (663 mg) as yellow oil.

$^1$H-NMR (200 MHz, CDCl$_3$) δ 1.05 (t, 3H, J=7.2 Hz), 1.81–1.88 (m, 2H), 2.82 (t, 2H, J=5.2 Hz), 3.34 (t, 2H, J=5.2 Hz), 3.82 (s, 3H), 3.88 (s, 3H), 3.95 (t, 2H, J=6.6 Hz), 4.56 (s, 2H), 6.76–7.15 (m, 6H), 7.26–7.35 (m, 2H), 7.45 (d, 2H, J=8.8 Hz), 7.57–7.60 (m, 1H), 7.84 (s, 1H).

Reference Example 195

To a solution of methyl 7-(propoxyphenyl)-1-(2-methoxybenzyl)-2,3-dihydro-1-benzazepine-4-carboxylate (601 mg) in a mixture of tetrahydrofuran (39 ml) and methanol (39 ml) was added 1N sodium hydroxide solution (13 ml), and the mixture was stirred at room temperature for 4 days. Then, to the mixture was added water at 0° C., and 1N hydrochloric acid was further added to neutral, and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-propoxyphenyl)-1-(2-methoxybenzyl)-2,3-dihydro-1-benzazepine-4-carboxylic acid (406 mg) as yellow crystals.

$^1$H-NMR (200 MHz, CDCl$_3$) δ 1.05 (t, 3H, J=7.2 Hz), 1.77–1.88 (m, 2H), 2.84 (t, 2H, J=4.8 Hz), 3.37 (t, 2H, J=4.8 Hz), 3.88 (s, 3H), 3.95 (t, 2H, J=6.6 Hz), 4.58 (s, 2H), 6.79 (d, 1H, J=8.8 Hz), 6.92–6.96 (m, 4H), 7.14 (d, 1H, J=6.0 Hz), 7.26–7.37 (m, 2H), 7.46 (d, 2H, J=8.8 Hz), 7.56 (d, 1H, J=2.2 Hz), 7.95 (s, 1H).

Anal. Calcd. C$_{29}$H$_{29}$NO$_4$·0.3H$_2$O Calcd. C, 75.56; H, 6.47; N, 3.04. Found C, 75.47; H, 6.58; N, 3.04.

Reference Example 196

To a suspension of 60% sodium hydride (1.5 g) in dry tetrahydrofuran (30 ml) which had been washed with hexane three times was added dropwise a solution of 4-bromopyrazole (5.0 g) in dry tetrahydrofuran (30 ml) under nitrogen atmosphere at 0° C., the temperature was returned to room temperature, and the mixture was stirred for 1 hour. To the mixture was added dropwise a solution of methyl iodide (5.31 g) in dry tetrahydrofuran (20 ml) under nitrogen atmosphere at 0° C., the temperature was returned to room temperature, and the mixture was stirred for 3 hours. The solution was diluted with tetrahydrofuran, and the insolubles were filtered with Celite. After the filtrate was concentrated under reduced pressure, hexane was further added, and the insolubles were filtered. The filtrate was concentrated under reduced pressure to give 4-bromo-1-methylpyrazole (5.12 g) as light yellow liquid.

$^1$H-NMR (200 MHz, CDCl$_3$) δ 3.89 (s, 3H), 7.38 (s, 1H), 7.44 (s, 1H).

Reference Example 197

To a solution of 4-bromo-1-methylpyrazole. (3.0 g) in dry tetrahydrofuran (50 ml) was added dropwise n-butyllithium (14.0 ml, 1.6M solution in hexane) under nitrogen atmosphere at −78° C. After 30 minutes, DMF (6.8 g) was added dropwise under nitrogen atmosphere at 78° C., the temperature was returned to room temperature, and the mixture was stirred for 1 hour. Then, 1N hydrochloric acid (50 ml) was added thereto at 0° C., and the mixture was stirred for 30 minutes, made basic with 1N sodium hydroxide solution and extracted with ethyl acetate three times. The extract was dried with magnesium sulfate, the solvent was evaporated under reduced pressure, and the resulting residue was purified with silica gel column chromatography (hexane:ethyl acetate=1:2) to give 1-methylpyrazole-4-carboxyaldehyde (540 mg) as light yellow oil.

$^1$H-NMR (200 MHz, CDCl$_3$) δ 3.97 (s, 3H), 7.91 (s, 1H), 7.96 (s, 1H), 9.86 (s, 1H).

Reference Example 198

To a solution of methyl 7-(4-butoxyethoxyphenyl)-2,3-dihydro-1-benzazepine-4-carboxylate (388 mg) and 1-methylpyrazole-4-carboxyaldehyde (540 mg) in 1,2-dichloroethane (5 ml) was added sodium triacetoxyborohydride (519 mg), and the mixture was stirred under nitrogen atmosphere at room temperature for 1 day. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate=2:3) to give methyl 7-(4-butoxyethoxyphenyl)-1-[(1-methylpyrazol-4-yl)methyl]-2,3-dihydro-1-benzazepine-4-carboxylate (321 mg) as yellow oil.

$^1$H-NMR (200 MHz, CDCl$_3$) δ 0.93 (t, 3H, J=7.4 Hz), 1.34–1.45 (m, 2H), 1.50–1.70 (m, 2H), 2.76 (t, 2H, J=5.0 Hz), 3.27 (t, 2H, J=5.0 Hz), 3.56 (t, 2H, J=7.0 Hz), 3.78–3.83 (m, 5H), 3.89 (s, 3H), 4.16 (t, 2H, J=5.2 Hz), 4.42 (s, 2H), 6.92–7.00 (m, 3H), 7.29 (s, 1H), 7.4 (dd, 1H, J=8.4, 1.8 Hz), 7.45–7.49 (m, 3H), 7.54 (d, 1H, J=2.2 Hz), 7.78 (s, 1H).

Reference Example 199

To a solution of methyl 7-(4-butoxyethoxyphenyl)-1-[(1-methylpyrazol-4-yl)methyl]-2,3-dihydro-1-benzazepine-4-carboxylate (321 mg) in a mixture of tetrahydrofuran (24 ml) and methanol (24 ml) was added 1N sodium hydroxide solution (8 ml), and the mixture was stirred at room temperature for 3 days. Then, to the mixture was added water at 0° C., and 1N hydrochloric acid was further added to neutralize, and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-[(1-methylpyrazol-4-yl)methyl]-2,3-dihydro-1-benzazepine-4-carboxylic acid (239 mg) as yellow crystals.

$^1$H-NMR (200 MHz, CDCl$_3$) δ 0.93 (t, 3H, J=7.4 Hz), 1.34–1.49 (m, 2H), 1.55–1.65 (m, 2H), 2.79 (t, 2H, J=4.2 Hz), 3.30 (t, 2H, J=4.2 Hz), 3.56 (t, 2H, J=8.6 Hz), 3.81 (t, 2H, J=4.8 Hz), 3.90 (s, 3H), 4.16 (t, 2H, J=5.2 Hz), 4.44 (s, 2H), 6.94–7.01 (m, 3H), 7.30 (s, 1H), 7.40–7.50 (m, 4H), 7.56 (d, 1H, J=2.0 Hz), 7.90 (s, 1H).

Anal. Calcd C$_{28}$H$_{33}$N$_3$O$_4$ Calcd. C, 70.71; H, 6.99; N, 8.84. Found C, 70.52; H, 6.90; N, 8.70.

Reference Example 200

To a solution of 1-methylpyrazole (10.0 g) in dry tetrahydrofuran (200 ml) was added dropwise n-butyllithium (91.3 ml, 1.6M solution in hexane) at −78° C. under nitrogen atmosphere. After 30 minutes, DMF (44.6 g) was added dropwise thereto at −78° C. under nitrogen atmosphere, the temperature was returned to room temperature, and the mixture was stirred for 2 hours. Then, to the mixture was added 1N hydrochloric acid (200 ml) at 0° C., the mixture was stirred for 30 minutes, made basic with 1N sodium hydroxide solution, and extracted with ethyl acetate three times. The mixture was dried with magnesium sulfate, and the solvent was evaporated under reduced pressure to give 1-methyl-5-pyrazolecarboxyaldehyde (11.7 g) as light yellow oil.

$^1$H-NMR (200 MHz, CDCl$_3$) δ 4.19 (s, 3H), 6.90 (d, 1H, J=2.2 Hz), 7.54 (d, 1H, J=1.8 Hz), 9.88 (s, 1H).

Reference Example 201

To a solution of methyl 7-(4-butoxyethoxyphenyl)-2,3-dihydro-1-benzazepine-4-carboxylate (50 mg) and 1-methylpyrazole-5-carboxyaldehyde (696 mg) in 1,2-dichloroethane (1 ml) was added sodium triacetoxyborohydride (670 mg), and the mixture was stirred under nitrogen atmosphere at room temperature for 1 day. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate=2:3) to give methyl 7-(4-butoxyethoxyphenyl)-1-[(1-methylpyrazol-5-yl)methyl]-2,3-dihydro-1-benzazepine-4-carboxylate (391 mg), as yellow oil.

$^1$H-NMR (200 MHz, CDCl$_3$) δ 0.93 (t, 3H, J=7.4 Hz), 1.34–1.45 (m, 2H), 1.55–1.70 (m, 2H), 2.58 (t, 2H, J=4.8 Hz), 3.27 (t, 2H, J=4.8 Hz), 3.56 (t, 2H, J=7.0 Hz), 3.79–3.83 (m, 8H), 4.17 (t, 2H, J=4.4 Hz), 4.52 (s, 2H), 6.22 (d, 1H, J=1.8 Hz), 6.92 (d, 1H, J=8.8 Hz), 6.99 (d, 2H, J=8.8 Hz), 7.40–7.50 (m, 4H), 7.57 (d, 1H, J=2.2 Hz), 7.79 (s, 1H).

Reference Example 202

To a solution of methyl 7-(4-butoxyethoxyphenyl)-1-[(1-methylpyrazol-5-yl)methyl]-2,3-dihydro-1-benzazepine-4-carboxylate (391 mg) in a mixture of tetrahydrofuran (24 ml) and methanol (24 ml) was added 1N sodium hydroxide solution (8 ml), and the mixture was stirred at room temperature for 3 days. Then, to the mixture was added water at 0° C., and 1N hydrochloric acid was further added to neutral, and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-[(1-methylpyrazol-5-yl)methyl]-2,3-dihydro-1-benzazepine-4-carboxylic acid (263 mg) as yellow crystals.

$^1$H-NMR (200 MHz, CDCl$_3$) δ 0.93 (t, 3H, J=7.0 Hz), 1.34–1.45 (m, 2H), 1.55–1.65 (m, 2H), 2.62 (br, 2H), 3.30 (br, 2H), 3.56 (t, 2H, J=7.0 Hz), 3.79–3.84 (m, 5H), 4.17 (t, 2H, J=5.0 Hz), 4.54 (s, 2H), 6.22 (d, 1H, J=1.8 Hz), 6.93 (d, 1H, J=8.8 Hz), 6.99 (d, 2H, J=8.8 Hz), 7.43–7.50 (m, 4H), 7.58 (d, 1H, J=2.2 Hz), 7.89 (s, 1H).

Anal. Calcd. C$_{28}$H$_{33}$N$_3$O$_4$ Calcd. C, 70.71; H, 6.99; N, 8.84. Found C, 70.48; H, 6.90; N, 8.80.

Reference Example 203

2,5-dimethylisooxazole (10.0 g) was dissolved in water (100 ml). To the solution were added concentrated sulfuric acid (35.3 g) and 40% aqueous formaldehyde solution (46.4 g) at 0° C., and the mixture was heated at 70° C. overnight. The mixture was neutralized with 1N sodium hydroxide solution at 0° C. and extracted with chloroform three times. The extract was dried with magnesium sulfate, the solvent was evaporated under reduced pressure, and the resulting residue was distilled under reduced pressure to give 4-hydroxymethyl-2,5-dimethylisooxazole (2.54 g) as colorless liquid.

$^1$H-NMR (200 MHz, CDCl$_3$) δ 2.31 (s, 3H), 2.39 (s, 3H), 4.48 (s, 2H).

Reference Example 204

To a solution of 4-hydroxymethyl-2,5-dimethylisooxazole (2.45 g) in ethyl acetate (500 ml) was added active manganese dioxide (24.5 g), and the mixture was stirred at room temperature for 3 days. The insolubles were filtered using Celite, and the filtrate was concentrated under reduced pressure to give 2,3-dimethylisooxazole-4-carboxyaldehyde (1.5 g) as colorless oil.

$^1$H-NMR (200 MHz, CDCl$_3$) δ 2.42 (s, 3H), 2.69 (s, 3H), 9.95 (s, 1H).

Reference Example 205

To a solution of methyl 7-(4-butoxyethoxyphenyl)-2,3-dihydro-1-benzazepine-4-carboxylate (500 mg) and 2,5-dimethylisooxazole-4-carboxyaldehyde (791 mg) in 1,2-dichloroethane (15 ml) was added sodium triacetoxyborohydride (2.0 g), and the mixture was stirred under nitrogen atmosphere at room temperature for 7 days. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate=3:1) to give methyl 7-(4-butoxyethoxyphenyl)-1-[(2,5-diethylisooxazol-4-yl)methyl]-2,3-dihydro-1-benzazepine-4-carboxylate (309 mg) as yellow oil.

$^1$H-NMR (200 MHz, CDCl$_3$) δ 0.94 (t, 3H, J=7.4 Hz), 1.34–1.48 (m, 2H), 1.49–1.68 (m, 2H), 2.19 (s, 3H), 2.27 (s, 3H), 2.59 (t, 2H, J=4.0 Hz), 3.13 (t, 2H, J=4.4 Hz), 3.56 (t, 2H, J=6.6 Hz), 3.79–3.84 (m, 5H), 4.17 (t, 2H, J=4.6 Hz), 4.26 (s, 2H), 6.93 (d, 1H, J=8.4 Hz), 6.99 (d, 2H, J=8.8 Hz), 7.42–7.50 (m, 3H), 7.57 (d, 1H, J=2.2 Hz), 7.78 (s, 1H).

Reference Example 206

To a solution of methyl 7-(4-butoxyethoxyphenyl)-1-[(1-methylpyrazol-5-yl)methyl]-2,3-dihydro-1-benzazepine-4-carboxylate (222 mg) in a mixture of tetrahydrofuran (13 ml) and methanol (13 ml) was added 1N sodium hydroxide solution (4.4 ml), and the mixture was stirred at room temperature for 4 days. Then, to the mixture was added water at 0° C., and 1N hydrochloric acid was further added to neutral, and the mixture was extracted with ethyl acetate. The organic layer was washed with water and saturated brine and dried with magnesium sulfate. The solvent was evaporated under reduced-pressure, which was recrystallized from hexane-ethyl acetate to give 7-(4-butoxyethoxyphenyl)-1-[(2,5-dimethylisoxazol-4-yl)methyl]-2,3-dihydro-1-benzazepine-4-carboxylic acid (164 mg) as yellow crystals.

$^1$H-NMR (200 MHz, CDCl$_3$) δ 0.94 (t, 3H, J=7.0 Hz), 1.34–1.45 (m, 2H), 1.55–1.65 (m, 2H), 2.20 (s, 3H), 2.39 (s, 3H), 2.62 (br, 2H), 3.16 (br, 2H), 3.56 (t, 2H, J=6.6 Hz), 3.81 (t, 2H, J=4.4 Hz), 4.17 (t, 2H, J=5.0 Hz), 4.28 (s, 2H), 6.93–7.02 (m, 3H), 7.46–7.51 (m, 3H), 7.58 (d, 1H, J=2.2 Hz), 7.87 (s, 1H).

Anal. Calcd. C$_{29}$H$_{35}$N$_2$O$_5$ Calcd. C, 70.85, H, 7.18; N, 5.70. Found C, 70.71; H, 6.90; N, 5.43.

Reference Example 207

To a solution of methyl 7-(4-butoxyethoxyphenyl)-2,3-dihydro-1-benzazepine-4-carboxylate (400 mg) and furfural (485 mg) in 1,2-dichloroethane (15 ml) was added sodium triacetoxyborohydride (536 mg), and the mixture was stirred under nitrogen atmosphere at room temperature for 1 day. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate=3:1) to give methyl 7-(4-butoxyethoxyphenyl)-1-(2-furylmethyl)-2,3-dihydro-1-benzazepine-4-carboxylate (319 mg) as yellow oil.

$^1$H-NMR (200 MHz, CDCl$_3$) δ 0.93 (t, 3H, J=7.4 Hz), 1.30–1.45 (m, 2H), 1.46–1.70 (m, 2H), 2.77 (t, 2H, J=4.0 Hz), 3.30 (t, 2H, J=4.4 Hz), 3.55 (t, 2H, J=6.6 Hz), 3.78–3.83 (m, 5H), 4.16 (t, 2H, J=5.0 Hz), 4.49 (s, 2H), 6.28 (d, 2H,

J=3.4 Hz), 6.37 (dd, 1H, J=2.8, 1.8 Hz), 6.98 (d, 2H, J=8.8 Hz), 7.06 (d, 1H, J=8.8 Hz), 7.41–7.50 (m, 4H), 7.54 (d, 1H, J=2.2 Hz), 7.79 (s, 1H).

Reference Example 208

To a solution of methyl 7-(4-butoxyethoxyphenyl)-1-(2-furylmethyl)-2,3-dihydro-1-benzazepine-4-carboxylate (319 mg) in a mixture of tetrahydrofuran (21 ml) and methanol (21 ml) was added 1N sodium hydroxide solution (7 ml), and the mixture was stirred at room temperature for 5 days. Then, to the mixture was added water at 0° C., and 1N hydrochloric acid was further added to neutral, and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-(2-furylmethyl)-2,3-dihydro-1-benzazepine-4-carboxylic acid (256 mg) as yellow crystals.

$^1$H-NMR (200 MHz, CDCl$_3$) δ 0.93 (t, 3H, J=7.0 Hz), 1.34–1.50 (m, 2H), 1.55–1.70 (m, 2H), 2.79 (t, 2H, J=4.4 Hz), 3.33 (t, 2H, J=4.4 Hz), 3.56 (t, 2H, J=6.6 Hz), 3.81 (t, 2H, J=4.8 Hz), 4.17 (t, 2H, J=4.8 Hz), 4.50 (s, 2H), 6.29 (d, 1H, J=3.2 Hz), 6.38 (dd, 1H, J=2.8, 1.8 Hz), 6.99 (d, 2H, J=8.8 Hz), 7.08 (d, 1H, J=9.0 Hz), 7.42–7.50 (m, 4H), 7.55 (d, 1H, J=2.2 Hz), 7.90 (s, 1H).

Anal. Calcd. C$_{28}$H$_{31}$NO$_5$ Calcd. C, 72.86; H, 6.77; N, 3.03. Found C, 72.63; H, 6.67; N, 2.82.

Reference Example 209

To a solution of methyl 7-(4-butoxyethoxyphenyl)-2,3-dihydro-1-benzazepine-4-carboxylate (400 mg) and pyridine-2-carboxyaldehyde (542 mg) in 1,2-dichloroethane (15 ml) was added sodium triacetoxyborohydride (1.07 g), and the mixture was stirred under nitrogen atmosphere at room temperature for 4 days. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate= 1:1) to give methyl 7-(4-butoxyethoxyphenyl)-1-(2-pyridylmethyl)-2,3-dihydro-1-benzazepine-4-carboxylate (378 mg) as yellow oil.

$^1$H-NMR (200 MHz, CDCl$_3$) δ 0.93 (t, 3H, J=7.2 Hz), 1.34–1.45 (m, 2H), 1.50–1.65 (m, 2H), 2.84 (t, 2H, J=4.4 Hz), 3.40 (t, 2H, J=4.4 Hz), 3.55 (t, 2H, J=6.8 Hz), 3.78–3.82 (m, 5H), 4.15 (t, 2H, J=5.2 Hz), 4.71 (s, 2H), 6.82 (d, 1H, J=8.8 Hz), 6.97 (d, 2H, J=8.8 Hz), 7.21–7.29 (m, 2H), 7.35 (dd, 1H, J=8.8, 2.2 Hz), 7.46 (d, 2H, J=8.8 Hz), 7.56 (d, 1H, J=2.2 Hz), 7.67 (td, 1H, J=9.0, 2.0 Hz), 7.83 (s, 1H), 8.62 (d, 1H, J=4.0 Hz).

Reference Example 210

To a solution of methyl 7-(4-butoxyethoxyphenyl)-1-(2-pyridylmethyl)-2,3-dihydro-1-benzazepine-4-carboxylate (378 mg) in a mixture of tetrahydrofuran (24 ml) and methanol (24 ml) was added 1N sodium hydroxide solution (8 ml), and the mixture was stirred at room temperature for 2 days. Then, to the mixture was added water at 0° C., and 1N hydrochloric acid was further added to neutral, and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-(2-pyridylmethyl)-2,3-dihydro-1-benzazepine-4-carboxylic acid (260 mg) as yellow crystals.

$^1$H-NMR (200 MHz, CDCl$_3$) δ 0.93 (t, 3H, J=7.4 Hz), 1.30–1.48 (m, 2H), 1.54–1.68 (m, 2H), 2.87 (t, 2H, J=4.4 Hz), 3.43 (t, 2H, J=4.4 Hz), 3.55 (t, 2H, J=6.6 Hz), 3.80 (t, 2H, J=5.6 Hz), 4.74 (s, 2H), 6.83 (d, 1H, J=8.8 Hz), 6.97 (d, 2H, J=8.8 Hz), 7.20–7.31 (m, 2H), 7.37 (dd, 1H, J=8.8, 2.2 Hz), 7.46 (d, 2H, J=8.4 Hz), 7.58 (d, 1H, J=1.8 Hz), 7.69 (td, 1H, J=7.8, 2.0 Hz), 7.94 (s, 1H), 8.64 (d, 1H, J=5.2 Hz).

Anal. Calcd. C$_{29}$H$_{32}$N$_2$O$_4$.0.3H$_2$O Calcd. C, 72.87; H, 6.87; N, 5.86. Found C, 72.74; H, 6.73; N, 5.69.

Reference Example 211

To a solution of acetamide (4.0 g) in tetrahydrofuran (300 ml) was added sodium hydrogen carbonate (28.4 g), followed by addition of 80% ethyl bromopyruvate (21.5 g) at 0° C. The mixture was heated at 85° C. overnight, the temperature was returned to room temperature, the insolubles were filtered using Celite and the solvent was evaporated under reduced pressure. The resulting residue was dissolved in tetrahydrofuran (150 ml), and to the solution was added dropwise trifluoroacetic anhydride at 0° C. After concentrated under reduced pressure, to the mixture was added ethyl acetate, and the mixture was washed with saturated sodium hydrogen carbonate solution twice and further with saturated brine and dried with magnesium sulfate. The solvent was evaporated under reduced pressure, followed by distillation under reduced pressure to give ethyl 2-methyloxazole-4-carboxylate (4.67 g).

$^1$H-NMR (200 MHz, CDCl$_3$) δ 1.38 (t, 3H, J=7.4 Hz), 2.54 (s, 3H), 4.39 (q, 2H, J=7.4 Hz), 8.14 (s, 1H).

Reference Example 212

A suspension of aluminum lithium hydride (553 mg) in tetrahydrofuran (20 ml) was added dropwise a solution of ethyl 2-methyl-oxazole-4-carboxylate (2.26 g) in tetrahydrofuran (20 ml) under nitrogen atmosphere, and the mixture was stirred at room temperature for 6 hours. To the mixture were successively added water (0.55 ml), 15% sodium hydroxide solution (0.55 ml) and water (1.65 ml), the mixture was stirred at room temperature for 2 hours and dried with magnesium sulfate. The insolubles were filtered using Celite, and the solvent was evaporated under reduced pressure to give 4-hydroxymethyl-2-methyloxazole (1.11 g).

$^1$H-NMR (20.0 MHz, CDCl$_3$) δ 2.45 (s, 3H), 4.56 (d, 2H, J=1.0 Hz), 7.48 (s, 1H).

Reference Example 213

To a solution of oxalyl chloride (3.53 g) in dichloromethane (100 ml) was added dropwise a solution of DMSO (2.89 g) in dichloromethane (10 ml) at −78° C. Then, to the mixture was added dropwise a solution of 4-hydroxymethyl-2-methyloxazole in dichloromethane (50 ml), and the mixture was stirred at −45° C. for 1 hour. Then, to the mixture was added dropwise triethylamine (10.3 g) at −45° C., and the mixture was stirred at 0° C. for 30 minutes. To the mixture were added saturated aqueous ammonium chloride solution (50 ml) and water (200 ml), and the mixture was extracted with ethyl acetate and dried with magnesium sulfate. The solvent was evaporated under reduced pressure, and the resulting residue was purified with silica gel column chromatography (hexane:ethyl acetate= 1:1) to give 2-methyloxazole-4-carboxyaldehyde (0.10 g) as brown crystals.

$^1$H-NMR (200 MHz, CDCl$_3$) δ 2.55 (s, 3H), 8.17 (s, 1H), 9.91 (s, 1H).

Reference Example 214

To a solution of thioacetamide (11.9 g) in tetrahydrofuran (600 ml) was added sodium hydrogen carbonate (66.4 g), followed by addition of 80% ethyl bromopyruvate (50.0 g) at 0° C. The mixture was stirred overnight, the insolubles were filtered using Celite and the solvent was evaporated under reduced pressure. The resulting residue was dissolved in tetrahydrofuran (170 ml), and to the solution was added dropwise trifluoroacetic anhydride (170 ml) at 0° C., and the mixture was stirred at room temperature for 1 hour. To the mixture was added dropwise pyridine (200 ml) at 0° C., and the mixture was stirred at room temperature for 3 hours. The solvent was evaporated under reduced pressure, to the mixture was added ethyl acetate, and the mixture was washed with saturated sodium hydrogen carbonate solution and further with saturated brine and dried with magnesium sulfate. The solvent was evaporated under reduced pressure, and the resulting residue was purified with silica gel column chromatography (hexane:ethyl acetate=2:1) to give ethyl 2-methylthiazole-4-carboxylate (13.0 g) as brown crystals.

$^1$H-NMR (200 MHz, CDCl$_3$) δ 1.41 (t, 3H, J=7.4 Hz), 2.78 (s, 3H), 4.43 (q, 2H, J=7.4 Hz), 8.04 (s, 1H).

Reference Example 215

A suspension of aluminum lithium hydride (0.89 g) in tetrahydrofuran (20 ml) was added dropwise a solution of ethyl 2-methylthiazole-4-carboxylate (4.00 g) in tetrahydrofuran (30 ml) under nitrogen atmosphere, and the mixture was stirred at room temperature for 2 hours. To the mixture were successively added water (0.9 ml), 15% sodium hydroxide solution (0.9 ml) and water (2.7 ml), the mixture was stirred at room temperature for 2 hours and dried with magnesium sulfate. The insolubles were filtered using Celite, and the solvent was evaporated under reduced pressure to give 4-hydroxymethyl-2-methylthiazole (2.18 g).

$^1$H-NMR (200 MHz, CDCl$_3$) δ 2.71 (s, 3H), 4.73 (d, 2H, J=0.8 Hz), 7.03 (s, 1H).

Reference Example 216

To a solution of 4-hydroxymethyl-2-methylthiazole (2.18 g) in ethyl acetate (50 ml) was added active manganese (21.8 g), and the mixture was stirred at room temperature for 1 day. The insolubles were filtered using Celite, and the filtrate was concentrated under reduced pressure to give 2-methylthiazole-4-carboxyaldehyde (0.9 g) as brown oil.

$^1$H-NMR (200 MHz, CDCl$_3$) δ 2.80 (s, 3H), 8.05 (s, 1H), 9.99 (s, 1H).

Reference Example 217

To a solution of methyl 7-(4-butoxyethoxyphenyl)-2,3-dihydro-1-benzazepine-4-carboxylate (500 mg) and 2-methylthiazole-4-carboxyaldehyde (804 mg) in 1,2-dichloroethane (20 ml) was added sodium triacetoxyborohydride (1.6 g), and the mixture was stirred under nitrogen atmosphere at room temperature for 4 days. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate=3:2) to give methyl 7-(4-butoxyethoxyphenyl)-1-[(2-methylthiazol-4-yl)methyl]-2,3-dihydro-1-benzazepine-4-carboxylate (550 mg) as yellow oil.

$^1$H-NMR (200 MHz, CDCl$_3$) δ 0.93 (t, 3H, J=7.0 Hz), 1.34–1.45 (m, 2H), 1.54–1.65 (m, 2H), 2.74 (s, 3H), 2.83 (t, 2H, J=4.4 Hz), 3.38 (t, 2H, J=4.0 Hz), 3.55 (t, 2H, J=6.6 Hz), 3.78–3.83 (m, 5H), 4.16 (t, 2H, J=5.0 Hz), 4.65 (s, 2H), 6.89–6.99 (m, 4H), 7.37 (dd, 1H, J=8.8, 2.2 Hz), 7.46 (d, 2H, J=8.8 Hz), 7.54 (d, 1H, J=2.2 Hz), 7.81 (s, 1H).

Reference Example 218

To a solution of methyl 7-(4-butoxyethoxyphenyl)-1-[(2-methylthiazol-4-yl)methyl]-2,3-dihydro-1-benzazepine-4-carboxylate (550 mg) in a mixture of tetrahydrofuran (33 ml) and methanol (33 ml) was added solution (11 ml), and the mixture was stirred at room temperature for 2 days. Then, to the mixture was added water at 0° C., and 1N hydrochloric acid was further added to neutral, and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-[(2-methylthiazol-4-yl)methyl]-2,3-dihydro-1-benzazepine-4-carboxylic acid (427 mg) as yellow crystals.

$^1$H-NMR (200 MHz, CDCl$_3$) δ 0.93 (t, 3H, J=7.2 Hz), 1.34–1.45 (m, 2H), 1.58–1.65 (m, 2H), 2.75 (s, 3H), 2.85 (t, 2H, J=4.4 Hz), 3.40 (t, 2H, J=4.4 Hz), 3.55 (t, 2H, J=6.6 Hz), 3.80 (t, 2H, J=4.4 Hz), 4.16 (t, 2H, J=5.4 Hz), 4.66 (s, 2H), 6.90–7.00 (m, 4H), 7.40 (dd, 1H, J=9.4, 2.6 Hz), 7.46 (d, 2H, J=8.8 Hz), 7.55 (d, 1H, J=2.2 Hz), 7.91 (s, 1H).

Anal. Calcd. C$_{28}$H$_{32}$N$_2$O$_4$ Calcd. C, 68.27; H, 6.55; N, 5.69. Found C, 68.25; H, 6.69; N, 5.82.

Reference Example 219

In water (28 ml) and ice (100 cc) was suspended 5-amino-3-methylisothiazole hydrochloride (10.0 g), and concentrated sulfuric acid (28 ml) was added to the suspension. Then, to the mixture was added dropwise a solution of sodium nitrite (4.82 g) in water (100 ml) at 0° C. The mixture was stirred at 0° C. for 1 hour, and a solution of potassium iodide (11.6 g) in water (70 ml) was added dropwise to the mixture at 0° C. Then, the mixture was heated at 80° C. for 1 hour, and to the mixture was added ethyl acetate at 0° C., and the mixture was neutralized with potassium carbonate. After separation, the organic layer was washed with saturated brine and dried with magnesium sulfate. The solvent was evaporated under reduced pressure, and origin components were removed by silica gel column chromatography (ethyl acetate) to give 5-iodo-3-methylisothiazole (10.6 g) as deep brown oil.

$^1$H-NMR (200 MHz, CDCl$_3$) δ 2.51 (s, 3H), 7.15 (s, 1H).

Reference Example 220

To a solution of 5-iodo-3-methylisothiazole (10.0 g) in dry tetrahydrofuran (150 ml) was added dropwise n-butyllithium (33.3 ml, 1.6M solution in hexane) at −78° C. under nitrogen atmosphere. After 30 minutes, to the mixture was added dropwise DMF (9.7 g) at −78° C. under nitrogen atmosphere, the temperature was returned to room temperature, and the mixture was stirred for 2 hours. Then, to the mixture was added 1N hydrochloric acid (75 ml) at 0° C., and the mixture was stirred for 30 minutes and extracted with ethyl acetate. The extract was dried with magnesium sulfate, the solvent was evaporated under reduced pressure, and the resulting residue was subjected to silica gel column chromatography (ethyl acetate) to remove origin components to give 3-methylisothiazole-5-carboxyaldehyde (5.0 g) as deep brown oil.

$^1$H-NMR (200 MHz, CDCl$_3$) δ 2.59 (s, 3H), 7.54 (s, 1H), 10.08 (s, 1H).

Reference Example 221

To a solution of methyl 7-(4-butoxyethoxyphenyl)-2,3-dihydro-1-benzazepine-4-carboxylate (500 mg) and 3-methylthiazole-5-carboxyaldehyde (803 mg) in 1,2-dichloroethane (15 ml) was added sodium triacetoxyborohydride (807 mg), and the mixture was stirred under nitrogen atmosphere at room temperature for 1 day. Then, water was added to the mixture, and the mixture was extracted with ethyl acetate. The organic layer was washed with saturated brine and dried with magnesium sulfate. The solvent was evaporated under reduced pressure, and the resulting residue was purified by silica gel column chromatography (hexane:ethyl acetate=2:1) to give methyl 7-(4-butoxyethoxyphenyl)-1-[(3-methylthiazol-5-yl)methyl]-2,3-dihydro-1-benzazepine-5-carboxylate (640 mg) as yellow oil.

$^1$H-NMR (200 MHz, CDCl$_3$) δ 0.93 (t, 3H, J=7.2 Hz), 1.34–1.45 (m, 2H), 1.50–1.70 (m, 2H), 2.48 (s, 3H), 2.85 (t, 2H, J=4.4 Hz), 3.34 (t, 2H, J=4.8 Hz), 3.55 (t, 2H, J=6.6 Hz), 3.78–3.82 (m, 5H), 4.16 (t, 2H, J=5.0 Hz), 4.76 (s, 2H), 6.87–7.00 (m, 4H), 7.41 (dd, 1H, J=8.8, 2.2 Hz), 7.47 (d, 2H, J=8.8 Hz), 7.56 (d, 1H, J=2.2 Hz), 7.80 (s, 1H).

Reference Example 222

To a solution of methyl 7-(4-butoxyethoxyphenyl)-1-[(3-methylthiazol-5-yl)methyl]-2,3-dihydro-1-benzazepine-4-carboxylate (640 mg) in a mixture of tetrahydrofuran (39 ml) and methanol (39 ml) was added 1N sodium hydroxide solution (13 ml), and the mixture was stirred at room temperature for 1 day. Then, to the mixture was added water at 0° C., and 1N hydrochloric acid was further added to neutral, and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-[(3-methylthiazol-5-yl)methyl]-2,3-dihydro-1-benzazepine-4-carboxylic acid (460 mg) as yellow crystals.

$^1$H-NMR (200 MHz, CDCl$_3$) δ 0.93 (t, 3H, J=7.2 Hz), 1.34–1.45 (m, 2H), 1.55–1.69 (m, 2H), 2.49 (s, 3H), 2.87 (t, 2H, J=4.4 Hz), 3.37 (t, 2H, J=4.4 Hz), 3.56 (t, 2H, J=6.6 Hz), 3.81 (t, 2H, J=4.4 Hz), 4.16 (t, 2H, J=5.0 Hz), 4.78 (s, 2H), 6.89–7.01 (m, 4H), 7.40–7.49 (m, 3H), 7.58 (d, 1H, J=1.8 Hz), 7.91 (s, 1H).

Anal. Calcd. C$_{28}$H$_{32}$N$_2$O$_4$S Calcd. C, 68.27; H, 6.55; N, 5.69. Found C, 67.94; H, 6.55; N, 5.97.

Reference Example 223

To a solution of methyl 7-bromo-2,3-dihydro-1-benzazepine-4-carboxylate (200 mg) and pyridine (123 mg) in tetrahydrofuran (10 ml) was added 2-thienyl chloride (208 mg) at 0° C., and the mixture was heated at 78° C. overnight. After allowing to cool, to the mixture was added water, and the mixture was extracted with ethyl acetate. The organic layer was washed with water and saturated brine and dried with magnesium sulfate. The solvent was evaporated, which was recrystallized from hexane-ethyl acetate to give methyl 7-bromo-1-(2-thienylcarbonyl)-2,3-dihydro-1-benzazepine-4-carboxylate (236 mg) as colorless crystals.

$^1$H-NMR (200 MHz, CDCl$_3$) δ 2.98 (br, 2H), 3.82 (s, 3H), 6.73 (dd, 1H, J=4.0, 1.0 Hz), 6.80–6.85 (m, 1H), 6.91 (d, 1H, 8.8), 7.26–7.31 (m, 1H), 7.37 (dd, 1H, J=5.2, 1.4 Hz), 7.68–7.69 (m, 2H).

Anal. Calcd. C$_{17}$H$_{14}$NO$_3$Br Calcd. C, 52.05; H, 3.60; N, 3.57. Found C, 52.05; H, 3.45; N, 3.38.

Reference Example 224

In toluene (10 ml), ethanol (1.0 ml) and water (1.0 ml) were suspended methyl 7-bromo-1-(2-thienylcarbonyl)-2,3-dihydro-1-benzazepine-4-carboxylate (210 mg), 4-butoxyethoxyphenyl borate (166 mg) and potassium carbonate (192 mg), and the mixture was stirred for 30 minutes under argon atmosphere. Then, to the suspension was added tetrakistriphenylphosphinepalladium (43 mg), and the mixture was heated at 100° C. for 5 hours under argon atmosphere. After allowing to cool, to the mixture was added water, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate= 1:1) to give methyl 7-(4-butoxyethoxyphenyl)-1-(2-thienylcarbonyl)-2,3-dihydro-1-benzazepine-4-carboxylate (201 mg) as colorless oil.

$^1$H-NMR (200 MHz, CDCl$_3$) δ 0.94 (t, 3H, J=7.4 Hz), 1.30–1.45 (m, 2H), 1.50–1.65 (m, 2H), 3.00 (br, 2H), 3.56 (t, 2H, J=7.0 Hz), 3.79–3.84 (m, 5H), 4.18 (t, 2H, J=4.8 Hz), 6.74–6.82 (m, 2H), 7.02 (d, 2H, J=8.8 Hz), 7.08 (d, 1H, J=8.4 Hz), 7.32–7.40 (m, 2H), 7.54 (d, 2H, J=8.8 Hz), 7.72 (d, 1H, J=2.2 Hz), 7.83 (s, 1H).

Reference Example 225

To a solution of methyl 7-(4-butoxyethoxyphenyl)-1-(2-thienylcarbonyl)-2,3-dihydro-1-benzazepine-4-carboxylate (200 mg) in a mixture of tetrahydrofuran (12 ml) and methanol (12 ml) was added 1N sodium hydroxide solution (4 ml), and the mixture was stirred at room temperature for 1 day. Then, to the mixture was added water at 0° C., and 1N hydrochloric acid was further added to neutral, and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-(2-thienylcarbonyl)-2,3-dihydro-1-benzazepine-4-carboxylic acid (171 mg) as yellow crystals.

$^1$H-NMR (200 MHz, CDCl$_3$) δ 0.94 (t, 3H, J=7.4 Hz), 1.34–1.45 (m, 2H), 1.50–1.70 (m, 2H), 3.02 (br, 2H), 3.56 (t, 2H, J=6.6 Hz), 3.82 (t, 2H, J=4.4 Hz), 4.18 (t, 2H, J=5.0 Hz), 6.72–6.83 (m, 2H), 7.02 (d, 2H, J=8.8 Hz), 7.09 (d, 1H, J=8.4 Hz), 7.34–7.42 (m, 2H), 7.54 (d, 2H, J=8.8 Hz), 7.74 (d, 1H, J=2.2 Hz), 7.92 (s, 1H).

Anal. Calcd. C$_{28}$H$_{29}$NOS Calcd. C, 68.41; H, 5.95; N, 2.85. Found C, 68.18; H, 6.03; N, 2.84.

Reference Example 226

To a suspension of 60% sodium hydride (2.3 g) in tetrahydrofuran (40 ml) which had been washed with hexane three times was added a solution of 4-bromopyrazole (7.0 g) in tetrahydrofuran (40 ml) at 0° C. under nitrogen atmosphere, the temperature was returned room temperature, and the mixture was stirred for 1 hour. To this mixture was added dropwise a solution of ethyl iodide (8.9 g) in tetrahydrofuran (30 ml) at 0° C. under nitrogen atmosphere, the temperature was returned to room temperature, and the mixture was stirred overnight. The solution was diluted with tetrahydrofuran, and the insolubles were filtered using Celite. The filtrate was concentrated under reduced pressure, hexane was added thereto, and the insolubles were filtered. The filtrate was concentrated under reduced pressure to give 4-bromo-1-ethylpyrazole (7.72 g) as light yellow liquid.

$^1$H-NMR (200 MHz, CDCl$_3$) δ 1.48 (t, 3H, J=7.8 Hz), 4.16 (q, 2H, J=7.4 Hz), 7.41 (s, 1H), 7.45 (s, 1H).

Reference Example 227

To a solution of 4-bromo-1-ethylpyrazole (7.0 g) in dry tetrahydrofuran (150 ml) was added dropwise n-butyllithium (30 ml, 1.6M solution in hexane) at −78° C. under nitrogen atmosphere. After 30 minutes, to the mixture was added dropwise DMF (14.6 g) at −78° C. under nitrogen atmosphere, the temperature was returned to room temperature, and the mixture was stirred for 1 hour. Then, to the mixture was added 1N hydrochloric acid (60 ml) at 0° C., and the mixture was stirred for 30 minutes, which was made basic with 1N sodium hydroxide solution, and the mixture was extracted with ethyl acetate five times. The extract was dried with magnesium sulfate, the solvent was evaporated under reduced pressure, and the resulting residue was subjected to silica gel column chromatography (hexane:ethyl acetate=1:2) to give 1-ethylpyrazole-4-carboxyaldehyde (2.9 g) as light yellow oil.

$^1$H-NMR (200 MHz, CDCl$_3$) δ 1.54 (t, 3H, J=7.2 Hz), 4.24 (q, 2H, J=7.4 Hz), 7.95 (s, 1H), 7.97 (s, 1H), 9.86 (s, 1H).

Reference Example 228

To a solution of methyl 7-(4-butoxyethoxyphenyl)-2,3-dihydro-1-benzazepine-4-carboxylate (300 mg) and 1-ethylpyrazole-4-carboxyaldehyde (471 mg) in 1,2-dichloroethane (10 ml) was added sodium triacetoxyborohydride (804 mg), and the mixture was stirred under nitrogen atmosphere at room temperature for 2 days. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate=1:1) to give methyl 7-(4-butoxyethoxyphenyl)-1-[(1-ethylpyrazol-4-yl)methyl]-2,3-dihydro-1-benzazepine 5-carboxylate (382 mg) as yellow oil.

$^1$H-NMR (200 MHz, CDCl$_3$) δ 0.93 (t, 3H, J=7.0 Hz), 1.34–1.70 (m, 7H), 2.76 (br, 2H), 3.27 (br, 2H), 3.56 (t, 2H, J=6.6 Hz), 3.39–3.83 (m, 5H), 4.07–4.29 (m, 4H), 4.42 (s, 2H), 6.94–7.00 (m, 3H), 7.33–7.54 (m, 6H), 7.79 (s, 1H).

Reference Example 229

To a solution of methyl 7-(4-butoxyethoxyphenyl)-1-[(1-ethylpyrazol-4-yl)methyl]-2,3-dihydro-1-benzazepine-4-carboxylate (382 mg) in a mixture of tetrahydrofuran (24 ml) and methanol (24 ml) was added 1N sodium hydroxide solution (8 ml), and the mixture was stirred at room temperature for 1 day. Then, to the mixture was added water at 0° C., and 1N hydrochloric acid was further added to neutral, and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-[(1-ethylpyrazol-4-yl)methyl]-2,3-dihydro-1-benzazepine-4-carboxylic acid (287 mg) as yellow crystals.

$^1$H-NMR (200 MHz, CDCl$_3$) δ 0.93 (t, 3H, J=7.2 Hz), 1.34–1.65 (m, 7H), 2.78 (br, 2H), 3.29 (br, 2H), 3.56 (t, 2H, J=6.6 Hz), 3.81 (t, 2H, J=5.2 Hz), 4.11–4.22 (m, 4H), 4.44 (s, 2H), 6.95–7.01 (m, 3H), 7.34 (s, 1H), 7.41–7.50 (m, 4H), 7.56 (d, 1H, J=2.2 Hz), 7.79 (s, 1H).

Anal. Calcd. C$_{29}$H$_{35}$N$_3$O$_4$ Calcd. C, 71.14; H, 7.21; N, 8.58. Found C, 70.84; H, 7.47; N, 8.48.

Reference Example 230

To a solution of ethyl 2-methyldioxolan-2-ylacetate (2.0 g) in methanol (69 ml) was added 1N sodium hydroxide solution (23 ml), and the mixture was stirred at room temperature overnight. Then, the mixture was neutralized with 1N hydrochloric acid, and the solvent was evaporated under reduced pressure. To the mixture was added ethyl acetate, and the mixture was dried with magnesium sulfate. The solvent was evaporated under reduced pressure to give 2-methyldioxolan-2-ylacetic acid (1.63 g) as colorless $^1$H-NMR (200 MHz, CDCl$_3$) δ 1.51 (s, 3H), 2.74 (s, 2H), 4.03 (s, 4H).

Reference Example 231

To a solution of 5-(2-hydroxyethyl)-4-methylthiazole (2.5 g) in dichloromethane (125 ml) was added Celite (10.0 g), and to the mixture was added PCC (18.9 g), which was stirred for 2 hours under nitrogen atmosphere. The insolubles were filtered, followed by washing with ether. The solvent was evaporated under reduced pressure, and the residue was subjected to Florisil column chromatography (ethyl acetate) to remove origin components, and the residue was recrystallized from hexane-ethyl acetate to give 4-methylthiazole-5-carboxyaldehyde (692 mg).

$^1$H-NMR (200 MHz, CDCl$_3$) δ 2.80 (s, 3H), 8.98 (s, 1H), 10.15 (s, 1H).

Reference Example 232

To a solution of methyl 7-(4-butoxyethoxyphenyl)-2,3-dihydro-1-benzazepine-4-carboxylate (300 mg) and 4-methylthiazole-5-carboxyaldehyde (482 mg) in 1,2-dichloroethane (15 ml) was added sodium triacetoxyborohydride (804 mg), and the mixture was stirred under nitrogen atmosphere at room temperature for 6 days. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate=1:1) to give methyl 7-(4-butoxyethoxyphenyl)-1-[(4-methylthiazol-5-yl)methyl]-2,3-dihydro-1-benzazepine-5-carboxylate (284 mg) as yellow oil.

$^1$H-NMR (200 MHz, CDCl$_3$) δ 0.93 (t, 3H, J=7.4 Hz), 1.34–1.45 (m, 2H), 1.50–1.70 (m, 2H), 2.50 (s, 3H), 2.76 (t, 2H, J=5.2 Hz), 3.26 (t, 2H, J=5.2 Hz), 3.55 (t, 2H, J=6.6 Hz), 3.78–3.83 (m, 5H), 4.16 (t, 2H, J=4.4 Hz), 4.65 (s, 2H), 6.93 (d, 1H, J=8.8 Hz), 6.98 (d, 2H, J=9.2 Hz), 7.41–7.50 (m, 3H), 7.56 (d, 1H, J=2.6 Hz), 7.78 (s, 1H), 8.66 (s, 1H).

Reference Example 233

To a solution of methyl 7-(4-butoxyethoxyphenyl)-1-[(4-methylthiazol-5-yl)methyl]-2,3-dihydro-1-benzazepine-4-carboxylate (284 mg) in a mixture of tetrahydrofuran (18 ml) and methanol (18 ml) was added 1N sodium hydroxide solution (6 ml), and the mixture was stirred at room temperature for 1 day. Then, to the mixture was added water at 0° C., and 1N hydrochloric acid was further added to neutral, and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-[(4-methylthiazol-5-yl)methyl]-2,3-dihydro-1-benzazepine-4-carboxylic acid (201 mg) as yellow crystals.

$^1$H-NMR (200 MHz, CDCl$_3$) δ 0.93 (t, 3H, J=7.2 Hz), 1.30–1.50 (m, 2H), 1.50–1.70 (m, 2H), 2.51 (s, 3H), 2.79 (br, 2H), 3.29 (br, 2H), 3.56 (t, 2H, J=6.6 Hz), 3.81 (t, 2H, J=4.8 Hz), 4.17 (t, 2H, J=5.2 Hz), 4.67 (s, 2H), 6.92–7.01 (m, 3H), 7.43–7.50 (m, 3H), 7.58 (d, 1H, J=2.6 Hz), 7.89 (s, 1H), 8.68 (s, 1H).

Anal. Calcd. C$_{28}$H$_{32}$N$_2$O$_4$ Calcd. C, 68.27; H, 6.55; N, 5.69. Found C, 67.95; H, 6.56; N, 5.63.

Reference Example 234

To a mixture (135.0 g) of methyl 7-bromo-1-[(4-methylphenyl)sulfonyl]-oxo-2,3,4,5-tetrahydro-1-benzazepine-4-carboxylate and ethyl 7-bromo-1-[(4-methylphenyl)sulfonyl]-oxo-2,3,4,5-tetrahydro-1-benzazepine-4-carboxylate in tetrahydrofuran (1200 ml) was added sodium borohydride (11.1 g) at −65° C., and to the mixture was added dropwise methanol (120 ml). After completion of the addition, the mixture was stirred at −15° C. to 25° C. for 1.5 hours, to the mixture was added dropwise acetone (67.8 g, 1.17 mol) at −25° C., and the mixture was further stirred for 30 minutes. To the mixture were added ethyl acetate and water at −45° C., which was separated, and the organic layer was washed with saturated brine and dried with magnesium sulfate. The solvent was evaporated under reduced pressure to give brown oil (152.3 g). The oil was dissolved in dry tetrahydrofuran (1000 ml) as it was, and to the solution was added dropwise methanesulfonyl chloride (50.1 g) at 0° C. under nitrogen atmosphere. After completion of the addition, the mixture was stirred at room temperature for 1 hour, and to the mixture was added dropwise DBU (66.6 g), which was stirred for 5 hours. To the mixture was added water, the mixture was extracted with ethyl acetate, and the organic layer was washed with 1N hydrochloric acid twice and further with water and saturated brine, followed by drying with magnesium sulfate. The solvent was evaporated under reduced pressure to give brown oil (148 g). This was dissolved in acetic acid (520 ml), to the solution was added concentrated sulfuric acid (260 ml, 4.88 mol) at 0° C., and the mixture was heated at 90° C. for 3 hours. After allowing to cool, to the mixture was added water (40 ml), and the mixture was heated again at 90° C. for 2.5 hours. After allowing to cool, the solvent was evaporated under reduced pressure. Ice was added to the resulting residue, and 6N sodium hydroxide solution was added to pH=4. The precipitated solid was collected by filtration, and the solid was dissolved in 1N sodium hydroxide solution (1500 ml). The insolubles were removed by filtration, 2N hydrochloric acid was added to the filtrate to adjust to pH=4 at 0° C., and the precipitated solid was collected by filtration. The solid was dried under reduced pressure to give 7-bromo-2,3-dihydro-1-benzazepine-4-carboxylic acid (69.4 g) as green solid.

$^1$H-NMR (200 MHz, DMSO-d$_6$) δ 2.36 (t, 2H, J=4.8 Hz), 2.87 (t, 2H, J=4.8 Hz), 6.35 (d, 1H, J=8.6, 2.6 Hz), 6.84 (dd, 1H, J=8.6, 2.6 Hz), 7.08 (d, 1H, J=2.6 Hz), 7.12 (s, 1H).

Reference Example 235

To a suspension of 7-bromo-2,3-dihydro-1-benzazepine-4-carboxylic acid (68.2 g) in methanol (100 ml) was added concentrated sulfuric acid (37.3 g) at 0° C., and the mixture was heated at 80° C. for 10 hours. After allowing to cool, the solvent was evaporated under reduced pressure. Ethyl acetate and water were added thereto and 1N sodium hydroxide solution was added to pH=4 at 0° C. The solution was separated, and the organic phase was washed with water and saturated brine and dried with magnesium sulfate. The solvent was evaporated under reduced pressure, the resulting residue was subjected to silica gel column to remove origin components (ethyl acetate), and the resulting solid was washed with diisopropyl ether to give methyl 7-bromo-2,3-dihydro-1-benzazepine-4-carboxylate (44.0 g). The filtrate was purified with silica gel column (hexane:ethyl acetate=4:1) to give methyl 7-bromo-2,3-dihydro-1-benzazepine-4-carboxylate (3.4 g).

$^1$H-NMR (200 MHz, CDCl$_3$) δ 2.86 (t, 2H, J=5.2 z), 3.36 (t, 2H, J=5.2 Hz), 3.80 (s, 3H), 4.57 (br, 1H), 6.49 (d, 1H, J=8.4 Hz), 7.15 (dd, 1H, J=8.4, 2.2 Hz), 7.38 (d, 1H, J=2.2 Hz), 7.53 (s, 1H).

Reference Example 236

In toluene (100 ml), ethanol (10 ml) and water (10 ml) were suspended methyl 7-bromo-2,3-dihydro-1-benzazepine-4-carboxylate (3.0 g), 4-propoxyethoxyphenyl borate (3.1 g) and potassium carbonate (3.8 g), and the suspension was stirred for 30 minutes under argon atmosphere. Then, to the suspension was added tetrakistriphenylphosphinepalladium (860 mg), and the mixture was heated at 100° C. for 8 hours under argon atmosphere. After allowing to cool, water was added thereto, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate=3:1) to give the solid, which was washed with hexane to give methyl 7-(4-propoxyethoxyphenyl)-2,3-dihydro-1-benzazepine-4-carboxylate (2.59 g) as yellow crystals.

$^1$H-NMR (200 MHz, CDCl$_3$) δ 0.94 (3H, t, J=7.2 Hz), 1.56–1.74 (2H, m), 2.88 (2H, t, J=4.8 Hz), 3.41 (2H, t, J=4.8 Hz), 3.51 (2H, t, J=7.0 Hz), 3.78–3.83 (m, 5H), 4.16 (2H, t, J=4.8 Hz), 6.66 (1H, d, J=8.0 Hz), 6.97 (2H, d, J=6.68 Hz), 7.31 (1H, dd, J=8.0, 2.2 Hz), 7.43–7.47 (3H, m), 7.725 (1H, s).

Reference Example 237

In toluene (200 ml) and ethanol (35 ml) were suspended methyl 7-bromo-2,3-dihydro-1-benzazepine-4-carboxylate (5.0 g), 4-butoxyethoxyphenyl borate (4.6 g) and 1M potassium carbonate solution (35 ml), and the mixture was stirred for 30 minutes under argon atmosphere. Then, to the mixture was added tetrakistriphenylphosphinepalladium (1 g), and the mixture was heated at 100° C. overnight under argon atmosphere. After allowing to cool, to the mixture was added water, and the mixture was extracted with ethyl acetate. The organic layer was washed a with saturated brine and dried with magnesium sulfate. The solvent was evaporated under reduced pressure, and the resulting residue was purified with silica gel column chromatography (hexane:ethyl acetate=4:1) to give the solid, which was washed with hexane to give methyl 7-(4-butoxyethoxyphenyl)-2,3-dihydro-1-benzazepine-4-carboxylate (5.7 g) as yellow crystals.

$^1$H-NMR (200 MHz, CDCl$_3$) δ 0.93 (3H, t, J=7.3 Hz), 1.29–1.49 (2H, m), 1.55–1.68 (2H, m), 2.86–2.95 (2H, m), 3.41–3.45 (2H, m), 3.56 (2H, t, J=6.6 Hz), 3.81 (2H, t, J=5.0 Hz), 4.16 (2H, t, J=5.0 Hz), 6.68 (1H, d, J=8.6 Hz), 6.98 (2H, d, J=8.8 Hz), 7.34 (1H, d, J=8.6, 2.0 Hz), 7.43–7.48 (3H, m), 7.85 (1H, s).

C$_{23}$H$_{27}$NO$_4$ Calcd. C, 72.42; H, 7.13; N, 3.67. Found C, 72.32; H, 7:01; N, 3.84.

Reference Example 238

To a suspension of 60% sodium hydride (4.2 g) in tetrahydrofuran (40 ml) which had been washed with hexane three times was added dropwise a solution of 4-bromopyrazole (7.0 g) in tetrahydrofuran (50 ml) at 0° C. under nitrogen atmosphere, the temperature was returned to room temperature, and the mixture was stirred for 1 hour. To the mixture was added dropwise a solution of ethyl iodide (17.8 g) in tetrahydrofuran (30 ml) at 0° C. under nitrogen atmosphere and the mixture was refluxed for 1 day. The solution was diluted with tetrahydrofuran, and the insolubles were filtered using Celite. After the filtrate was concentrated under reduced pressure, hexane was further added, and the insolubles were removed by filtration. The filtrate was concentrated under reduced pressure, followed by distillation under reduced pressure to give 4-bromo-1-isopropylpyrazole (5.8 g) as light yellow liquid.

$^1$H-NMR (200 MHz, CDCl$_3$) δ 1.50 (d, 6H, J=6.6 Hz), 4.40–4.54 (m, 1H), 7.43 (s, 1H), 7.45 (s, 1H).

Reference Example 239

To a solution of 4-bromo-1-isopropylpyrazole (5.0 g) in dry ether (75 ml) was added dropwise n-butyllithium (22 ml, 1.6M solution in hexane) at −78° C. under nitrogen atmosphere. After 30 minutes, to the mixture was added dropwise DMF (9.7 g) at −78° C. under nitrogen atmosphere, the temperature was returned to room temperature and the mixture was stirred for 1 hour. Then, to the mixture was added 1N hydrochloric acid (40 ml) at 0° C., and the mixture was stirred for 30 minutes, made basic with 1N sodium hydroxide solution, extracted with ethyl acetate five times and dried with magnesium sulfate. The solvent was evaporated under reduced pressure to give 1-isopropylpyrazole-4-carboxaldehyde (3.6 g) as light yellow oil.

$^1$H-NMR (200 MHz, CDCl$_3$) δ 1.55 (d, 6H, J=6.6 Hz), 4.48–4.61 (m, 1H), 7.98 (s, 2H), 9.86 (s, 1H).

Reference Example 240

To a solution of methyl 7-(4-butoxyethoxyphenyl)-2,3-dihydro-1-benzazepine-4-carboxylate (300 mg) and 1-isopropylpyrazole-4-carboxaldehyde (524 mg) in 1,2-dichloroethane (10 ml) was added sodium triacetoxyborohydride (964 mg), and the mixture was stirred under nitrogen atmosphere at room temperature for 4 days. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate=3:1) to give methyl 7-(4-butoxyethoxyphenyl)-1-[(1-isopropylpyrazol-4-yl)methyl]-2,3-dihydro-1-benzazepine-5-carboxylate (392 mg) as yellow oil.

$^1$H-NMR (200 MHz, CDCl$_3$) δ 0.93 (t, 3H, J=7.0 Hz), 1.34–1.65 (m, 10H), 2.75 (t, 2H, J=5.0 Hz), 3.26 (t, 2H, J=5.0 Hz), 3.55 (t, 2H, J=6.6 Hz), 3.78–3.83 (m, 5H), 4.16 (t, 2H, J=4.8 Hz), 4.42 (s, 2H), 4.44–4.61 (m, 1H), 6.94–7.00 (m, 3H), 7.36–7.50 (m, 5H), 7.55 (d, 1H, J=2.6 Hz), 7.79 (s, 1H).

Reference Example 241

To a solution of methyl 7-(4-butoxyethoxyphenyl)-1-[(1-ethylpyrazol-4-yl)methyl]-2,3-dihydro-1-benzazepine-4-carboxylate (392 mg) in a mixture of tetrahydrofuran (24 ml) and methanol (24 ml) was added 1N sodium hydroxide solution (8 ml), and the mixture was stirred at room temperature for 3 days. Then, to the mixture was added water at 0° C., and 1N hydrochloric acid was further added to neutral, and the mixture was extracted with ethyl acetate. The organic layer was washed with water and saturated brine and dried with magnesium sulfate. The solvent was evaporated under reduced pressure, which was recrystallized from hexane-ethyl acetate to give 7-(4-butoxyethoxyphenyl)-1-[(1-isopropylpyrazol-4-yl)methyl]-2,3-dihydro-1-benzazepine-4-carboxylic acid (229 mg) as yellow crystals.

$^1$H-NMR (200 MHz, CDCl$_3$) δ 0.93 (t, 3H, J=7.0 Hz), 1.34–1.45 (m, 2H), 1.50 (d, 6H, J=6.6 Hz), 1.53–1.68 (m, 2H), 2.77 (br, 2H), 3.29 (br, 2H), 3.56 (t, 2H, J=6.6 Hz), 3.81 (t, 2H, J=5.2 Hz), 4.16 (t, 2H, J=5.0 Hz), 4.43–4.52 (m, 3H), 6.96–7.00 (m, 3H), 7.36–7.55 (m, 6H), 7.89 (s, 1H).

Anal. Calcd. C$_{30}$H$_{37}$N$_3$O$_4$ Calcd. C, 71.54; H, 7.40; N, 8.34. Found C, 71.16; H, 7.24; N, 8.23.

Reference Example 242

To a solution of methyl 7-bromo-2,3-dihydro-1-benzazepine-4-carboxylate (800 mg) and 1-ethylpyrazole-4-carboxaldehyde (1.05 g) in 1,2-dichloroethane (30 ml) were added sodium triacetoxyborohydride (3.0 g) and acetic acid (853 mg) and the mixture was stirred under nitrogen atmosphere at room temperature for 2 days. Then, water was added to the mixture, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate=1:1) to give methyl 7-bromo-1-[(1-ethylpyrazol-4-yl)methyl]-2,3-dihydro-1-benzazepine-5-carboxylate (593 mg) as yellow oil.

$^1$H-NMR (200 MHz, CDCl$_3$) δ 1.48 (t, 3H, J=6.6 Hz), 2.73 (t, 2H, J=4.8 Hz), 3.22 (t, 2H, J=4.8 Hz), 3.80 (s, 3H), 4.15 (q, 2H, J=7.4 Hz), 4.36 (s, 2H), 6.77 (d, 1H, J=8.8 Hz), 7.22–7.29 (m, 2H), 7.42 (s, 1H), 7.45 (d, 1H, J=2.2 Hz), 7.60 (s, 1H).

Reference Example 243

In toluene (15 ml), ethanol (1.5 ml) and water (1.5 ml) were suspended methyl 7-bromo-[(1-ethylpyrazol-4-yl)methyl]-2,3-dihydro-1-benzazepine-4-carboxylate (550 mg), 4-propoxyethoxyphenyl borate (320 mg) and potassium carbonate (506 mg), and the suspension was stirred for 30 minutes under argon atmosphere. Then, to the suspension was added tetrakistriphenylphosphinepalladium (81 mg), and the mixture was heated at 100° C. for 6 hours under argon atmosphere. After allowing to cool, water was added thereto, and the mixture was extracted with ethyl acetate. The organic layer was washed with saturated brine and dried with magnesium sulfate. The solvent was evaporated under reduced pressure, and the resulting residue was purified with silica gel column chromatography (hexane:ethyl acetate=1:1) to give methyl 1-[(1-ethylpyrazol-4-yl)methyl]-7-(4-propoxyphenyl)-2,3-dihydro-1-benzazepine-4-carboxylate (370 mg) as yellow oil.

$^1$H-NMR (200 MHz, CDCl$_3$) δ 1.06 (t, 3H, J=7.6 Hz), 1.48 (t, 3H, J=7.4 Hz), 1.75–1.95 (m, 2H), 2.76 (t, 2H, J=5.4 Hz), 3.27 (t, 2H, J=5.4 Hz), 3.81 (s, 3H), 3.96 (t, 2H, J=6.6 Hz), 4.16 (q, 2H, J=7.4 Hz), 4.42 (s, 2H), 6.93–6.97 (m, 3H), 7.33 (s, 1H), 7.38–7.49 (m, 4H), 7.54 (d, 1H, J=2.4 Hz), 7.79 (s, 1H).

Reference Example 244

To a solution of methyl 1-[(1-ethylpyrazol-4-yl)methyl]-7-(4-propoxyphenyl)-2,3-dihydro-1-benzazepine-4- carboxylate (370 mg) in a mixture of tetrahydrofuran (24 ml) and methanol (24 ml) was added 1N sodium hydroxide solution (8 ml), and the mixture was stirred at room temperature for 1 day. Then, to the mixture was added water at 0° C., and 1N hydrochloric acid was further added to neutral, and the mixture was extracted with ethyl acetate. The organic layer was washed with water and saturated brine and dried with magnesium sulfate. The solvent was evaporated under reduced pressure to give 1-[(1-ethylpyrazol-4-yl) methyl]-7-(4-propoxyphenyl)-2,3-dihydro-1-benzazepine-4-carboxylic acid (330 mg) as yellow oil.

$^1$H-NMR (200 MHz, CDCl$_3$) δ 1.06 (t, 3H, J=7.6 Hz), 1.49 (t, 3H, J=7.4 Hz), 1.78–1.89 (m, 2H), 2.78 (br, 2H), 3.30 (br, 2H), 3.96 (t, 2H, J=6.6 Hz), 4.16 (q, 2H, J=7.4 Hz), 4.44 (s, 2H), 6.93–6.99 (m, 3H), 7.34 (s, 1H), 7.40–7.50 (m, 4H), 7.56 (d, 1H, J=2.2 Hz), 7.89 (s, 1H).

Reference Example 245

In methanol (25 ml) and THF (10 ml) was dissolved methyl 7-[(4-(2-butoxyethoxy)phenyl]-1-(2-methylthiazol-4-yl)-2,3-dihydro-1H-1-benzazepine-4-carboxylate (0.17 g). To the solution was added 1N sodium hydroxide solution (4 ml), and the mixture was stirred at room temperature overnight, heated at 60° C. for 5 hours, concentrated, neutralized with 1N hydrochloric acid and extracted with ethyl acetate. The organic layer was washed with water and saturated brine and dried with anhydrous magnesium sulfate. The solvent was evaporated to give 7-[4-(2-butoxyethoxy)phenyl]-1-(2-methylthiazol-4-yl)-2,3-dihydro-1H-1-benzazepine-4-carboxylic acid (0.12 g) as yellow crystals.

mp 155–158° C.

$^1$-NMR (δ ppm, CDCl$_3$) 0.94 (3H, t, J=7.2 Hz), 1.31–1.49 (2H, m), 1.55–1.69 (2H, m), 2.67 (3H, s), 2.87 (2H, t-like), 3.56 (2H, t, J=6.6 Hz), 3.82 (2H, t, J=4.9 Hz), 3.96 (2H, t-like), 4.17 (2H, t, J=4.9 Hz), 5.97 (1H, s), 7.00 (2H, d, J=8.6 Hz), 7.44 (2H, s), 7.51 (2H, d, J=8.6 Hz), 7.63 (1H, s), 7.88 (1H, s).

IR (KBr) ν: 2926, 1674, 1530, 1495 cm$^{-1}$.

Reference Example 246

In THF (6.0 ml) was dissolved methyl 7-[4-(2-butoxyethoxy)phenyl]-2,3-dihydro-1-benzazepine-4-carboxylate (0.30 g). To the solution was added 60% sodium hydride (61 mg) under ice-cooling and the mixture was stirred at room temperature for 1 hour. To the mixture was added crotyl bromide (0.31 ml), and the mixture was stirred at 60° C. for 4 days. After cooled to room temperature, the reaction solution was added to water, and the mixture was extracted with ethyl acetate. The extract was washed with saturated brine and dried with magnesium sulfate. The solvent was removed under reduced pressure, and the resulting residue was purified with silica gel column chromatography (hexane/ethyl acetate=4/1) to give methyl 7-[4-(2-butoxyethoxy)phenyl]-1-crotyl-2,3-dihydro-1-benzazepine-4-carboxylate (0.23 g).

$^1$H-NMR (200 MHz, CDCl$_3$) δ 0.93 (3H, t, J=7.2 Hz), 1.33–1.45 (2H, m), 1.54–1.65 (2H, m), 1.75 (3H, d, J=5.2 Hz), 2.71–2.82 (2H, m), 3.22–3.27 (2H, m), 3.55 (2H, t, J=6.6 Hz), 3.77–3.82 (2H, m), 3.81 (3H, s), 3.88 (2H, d, J=4.4 Hz), 5.22 (1H, m), 5.63 (1H, m), 6.85–7.01 (3H, m), 7.36–7.49 (4H, m), 7.77 (1H, s).

Reference Example 247

In THF (4.4 ml)/methanol (4.4 ml) was dissolved methyl 7-[4-(2-butoxyethoxy)phenyl]-1-crotyl-2,3-dihydro-1-benzazepine-4-carboxylate (0.22 g). To the solution was added 1N sodium hydroxide solution (2.2 ml), and the mixture was stirred at 40° C. for 6 hours. pH was adjusted to approximate 5 with 1N hydrochloric acid, and the solvent was concentrated to half under reduced pressure. The concentrated material was extracted with ethyl acetate, washed with saturated brine and dried with magnesium sulfate. The solvent was removed under reduced pressure, and the resulting residue was washed with hexane/ethyl acetate=8/1) to give 7-[4-(2-butoxyethoxy)phenyl]-1-crotyl-2,3-dihydro-1-benzazepine-4-carboxylic acid (198 mg).

$^1$H-NMR (200 MHz, CDCl$_3$) δ 0.93 (3H, t, J=7.2 Hz), 1.34–1.45 (2H, m), 1.54–1.65 (2H, m), 1.76 (3H, d, J=5.4 Hz), 2.82 (2H, m), 3.27 (2H, m), 3.55 (2H, t, J=6.6 Hz), 3.78–3.83 (2H, m), 3.89 (3H, s), 4.13–4.18 (2H, m), 5.23 (1H, m), 5.66 (1H, m), 6.88 (1H, d, J=6.2 Hz), 6.98 (2H, d, J=8.8 Hz), 7.38–7.53 (4H, m), 7.88 (1H, s).

Working Example 83

Production of Compound 83

In DMF (3.9 ml) was dissolved 7-[4-(2-butoxyethoxy) phenyl)-1-crotyl-2,3-dihydro-1-benzazepine-4-carboxylic acid (0.20 g). To the solution was added thionyl chloride (82 µl), and the mixture was stirred at room temperature for 1 hour. The solvent was removed under reduced pressure, and a solution of the resulting residue in THF was added dropwise to a solution of 4-[methyl(tetrahydropyranyl-4-yl) aminomethyl]aniline (111 mg) and triethylamine (0.31 ml) in THF (3.3 ml) under ice-cooling, and the mixture was stirred at room temperature for 2 hours. The reaction solution was added to water, and the mixture was extracted with ethyl acetate, washed with saturated brine and dried with magnesium sulfate. The solvent was removed under reduced pressure, and the resulting residue was purified with silica gel column chromatography (ethyl acetate/ethanol=4/1), which was recrystallized from isopropyl ether/ethyl acetate to give 7-[4-(2-butoxyethoxy)phenyl]-1-crotyl-N-[4-[N-methyl-N-(tetrahydropyran-4-yl)aminomethyl]phenyl]-2,3-dihydro-1-benzazepine-4-carboxamide (Compound 83) (9 mg).

$^1$H-NMR (200 MHz, CDCl$_3$) δ 0.93 (3H, t, J=7.2 Hz), 1.25–1.45 (2H, m), 1.53–1.78 (6H, m), 2.20 (3H, s), 2.68 (1H, m), 3.33–3.43 (4H, m), 3.55 (2H, t, J=7.0 Hz), 3.59 (2H, s), 3.77–3.80 (2H, m), 3.88 (2H, m), 3.98–4.07 (2H, m), 4.12–4.18 (2H, m), 5.24 (1H, m), 5.62 (1H, m), 6.68 (3H, s), 6.90 (1H, d, J=8.4 Hz), 6.97 (2H, d, J=8.8 Hz), 7.27–7.58 (7H, m).

Reference Example 248

Methyl 7-bromo-2,3-dihydro-1-benzazepine-4-carboxylate (2.0 g) was dissolved in 1,2-dichloroethane (70 ml). To the solution were added isobutylaldehyde (3.2 ml) and sodium triacetoxyborohydride (5.26 g), and the mixture was stirred at room temperature for 12 hours. The solvent was removed under reduced pressure, and the resulting residue was added to water and extracted with ethyl acetate. The extract was washed with saturated brine and dried with magnesium sulfate. The solvent was removed under reduced pressure and the resulting residue was purified with silica gel column chromatography (hexane/ethyl acetate=6/1) to give methyl 7-bromo-1-isobutyl-2,3-dihydro-1-benzazepine-4-carboxylate (1.82 g).

$^1$H-NMR (200 MHz, CDCl$_3$) δ 0.92 (6H, d, J=6.6 Hz), 2.03 (1H, m), 2.77–2.82 (2H, m), 3.10 (2H, d, J=7.4 Hz), 3.21–3.26 (2H, m), 3.80 (3H, s), 6.71 (1H, d, J=8.8 Hz), 7.19–7.26 (1H, m), 7.42 (1H, d, J=2.6 Hz), 7.58 (1H, s).

Reference Example 249

In toluene/ethanol/water (=10/1/1, 41 ml) was dissolved methyl 7-bromo-1-isobutyl-2,3-dihydro-1-benzazepine-4-carboxylate (0.90 g). To the solution were added 4-(2-propoxyethoxy)phenyl borate (0.72 g) and potassium carbonate (0.81 g) and the mixture was stirred for 30 minutes under argon atmosphere. To the mixture was added tetrakistriphenylphosphinepalladium (123 mg) and the mixture was heated to reflux for 14 hours. After cooling to room temperature, the solution was added to water, and the mixture was extracted with ethyl acetate. The extract was washed with saturated brine, and dried with magnesium sulfate. The solvent was removed under reduced pressure, and the resulting residue was purified with silica gel column chromatography (hexane/ethyl acetate=8/1) to give methyl 1-isobutyl-7-[4-(2-propoxyethoxy)phenyl]-2,3-dihydro-1-benzazepine-4-carboxylate (0.79 g).

$^1$H-NMR (200 MHz, CDCl$_3$) δ 0.94 (3H, t, J=7.2 Hz), 0.95 (6H, d, J=6.6 Hz), 1.57–1.72 (2H, m), 1.98–2.15 (1H, m), 2.80–2.85 (2H, m), 3.16 (2H, d, J=7.2 Hz), 3.27–3.32 (2H, m), 3.51 (2H, t, J=6.6 Hz), 3.78–3.83 (2H, m), 3.81 (3H, s), 4.13–4.19 (2H, m), 6.89 (1H, d, J=8.8 Hz), 6.95–7.00 (2H, m), 7.39 (1H, dd, J=8.8, 2.2 Hz), 7.43–7.49 (3H, m), 7.77 (1H, s).

IR (KBr) 2961, 2870, 1701, 1607, 1499, 1248, 1180, 927, 820 cm$^{-1}$.

Reference Example 250

In THF (15.8 ml)/methanol (15.8 ml) was dissolved methyl 1-isobutyl-7-[4-(2-propoxyethoxy)phenyl]-2,3-dihydro-1-benzazepine-4-carboxylate (0.79 g). To the solution was added 1N sodium hydroxide solution (7.9 ml) and the mixture was stirred at room temperature for 20 hours. pH was adjusted to approximate 4 with 1N hydrochloric acid, and the solvent was concentrated to half under reduced pressure. The concentrated material was extracted with ethyl acetate, and the extract was washed with saturated brine and dried with magnesium sulfate. The solvent was removed under reduced pressure, and the resulting residue was washed With hexane/ethyl acetate (=6/1) to give 1-isobutyl-7-[4-(2-propoxyethoxy)phenyl]-2,3-dihydro-1-benzazepine-4-carboxylic acid (0.57 g).

$^1$H-NMR (200 MHz, CDCl$_3$) δ 0.95 (3H, t, J=7.2 Hz), 0.96 (6H, d, J=6.6 Hz), 1.59–1.71 (2H, m), 2.00–2.17 (1H, m), 2.80–2.86 (2H, m), 3.19 (2H, d, J=7.2 Hz), 3.30–3.35 (2H, m), 3.52 (2H, t, J=6.6 Hz), 3.81 (2H, t, J=4.8 Hz), 4.17 (2H, t, J=4.8 Hz), 6.90 (1H, d, J=8.8 Hz), 6.98 (2H, d, J=8.8 Hz), 7.38–7.53 (4H, m), 7.89 (1H, s).

Working Example 84

Production of Compound 84

In THF (11.4 ml) was dissolved 1-isobutyl-7-[4-(2-propoxyethoxy)phenyl]-2,3-dihydro-1-benzazepine-4-carboxylic acid (0.57 g). To the solution was added oxalyl chloride (0.23 ml), and the mixture was stirred at room temperature for 1 hour. The solvent was removed under reduced pressure, a solution of the resulting residue in THF was added dropwise to a solution of 4-[methyl (tetrahydropyranyl-4-yl)aminomethyl]aniline (0.33 g) and triethylamine (0.94 ml) in THF (9.9 ml) under ice-cooling, and the mixture was stirred at room temperature for 14 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=4/1), which was recrystallized from hexane/ethyl acetate to give 1-isobutyl-N-[4-[N-methyl-N-(tetrahydropyran-4-yl)aminomethyl]phenyl]-7-[4-(2-propoxyethoxy)phenyl]-2,3-dihydro-1-benzazepine-4-carboxamide (Compound 84) (0.56 g).

$^1$H-NMR (200 MHz, CDCl$_3$) δ 0.94 (3H, t, J=7.2 Hz), 0.97 (6H, d, J=6.6 Hz), 1.62–1.82 (6H, m), 2.00–2.17 (1H, m), 2.20 (3H, s), 2.64 (1H, m), 2.87–2.95 (2H, m), 3.18 (2H, d, J=7.4 Hz), 3.30–3.43 (4H, m), 3.51 (2H, t, J=7.0 Hz), 3.56 (2H, s), 3.78–3.83 (2H, m), 3.99–4.07 (2H, m), 4.13–4.19 (2H, m), 6.91 (1H, d, J=8.8 Hz), 6.97 (2H, d, J=8.8 Hz), 7.27–7.57 (10H, m).

IR (KBr) 3303, 2957, 1636, 1607, 1499, 1244, 1122, 926, 812 cm$^{-1}$.

Anal. Calcd. C$_{39}$H$_{51}$N$_3$O$_4$ Calcd. C, 74.85; N, 6.71; H, 8.21. Found C, 74.69; N, 6.92; H, 8.34.

Reference Example 251

Methyl 7-bromo-1-isobutyl-2,3-dihydro-1-benzazepine-4-carboxylate (0.90 g) was dissolved in toluene/ethanol/water (=10/1/1, 41 ml). To the solution were added 4-(2-butoxyethoxy)phenyl borate (0.76 g) and potassium carbonate (0.18 g), and the mixture was stirred under argon atmosphere for 30 minutes. To the mixture was added tetrakistriphenylphosphinepalladium (123 mg), and the mixture was heated to reflux for 14 hours. After cooled to room temperature, the reaction solution was added to water, and the mixture was extracted with ethyl acetate. The extract was washed with saturated brine and dried with magnesium sulfate. The solvent was removed under reduced pressure, and the resulting residue was purified with silica gel column chromatography (hexane/ethyl acetate=8/1) to give methyl 7-[4-(2-butoxyethoxy)phenyl]-1-isobutyl-2,3-dihydro-1-benzazepine-4-carboxylate (0.75 g).

$^1$H-NMR (200 MHz, CDCl$_3$) δ 0.93 (3H, t, J=7.2 Hz), 0.95 (6H, d, J=6.6 Hz), 1.37–1.67 (4H, m), 2.26 (1H, m), 2.82 (2H, m), 3.17 (2H, d, J=4.8 Hz), 3.30 (2H, t, J=4.8 Hz), 3.55 (2H, t, J=6.6 Hz), 3.77–3.83 (2H, m), 3.81 (3 s), 4.13–4.18 (2H, m), 6.89 (1H, d, J=8.4 Hz), 6.94–7.00 (2H, m), 7.36–7.52 (4H, m), 7.77 (1H, s).

IR (KBr) 2959, 1703, 1607, 1499, 1244, 1181, 814 cm$^{-1}$.

Reference Example 252

In THF (15.0 ml)/methanol (15.0 ml) was dissolved methyl 7-[4-(2-butoxyethoxy)phenyl]-1-isobutyl-2,3-dihydro-1-benzazepine-4-carboxylate (0.75 g). To the solution was added 1N sodium hydroxide solution (7.5 ml), and the mixture was stirred at room temperature for 20 hours. pH was adjusted to approximate 4 with 1N hydrochloric acid, and the solvent was concentrated to half under reduced pressure. The concentrated material was extracted with ethyl acetate, washed with saturated brine and dried with magnesium sulfate. The solvent was removed under reduced pressure, and the resulting residue was washed with hexane/ethyl acetate (=6/1) to give 7-[4-(2-butoxyethoxy)phenyl]-1-isobutyl-2,3-dihydro-1-benzazepine-4-carboxylic acid (0.61 g).

$^1$H-NMR (200 MHz, CDCl$_3$) δ 0.93 (3H, t, J=7.0 Hz), 0.96 (6H, d, J=6.6 Hz), 1.34–1.47 (2H, m), 1.54–1.66 (2H, m), 2.08 (1H, m), 2.79–2.85 (2H, m), 3.19 (2H, d, J=6.8 Hz), 3.30–3.35 (2H, m), 3.56 (2H, t, J=6.6 Hz), 3.81 (2H, t, J=4.8 Hz), 4.16 (2H, J=4.8 Hz), 6.90 (1H, d, J=8.8 Hz), 6.98 (2H, d, J=8.8 Hz), 7.38–7.53 (4H, m), 7.89 (1H, s).

Working Example 85

Production of Compound 85

In THF (12.0 ml) was dissolved 7-[4-(2-butoxyethoxy)phenyl]-1-isobutyl-2,3-dihydro-1-benzazepine-4-carboxylic acid (0.60 g). To the solution was added oxalyl chloride (0.24 ml), and the mixture was stirred at room temperature for 1 hour. The solvent was removed under reduced pressure, a solution of the resulting residue in THF was added dropwise to a solution of 4-[methyl(tetrahydropyranyl-4-yl)aminomethyl]aniline (0.33 g) and triethylamine (0.96 ml) in THF (9.6 ml) under ice-cooling, and the mixture was stirred at room temperature for 14 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=4/1), which was recrystallized from hexane/ethyl acetate to give 7-[4-(2-butoxyethoxy)phenyl]-1-isobutyl-N-[4-[N-methyl-N-](tetrahydropyran-4-yl)aminomethyl]phenyl]-2,3-dihydro-1-benzazepine-4-carboxamide (Compound 85) (0.49 g).

$^1$H-NMR (200 MHz, CDCl$_3$) δ 0.93 (3H, t, J=7.2 Hz), 1.97 (6H, d, J=6.6 Hz), 1.33–1.46 (2H, m), 1.54–1.77 (6H, m), 2.07 (1H, m), 2.20 (3H, s), 2.64 (1H, m), 2.88–2.95 (2H, m), 3.18 (2H, d, J=7.4 Hz), 3.30–3.43 (4H, m), 3.51–3.59 (2H, m), 3.56 (2H, s), 3.77–3.83 (2H, m), 3.98–4.07 (2H, m), 4.12–4.18 (2H, m), 6.91 (1H, d, J=8.8 Hz), 6.99 (2H, d, J=8.4 Hz), 7.29 (1H, d, J=8.4 Hz), 7.36–7.58 (9H, m).

IR (KBr) 3303, 2955, 1636, 1597, 1499, 1242, 1121, 926, 812 cm$^{-1}$.

Anal. Calcd. C$_{40}$H$_{53}$N$_3$O$_4$ Calcd. C, 75.08; N, 6.57; H, 8.35. Found C, 74.99; N, 6.69; H, 8.16.

Reference Example 253

In 1,2-dichloroethane (60 ml) was dissolved methyl 7-bromo-2,3-dihydro-1-benzazepine-4-carboxylate (1.7 g). To the solution were added isopentylaldehyde (3.1 g) and sodium triacetoxyborohydride (4.5 g), and the mixture was stirred at room temperature for 12 hours. The solvent was removed under reduced pressure, and the resulting residue was added to water, and the mixture was extracted with ethyl acetate. The extract was washed with saturated brine and dried with magnesium sulfate. The solvent was removed under reduced pressure, and the resulting residue was purified with silica gel column chromatography (hexane/ethyl acetate=5/1) to give methyl 7-bromo-1-isopentyl-2,3-dihydro-1-benzazepine-4-carboxylate (1.84 g).

$^1$H-NMR (200 MHz, CDCl$_3$) δ 0.95 (6H, d, J=6.2 Hz), 1.48–1.62 (3H, m), 2.79 (2H, t, J=4.4 Hz), 3.21 (2H, t, J=4.4 Hz), 3.24–3.33 (2H, m), 3.80 (3H, s), 6.68 (1H, d, J=8.8 Hz), 7.20–7.26 (1H, m), 7.41 (1H, d, J=2.2 Hz), 7.56 (1H, s).

Reference Example 254

In THF (36 ml)/methanol (36 ml) was dissolved methyl 7-bromo-1-isopentyl-2,3-dihydro-1-benzazepine-4-carboxylate (1.8 g). To the solution was added 1N sodium hydroxide solution (18 ml), and the mixture was stirred at room temperature for 24 hours. pH was adjusted to approximate 5 with 1N hydrochloric acid, and the solvent was concentrated to half under reduced pressure. The concentrated material was extracted with ethyl acetate, washed with saturated brine and dried with magnesium sulfate. The solvent was removed under reduced pressure, and the resulting residue was washed with hexane/ethyl acetate (=6/1) to give 7-bromo-1-isopentyl-2,3-dihydro-1-benzazepine-4-carboxylic acid (1.51 g).

$^1$H-NMR (200 MHz, CDCl$_3$) δ 0.96 (6H, d, J=6.2 Hz), 1.52–1.71 (3H, m), 2.78–2.84 (2H, m), 3.21–3.26 (2H, m), 3.32 (2H, d, J=8.2 Hz), 6.69 (1H, d, J=8.8 Hz), 7.22–7.29 (1H, m), 7.43 (1H, d, J=2.2 Hz), 7.68 (1H, s).

Reference Example 255

In DMF (30 ml) was dissolved 7-bromo-1-isopentyl-2,3-dihydro-1-benzazepine-4-carboxylic acid (1.5 g). To the solution was added thionyl chloride (0.84 ml), and the mixture was stirred at room temperature for 1 hour. The solvent was removed under reduced pressure, a solution of the resulting residue in THF was added dropwise to a solution of 4-[methyl(tetrahydropyranyl-4-yl)aminomethyl]aniline (1.04 g) and triethylamine (3.2 ml) in THF (20.8 ml) under ice-cooling, and the mixture was stirred at room temperature for 16 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=3/1) to give 7-bromo-1-isopentyl-N-[4-[N-methyl-N-(tetrahydropyran-4-yl)aminomethyl]phenyl]-2,3-dihydro-1-benzazepine-4-carboxamide (1.35 g).

$^1$H-NMR (200 MHz, CDCl$_3$) δ 0.96 (6H, d, J=6.2 Hz), 1.54–1.86 (5H, m), 2.21 (3H, s), 2.66 (1H, m), 2.88 (2H, m), 3.26 (2H, m), 3.28–3.44 (2H, m), 3.57 (2H, s), 3.98–4.11 (2H, m), 6.70 (1H, d, J=8.8 Hz), 7.18–7.40 (3H, m), 7.54 (2H, d, J=8.4 Hz), 7.64 (1H, s), 8.02 (1H, s).

Working Example 86

Production of Compound 86

In toluene/ethanol/water (=10/1/1, 31.5 ml) was dissolved 7-bromo-1-isopentyl-N-[4-[N-methyl-N-(tetrahydropyran-4-yl)aminomethyl]phenyl]-2,3-dihydro-1-benzazepine-4-carboxamide (0.66 g). To the solution were added 4-(2-propoxyethoxy)phenyl borate (0.33 g) and potassium carbonate (0.37 g), and the mixture was stirred for 30 minutes under argon atmosphere. To the mixture was added tetrakistriphenylphosphinepalladium (56 mg), and the mixture was heated to reflux for 16 hours. After cooled to room temperature, the reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=3/1). The purified residue was dissolved in ethyl acetate and filtered to give a solution. The solvent was removed under reduced pressure, followed by recrystallization from isopropyl ether/ethyl acetate to give 1-isopentyl-N-[4-[N-methyl-N-(tetrahydropyran-4-yl)aminomethyl]phenyl]-7-[4-(2-propoxyethoxy)phenyl]-2,3-dihydro-1-benzazepine-4-carboxamide (Compound 86) (80 mg).

$^1$H-NMR (200 MHz, CDCl$_3$) δ 0.94 (3H, t, J=7.4 Hz), 0.96 (6H, d, J=6.0 Hz), 1.54–1.76 (6H, m), 2.21 (3H, s), 2.68 (1H, m), 2.89 (2H, m), 3.30–3.50 (9H, m), 3.51 (2H, t, J=6.2 Hz), 3.58 (2H, s), 3.98–4.07 (2H, m), 4.15 (2H, t, J=4.8 Hz), 6.65 (1H, s), 6.70–6.81 (1H, m), 6.88 (1H, d, J=9.2 Hz), 6.96 (2H, d, J=8.6 Hz), 7.30–7.69 (9H, m).

IR (KBr) 3312, 2953, 2867, 1644, 1605, 1501, 1244, 829 cm$^{-1}$.

Working Example 87

Production of Compound 87

In toluene/ethanol/water (=10/1/1, 31.5 ml) was dissolved 7-bromo-1-isopentyl-N-[4-[N-methyl-N-(tetrahydropyran-4-yl)aminomethyl]phenyl]-2,3-dihydro-1-benzazepine-4-carboxamide (0.66 g). To the solution were added 4-(2-butoxyethoxy)phenyl borate (0.35 g) and potassium carbonate (0.37 g), and the mixture was stirred for 30 minutes under argon atmosphere. To the mixture was added tetrakistriphenylphosphinepalladium (56 mg), and the mixture was heated to reflux for 16 hours. After cooled to room temperature, the reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=3/1). The purified residue was dissolved in ethyl acetate and filtered to give a solution. The solvent was removed under reduced pressure, followed by recrystallization from isopropyl ether/ethyl acetate to give 7-[4-(2-butoxyethoxy)phenyl]-1-isopentyl-N-[4-[N-methyl-N-(tetrahydropyran-4-yl)aminomethyl]phenyl]-2,3-dihydro-1-benzazepine-4-carboxamide (Compound 87) (74 mg).

$^1$H-NMR (200 MHz, CDCl$_3$) δ 0.93 (3H, t, J=7.2 Hz), 0.98 (6H, d, J=6.2 Hz), 1.33–1.45 (2H, m), 1.54–1.75 (6H, m), 2.21 (3H, s), 2.67 (1H, m), 2.85–2.92 (2H, m), 3.30–3.43 (9H, m), 3.55 (2H, t, J=6.6 Hz), 3.58 (2H, s), 3.77–3.83 (2H, m), 4.00–4.06 (2H, m), 4.12–4.17 (2H, m), 6.66 (1H, s), 6.89 (1H, d, J=8.8 Hz), 6.97 (2H, d, J=8.8 Hz), 7.29 (2H, d, J=8.4 Hz), 7.38–7.63 (7H, m).

IR (KBr) 3328, 2957, 2870, 1642, 1607, 1503, 1242, 1140, 823 cm$^{-1}$.

Reference Example 256

In THF (14.0 ml) was dissolved methyl 7-[4-(2-butoxyethoxy)phenyl]-2,3-dihydro-1-benzazepine-4-carboxylate (0.70 g). To the solution was added 60% sodium hydride (142 mg) at 0° C., and the mixture was stirred at room temperature for 1 hour. To the mixture was added 1-bromo-3-methyl-2-butene (0.83 ml), and the mixture was stirred at 60° C. for 60 hours. After cooled to room temperature, the mixture was added to water, and the mixture was extracted with ethyl acetate. The extract was washed with saturated brine and dried with magnesium sulfate. The solvent was removed under reduced pressure, and the resulting residue was purified with silica gel column chromatography (hexane/ethyl/acetate=4/1) to give methyl 7-[4-(2-butoxyethoxy)phenyl]-1-(3-methyl-2-butenyl)-2,3-dihydro-1-benzazepine-4-carboxylate (0.71 g).

$^1$H-NMR (200 MHz, CDCl$_3$) δ 0.93 (3H, d, J=7.2 Hz), 1.33–1.45 (2H, m), 1.54–1.68 (2H, m), 1.75 (3H, s), 1.78 (3H, s), 2.78–2.83 (2H, m), 3.19–3.25 (2H, m), 3.55 (2H, t, J=6.6 Hz), 3.77–3.80 (2H, m), 3.93 (2H, d, J=6.2 Hz), 4.10–4.18 (2H, m), 5.32 (1H, m), 6.86 (1H, d, J=8.4 Hz), 6.97 (2H, d, J=8.8 Hz), 7.37–7.52 (4H, m), 7.76 (1H, s).

Reference Example 257

In THF (14.0 ml)/methanol (14.0 ml) was dissolved methyl 7-[4-(2-butoxyethoxy)phenyl]-1-(3-methyl-2-butenyl)-2,3-dihydro-1-benzazepine-4-carboxylate (0.70 g). To the solution was added 1N sodium hydroxide (7.0 ml), and the mixture was stirred at room temperature for 24 hours. pH was adjusted to approximate 4 with 1N hydrochloric acid, and the solvent was concentrated to half under reduced pressure. The concentrated material was extracted with ethyl acetate, and the extract was washed with saturated brine and dried with magnesium sulfate. The solvent was removed under reduced pressure, and the resulting residue was washed with hexane/ethyl acetate (=6/1) to give 7-[4-(2-butoxyethoxy)phenyl]-1-(3-methyl-2-butenyl)-2,3-dihydro-1-benzazepine-4-carboxylic acid (0.46 g).

$^1$H-NMR (200 MHz, CDCl$_3$) δ 0.93 (3H, d, J=7.2 Hz), 1.35–1.47 (2H, m), 1.54–1.65 (2H, m), 1.76 (3H, s), 1.79 (3H, s), 2.79–2.85 (2H, m), 3.21–3.29 (2H, m), 3.56 (2H, t, J=6.6 Hz), 3.78–3.83 (2H, m), 3.95 (2H$_1$, d, J=5.8 Hz), 4.13–4.19 (2H, m), 5.33 (1H, m), 6.87 (1H, d, J=8.4 Hz), 6.98 (2H, d, J=8.8 Hz), 7.38–7.54 (2H, m), 7.47 (2H, d, J=8.8 Hz), 7.89 (1H, s).

Working Example 88

Production of Compound 88

In THF (9.0 ml) was dissolved 7-[4-(2-butoxyethoxy)phenyl]-1-(3-methyl-2-butenyl)-2,3-dihydro-1-benzazepine-4-carboxylic acid (0.40 g). To the solution was added oxalyl chloride (0.18 ml), and the mixture was stirred at room temperature for 1 hour. The solvent was removed under reduced pressure, a solution of the resulting residue in THF was added dropwise to a solution of 4-[methyl(tetrahydropyranyl-4-yl)aminomethyl]aniline (0.24 g) and triethylamine (0.70 ml) in THF (7.2 ml) under ice-cooling, and the mixture was stirred at room temperature for 14 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=4/1), which was recrystallized from hexane/ethyl acetate to give 7-[4-(2-butoxyethoxy)phenyl]-1-isobutyl-N-[4-[N-methyl-N-(tetrahydropyran-4-yl)aminomethyl]phenyl]-2,3-dihydro-1-benzazepine-4-carboxamide (Compound 88) (0.33 g).

$^1$H-NMR (200 MHz, CDCl$_3$) δ 0.93 (3H, d, J=7.2 Hz), 1.33–1.45 (2H, m), 1.54–1.67 (6H, m), 1.77 (3H, s), 1.80 (3H, s), 2.21 (3H, m), 2.65 (1H, m), 2.91 (2H, m), 3.25–3.44 (4H, m), 3.55 (2H, t, J=6.6 Hz), 3.57 (2H, s), 3.80 (2H, t, J=4.8 Hz), 3.95 (2H, d, J=6.2 Hz), 4.00–4.08 (2H, m), 4.16 (2H, t, J=4.6 Hz), 5.34 (1H, m), 6.89 (1H, d, J=8.8 Hz), 6.97 (2H, d, J=8.8 Hz), 7.27–7.56 (10H, m).

IR (KBr) 2926, 2865, 1703, 1607, 1499, 1244, 1181, 814 cm$^{-1}$.

Anal. Calcd. $C_{41}H_{53}N_3O_4$ Calcd. C, 75.54; N, 6.45; H, 8.19. Found C, 75.39; N, 6.40; H, 8.03.

Reference Example 258

In THF (228 ml) was dissolved 2-ethoxyethanol (22.8 g). To the solution were added triethylamine (49.3 ml) and methanesulfonyl chloride (23.6 ml) at 0° C., and the mixture was stirred at room temperature for 1 hour. The reaction solution was added to water, and the mixture was extracted with ethyl acetate. The extract was washed with saturated brine and dried with magnesium sulfate. The solvent was removed under reduced pressure, and the resulting residue was added dropwise to a solution of 4-[(benzyloxycarbonyl)amino]butyric acid (30.0 g) and 60% sodium hydride (10.1 g) in THF (450 ml). The mixture was stirred at 60° C. for 16 hours, cooled to room temperature, and the reaction solution was added to water. To the mixture was added 1N sodium hydroxide (50 ml), and the mixture was washed with ethyl acetate. The mixture was neutralized with 1N hydrochloric acid and extracted with ethyl acetate. The extract was washed with saturated sodium thiosulfate solution and dried with magnesium sulfate. The solvent was removed under reduced pressure, and the resulting residue was dissolved in methylene chloride (54.6 ml), which was added dropwise to a solution of concentrated sulfuric acid (8.23 ml) and magnesium sulfate (28.3 g) in methylene chloride (273 ml). To the mixture was added 2-methyl-2-propanol (28.1 ml), and the mixture was stirred at room temperature for 18 hours. To the mixture was added an aqueous solution of sodium hydrogen carbonate to adjust pH to approximate 8, and the mixture was extracted with ethyl acetate. The extract was washed with water and saturated brine, and dried with magnesium sulfate. The solvent was removed under reduced pressure, and the resulting residue was purified with silica gel column chromatography (hexane/ethyl acetate=6/1→5/1) to give tert-butyl 4-[(benzyloxycarbonyl)(2-ethoxyethyl)amino]butyrate (8.7 g).

$^1$H-NMR (200 MHz, CDCl$_3$) δ 1.20 (3H, d, J=7.4 Hz), 1.44 (9H, s), 1.71–1.82 (2H, m), 2.27 (2H, t, J=7.2 Hz), 2.64 (2H, t, J=7.4 Hz), 2.72–2.81 (2H, m), 3.50 (2H, q, J=7.4 Hz), 3.50–3.56 (2H, m).

Reference Example 259

In methanol (87 ml) was dissolved tert-butyl 4-[(benzyloxycarbonyl)(2-ethoxyethyl)amino]butyrate (8.7 g). To the solution was added 10% palladium/carbon (0.87 g), and the mixture was stirred for 3 hours under hydrogen atmosphere. 10% palladium/carbon was removed by filtration with Celite, and the solvent of the resulting solution was removed under reduced pressure to give tert-butyl 4-[(2-ethoxyethyl)amino]butyrate (5.5 g).

$^1$H-NMR (200 MHz, CDCl$_3$) δ 1.26 (3H, d, J=7.0 Hz), 1.43 (9H, s), 1.77–1.87 (2H, m), 2.18–2.27 (2H, m), 3.31–3.57 (6H, m), 5.13 (2H, s), 7.32–7.37 (5H, m).

Reference Example 260

In DMF (43.9 ml) was dissolved tert-butyl 4-[(2-ethoxyethyl)amino]butyrate (5.5 g). To the solution was added 5-bromo-2-fluorobenzaldehyde (4.4 g), followed by addition of potassium carbonate (3.6 g). The mixture was stirred at 90° C. for 60 hours and cooled to room temperature. The reaction solution was added to water, the mixture was extracted with ethyl acetate, washed with saturated brine and dried with magnesium sulfate. The solvent was removed under reduced pressure, and the resulting residue was purified with silica gel column chromatography (hexane/ethyl acetate=6/1→5/1) to give tert-butyl 4-(4-bromo(2-ethoxyethyl)-2-formylanilino]butyrate (2.3 g).

$^1$H-NMR (200 MHz, CDCl$_3$) δ 1.12 (3H, d, J=7.0 Hz), 1.41 (9H, s), 1.76–1.81 (2H, m), 2.16–2.24 (2H, m), 3.23 (2H, t, J=7.4 Hz), 3.28–3.39 (4H, m), 3.37 (2H, q, J=7.0 Hz), 3.43–3.49 (2H, m), 7.14 (1H, d, J=8.6 Hz), 7.59 (1H, dd, J=8.8, 2.6 Hz), 7.91 (1H, d, J=2.4 Hz), 10.30 (1H, s).

Reference Example 261

In toluene (4.8 ml)/2-methyl-2-propanol (0.48 ml) was dissolved tert-butyl 4-[4-bromo(2-ethoxyethyl)-2-formylanilino]butyrate (2.4 g). To the solution was added potassium tert-butoxide. (72 mg), the mixture was stirred at 100° C. for 1 hour and cooled to room temperature. The reaction solution was added to water, the mixture was extracted with ethyl acetate, and the extract was washed with saturated brine and dried with magnesium sulfate. The solvent was removed under reduced pressure, and the resulting residue was purified with silica gel column chromatography (hexane/ethyl acetate=6/1) to give tert-butyl 7-bromo-1-(2-ethoxyethyl)-2,3-dihydro-1-benzazepine-4-carboxylate (0.15 g).

$^1$H-NMR (200 MHz, CDCl$_3$) δ 1.21 (3H, t, J=7.0 Hz), 1.53 (9H, s), 2.76 (2H, t, J=4.4 Hz), 3.26 (2H, t, J=4.4 Hz), 3.44–3.54 (2H, m), 3.52 (2H, q, J=7.0 Hz), 3.62–3.69 (2H, m), 6.82 (1H, d, J=8.8 Hz), 7.22 (1H, dd, J=8.8, 2.6 Hz), 7.39 (1H, d, J=2.2 Hz), 7.46 (1H, s).

Reference Example 262

In ethyl acetate (22 ml) was dissolved tert-butyl 7-bromo-1-(2-ethoxyethyl)-2,3-dihydro-1-benzazepine-4-carboxylate (1.1 g). To the solution was added 4N hydrochloric acid/ethyl acetate (11 ml) at room temperature, and the mixture was stirred for 24 hours. An aqueous saturated solution of sodium hydrogen carbonate was added to adjust pH to approximate 4, followed by extraction with ethyl acetate. The extract was washed with saturated brine and dried with magnesium sulfate. The solvent was removed under reduced pressure, and the resulting residue was washed with hexane/ethyl acetate (=8/1) to give 7-bromo-1-(2-ethoxyethyl)-2,3-dihydro-1-benzazepine-4-carboxylic acid (0.73 g).

$^1$H-NMR (200 MHz, CDCl$_3$) δ 1.21 (3H, t, J=7.0 Hz), 2.82 (2H, t, J=4.4 Hz), 3.30 (2H, t, J=4.4 Hz), 3.51 (2H, t, J=4.4 Hz), 3.52 (2H, q, J=7.0 Hz), 3.67 (2H, t, J=5.2 Hz), 6.85 (1H, d, J=8.8 Hz), 7.23–7.29 (1H, m), 7.44 (1H, d, J=2.2 Hz), 7.69 (1H, s).

Reference Example 263

In DMF (14.6 ml) was dissolved 7-bromo-1-(2-ethoxyethyl)-2,3-dihydro-1-benzazepine-4-carboxylic acid (0.73 g). To the solution was added thionyl chloride (0.39 ml), and the mixture was stirred at room temperature for 1 hour. The solvent was removed under reduced pressure, a solution of the resulting residue in THF was added dropwise to a solution of 4-[methyl(tetrahydropyranyl-4-yl) aminomethyl]aniline (0.53 g) and triethylamine (1.5 ml) in THF (15.9 ml) under ice-cooling, and the mixture was stirred at room temperature for 2 hours. The reaction solution was added to water, the mixture was extracted with ethyl acetate, and the extract was washed with saturated brine and dried with magnesium sulfate. The solvent was removed under reduced pressure, and the resulting residue was purified with silica gel column chromatography (ethyl acetate/ethanol=3/1) to give 7-bromo-1-(2-ethoxyethyl)-N-[4-[4-[N-methyl-N-(tetrahydropyran-4-yl)aminomethyl]phenyl]-2,3-dihydro-1-benzazepine-4-carboxamide (0.66 g).

$^1$H-NMR (200 MHz, CDCl$_3$) δ 1.21 (3H, t, J=7.0 Hz), 1.63–1.82 (4H, m), 2.20 (3H, s), 2.64 (1H, m), 2.87–2.96 (4H, m), 3.31–3.38 (4H, m), 3.47–3.58 (2H, m), 3.56 (2H, s), 3.64–3.70 (2H, m), 3.97–4.09 (2H, m), 6.85 (1H, d, J=8.8 Hz), 7.19–7.32 (4H, m), 7.40 (1H, d, J=2.6 Hz), 7.50–7.56 (2H, m), 8.01 (1H, s).

Working Example 89

Production of Compound 89

In toluene/ethanol/water (=20/1/1, 14.3 ml) was dissolved 7-bromo-1-(2-ethoxyethyl)-N-[4-[4-[N-methyl-N-(tetrahydropyran-4-yl)aminomethyl]phenyl]-2,3-dihydro-1-benzazepine-4-carboxamide (0.32 g). To the solution were added 4-(2-propoxyethoxy)phenyl borate (0.16 g) and potassium carbonate (0.18 g), and the mixture was stirred for 30 minutes under argon atmosphere. To the mixture was added tetrakistriphenylphosphinpalladium (27 mg), and the mixture was heated to reflux for 14 hours. After cooled to room temperature, the reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=3/1). The purified residue was dissolved in ethyl acetate, which was filtered to give a solution. The solvent was removed under reduced pressure, which was recrystallized from isopropyl ether/ethyl acetate to give 1-(2-ethoxyethyl)-N-[4-[N-methyl-N-(tetrahydropyran-4-yl)aminomethyl]phenyl]-7-[4-(2-propoxyethoxy)phenyl]-2,3-dihydro-1-benzazepine-4-carboxamide (Compound 89) (60 mg).

$^1$H-NMR (200 MHz, CDCl$_3$) δ 0.94 (3H, t, J=7.2 Hz), 1.59–1.80 (6H, m), 2.21 (3H, s), 2.65 (1H, m), 2.92 (2H, m), 3.22–3.69 (8H, m), 3.57 (2H, s), 3.69–3.73 (2H, m), 3.78–3.84 (2H, m), 3.99–4.17 (2H, m), 4.16 (2H, t, J=4.8 Hz), 6.69 (1H, s), 6.95–7.03 (3H, m), 7.30–7.56 (9H, m).

Working Example 90

Production of Compound 90

In toluene/ethanol/water (=20/1/1, 14.3 ml) was dissolved 7-bromo-1-(2-ethoxyethyl)-N-[4-[N-methyl-N-(tetrahydropyran-4-yl)aminomethyl]phenyl]-2,3-dihydro-1-benzazepine-4-carboxamide (0.32 g). To the solution were added 4-(2-butoxyethoxy)phenyl borate (0.17 g) and potassium carbonate (0.18 g), and the mixture was stirred for 30 minutes under argon atmosphere. To the mixture was added tetrakistriphenylphosphinepalladium (27 mg), and the mixture was heated to reflux for 14 hours. After cooled to room temperature, the reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=3/1). The purified residue was dissolved in ethyl acetate, which was filtered to give a solution. The solvent was removed under reduced pressure, which was recrystallized from isopropyl ether/ethyl acetate to give 7-[4-(2-butoxyethoxy)phenyl]-1-(2-ethoxyethyl)-N-[4-[N-methyl-N-(tetrahydropyran-4-yl)aminomethyl]phenyl]-2,3-dihydro-1-benzazepine-4-carboxamide (Compound 90) (15 mg).

$^1$H-NMR (200 MHz, CDCl$_3$) δ 0.93 (3H, t, J=7.2 Hz), 1.23 (3H, t, J=7.0 Hz), 1.29–1.45 (2H, m), 1.54–1.75 (6H, m), 2.21 (3H, s), 2.65 (1H, m), 2.92 (2H, m), 3.30–3.44 (4H, m), 3.50–3.60 (4H, m), 3.57 (2H, s), 3.67–3.72 (2H, m), 3.98–4.07 (2H, m), 4.13–4.18 (2H, t, J=4.8 Hz), 6.70 (1H, s), 6.95–7.03 (3H, m), 7.27–7.55 (9H, m).

Reference Example 264

In THF (400 ml) was dissolved 2-methoxyethanol (20 g). To the solution were added triethylamine (47.6 ml), 4-dimethylaminopyridine (9.66 g) and p-toluenesulfonyl chloride (60.2 g), and the mixture was stirred at room temperature for 2 hours. The mixture was stirred at 60° C. for 3 hours, the reaction solution was added to water, and the mixture was extracted with ethyl acetate. The extract was washed with saturated brine and dried with magnesium sulfate. The solvent was removed under reduced pressure, the resulting residue was added dropwise to a solution of 4-[(benzyloxycarbonyl)amino]butyric acid (30.2 g) and 60% sodium hydride (10.2 g) in THF (453 ml). The mixture was stirred at 65° C. for 24 hours and cooled to room temperature. The reaction solution was added to water, followed by addition of 1N sodium hydroxide (50 ml) and washing with ethyl acetate. The mixture was neutralized with 1N hydrochloric acid, and extracted with ethyl acetate. The extract was washed with saturated sodium thiosulfate solution and dried with magnesium sulfate. The solvent was removed under reduced pressure, and the resulting residue was dissolved in methylene chloride (90 ml), which was added dropwise to a solution of concentrated sulfuric acid (5.4 ml) and magnesium sulfate (48.9 g) in methylene chloride (450 ml). To the mixture was added 2-methyl-2-propanol (48.6 ml), and the mixture was stirred at room temperature for 18 hours. An aqueous saturated solution of sodium hydrogen carbonate was added to adjust pH to approximate 8, which was extracted with ethyl acetate. The extract was washed with water and saturated brine and dried with magnesium sulfate. The solvent was removed under reduced pressure, and the resulting residue was purified with silica gel column chromatography (hexane/ethyl acetate=6/1→5/1) to give tert-butyl 4-[(benzyloxycarbonyl)(2-methoxyethyl)amino]butyrate (10.7 g).

$^1$H-NMR (200 MHz, CDCl$_3$) δ 1.43 (9H, s), 1.75–1.87 (2H, m), 2.27 (2H, t, J=7.2 Hz), 3.18–3.58 (9H, m), 5.13 (2H, s).

Reference Example 265

In methanol (300 ml) was dissolved tert-butyl 4-[(benzyloxycarbonyl)(2-methoxyethyl)amino]butyrate (30.0 g). To the solution was added 10% palladium/carbon (3.0 g), and the mixture was stirred for 3 hours under hydrogen atmosphere. 10% palladium/carbon was removed by filtration with Celite, the solvent was removed under reduced pressure, and the resulting residue was added dropwise to a solution of 5-bromo-2-fluorobenzaldehyde (15.8 g) and sodium carbonate (9.9 g) in DMF (186 ml). The mixture was stirred at 90° C. for 65 hours. After cooled to room temperature, the reaction solution was added to water, and the mixture was extracted with ethyl acetate. The extract was washed with saturated brine and dried with magnesium sulfate. The solvent was removed under reduced pressure, and the resulting residue was purified with silica gel column chromatography (hexane/ethyl acetate=4/1) to give tert-butyl 4-[4-bromo(2-methoxyethyl)-2-formylanilino]butyrate (6.0 g). Tert-butyl 4-[4-bromo(2-methoxyethyl)-2-formylanilino]butyrate (6.0 g) was dissolved in toluene (60 ml)/2-methyl-2-propanol (6.0 ml). To the solution was added potassium tert-butoxide (1.85 g), and the mixture was stirred at 100° C. for 1 hour. After cooled to room temperature, the reaction solution was added to water, and the mixture was extracted with ethyl acetate. The extract was washed with saturated brine and dried with magnesium sulfate. The solvent was removed under reduced pressure, and the resulting residue was purified with silica gel column chromatography (hexane/ethyl acetate=5/1) to give tert-butyl 7-bromo-1-(2-methoxyethyl)-2,3-dihydro-1-benzazepinecarboxylate (1.8 g).

$^1$H-NMR (200 MHz, CDCl$_3$) δ 1.53 (9H, s), 2.75 (2H, t, J=4.4 Hz), 3.24 (2H, t, J=4.8 Hz), 3.39 (3H, s), 3.55–3.65 (4H, m), 6.73 (1H, d, J=9.0 Hz), 7.19–7.40 (3H, m), 7.46 (1H, s).

Reference Example 266

In toluene/ethanol/water (=10/1/1, 62.4 ml) was dissolved tert-butyl 7-bromo-1-(2-methoxyethyl)-2,3-dihydro-1- benzazepine-4-carboxylate (1.8 g). To the solution were added 4-(2-butoxyethoxy)phenyl borate (1.68 g) and potassium carbonate (1.55 g), and the mixture was stirred for 30 minutes under argon atmosphere. To the mixture was added tetrakistriphenylphosphinpalladium (0.22 g), and the mixture was heated to reflux for 16 hours. After cooled to room temperature, the reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=5/1) to give tert-butyl 7-[4-(2-butoxyethoxy)phenyl]-1-(2-methoxyethyl)-2,3-dihydro-1-benzazepine-4-carboxylate (1.4 g).

$^1$H-NMR (200 MHz, CDCl$_3$) δ 0.93 (3H, t, J=7.2 Hz), 1.33–1.45 (2H, m), 1.54 (9H, s), 1.53–1.65 (2H, m), 2.75–2.80 (2H, m), 3.32 (2H, m), 3.41 (3H, s), 3.49–3.58 (4H, m), 3.63–3.67 (2H, m), 3.72–3.83 (2H, m), 4.13–4.18 (2H, m), 6.78 (1H, d, J=5.4 Hz), 6.87 (2H, d, J=8.8 Hz), 7.38 (1H, dd, J=8.4, 2.2 Hz), 7.43–7.48 (3H, m), 7.65 (1H, s).

Reference Example 267

In ethyl acetate (28 ml) was dissolved tert-butyl 7-[4-(2-butoxyethoxy)phenyl]-1-(2-methoxyethyl)-2,3-dihydro-1-benzazepine-4-carboxylate (1.4 g). To the solution was added 4N hydrochloric acid/ethyl acetate (14 ml) at room temperature, and the mixture was stirred at 60° C. for 2 hours. After cooled to room temperature, an aqueous saturated solution of sodium hydrogen carbonate was added to adjust pH to approximate 5. The solvent was removed under reduced pressure, and the resulting residue was washed with hexane/ethyl acetate (=6/1) to give 7-[4-(2-butoxyethoxy) phenyl]-1-(2-ethoxyethyl)-2,3-dihydro-1-benzazepine-4-carboxylic acid (0.61 g, 49%).

$^1$H-NMR (200 MHz, CDCl$_3$) δ 0.93 (3H, t, J=7.2 Hz), 1.33–1.45 (2H, m), 1.54–1.66 (2H, m), 2.84 (2H, m), 3.34–3.44 (2H, m), 3.41 (3H, s), 3.56 (2H, t, J=6.6 Hz), 3.52–3.59 (2H, m), 3.65–3.71 (2H, m), 4.13–4.18 (2H, m), 6.98 (2H, d, J=8.4 Hz), 7.00 (1H, d, J=8.8 Hz), 7.40–7.50 (4H, m), 7.89 (1H, s).

Working Example 91

Production of Compound 91

In THF (12.0 ml) was dissolved 7-[4-(2-butoxyethoxy) phenyl]-1-(2-methoxyethyl)-2,3-dihydro-1-benzazepine-4-carboxylic acid (0.60 g). To the solution was added oxalyl chloride (0.24 ml), and the mixture was stirred at room temperature for 1 hour. The solvent was removed under reduced pressure, a solution of the resulting residue in THF was added dropwise to a solution of 4-[methyl (tetrahydropyranyl-4-yl)aminomethyl]aniline (0.33 g) and triethylamine (0.95 ml) in THF (9.9 ml) under ice-cooling, and the mixture was stirred at room temperature for 14 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=4/1), which was recrystallized from hexane/ethyl acetate to give 7-[4-(2-butoxyethoxy)phenyl]-1-(2-methoxyethyl)-N-[4-[N-methyl-N-(tetrahydropyran-4-yl)aminomethyl]phenyl]-2,3-dihydro-1-benzazepine-4-carboxamide (Compound 91) (0.57 g).

$^1$H-NMR (200 MHz, CDCl$_3$) δ 0.93 (3H, t, J=7.2 Hz), 1.30–1.45 (2H, m), 1.54–1.76 (2H, m), 2.20 (3H, s), 2.64 (1H, m), 2.91 (2H, m), 3.30–3.41 (2H, m), 3.41 (3H, s), 3.51–3.59 (2H, m), 3.56 (2H, s), 3.65–3.71 (2H, m), 3.77–3.83 (2H, m), 4.00–4.17 (2H, m), 4.15 (2H, t, J=4.8 Hz), 6.97 (2H, d, J=8.8 Hz), 6.99 (1H, d, J=8.4 Hz), 7.30 (1H, d, J=8.8 Hz), 7.39–7.56 (9H, m).

IR (KBr) 3321, 2922, 1640, 1609, 1501, 1244, 1140, 822 cm$^{-1}$.

Reference Example 268

In THF (12.0 ml) was dissolved methyl 7-[4-(2-butoxyethoxy)phenyl]-2,3-dihydro-1-benzazepine-4-carboxylate (0.60 g). To the solution were added pyridine (0.37 ml) and 4-dimethylaminopyridine (56 mg), followed by addition of crotonic anhydride (0.58 ml). The mixture was stirred at 50° C. for 24 hours, and cooled to room temperature. The reaction solution was added to water and the mixture was extracted with ethyl acetate. The extract was washed with saturated brine and dried with magnesium sulfate. The solvent was removed under reduced pressure, and the resulting residue was purified with silica gel column chromatography (hexane:ethyl acetate=3/1) to give methyl 7-[4-(2-butoxyethoxy)phenyl]-1-[(E)-2-butenoyl]-2,3-dihydro-1-benzazepine-4-carboxylate (0.53 g).

$^1$H-NMR (200 MHz, CDCl$_3$) δ 0.94 (3H, t, J=7.0 Hz), 1.34–1.46 (2H, m), 1.55–1.66 (2H, m), 3.52–3.60 (2H, t, J=6.2 Hz), 3.79–3.85 (2H, m), 3.83 (3H, s), 4.15–4.21 (2H, m), 4.94–5.11 (1H, m), 5.88–6.04 (1H, m), 7.02 (2H, d, J=8.8 Hz), 7.24–7.29 (1H, m), 7.53 (3H, d, J=8.4 Hz), 7.66 (1H, s), 7.74 (1H, s).

Reference Example 269

In THF (10.6 ml)/methanol (10.6 ml) was dissolved methyl 7-[4-(2-butoxyethoxy)phenyl]-1-[(E)-2-butenoyl]-2,3-dihydro-1-benzazepine-4-carboxylate (0.53 g). To the solution was added 1N sodium hydroxide (5.3 ml), and the mixture was stirred at room temperature for 20 hours. pH was adjusted to approximate 5 with 1N hydrochloric acid, and the solvent was concentrated to half under reduced pressure. The concentrated material was extracted with ethyl acetate, and the extract was washed with saturated brine and dried with magnesium sulfate. The solvent was removed under reduced pressure, and the resulting residue was washed with hexane/ethyl acetate (=8/1) to give 7-[4-(2-butoxyethoxy)phenyl]-1-[(E)-2-butenoyl]-2,3-dihydro-1-benzazepine-4-carboxylate (0.40 g).

$^1$H-NMR (200 MHz, CDCl$_3$) δ 0.97 (3H, t, J=6.8 Hz), 1.31–1.50 (2H, m), 1.54–1.63 (2H, m), 1.80 (3H, d, J=6.4 Hz), 3.57 (2H, t, J=6.6 Hz), 3.82 (2H, m), 4.19 (2H, m), 4.90 (1H, m), 6.01 (1H, m), 7.03 (2H, d, J=8.4 Hz), 7.21 (1H, d, J=8.4 Hz), 7.52–7.57 (3H, m), 7.67 (1H, s), 7.84 (1H, s).

Working Example 92

Production of Compound 92

In THF (7.5 ml) was dissolved 7-[4-(2-butoxyethoxy) phenyl]-1-[(E)-2-butenoyl]-2,3-dihydro-1-benzazepine-4-carboxylic acid (0.39 g). To the solution were added DMF (two droplets) and oxalyl chloride (0.15 ml), and the mixture was stirred at room temperature for 1 hour. The solvent was removed under reduced pressure, a solution of the resulting residue in THF was added dropwise to a solution of 4-[methyl(tetrahydropyranyl-4-yl)aminomethyl]aniline (210 mg) and triethylamine (0.60 ml) in THF (6.3 ml) under ice-cooling, and the mixture was stirred at room temperature for 14 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=4/1), which was recrystallized from isopropyl ether/ethyl acetate to give 1-[(E)-2-butenoyl]-7-[4-(2-butoxyethoxy)phenyl]-N-[4-[N-methyl-N-(tetrahydropyran-4-yl)aminomethyl]phenyl]-2,3-dihydro-1-benzazepine-4-carboxamide (Compound 92) (168 mg).

$^1$H-NMR (200 MHz, CDCl$_3$) δ 0.94 (3H, t, J=7.2 Hz), 1.25–1.49 (2H, m), 1.54–1.82 (9H, m), 2.21 (3H, s), 2.65 (1H, m), 2.93 (3H, s), 3.16–3.43 (3H, m), 3.52–3.60 (2H, m), 3.56 (2H, s), 3.79–3.85 (2H, m), 3.98–4.09 (2H, m), 4.91 (1H, m), 6.00–6.09 (1H, m), 7.03 (2H, d, J=8.8 Hz), 7.18–7.33 (3H, m), 7.39–7.67 (8H, m).

IR (KBr) 2936, 2851, 1659, 1609, 1495, 1250, 1140, 826 cm$^{-1}$.

Anal. Calcd. C$_{40}$H$_{49}$N$_3$O$_5$·0.7H$_2$O Calcd. C, 72.51; H, 6.32; N, 7.65. Found C, 72.33; H, 6.05; N, 7.42.

Reference Example 270

4N sodium hydroxide (36 ml) was added to 1-isopropyl-2-pyrrolidone (9.2 g), and the mixture was stirred for 3.5 hours. After cooled to 0° C., the mixture was neutralized with concentrated hydrochloric acid. After sodium carbonate (15.3 g) was added thereto, a solution of 5-bromo-2-fluorobenzaldehyde (7.3 g) in dimethyl sulfoxide (96 ml) was added thereto, and the mixture was heated to reflux for 5 hours. After cooled to room temperature, pH was adjusted to approximate 4 with 6N hydrochloric acid, and the mixture was extracted with ethyl acetate/THF. The extract was washed with saturated brine and dried with magnesium sulfate. The solvent was removed under reduced pressure, and the resulting residue was purified with silica gel column chromatography (hexane/ethyl acetate=4/1→3/2) to give 4-(4-bromo-2-formylisopropylanilino)butyric acid (0.92 g).

$^1$H-NMR (200 MHz, CDCl$_3$) δ 1.12 (6H, d, J=6.6 Hz), 1.74 (2H, m), 2.37 (2H, t, J=7.0 Hz), 3.16 (2H, t, J=6.6 Hz), 3.30 (1H, m), 7.12 (1H, d, J=8.8 Hz), 7.60 (1H, d, J=8.8, 2.4 Hz), 7.95 (1H, d, J=2.4 Hz), 10.21 (1H, s).

Reference Example 271

In DMF (4.5 ml) was dissolved 4-(4-bromo-2-formylisopropylanilino)butyric acid (0.9 g). To the solution was added potassium carbonate (0.49 g), followed by addition of methyl iodide (0.2 ml) and stirring at room temperature 1 hour. To the mixture was added dimethyl carbonate (9 ml), followed by addition of a 28% sodium methoxide/methanol solution (1.27 g) and stirring at 50° C. for 1 hour. After cooled to room temperature, the mixture was neutralized with 2N hydrochloric acid, and extracted with ethyl acetate. The extract was washed with saturated brine and dried with magnesium sulfate. The solvent was removed under reduced pressure, and the resulting residue was purified with silica gel column chromatography (hexane/ethyl acetate=20/1→6/1) to give methyl 7-bromo-1-isopropyl-2,3-dihydro-1-benzazepine-4-carboxylate (0.50 g).

$^1$H-NMR (200 MHz, CDCl$_3$) δ 1.24 (6H, d, J=6.6 Hz), 2.73–2.79 (2H, m), 3.15 (2H, t, J=4.8 Hz), 3.80 (3H, s), 3.98 (1H, s), 6.70 (1H, d, J=9.0 Hz), 7.22 (1H, d, J=2.6 Hz), 7.42 (1H, d, J=2.6 Hz), 7.55 (1H, s).

Reference Example 272

In toluene/ethanol/water (=10/1/1, 20.4 ml) was dissolved methyl 7-bromo-1-isopropyl-2,3-dihydro-1-benzazepine-4-carboxylate (0.50 g). To the solution were added 4-(2-butoxyethoxy)phenyl borate (0.48 g) and potassium carbonate (0.47 g), and the mixture was stirred for 30 minutes under argon atmosphere. To the mixture was added tetrakistriphenylphosphinepalladium (0.10 g), and the mixture was heated to reflux for 14 hours. After cooled to room temperature, the reaction solution was added to water, and the mixture was extracted with ethyl acetate. The extract was washed with saturated brine and dried with magnesium sulfate. The solvent was removed under reduced pressure, and the resulting residue was purified with silica gel column chromatography (hexane/ethyl acetate=20/1→8/1) to give methyl 7-[4-(2-butoxyethoxy)phenyl]-1-isopropyl-2,3-dihydro-1-benzazepine-4-carboxylate (0.44 g). Methyl 7-[4-(2-butoxyethoxy)phenyl]-1-isopropyl-2,3-dihydro-1-benzazepine-4-carboxylate (0.44 g) was dissolved in THF (8.8 ml)/methanol (8.8 ml). To the solution was added 1N sodium hydroxide (4.4 ml), and the mixture was stirred at 50° C. for 4 hours. After cooled to room temperature, pH was adjusted to approximate. 5 with 1N hydrochloric acid, and the solvent was concentrated to half under reduced pressure. The concentrated material was extracted with ethyl acetate/THF, and the extract was washed with saturated brine and dried with magnesium sulfate. The solvent was removed under reduced pressure, and the resulting residue was washed with hexane/ethyl acetate (12/1) to give 7-[4-(2-butoxyethoxy)phenyl]-1-isopropyl-2,3-dihydro-1-benzazepine-4-carboxylic acid (320 mg).

$^1$H-NMR (200 MHz, CDCl$_3$) δ 0.93 (3H, t, J=7.2 Hz), 1.28 (6H, d, J=6.6 Hz), 1.28–1.68 (4H, m), 2.77–2.83 (2H, m), 3.20–3.26 (2H, m), 3.56 (2H, t, J=6.6 z), 3.81 (2H, t, J=4.8 Hz), 4.11 (1H, m), 4.13–4.18 (2H, m), 6.90 (1H, d, J=8.8 Hz), 6.98 (2H, d, J=8.4 Hz), 7.25–7.54 (4H, m), 7.87 (1H, s).

Working Example 93

Production of Compound 93

In THF (6.4 ml) was dissolved 7-[4-(2-butoxyethoxy)phenyl]-1-isopropyl-2,3-dihydro-1-benzazepine-4-carboxylic acid (0.32 g), followed by addition of DMF (two droplets). To the mixture was added oxalyl chloride (165 μl), and the mixture was stirred at room temperature for 1 hour. The solvent was removed under reduced pressure, a solution of the resulting residue in THF was added dropwise to a solution of 4-[methyl(tetrahydropyranyl-4-yl)aminomethyl] aniline (183 mg) and triethylamine (0.63 ml) in THF (5.5 ml) under ice-cooling, and the mixture was stirred at room temperature for 3 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=4/1) to give 7-[4-(2-butoxyethoxy)phenyl]-1-isopropyl-N-[4-[N-methyl-N-(tetrahydropyran-4-yl)aminomethyl]phenyl]-2,3-dihydro-1-benzazepine-4-carboxamide (Compound 93) (284 mg).

$^1$H-NMR (200 MHz, CDCl$_3$) δ 0.93 (3H, t, J=7.0 Hz), 1.29 (6H, d, J=6.6 Hz), 1.32–1.54 (2H, m), 1.57–1.76 (6H, m), 2.20 (3H, s), 2.64 (1H, s), 2.89 (2H, m), 3.24–3.43 (4H, m), 3.55 (2H, t, J=6.2 Hz), 3.56 (2H, s), 3.80 (2H, m), 4.00–4.08 (2H, m), 4.10 (1H, m), 4.16 (2H, m), 6.92 (1H, d, J=8.8 Hz), 6.97 (2H, d, J=8.8 Hz), 7.29 (2H, d, J=8.8 Hz), 7.40–7.56 (8H, m).

IR (KBr) 2959, 2870, 1667, 1597, 1514, 1497, 1404, 1242, 820 cm$^{-1}$.

Anal. Calcd. C$_{39}$H$_{51}$N$_3$O$_4$·0.5H$_2$O Calcd. C, 73.78; N, 6.62; H, 8.26. Found C, 74.04; N, 6.53; H, 8.41.

Reference Example 273

In THF (27.4 ml) was dissolved methyl 7-[4-(2-butoxyethoxy)phenyl]-2,3-dihydro-1-benzazepine-4-carboxylate (1.37 g). To the solution was added 60% sodium hydride (0.27 g) at 0° C., and the mixture was stirred at room temperature for 1 hour. To the mixture was added 3-bromo-1-(trimethylsilyl)-1-propyne (1.48 ml), and the mixture was stirred at 65° C. for 90 hours. After cooled to room temperature, the reaction solution was added to water, and the mixture was extracted with ethyl acetate. The extract was washed with saturated brine and dried with magnesium sulfate. The solvent was removed under reduced pressure, and the resulting residue was purified with silica gel column chromatography (hexane/ethyl acetate=3/1) to give methyl 7-[4-(2-butoxyethoxy)phenyl]-1-(3-trimethylsilyl-2-propynyl)-2,3-dihydro-1-benzazepine-4-carboxylate (0.78 g).

$^1$H-NMR (200 MHz, CDCl$_3$) δ 0.18 (9H, s), 0.93 (3H, t, J=7.4 Hz), 1.34–1.44 (2H, m), 1.55–1.64 (2H, m), 2.82–2.90 (2H, m), 3.33–3.40 (4H, m), 3.56 (2H, t, J=6.2 Hz), 3.78–3.84 (2H, m), 3.82 (3H, s), 4.07 (2H, s), 4.10–4.19 (2H, m), 6.97–7.06 (3H, m), 7.43 (4H, m), 7.76 (1H, s).

Reference Example 274

In THF (7.8 ml)/methanol (7.8 ml) was dissolved methyl 7-[4-(2-butoxyethoxy)phenyl]-1-(3-trimethylsilyl-2-propynyl)-2,3-dihydro-1-benzazepine-4-carboxylate (0.78 g). To the solution was added 2N potassium hydroxide (7.8 ml), and the mixture was stirred at room temperature for 16 hours. pH was adjusted to approximate 4 with 6N hydrochloric acid, and the solvent was concentrated to half under reduced pressure. The concentrated material was extracted with ethyl acetate, and the extract was washed with saturated brine and dried with magnesium sulfate. The solvent was removed under reduced pressure and the resulting residue was washed with hexane/ethyl acetate (=8/1) to give 7-[4-(2-butoxyethoxy)phenyl]-1-(2-propynyl)-2,3-dihydro-1-benzazepine-4-carboxylic acid (0.52 g).

$^1$H-NMR (200 MHz, CDCl$_3$) δ 0.93 (3H, t, J=7.4 Hz), 1.34–1.47 (2H, m), 1.55–1.68 (2H, m), 2.31 (1H, m), 2.84–2.95 (2H, m), 3.37–3.43 (2H, m), 3.56 (2H, t, J=6.6 Hz), 3.78–3.84 (2H, m), 4.08 (2H, d, J=2.2 Hz), 4.14–4.19 (2H, m), 6.99 (2H, d, J=8.8 Hz), 7.06 (1H, d, J=8.8 Hz), 7.45–7.56 (4H, m), 7.87 (1H, s).

Reference Example 94

Production of Compound 94

In THF (10.4 ml) was dissolved 7-[4-(2-butoxyethoxy)phenyl]-1-(2-propynyl)-2,3-dihydro-1-benzazepine-4-carboxylic acid (0.52 g). To the solution was added DMF (two droplets), followed by addition of oxalyl chloride (0.27 ml) and stirring at room temperature for 2 hours. The solvent was removed under reduced pressure, a solution of the resulting residue in THF was added dropwise to a solution of 4-[methyl(tetrahydropyranyl-4-yl)aminomethyl]aniline (0.30 g) and triethylamine (1.04 ml) in THF (9.0 ml) under ice-cooling, and the mixture was stirred at room temperature for 15 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=4/1), which was recrystallized from ethyl acetate to give 7-[4-(2-butoxyethoxy)phenyl]-N-[4-[N-methyl-N-(tetrahydropyran-4-yl)aminomethyl]phenyl]-1-(2-propynyl)-2,3-dihydro-1-benzazepine-4-carboxamide (Compound 94) (570 mg).

$^1$H-NMR (200 MHz, CDCl$_3$) δ 0.93 (3H, t, J=7.0 Hz), 1.33–1.46 (2H, m), 1.54–1.75 (6H, m), 2.20 (3H, s), 2.32 (1H, m), 2.64 (1H, m), 2.90–2.97 (2H, m), 3.30–3.42 (6H, m), 3.51–3.59 2H, m), 3.55 (2H, s), 3.77–3.83 (2H, m), 4.00–4.17 (4H, m), 4.06 (1H, m), 6.97 (2H, d, J=8.8 Hz), 7.05 (2H, d, J=8.8 Hz), 7.31–7.56 (8H, m), 7.67 (1H, s)

IR (KBr) 3322, 3249, 2948, 1642, 1607, 1499, 1240, 1140, 810 cm$^{-1}$.

Anal. Calcd. C$_{39}$H$_{47}$N$_3$O$_4$ Calcd. C, 75.33; N, 6.76; H, 7.62. Found C, 75.39; N, 6.74; H, 7.53.

Reference Example 275

In THF (24.0 ml) was dissolved methyl 7-[4-(2-butoxyethoxy)phenyl]-2,3-dihydro-1-benzazepine-4-carboxylate (1.20 g). To the solution was added 60% sodium hydride (0.24 g), and the mixture was stirred at room temperature for 1 hour. To the mixture was added 1-bromo-2-butyne (0.80 ml), and the mixture was stirred at 65° C. for 4 days. After cooled to room temperature, the reaction solution was added to water, and the mixture was extracted with ethyl acetate. The extract was washed with saturated brine and dried with magnesium sulfate. The solvent was removed under reduced pressure, and the resulting residue was purified with silica gel column chromatography (hexane/ethyl acetate=4/1) to give methyl 7-[4-(2-butoxyethoxy)phenyl]-1-(2-butynyl)-2,3-dihydro-1-benzazepine-4-carboxylate (0.50 g).

$^1$H-NMR (200 MHz, CDCl$_3$) δ 0.93 (3H, t, J=7.4 Hz), 1.30–1.45 (2H, m), 1.53–1.68 (2H, m), 1.83–1.86 (3H, m), 2.83–2.89 (2H, m), 3.30–3.38 (2H, m), 3.56 (2H, t, J=6.6 Hz), 3.78–3.84 (2H, m), 3.81 (3H, s), 4.01 (2H, d, J=2.2 Hz), 4.13–4.18 (2H, m), 6.98 (2H, d, J=8.8 Hz), 7.04 (1H, d, J=8.8 Hz), 7.42–7.54 (4H, m), 7.76 (1H, s).

Reference Example 276

In THF (5.0 ml)/methanol (5.0 ml) was dissolved methyl 7-[4-(2-butoxyethoxy)phenyl]-1-(2-butynyl)-2,3-dihydro-1-benzazepine-4-carboxylate (0.50 g). To the solution was added 2N potassium hydroxide (5.0 ml), and the mixture was stirred at 50° C. for 3 hours. pH was adjusted to approximate 4 with 6N hydrochloric acid, and the solvent was concentrated to half under reduced pressure. The concentrated material was extracted with ethyl acetate, and the extract was washed with saturated brine and dried with magnesium sulfate. The solvent was removed under reduced pressure, and the resulting residue was washed with hexane/ethyl acetate (=8/1) to give 7-[4-(2-butoxyethoxy)phenyl]-1-(2-butynyl)-2,3-dihydro-1-benzazepine-4-carboxylic acid (0.40 g).

$^1$H-NMR (200 MHz, CDCl$_3$) δ 0.93 (3H, t, J=7.0 Hz), 1.35–1.45 (2H, m), 1.55–1.64 (2H, m), 1.86 (3H, s), 2.88 (2H, m), 3.38 (2H, m), 3.56 (2H, t, J=6.6 Hz), 3.78–3.84 (2H, m), 4.02 (2H, d, J=2.0 Hz), 4.17 (2H, t, J=4.8 Hz), 6.98 (2H, d, J=8.6 Hz), 7.05 (1H, d, J=8.4 Hz), 7.44–7.55 (4H, m), 7.87 (1H, s).

IR (KBr) 2922, 1677, 1607, 1503, 1275, 1248, 1192, 924, 806 cm$^{-1}$.

Working Example 95

Production of Compound 95

In THF (8.0 ml) was dissolved 7-[4-(2-butoxyethoxy)phenyl]-1-(2-butynyl)-2,3-dihydro-1-benzazepine-4- carboxylic acid (0.40 g). To the solution was added DMF (two droplets), followed by addition of oxalyl chloride (0.20 ml) and stirring at room temperature for 1 hour. The solvent was removed under reduced pressure, a solution of the resulting residue in THF was added dropwise to a solution of 4-[methyl(tetrahydropyranyl-4-yl)aminomethyl]aniline (224 mg) and triethylamine (0.64 ml) in THF (6.7 ml) under ice-cooling, and the mixture was stirred at room temperature for 12 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=4/1→3/1), which was recrystallized from hexane/ethyl acetate to give 7-[4-(2-butoxyethoxy)phenyl]-1-(2-butynyl)-N-[4-[N-methyl-N-(tetrahydropyran-4-yl)aminomethyl]phenyl]-2,3-dihydro-1-benzazepine-4-carboxamide (Compound 95) (359 mg).

m.p 129–131° C.

$^1$H-NMR (200 MHz, CDCl$_3$) δ 0.93 (3H, t, J=7.0 Hz), 1.26–1.48 (2H, m), 1.54–1.76 (6H, m), 1.86 (23H, s), 2.21 (3H, s), 2.64 (1H, m), 2.96 (2H, m), 3.30–3.44 (4H, m), 3.55 (2H, t, J=6.2 Hz), 3.56 (2H, s), 3.80 (2H, t, J=4.8 Hz), 4.00–4.10 (4H, m), 4.13–4.18 (2H, m), 6.98 (2H, d, J=8.8 Hz), 7.07 (2H, d, J=8.8 Hz), 7.30 (2H, m), 7.39–7.58 (8H, m).

IR (KBr) 2953, 1655, 1605, 1514, 1499, 1244, 1138, 814 cm$^{-1}$.

Anal. Calcd. C$_{40}$H$_{49}$N$_3$O$_4$ Calcd. C, 75.56; N, 6.61; H, 7.77. Found C, 75.53; N, 6.52; H, 7.79.

Reference Example 277

In THF (11.2 ml) was dissolved methyl 7-[4-(2-butoxyethoxy)phenyl]-2,3-dihydro-1-benzazepine-4-carboxylate (0.56 g). To the solution were added pyridine (0.17 ml) and ethyl chloroformate (0.18 ml, and the mixture was stirred at room temperature for 3 hours. To the mixture was added 4-dimethylaminopyridine (169 mg), and the mixture was stirred at room temperature for 2 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (hexane/ethyl acetate=3/1) to give methyl 7-[4-(2-butoxyethoxy)phenyl]-1-(ethoxycarbonyl)-2,3-dihydro-1-benzazepine-4-carboxylate (580 mg).

$^1$H-NMR (200 MHz, CDCl$_3$) δ 0.93 (3H, t, J=7.0 Hz), 1.26–1.42 (5H, m), 1.55–1.62 (2H, m), 2.93 (2H, m), 3.56 (2H, t, J=6.6 Hz), 3.66–3.84 (4H, m), 3.83 (3H, s), 4.14–4.29 (4H, m), 7.00 (2H, d, J=8.8 Hz), 7.47–7.59 (5H, m), 7.73 (1H, s).

Reference Example 278

In THF (8.7 ml)/methanol (8.7 ml) was dissolved methyl 7-[4-(2-butoxyethoxy)phenyl]1-(ethoxycarbonyl)-2,3-dihydro-1-benzazepine-4-carboxylate (0.58 g). To the solution was added 1N sodium hydroxide (8.7 ml), and the mixture was stirred at 50° C. for 4 hours. pH was adjusted to approximate 4 with 6N hydrochloric acid, and the solvent was concentrated to half under reduced pressure. The concentrated material was extracted with ethyl acetate, and the extract was washed with saturated brine and dried with magnesium sulfate. The solvent was removed under reduced pressure, and the resulting residue was washed with hexane/ethyl acetate (=8/1) to give 7-[4-(2-butoxyethoxy)phenyl]-1-(ethoxycarbonyl)-2,3-dihydro-1-benzazepine-4-carboxylic acid (0.46 g).

$^1$H-NMR (200 MHz, CDCl$_3$) δ 0.93 (3H, t, J=7.0 Hz), 1.29 (3H, t, J=6.6 Hz), 1.56–1.66 (2H, m), 2.95 (2H, m), 3.56 (2H, t, J=6.6 Hz), 3.75–3.85 (4H, m), 4.17 (2H, t, J=4.8 Hz), 4.23 (2H, q, J=6.6 Hz), 7.01 (2H, d, J=8.4 Hz), 7.51–7.62 (5H, m), 7.84 (1H, s).

Working Example 96

Production of Compound 96

In THF (9.2 ml) was dissolved 7-[4-(2-butoxyethoxy) phenyl]-1-(ethoxycarbonyl)-2,3-dihydro-1-benzazepine-4-carboxylic acid (0.46 g). To the solution was added DMF (two droplets), followed by addition of oxalyl chloride (0.22 ml) and stirring at room temperature for 1 hour. The solvent was removed under reduced pressure, a solution of the resulting residue in THF was added dropwise to a solution of 4-[methyl(tetrahydropyranyl-4-yl)aminomethyl]aniline (246 mg) and triethylamine (0.71 ml) in THF (7.4 ml) under ice-cooling, and the mixture was stirred at room temperature for 12 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=4/1→3/1), which was recrystallized from hexane/ethyl acetate to give 7-[4-(2-butoxyethoxy)phenyl]-1-(ethoxycarbonyl)-4-[4-[N-methyl-N-(tetrahydropyran-4-yl)aminomethyl]phenyl]-2,3-dihydro-1-benzazepine-4-carboxamide (Compound 96) (0.48 g).

m.p 152–154° C.

$^1$H-NMR (200 MHz, CDCl$_3$) δ 0.93 (3H, t, J=7.2 Hz), 1.29 (3H, t, J=6.4 Hz), 1.33–1.45 (2H, m), 1.54–1.75 (6H, m), 2.21 (3H, s), 2.65 (1H, m), 3.00 (2H, m), 3.30–3.43 (2H, m), 3.55 (2H, t, J=6.6 Hz), 3.57 (2H, s), 3.81 (2H, m), 4.00–4.20 (2H, m), 4.17 (2H, t, J=4.8 Hz), 4.23 (2H, q, J=6.4 Hz), 7.00 (2H, d, J=8.8 Hz), 7.31 (2H, d, J=8.8 Hz), 7.46–7.60 (8H, m).

IR (KBr) 3308, 2955, 2870, 1699, 1609, 1497, 1250, 1208, 1140, 922, 826, 731 cm$^{-1}$.

Anal. Calcd. C$_{38}$H$_{48}$N$_3$O$_6$ Calcd. C, 71.00; N, 6.54; H, 7.53. Found C, 71.14; N, 6.26; H, 7.36.

Reference Example 279

In pyridine (4.3 ml) was dissolved methyl 7-[4-(2-butoxyethoxy)phenyl]-2,3-dihydro-1-benzazepine-4-carboxylate (0.43 g). To the solution was added allyl chloroformate (0.23 ml), and the mixture was stirred at room temperature for 14 hours. To the mixture was added 4-dimethylaminopyridine (40 mg), and the mixture was stirred at room temperature for 2 hours. The reaction solution was added to water, and the mixture was extracted with ethyl acetate. The extract was washed with saturated brine, and dried with magnesium sulfate. The solvent was removed under reduced pressure, and the resulting residue was purified with silica gel column chromatography (hexane/ethyl acetate→3/1) to give methyl 1-(allyloxycarbonyl)-7-[4-(2-butoxyethoxy)phenyl]-2,3-dihydro-1-benzazepine-4-carboxylate (0.30 g).

$^1$H-NMR (200 MHz, CDCl$_3$) δ 0.93 (3H, t, J=7.0 Hz), 1.28–1.45 (2H, m), 1.54–1.66 (2H, m), 2.94 (2H, m), 3.56 (2H, t, J=6.6 Hz), 3.78–3.85 (4H, m), 3.83 (3H, s), 4.15–4.19 (2H, m), 4.67 (1H, m), 5.24 (1H, m), 5.94 (1H, m), 7.00 (2H, d, J=8.8 Hz), 7.43–7.60 (5H, m), 7.73 (1H, s).

Reference Example 280

In THF (4.5 ml)/ethanol (4.5 ml) was dissolved methyl 1-(allyloxycarbonyl)-7-[4-(2-butoxyethoxy)phenyl]-2,3-dihydro-1-benzazepine-4-carboxylate (0.30 g). To the solution was added 1N sodium hydroxide (3.0 ml), and the mixture was stirred at room temperature for 4 hours. pH was adjusted to approximate 4 with 1N hydrochloric acid, and the solvent was concentrated to half under reduced pressure. The concentrated material was extracted with ethyl acetate, the extract was washed with saturated brine and dried with magnesium sulfate. The solvent was removed under reduced pressure, and the resulting residue was washed with hexane/ethyl acetate (=8/1) to give 1-(allyloxycarbonyl)-7-[4-(2-butoxyethoxy)phenyl]-2,3-dihydro-1-benzazepine-4-carboxylic acid (0.25 g).

$^1$H-NMR (200 MHz, CDCl$_3$) δ 0.94 (3H, t, J=7.2 Hz), 1.30–1.49 (2H, m), 1.54–1.69 (2H, m), 2.97 (2H, m), 3.56 (2H, t, J=6.6 Hz), 3.75–3.87 (4H, m), 4.18 (2H, d, J=4.8 Hz), 4.68 (1H, m), 5.24 (1H, m), 5.96 (1H, m), 7.01 (2H, d, J=8.4 Hz), 7.49–7.61 (5H, m), 7.85 (1H, s).

Working Example 97

Production of Compound 97

In THF (4.8 ml) was dissolved 1-(allyloxycarbonyl)-7-[4-(2-butoxyethoxy)phenyl]-2,3-dihydro-1-benzazepine-4-carboxylic acid (0.24 g). To the solution was added DMF (two droplets), followed by addition of oxalyl chloride (0.11 ml) and stirring at room temperature for 1 hour. The solvent was removed under reduced pressure, a solution of the resulting residue in THF was added dropwise to a solution of 4-[methyl(tetrahydropyranyl-4-yl)aminomethyl]aniline (125 mg) and triethylamine (0.36 ml) in THF (5.0 ml) under ice-cooling, and the mixture was stirred at room temperature for 12 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=4/1→3/1), which was recrystallized from hexane/ethyl acetate to give 1-(allyloxycarbonyl)-7-[4-(2-butoxyethoxy)phenyl]-4-[4-[N-methyl-N-(tetrahydropyran-4-yl)aminomethyl]phenyl]-2,3-dihydro-1-benzazepine-4-carboxamide (Compound 97) (0.23 g).

mp 160–162° C.

$^1$H-NMR (200 MHz, CDCl$_3$) δ 0.93 (3H, t, J=7.2 Hz), 1.33–1.49 (2H, m), 1.54–1.75 (6H, m), 2.21 (3H, s), 2.65 (1H, m), 3.02 (2H, m), 3.37 (2H, td, J=11.0, 2.8 Hz), 3.56 (2H, t, J=6.6 Hz), 3.57 (2H, s), 3.81 (2H, m), 3.99–4.08 (2H, m), 3.99–4.08 (2H, m), 4.14–4.20 (2H, m), 4.67 (1H, m), 5.25 (1H, m), 5.92 (1H, m), 7.00 (2H, d, J=8.4 Hz), 7.31 (2H, d, J=8.4 Hz), 7.47–7.58 (9H, m).

IR (KBr) 3353, 2953, 2845, 1686, 1658, 1611, 1533, 1316, 1206, 1086, 922, 829, 764 cm$^{-1}$.

Anal. Calcd. C$_{40}$H$_{49}$N$_3$O$_6$ Calcd. C, 71.94; N, 6.29; H, 7.40. Found C, 71.69; N, 6.33; H, 7.49.

Reference Example 281

In 1,2-dichloroethane (15 ml) was dissolved methyl 7-[4-(2-butoxyethoxy)phenyl]-1-benzazepine-4-carboxylate (0.50 g). To the solution were added 1,3-thiazole-5-carbaldehyde 10.43 g) and sodium triacetoxyborohydride (0.80 g), and the mixture was stirred at room temperature for 24 hours. To the mixture was added sodium triacetoxyborohydride (0.27 g), and the mixture was stirred for 6 hours. The solvent was removed under reduced pressure, the resulting residue was added to water, and the mixture was extracted with ethyl acetate. The extract was washed with saturated brine and dried with magnesium sulfate. The solvent was removed under reduced pressure, and the resulting residue was purified with silica gel column chromatography (hexane/ethyl acetate=3/2→2/3) to give methyl 7-[4-(2-butoxyethoxy)phenyl]-1-(1,3-thiazol-5-ylmethyl)-2,3-dihydro-1-benzazepine-4-carboxylate (0.50 g).

$^1$H-NMR (200 MHz, CDCl$_3$) δ 0.93 (3H, t, J=7.2 Hz), 1.34–1.44 (2H, m), 1.54–1.65 (2H, m), 2.79 (2H, m), 3.30 (2H, m), 3.55 (2H, t, J=6.6 Hz), 3.78–3.83 (2H, m), 3.81 (3H, s), 4.16 (2H, m), 6.94–7.10 (3H, m), 7.39–7.57 (3H, m), 7.56 (1H, d, J=2.2 Hz), 7.79 (1H, s), 7.83 (1H, s), 8.78 (1H, s).

Reference Example 282

In THF (5.0 ml)/methanol (10 ml) was dissolved methyl 7-[4-(2-butoxyethoxy)phenyl]-1-(1,3-thiazol-5-ylmethyl)-2,3-dihydro-1-benzazepine-4-carboxylate (0.50 g). To the solution was added 1N sodium hydroxide solution (5.0 ml), and the mixture was stirred at room temperature for 16 hours. pH was adjusted to approximate 5 with 1N hydrochloric acid, and the solvent was concentrated to half under reduced pressure. The concentrated material was extracted with ethyl acetate/THF, and the extract was washed with saturated brine and dried with magnesium sulfate. The solvent was removed under reduced pressure, and the resulting residue was washed with hexane ethyl acetate (8/1) to give 7-[4-(2-butoxyethoxy)phenyl]-1-(1,3-thiazol-5-ylmethyl)-2,3-dihydro-1-benzazepine-4-carboxylic acid (385 mg).

$^1$H-NMR (200 MHz, CDCl$_3$) δ 0.93 (3H, t, J=7.4 Hz), 1.34–1.44 (2H, m), 1.55–1.67 (2H, m), 2.82 (2H, m), 3.33 (2H, m), 3.56 (2H, t, J=6.6 Hz), 3.81 (2H, t, J=4.8 Hz), 4.17 (2H, m), 4.77 (2H, s), 6.97 (1H, d, J=8.8 Hz), 6.99 (2H, d, J=8.8 Hz), 7.41–7.50 (3H, m), 7.58 (1H, d, J=1.8 Hz), 7.85 (1H, s), 7.91 (1H, s), 8.81 (1H, s).

Working Example 98

Production of Compound 98

In methylene chloride (19 ml) was dissolved 7-[4-(2-butoxyethoxy)phenyl]-1-(1,3-thiazol-5-ylmethyl)-2,3-dihydro-1-benzazepine-4-carboxylic acid (0.38 g). To the solution was added DMF (two droplets), followed by addition of oxalyl chloride (90 μl) and stirring at room temperature for 2 hours to give a solution, which was added dropwise to a solution of 4-[methyl(tetrahydropyranyl-4-yl)aminomethyl]aniline (198 mg) and triethylamine (2.75 ml) in methylene chloride (7.6 ml), and the mixture was stirred at room temperature for 2 hours. The reaction solution was added to water, and the mixture was extracted with methylene chloride. The extract was washed with saturated brine and dried with magnesium sulfate. The solvent was removed under reduced pressure, and the resulting residue was purified with silica gel column chromatography (ethyl acetate/ethanol=2/1) to give 7-[4-(2-butoxyethoxy)phenyl]-N-[4-[N-methyl-N-(tetrahydropyran-4-aminomethyl]phenyl]-1-(1,3-thiazol-5-ylmethyl)-2,3-dihydro-1-benzazepine-4-carboxamide (Compound 98) (190 mg).

$^1$H-NMR (200 MHz, CDCl$_3$) δ 0.93 (3H, t, J=7.2 Hz), 1.30–1.48 (2H, m), 1.53–1.72 (2H, m), 2.21 (3H, s), 2.66

(1H, m), 2.87 (2H, m), 3.30–3.43 (4H, m), 3.55 (2H, t, J=6.6 Hz), 3.57 (2H, s), 3.80 (2H, m), 3.97–4.09 (2H, m), 4.16 (2H, m), 4.77 (2H, m), 6.98 (4H, d, J=8.8 Hz), 7.27–7.58 (9H, m), 7.84 (1H, s), 8.79 (1H, s).

IR (KBr) 3293, 2955, 1645, 1609, 1518, 1499, 1406, 1242, 1140, 821 $cm^{-1}$.

Reference Example 283

In ethanol (50 ml) was dissolved acetyl thioamide (5.0 g). To the solution was added ethyl 2-chloroacetoacetate (11.0 g), and the mixture was heated to reflux for 16 hours. After cooled to room temperature, the solvent was removed under reduced pressure, the resulting residue was added to water, and the mixture was extracted with ethyl acetate. The extract was washed with saturated brine and dried with magnesium sulfate. The solvent was removed under reduced pressure, and the resulting residue was purified with silica gel column chromatography (hexane/ethyl acetate=1/1) to give ethyl 2,3-dimethyl-1,3-thiazole-5-carboxylate (9.1 g).

$^1$H-NMR (200 MHz, $CDCl_3$) δ 1.36 (3H, t, J=7.2 Hz), 2.68 (3H, m), 2.69 (3H, s), 4.32 (2H, q, J=7.2 Hz).

Reference Example 284

A solution of ethyl 2,4-dimethyl-1,3-thiazole-5-carboxylate (5.0 g) in THF (50 ml) was added dropwise to a solution of aluminum lithium hydride (1.1 g) in THF (150 ml) under ice-cooling. After stirred at room temperature for 4 hours, water (1.1 ml), 15% sodium hydroxide solution (1.1 ml) and water (3.3 ml) were added thereto, and the mixture was stirred for 10 minutes. The mixture was filtered with Celite, and washed with methanol. The solvent was removed under reduced pressure, and the resulting residue was purified with silica gel column chromatography (hexane/ethyl acetate=1/2) to give (2,4-dimethyl-1,3-thiazol-5-yl) methanol (2.0 g).

$^1$H-NMR (200 MHz, $CDCl_3$) δ 2.31 (3H, s), 2.62 (3H, s), 3.14 (1H, br), 4.72 (2H, d, J=5.0 Hz).

Reference Example 285

In THF (20 ml) was dissolved (2,4-dimethyl-1,3-thiazol-5-yl)methanol (1.0 g). To the solution was added active manganese dioxide (6.0 g), and the mixture was stirred at room temperature for 3 hours. To the mixture was added active manganese dioxide (3.0 g), and the mixture was stirred at room temperature for 1 hour. The mixture was filtered with Celite and washed with methanol. The solvent was removed under reduced pressure, and the resulting residue was purified with silica gel column chromatography (hexane/ethyl acetate/methanol=10/10/1) to give 2,4-dimethyl-1,3-thiazole-5-carbaldehyde (0.32 g).

$^1$H-NMR (200 MHz, $CDCl_3$) δ 2.70 (3H, s), 2.73 (3H, s), 10.13 (1H, s).

Reference Example 286

In 1,2-dichloroethane (21 ml) was dissolved methyl 7-[4-(2-butoxyethoxy)phenyl]-1-benzazepine-4-carboxylate (0.70 g). To the solution were added 2,4-dimethyl-1,3-thiazole-5-carbaldehyde (0.62 g) and sodium triacetoxyborohydride (1.5 g), and the mixture was stirred at room temperature for 36 hours. After stirred at 60° C. for 12 hours, the mixture was cooled to room temperature, and the solvent was removed under reduced pressure. The residue was added to water, and the mixture was extracted with ethyl acetate. The extract was washed with saturated brine and dried with magnesium sulfate. The solvent was removed under reduced pressure, and the resulting residue was purified with silica gel column chromatography (hexane/ethyl acetate=1/1) to give methyl 7-[4-(2-butoxyethoxy)phenyl]-1-(2,4-dimethyl-1,3-thiazol-5-ylmethyl)-2,3-dihydro-1-benzazepine-4-carboxylate (0.26 g).

$^1$H-NMR (200 MHz, $CDCl_3$) δ 0.93 (3H, t, J=7.2 Hz), 1.37–1.44 (2H, m), 1.54–1.67 (2H, m), 2.40 (3H, s), 2.62 (3H, s), 2.76 (2H, t, J=4.4 Hz), 3.24 (2H, m), 3.55 (2H, t, J=6.6 Hz), 3.78–3.83 (2H, m), 3.81 (3H, s), 4.16 (2H, m), 4.56 (2H, s), 6.93 (1H, d, J=8.8 Hz), 6.98 (2H, d, J=8.8 Hz), 7.39–7.49 (3H, m), 7.55 (1H, d, J=2.2 Hz), 7.78 (1H, s).

Reference Example 287

In THF (5.0 ml)/methanol (2.5 ml) was dissolved methyl 7-[4-(2-butoxyethoxy)phenyl]-1-(2,4-dimethyl-1,3-thiazol-5-ylmethyl)-2,3-dihydro-1-benzazepine-4-carboxylate (0.25 g). To the solution was added 1N sodium hydroxide solution (2.5 ml), and the mixture was stirred at room temperature for 16 hours. pH was adjusted to approximate with 1N hydrochloric acid, and the solvent was concentrated to half under reduced pressure. The concentrated material was extracted with ethyl acetate/THF, and the extract was washed with saturated brine and dried with magnesium sulfate. The solvent was removed under reduced pressure, and the resulting residue was washed with hexane/ethyl acetate (8/1) to give 7-(4-(2-butoxyethoxy)phenyl]-1-(2,4-dimethyl-1,3-thiazol-5-ylmethyl)-2,3-dihydro-1-benzazepine-4-carboxylic acid (190 mg).

$^1$H-NMR (200 MHz, $CDCl_3$) δ 0.93 (3H, t, J=7.2 Hz), 1.32–1.46 (2H, m), 1.56–1.68 (2H, m), 2.42 (3H, s), 2.64 (3H, s), 2.78 (2H, m), 3.27 (2H, m), 3.56 (2H, t, J=6.6 Hz), 3.81 (2H, t, J=4.8 Hz), 4.17 (2H, t, J=4.8 Hz), 4.59 (2H, s), 6.92–7.10 (3H, m), 7.42–7.50 (3H, m), 7.57 (1H, d, J=1.8 Hz), 7.89 (1H, s).

IR (KBr) 2924, 1684, 1607, 1501, 1235, 1126, 968, 810 $cm^{-1}$.

Working Example 99

Production of Compound 99

In methylene chloride (9.5 ml) was dissolved 7-[4-(2-butoxyethoxy)phenyl]-1-(2,4-dimethyl-1,3-thiazol-5-ylmethyl)-2,3-dihydro-1-benzazepine-4-carboxylic acid (0.19 g). To the solution was added DMF (two droplets), followed by addition of thionyl chloride (32 μl) and stirring at room temperature for 2 hours, to give a solution, which was added dropwise to a solution of 4-[methyl (tetrahydropyranyl-4-yl)aminomethylaniline (91 mg) and triethylamine (1.0 ml) in methylene chloride (5.6 ml), and the mixture was stirred at room temperature for 2 hours. The reaction solution was added to water, and the mixture was extracted with methylene chloride. The extract was washed with saturated brine and dried with magnesium sulfate. The solvent was removed under reduced pressure, and the resulting residue was purified with silica gel column chromatography (ethyl acetate/ethanol=2/1), which was recrystallized from hexane/ethyl acetate to give 7-[4-(2-butoxyethoxy)phenyl]-1-(2,4-dimethyl-1,3-thiazol-5-ylmethyl)-N-[4-[N-methyl-N-(tetrahydropyran-4-yl)amino]methylphenyl]-2,3-dihydro-1-benzazepine-4-carboxamide (Compound 99) (135 mg).

mp 125–128° C.

$^1$H-NMR (200 MHz, $CDCl_3$) δ 0.93 (3H, t, J=7.2 Hz), 1.37–1.45 (2H, m), 1.57–1.77 (6H, m), 2.21 (3H, s), 2.43 (3H, s), 2.64 (3H, s), 2.84 (2H, m), 3.28–3.44 (2H, m), 3.52–3.59 (2H, m), 3.55 (2H, s), 3.81 (2H, t, J=4.8 Hz), 3.98–4.08 (2H, m), 4.16 (2H, t, J=4.8 Hz), 4.59 (2H, s), 6.96 (1H, d, J=8.8 Hz), 6.99 (2H, d, J=8.8 Hz), 7.30 (2H, d, J=8.4 Hz), 7.40–7.56 (8H, m).

IR (KBr) 3227, 2959, 1655, 1603, 1499, 1406, 1315, 1248, 1177, 820 cm$^{-1}$.

Anal. Calcd. $C_{42}H_{52}N_4O_4 \cdot 0.5H_2O$ Calcd. C, 70.26; N, 7.80; H, 7.44. Found C, 70.36; N, 7.47; H, 7.54.

Reference Example 288

To a solution of aluminum lithium hydride (2.5 g) in THF (282 ml) was added dropwise a solution of ethyl tetrazole-5-carboxylate (9.4 g) in THF (94 ml) under ice-cooling. The mixture was stirred at room temperature for 3 hours, followed by addition of water (2.5 ml), 15% sodium hydroxide solution (2.5 ml) and water (7.5 ml), and stirring for 10 minutes. The mixture was filtered with Celite and washed with methanol. The solvent was removed under reduced pressure, and the resulting residue was dissolved in DMF (190 ml). To the solution was added active manganese dioxide (37 g), and the mixture was stirred at room temperature for 16 hours. The mixture was filtered with Celite and washed with methanol. The solvent was removed under reduced pressure, and the resulting residue was washed with hexane/ethyl acetate (=1/1) to give tetrazole-5-carbaldehyde (4.6 g).

$^1$H-NMR (200 MHz, DMSO-d$_6$) δ 10.10 (1H, s).

Reference Example 289

In 1,2-dichloroethane (14 ml)/acetic acid (7 ml) was dissolved methyl 7-[4-(2-butoxyethoxy)phenyl]-2,3-dihydro-1-benzazepine-4-carboxylate (0.70 g). To the solution were added tetrazole-5-carbaldehyde (0.31 g) and sodium triacetoxyborohydride (1.5 g), and the mixture was stirred at 40° C. for 18 hours. The mixture was cooled to room temperature, and the solvent was removed under reduced pressure. The resulting residue was added to water, and the mixture was extracted with ethyl acetate. The extract was washed with saturated brine, and dried with magnesium sulfate. The solvent was removed under reduced pressure, and the resulting residue was purified with silica gel column chromatography (ethyl acetate/ethanol=15:1) to give methyl 7-[4-(2-butoxyethoxy)phenyl]-1-(tetrazol-5-ylmethyl)-2,3-dihydro-1-benzazepine-4-carboxylate (0.67 g).

$^1$H-NMR (200 MHz, CDCl$_3$) δ 0.93 (3H, t, J=7.2 Hz), 1.36–1.45 (2H, m), 1.55–1.66 (2H, m), 2.74 (2H, m), 3.33 (2H, m), 3.59 (2H, t, J=6.6 Hz), 3.67 (3H, s), 3.83 (2H, t, J=4.6 Hz), 4.15 (2H, m), 4.85 (2H, s), 6.79 (1H, d, J=8.6 Hz), 6.88 (2H, d, J=8.6 Hz), 7.27–7.37 (3H, m), 7.45 (1H, d, J=2.0 Hz), 7.68 (1H, s).

Reference Example 290

In THF (6.7 ml)/methanol (6.7 ml) was dissolved methyl 7-[4-(2-butoxyethoxy)phenyl]-1-(tetrazol-5-ylmethyl)-2,3-dihydro-1-benzazepine-4-carboxylate (0.25 g). To the solution was added 1N sodium hydroxide solution (6.7 ml), and the mixture was stirred at 50° C. for 4 hours. pH was adjusted to approximate 4 with 1N hydrochloric acid, and the solvent was concentrated to half under reduced pressure. The concentrated material was extracted with ethyl acetate/THF, and the extract was washed with saturated brine and dried with magnesium sulfate. The solvent was removed under reduced pressure, and the resulting residue was washed with hexane/ethyl acetate (2/1) to give 7-[4-(2-butoxyethoxy)phenyl]-1-(tetrazol-5-ylmethyl)-2,3-dihydro-1-benzazepine-4-carboxylic acid (0.45 g).

$^1$H-NMR (200 MHz, DMSO-d$_6$) δ 0.89 (3H, t, J=7.2 Hz), 1.04–1.55 (4H, m), 2.72 (2H, m), 3.33 (2H, m), 3.46 (2H, t, J=6.6 Hz), 3.72 (3H, s), 4.11 (2H, t, J=4.6 Hz), 4.91 (2H, s), 6.91–7.00 (3H, m), 7.43–7.71 (5H, m).

Working Example 100

Production of Compound 100

In THF (8.1 ml) was dissolved 7-[4-(2-butoxyethoxy)phenyl]-1-(tetrazol-5-ylmethyl)-2,3-dihydro-1-benzazepine-4-carboxylic acid (0.27 g). To the solution was added DMF (two droplets), followed by addition of thionyl chloride (51 μl) and stirring at room temperature for 1 hour, to give a solution, which was added dropwise to a solution of 4-[methyl(tetrahydropyranyl-4-yl)aminomethyl]aniline (145 mg) and triethylamine (1.62 ml) in THF (8.1 ml) under ice-cooling, and the mixture was stirred at room temperature for 2 hours. The reaction solution was added to water, and the mixture was extracted with ethyl acetate. The extract was washed with saturated brine and dried with magnesium sulfate. The solvent was removed under reduced pressure, and the resulting residue was dissolved in ethanol. To the solution was added ethyl acetate, and the precipitates were collected by filtration, which was recrystallized from hexane/ethanol to give 7-[4-(2-butoxyethoxy)phenyl]-N-[4-[N-methyl-N-(tetrahydropyran-4-yl)aminomethyl]phenyl]-1-(tetrazol-5-ylmethyl)-2,3-dihydro-1-benzazepine-4-carboxamide (Compound 100) (42 mg).

$^1$H-NMR (200 MHz, DMSO-d$_6$) δ 0.89 (3H, t, J=7.2 Hz), 1.28–1.39 (2H, m), 1.47–1.55 (2H, m), 1.55–1.92 (4H, m), 2.28–2.38 (1H, m), 2.34 (3H, s), 2.83 (2H, m), 3.24–3.45 (4H, m), 3.46 (2H, t, J=6.4 Hz), 3.71 (2H, m), 3.86–3.99 (4H, m), 4.11 (2H, m), 4.81 (2H, s), 6.58 (1H, d, J=8.8 Hz), 6.99 (2H, d, J=8.8 Hz), 7.11 (2H, d, J=8.4 Hz), 7.33–7.75 (7H, m), 9.89 (1H, s).

Reference Example 291

In acetonitrile (100 ml) was dissolved methyl 7-[4-(2-butoxyethoxy)phenyl]-1-(tetrazol-4-ylmethyl)-2,3-dihydro-1-benzazepine-4-carboxylate (1.0 g). To the solution were added potassium carbonate (0.87 g) and methyl iodide (0.31 ml), and the mixture was stirred at room temperature for 4 hours. The solvent was concentrated to half under reduced pressure, which was added to water, and the mixture was extracted with ethyl acetate. The extract was washed with saturated brine and dried with magnesium sulfate. The solvent was removed under reduced pressure, and the resulting residue was washed with hexane/ethyl acetate (=8/1) to give methyl 7-[4-(2-butoxyethoxy)phenyl]-1-(1-methyltetrazol-5-ylmethyl)-2,3-dihydro-1-benzazepine-4-carboxylate (0.33 g) and methyl 7-[4-(2-butoxyethoxy)phenyl]-1-(2-methyltetrazol-5-ylmethyl)-2,3-dihydro-1-benzazepine-4-carboxylate (0.44 g).

$^1$H-NMR (1-methyl compound; 200 MHz, CDCl$_3$) δ 0.93 (3H, t, J=7.2 Hz), 1.30–1.44 (2H, m), 1.45–1.66 (2H, m), 2.59 (2H, m), 3.55 (2H, m), 3.55 (2H, t, J=6.6 Hz), 3.81 (2H, t, J=4.8 Hz), 3.95 (3H, s), 4.16 (2H, t, J=4.8 Hz), 1 4.86 (2H, s), 6.96 (1H, d, J=8.4 Hz), 6.99 (2H, d, J=8.8 Hz), 7.26–7.48 (3H, m), 7.57 (1H, d, J=2.2 Hz), 7.78 (1H, s).

$^1$H-NMR (2-methyl compound; 200 MHz, CDCl$_3$) δ 0.93 (3H, t, J=7.2 Hz), 1.22–1.44 (2H, m), 1.55–1.65 (2H, m), 2.86 (2H, m), 3.42 (2H, m), 3.55 (2H, t, J=6.6 Hz), 3.77–3.83 (2H, m), 3.81 (3H, s), 4.15 (2H, t, J=4.8 Hz), 4.36 (23H, s), 4.75 (2H, s), 6.97 (2H, d, J=8.2 Hz), 7.13 (1H, d, J=8.8 Hz), 7.39–7.54 (3H, m), 7.78 (1H, s).

Reference Example 292

In THF (6.4 ml)/methanol (3.2 ml) was dissolved methyl 7-[4-(2-butoxyethoxy)phenyl]-1-(1-methyltetrazol-5- ylmethyl)-2,3-dihydro-1-benzazepine-4-carboxylate (0.32 g). To the solution was added 1N sodium hydroxide solution (3.2 ml), and the mixture was stirred at room temperature for 14 hours. pH was adjusted to approximate 4 with 1N hydrochloric acid, and the solvent was concentrated to half under reduced pressure. The concentrated material was extracted with ethyl acetate/THF, and the extract was washed with saturated brine and dried with magnesium sulfate. The solvent was removed under reduced pressure, and the resulting residue was washed with hexane/ethyl acetate (5/1) to give 7-[4-(2-butoxyethoxy)phenyl]-1-(1-methyltetrazol-5-ylmethyl)-2,3-dihydro-1-benzazepine-4-carboxylic acid (0.25 g).

$^1$H-NMR (200 MHz, DMSO-d$_6$) δ 0.89 (3H, t, J=7.2 Hz), 1.27–1.41 (2H, m), 1.44–1.57 (2H, m), 2.69 (2H, m), 3.32 (2H, m), 3.47 (2H, t, J=6.6 Hz), 3.72 (2H, m), 4.03 (3H, s), 4.09 (2H, m), 4.96 (2H, s), 6.87–6.99 (3H, m), 7.43 (1H, d, J=8.8 Hz), 7.53–7.63 (3H, m), 7.71 (1H, s).

IR (KBr) 2957, 2932, 1667, 1609, 1505, 1435, 1273, 1244, 1119, 828, 797 cm$^{-1}$.

Working Example 101

Production of Compound 101

In THF (6.9 ml) was dissolved 7-[4-(2-butoxyethoxy)phenyl]-1-(1-methyltetrazol-5-ylmethyl)-2,3-dihydro-1-benzazepine-4-carboxylic acid (230 mg). To the solution was added DMF (two droplets), followed by addition of oxalyl chloride (63 ml) and stirring at room temperature for 1 hour, to give a solution, which was added dropwise to a solution of 4-[methyl(tetrahydropyranyl-4-yl)aminomethyl]aniline (120 mg) and triethylamine (1.34 ml) in THF (6.9 ml) under ice-cooling, and the mixture was stirred at room temperature for 3 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=3/1), which was recrystallized from hexane/ethyl acetate to give 7-[4-(2-butoxyethoxy)phenyl]-N-[4-[N-methyl-N-(tetrahydropyran-4-yl)aminomethyl]phenyl]-1-(1-methyltetrazol-5-ylmethyl)-2,3-dihydro-1-benzazepine-4-carboxamide (Compound 101) (114 mg).

mp 132–135° C.

$^1$H-NMR (200 MHz, CDCl$_3$) δ 0.93 (3H, t, J=7.2 Hz), 1.31–1.46 (2H, m), 1.56–1.81 (6H, m), 2.20 (3H, s), 2.54–2.73 (3H, m), 2.95 (2H, m), 3.30–3.42 (4H, m), 3.51–3.59 (2H, t, J=6.2 Hz), 3.56 (2H, s), 3.78–3.84 (2H, m), 3.96–4.17 (2H, m), 3.98 (3H, s), 4.15 (2H, t, J=4.8 Hz), 4.81 (2H, s), 6.96 (2H, d, J=8.4 Hz), 6.98 (1H, d, J=8.4 Hz), 7.40–7.58 (7H, m), 7.70 (1H, s).

IR (KBr) 3294, 2932, 1659, 1607, 1516, 1501, 1406, 1360, 1244, 1138, 820 cm$^{-1}$.

Anal. Calcd. C$_{39}$H$_{49}$N$_7$O$_4$ Calcd. C, 68.90; N, 14.42; H, 7.26. Found C, 68.82; N, 14.14; H, 7.08.

Reference Example 293

In THF (4.3 ml)/methanol (3.2 ml) was dissolved methyl 7-[4-(2-butoxyethoxy)phenyl]-1-(2-methyltetrazol-5-ylmethyl)-2,3-dihydro-1-benzazepine-4-carboxylate (0.43 g). To the solution was added 1N sodium hydroxide solution (4.3 ml), and the mixture was stirred at room temperature for 14 hours. pH was adjusted to approximate 4 with 1N hydrochloric acid, and the solvent was concentrated to half under reduced pressure. The concentrated material was extracted with ethyl acetate, and the extract was washed with saturated brine and dried with magnesium sulfate. The solvent was removed under reduced pressure, and the resulting residue was washed with hexane/ethyl acetate (=5/1) to give 7-[4-(2-butoxyethoxy)phenyl]-1-(2-methyltetrazol-5-ylmethyl)-2,3-dihydro-1-benzazepine-4-carboxylic acid (0.37 g).

$^1$H-NMR (200 MHz, DMSO-d$_6$) δ 0.89 (3H, t, J=7.2 Hz), 1.27–1.41 (2H, m), 1.43–1.58 (2H, m), 2.76 (2H, m), 3.33 (2H, m), 3.47 (2H, t, J=6.6 Hz), 3.69–3.74 (2H, m), 4.07–4.12 (2H, m), 4.37 (3H, s), 4.81 (2H, s), 6.97 (2H, d), 7.06 (1H, d, J=8.8 Hz), 7.42–7.60 (4H, m), 7.70 (1H, s).

IR (KBr) 3034, 2934, 1672, 1607, 1501, 1404, 1246, 1190, 1132, 816 cm$^{-1}$.

Working Example 102

Production of Compound 102

In THF (10.2 ml) was dissolved 7-[4-(2-butoxyethoxy)phenyl]-1-(2-methyltetrazol-5-ylmethyl)-2,3-dihydro-1-benzazepine-4-carboxylic acid (0.34 mg). To the solution was added DMF (two droplets), followed by addition of oxalyl chloride (93 ml) and stirring at room temperature for 1 hour, to give a solution, which was added dropwise to a solution of 4-[methyl(tetrahydropyranyl-4-yl)aminomethyl]aniline (177 mg) and triethylamine (1.98 ml) in THF (10.2 ml) under ice-cooling, and the mixture was stirred at room temperature for 2 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=3/1), which was recrystallized from hexane/ethyl acetate to give 7-[4-(2-butoxyethoxy)phenyl]-N-[4-[N-methyl-N-(tetrahydropyran-4-yl)aminomethyl]phenyl]-1-(2-methyltetrazol-5-ylmethyl)-2,3-dihydro-1-benzazepine-4-carboxamide (Compound 102) (193 mg).

$^1$H-NMR (200 MHz, CDCl$_3$) δ 0.93 (3H, t, J=7.2 Hz), 1.32–1.45 (2H, m), 1.57–1.76 (6H, m), 2.21 (3H, s), 2.65 (1H, m), 2.95 (2H, m), 3.30–3.48 (4H, m), 3.55 (2H, t, J=6.6 Hz), 3.57 (2H, s), 3.77–3.83 (2H, m), 3.98–4.08 (2H, m), 4.10–4.18 (2H, m), 4.37 (3H, s), 4.78 (2H, s), 6.97 (2H, d, J=8.8 Hz), 7.05 (1H, d, J=8.4 Hz), 7.30 (2H, d, J=8.4 Hz), 7.39–7.56 (8H, m).

IR (KBr) 3312, 2930, 1644, 1607, 1503, 1406, 1360, 1242, 1140, 810 cm$^{-1}$.

Working Example 103

Production of Compound 103

To a solution of 1-(3-methoxypropyl)-7-[4-(2-propoxyethoxy)phenyl]-2,3-dihydro-1H-1-benzazepine-4-carboxylic acid (250 mg) in THF (10 ml) were added thionyl chloride (0.083 ml) and DMF (one droplet) at room temperature, and the mixture was stirred for 1.5 hours. The solvent was evaporated under reduced pressure, and the resulting residue was dissolved in THF (15 ml), which was added dropwise to a solution of 4-[[N-methyl-N-(tetrahydropyran-4-yl)amino]methyl]aniline (138 mg) and triethylamine (0.48 ml) in THF (3 ml) at 0° C. The mixture was stirred at room temperature for 3 hours, water was added thereto, and the mixture was extracted with ethyl acetate. The organic layer was washed with water and saturated brine, and dried with magnesium sulfate. After concentration under reduced pressure, the residue was purified with column chromatography (ethanol:ethyl acetate=1:4→1:3→1:2), and the resulting crystals were purified by recrystallization (hexane-ethyl acetate) to give 1-(3-methoxypropyl)-N-[4-[[N-methyl-N-(tetrahydropyran-4-yl)amino]methyl]phenyl]-7-[4-(2-propoxyethoxy)phenyl]-2,3-dihydro-1H-1-benzazepine-4-carboxamide (Compound 103) (264 mg) as yellow crystals.

mp 87–90° C.

$^1$H-NMR (200 MHz, CDCl$_3$) δ 0.93 (3H, t, J=7.5 Hz), 1.53–1.82 (6H, m), 1.90–2.06 (2H, m), 2.21 (3H, s), 2.51–2.74 (1H, m), 2.86–2.97 (2H, m), 3.28–3.66 (15H, m), 3.81 (2H, t, J=4.9 Hz), 3.98–4.11 (2H, m), 4.16 (2H, t, J=4.9 Hz), 6.95 (1H, d, J=8.8 Hz), 6.98 (2H, d, J=8.8 Hz), 7.30 (2H, d, J=8.4 Hz), 7.38–7.57 (8H, m).

IR (KBr) 3233, 1638, 1607, 1516, 1501, 1314, 1246, 1186, 1117 cm$^{-1}$.

Anal. Calcd. C$_{39}$H$_{51}$N$_3$O$_5$ Calcd. C, 72.98; H, 8.01; N, 6.55. Found C, 72.65; H, 7.98; N, 6.35.

Working Example 104

Production of Compound 104

To a solution of 7-[4-(2-butoxyethoxy)phenyl]-1-(3-methoxypropyl)-2,3-dihydro-1H-1-benzazepine-4-carboxylic acid (200 mg) in THF (10 ml) were added thionyl chloride (0.064 ml) and DMF (one droplet) at room temperature, and the mixture was stirred for 1 hour. The solvent was evaporated under reduced pressure, and the resulting residue was dissolved in THF (15 ml), which was added dropwise to a solution of 4-[[N-methyl-N-(tetrahydropyran-4-yl)amino]methyl]aniline (107 mg) and triethylamine (0.37 ml) in THF (5 ml) at 0° C. The mixture was stirred at room temperature for 18 hours, water was added thereto, and the mixture was extracted with ethyl acetate. The organic layer was washed with saturated brine, and dried with magnesium sulfate. After concentration under reduced pressure, the residue was purified with column chromatography (ethanol:ethyl acetate=1:3), and the resulting crystals were purified by recrystallization (hexane-ethyl acetate) to give 7-[4-(2-butoxyethoxy)phenyl]-1-(3-methoxypropyl)-N-[4-[[N-methyl-N-(tetrahydropyran-4-yl)amino]methyl]phenyl]-2,3-dihydro-1H-1-benzazepine-4-carboxamide (Compound 104) (264.2 mg) as yellow crystals.

mp 87–90° C.

$^1$H-NMR (200 MHz, CDCl$_3$) δ 0.93 (3H, t, J=7.3 Hz), 1.32–1.46 (2H, m), 1.50–1.82 (6H, m), 1.89–2.03 (2H, m), 2.21 (3H, s), 2.55–2.72 (1H, m), 2.84–2.96 (2H, m), 3.28–3.61 (15H, m), 3.80 (2H, t, J=4.8 Hz), 3.98–4.09 (2H, m), 4.16 (2H, t, J=4.8 Hz), 6.95 (1H, d, J=8.8 Hz), 6.98 (2H, d, J=8.8 Hz), 7.31 (2H, d, J=8.4 Hz), 7.36–7.57 (8H, m).

IR (KBr) 3334, 1640, 1609, 1516, 1503, 1314, 1244, 1184, 1119 cm$^{-1}$.

Anal. Calcd. C$_{40}$H$_{53}$N$_3$O$_5$.0.5H$_2$O Calcd. C, 72.26; H, 8.18; N, 6.32. Found C, 72.51; H, 7.93; N, 6.10.

Working Example 105

Production of Compound 105

To a solution of 1-(3-ethoxypropyl)-7-[4-(2-propoxyethoxy)phenyl]-2,3-dihydro-1H-1-benzazepine-4-carboxylic acid (250 mg) in THF (10 ml) were added thionyl chloride (0.080 ml) and DMF (one droplet) at room temperature, and the mixture was stirred for 1.5 hours. The solvent was evaporated under reduced pressure, and the resulting residue was dissolved in THF (20 ml), which was added dropwise to a solution of 4-[[N-methyl-N-(tetrahydropyran-4-yl)amino]methyl]aniline (133 mg) and triethylamine (0.46 ml) in THF (3 ml) at 0° C. The mixture was stirred at room temperature for 2.5 hours, water was added thereto, and the mixture was extracted with ethyl acetate. The organic layer was washed with saturated brine, and dried with magnesium sulfate. After concentration under reduced pressure, the residue was purified with column chromatography (ethanol:ethyl acetate=1:9→1:3), and the resulting crystals were purified by recrystallization (hexane-ethyl acetate) to give 1-(3-ethoxypropyl)-N-[4-[[N-methyl-N-tetrahydropyran-4-yl)amino]methyl]phenyl]-7-[4-(2-propoxyethoxy)phenyl]-2,3-dihydro-1H-1-benzazepine-4-carboxamide (Compound 105) (242 mg) as yellow crystals.

mp 99–101° C.

$^1$H-NMR (200 MHz, CDCl$_3$) δ 0.94 (3H, t, J=7.5 Hz), 1.23 (3H, t, J=6.9 Hz), 1.53–1.82 (6H, m), 1.90–2.04 (2H, m), 2.21 (3H, s), 2.53–2.73 (1H, m), 2.87–2.96 (2H, m), 3.30–3.60 (14H, m), 3.81 (2H, t, J=5.0 Hz), 3.98–4.10 (2H, m), 4.17 (2H, t, J=5.0 Hz), 6.95–7.00 (3H, m), 7.30 (2H, d, J=8.4 Hz), 7.36–7.58 (8H, m).

IR (KBr) 3305, 1640, 1607, 1501, 1406, 1314, 1244, 1123 cm$^{-1}$.

Anal. Calcd. C$_{40}$H$_{53}$N$_3$O$_5$.0.25H$_2$O Calcd. C, 72.75; H, 8.18; N, 6.36. Found C, 72.81; H, 8.08; N, 6.27.

Working Example 106

Production of Compound 106

To a solution of 7-[4-(2-butoxyethoxy)phenyl]-1-(3-ethoxypropyl)-2,3-dihydro-1H-1-benzazepine-4-carboxylic acid (250 mg) in THF (10 ml) were added thionyl chloride (0.078 ml) and DMF (one droplet) at room temperature, and the mixture was stirred for 1.5 hours. The solvent was evaporated under reduced pressure, and the resulting residue was dissolved in THF (20 ml), which was added dropwise to a solution of 4-[[N-methyl-N-(tetrahydropyran-4-yl)amino]methyl]aniline (128 mg) and triethylamine (0.44 ml) in THF (3 ml) at 0° C. The mixture was stirred at room temperature for 64 hours, water was added thereto, and the mixture was extracted with ethyl acetate. The organic layer was washed with saturated brine, and dried with magnesium sulfate. After concentration under reduced pressure, the residue was purified with column chromatography (ethanol:ethyl acetate=1:4), and the resulting crystals were purified by recrystallization (hexane-ethyl acetate) to give 7-[4-(2-butoxyethoxy)phenyl]-1-(3-ethoxypropyl)-N-[4-[N-methyl-N-tetrahydropyran-4-yl)amino]methyl]phenyl]-2,3-dihydro-1H-1-benzazepine-4-carboxamide (Compound 106) (224 mg) as yellow crystals.

mp 95–97° C.

$^1$H-NMR (200 MHz, CDCl$_3$) δ 0.93 (3H, t, J=7.3 Hz), 1.24 (3H, t, J=6.9 Hz), 1.30–1.48 (2H, m), 1.52–1.84 (6H, m), 1.90–2.06 (2H, m), 2.21 (3H, s), 2.52–2.75 (1H, m), 2.86–2.97 (2H, m), 3.30–3.60 (14H, m), 3.80 (2H, t, J=5.0 Hz), 3.98–4.09 (2H, m), 4.16 (2H, t, J=4.9 Hz), 6.94–7.03 (3H, m), 7.30 (2H, d, J=8.4 Hz), 7.36–7.57 (8H, m).

IR (KBr) 3323, 1638, 1607, 1516, 1501, 1406, 1314, 1244, 1123 cm$^{-1}$.

Anal. Calcd. C$_{41}$H$_{55}$N$_3$O$_5$ Calcd. C, 73.51; H, 8.28; N, 6.27. Found C, 73.60; H, 8.16; N, 6.23.

Working Example 107

Production of Compound 107

To a solution of 7-[4-(2-butoxyethoxy)phenyl]-1-[(2-methyl-1,3-dioxolan-2-yl)methyl]-2,3-dihydro-1H-1- benzazepine-4-carboxylic acid (300 mg) in THF (10 ml) were added thionyl chloride (0.068 ml) and DMF (one droplet) at room temperature, and the mixture was stirred for 1 hour. The reaction mixture was added dropwise to a solution of 4-[[N-methyl-N-(tetrahydropyran-4-yl)amino]methyl]aniline (151 mg) and triethylamine (0.7 ml) in THF (3 ml) at 0° C. The mixture was stirred at room temperature for 20 hours, water was added thereto, and the mixture was extracted with ethyl acetate. The organic layer was washed with saturated brine, and dried with magnesium sulfate. After concentration under reduced pressure, the residue was separated and purified with column chromatography (ethanol:ethyl acetate=1:19→1:10), and the resulting crystals were purified by recrystallization (ethyl acetate-diisopropyl ether) to give 7-[4-(2-butoxyethoxy)phenyl]-1-[(2-methyl-1,3-dioxolan-2-yl)methyl]-N-[4-[[N-methyl-N-tetrahydropyran-4-yl)amino]methyl]phenyl]-2,3-dihydro-1H-1-benzazepine-4-carboxamide (Compound 107) (144 mg) as yellow crystals.

mp 123–126° C.

$^1$H-NMR (200 MHz, CDCl$_3$) δ 0.93 (3H, t, J=7.3 Hz), 1.31–1.47 (5H, m), 1.51–1.83 (6H, m), 2.21 (3H, s), 2.54–2.73 (1H, m), 2.86–2.97 (2H, m), 3.28–3.60 (10H, m), 3.80 (2H, t, J=5.0 Hz), 3.93–4.09 (6H, m), 4.16 (2H, t, J=5.0 Hz), 6.98 (2H, d, J=8.8 Hz), 7.26–7.32 (3H, m), 7.39–7.50 (8H, m).

IR (KBr) 3245, 1645, 1607, 1516, 1499, 1406, 1316, 1244, 1175, 1140, 1046 cm$^{-1}$.

Anal. Calcd. C$_{41}$H$_{53}$N$_3$O$_5$·0.25H$_2$O Calcd. C, 71.54; H, 7.83; N, 6.10. Found C, 71.49; H, 7.96; N, 6.03.

Working Example 108

Production of Compound 108

A mixture of 7-[4-(2-butoxyethoxy)phenyl]-1-[(2-methyl-1,3-dioxolan-2-yl)methyl]-N-[4-[[N-methyl-N-(tetrahydropyran-4-yl)amino]methyl]phenyl]-2,3-dihydro-1H-1-benzazepine-4-carboxamide (100 mg), cerium chloride heptahydrate (300 mg), sodium iodide (19 mg) and acetonitrile (5 ml) was stirred at 60° C. for 5 days. Water was added to the reaction system, and the mixture was extracted with ethyl acetate. The organic layer was washed with saturated brine and dried with magnesium sulfate. After concentration under reduced pressure, the residue was separated and purified with column chromatography (ethanol:ethyl acetate=1:3) to give 7-[4-(2-butoxyethoxy)phenyl]-1-(2-oxopropyl)-N-[4-[[N-methyl-N-(tetrahydropyran-4-yl)amino]methyl]phenyl]-2,3-dihydro-1H-1-benzazepine-4-carboxamide (Compound 108) (52 mg) as yellow crystals.

$^1$H-NMR (200 MHz, CDCl$_3$) δ 0.93 (3H, t, J=7.3 Hz), 1.32–1.47 (2H, m), 1.53–2.05 (6H, m), 2.26 (3H, s), 2.38 (3H, s), 3.29–3.47 (4H, m), 3.55 (2H, t, J=6.6 Hz), 3.74–3.86 (4H, m), 4.01–4.21 (6H, m), 6.54 (1H, d, J=8.0 Hz), 6.98 (2H, d, J=8.8 Hz), 7.26–7.67 (10H, m).

IR (KBr) 3302, 1728, 1651, 1607, 1518, 1501, 1244, 914 cm$^{-1}$.

Working Example 109

Production of Compound 109

To a solution of 7-[4-(2-butoxyethoxy)phenyl]-1-propyl-N-[4-[[N-methyl-N-(tetrahydropyran-4-yl)amino]methyl]phenyl]-2,3-dihydro-1H-1-benzazepine-4-carboxamide (16.4 g) in ethyl acetate (1500 ml) was added 4N hydrochloric acid-ethyl acetate (25 ml) at room temperature, and the mixture was stirred for 1 hour. The precipitated crystals were collected by filtration, which was purified by recrystallization (2-propanol) to give 7-[4-(2-butoxyethoxy) phenyl]-1-propyl-N-[4-[[N-methyl-N-(tetrahydropyran-4-yl)amino]methyl]phenyl]-2,3-dihydro-1H-1-benzazepine-4-carboxamide dihydrochloride (Compound 109) (8.61 g) as pale yellow crystals.

$^1$H-NMR (200 MHz, DMSO-d$_6$) δ 0.88 (3H, t, J=7.1 Hz), 0.94 (3H, t, J=7.3 Hz), 1.22–2.18 (10H, m), 2.57 (3H, s), 2.78–2.90 (2H, m), 3.21–3.41 (7H, m), 3.46 (2H, t, J=6.4 Hz), 3.68–3.73 (2H, m), 3.91–4.15 (5H, m), 4.35–4.60 (1H, m), 6.97–7.02 (3H, m), 7.42–7.58 (6H, m), 7.65 (1H, s), 7.81 (2H, d, J=8.4 Hz), 10.03 (1H, s), 10.45–10.59 (1H, m).

IR (KBr) 3248, 1663, 1609, 1521, 1501, 1464, 1312, 1248, 1180, 1121, 831 cm$^{-1}$.

Anal. Calcd. C$_{39}$H$_{53}$N$_3$O$_4$Cl$_2$ Calcd. C, 67.04; H, 7.65; N, 6.01. Found C, 67.10; H, 7.51; N, 6.14.

Working Example 110

Production of Compound 110

To a solution of 7-[4-(2-butoxyethoxy)phenyl]-1-propyl-N-[4-[[N-methyl-N-(tetrahydropyran-4-yl)amino]methyl]phenyl]-2,3-dihydro-1H-1-benzazepine-4-carboxamide (2.0 g) in ethanol (150 ml) was added fumaric acid (371 mg) at room temperature, and the mixture was stirred for 0.5 hour. After concentration under reduced pressure, to the residue was added ethyl acetate, and the precipitated crystals were collected by filtration, (2-propanol) to give 7-[4-(2-butoxyethoxy)phenyl]-1-propyl-N-[4-[[N-methyl-N-(tetrahydropytan-4-yl)amino]methyl]phenyl]-2,3-dihydro-1H-1-benzazepine-4-carboxamide fumarate (Compound 110) (1.86 g) as yellow crystals.

mp 159–161° C.

$^1$H-NMR (200 MHz, CDCl$_3$) δ 0.93 (3H, t, J=7.3 Hz), 0.99 (3H, t, J=7.2 Hz), 1.30–1.45 (2H, m), 1.51–1.86 (8H, m), 2.24 (3H, s), 2.61–2.79 (1H, m), 2.86–2.95 (2H, m), 3.24–3.43 (6H, m), 3.55 (2H, t, J=6.4 Hz), 3.62 (2H, s), 3.81 (2H, t, J=5.0 Hz), 3.98–4.09 (2H, m), 4.16 (2H, t, J=5.0 Hz), 6.90 (1H, d, J=8.8 Hz), 6.98 (2H, d, J=8.8 Hz), 7.26–7.57 (12H, m).

IR (KBr) 3365, 1653, 1609, 1520, 1501, 1316, 1246, 1177 cm$^{-1}$.

Anal. Calcd. C$_{43}$H$_{55}$N$_3$O$_8$ Calcd. C, 69.61; H, 7.47; N, 5.66. Found C, 69.51; H, 7.46; N, 5.88.

Reference Example 294

To a solution of methyl 7-bromo-2,3-dihydro-1H-1-benzazepine-4-carboxylate (0.80 g) and 3-methoxypropionaldehyde (1.25 g) in 1,2-dichloroethane (10 ml) was added sodium triacetoxyborohydride (1.81 g) at room temperature, and the mixture was stirred for 24 hours. Water was added to the reaction system, and the mixture was extracted with ethyl acetate. The organic layer was washed with saturated brine and dried with magnesium sulfate. After concentration under reduced pressure, the resulting residue was separated and purified with column chromatography (ethyl acetate hexane=1:3→1:2) to give methyl 7-bromo-1-(3-methoxypropyl)-2,3-dihydro-1H-1-benzazepine-4-carboxylate (935 mg) as yellow oil.

$^1$H-NMR (200 MHz, CDCl$_3$) δ 1.83–1.96 (2H, m), 2.79 (2H, t, J=4.0 Hz), 3.22 (2H, t, J=4.9 Hz), 3.34 (3H, s), 3.37–3.45 (4H, m), 3.80 (3H, s), 6.75 (1H, d, J=9.2 Hz), 7.21–7.26 (1H, m), 7.42 (1H, d, J=2.6 Hz), 7.57 (1H, s).

IR (neat) 1699, 1626, 1588, 1539, 1495, 1435, 1256, 1177, 1117, 1086 cm$^{-1}$.

Reference Example 295

A mixture of methyl 7-bromo-1-(3-methoxypropyl)-2,3-dihydro-1H-1-benzazepine-4-carboxylate (450 mg), 4-(2-propoxyethoxy)phenyl borate (313 mg) and potassium carbonate (351 mg) in toluene-ethanol-water (15-1.5-1.5 ml) was stirred at room temperature for 1 hour under argon atmosphere. To the reaction system was added tetrakistriphenylphosphinepalladium (73 mg), and the mixture was heated to reflux for 20 hours. After cooled to room temperature, the mixture was extracted with ethyl acetate. The organic layer was washed with water and saturated brine and dried with magnesium sulfate. After concentration under reduced pressure, the residue was separated and purified with column chromatography (ethyl acetate:hexane= 1:4→1:2) to give methyl 1-(3-methoxypropyl)-7-[4-(2-propoxyethoxy)phenyl]-2,3-dihydro-1H-1-benzazepine-4-carboxylate (376 mg) as yellow oil.

$^1$H-NMR (200 MHz, CDCl$_3$) δ 0.94 (3H, t, J=7.3 Hz), 1.55–1.73 (2H, m), 1.86–2.03 (2H, m), 2.79–2.84 (2H, m), 3.26–3.31 (2H, m), 3.36 (3H, s), 3.42–3.55 (6H, m), 3.81 (3H, s), 3.83 (2H, t, J=4.9 Hz), 4.16 (2H, t, J=4.9 Hz), 6.92 (1H, d, J=8.8 Hz), 6.97 (2H, d, J=8.8 Hz), 7.38–7.51 (4H, m), 7.76 (1H, s).

IR (neat) 1699, 1607, 1505, 1456, 1435, 1244, 1181, 1119 cm$^{-1}$.

Reference Example 296

To a solution of methyl 1-(3-methoxypropyl)-7-[4-(2-propoxyethoxy)phenyl]-2,3-dihydro-1H-1-benzazepine-4-carboxylate (376 mg) in a mixture of THF-methanol (5-10 ml) was added 1N sodium hydroxide solution (3.0 ml) at room temperature, and the mixture was stirred at 50° C. for 24 hours. After concentration under reduced pressure, 1N hydrochloric acid was added to pH 3–4, and the mixture was extracted with ethyl acetate. The organic layer was washed with saturated brine and dried with magnesium sulfate. After concentration under reduced pressure, the resulting crystals were collected by filtration. The crystals were washed with diisopropyl ether and hexane to give 1-(3-methoxypropyl)-7-[4-(2-propoxyethoxy)phenyl]-2,3-dihydro-1H-1-benzazepine-4-carboxylic acid (346 mg) as yellow crystals.

mp 114–115° C.

$^1$H-NMR (200 MHz, CDCl$_3$) δ 0.94 (3H, t, J=7.3 Hz), 1.56–1.73 (2H, m), 1.88–2.04 (2H, m), 2.78–2.89 (2H, m), 3.24–3.35 (2H, m), 3.36 (3H, s), 3.43–3.55 (6H, m), 3.81 (2H, t, J=5.0 Hz), 4.17 (2H, t, J=5.0 Hz), 6.94 (1H, d, J=8.4 Hz), 6.98 (2H, d, J=8.8 Hz), 7.40–7.53 (4H, m), 7.88 (1H, s).

IR (KBr) 1671, 1607, 1501, 1273, 1252, 1186, 1115 cm$^{-1}$.

Anal. Calcd. C$_{26}$H$_{33}$NO$_5$ Calcd. C, 71.05; H, 7.57; N, 3.19. Found C, 70.78; H, 7.38; N, 3.01.

Reference Example 297

A mixture of methyl 7-bromo-1-(3-methoxypropyl)-2,3-dihydro-1H-1-benzazepine-4-carboxylate (478.2 mg), 4-(2-butoxyethoxy)phenyl borate (354 mg) and potassium carbonate (373 mg) in toluene-ethanol-water (15-1.5-1.5 ml) was stirred at room temperature for 1 hour under argon atmosphere. To the reaction system was added tetrakistriphenylphosphinepalladium (78 mg), and the mixture was heated to reflux for 16 hours. After cooled to room temperature, the mixture was extracted with ethyl acetate. The organic layer was washed with water and saturated brine and dried with magnesium sulfate. After concentration under reduced pressure, the residue was separated and purified with column chromatography (ethyl acetate:hexane= 1:4→1:3→1:2) to give an end product (362 mg) as yellow oil.

$^1$H-NMR (200 MHz, CDCl$_3$) δ 0.93 (3H, t, J=7.3 Hz), 1.30–1.49 (2H, m), 1.53–1.69 (2H, m), 1.87–2.03 (2H, m), 2.78–2.86 (2H, m), 3.28 (2H, t, J=4.8 Hz), 3.36 (3H, s), 3.42–3.50 (4H, m), 3.55 (2H, t, J=6.7 Hz), 3.78–3.83 (5H, m), 4.16 (2H, t, J=5.0 Hz), 6.90–7.00 (3H, m), 7.38–7.51 (4H, m), 7.76 (1H, s).

IR (neat) 1699, 1622, 1607, 1505, 1456, 1435, 1246, 1182, 1119, 818 cm$^{-1}$.

Reference Example 298

To a solution of methyl 7-[4-(2-butoxyethoxy)phenyl]-1-(3-methoxypropyl)-2,3-dihydro-1H-1-benzazepine-4-carboxylate (362.3 mg) in a mixture of THF-methanol (5-10 ml) was added 1N sodium hydroxide solution (2.8 ml) at room temperature, and the mixture was stirred at 50° C. for 15 hours. After concentration under reduced pressure, 1N hydrochloric acid was added to pH 3–4, and the mixture was extracted with ethyl acetate. The organic layer was washed with saturated brine and dried with magnesium sulfate. After concentration under reduced pressure, the resulting crystals were collected by filtration. The crystals were washed with diisopropyl ether and hexane to give 7-[4-(2-butoxyethoxy)phenyl]-1-(3-methoxypropyl)-2,3-dihydro-1H-1-benzazepine-4-carboxylic acid (283 mg) as yellow crystals.

mp 99–101° C.

$^1$H-NMR (200 MHz, CDCl$_3$) δ 0.93 (3H, t, J=7.2 Hz), 1.29–1.48 (2H, m), 1.53–1.70 (2H, m), 1.88–2.04 (2H, m), 2.80–2.89 (2H, m), 3.25–3.35 (2H, m), 3.37 (3H, s), 3.43–3.49 (4H, m), 3.56 (2H, t, J=6.6 Hz), 3.81 (2H, t, J=5.0 Hz), 4.16 (2H, t, J=5.0 Hz), 6.94 (1H, d, J=8.6 Hz), 6.98 (2H, d, J=8.4 Hz), 7.40–7.53 (4H, m), 7.88 (1H, s).

IR (KBr) 1671, 1607, 1501, 1269, 1246, 1184, 1115 cm$^{-1}$.

Anal. Calcd. C$_{27}$H$_{35}$NO$_5$ Calcd. C, 71.50; H, 7.78; N, 3.09. Found C, 71.31; H, 7.75; N, 2.99.

Reference Example 299

To a solution of methyl 7-[4-(2-propoxyethoxy)phenyl]-2,3-dihydro-1H-1-benzazepine-4-carboxylate (400 mg) and 3-ethoxypropionaldehyde (0.53 g) in 1,2-dichloroethane (10 ml) was added sodium triacetoxyborohydride (0.66 g) at room temperature, and the mixture was stirred for 20 hours. To the reaction system was added water, and the mixture was extracted with ethyl acetate. The organic layer was washed with water and saturated brine and dried with magnesium sulfate. After concentration under reduced pressure, the residue was separated and purified with column chromatography (ethyl acetate:hexane=1:4→1:3) to give methyl 1-(3-ethoxypropyl)-7-[4-(2-propoxyethoxy)phenyl]-2,3-dihydro-1H-1-benzazepine-4-carboxylate (475 mg) as yellow oil.

$^1$H-NMR (200 MHz, CDCl$_3$) δ 0.95 (3H, t, J=7.5 Hz), 1.23 (3H, t, J=6.9 Hz), 1.52–1.72 (2H, m), 1.88–2.03 (2H, m), 2.80–2.84 (2H, m), 3.26–3.31 (2H, m), 3.43–3.55 (8H, m), 3.79–3.84 (5H, m), 4.16 (2H, t, J=5.0 Hz), 6.94 (1H, d, J=8.8 Hz), 6.98 (2H, d, J=8.8 Hz), 7.40 (1H, dd, J=8.8, 2.2 Hz), 7.47 (2H, d, J=8.8 Hz), 7.51 (1H, d, J=2.2 Hz), 7.76 (1H, s).

Reference Example 300

To a solution of methyl 1-(3-ethoxypropyl)-7-[4-(2-propoxyethoxy)phenyl]-2,3-dihydro-1H-1-benzazepine-4-carboxylate (475 mg) in a mixture of THF-methanol (5-10 ml) was added 1N sodium hydroxide solution (3.0 ml) at room temperature, and the mixture was stirred at 50° C. for 62 hours. After concentration under reduced pressure, to the mixture was added 1N hydrochloric acid (3.0 ml), and the mixture was extracted with ethyl acetate. The organic layer was washed with saturated brine and dried with magnesium sulfate. After concentration under reduced pressure, the resulting crystals were collected by filtration. The crystals were washed with diisopropyl ether and hexane to give 1-(3-ethoxypropyl)-7-[4-(2-propoxyethoxy)phenyl]-2,3-dihydro-1H-1-benzazepine-4-carboxylic acid (390 mg) as yellow crystals.

mp 98–100° C.

$^1$H-NMR (200 MHz, CDCl$_3$) δ 0.95 (3H, t, J=7.0 Hz), 1.23 (3H, t, J=7.2 Hz), 1.53–1.74 (2H, m), 1.89–2.04 (2H, m), 2.79–2.89 (2H, m), 3.26–3.35 (2H, m), 3.44–3.55 (8H, m), 3.81 (2H, t, J=5.0 Hz), 4.17 (2H, t, J=5.0 Hz), 6.96 (1H, d, J=8.4 Hz), 6.98 (2H, d, J=8.8 Hz), 7.39–7.52 (4H, m), 7.87 (1H, s).

IR (KBr) 1669, 1607, 1501, 1275, 1248, 1184, 1125 cm$^{-1}$.

Anal. Calcd. C$_{27}$H$_{35}$NO$_5$ Calcd. C, 71.50; H, 7.78; N, 3.09. Found C, 71.23; H, 7.84; N, 3.16.

Reference Example 301

To a solution of methyl 7-[4-(2-butoxyethoxy)phenyl]-2,3-dihydro-1H-1-benzazepine-4-carboxylate (400 mg) and 3-ethoxypropionaldehyde (0.52 g) in 1,2-dichloroethane (10 ml) was added sodium triacetoxyborohydride (0.64 g) at room temperature, and the mixture was stirred for 20 hours. To the reaction system was added water, and the mixture was extracted with ethyl acetate. The organic layer was washed with water and saturated brine and dried with magnesium sulfate. After concentration under reduced pressure, the residue was separated and purified with column chromatography (ethyl acetate:hexane=1:4→1:3) to give methyl 7-[4-(2-butoxyethoxy)phenyl]-1-(3-ethoxypropyl)-2,3-dihydro-1H-1-benzazepine-4-carboxylate (452 mg) as yellow oil.

$^1$H-NMR (200 MHz, CDCl$_3$) δ 0.93 (3H, t, J=7.2 Hz), 1.23 (3H, t, J=7.1 Hz), 1.28–1.68 (4H, m), 1.89–2.06 (2H, m), 2.78–2.87 (2H, m), 3.27–3.31 (2H, m), 3.43–3.59 (1H, m), 3.78–3.83 (5H, m), 4.16 (2H, t, J=4.9 Hz), 6.94 (1H, d, J=8.4 Hz), 6.98 (2H, d, J=8.8 Hz), 7.37–7.52 (4H, m), 7.76 (1H, s).

IR (neat) 1699, 1622, 1609, 1501, 1454, 1435, 1373, 1354, 1246, 1181, 1125, 818 cm$^{-1}$.

Reference Example 302

To a solution of methyl 7-[4-(2-butoxyethoxy)phenyl]-1-(3-ethoxypropyl)-2,3-dihydro-1H-1-benzazepine-4-carboxylate (452 mg) in a mixture of THF-methanol (5-10 ml) was added 1N sodium hydroxide solution (3.0 ml) at room temperature, and the mixture was stirred at 50° C. for 40 hours. After concentration under reduced pressure, to the mixture was added 1N hydrochloric acid (3.0 ml), and the mixture was extracted with ethyl acetate. The organic layer was washed with saturated brine and dried with magnesium sulfate. After concentration under reduced pressure, the resulting crystals were collected by filtration. The crystals were washed with hexane to 7-[4-(2-butoxyethoxy)phenyl]-1-(3-ethoxypropyl)-2,3-dihydro-1H-1-benzazepine-4-carboxylic acid (340 mg) as yellow crystals.

mp 76–78° C.

$^1$H-NMR (200 MHz, CDCl$_3$) δ 0.93 (3H, t, J=7.4 Hz), 1.23 (3H, t, J=7.0 Hz), 1.30–1.47 (2H, m), 1.53–1.68 (2H, m), 1.88–2.04 (2H, m), 2.79–2.88 (2H, m), 3.26–3.37 (2H, m), 3.44–3.59 (8H, m), 3.81 (2H, t, J=4.9 Hz), 4.16 (2H, t, J=4.9 Hz), 6.96 (1H, d, J=8.8 Hz), 6.98 (2H, d, J=8.8 Hz), 7.40–7.54 (4H, m), 7.88 (1H, s).

IR (KBr) 1667, 1607, 1501, 1271, 1248, 1184, 1125 cm$^{-1}$.

Anal. Calcd. C$_{28}$H$_{37}$NO$_5$ Calcd. C, 71.92; H, 7.98; N, 3.00. Found C, 71.89; H, 8.08; N, 2.68.

Reference Example 303

A mixture of palladium chloride (96 mg) and curious chloride (218 mg) in DMF-water (7-1 ml) was stirred at 60° C. for 18 hours under oxygen atmosphere. To the reaction system was added a solution of methyl 7-bromo-1-(2-propenyl)-2,3-dihydro-1H-1-benzazepine-4-carboxylate (500 mg) in DMF-water (7-1 ml) was added, and the mixture was stirred at 60° C. for 7 hours. To the reaction system was added saturated brine, and the mixture was extracted with ethyl acetate. The organic layer was washed with saturated brine and dried with magnesium sulfate. After concentration under reduced pressure, the residue was separated and purified with column chromatography (ethyl acetate:hexane=1:4→1:2) to give methyl 7-bromo-1-(2-oxopropyl)-2,3-dihydro-1H-1-benzazepine-4-carboxylate (311 mg) as yellow crystals.

$^1$H-NMR (200 MHz, CDCl$_3$) δ 2.21 (3H, s), 2.82 (2H, t, J=4.6 Hz), 3.30 (2H, t, J=4.6 Hz), 3.81 (3H, s), 4.08 (2H, s), 6.31 (1H, d, J=8.8 Hz), 7.21 (1H, dd, J=8.8, 2.2 Hz), 7.46 (1H, d, J=2.2 Hz), 7.59 (1H, s).

Reference Example 304

A solution of methyl 7-bromo-1-(2-oxopropyl)-2,3-dihydro-1H-1-benzazepine-4-carboxylate (1.29 g), ethylene glycol (2.3 g) and p-toluenesulfonic acid monohydrate (36 mg) in toluene (10 ml) was heated to reflux for 3 days while removing water. After cooled to room temperature, an aqueous solution of sodium hydrogen carbonate was added to alkaline, and the mixture was extracted with ethyl acetate. The organic layer was washed with saturated brine and dried with magnesium sulfate. After concentration under reduced pressure, the residue was separated and purified with column chromatography (ethyl acetate:hexane=1:4) to give methyl 7-bromo-1-[(2-methyl-1,3-dioxolan-2-yl)methyl]-2,3-dihydro-1H-1-benzazepine-4-carboxylate (992 mg).

mp 96–99° C.

$^1$H-NMR (200 MHz, CDCl$_3$) δ 1.57 (3H, s), 2.78–2.83 (2H, m), 3.34–3.39 (2H, m), 3.43 (2H, s), 3.80 (3H, s), 3.88–3.99 (4H, m), 7.13 (1H, d, J=9.2 Hz), 7.22–7.27 (1H, m), 7.42 (1H, d, J=2.2 Hz), 7.58 (1H, s).

IR (KBr) 1703, 1626, 1495, 1435, 1258, 1217, 1179, 1086, 1047 cm$^{-1}$.

Anal. Calcd. C$_{17}$H$_{20}$NO$_4$Br Calcd. C, 53.42; H, 5.27; N, 3.66. Found C, 53.34; H, 5.50; N, 3.64.

Reference Example 305

A mixture of methyl 7-bromo-1-[(2-methyl-1,3-dioxolan-2-yl)methyl]-2,3-dihydro-1H-1-benzazepine-4-carboxylate (960 mg), 4-(2-butoxyethoxy)phenyl borate (0.66 g) and potassium carbonate (0.69 g) in a mixture of toluene-ethanol-water (25-2.5-2.5 ml) was stirred at room temperature for 1 hour under argon atmosphere. To the reaction system was added tetrakistriphenylphosphinepalladium (144 mg), and the mixture was heated to reflux for 8 hours. After cooled to room temperature, the mixture was extracted with ethyl acetate, and the mixture was dried with magnesium sulfate. After concentration under reduced pressure, the residue was separated and purified with column chromatography to give methyl 7-[4-(2-butoxyethoxy)phenyl]-1-[(2- methyl-1,3-dioxolan-2-yl)methyl-7-[4-(2-butoxyethoxy) phenyl]-2,3-dihydro-1H-1-benzaepine-4-carboxylate (796 mg) as yellow oil.

$^1$H-NMR (200 MHz, CDCl$_3$) δ 0.93 (3H, t, J=7.4 Hz), 1.31–1.47 (5H, m), 1.52–1.67 (2H, m), 1.78–1.86 (2H, m), 3.41–3.45 (2H, m), 3.49 (2H, s), 3.56 (2H, t, J=6.6 Hz), 3.78–3.83 (5H, m), 3.97 (4H, s), 4.16 (2H, t, J=5.0 Hz), 6.98 (2H, d, J=8.8 Hz), 7.26–7.30 (1H, m), 7.39–7.51 (4H, m), 7.77 (1H, s).

IR (neat) 1699, 1609, 1505, 1495, 1435, 1242, 1181, 1127, 1047 cm$^{-1}$.

Reference Example 306

To a solution of methyl 7-[4-(2-butoxyethoxy)phenyl-1-[(2-methyl-1,3-dioxolan-2-yl)methyl]-7-[4-(2-propoxyethoxy)phenyl]-2,3-dihydro-1H-1-benzazepine-4-carboxylate (795.7 mg) in a mixture of THF-methanol (5-5 ml) was added 1N sodium hydroxide solution (3.2 ml) at room temperature, and the mixture was stirred at 50° C. for 16 hours. After concentration under reduced pressure, to the mixture was added 1N hydrochloric acid (4 ml) and the mixture was extracted with ethyl acetate. The organic layer was washed with saturated brine and dried with magnesium sulfate. After concentration under reduced pressure, the resulting crystals were collected by filtration. The crystals were washed with diisopropyl ether to give 7-[4-(2-butoxyethoxy)phenyl]-1-[(2-methyl-1,3-dioxolan-2-yl) methyl]-7-[4-(2-propoxyethoxy)phenyl]-2,3-dihydro-1H-1-benzazepine-4-carboxylic acid (664 mg) as yellow crystals.

mp 127–129° C.

$^1$H-NMR (200 MHz, CDCl$_3$) δ 0.93 (3H, t, J=7.4 Hz), 1.30–1.49 (5H, m), 1.52–1.68 (2H, m), 2.81–2.89 (2H, m), 3.41–3.49 (2H, m), 3.51 (2H, s), 3.56 (2H, t, J=6.6 Hz), 3.81 (2H, t, J=5.0 Hz), 3.91–4.01 (4H, m), 4.17 (2H, t, J=5.0 Hz), 6.98 (2H, t, J=8.8 Hz), 7.26–7.32 (1H, m), 7.41–7.53 (4H, m), 7.89 (1H, s).

IR (KBr) 1665, 1611, 1503, 1427, 1246, 1184, 1046 cm$^{-1}$.

Anal. Calcd. C$_{28}$H$_{35}$NO$_6$ Calcd. C, 69.83; H, 7.33; N, 2.91. Found C, 69.78; H, 7.39; N, 2.81.

Reference Example 307

To a solution of 7-bromo-2,3,4,5-tetrahydro-1H-1-benzazepine-5-one (5.0 g), propionaldehyde (15 ml) and acetic acid (4.7 ml) in 1,2-dichloroethane (250 ml) was added sodium triacetoxyborohydride (22.0 g) at room temperature, and the mixture was stirred for 6 hours. To the reaction system was added water, and the mixture was extracted with ethyl acetate. The organic layer was washed with an aqueous solution of sodium hydrogen carbonate and saturated brine, and dried with magnesium sulfate. After concentration under reduced pressure, the residue was separated and purified with column chromatography (ethyl acetate:hexane=1:4) to give 7-bromo-1-propyl-2,3,4,5-tetrahydro-1H-1-benzazepine-5-one (5.89 g) as yellow oil.

$^1$H-NMR (200 MHz, CDCl$_3$) δ 1.00 (3H, t, J=7.4 Hz), 1.58–1.81 (2H, m), 2.18–2.33 (2H, m), 2.75 (2H, t, J=7.2 Hz), 3.26 (2H, t, J=6.6 Hz), 3.38 (2H, t, J=7.7 Hz), 6.76 (1H, d, J=9.0 Hz), 7.34 (1H, dd, J=9.0, 2.6 Hz), 7.84 (1H, d, J=2.6 Hz).

IR (neat) 1667, 1590, 1487, 1443, 1412, 1381, 1366, 1337, 1296, 1281, 1252, 1223, 1206, 1161, 1136, 1117, 808 cm$^{-1}$.

Reference Example 308

A mixture of 7-bromo-1-propyl-2,3,4,5-tetrahydro-1H-1-benzazepine-5-one (5.89 g), 4-(2-butoxyethoxy)phenyl borate (5.45 g) and potassium carbonate (5.74 g) in toluene-ethanol-water (200-20-20 ml) was stirred at room temperature for 1 hour under argon atmosphere. To the reaction system was added tetrakistriphenylphosphinepalladium (0.72 g), and the mixture was heated to reflux for 3 hours. After cooled to room temperature, the mixture was extracted with ethyl acetate. The organic layer was washed with saturated brine and dried with magnesium sulfate. After concentration under reduced pressure, the residue was separated and purified with column chromatography (ethyl acetate:hexane=1:9→1:4) to give 7-[4-(2-butoxyethoxy) phenyl]-1-propyl-2,3,4,5-tetrahydro-1H-1-benzazepine-5-one (7.15 g) as yellow oil.

$^1$H-NMR (200 MHz, CDCl$_3$) δ 0.93 (3H, t, J=7.3 Hz), 1.02 (3H, t, J=7.5 Hz), 1.29–1.47 (2H, m), 1.52–1.84 (4H, m), 2.18–2.35 (2H, m), 2.80 (2H, t, J=7.1 Hz), 3.31 (2H, t, J=6.6 Hz), 3.44 (2H, t, J=7.5 Hz), 3.55 (2H, t, J=6.8 Hz), 3.80 (2H, t, J=4.9 Hz), 4.15 (2H, t, J=4.9 Hz), 6.92–6.98 (3H, m), 7.46–7.54 (3H, m), 7.96 (1H, d, J=2.6 Hz).

Reference Example 309

To a solution of 7-[4-(2-butoxyethoxy)phenyl]-1-propyl-2,3,4,5-tetrahydro-1H-1-benzazepine-5-one (500 mg) in THF (15 ml) was added dropwise lithium bis(trimethylsilyl) amide (1.0M solution in hexane, 3.8 ml) at −78° C. under argon atmosphere. After stirred at −76° C. for 2 hours, argon was removed under reduced pressure to replace it with carbon dioxide. The reaction mixture was removed from an acetone-dry ice bath, and stirred at room temperature for 2 hours. To the reaction system were added water and ethyl acetate, and 1N hydrochloric acid was slowly added at 0° C. until pH 6. The mixture was extracted with ethyl acetate, the organic layer was washed with saturated brine and dried with magnesium sulfate. Concentration by rotary evaporator under reduced pressure afforded yellow oil (981 mg).

To a solution of the oil (980.9 mg) in ethanol (20 ml) was added sodium borohydride (0.48 g), and the mixture was stirred at room temperature for 2 hours under nitrogen atmosphere. Ethanol was evaporated under reduced pressure, and water and ethyl acetate were added thereto. 1N hydrochloric acid was slowly added at 0° C. until pH 6. The mixture was extracted with ethyl acetate, and the extract was washed with saturated brine and dried with magnesium sulfate. After concentration by rotary evaporator under reduce pressure, concentrated hydrochloric acid (1.5 ml) was added to a solution of the residue (769 mg) in 1,2-dimethoxyethane (20 ml) at room temperature, and the mixture was heated to reflux for 1 hour. After cooled to room temperature, water and ethyl acetate were added thereto. 1N sodium hydroxide solution was added dropwise at 0° C. until pH=4. The mixture was extracted with ethyl acetate, and water was added to the organic layer, followed by addition of 1N sodium hydroxide solution until pH 6. The solution was separated, and the organic layer was washed with water and saturated brine and dried with magnesium sulfate. After concentration under reduced pressure, the residue was separated and purified with silica gel column chromatography (ethyl acetate:hexane=1:2→1:1) to give 7-[4-(2-butoxyethoxy)phenyl]-1-propyl-2,3-dihydro-1H-1-benzazepine-4-carboxylic acid (374 mg).

$^1$H-NMR (200 MHz, CDCl$_3$) δ 0.96–1.02 (6H, m), 1.34–1.45 (2H, m), 1.54–1.80 (4H, m), 2.84 (2H, m), 3.28–3.35 (4H, m), 3.55 (2H, t, J=6.6 Hz), 3.80 (2H, t, J=5.0 Hz), 4.16 (2H, t, J=5.0 Hz), 6.88 (1H, d, J=8.8 Hz), 6.98 (2H, t, J=8.8 Hz), 7.39–7.52 (4H, m), 7.88 (1H, s).

Reference Example 310

To a solution of methyl 7-[4-(2-butoxyethoxy)phenyl]-2, 3-dihydro-1H-1-benzazepine-4-carboxylate (1.0 g, 2.53 mmol) and propionaldehyde (1 ml, 13.86 mmol) in 1,2-dichloroethane (30 ml) was added sodium triacetoxyborohydride (1.9 g, 8.96 mmol) at room temperature, and the mixture was stirred for 24 hours. To the reaction system was added 1N sodium hydroxide solution, and the mixture was extracted with ethyl acetate. The organic layer was washed with water and saturated brine and dried with magnesium sulfate. After concentration under reduced pressure, the residue was dissolved in THF (50 ml) and methanol (50 ml), and to the solution was added 1N sodium hydroxide solution. After heating to reflux for 1 hour, the mixture was concentrated under reduced pressure. To the residue was added 1N hydrochloric acid, and the mixture was extracted with ethyl acetate. The organic layer was washed with water and saturated brine and dried with magnesium sulfate. After concentration under reduced pressure, the resulting crystals were collected by filtration to give 7-[4-(2-butoxyethoxy)phenyl]-1-propyl-2,3-dihydro-1H-1-benzazepine-4-carboxylic acid (0.895 g) as yellow crystals.

mp 145–146° C.

$^1$H-NMR (200 MHz, CDCl$_3$) δ 0.96–1.02 (6H, m), 1.34–1.45 (2H, m), 1.54–1.80 (4H, m), 2.84 (2H, m), 3.28–3.35 (4H, m), 3.55 (2H, t, J=6.6 Hz), 3.80 (2H, t, J=5.0 Hz), 4.16 (2H, t, J=0 Hz), 6.88 (1H, d, J=8.8 Hz), 6.98 (2H, t, J=8.8 Hz), 7.39–7.52 (4H, m), 7.88 (1H, s).

IR (KBr) 2975, 2925, 2870, 1670, 1605, 1500 cm$^{-1}$.

Anal. Calcd. C$_{26}$H$_{33}$NO$_4$ Calcd. C, 73.73; H, 7.85; N, 3.31. Found C, 73.68; H, 8.11; N, 3.23.

Reference Example 311

4-morpholinophenyl borate (237 mg) and 7-bromo-1-propyl-N-[4-[[N-methyl-N-(tetrahydropyran-4-yl)amino]methyl]phenyl]-2,3-dihydro-1-benzazepine-4-carboxamide (391 mg) were dissolved in water:ethanol toluene (=1:1:10, v/v, 18.0 ml), and potassium carbonate (253 mg) was added thereto. This mixture was stirred at room temperature for 30 minutes under argon atmosphere, tetrakistriphenylphosphinepalladium (35 mg) was added thereto, and the mixture was heated to reflux for 10 hours under argon atmosphere. The reaction mixture was diluted with ethyl acetate, and washed with water and saturated brine. The organic layer was dried with anhydrous magnesium sulfate, and the solvent was evaporated under reduced pressure. The residue was purified with silica gel column chromatography (ethyl acetate→ethyl acetate:ethanol=10:1), which was further recrystallized from ethyl acetate-diisopropyl ether-hexane to give N-[4-[[N-methyl-N-(tetrahydropyran-4-yl)amino]methyl]phenyl]-7-(4-morpholinophenyl)-1-propyl-2,3-dihydro-1-benzazepine-4-carboxamide (222 mg) as yellow crystals.

mp 114–118° C.

$^1$H-NMR (200 MHz, CDCl$_3$) δ 0.99 (3H, t, J=7.4 Hz), 1.64–1.81 (6H, m), 2.21 (3H, s), 2.57–2.70 (1H, m), 2.92 (2H, t, J=4.8 Hz), 3.20 (4H, t, J=4.8 Hz), 3.28–3.43 (6H, m), 3.57 (2H, s), 3.89 (4H, t, J=4.8 Hz), 4.01–4.07 (2H, m), 6.90 (1H, d, J=8.8 Hz), 6.97 (2H, d, J=8.8 Hz), 7.30 (2H, d, J=8.8 Hz), 7.39–7.56 (8H, m).

IR (KBr) 2955, 1649, 1605, 1512, 1503, 1451, 1406, 1312, 1233, 1175, 111.9, 928, 812, 733 cm$^{-1}$.

Anal. Calcd. for C$_{37}$H$_{45}$N$_4$O$_3$ (1.1H$_2$O): C, 72.31; H, 7.90; N, 9.12. Found C, 72.09; H, 7.66; N, 8.87.

Reference Example 312

One droplet of DMF was added to a solution of 1-(2-methoxybenzyl)-7-(4-propoxyphenyl)-2,3-dihydro-1-benzazepine-4-carboxylic acid (340 mg) in tetrahydrofuran (10 ml). Then, thionyl chloride (267 mg) was added thereto at 0° C., the temperature was returned to room temperature, and the mixture was stirred for 1 hour under nitrogen atmosphere. The solvent and excess thionyl chloride were evaporated under reduced pressure, and the resulting residue was suspended in tetrahydrofuran (30 ml), which was added to a solution of 4-[[N-methyl-N-(tetrahydropyran-4-yl)amino]methyl]aniline (197 mg) and triethylamine (906 mg) in tetrahydrofuran (10 ml) at 0° C. The mixture was stirred at room temperature for 1 hour under nitrogen atmosphere, water was added thereto, and the mixture was extracted with ethyl acetate. The organic layer was washed with saturated brine and dried with magnesium sulfate. The solvent was evaporated under reduced pressure, and the resulting residue was separated and purified with silica gel column chromatography (methanol:ethyl acetate=1:8), which was recrystallized from hexane-ethyl acetate to give 1-(2-methoxybenzyl)-N-[4-[[N-methyl N-(tetrahydropyran-4-yl)amino]methyl]phenyl]-7-(4-propoxyphenyl)-2,3-dihydro-1-benzazepine-4-carboxamide (337 mg) as yellow crystals.

$^1$H-NMR (200 MHz, CDCl$_3$) δ 1.05 (t, 3H, J=7.2 Hz), 1.60–1.88 (m, 6H), 2.21 (s, 3H), 2.64 (br, 1H), 2.90 (br, 2H), 3.32–3.45 (m, 4H), 3.57 (s, 2H), 3.89 (s, 3H), 3.92–4.08 (m, 4H), 4.59 (s, 2H), 6.82 (d, 1H, J=8.8 Hz), 6.92–6.97 (m, 4H), 7.15–7.22 (m, 1H), 7.26–7.38 (m, 4H), 7.44–7.60 (m, 7H).

Reference Example 313

One droplet of DMF was added to a solution of 1-[(1-ethylpyrazol-4-yl)methyl]-7-(4-propoxyphenyl)-2,3-dihydro-1-benzazepine-4-carboxylic acid (330 mg) in dichloromethane (15 ml). Then, thionyl chloride (118 mg) was added thereto at 0° C., the temperature was returned to room temperature, and the mixture was stirred for 1 hour under nitrogen atmosphere. Then, this solution was added to a solution of 4-[[N-methyl-N-(tetrahydropyran-4-yl)amino]methyl]aniline (219 mg) and triethylamine (2.01 g) in dichloromethane (15 ml) at 0° C. The mixture was stirred at room temperature for overnight under nitrogen atmosphere, water was added thereto, and the mixture was extracted with ethyl acetate. The organic layer was washed with saturated brine and dried with magnesium sulfate. The solvent was evaporated under reduced pressure, and the resulting residue was separated and purified with silica gel column chromatography (methanol:ethyl acetate=1:4), which was recrystallized from hexane-ethyl acetate to give 1-[(1-ethylpyrazol-4-yl)methyl]-N-[4-[[N-methyl-N-(tetrahydropyran-5-yl)amino]methyl]phenyl]-7-(4-propoxyphenyl)-2,3-dihydro-1-benzazepine-4-carboxamide (362 mg) as yellow crystals.

$^1$H-NMR (t, 3H, J=7.4 Hz), 1.49 (t, 3H, J=7.4 Hz), 1.58–1.88 (m, 6H), 2.21 (s, 3H), 2.65 (br, 1H), 2.84 (br, 2H), 3.25–3.42 (m, 4H), 3.57 (s, 2H), 3.93–4.06 (m, 4H), 4.16 (q, 2H, J=7.4 Hz), 4.40 (s, 2H), 6.94–7.01 (m, 3H), 7.26–7.40 (m, 4H), 7.45–7.56 (m, 8H).

Anal. Calcd. C$_{39}$H$_{47}$N$_5$O$_3$ Calcd. C, 73.90; H, 7.47; N, 11.05. Found C, 73.58; H, 7.47; N, 10.86.

Reference Example 314

Methyl 7-[4-(2-butoxyethoxy)phenyl]-1-(tetrazol-5-ylmethyl)-2,3-dihydro-1-benzazepine-4-carboxylate (1.9 g) was dissolved in acetonitrile (190 ml). To the solution were added potassium carbonate (1.65 g) and ethyl iodide (0.76 ml), and the mixture was stirred at 50° C. for 16 hours. The solvent was concentrated to 1/3 under reduced pressure, which was added to water, and the mixture was extracted with ethyl acetate. The extract was washed with saturated brine and dried with magnesium sulfate. The solvent was removed under reduced pressure, and the resulting residue was purified with silica gel column chromatography (hexane/ethyl acetate=3/1→1/2) to give methyl 7-[4-(2-butoxyethoxy)phenyl]-1-(1-ethyltetrazol-5-ylmethyl)-2,3-dihydro-1-benzazepine-4-carboxylate (1.05 g) and methyl 7-[4-(2-butoxyethoxy)phenyl]-1-(2-ethyltetrazol-5-ylmethyl)-2,3-dihydro-1-benzazepine-4-carboxylate (0.42 g).

$^1$H-NMR (1-ethyl compound; 200 MHz, CDCl$_3$) δ 0.93 (3H, t, J=7.2 Hz), 1.33–1.45 (2H, m), 1.44 (3H, t, J=7.0 Hz), 1.47–1.66 (2H, m), 2.58 (2H, t, J=4.6 Hz), 3.37 (2H, t, J=5.0 Hz), 3.56 (2H, t, J=6.6 Hz), 3.78–3.84 (2H, m), 3.81 (3H, s), 4.13–4.19 (2H, m), 4.31 (2H, q, J=7.0 Hz), 4.84 (2H, s), 6.95–7.02 (3H, m), 7.42–7.49 (3H, m), 7.57 (1H, m), 7.78 (1H, s).

$^1$H-NMR (2-ethyl compound; 200 MHz, CDCl$_3$) δ 0.93 (3H, t, J=7.0 Hz), 1.33–1.49 (2H, m), 1.57–1.65 (2H, m), 1.65 (3H, t, J=7.4 Hz), 2.83–2.91 (2H, m), 3.39–3.45 (2H, m), 3.55 (2H, t, J=6.6 Hz), 3.78–3.83 (2H, m), 3.82 (3H, s), 4.07–4.18 (2H, m), 4.67 (2H, q, J=7.4 Hz), 4.75 (2H, s), 6.98 (2H, d, J=8.8 Hz), 7.16 (1H, d, J=8.4 Hz), 7.40–7.54 (4H, m), 7.79 (1H, s).

Reference Example 315

Methyl 7-[4-(2-butoxyethoxy)phenyl]-1-(1-ethyltetrazol-4-ylmethyl)-2,3-dihydro-1-benzazepine-4-carboxylate (0.11 g) was dissolved in THF (2.2 ml)/methanol (2.2 ml). To the solution was added 1N sodium hydroxide (1.1 ml), and the mixture was stirred at 50° C. for 4 hours. After cooled to room temperature, pH was adjusted to approximate 5 with 6N hydrochloric acid, and the solvent was removed to half under reduced pressure. The material was extracted with ethyl acetate, and the extract was washed with saturated brine and dried with magnesium sulfate. The solvent was removed under reduced pressure, and the residue was washed with hexane/ethyl acetate (8/1) to give 7-[4-(2-butoxyethoxy)phenyl]-1-(1-ethyltetrazol-5-ylmethyl)-2,3-dihydro-1-benzazepine-4-carboxylic acid (0.10 g).

$^1$H-NMR (200 MHz, CDCl$_3$) δ 0.93 (3H, t, J=7.0 Hz), 1.34–1.45 (2H, m), 1.46 (3H, t, J=7.4 Hz), 1.54–1.65 (2H, m), 2.62 (2H, m), 3.40 (2H, m), 3.56 (2H, t, J=6.6 Hz), 3.78–3.84 (2H, m), 4.14–4.19 (2H, m), 4.29 (2H, q, J=7.4 Hz), 4.86 (2H, s), 6.99 (3H, d, J=8.8 Hz), 7.44–7.49 (3H, m), 7.58 (1H, d, J=2.2 Hz), 7.88 (1H, s).

IR (KBr) 2957, 2932, 1667, 1609, 1505, 1435, 1273, 1244, 1119, 828, 797 cm$^{-1}$.

Working Example 111

Production of Compound 111

In THF (6.0 ml) was dissolved 7-[4-(2-butoxyethoxy)phenyl]-1-(1-ethyltetrazol-5-ylmethyl)-2,3-dihydro-1-benzazepine-4-carboxylic acid (0.10 g). To the solution was added DMF (two droplets), followed by addition of oxalyl chloride (35 μl) at 0° C. and stirring at room temperature for 1 hour. The solvent was removed under reduced pressure, a solution of the resulting residue in THF was added dropwise to a solution of 4-[methyl(tetrahydropyranyl-4-yl)aminomethyl]phenylalanine (50 mg) and triethylamine (0.17 ml) in THF (6.0 ml) at 0° C., and the mixture was stirred at room temperature for 2 hours. The reaction solution was added to water, and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=3/1), which was recrystallized from hexane/ethyl acetate to give 7-[4-(2-butoxyethoxy)phenyl]-1-(1-ethyltetrazol-5-ylmethyl)-N-[4-[N-methyl-N-(tetrahydropyran-4-yl)aminomethyl]phenyl]-2,3-dihydro-1-benzazepine-4-carboxamide (Compound 111) (34 mg).

$^1$H-NMR (200 MHz, CDCl$_3$) δ 0.93 (3H, t, J=7.2 Hz), 1.33–1.45 (2H, m), 1.46 (3H, t, J=7.2 Hz), 1.57–1.75 (6H, m), 2.21 (3H, s), 2.68 (3H, m), 3.36–3.43 (4H, m), 3.51–3.59 (2H, m), 3.59 (2H, s), 3.77–3.83 (2H, m), 4.00–4.17 (4H, m), 4.32 (2H, q, J=7.2 Hz), 4.81 (2H, s), 6.98 (3H, d, J=8.8 Hz), 7.30 (2H, d, J=8.4 Hz), 7.42–7.82 (8H, m).

IR (KBr) 3277, 2934, 1651, 1607, 1505, 1242, 822 cm$^{-1}$.

Reference Example 316

In THF (20.8 ml)/methanol (20.8 ml) was dissolved methyl 7-[4-(2-butoxyethoxy)phenyl]-1-(2-ethyltetrazol-5-ylmethyl)-2,3-dihydro-1-benzazepine-4-carboxylate (1.04 g). To the solution was added 1N sodium hydroxide (10.4 ml), and the mixture was stirred at 50° C. for 4 hours. After cooled to room temperature, pH was adjusted to approximate 5 with 6N hydrochloric acid, and the solvent was removed to half under reduced pressure. The material was extracted with ethyl acetate, and the extract was washed with saturated brine and dried with magnesium sulfate. The solvent was removed under reduced pressure, and the resulting residue was washed with hexane/ethyl acetate (8/1) to give 7-[4-(2-butoxyethoxy)phenyl]-1-(2-ethyltetrazol-4-ylmethyl)-2,3-dihydro-1-benzazepine-4-carboxylic acid (0.76 g).

$^1$H-NMR (200 MHz, CDCl$_3$) δ 0.93 (3H, t, J=7.0 Hz), 1.33–1.45 (2H, m), 1.55–1.65 (2H, m), 1.66 (3H, t, J=7.4 Hz), 2.88 (2H, m), 3.45 (2H, m), 3.56 (2H, t, J=6.6 Hz), 3.81 (2H, m), 4.13–4.18 (2H, m), 4.68 (2H, q, J=7.4 Hz), 4.77 (2H, s), 6.98 (2H, d, J=8.8 Hz), 7.17 (1H, d, J=8.8 Hz), 7.41–7.49 (3H, m), 7.55 (1H, d, J=2.2 Hz), 7.91 (1H, s).

IR (KBr) 3034, 2934, 1672, 1607, 1501, 1404, 1246, 1190, 1132, 816 cm$^{-1}$.

Working Example 112

Production of Compound 112

In THF (15 ml) was dissolved 7-[4-(2-butoxyethoxy)phenyl]-1-(2-ethyltetrazol-5-ylmethyl)-2,3-dihydro-1-benzazepine-4-carboxylic acid (0.75 mg). To the solution was added DMF (three droplets), followed by addition of oxalyl chloride (0.26 ml) at 0° C. and stirring at room temperature for 1 hour. The solvent was removed under reduced pressure a solution of the resulting residue in THF was added dropwise to a solution of 4-[methyl(tetrahydropyranyl-4-yl)aminomethyl]phenylalanine (0.38 g) and triethylamine (1.26 ml) in THF (11.4 ml) at 0° C., and the mixture was stirred at room temperature for 2 hours. The reaction solution was added to water and the mixture was extracted with ethyl acetate. The extract was washed with saturated brine and dried with magnesium sulfate. The solvent was removed under reduced pressure, and the resulting residue was purified with silica gel column chromatography (ethyl acetate/ethanol=3/1), which was recrystallized from hexane/ethyl acetate to give 7-[4-(2-butoxyethoxy)phenyl]-1-(2-ethyltetrazol-5-ylmethyl)-N-[4-[N-methyl-N-(tetrahydropyran-4-yl)aminomethyl]phenyl]-2,3-dihydro-1-benzazepine-4-carboxamide (Compound 112) (0.48 g).

$^1$H-NMR (200 MHz, CDCl$_3$) δ 0.93 (3H, t, J=7.2 Hz), 1.33–1.45 (2H, m), 1.54–1.78 (6H, m), 1.66 (3H, t, J=7.2

Hz), 2.21 (3H, s), 2.65 (1H, m), 2.95 (2H, m), 3.30–3.43 (2H, m), 3.46–3.50 (2H, m), 3.55 (2H, t, J=6.6 Hz), 3.57 (2H, s), 3.77–3.83 (2H, m), 3.99–4.08 (2H, m), 4.12–4.18 (2H, m), 4.68 (2H, q, J=7.2 Hz), 4.78 (2H, s), 6.98 (2H, d, J=8.8 Hz), 7.18 (1H, d, J=8.4 Hz), 7.30 (2H, d, J=8.8 Hz), 7.39–7.59 (8H, m).

IR (KBr) 3306, 2934, 1644, 1505, 1244, 1140, 812 cm$^{-1}$.

Anal. Calcd. $C_{40}H_{51}N_7O_4$ Calcd. C, 69.24; N, 14.13; H, 7.41. Found C, 69.04; N, 14.04; H, 7.44.

Working Example 113

Production of Compound 27

To a solution of 7-[4-(2-butoxyethoxy)phenyl]-1-propyl-N-[4-[[N-methyl-N-(tetrahydropyran-4-yl)amino]methyl]phenyl]-2,3-dihydro-1H-1-benzazepine-4-carboxylic acid (4.00 g) in THF (40 ml) were added thionyl chloride (1.72 ml) and DMF (0.5 ml) at room temperature, and the mixture was stirred for 1 hour. After concentration under reduced pressure, the residue was dissolved in THF (50 ml) and DMF (10 ml), which was added dropwise to a mixture of 4-[[N-methyl-N-(tetrahydropyran-4-yl)amino]methyl]aniline dihydrochloride (3.05 g) and triethylamine (7.9 ml) in THF (30 ml) at 0° C. After stirred at room temperature for 16 hours, water was added to the reaction system, and the mixture was extracted with ethyl acetate. The organic layer was washed with saturated brine and dried with magnesium sulfate. After concentrated under reduced pressure, the residue was separated and purified with column chromatography (ethanol:ethyl acetate=1:19), which was further purified by recrystallization (2-propanol) to give an end product (Compound 27) (4.19 g) as yellow crystals.

Industrial Applicability

The compound of the formula (I) of the present invention or a salt thereof has potent CC chemokine receptor (CCR) antagonistic activity, in particular, potent CCR5 antagonistic activity and, thus, it can be advantageously used for the treatment or prevention of infectious disease of various HIV in human (e.g., AIDS).

What is claimed is:

1. A compound of the formula (I):

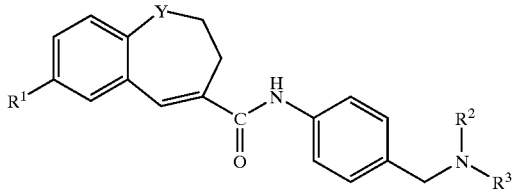

wherein $R^1$ is a 5- to 6-membered aromatic ring which has a group of the formula: $R-Z^1-X-Z^2-$ wherein R is a hydrogen atom or a substituted or unsubstituted hydrocarbon group, X is a substituted or unsubstituted alkylene chain, and $Z^1$ and $Z^2$ are respectively hetero-atoms, and which may have a further substituent, the group R may bind to the 5- to 6-membered aromatic ring to form a ring, Y is a substituted or unsubstituted imino group, $R^2$ and $R^3$ are respectively a substituted or unsubstituted aliphatic hydrocarbon group or a substituted or unsubstituted alicyclic heterocyclic group; or a salt thereof.

2. The compound according to claim 1, wherein the 5- to 6-membered aromatic ring is benzene, furan or thiophene.

3. The compound according to claim 1, wherein the 5- to 6-membered aromatic ring is benzene.

4. The compound according to claim 1, wherein R is a halogenated or unhalogenated lower alkyl group.

5. The compound according to claim 1, wherein X is —$(CH_2)_n$— wherein n is an integer of 1–4.

6. The compound according to claim 1, wherein $Z^1$ and $Z^2$ are respectively —O—, —$S(O)_m$— wherein m is an integer of 0–2 or —$N(R^4)$— wherein $R^4$ is a hydrogen atom or a substituted or unsubstituted lower alkyl group.

7. The compound according to claim 1, wherein $Z^1$ is —O— or —$S(O)_m$— wherein m is an integer of 0–2.

8. The compound according to claim 1, wherein $Z^1$ is —O—.

9. The compound according to claim 1, wherein $Z^2$ is —O— or —$N(R^4)$— wherein $R^4$ is a hydrogen atom or a substituted or unsubstituted lower alkyl group.

10. The compound according to claim 1, wherein $Z^2$ is —O—.

11. The compound according to claim 1, wherein Y is —$N(R^5)$— wherein $R^5$ is a hydrogen atom, a substituted or unsubstituted hydrocarbon group or a substituted or unsubstituted acyl group.

12. The compound according to claim 11, wherein $R^5$ is $C_{1-4}$ alkyl, formyl or $C_{2-5}$ alkanoyl.

13. The compound according to claim 11, wherein $R^5$ is a group represented by the formula —$(CH_2)_k$—$R^6$; wherein k is 0 or 1, and $R^6$ is a substituted or unsubstituted 5- to 6-membered monocyclic aromatic group.

14. The compound according to claim 1, wherein $R^2$ is a substituted or unsubstituted straight chain hydrocarbon group.

15. The compound according to claim 1, wherein $R^2$ is a substituted or unsubstituted lower alkyl group.

16. The compound according to claim 1, wherein $R^3$ is a substituted or unsubstituted alicyclic hydrocarbon group or a substituted or unsubstituted alicyclic heterocyclic group.

17. The compound according to claim 16, wherein the alicyclic hydrocarbon group is a lower cycloalkyl group.

18. The compound according to claim 16, wherein the alicyclic hydrocarbon group is cyclohexyl.

19. The compound according to claim 16, wherein the alicyclic heterocyclic group is a saturated alicyclic heterocyclic group.

20. The compound according to claim 16, wherein the alicyclic heterocyclic group is tetrahydropyranyl, tetrahydrothiopyranyl or piperidyl.

21. The compound according to claim 16, wherein the alicyclic heterocyclic group is tetrahydropyranyl.

22. A compound selected from the group consisting of 7-(4-ethoxyethoxyphenyl)-1-ethyl-N-[4-[[N-methyl-N-(tetrahydropyran-4-yl)amino]methyl]phenyl]-2,3-dihydro-1-benzazepine-4-carboxamide, 1-ethyl-7-(4-propoxyethoxyphenyl)-N-[4-[[N-methyl-N-(tetrahydropyran-4-yl)amino]methyl]phenyl]-2,3-dihydro-1-benzazepine-4-carboxamide, 7-(4-butoxyethoxyphenyl)-1-ethyl-N-[4-[[N-methyl-N-(tetrahydropyran-4-yl)amino]methyl]phenyl]-2,3-dihydro-1-benzazepine-4-carboxamide, 7-(4-ethoxyethoxyphenyl)-1-formyl-N-[4-[[N-methyl-N-(tetrahydropyran-4-yl)amino]methyl]phenyl]-2,3-dihydro-1-benzazepine-4-carboxamide, 1-formyl-7-(4-propoxyethoxyphenyl)-N-[4-[[N-methyl-N-(tetrahydropyran-4-yl)amino]methyl]phenyl]-2,3-dihydro-1-benzazepine-4-carboxamide, 7-(4-butoxyethoxyphenyl)-1-formyl-N-[4-[[N-methyl-N-(tetrahydropyran-4-yl)amino]methyl]phenyl]-2,3-dihydro-1-benzazepine-4-carboxamide, 7-(4-butoxyethoxyphenyl)-N-[4-[[N-methyl-N-(tetrahydropyran-5-yl)amino]methyl]phenyl]-1-propyl-2,3-dihydro-1-benzazepine-4-carboxamide, N-[4-[[N-methyl-N-(tetrahydropyran-5-yl)amino]methyl]phenyl]-7-(4-propoxyethoxyphenyl)-1-propyl-2,3-dihydro-1- benzazepine-4-carboxamide, 1-benzyl-7-(4-butoxyethoxyphenyl)-N-[4-[[N-methyl-N-(tetrahydropyran-4-yl)amino]methyl]phenyl]-2,3-dihydro-1-benzazepine-4-carboxamide, 7-(4-butoxyethoxyphenyl)-1-cyclopropylmethyl-N-[4-[[N-methyl-N-(tetrahydropyran-4-yl)amino]methyl]phenyl]-2,3-dihydro-1-benzazepine-4-carboxamide, 7-(4-butoxyethoxyphenyl)-N-[4-[[N-methyl-N-(tetrahydropyran-4-yl)amino]methyl]phenyl]-1-phenyl-2,3-dihydro-1-benzazepine-4-carboxamide, 7-(4-butoxyethoxyphenyl)-1-(3,4-methylenedioxy)phenyl-N-[4-[[N-methyl-N-(tetrahydropyran-4-yl)amino]methyl]phenyl]-2,3-dihydro-1-benzazepine-4-carboxamide, 7-(4-butoxyethoxyphenyl)-1-(2-methyloxazol-5-yl)-N-[4-[[N-methyl-N-(tetrahydropyran-4-yl)amino]methyl]phenyl]-2,3-dihydro-1-benzazepine-4-carboxamide, 1-allyl-7-(4-butoxyethoxyphenyl)-N-[4-[[N-methyl-N-(tetrahydropyran-4-yl)amino]methyl]phenyl]-2,3-dihydro-1-benzazepine-4-carboxamide, 7-(4-butoxyethoxyphenyl)-N-[4-[[N-methyl-N-(tetrahydropyran-4-yl)amino]methyl]phenyl]-1-(3-thienyl)methyl-2,3-dihydro-1-benzazepine-4-carboxamide, 7-(4-butoxyethoxyphenyl)-N-[4-[[N-methyl-N-(tetrahydropyran-4-yl)amino]methyl]phenyl]-1-(thiazol-2-yl)methyl-2,3-dihydro-1-benzazepine-4-carboxamide, 7-(4-butoxyethoxyphenyl)-1-(1-methylpyrazol-4-yl)methyl-N-[4-[[N-methyl-N-(tetrahydropyran-4-yl)amino]methyl]phenyl]-2,3-dihydro-1-benzazepine-4-carboxamide, 7-(4-butoxyethoxyphenyl)-1-(3-methylisothiazol-4-yl)methyl-N-[4-[[N-methyl-N-(tetrahydropyran-5-yl)amino]methyl]phenyl]-2,3-dihydro-1-benzazepine-4-carboxamide, 7-(4-butoxyethoxyphenyl)-1-(1-ethylpyrazol-4-yl)methyl-N-[4-[[N-methyl-N-(tetrahydropyran-4-yl)amino]methyl]phenyl]-2,3-dihydro-1-benzazepine-4-carboxamide, 7-(4-butoxyethoxyphenyl)-1-isobutyl-N-[4-[[N-methyl-N-(tetrahydropyran-5-yl)amino]methyl]phenyl]-2,3-dihydro-1-benzazepine-4-carboxamide, 1-isobutyl-N-[4-[[N-methyl-N-(tetrahydropyran-5-yl)amino]methyl]phenyl]-7-(4-propoxyethoxyphenyl)-2,3-dihydro-1-benzazepine-4-carboxamide, 7-(4-butoxyethoxyphenyl)-N-[4-[[N-methyl-N-(tetrahydropyran-4-yl)amino]methyl]phenyl]-1-(thiazol-5-yl)methyl-2,3-dihydro-1-benzazepine-4-carboxamide, 7-(4-butoxyethoxyphenyl)-N-[4-[[N-methyl-N-(tetrahydropyran-4-yl)amino]methyl]phenyl]-1-(1-methyltetrazol-5-yl)methyl-2,3-dihydro-1-benzazepine-4-carboxamide, 7-(4-butoxyethoxyphenyl)-N-[4-[[N-methyl-N-(tetrahydropyran-4-yl)amino]methyl]phenyl]-1-(2-methyltetrazol-5-yl)methyl-2,3-dihydro-1-benzazepine-4-carboxamide and salts thereof.

23. A method for producing a compound of the formula I:

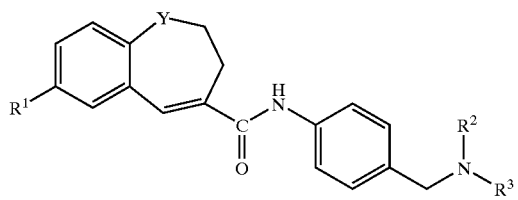

wherein $R^1$ is a 5- to 6-membered aromatic ring which has a group of the formula: R-$Z^1$-X-$Z^2$- wherein R is a hydrogen atom or a substituted or unsubstituted hydrocarbon group, X is a substituted or unsubstituted alkylene chain, and $Z^1$ and $Z^2$ are respectively heteroatoms, and which may have a further substituent, the group R may bind to the 5- to 6-membered aromatic ring to form a ring, Y is a substituted or unsubstituted imino group, $R^2$ and $R^3$ are respectively a substituted or unsubstituted aliphatic hydrocarbon group or a substituted or unsubstituted alicyclic heterocyclic group; or a salt thereof, which comprises subjecting a compound of the formula:

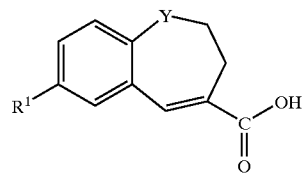

wherein $R^1$ and Y are as defined above, a salt or a reactive derivative thereof to a condensation reaction with a compound of the formula:

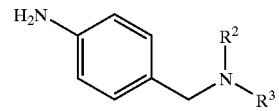

wherein $R^2$ and $R^3$ are as defined above, or a salt thereof; and then optionally isolating said compound of formula I or a salt thereof.

24. A pharmaceutical composition which comprises the compound according to claim 1 or a salt thereof and a pharmaceutically acceptable carrier, excipient, binder or diluent.

25. A method for treating infectious diseases of HIV comprising administering a pharmaceutically effective amount of a compound of claim 1 or a salt thereof in combination with a protease inhibitor, a reverse transcriptase inhibitor or a combination thereof to a mammal in need thereof.

26. A method for treating AIDS comprising administering a pharmaceutically effective amount of a compound of claim 1 or a salt thereof to a mammal in need thereof.

27. A method for treatment of infectious diseases of HIV comprising administering an effective amount of a compound of claim 1 or a salt thereof to a mammal in need thereof.

* * * * *

UNITED STATES PATENT AND TRADEMARK OFFICE
CERTIFICATE OF CORRECTION

PATENT NO. : 6,936,602 B1
DATED : August 30, 2005
INVENTOR(S) : Mitsuru Shiraishi et al.

It is certified that error appears in the above-identified patent and that said Letters Patent is hereby corrected as shown below:

<u>Title page,</u>
Item [*] Notice, please add:
-- This patent is subject to terminal disclaimers. --.

Signed and Sealed this

Thirteenth Day of December, 2005

JON W. DUDAS
*Director of the United States Patent and Trademark Office*